US009493454B2

(12) United States Patent
Zeng et al.

(10) Patent No.: US 9,493,454 B2
(45) Date of Patent: Nov. 15, 2016

(54) MULTIPLE KINASE PATHWAY INHIBITORS

(71) Applicants: MANNKIND CORPORATION, Valencia, CA (US); TOLERO PHARMACEUTICALS, INC., Lehi, UT (US)

(72) Inventors: Qingping Zeng, Thousand Oaks, CA (US); Mary Faris, Los Angeles, CA (US); Alexis Mollard, Salt Lake City, UT (US); Steven L. Warner, Sandy, UT (US); Gary A. Flynn, Oro Valley, AZ (US)

(73) Assignees: Tolero Pharmaceuticals, Inc., Lehi, UT (US); Mannkind Corporation, Valencia, CA (US)

( * ) Notice: Subject to any disclaimer, the term of this patent is extended or adjusted under 35 U.S.C. 154(b) by 0 days.

(21) Appl. No.: 14/431,476

(22) PCT Filed: Sep. 25, 2013

(86) PCT No.: PCT/US2013/061548
§ 371 (c)(1),
(2) Date: Mar. 26, 2015

(87) PCT Pub. No.: WO2014/052365
PCT Pub. Date: Apr. 3, 2014

(65) Prior Publication Data
US 2015/0266870 A1 Sep. 24, 2015

Related U.S. Application Data

(60) Provisional application No. 61/785,992, filed on Mar. 14, 2013, provisional application No. 61/757,331, filed on Jan. 28, 2013, provisional application No. 61/706,084, filed on Sep. 26, 2012.

(51) Int. Cl.
*C07D 471/04* (2006.01)
*A61K 31/4375* (2006.01)

(52) U.S. Cl.
CPC .................. *C07D 471/04* (2013.01)

(58) Field of Classification Search
CPC ............. C07D 471/04; A61K 31/4375
USPC .......................................... 546/122
See application file for complete search history.

(56) References Cited

U.S. PATENT DOCUMENTS

| | | | |
|---|---|---|---|
| 5,945,422 A | | 8/1999 | Doherty et al. |
| 6,150,359 A | * | 11/2000 | Barvian et al. ............ 514/234.5 |
| 8,604,031 B2 | | 12/2013 | Flynn et al. |
| 2003/0144351 A1 | | 7/2003 | Uckun et al. |

FOREIGN PATENT DOCUMENTS

| | | |
|---|---|---|
| WO | 9634867 A1 | 11/1996 |
| WO | 2004/065378 A1 | 8/2004 |
| WO | 2005/034869 A2 | 4/2005 |
| WO | 2007/136465 A2 | 11/2007 |

OTHER PUBLICATIONS

Thompson et al., Journal of Medicinal Chemistry (2000), 43(16), 3134-3147.*
Boschelli et al., "Synthesis and Tyrosine Kinase Inhibitory Activity of a Series of 2-Amino-8H-pyrido[2,3-d] pyrimidines: Identification of Potent, Selective Platelet-Derived Growth Factor Receptor Tyrosine Kinase Inhibitors," J. Med. Chem. 41, 4365-77, 1998.
Dalgarno et al., "Structural basis of Src tyrosine kinase inhibition with a new class of potent and selective trisubstituted purine-based compounds," Chem. Biol. Drug Des. 67, 46-57, 2006.
International Search Report and Written Opinion mailed Jan. 29, 2014 (PCT/US2013/061548); ISA/KR.
Lou et al., "Bruton's tyrosine kinase inhibitors: Approaches to potent and selective inhibition, preclinical and clinical evaluation for inflammatory diseases and B cell malignancies," J. Med. Chem. 55, 4539-50, 2012.
Klutchko et al., "2-Substituted Aminopyrido[2,3-d]pyrimidin-7(8H)-ones. Structure-Activity Relationships Against Selected Tyrosine Kinases and in Vitro and in Vivo Anticancer Activity," J. Med. Chem. 41, 3276-92, 1998.
Moasser et al., "Inhibition of Src kinases by a selective tyrosine kinase inhibitor causes mitotic arrest," Cancer Res. 59, 6145-52, 1999.
Thompson et al., "Synthesis and Structure-Activity Relationships of 7-Substituted 3-(2,6-Dichlorophenyl)-1,6-naphthyridin-2(1H)-ones as Selective Inhibitors of pp60c-src," J. Med. Chem. 43, 3134-47, 2000.
Wiestner, "Emerging role of kinase-targeted strategies in chronic lymphocytic leukemia," Blood 120, 4681-91, 2012.
Wiestner, "Targeting B-Cell Receptor Signaling for Anticancer Therapy: The Bruton's Tyrosine Kinase Inhibitor Ibrutinib Induces Impressive Responses in B-Cell Malignancies," J. Clin. Oncol. 31, 128-30, 2013.
Buggy et al., "Bruton Tyrosine Kinase (BTK) and Its Role in B-cell Malignancy," *International Reviews of Immunology* 31(2):119-132, 2012.
Evans et al., "Clinical Development of AVL-292; a Potent, Selective Covalent Btk Inhibitor for the Treatment of B Cell Malignancies," *Blood (ASH Annual Meeting Abstracts)* 118(21), 2011, 1 page. (Poster).
Hantschel et al., "Target spectrum of the BCR-ABL inhibitors imatinib, nilotinib and dasatinib," *Leukemia & Lymphoma* 49(4):615-619, 2008.
Lombardo et al., "Discovery of N-(2-chloro-6-methyl-phenyl)-2-(6-(4-(2-hydroxyethyl)-piperazin-1-yl)-2-methylpyrimidin-4-ylamino) thiazole-5-carboxamide (BMS-354825), a Dual Src/Abl Kinase Inhibitor with Potent Antitumor Activity in Preclinical Assays," *Journal of Medicinal Chemistry* 47(27):6658-6661, 2004.

* cited by examiner

*Primary Examiner* — Niloofar Rahmani
(74) *Attorney, Agent, or Firm* — Seed IP Law Group LLP

(57) ABSTRACT

Kinase with inhibitory activity against kinases disposed in multiple signaling pathways and their therapeutic uses.

24 Claims, 11 Drawing Sheets

MULTIPLE KINASE PATHWAY INHIBITORS

This application claims priority to Ser. No. 61/706,084 filed on Sep. 26, 2012; Ser. No. 61/757,331 filed on Jan. 28, 2013; and Ser. No. 61/785,992 filed on Mar. 14, 2013. Each of these applications is incorporated herein by reference in its entirety.

All documents cited in this disclosure are incorporated herein by reference in their entireties.

TECHNICAL FIELD

The invention relates to kinase inhibitors with inhibitory activity against kinases disposed in multiple signaling pathways and their therapeutic uses.

BACKGROUND

Cancer chemotherapy initially relied on agents with broad cytotoxicity. As greater understanding of the cancer cell biology was gained, targeted therapies were developed that inhibited the activity of signaling proteins, often kinases, involved in the regulation of vital cellular functions and uniquely or excessively expressed in cancer cells. Compounds with activity solely against a particular target enzyme were generally sought in developing such drugs, although as more of the kinome became experimentally accessible, it became clear that many of these drugs had activity against additional kinases. Differences in effectiveness but also general toxicity could often be attributed to these additional inhibitory activities. Additionally, cancers often develop resistance to such targeted therapies and in relatively short periods of time. Thus, there exists a need for further and more effective drugs.

DETAILED DESCRIPTION

Figure 1:
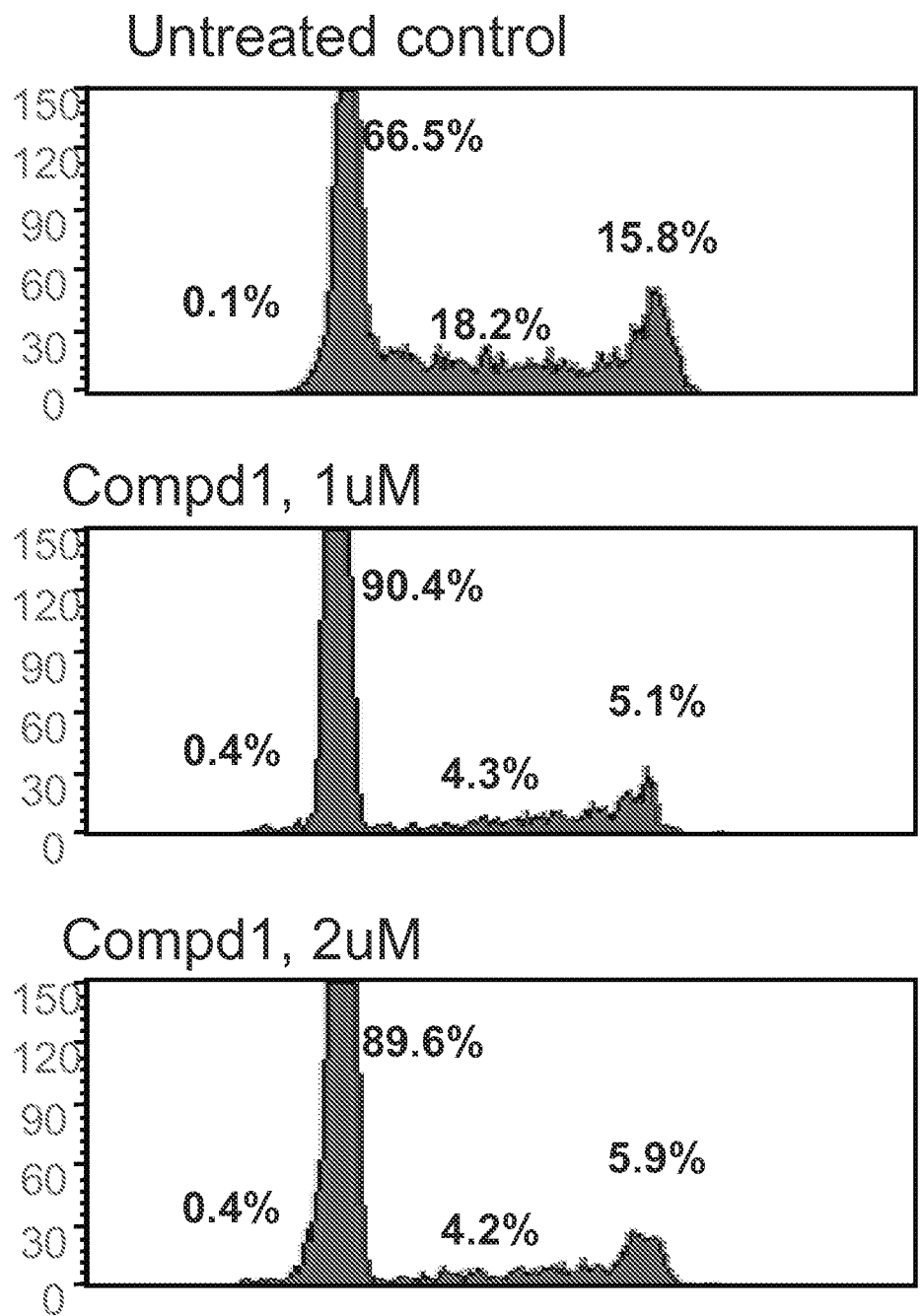
FIG. 1. Representative graphs showing cell cycle analysis of DoHH2 cells by flow cytometry.

Embodiments disclosed herein provide compounds, especially amino naphthyridinones, that reversibly inhibit two or more kinases disposed in two or more semi-independent but compensatory signaling pathways involved in the regulation of cellular proliferation and survival. Inhibition of a first pathway arises from the inhibition of Bruton's tyrosine kinase (BTK), particularly in cells of hematologic origin, or of bone marrow kinase on chromosome X (BMX), particularly in cells of epithelial or endothelial origin Inhibition of the second pathway, the SRC-family kinase pathway, arises from inhibition of one or more SRC-family kinases (SFK) such as SRC, LYN, or Hemopoietic Cell Kinase (HCK) or any combination thereof. Embodiments disclosed herein also include methods of using the disclosed compounds to inhibit one or more of the targeted kinases disposed in either or both pathways, to indirectly inhibit the activation, activity, or generation of signal mediators disposed downstream of one or more of the targeted kinases in either or both pathways, to inhibit the function, proliferation, or survival of cells in which one or more of the targeted kinases are activated, and to treat diseases or disorders associated with the abnormal or undesired function, proliferation, or survival of cells in which one or more of the targeted kinases are activated. Such diseases or disorders include those that are immunologic or neoplastic in nature. Further embodiments include methods of synthesizing the compounds, methods of synthesizing intermediates, and the intermediates themselves.

Intracellular signaling involves a complex network of interacting proteins. Although often presented in simplified forms involving linear paths from extra-cellular or endogenous stimulus to ultimate cellular response, there are in fact multiple possible branch points, convergences, and feedback loops. In normal physiology this allows for integration of signals from multiple stimuli. Many pathologic conditions, including various cancers and immunologic disorders, are associated with dysregulated signal transduction. Thus, even in the absence of a particular stimulus, a receptor or any of the downstream signal transduction mediators can become aberrantly activated, leading to inappropriate cellular activation resulting in unchecked cellular proliferation or pathologically exhibited function. It has become possible to treat the resulting pathologies by inhibiting the activity of such aberrantly or inappropriately activated signal transduction proteins. However, alternative signaling pathways, in some instances leading to the activation of distinct downstream intermediates for common biological responses, complicate such treatments. Such downstream intermediates include phospholipase C-γ (PLC-γ), phosphoinosital-3 kinase (PI3K), the mitogen-activated protein (MAP) kinases, Grb2/SOS complex (growth factor receptor-bound protein 2 complexed with Ras-guanine exchange factor SOS), FAK (focal adhesion kinase), AKT (protein kinase B), STAT3 (signal transducer and activator of transcription 3), and NF-κB (nuclear factor kappa-light-chain-enhancer of activated B cells), among others. The effectiveness of the inhibitor of the targeted pathway will be reduced or lost if a second pathway already is activated. Even if only a single signaling pathway is activated initially, its inhibition can provide selective pressure for another to become activated and establish resistance to the inhibitor of the first pathway. Thus, it is advantageous to use an agent that simultaneously inhibits multiple relevant targets.

A major class of signal transduction proteins is the tyrosine kinases. These kinases phosphorylate critical tyrosine residues in their substrates, which can themselves have kinase or other enzymatic activity which is regulated by the extent of phosphorylation. Alternatively, kinase substrates can in turn regulate their targets by phosphorylation-sensitive binding. Signaling kinases can themselves also have critical tyrosine residues that can be phosphorylated. In a common scheme there are two critical tyrosine residues. The enzyme is inactive when neither of the tyrosine residues is phosphorylated and is fully active when both tyrosine residues are phosphorylated. When one of the tyrosine residues is phosphorylated, the enzyme has partial activity. The partial activity may be minimal, as with BTK, or substantial, as with SRC In other instances, there can be a single critical tyrosine or several. Signaling is typically initiated by a binding event that exposes otherwise inaccessible tyrosine residues, allowing a first kinase to become activated. Such binding events are also important in the activation process for bringing about the co-localization of various signaling pathway components. Examples of such binding events are the binding of the ITAM (immunoreceptor tyrosine-based activation) motif of the BCR (B cell receptor) co-receptor molecules CD79A and CD79B by SYK (spleen tyrosine kinase), and phosphatitdylinositol-3,4,5-triphosphate (PIP3) by BTK, resulting in both conformational change and co-localization near the inner face of the plasma membrane, thus facilitating the phosphorylation of BTK by SYK.

The observable level of activity of a particular kinase is related to the degree of phosphorylation at both the molecular and population level as well as to the amount of kinase present. Thus, kinase activation or up-regulation can reflect an increase in the degree of phosphorylation, the level of expression, or both. Similarly, down-regulation can reflect a decrease in the degree of phosphorylation, level of expression, or both. The degree of pathway activation reflects the net effect of the degree of activation of all of the components of the pathway.

At this point several cancer drugs that inhibit signaling kinases have reached the market and many more are in development. These agents typically have been developed to inhibit a single target kinase relevant to a disease sought to be treated. In actuality many of these drugs inhibit numerous kinases with various effects. These additional inhibitory activities can contribute to the effectiveness of the drug against the disease(s) sought to be treated, that is, effectiveness can be due to inhibition of more than just the originally targeted kinase; or the additional activities can allow the drug to be used for additional indications; or the additional activities can contribute to undesirable side effects and toxicities. In some instances these different effects can be due to the same additional activity or activities. In other instances these different effects can be due to distinct additional activities. Similarly in various embodiments there are amino naphthyridinones that inhibit other than just the originally targeted kinases and thus there are associated methods of inhibition of these kinases as well as methods of treatment of diseases or disorders that are associated with the activation or activity of such other inhibited kinase(s) whether such association is in addition to or instead of the association one or another of the originally targeted kinases with a particular disease or disorder. Typically in such embodiments the level of activity, measured as $IC_{50}$, $EC_{50}$, or $K_i$, and the like, against the other kinase(s) is similar to that against originally targeted kinases being within 2-fold, 5-fold, or 10-fold of each other. Further in various embodiments the amino naphthyridinones lack substantial activity against one, two, or more kinases the activity of which is associated with undesirable side effects and toxicities when administered to a mammal, for example a human.

Despite the success of such marketed agents in bringing about the control or regression of various tumors, the common experience with such targeted therapies is that resistance eventually emerges. Two mechanisms of resistance are understood. By one, the treatment selects mutants of the targeted kinase that are resistant to inhibition. By the other, the treatment selects cells in which the expression/activation of another kinase in the network is increased, thereby generating a compensatory signal. A compensatory signal is one that substitutes for a blocked or inhibited signal, especially in promoting the activation, productivity, proliferation, or survival of cells, and without which such blockage or inhibition of the signal would lead to a reduced level of activation, productivity, proliferation or survival. The other kinase can be in a parallel arm of the network, providing a bypass to the block caused by inhibition of the first kinase. Alternatively, for kinases disposed in serial positions in the network, the increased signal from the other kinase can compensate for the reduced signal if upstream, or simply replace it if downstream. Targeting of multiple strategically selected nodes in the signaling network substantially reduces the emergence of resistance by requiring simultaneous selection of two mutations in the case of the first mechanism or by also inhibiting the compensatory signal in the case of the second mechanism.

There are many possible combinations of targets among the kinases, among the tyrosine kinases, and even among the non-receptor tyrosine kinases, whose activity are known or suspected to contribute to dysregulation of cellular function or proliferation, and thus whose inhibition might be effective in the treatment of an associated disease or disorder. However, due to the complexity of the signaling network, it is not readily apparent what combination of targets will actually lead to improved effectiveness. Data disclosed herein show greater inhibition of tumor cell line proliferation in vitro and in animal models (see Examples 77, 84, and 85) by compounds that inhibit certain non-receptor tyrosine kinases, BTK and various Src-family kinases, thus providing indications of synergy and compensatory mechanisms between the Tec kinase family member BTK, which acts downstream through PLC-γ, and members of the SFK, some of which can participate in the BTK pathway but can also act downstream through PI3 kinase.

One SFK member, SRC, a known contributor to tumorigenesis and a member of SFK group A, is involved in cellular proliferation, migration, adhesion, invasion and angiogenesis. LYN, a member of SFK group B whose members are specific to hematopoietic cells, is a key initiator of the B cell signaling process and is involved in modulating immune responses and determining cell fate decision, including cell activation, apoptosis and survival. LYN can act at multiple sites in the signaling network and its activation can have either stimulatory or inhibitory net effect on cell growth and survival, depending on the nature of the activating stimulus. However, in tumor cells LYN activation is associated with growth and survival. A third SFK member, HCK, is involved in phagocytosis, adhesion, migration, lysosome exocytosis and actin polymerization. HCK shows a restricted expression profile with primary expression in myelomonocytic cell lineages. HCK plays a role in immune function and cancer. HCK mimics adhesion-dependent priming of leukocytes and regulates the phagocytic activity of macrophages, thereby enhancing innate immune responses. In addition, HCK mediates toll-like receptor 4 function in host defense to infection.

When activated, LYN, HCK, and SRC have oncogenic potential and can initiate tumor formation. More to the point, these kinases activate downstream intermediates including PI3K/AKT, RAC, and STAT, constituting a second arm in the network leading to the activation of biological responses similar to those activated by BTK. Thus, treating neoplastic or immunological disorders by inhibiting only one of these pathways at a time may not be sufficient to significantly alter biological responses and the course of the disease. In addition to their activation downstream of the BCR, BTK and Src-family kinases such as HCK, LYN, and SRC show increased expression and/or activation in tumor cells. The expression and/or constitutive activation of these kinases in B cell malignancies correlate with disease progression and are also associated drug resistance, again indicating that inhibiting both arms of the network (that is, signaling through PLCγ, NF-AT and NFkB one the one hand and signaling through PI3K/AKT, RAC, and STAT on the other) will provide more robust treatment. Thus, embodiments include compounds that are capable of down-modulating signaling through either or both the PLC-γ and PI3 kinase nodes of the intracellular signaling network. In some of these embodiments down-modulation of signaling through PLC-γ includes inhibition of BTK. In alternative embodiments down-modulation of signaling through PLC-γ includes inhibition of BMX. In some of these embodiments down-modulation of signaling through PLC-γ includes inhibition of a SFK. In various aspects of these embodiments the SFK can include SRC, LYN, HCK, or any combination thereof. In some of these embodiments down-modulation of signaling through PLC-γ includes inhibition of LYN.

BTK is a member of the Tec family of intracellular tyrosine kinases, and is primarily expressed in lymphocytes of B cell lineage, mast cells, granulocytes, basophils, and monocytic cells. BTK is a key node in the B cell receptor (BCR) activation pathway, for example, in that it is limiting for the transmission of mitogenic signals from the BCR (Buggy, J. J, and Elias, L. *Bruton tyrosine kinase (BTK) and its role in B-cell malignancy Int Rev Immunol.* 31: 119-32, 2012). BCR ligation on the surface of B cell results in the tyrosine phosphorylation in the ITAM motif of the BCR by Src family member tyrosine kinases (e.g., Lyn, Fyn). The phosphorylated ITAMs recruit and enhance the phosphorylation of SYK and BTK, leading to the activation of downstream intermediates, particularly PLCγ, NF-AT and NF-κB, and biological responses including proliferation, anti-apoptosis and immunologic functions. BTK can also become activated downstream of the activation of various receptors, whether by ligand binding or otherwise, importantly including FcγR, CXCR4, CXCR5 as mentioned above. This portion of the signaling network can include other Tec kinases, SYK, and various SRC-family kinases including SRC, LYN, and HCK. These kinases can be disposed serially in a pathway or in parallel arms of the network, and indeed they can act at multiple loci within the network.

In addition to its role in BCR mediated signal transduction, BTK also functions in other receptor pathways, including immunoglobulin Fc receptor signaling such as the high-affinity IgE receptor (FcεRI), the G-protein coupled chemokine receptors CXCR4 and CXCR5, as well as integrin α4β1 (VLA-4). BTK also interacts with members of the Toll-like receptor (TLR) family, including TLR8 and TLR9. As a result, BTK regulates innate immune activation, inflammatory cytokine production, immunoglobulin expression, B-cell trafficking, tissue homing, adhesion to cellular substrates and basophil/mast cell degranulation. Some of these mechanisms also involve the SFK LYN.

The cellular and molecular mode of action of BTK explains its role in allergic, immune and inflammatory diseases. For example, BTK activation plays a detrimental role in systemic lupus erythematosus (SLE) as well as rheumatoid arthritis (RA) patients and synovitis. BTK also regulates immune hypersensitivity responses such as allergic rhinitis, dermatitis, anaphylactic reaction, and passive cutaneous anaphylaxis. Finally, BTK mediates the amplification of inflammatory reactions driven through cytokine production and immune complex formation. These have direct implication in the different phases of immune diseases.

Basal levels of BTK activity provide a tonic signal supporting cellular viability, whereas higher levels of activity associated with activation of the pathway, for example upon BCR engagement, support cellular proliferation. BTK can also be activated downstream of immunoglobulin receptor FcγR, selectin, and various chemokine receptors, particularly CXCR4 and CXCR5. Thus BTK plays a critical role in B cell differentiation, proliferation, and function (examples include degranulation, migration, homing, and immunoglobulin and cytokine production); the particular response depending on factors such as cell type, stage of differentiation, and what other signals may be present. Additionally, BTK can become activated in the absence of receptor engagement, for example it can be activated by the oncogenic kinase BCR/ABL, an aberrant fusion protein, or by becoming constitutively activated. Such chronic signaling has been associated with various neoplastic and immunologic disorders; thus, BTK has been recognized as a target for interventions in immune disorders and more recently in oncology.

BTK is involved in several inflammatory processes mediated by B cells, mast cells and neutrophils. BTK plays a critical role in neutrophil activation and recruitment after stimulation with chemokines or through selectins, and is necessary for efficient B-cell function, including cytokine secretion, integrin-mediated interactions, all of which activate immune responses and may become aberrantly activated in immune disorders, including in autoimmune and inflammatory disease such as rheumatoid arthritis, systemic lupus erythematosus, immune hypersensitivity, atopic asthma and other allergic disorders. Thus compounds that inhibit BTK can be used in the treatment of these disorders.

BTK participates in the transformation, proliferation, and drug resistance of hematologic malignancies such as:
  a. B cell leukemias, for example, Acute Lymphocytic Leukemia (ALL), Chronic Lymphocytic Leukemia (CLL), Acute Myeloid Leukemia (AML), Chronic Myeloid Leukemia, (CML);
  b. B cell lymphomas, for example, Hodgkin's lymphoma (HL), and Non-Hodgkin's lymphoma (NHL) including the following types: Diffuse Large B-Cell Lymphoma (DLBCL), Follicular Lymphoma (FL), Mucosa-Associated Lymphatic Tissue (MALT) Lymphoma Small Cell Lymphocytic Lymphoma-Chronic Lymphocytic Leukemia (SLL/CLL), Mantle Cell Lymphoma (MCL), Large B-Cell Lymphoma, Lymphoplasmacytic Lymphoma (aka Waldenström Macroglobulinemia), Marginal Zone Lymphoma (MZL), Hairy cell leukemia (HCL) and Burkitt Lymphoma-Burkitt Leukemia (BL);

c. Myelomas, including multiple myeloma (MM) and plasmacytoma; and d. Mast cell malignancies, including mastocytoma and mast cell leukemia.

Besides its involvement in hematologic malignancies BTK has also been associated with certain solid tumors including pancreatic and colorectal cancers.

Resistance, that is lack of or loss or responsiveness, to standard of care therapy has been reported in numerous hematologic tumors, and can be attributed to a variety of mechanisms, including complementary (i.e., compensatory) pathways activated in a tumor environment. Emerging evidence indicates that BTK plays a role in tumor survival and resistance to targeted therapies. In particular, chronic activation of BTK has been observed in cancers that have become resistant to a variety of targeted drugs including:

e. imatinib which inhibits the Abelson proto-oncogene product (ABL) and the breakpoint cluster region gene product (BCR)/ABL fusion protein, Mast/stem cell growth factor receptor (c-Kit), and platelet-derived growth factor receptor (PDGFR). It is approved to treat Ph$^+$ CML, c-Kit$^+$ gastrointestinal stromal tumors (GIST), Ph$^+$ ALL, myelodysplastic/myeloproliferative diseases associated with PDGFR gene re-arrangements, aggressive systemic mastocytosis (ASM) without or an unknown D816V c-KIT mutation, hypereosinophilic syndrome (HES) and/or chronic eosinophilic leukemia (CEL) who have the FIP1L1-PDGFRα fusion kinase (CHIC2 allele deletion) or FIP1L1-PDGFRα fusion kinase negative or unknown, unresectable, recurrent and/or metastatic dermatofibrosarcoma protuberans.

f. dasatinib which inhibits BCR/ABL, SRC family kinases (SRC, LCK, YES, FYN), c-Kit, ephrin receptor EPHA2, and PDGFRβ. Although not noted in its prescribing information dasatinib also inhibits BTK and indeed a broad array of tyrosine kinases. It is approved to treat Ph$^+$ CML and Ph$^+$ ALL.

g. bortezomib a proteasome inhibitor, which is currently a primary treatment in MM, although the mechanism is not apparent.

h. rituximab and other anti-CD20 therapies which are primary treatment in non-Hodgkin's lymphoma and can be used in other B cell malignancies.

Additionally, the SFKs LYN and HCK have been frequently implicated in treatment resistance and progression of CML. HCK and LYN are often over-expressed in imatinib-resistant CML cells that lack BCR-ABL mutations Inhibition of HCK alone or LYN alone can be sufficient to re-sensitize CML cells to imatinib or dasatinib. Thus a compound inhibiting at least one of these kinases could be useful in combination with imatinib or dasatinib in treating such resistant cancers. A compound inhibiting HCK and/or LYN as well as BCR-ABL could be similarly useful.

Perhaps the first compound with experimentally useful BTK-inhibitory activity was LFM-A13, however it was relatively non-specific, inhibiting a wide array of kinases and, with an IC50 of around 17 μM, not clinically suitable. More recent compounds targeting BTK are currently in clinical development: AVL-292 (Avila Therapeutics) and PCI-32765 (ibrutinib; Pharmacyclics). Both of these compounds are irreversible (covalent) inhibitors of BTK (as was LFM-A13), with several orders of magnitude greater activity against BTK than against other kinases including the SFKs SRC, LYN, and HCK (Evans, et al. ASH Annual Meeting Abstracts. 2011; 118: 3485; Buggy & Elias, Int'l. Rev. Immunol. 2012, 31:119-132). In contrast, embodiments disclosed herein relate to compounds that bind reversibly (non-covalently) to BTK, and their use in treating neoplastic and immunologic disorders. In some of these embodiments the compound(s) have activity against one or more of the SFKs that is within an order of magnitude of its activity against BTK. In one aspect activity can be expressed as an $IC_{50}$. In another aspect activity can be expressed as a In another aspect activity can be expressed as an $EC_{50}$. In some of these embodiments the activity against BTK or SRC or LYN or HCK or any combination thereof is an order of magnitude better than against one or more other kinases, for example, without limitation, ABL, BCR/ABL, c-Kit, PLK, JAK2, ephrin receptor EPHA2, or PDGFRβ.

BMX, also known as ETK, is another Tec kinase that can be inhibited by amino naphthyridinone compounds disclosed herein. The expression and activation of BMX has been associated with angiogenesis, self-renewal of cancer stem cells, and is up-regulated in a variety of cancers (see for example Holopainen T, et al. *Deletion of the Endothelial Bmx Tyrosine Kinase Decreases Tumor Angiogenesis and Growth*. Cancer Res. 2012 Jul. 15; 72(14):3512-3521; Fujisawa Y, et al. *Ligand-independent activation of the arylhydrocarbon receptor by ETK (Bmx) tyrosine kinase helps MCF10AT1 breast cancer cells to survive in an apoptosis-inducing environment*. Biol Chem. 2011 October; 392(10): 897-908. Epub 2011 Aug. 24; Guryanova O A, et al. *Nonreceptor tyrosine kinase BMX maintains self-renewal and tumorigenic potential of glioblastoma stem cells by activating STAT3*. Cancer Cell. 2011 Apr. 12; 19(4):498-511; Guo S, et al. *Tyrosine kinase ETK/BMX is up-regulated in bladder cancer and predicts poor prognosis in patients with cystectomy*. PLoS One. 2011 Mar. 7; 6(3):e17778; Dai B, et al. *Compensatory upregulation of tyrosine kinase Etk/BMX in response to androgen deprivation promotes castration-resistant growth of prostate cancer cells*. Cancer Res. 2010 Jul. 1; 70(13):5587-96. Epub 2010 Jun. 22; and Guo L, et al. *Non-receptor tyrosine kinase Etk is involved in the apoptosis of small cell lung cancer cells*. Exp Mol Pathol. 2010 June; 88(3):401-6). Thus various embodiments involve methods of inhibiting BMX including in cancer cells, endothelial cells, or otherwise; methods of inhibiting angiogenesis, cancer-related or otherwise; and methods of inhibiting tumor growth and survival. In various aspects of these embodiments the cancer can include breast cancer, bladder cancer, glioblastoma, prostate cancer, small-cell lung cancer, or hepatocellular cancer.

Additional kinases the inhibition of which can contribute to therapeutic effectiveness include SYK, ABL, BCR/ABL, and c-Kit. SYK participates in the activation of BTK as noted above. Inhibition of ABL or BCR/ABL is useful in the treatment of Ph$^+$ leukemias. C-Kit has been associated with mast cell leukemias and gastrointestinal stromal tumors. Like the SFKs, its signal is transmitted through the PI3 kinase node. Thus in some embodiments amino naphthyridinone compounds will have substantial inhibitory activity against one or more of these tyrosine kinases in addition to the above described targeted kinases and can be used in the treatment of diseases involving the activation of these kinases.

While improved therapeutic effectiveness can be associated with inhibiting multiple kinases, inhibition of some kinases will lead to undesirable side-effects. Such side-effects can be due to inhibition of the kinase(s) responsible for or contributing to the therapeutic effect, that is, be due to an on-target effect. Such side effects can also be due to inhibition of one of more kinases that do not contribute to the therapeutic effect, that is, an off-target effect. Depending on the severity of an undesirable side-effect and the seriousness of the disease or disorder being treated, the side-effect may or may not be tolerable with respect to any particular indication. However, while it may be necessary to tolerate side-effects due to on-target activity, it will be generally desirable to reduce or eliminate side-effects due to off-target activity. Thus, various embodiments comprise amino naphthyridinone compounds that lack substantial inhibitory activity against one or more kinases. Such embodiments can exclude inhibitory activity against any one, some, or all of the following, non-exhaustively listed, kinases or kinase groups in any combination: tyrosine kinases other than the targeted kinases and such as Met, JAK3, and ZAP-70; receptor tyrosine kinases generally; tyrosine kinases-like kinases generally and such as c-RAF and IRAK-3; serine-threonine kinases generally and such as ASK1, MEK1, MKK6, and PAK2; Calcium/calmodulin-dependent kinases generally and such as CaMK1, CHK1, MAPKAP-K2, and Pim-1; CMGC (CDK, MAPK, GSK, CLK family) kinases generally and such as CDK2/cyclinA, CDK7/cyclinH/MAT1, CDK9/cyclinT1, GSK3α, GSK3B, JNK1α1, JNK2α2, p38, MAPK1, SAPK2a, and SAPk2b; casein kinases generally and such as CK1 and CK1δ; AGC (PKA, PKG, PKC family) kinases generally and such as PKCα, p70S6K, and ROCK1; lipid/atypical kinases generally and such as mTOR, PI3 kinase (p110α/p85α), and PI3 kinase (p110β/p85α); miscellaneous kinases generally and such as Aurora-A, Aurora-B, IKKα, IKKβ, and Plk1; and non-tyrosine kinases generally. In various aspects of such embodiments a lack of substantial inhibitory activity corresponds to an $IC_{50}$ of >5 μM, >3 μM, >2 μM, >1 μM, >0.5 μM, or more than 10-fold, 20-fold, 50-fold or 100-fold greater than the $IC_{50}$ of a targeted kinase. In further various aspects of such embodiments a lack substantial inhibitory activity corresponds to an $EC_{50}$ of >10 μM, >5 μM, >3 μM, >2 μM, or more than 10-fold, 20-fold, 50-fold or 100-fold greater than the $EC_{50}$ of a targeted kinase.

The kinase selectivity profiles of the amino naphthyridinone compounds herein disclosed differ from other known compounds with BTK or SFK inhibitory activity. The irreversible BTK inhibitors have a narrow specificity as the residue that becomes covalently modified is not widely distributed in the kinome. Activity against the closely related kinase ITK has been observed (see for example US 2007-0293499 A1). The amino naphthyridinones are reversible inhibitors without notable activity against ITK. Reversible inhibitors targeting ABL or SFK have tended to be multi-kinase inhibitors that also have inhibitory activity against BTK. The amino naphthyridinones indeed inhibit BTK and SFK, and also ABL, but overall are focused on non-receptor protein tyrosine kinases whereas the inhibitors in the art, such as dasatinib, have a broader selectivity profile including for example, CMGC kinases such as p38 and MAPK1 (Lombardo, *J. Med. Chem.* 2004; Haxtschel, *Leukemi Lymphoma*, 2008).

Definitions

"Amino naphthyridinone"—For convenience the kinase inhibitors herein disclosed are referred to simply as "amino naphthyridinones" or "amino napthyridinone compounds". The plural form should be read as including the possibility of the singular.

"Alkyl" as used herein is a linear or branched saturated aliphatic hydrocarbon.

"Alkenyl" is linear or branched unsaturated aliphatic hydrocarbon containing at least one double bond.

"Alkynyl" is a linear or branched unsaturated aliphatic hydrocarbon containing at least one triple bond.

"Alkoxyl" is an alkyl, as defined above, bound to an oxygen atom.

"Alkylamino" is a

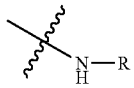

group, in which R is alkyl, as defined above.

"Alkylaminoalkyl" is a

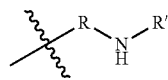

group, in which R and R' are alkyl as defined above and in which R and R' are the same or different alkyls.

"Alkylaminoalkoxyl" is a

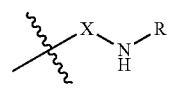

group, in which R is alkyl, as defined, above and X is alkoxyl, as defined above.

"Alkylaminoalkylamino" is a

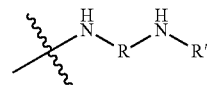

group, in which R and R' are alkyl, as defined above, and in which R and R' are the same or different alkyls.

"Alkoxylalkylamino" is a

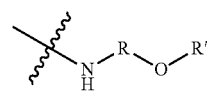

group in which R and R' are alkyl as defined above, and in which R and R' are the same or different alkyls.

"Alkoxyldialkylamino" is a

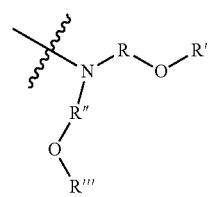

group in which R, R', R", and R'" are alkyl, as defined above, and in which R, R', R", and R'" independently are the same or different alkyls. If the number of carbon atoms in the dialkylamino portion is specified with a single designation, e.g., alkoxyl(C2-C3)dialkylamino, this means each alkyl of the dialkylamino independently is (C2-C3)alkyl. If the number of carbon atoms in the dialkylamino portion is specified with two designations, e.g., alkoxyl(C2-C3)(C1)dialkylamino, this means one alkyl of the dialkylamino is C2-C3 alkyl and the other alkyl of the dialkylamino is C1 alkyl.

"Alkylaminodialkylamino" is a

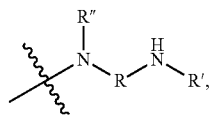

in which R, R', and R" are alkyl, as defined above, and in which R, R', and R" independently are the same or different alkyls. If the number of carbon atoms in the dialkylamino portion is specified with a single designation, e.g., alkylamino(C2-C3)dialkylamino, this means each alkyl of the dialkylamino independently is (C2-C3)alkyl. If the number of carbon atoms in the dialkylamino portion is specified with two designations, e.g., alkylamino(C2-C3)(C1)dialkylamino, this means one alkyl of the dialkylamino is C2-C3 alkyl and the other alkyl of the dialkylamino is C1 alkyl.

"Cycloalkyl" is a cyclic, saturated aliphatic hydrocarbon.

"Dialkyamino" is a

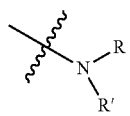

group in which R and R' are alkyl, as defined above, and in which R and R' are the same or different alkyls. If the number of carbon atoms in the dialkylamino is specified with a single designation, e.g., (C2-C3)dialkylamino, this means each alkyl of the dialkylamino independently is (C2-C3)alkyl. If the number of carbon atoms in the dialkylamino is specified with two designations, e.g., (C2-C3)(C1) dialkylamino, this means one alkyl of the dialkylamino is C2-C3 alkyl and the other alkyl of the dialkylamino is C1 alkyl.

"Dialkylaminoalkoxyl" is a

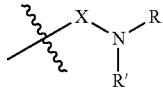

group, in which X is alkoxyl, as defined above, R and R' are alkyl, as defined above, and in which R and R' are the same or different alkyls. If the number of carbon atoms in the dialkylamino portion is specified with a single designation, e.g., (C2-C3)dialkylaminoalkoxyl, this means each alkyl of the dialkylamino independently is (C2-C3)alkyl. If the number of carbon atoms in the dialkylamino portion is specified with two designations, e.g., (C2-C3)(C1)dialkylaminoalkoxyl, this means one alkyl of the dialkylamino is C2-C3 alkyl and the other alkyl of the dialkylamino is C1 alkyl.

"Dialkylaminoalkyl" is a

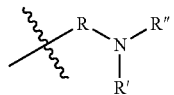

group, in which R, R', and R" are alkyl, as defined above, and in which R, R', and R" independently are the same or different alkyls. If the number of carbon atoms in the dialkylamino portion is specified with a single designation, e.g., (C2-C3)dialkylaminoalkyl, this means each alkyl of the dialkylamino independently is (C2-C3)alkyl. If the number of carbon atoms in the dialkylamino portion is specified with two designations, e.g., (C2-C3)(C1)dialkylaminoalkyl, this means one alkyl of the dialkylamino is C2-C3 alkyl and the other alkyl of the dialkylamino is C1 alkyl.

"Dialkylaminoalkylamino" is a

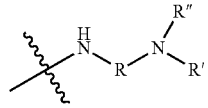

group, in which R, R', R", and R'" are alkyl, as defined above, and in which R, R', R", and R'" independently are the same or different alkyls. If the number of carbon atoms in the dialkylamino portion is specified with a single designation, e.g., (C2-C3)dialkylaminoalkylamino, this means each alkyl of the dialkylamino independently is (C2-C3)alkyl. If the number of carbon atoms in the dialkylamino portion is specified with two designations, e.g., (C2-C3)(C1)dialkylaminoalkylamino, this means one alkyl of the dialkylamino is C2-C3 alkyl and the other alkyl of the dialkylamino is C1 alkyl.

"Dialkylaminodialkylamino" is a

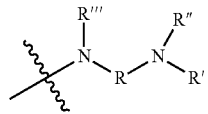

group, in which R, R', and R" are alkyl, as defined above, and in which R, R', and R" independently are the same or different alkyls. If the number of carbon atoms in either or both of the dialkylamino portions is specified with a single designation, e.g., (C2-C3)dialkylamino(C2-C3)dialkylamino, this means each of the four alkyls of the dialkylaminodialkylamino independently is (C2-C3)alkyl. If the number of carbon atoms in either or both of the dialkylamino portions is specified with two designations, e.g., (C2-C3)(C1)dialkylaminoalkylamino, this means one alkyl of the dialkylamino is C2-C3 alkyl and the other alkyl of the dialkylamino is C1 alkyl.

"Heterocyclic ring" is a saturated, unsaturated, or carbon-containing ring having at least one atom that is not carbon (e.g., N, S, O, boron, phosphorus, arsenic, antimony, bismuth, silicon, tin).

"Heteroaryl" is an aromatic carbon-containing ring having at least one atom that is not carbon (e.g., N, S, O, boron, phosphorus, arsenic, antimony, bismuth, silicon, tin).

"Hydroxylalkylamino" is a

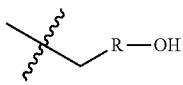

group in which R is alkyl, as defined above.

"Hydroxyldialkylamino" is a

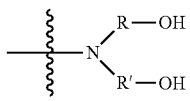

group in which R and R' are alkyl as defined above and in which R and R' are the same or different alkyls. If the number of carbon atoms in the dialkylamino portion is specified with a single designation, e.g., hydroxyl(C2-C3) dialkylamino, this means each alkyl of the dialkylamino independently is (C2-C3)alkyl. If the number of carbon atoms in the dialkylamino portion is specified with two designations, e.g., hydroxyl(C2-C3)(C1)dialkylamino, this means one alkyl of the dialkylamino is C2-C3 alkyl and the other alkyl of the dialkylamino is C1 alkyl.

"Perfluoroalkyl" is an alkyl, as defined above, in which the hydrogen atoms are replaced by fluorine atoms.

"IC50" (or "$IC_{50}$")—A concentration of a drug that reduces the observed activity of an enzyme by 50%. An IC50 is not a true affinity constant and the specific value determined can vary depending on the particular assay used. Nonetheless the rank order of IC50 for a set of compounds will typically be similar from one assay to another. (The true affinity constant for an inhibitor binding to an enzyme, can of course also be used for the same purposes as described herein for IC50). With respect to the kinases that are targeted by the compounds disclosed herein, kinase activity can be assayed, without limitation, as consumption of ATP or as incorporation of phosphate into a substrate. For example, the assay used in Example 76 assesses consumption of ATP based on luminescent detection of ADP. As an alternate example, the assay used in Example 78 assesses incorporation of phosphate based on the radiologic detection of $^{33}$P-labeled artificial substrates. Myriad other kinase assays are known in the art many of which are commercially available either as a kit or a service and one of skill in the art will recognize their particular usefulness for generating IC50 data.

"EC50" (or "$EC_{50}$")—A concentration of a drug that reduces by 50% an effect downstream of the direct inhibition of the drug's target(s). An EC50 can be based on a reduction of a disease symptom (e.g., tumor growth, inflammation), modulation of a cellular function (e.g., degranulation, secretion of antibody or cytokines), or modulation of the level of expression or activity of some biochemical marker, for example CD69. An EC50 will be influenced by factors such as solubility of the compound, cellular permeability and metabolism in tissue culture based assays and also adsorption, distribution, metabolism, elimination, and toxicity (ADMET) in whole animal based assays. As such, the specific value determined for any particular compound will vary from assay to assay, as can the rank order for a set of compounds. Similarly it is common that the rank orders for a set of compounds based on IC50 and EC50 will differ. With respect to the kinases that are targeted by the compounds disclosed herein, EC50 can be assessed by numerous measures including, without limitation, tumor growth as in Example 85, cellular proliferation as in Example 77, phosphorylation of PLC-γ as in Example 82, phosphorylation of BTK or SRC as in Example 83, induction of apoptosis as in Example 81, inhibition of basophil degranulation, inhibition of antibody secretion, and inhibition of cytokine secretion.

"Patient"—An individual in need of treatment with respect to a disease or disorder. In some embodiments the patient is specifically a human patient. In other embodiments the patient is specifically a veterinary patient, for example a dog, or includes such veterinary patients.

"Signal Mediator"—A signal mediator can be an enzyme that transmits the signal by activating another enzyme in the signaling pathway or generating a signaling biochemical (examples include kinases and other enzymes such as PI3 kinase and PLC-γ) or the signaling biochemical itself (examples include $IP_3$, NF-κB, and STAT).

"Targeted Kinase"—A kinase an inhibitor is designed or developed to inhibit. Alternatively, a kinase, the inhibition of which is associated with a clinical benefit or a biological response predictive of clinical benefit.

"Treat"—to slow or halt the progression of, to ameliorate or eliminate the symptoms of, to inhibit or disrupt the pathologic mechanism of, to reduce the extent or severity of, or to cure a disease or disorder; alternatively, to act with the goal of bringing about a clinical benefit.

Compounds

Disclosed herein are compounds which inhibit tyrosine kinases, particularly non-receptor tyrosine kinases, the inhibition of which can be useful in the treatment of various diseases and disorders. In preferred embodiments the compounds inhibit BTK and an SFK. In various embodiments the SFK is SRC, LYN, HCK or any combination thereof. The affinity of a compound for these various targeted kinases can be assessed as an $IC_{50}$. These compounds bind reversibly, typically with affinities at least sufficient to provide an $IC_{50}$ of <1 µM, and, without being bound by theory, are presumed to operate by an ATP-competitive mechanism. More useful compounds have an $IC_{50}$ of <200 nM or <100 nM. The $IC_{50}$ of reversibly-binding small molecule drugs, such as the compounds herein disclosed, are typically measured at no better than about 100 pM and thus in some embodiments the $IC_{50}$ is >50 or >100 pM. In some embodiments the $IC_{50}$ for BTK and the $IC_{50}$ for one, two, or three SFKs can be within 10-fold, 5-fold, 3-fold, or 2-fold of each other. For example for Compounds 16, 18, 36, 45, 46, 52, 56, 70, 73 the $IC_{50}$ for BTK and LYN are within 10-fold of each other in that they all have an $IC_{50}$ between 0.1 and 1 µM (see table 1). Alternatively a different range can be specified or no range need be specified. Similarly, in some embodiments the $IC_{50}$ for BTK and one or two SFK are less than some level. For example, the $IC_{50}$ with respect to BTK and LYN is <1 µM for each of Compounds 1, 5, 14-16, 18, 22-24, 27, 34-36, 43, 45-47, 52, 55, 56, 66, 67, 70, 73, 75-77, 79-83, 86, 92-101, 106-111, 115-125, 127, 129-148, 150, and 152. As another example, the IC50 with respect to BTK and SRC is <1 µM for each of Compounds 1, 7, 14-16, 18, 22-24, 27, 34-36, 43, 45-47, 52, 55, 56, 60, 66, 67, 70, 73, 75-77, 81-83, 88, 92-101, 107-111, 114-125, 127, 129-148, 150, and 152. As another example, the IC50 with respect to BTK, SRC, and LYN is <1 µM for each of Compounds 1, 14-16, 18, 22-24, 27, 34-36, 43, 45-47, 52, 55, 56, 66, 67, 70, 73, 75-77, 1-83, 92-101, 106-111, 115-125, 127, 129-148, 150, and 152. Other exemplary classes of compounds based on $IC_{50}$ with respect to one or more targeted kinase are apparent from Table 1. Such embodiments can be further limited by any of the disclosed structural criteria and such affinity criteria can further limit any of the structurally defined embodiments. Similarly, further embodiments can be limited by $EC_{50}$ as discussed below.

Further embodiments provide methods of making the compounds, methods of making intermediates in their synthetic pathways, and the intermediates themselves.

Due to the complexity of the signaling network there are many ways to assess the biological effects brought about the kinase inhibitors, though generally it is the aggregate effect which cannot readily be attributed to inhibition of any individual kinase. An $EC_{50}$ can be determined for any biological readout. Such biological effects include prolonged survival, reversal or amelioration of disease symptoms such as tumor growth (as in Example 85), allergy, inflammation or autoimmunity such as in rheumatoid arthritis; inhibition of cellular proliferation on one or another cell line or culture (as in Examples 77, 79 and 84); induction of apoptosis (as in Example 81); cellular activation; inhibition of immunologic function such as cytokine secretion, antibody secretion, or degranulation (as in Example 86); phosphorylation of kinases in the signaling pathway(s) such as BTK, SRC, or LYN (as in Example 83); phosphorylation of downstream signaling intermediates, such as PLC-γ (as in Example 82); or the expression of various biomarkers. Assays based on many of such biological effects are found in the Examples below. Useful $EC_{50}$s will often be somewhat higher than an $IC_{50}$ but still <10 µM. More useful compounds have an $EC_{50}$<5, <3, <2, or <1 µM. There may also be a differential in $EC_{50}$ as measured in a targeted versus a non-targeted system; for example between the inhibition of a B cell derived tumor cell line such as DoHH2 and a T cell or prostate tumor cell line such as H9 or PC3, respectively. Thus in some embodiments the $EC_{50}$ determined in a targeted system is 5-fold, 10-fold, 20-fold less than the $EC_{50}$ determined in a non-targeted system. In other embodiments an $EC_{50}$ can be below some level. Exemplary classes of compounds based on $EC_{50}$ with respect to one or more targeted kinase are apparent from Table 1 and the Examples. For example, $EC_{50}$ for inhibition of proliferation of DoHH2 cells is <1 µM for Compounds 1, 15-18, 22-25 27, 35, 42-44, 46, 47, 55, 56, 61, 62, 64-67, 70, 73, 75-80, 82, 83, 88-89, 92-97, 99-101, 106-111, 115-116, 118-125, 129-148, and 152 (see Table 1). Further embodiments can be defined by limits on $EC_{50}$ values other than those reported in Table 1. Such embodiments may be further limited by any of the disclosed structural criteria and such effectiveness criteria can further limit any of the structurally defined embodiments. Similarly, further embodiments can be limited by $IC_{50}$ as discussed above.

Embodiment Groups

1. In some embodiments, the compound is a compound of Structural Formula (I):

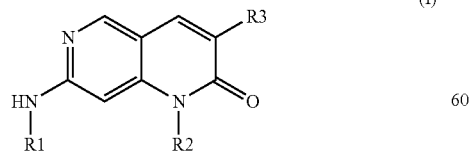

(I)

or a pharmaceutically acceptable salt thereof, wherein:
R1 is a nitrogen-containing five- or six-member heteroaryl in which at least one ring nitrogen atom is adjacent to the carbon linking R1 to the amino group, optionally substituted with 1, 2, or 3 groups independently selected from the group consisting of:
hydroxyl;
halogen;
C1-C3 alkyl;
hydroxyl (C1-C3)alkylamino, optionally linked to R1 through a carbonyl group;
hydroxyl (C1-C3)dialkylamino, optionally linked to R1 through a carbonyl group;
C1-C3 alkylamino, optionally linked to R1 through a carbonyl group;
C1-C3 dialkylamino; optionally linked to R1 through a carbonyl group;
(C1-C3)alkylamino(C1-C3)alkyl, optionally linked to R1 through a carbonyl group;
(C1-C3)dialkylamino(C1-C3)alkyl, optionally linked to R1 through a carbonyl group;
(C1-C3)alkylamino(C2-C3)alkoxyl, optionally linked to R1 through a carbonyl group;
(C1-C3)dialkylamino(C2-C3)alkoxyl, optionally linked to R1 through a carbonyl group;
(C1-C3)alkylamino(C2-C3)alkylamino, optionally linked to R1 through a carbonyl group;
(C1-C3)dialkylamino(C2-C3)alkylamino, optionally linked to R1 through a carbonyl group;
(C1-C3)alkylamino(C2-C3)dialkylamino, optionally linked to R1 through a carbonyl group
(C1-C3)dialkylamino(C2-C3)dialkylamino, optionally linked to R1 through a carbonyl group;
(C1-C3)alkoxyl(C2-C3)alkylamino, optionally linked to R1 through a carbonyl group;
(C1-C3)alkoxyl(C2-C3)dialkylamino, optionally linked to R1 through a carbonyl group; and
a three- to six-member heterocyclic ring containing 1 or 2 heteroatoms selected from O, N, and S; and, independently,
(1) optionally is substituted with (C1-C3)alkyl, (C1-C3) hydroxylalkyl, (C1-C3)alkoxyl(C1-C3)alkyl, or (C1-C3)alkylamino(C1-C3)alkyl and
(2) optionally is linked to the five- or six-member heteroaryl through a carbonyl group;
R2 is:
hydrogen;
C1-C6 alkyl, optionally substituted with 1, 2, or 3 groups selected from hydroxyl, methoxyl, ethoxyl, methylamino, N,N-dimethyl amino, ethylamino, N,N-diethylamino, and methylsulfanyl;
a three- to six-member cycloalkyl, optionally substituted with 1, 2, or 3 groups selected from hydroxyl, methoxyl, ethoxyl, methylamino, N,N-dimethyl amino, ethylamino, N,N-diethylamino, and methylsulfanyl;
a three- to six-member heterocyclic ring, optionally substituted with 1, 2, or 3 groups selected from hydroxyl, C1-C3 alkyl, methoxyl, ethoxyl, methylamino, N,N-dimethyl amino, ethylamino, N,N-diethylamino, and methylsulfanyl;
phenyl, optionally substituted with 1, 2, or 3 groups selected from hydroxyl, methoxyl, ethoxyl, methylamino, N,N-dimethyl amino, ethylamino, N,N-diethylamino, and methylsulfanyl; or
heteroaryl, optionally substituted with 1, 2, or 3 groups selected from hydroxyl, methoxyl, ethoxyl, methylamino, N,N-dimethyl amino, ethylamino, N,N-diethylamino, and methylsulfanyl; and R3 is:
- halogen;
- C1-C6 alkyl;
- C1-C6 hydroxylalkyl;
- C1-C6 alkylcarbonyl;
- C1-C6 perfluoroalkyl;
- C3-C6 cycloalkyl;
- C2-C6 alkenyl, optionally substituted with 1, 2, or 3 substituents selected from the group consisting of C1-C3 alkoxyl, C1-C3 alkoxylcarbonyl, and trifluoromethyl;
- C2-C6 alkynyl, optionally substituted with 1, 2, or 3 substituents selected from the group consisting of C1-C3 alkoxyl, hydroxyl, C1-C6 alkyl, trifluoromethyl;
- phenyl, optionally substituted with 1, 2, or 3 substituents selected from the group consisting of halogen, C1-C3 alkoxyl, and trifluoromethyl; and
- a five- to six-member heteroaryl, optionally substituted with 1, 2, or 3 substituents selected from the group consisting of halogen, C1-C3 alkoxyl, and trifluoromethyl.

2. In some embodiments, the compound is a compound of Embodiment Group 1, or a pharmaceutically acceptable salt thereof, in which R1 is a nitrogen-containing five-member heteroaryl.

3. In some embodiments, the compound is a compound of Embodiment Group 1, or a pharmaceutically acceptable salt thereof, in which R1 is a nitrogen-containing five-member heteroaryl selected from the group consisting of pyrrolyl, imidazolyl, pyrazolyl, oxazolyl, isoxazolyl, thiazolyl, isothiazolyl, triazolyl, furazanyl, oxadiazolyl, thiadiazolyl, dithiadiazolyl, and tetrazolyl.

4. In some embodiments, the compound is a compound of Embodiment Group 1, or a pharmaceutically acceptable salt thereof, in which R1 is a nitrogen-containing six-member heteroaryl.

5. In some embodiments, the compound is a compound of Embodiment Group 1, or a pharmaceutically acceptable salt thereof, in which R1 is a nitrogen-containing six-member heteroaryl selected from the group consisting of pyridinyl, diazinyl, oxazinyl, thiazinyl, triazinyl, and tetrazinyl.

6. In some embodiments, the compound is a compound of Embodiment Group 1, 2, 3, 4, or 5, or a pharmaceutically acceptable salt thereof, in which R1 is unsubstituted.

7. In some embodiments, the compound is a compound of Embodiment Group 1, 2, 3, 4, or 5, or a pharmaceutically acceptable salt thereof, in which R1 is substituted with 1 group.

8. In some embodiments, the compound is a compound of Embodiment Group 1, 2, 3, 4, or 5, or a pharmaceutically acceptable salt thereof, in which R1 is substituted with 2 groups.

9. In some embodiments, the compound is a compound of Embodiment Group 1, 2, 3, 4, or 5, or a pharmaceutically acceptable salt thereof, in which R1 is substituted with 3 groups.

10. In some embodiments, the compound is a compound of Embodiment Group 7, 8, or 9, or a pharmaceutically acceptable salt thereof, in which R1 is substituted with hydroxyl.

11. In some embodiments, the compound is a compound of Embodiment Group 7, 8, 9, or 10, or a pharmaceutically acceptable salt thereof, in which R1 is substituted with halogen.

12. In some embodiments, the compound is a compound of Embodiment Group 11, or a pharmaceutically acceptable salt thereof, in which R1 is substituted with F.

13. In some embodiments, the compound is a compound of Embodiment Group 11 or 12, or a pharmaceutically acceptable salt thereof, in which R1 is substituted with Br.

14. In some embodiments, the compound is a compound of Embodiment Group 11, 12, or 13, or a pharmaceutically acceptable salt thereof, in which R1 is substituted with Cl.

15. In some embodiments, the compound is a compound of Embodiment Group 11, 12, 13, or 14, or a pharmaceutically acceptable salt thereof, in which R1 is substituted with I.

16. In some embodiments, the compound is a compound of Embodiment Group 7, 8, 9, 10, 11, 12, 13, 14, or 15, or a pharmaceutically acceptable salt thereof, in which R1 is substituted with C1-C3 alkyl.

17. In some embodiments, the compound is a compound of Embodiment Group 16, or a pharmaceutically acceptable salt thereof, in which R1 is substituted with C1 alkyl, C2 alkyl, C3 alkyl, C1-C2 alkyl, C2-C3 alkyl, or C1-C3 alkyl.

18. In some embodiments, the compound is a compound of Embodiment Group 7, 8, 9, 10, 11, 12, 13, 14, 15, 16, or 17, or a pharmaceutically acceptable salt thereof, in which R1 is substituted with hydroxyl (C1-C3)alkylamino, optionally linked to R1 through a carbonyl group.

19. In some embodiments, the compound is a compound of Embodiment Group 18, or a pharmaceutically acceptable salt thereof, in which R1 is substituted with hydroxyl (C1)alkylamino, hydroxyl (C2)alkylamino, hydroxyl (C3)alkylamino, hydroxyl (C1-C2)alkylamino, hydroxyl (C1-C3)alkylamino, or hydroxyl (C2-3)alkylamino.

20. In some embodiments, the compound is a compound of Embodiment Group 18 or 19, or a pharmaceutically acceptable salt thereof, in which the hydroxyl (C1-C3) alkylamino is directly linked to R1.

21. In some embodiments, the compound is a compound of Embodiment Group 18 or 19, or a pharmaceutically acceptable salt thereof, in which the hydroxyl (C1-C3) alkylamino is linked to R1 through a carbonyl.

22. In some embodiments, the compound is a compound of Embodiment Group 7, 8, 9, 10, 11, 12, 13, 14, 15, 16, 17, 18, 19, 20, or 21, or a pharmaceutically acceptable salt thereof, in which R1 is substituted with hydroxyl (C1-C3)dialkylamino, optionally linked to R1 through a carbonyl group.

23. In some embodiments, the compound is a compound of Embodiment Group 22, or a pharmaceutically acceptable salt thereof, in which R1 is substituted with hydroxyl (C1-C3)dialkylamino, hydroxyl (C1-C2)dialkylamino, hydroxyl (C2-C3)dialkylamino, hydroxyl (C1)dialkylamino, hydroxyl (C2)dialkylamino, or hydroxyl (C3) dialkylamino.

24. In some embodiments, the compound is a compound of Embodiment Group 22, or a pharmaceutically acceptable salt thereof, in which R1 is substituted with hydroxyl (C1-C3)(C1-C3)dialkylamino, hydroxyl (C1-C3)(C1-C2) dialkylamino, hydroxyl (C1-C3)(C2-C3)dialkylamino, hydroxyl (C1-C3)(C1)dialkylamino, hydroxyl (C1-C3) (C2)dialkylamino, or hydroxyl (C1-C3)(C3)dialkylamino.

25. In some embodiments, the compound is a compound of Embodiment Group 22, or a pharmaceutically acceptable salt thereof, in which R1 is substituted with hydroxyl (C1-C2)(C1-C3)dialkylamino, hydroxyl (C1-C2)(C1-C2)

dialkylamino, hydroxyl (C1-C2)(C2-C3)dialkylamino, hydroxyl (C1-C2)(C1)dialkylamino, hydroxyl (C1-C2)(C2)dialkylamino, or hydroxyl (C1-C2)(C3)dialkylamino.

26. In some embodiments, the compound is a compound of Embodiment Group 22, or a pharmaceutically acceptable salt thereof, in which R1 is substituted with hydroxyl (C2-C3)(C1-C3)dialkylamino, hydroxyl (C2-C3)(C1-C2)dialkylamino, hydroxyl (C2-C3)(C2-C3)dialkylamino, hydroxyl (C2-C3)(C1)dialkylamino, hydroxyl (C2-C3)(C2)dialkylamino, or hydroxyl (C2-C3)(C3)dialkylamino.

27. In some embodiments, the compound is a compound of Embodiment Group 22, or a pharmaceutically acceptable salt thereof, in which R1 is substituted with hydroxyl (C1)(C1-C3)dialkylamino, hydroxyl (C1)(C1-C2)dialkylamino, hydroxyl (C1)(C2-C3)dialkylamino, hydroxyl (C1)(C1)dialkylamino, hydroxyl (C1)(C2)dialkylamino, or hydroxyl (C1)(C3)dialkylamino.

28. In some embodiments, the compound is a compound of Embodiment Group 22, or a pharmaceutically acceptable salt thereof, in which R1 is substituted with hydroxyl (C2)(C1-C3)dialkylamino, hydroxyl (C2)(C1-C2)dialkylamino, hydroxyl (C2)(C2-C3)dialkylamino, hydroxyl (C2)(C1)dialkylamino, hydroxyl (C2)(C2)dialkylamino, or hydroxyl (C2)(C3)dialkylamino.

29. In some embodiments, the compound is a compound of Embodiment Group 22, or a pharmaceutically acceptable salt thereof, in which R1 is substituted with hydroxyl (C3)(C1-C3)dialkylamino, hydroxyl (C3)(C1-C2)dialkylamino, hydroxyl (C3)(C2-C3)dialkylamino, hydroxyl (C3)(C1)dialkylamino, hydroxyl (C3)(C2)dialkylamino, or hydroxyl (C3)(C3)dialkylamino.

30. In some embodiments, the compound is a compound of Embodiment Group 22, 23, 24, 25, 26, 27, 28, or 29, or a pharmaceutically acceptable salt thereof, in which the hydroxyl (C1-C3)dialkylamino is directly linked to R1.

31. In some embodiments, the compound is a compound of Embodiment Group 22, 23, 24, 25, 26, 27, 28, or 29, or a pharmaceutically acceptable salt thereof, in which the hydroxyl (C1-C3)dialkylamino is linked to R1 through a carbonyl.

32. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, or 31, or a pharmaceutically acceptable salt thereof, in which R1 is substituted with C1-C3 alkylamino, optionally linked to R1 through a carbonyl group.

33. In some embodiments, the compound is a compound of Embodiment Group 32, or a pharmaceutically acceptable salt thereof, in which R1 is substituted with C1-C3 alkylamino, C1-C2 alkylamino, C2-C3 alkylamino, C1 alkylamino, C2 alkylamino, or C3 alkylamino.

34. In some embodiments, the compound is a compound of Embodiment Group 32 or 33, or a pharmaceutically acceptable salt thereof, in which the C1-C3 alkylamino is directly linked to R1.

35. In some embodiments, the compound is a compound of Embodiment Group 32 or 33, or a pharmaceutically acceptable salt thereof, in which the C1-C3 alkylamino is linked to R1 through a carbonyl.

36. In some embodiments, the compound is a compound of Embodiment Group, 7, 8, 9, 10, 11, 12, 13, 14, 15, 16, 17, 18, 19, 20, 21, 22, 23, 24, 25, 26, 27, 28, 29, 30, 31, 32, 33, 34, or 35, or a pharmaceutically acceptable salt thereof, in which R1 is substituted with C1-C3 dialkylamino, optionally linked to R1 through a carbonyl group.

37. In some embodiments, the compound is a compound of Embodiment Group 36, or a pharmaceutically acceptable salt thereof, in which R1 is substituted with (C1-C3)dialkylamino, (C1-C2)dialkylamino, (C2-C3)dialkylamino, (C1)dialkylamino, (C2)dialkylamino, or (C3)dialkylamino.

38. In some embodiments, the compound is a compound of Embodiment Group 36, or a pharmaceutically acceptable salt thereof, in which R1 is substituted with (C1-C3)(C1-C3)dialkylamino, (C1-C3)(C1-C2)dialkylamino, (C1-C3)(C2-C3)dialkylamino, (C1-C3)(C1)dialkylamino, (C1-C3)(C2)dialkylamino, or (C1-C3)(C3)dialkylamino.

39. In some embodiments, the compound is a compound of Embodiment Group 36, or a pharmaceutically acceptable salt thereof, in which R1 is substituted with (C1-C2)(C1-C3)dialkylamino, (C1-C2)(C1-C2)dialkylamino, (C1-C2)(C2-C3)dialkylamino, (C1-C2)(C1)dialkylamino, (C1-C2)(C2)dialkylamino, or (C1-C2)(C3)dialkylamino.

40. In some embodiments, the compound is a compound of Embodiment Group 36, or a pharmaceutically acceptable salt thereof, in which R1 is substituted with (C2-C3)(C1-C3)dialkylamino, (C2-C3)(C1-C2)dialkylamino, (C2-C3)(C2-C3)dialkylamino, (C2-C3)(C1)dialkylamino, (C2-C3)(C2)dialkylamino, or (C2-C3)(C3)dialkylamino.

41. In some embodiments, the compound is a compound of Embodiment Group 36, or a pharmaceutically acceptable salt thereof, in which R1 is substituted with (C1)(C1-C3)dialkylamino, (C1)(C1-C2)dialkylamino, (C1)(C2-C3)dialkylamino, (C1)(C1)dialkylamino, (C1)(C2)dialkylamino, or (C1)(C3)dialkylamino.

42. In some embodiments, the compound is a compound of Embodiment Group 36, or a pharmaceutically acceptable salt thereof, in which R1 is substituted with (C2)(C1-C3)dialkylamino, (C2)(C1-C2)dialkylamino, (C2)(C2-C3)dialkylamino, (C2)(C1)dialkylamino, (C2)(C2)dialkylamino, or (C2)(C3)dialkylamino.

43. In some embodiments, the compound is a compound of Embodiment Group 36, or a pharmaceutically acceptable salt thereof, in which R1 is substituted with (C3)(C1-C3)dialkylamino, (C3)(C1-C2)dialkylamino, (C3)(C2-C3)dialkylamino, (C3)(C1)dialkylamino, (C3)(C2)dialkylamino, or (C3)(C3)dialkylamino.

44. In some embodiments, the compound is a compound of Embodiment Group 36, 37, 38, 39, 40, 41, 42, or 43, or a pharmaceutically acceptable salt thereof, in which the C1-C3 dialkylamino is directly linked to R1.

45. In some embodiments, the compound is a compound of Embodiment Group 36, 37, 38, 39, 40, 41, 42, or 43, or a pharmaceutically acceptable salt thereof, in which the C1-C3 dialkylamino is linked to R1 through a carbonyl.

46. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45, or a pharmaceutically acceptable salt thereof, in which R1 is substituted with (C1-C3)alkylamino(C1-C3)alkyl, optionally linked to R1 through a carbonyl group.

47. In some embodiments, the compound is a compound of Embodiment Group 46, or a pharmaceutically acceptable salt thereof, in which R1 is substituted with (C1-C3)alkylamino(C1-C3)alkyl, (C1-C3)alkylamino(C1-C2)alkyl, (C1-C3)alkylamino(C2-C3)alkyl, (C1-C3)alkylamino(C1)alkyl, (C1-C3)alkylamino(C2)alkyl, or (C1-C3)alkylamino(C3)alkyl.

48. In some embodiments, the compound is a compound of Embodiment Group 46, or a pharmaceutically acceptable salt thereof, in which R1 is substituted with (C1-C2)

alkylamino(C1-C3)alkyl, (C1-C2)alkylamino(C1-C2)alkyl, (C1-C2)alkylamino(C2-C3)alkyl, (C1-C2)alkylamino(C1)alkyl, (C1-C2)alkylamino(C2)alkyl, or (C1-C2)alkylamino(C3)alkyl.

49. In some embodiments, the compound is a compound of Embodiment Group 46, or a pharmaceutically acceptable salt thereof, in which R1 is substituted with (C2-C3)alkylamino(C1-C3)alkyl, (C2-C3)alkylamino(C1-C2)alkyl, (C2-C3)alkylamino(C2-C3)alkyl, (C2-C3)alkylamino(C1)alkyl, (C2-C3)alkylamino(C2)alkyl, or (C2-C3)alkylamino(C3)alkyl.

50. In some embodiments, the compound is a compound of Embodiment Group 46, or a pharmaceutically acceptable salt thereof, in which R1 is substituted with (C1)alkylamino(C1-C3)alkyl, (C1)alkylamino(C1-C2)alkyl, (C1)alkylamino(C2-C3)alkyl, (C1)alkylamino(C1)alkyl, (C1)alkylamino(C2)alkyl, or (C1)alkylamino(C3)alkyl.

51. In some embodiments, the compound is a compound of Embodiment Group 46, or a pharmaceutically acceptable salt thereof, in which R1 is substituted with (C2)alkylamino(C1-C3)alkyl, (C2)alkylamino(C1-C2)alkyl, (C2)alkylamino(C2-C3)alkyl, (C2)alkylamino(C1)alkyl, (C2)alkylamino(C2)alkyl, or (C2)alkylamino(C3)alkyl.

52. In some embodiments, the compound is a compound of Embodiment Group 46, or a pharmaceutically acceptable salt thereof, in which R1 is substituted with (C3)alkylamino(C1-C3)alkyl, (C3)alkylamino(C1-C2)alkyl, (C3)alkylamino(C2-C3)alkyl, (C3)alkylamino(C1)alkyl, (C3)alkylamino(C2)alkyl, or (C3)alkylamino(C3)alkyl.

53. In some embodiments, the compound is a compound of Embodiment Group 46, 47, 48, 49, 50, 51, or 52, or a pharmaceutically acceptable salt thereof, in which the (C1-C3)alkylamino(C1-C3)alkyl is directly linked to R1.

54. In some embodiments, the compound is a compound of Embodiment Group 46, 47, 48, 49, 50, 51, or 52, or a pharmaceutically acceptable salt thereof, in which the (C1-C3)alkylamino(C1-C3)alkyl is linked to R1 through a carbonyl.

55. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54, or a pharmaceutically acceptable salt thereof, in which R1 is substituted with (C1-C3)dialkylamino(C1-C3)alkyl, optionally linked to R1 through a carbonyl group.

56. In some embodiments, the compound is a compound of Embodiment Group 55, or a pharmaceutically acceptable salt thereof, in which R1 is substituted with (C1-C3)dialkylamino(C1-C3)alkyl, (C1-C3)dialkylamino(C1-C2)alkyl, (C1-C3)dialkylamino(C2-C3)alkyl, (C1-C3)dialkylamino(C1)alkyl, (C1-C3)dialkylamino(C2)alkyl, or (C1-C3)dialkylamino(C3)alkyl.

57. In some embodiments, the compound is a compound of Embodiment Group 55, or a pharmaceutically acceptable salt thereof, in which R1 is substituted with (C1-C2)dialkylamino(C1-C3)alkyl, (C1-C2)dialkylamino(C1-C2)alkyl, (C1-C2)dialkylamino(C2-C3)alkyl, (C1-C2)dialkylamino(C1)alkyl, (C1-C2)dialkylamino(C2)alkyl, or (C1-C2)dialkylamino(C3)alkyl.

58. In some embodiments, the compound is a compound of Embodiment Group 55, or a pharmaceutically acceptable salt thereof, in which R1 is substituted with (C2-C3)dialkylamino(C1-C3)alkyl, (C2-C3)dialkylamino(C1-C2)alkyl, (C2-C3)dialkylamino(C2-C3)alkyl, (C2-C3)dialkylamino(C1)alkyl, (C2-C3)dialkylamino(C2)alkyl, or (C2-C3)dialkylamino(C3)alkyl.

59. In some embodiments, the compound is a compound of Embodiment Group 55, or a pharmaceutically acceptable salt thereof, in which R1 is substituted with (C1)dialkylamino(C1-C3)alkyl, (C1)dialkylamino(C1-C2)alkyl, (C1)dialkylamino(C2-C3)alkyl, (C1)dialkylamino(C1)alkyl, (C1)dialkylamino(C2)alkyl, or (C1)dialkylamino(C3)alkyl.

60. In some embodiments, the compound is a compound of Embodiment Group 55, or a pharmaceutically acceptable salt thereof, in which R1 is substituted with (C2)dialkylamino(C1-C3)alkyl, (C2)dialkylamino(C1-C2)alkyl, (C2)dialkylamino(C2-C3)alkyl, (C2)dialkylamino(C1)alkyl, (C2)dialkylamino(C2)alkyl, or (C2)dialkylamino(C3)alkyl.

61. In some embodiments, the compound is a compound of Embodiment Group 55, or a pharmaceutically acceptable salt thereof, in which R1 is substituted with (C3)dialkylamino(C1-C3)alkyl, (C3)dialkylamino(C1-C2)alkyl, (C3)dialkylamino(C2-C3)alkyl, (C3)dialkylamino(C1)alkyl, (C3)dialkylamino(C2)alkyl, or (C3)dialkylamino(C3)alkyl.

62. In some embodiments, the compound is a compound of Embodiment Group 55, or a pharmaceutically acceptable salt thereof, in which R1 is substituted with (C1-C3)(C1-C3)dialkylamino(C1-C3)alkyl, (C1-C3)(C1-C3)dialkylamino(C1-C2)alkyl, (C1-C3)(C1-C3)dialkylamino(C2-C3)alkyl, (C1-C3)(C1-C3)dialkylamino(C1)alkyl, (C1-C3)(C1-C3)dialkylamino(C2)alkyl, or (C1-C3)(C1-C3)dialkylamino(C3)alkyl.

63. In some embodiments, the compound is a compound of Embodiment Group 55, or a pharmaceutically acceptable salt thereof, in which R1 is substituted with (C1-C3)(C1-C2)dialkylamino(C1-C3)alkyl, (C1-C3)(C1-C2)dialkylamino(C1-C2)alkyl, (C1-C3)(C1-C2)dialkylamino(C2-C3)alkyl, (C1-C3)(C1-C2)dialkylamino(C1)alkyl, (C1-C3)(C1-C2)dialkylamino(C2)alkyl, or (C1-C3)(C1-C2)dialkylamino(C3)alkyl.

64. In some embodiments, the compound is a compound of Embodiment Group 55, or a pharmaceutically acceptable salt thereof, in which R1 is substituted with (C1-C3)(C2-C3)dialkylamino(C1-C3)alkyl, (C1-C3)(C2-C3)dialkylamino(C1-C2)alkyl, (C1-C3)(C2-C3)dialkylamino(C2-C3)alkyl, (C1-C3)(C2-C3)dialkylamino(C1)alkyl, (C1-C3)(C2-C3)dialkylamino(C2)alkyl, or (C1-C3)(C2-C3)dialkylamino(C3)alkyl.

65. In some embodiments, the compound is a compound of Embodiment Group 55, or a pharmaceutically acceptable salt thereof, in which R1 is substituted with (C1-C3)(C1)dialkylamino(C1-C3)alkyl, (C1-C3)(C1)dialkylamino(C1-C2)alkyl, (C1-C3)(C1)dialkylamino(C2-C3)alkyl, (C1-C3)(C1)dialkylamino(C1)alkyl, (C1-C3)(C1)dialkylamino(C2)alkyl, or (C1-C3)(C1)dialkylamino(C3)alkyl.

66. In some embodiments, the compound is a compound of Embodiment Group 55, or a pharmaceutically acceptable salt thereof, in which R1 is substituted with (C1-C3)(C2)dialkylamino(C1-C3)alkyl, (C1-C3)(C2)dialkylamino(C1-C2)alkyl, (C1-C3)(C2)dialkylamino(C2-C3)alkyl, (C1-C3)(C2)dialkylamino(C1)alkyl, (C1-C3)(C2)dialkylamino(C2)alkyl, or (C1-C3)(C2)dialkylamino(C3)alkyl.

67. In some embodiments, the compound is a compound of Embodiment Group 55, or a pharmaceutically acceptable salt thereof, in which R1 is substituted with (C1-C3)(C3)dialkylamino(C1-C3)alkyl, (C1-C3)(C3)dialkylamino(C1-C2)alkyl, (C1-C3)(C3)dialkylamino(C2-C3)alkyl, (C1-C3)(C3)dialkylamino(C1)alkyl, (C1-C3)(C3)dialkylamino(C2)alkyl, or (C1-C3)(C3)dialkylamino(C3)alkyl.

68. In some embodiments, the compound is a compound of Embodiment Group 55, or a pharmaceutically acceptable salt thereof, in which R1 is substituted with (C1-C2)(C1-C3)dialkylamino(C1-C3)alkyl, (C1-C2)(C1-C3)dialkylamino(C1-C2)alkyl, (C1-C2)(C1-C3)dialkylamino(C2-C3)alkyl, (C1-C2)(C1-C3)dialkylamino(C1)alkyl, (C1-C2)(C1-C3)dialkylamino(C2)alkyl, or (C1-C2)(C1-C3)dialkylamino(C3)alkyl.

69. In some embodiments, the compound is a compound of Embodiment Group 55, or a pharmaceutically acceptable salt thereof, in which R1 is substituted with (C1-C3)(C1-C2)dialkylamino(C1-C3)alkyl, (C1-C3)(C1-C2)dialkylamino(C1-C2)alkyl, (C1-C3)(C1-C2)dialkylamino(C2-C3)alkyl, (C1-C2)(C1-C2)dialkylamino(C1)alkyl, (C1-C2)(C1-C2)dialkylamino(C2)alkyl, or (C1-C2)(C1-C2)dialkylamino(C3)alkyl.

70. In some embodiments, the compound is a compound of Embodiment Group 55, or a pharmaceutically acceptable salt thereof, in which R1 is substituted with (C1-C2)(C2-C3)dialkylamino(C1-C3)alkyl, (C1-C2)(C2-C3)dialkylamino(C1-C2)alkyl, (C1-C2)(C2-C3)dialkylamino(C2-C3)alkyl, (C1-C2)(C2-C3)dialkylamino(C1)alkyl, (C1-C2)(C2-C3)dialkylamino(C2)alkyl, or (C1-C2)(C2-C3)dialkylamino(C3)alkyl.

71. In some embodiments, the compound is a compound of Embodiment Group 55, or a pharmaceutically acceptable salt thereof, in which R1 is substituted with (C1-C2)(C1)dialkylamino(C1-C3)alkyl, (C1-C2)(C1)dialkylamino(C1-C2)alkyl, (C1-C2)(C1)dialkylamino(C2-C3)alkyl, (C1-C2)(C1)dialkylamino(C1)alkyl, (C1-C2)(C1)dialkylamino(C2)alkyl, or (C1-C2)(C1)dialkylamino(C3)alkyl.

72. In some embodiments, the compound is a compound of Embodiment Group 55, or a pharmaceutically acceptable salt thereof, in which R1 is substituted with (C1-C2)(C2)dialkylamino(C1-C3)alkyl, (C1-C2)(C2)dialkylamino(C1-C2)alkyl, (C1-C2)(C2)dialkylamino(C2-C3)alkyl, (C1-C2)(C2)dialkylamino(C1)alkyl, (C1-C2)(C2)dialkylamino(C2)alkyl, or (C1-C2)(C2)dialkylamino(C3)alkyl.

73. In some embodiments, the compound is a compound of Embodiment Group 55, or a pharmaceutically acceptable salt thereof, in which R1 is substituted with (C1-C2)(C3)dialkylamino(C1-C3)alkyl, (C1-C2)(C3)dialkylamino(C1-C2)alkyl, (C1-C2)(C3)dialkylamino(C2-C3)alkyl, (C1-C2)(C3)dialkylamino(C1)alkyl, (C1-C2)(C3)dialkylamino(C2)alkyl, or (C1-C2)(C3)dialkylamino(C3)alkyl.

74. In some embodiments, the compound is a compound of Embodiment Group 55, or a pharmaceutically acceptable salt thereof, in which R1 is substituted with (C2-C3)(C1-C3)dialkylamino(C1-C3)alkyl, (C2-C3)(C1-C3)dialkylamino(C1-C2)alkyl, (C2-C3)(C1-C3)dialkylamino(C2-C3)alkyl, (C2-C3)(C1-C3)dialkylamino(C1)alkyl, (C2-C3)(C1-C3)dialkylamino(C2)alkyl, or (C2-C3)(C1-C3)dialkylamino(C3)alkyl.

75. In some embodiments, the compound is a compound of Embodiment Group 55, or a pharmaceutically acceptable salt thereof, in which R1 is substituted with (C2-C3)(C1-C2)dialkylamino(C1-C3)alkyl, (C2-C3)(C1-C2)dialkylamino(C1-C2)alkyl, (C2-C3)(C1-C2)dialkylamino(C2-C3)alkyl, (C2-C3)(C1-C2)dialkylamino(C1)alkyl, (C2-C3)(C1-C2)dialkylamino(C2)alkyl, or (C2-C3)(C1-C2)dialkylamino(C3)alkyl.

76. In some embodiments, the compound is a compound of Embodiment Group 55, or a pharmaceutically acceptable salt thereof, in which R1 is substituted with (C2-C3)(C2-C3)dialkylamino(C1-C3)alkyl, (C2-C3)(C2-C3)dialkylamino(C1-C2)alkyl, (C2-C3)(C2-C3)dialkylamino(C2-C3)alkyl, (C2-C3)(C2-C3)dialkylamino(C1)alkyl, (C2-C3)(C2-C3)dialkylamino(C2)alkyl, or (C2-C3)(C2-C3)dialkylamino(C3)alkyl.

77. In some embodiments, the compound is a compound of Embodiment Group 55, or a pharmaceutically acceptable salt thereof, in which R1 is substituted with (C2-C3)(C1)dialkylamino(C1-C3)alkyl, (C2-C3)(C1)dialkylamino(C1-C2)alkyl, (C2-C3)(C1)dialkylamino(C2-C3)alkyl, (C2-C3)(C1)dialkylamino(C1)alkyl, (C2-C3)(C1)dialkylamino(C2)alkyl, or (C2-C3)(C1)dialkylamino(C3)alkyl.

78. In some embodiments, the compound is a compound of Embodiment Group 55, or a pharmaceutically acceptable salt thereof, in which R1 is substituted with (C2-C3)(C2)dialkylamino(C1-C3)alkyl, (C2-C3)(C2)dialkylamino(C1-C2)alkyl, (C2-C3)(C2)dialkylamino(C2-C3)alkyl, (C2-C3)(C2)dialkylamino(C1)alkyl, (C2-C3)(C2)dialkylamino(C2)alkyl, or (C2-C3)(C2)dialkylamino(C3)alkyl.

79. In some embodiments, the compound is a compound of Embodiment Group 55, or a pharmaceutically acceptable salt thereof, in which R1 is substituted with (C2-C3)(C3)dialkylamino(C1-C3)alkyl, (C2-C3)(C3)dialkylamino(C1-C2)alkyl, (C2-C3)(C3)dialkylamino(C2-C3)alkyl, (C2-C3)(C3)dialkylamino(C1)alkyl, (C2-C3)(C3)dialkylamino(C2)alkyl, or (C2-C3)(C3)dialkylamino(C3)alkyl.

80. In some embodiments, the compound is a compound of Embodiment Group 55, or a pharmaceutically acceptable salt thereof, in which R1 is substituted with (C1)(C1-C3)dialkylamino(C1-C3)alkyl, (C1)(C1-C3)dialkylamino(C1-C2)alkyl, (C1)(C1-C3)dialkylamino(C2-C3)alkyl, (C1)(C1-C3)dialkylamino(C1)alkyl, (C1)(C1-C3)dialkylamino(C2)alkyl, or (C1)(C1-C3)dialkylamino(C3)alkyl.

81. In some embodiments, the compound is a compound of Embodiment Group 55, or a pharmaceutically acceptable salt thereof, in which R1 is substituted with (C1)(C1-C2)dialkylamino(C1-C3)alkyl, (C1)(C1-C2)dialkylamino(C1-C2)alkyl, (C1)(C1-C2)dialkylamino(C2-C3)alkyl, (C1)(C1-C2)dialkylamino(C1)alkyl, (C1)(C1-C2)dialkylamino(C2)alkyl, or (C1)(C1-C2)dialkylamino(C3)alkyl.

82. In some embodiments, the compound is a compound of Embodiment Group 55, or a pharmaceutically acceptable salt thereof, in which R1 is substituted with (C1)(C2-C3)dialkylamino(C1-C3)alkyl, (C1)(C2-C3)dialkylamino(C1-C2)alkyl, (C1)(C2-C3)dialkylamino(C2-C3)alkyl, (C1)(C2-C3)dialkylamino(C1)alkyl, (C1)(C2-C3)dialkylamino(C2)alkyl, or (C1)(C2-C3)dialkylamino(C3)alkyl.

83. In some embodiments, the compound is a compound of Embodiment Group 55, or a pharmaceutically acceptable salt thereof, in which R1 is substituted with (C1)(C1)dialkylamino(C1-C3)alkyl, (C1)(C1)dialkylamino(C1-C2)alkyl, (C1)(C1)dialkylamino(C2-C3)alkyl, (C1)(C1)dialkylamino(C1)alkyl, (C1)(C1)dialkylamino(C2)alkyl, or (C1)(C1)dialkylamino(C3)alkyl.

84. In some embodiments, the compound is a compound of Embodiment Group 55, or a pharmaceutically acceptable salt thereof, in which R1 is substituted with (C1)(C2)dialkylamino(C1-C3)alkyl, (C1)(C2)dialkylamino(C1-C2)alkyl, (C1)(C2)dialkylamino(C2-C3)alkyl, (C1)(C2)dialkylamino(C1)alkyl, (C1)(C2)dialkylamino(C2)alkyl, or (C1)(C2)dialkylamino(C3)alkyl.

85. In some embodiments, the compound is a compound of Embodiment Group 55, or a pharmaceutically acceptable salt thereof, in which R1 is substituted with (C1)(C3)dialkylamino(C1-C3)alkyl, (C1)(C3)dialkylamino(C1-C2)alkyl, (C1)(C3)dialkylamino(C2-C3)alkyl, (C1)(C3)dialkylamino(C1)alkyl, (C1)(C3)dialkylamino(C2)alkyl, or (C1)(C3)dialkylamino(C3)alkyl.

86. In some embodiments, the compound is a compound of Embodiment Group 55, or a pharmaceutically acceptable salt thereof, in which R1 is substituted with (C2)(C1-C3) dialkylamino(C1-C3)alkyl, (C2)(C1-C3)dialkylamino (C1-C2)alkyl, (C2)(C1-C3)dialkylamino(C2-C3)alkyl, (C2)(C1-C3)dialkylamino(C1)alkyl, (C2)(C1-C3)dialkylamino(C2)alkyl, or (C2)(C1-C3)dialkylamino(C3)alkyl.

87. In some embodiments, the compound is a compound of Embodiment Group 55, or a pharmaceutically acceptable salt thereof, in which R1 is substituted with (C2)(C1-C2) dialkylamino(C1-C3)alkyl, (C2)(C1-C2)dialkylamino (C1-C2)alkyl, (C2)(C1-C2)dialkylamino(C2-C3)alkyl, (C2)(C1-C2)dialkylamino(C1)alkyl, (C2)(C1-C2)dialkylamino(C2)alkyl, or (C2)(C1-C2)dialkylamino(C3)alkyl.

88. In some embodiments, the compound is a compound of Embodiment Group 55, or a pharmaceutically acceptable salt thereof, in which R1 is substituted with (C2)(C2-C3) dialkylamino(C1-C3)alkyl, (C2)(C2-C3)dialkylamino (C1-C2)alkyl, (C2)(C2-C3)dialkylamino(C2-C3)alkyl, (C2)(C2-C3)dialkylamino(C1)alkyl, (C2)(C2-C3)dialkylamino(C2)alkyl, or (C2)(C2-C3)dialkylamino(C3)alkyl.

89. In some embodiments, the compound is a compound of Embodiment Group 55, or a pharmaceutically acceptable salt thereof, in which R1 is substituted with (C2)(C1) dialkylamino(C1-C3)alkyl, (C2)(C1)dialkylamino(C1-C2)alkyl, (C2)(C1)dialkylamino(C2-C3)alkyl, (C2)(C1) dialkylamino(C1)alkyl, (C2)(C1)dialkylamino(C2)alkyl, or (C2)(C1)dialkylamino(C3)alkyl.

90. In some embodiments, the compound is a compound of Embodiment Group 55, or a pharmaceutically acceptable salt thereof, in which R1 is substituted with (C2)(C2) dialkylamino(C1-C3)alkyl, (C2)(C2)dialkylamino(C1-C2)alkyl, (C2)(C2)dialkylamino(C2-C3)alkyl, (C2)(C2) dialkylamino(C1)alkyl, (C2)(C2)dialkylamino(C2)alkyl, or (C2)(C2)dialkylamino(C3)alkyl.

91. In some embodiments, the compound is a compound of Embodiment Group 55, or a pharmaceutically acceptable salt thereof, in which R1 is substituted with (C2)(C3) dialkylamino(C1-C3)alkyl, (C2)(C3)dialkylamino(C1-C2)alkyl, (C2)(C3)dialkylamino(C2-C3)alkyl, (C2)(C3) dialkylamino(C1)alkyl, (C2)(C3)dialkylamino(C2)alkyl, or (C2)(C3)dialkylamino(C3)alkyl.

92. In some embodiments, the compound is a compound of Embodiment Group 55, or a pharmaceutically acceptable salt thereof, in which R1 is substituted with (C3)(C1-C3) dialkylamino(C1-C3)alkyl, (C3)(C1-C3)dialkylamino (C1-C2)alkyl, (C3)(C1-C3)dialkylamino(C2-C3)alkyl, (C3)(C1-C3)dialkylamino(C1)alkyl, (C3)(C1-C3)dialkylamino(C2)alkyl, or (C3)(C1-C3)dialkylamino(C3)alkyl.

93. In some embodiments, the compound is a compound of Embodiment Group 55, or a pharmaceutically acceptable salt thereof, in which R1 is substituted with (C3)(C1-C2) dialkylamino(C1-C3)alkyl, (C3)(C1-C2)dialkylamino (C1-C2)alkyl, (C3)(C1-C2)dialkylamino(C2-C3)alkyl, (C3)(C1-C2)dialkylamino(C1)alkyl, (C3)(C1-C2)dialkylamino(C2)alkyl, or (C3)(C1-C2)dialkylamino(C3)alkyl.

94. In some embodiments, the compound is a compound of Embodiment Group 55, or a pharmaceutically acceptable salt thereof, in which R1 is substituted with (C3)(C2-C3) dialkylamino(C1-C3)alkyl, (C3)(C2-C3)dialkylamino (C1-C2)alkyl, (C3)(C2-C3)dialkylamino(C2-C3)alkyl, (C3)(C2-C3)dialkylamino(C1)alkyl, (C3)(C2-C3)dialkylamino(C2)alkyl, or (C3)(C2-C3)dialkylamino(C3)alkyl.

95. In some embodiments, the compound is a compound of Embodiment Group 55, or a pharmaceutically acceptable salt thereof, in which R1 is substituted with (C3)(C1) dialkylamino(C1-C3)alkyl, (C3)(C1)dialkylamino(C1-C2)alkyl, (C3)(C1)dialkylamino(C2-C3)alkyl, (C3)(C1) dialkylamino(C1)alkyl, (C3)(C1)dialkylamino(C2)alkyl, or (C3)(C1)dialkylamino(C3)alkyl.

96. In some embodiments, the compound is a compound of Embodiment Group 55, or a pharmaceutically acceptable salt thereof, in which R1 is substituted with (C3)(C2) dialkylamino(C1-C3)alkyl, (C3)(C2)dialkylamino(C1-C2)alkyl, (C3)(C2)dialkylamino(C2-C3)alkyl, (C3)(C2) dialkylamino(C1)alkyl, (C3)(C2)dialkylamino(C2)alkyl, or (C3)(C2)dialkylamino(C3)alkyl.

97. In some embodiments, the compound is a compound of Embodiment Group 55, or a pharmaceutically acceptable salt thereof, in which R1 is substituted with (C3)(C3) dialkylamino(C1-C3)alkyl, (C3)(C3)dialkylamino(C1-C2)alkyl, (C3)(C3)dialkylamino(C2-C3)alkyl, (C3)(C3) dialkylamino(C1)alkyl, (C3)(C3)dialkylamino(C2)alkyl, or (C3)(C3)dialkylamino(C3)alkyl.

98. In some embodiments, the compound is a compound of Embodiment Group 55, 56, 57, 58, 59, 60, 61, 62, 63, 64, 65, 66, 67, 68, 69, 70, 71, 72, 73, 74, 75, or 76, 77, 78, 79, 80, 81, 82, 83, 84, 85, 86, 87, 88, 89, 90, 91, 92, 93, 94, 95, 96, or 97, or a pharmaceutically acceptable salt thereof, in which the (C1-C3)dialkylamino(C1-C3)alkyl is directly linked to R1.

99. In some embodiments, the compound is a compound of Embodiment Group 55, 56, 57, 58, 59, 60, 61, 62, 63, 64, 65, 66, 67, 68, 69, 70, 71, 72, 73, 74, 75, or 76, 77, 78, 79, 80, 81, 82, 83, 84, 85, 86, 87, 88, 89, 90, 91, 92, 93, 94, 95, 96, or 97, or a pharmaceutically acceptable salt thereof, in which the (C1-C3)dialkylamino(C1-C3)alkyl is linked to R1 through a carbonyl.

100. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, Group 55, 56, 57, 58, 59, 60, 61, 62, 63, 64, 65, 66, 67, 68, 69, 70, 71, 72, 73, 74, 75, or 76, 77, 78, 79, 80, 81, 82, 83, 84, 85, 86, 87, 88, 89, 90, 91, 92, 93, 94, 95, 96, 97, 98, or 99,or a pharmaceutically acceptable salt thereof, in which R1 is substituted with (C1-C3)alkylamino(C2-C3)alkoxyl, optionally linked to R1 through a carbonyl group.

101. In some embodiments, the compound is a compound of Embodiment Group 100, or a pharmaceutically acceptable salt thereof, in which R1 is substituted with (C1-C3) alkylamino(C2-C3)alkoxyl, (C1-C3)alkylamino(C2) alkoxyl, or (C1-C3)alkylamino(C3)alkoxyl.

102. In some embodiments, the compound is a compound of Embodiment Group 100, or a pharmaceutically acceptable salt thereof, in which R1 is substituted with (C2-C3) alkylamino(C2-C3)alkoxyl, (C2-C3)alkylamino(C2) alkoxyl, or (C2-C3)alkylamino(C3)alkoxyl.

103. In some embodiments, the compound is a compound of Embodiment Group 100, or a pharmaceutically acceptable salt thereof, in which R1 is substituted with (C1-C2) alkylamino(C2-C3)alkoxyl, (C1-C2)alkylamino(C2) alkoxyl, or (C1-C2)alkylamino(C3)alkoxyl.

104. In some embodiments, the compound is a compound of Embodiment Group 100, or a pharmaceutically acceptable salt thereof, in which R1 is substituted with (C1) alkylamino(C2-C3)alkoxyl, (C1)alkylamino(C2)alkoxyl, or (C1)alkylamino(C3)alkoxyl.

105. In some embodiments, the compound is a compound of Embodiment Group 100, or a pharmaceutically acceptable salt thereof, in which R1 is substituted with (C2) alkylamino(C2-C3)alkoxyl, (C2)alkylamino(C2)alkoxyl, or (C2)alkylamino(C3)alkoxyl.

106. In some embodiments, the compound is a compound of Embodiment Group 100, or a pharmaceutically acceptable salt thereof, in which R1 is substituted with (C3)alkylamino(C2-C3)alkoxyl, (C3)alkylamino(C2)alkoxyl, or (C3)alkylamino(C3)alkoxyl.

107. In some embodiments, the compound is a compound of Embodiment Group 100, 101, 102, 103, 104, 105, or 106, or a pharmaceutically acceptable salt thereof, in which the (C1-C3)alkylamino(C2-C3)alkoxyl is directly linked to R1.

108. In some embodiments, the compound is a compound of Embodiment Group 100, 101, 102, 103, 104, 105, or 106, or a pharmaceutically acceptable salt thereof, in which the (C1-C3)alkylamino(C2-C3)alkoxyl is linked to R1 through a carbonyl.

109. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, or 108, or a pharmaceutically acceptable salt thereof, in which R1 is substituted with (C1-C3)dialkylamino(C2-C3)alkoxyl, optionally linked to R1 through a carbonyl group.

110. In some embodiments, the compound is a compound of Embodiment Group 109, or a pharmaceutically acceptable salt thereof, in which R1 is substituted with (C1-C3)dialkylamino(C2-C3)alkoxyl, (C1-C3)dialkylamino(C2)alkoxyl, or (C1-C3)dialkylamino(C3)alkoxyl.

111. In some embodiments, the compound is a compound of Embodiment Group 109, or a pharmaceutically acceptable salt thereof, in which R1 is substituted with (C1-C2)dialkylamino(C2-C3)alkoxyl, (C1-C2)dialkylamino(C2)alkoxyl, or (C1-C2)dialkylamino(C3)alkoxyl.

112. In some embodiments, the compound is a compound of Embodiment Group 109, or a pharmaceutically acceptable salt thereof, in which R1 is substituted with (C2-C3)dialkylamino(C2-C3)alkoxyl, (C2-C3)dialkylamino(C2)alkoxyl, or (C2-C3)dialkylamino(C3)alkoxyl.

113. In some embodiments, the compound is a compound of Embodiment Group 109, or a pharmaceutically acceptable salt thereof, in which R1 is substituted with (C1)dialkylamino(C2-C3)alkoxyl, (C1)dialkylamino(C2)alkoxyl, or (C1)dialkylamino(C3)alkoxyl.

114. In some embodiments, the compound is a compound of Embodiment Group 109, or a pharmaceutically acceptable salt thereof, in which R1 is substituted with (C2)dialkylamino(C2-C3)alkoxyl, (C2)dialkylamino(C2)alkoxyl, or (C2)dialkylamino(C3)alkoxyl.

115. In some embodiments, the compound is a compound of Embodiment Group 109, or a pharmaceutically acceptable salt thereof, in which R1 is substituted with (C3)dialkylamino(C2-C3)alkoxyl, (C3)dialkylamino(C2)alkoxyl, or (C3)dialkylamino(C3)alkoxyl.

116. In some embodiments, the compound is a compound of Embodiment Group 109, or a pharmaceutically acceptable salt thereof, in which R1 is substituted with (C1-C3)(C1-C3)dialkylamino(C2-C3)alkoxyl, (C1-C3)(C1-C3)dialkylamino(C2)alkoxyl, or (C1-C3)(C1-C3)dialkylamino(C3)alkoxyl.

117. In some embodiments, the compound is a compound of Embodiment Group 109, or a pharmaceutically acceptable salt thereof, in which R1 is substituted with (C1-C3)(C1-C2)dialkylamino(C2-C3)alkoxyl, (C1-C3)(C1-C2)dialkylamino(C2)alkoxyl, or (C1-C3)(C1-C2)dialkylamino(C3)alkoxyl.

118. In some embodiments, the compound is a compound of Embodiment Group 109, or a pharmaceutically acceptable salt thereof, in which R1 is substituted with (C1-C3)(C2-C3)dialkylamino(C2-C3)alkoxyl, (C1-C3)(C2-C3)dialkylamino(C2)alkoxyl, or (C1-C3)(C2-C3)dialkylamino(C3)alkoxyl.

119. In some embodiments, the compound is a compound of Embodiment Group 109, or a pharmaceutically acceptable salt thereof, in which R1 is substituted with (C1-C3)(C1)dialkylamino(C2-C3)alkoxyl, (C1-C3)(C1)dialkylamino(C2)alkoxyl, or (C1-C3)(C1)dialkylamino(C3)alkoxyl.

120. In some embodiments, the compound is a compound of Embodiment Group 109, or a pharmaceutically acceptable salt thereof, in which R1 is substituted with (C1-C3)(C2)dialkylamino(C2-C3)alkoxyl, (C1-C3)(C2)dialkylamino(C2)alkoxyl, or (C1-C3)(C2)dialkylamino(C3)alkoxyl.

121. In some embodiments, the compound is a compound of Embodiment Group 109, or a pharmaceutically acceptable salt thereof, in which R1 is substituted with (C1-C3)(C3)dialkylamino(C2-C3)alkoxyl, (C1-C3)(C3)dialkylamino(C2)alkoxyl, or (C1-C3)(C3)dialkylamino(C3)alkoxyl.

122. In some embodiments, the compound is a compound of Embodiment Group 109, or a pharmaceutically acceptable salt thereof, in which R1 is substituted with (C1-C2)(C1-C3)dialkylamino(C2-C3)alkoxyl, (C1-C2)(C1-C3)dialkylamino(C2)alkoxyl, or (C1-C2)(C1-C3)dialkylamino(C3)alkoxyl.

123. In some embodiments, the compound is a compound of Embodiment Group 109, or a pharmaceutically acceptable salt thereof, in which R1 is substituted with (C1-C3)(C1-C2)dialkylamino(C2-C3)alkoxyl, (C1-C2)(C1-C2)dialkylamino(C2)alkoxyl, or (C1-C2)(C1-C2)dialkylamino(C3)alkoxyl.

124. In some embodiments, the compound is a compound of Embodiment Group 109, or a pharmaceutically acceptable salt thereof, in which R1 is substituted with (C1-C2)(C2-C3)dialkylamino(C2-C3)alkoxyl, (C1-C2)(C2-C3)dialkylamino(C2)alkoxyl, or (C1-C2)(C2-C3)dialkylamino(C3)alkoxyl.

125. In some embodiments, the compound is a compound of Embodiment Group 109, or a pharmaceutically acceptable salt thereof, in which R1 is substituted with (C1-C2)(C1)dialkylamino(C2-C3)alkoxyl, (C1-C2)(C1)dialkylamino(C2)alkoxyl, or (C1-C2)(C1)dialkylamino(C3)alkoxyl.

126. In some embodiments, the compound is a compound of Embodiment Group 109, or a pharmaceutically acceptable salt thereof, in which R1 is substituted with (C1-C2)(C2)dialkylamino(C2-C3)alkoxyl, (C1-C2)(C2)dialkylamino(C2)alkoxyl, or (C1-C2)(C2)dialkylamino(C3)alkoxyl.

127. In some embodiments, the compound is a compound of Embodiment Group 109, or a pharmaceutically acceptable salt thereof, in which R1 is substituted with (C1-C2)(C3)dialkylamino(C2-C3)alkoxyl, (C1-C2)(C3)dialkylamino(C2)alkoxyl, or (C1-C2)(C3)dialkylamino(C3)alkoxyl.

128. In some embodiments, the compound is a compound of Embodiment Group 109, or a pharmaceutically acceptable salt thereof, in which R1 is substituted with (C2-C3)

(C1-C3)dialkylamino(C2-C3)alkoxyl, (C2-C3)(C1-C3) dialkylamino(C2)alkoxyl, or (C2-C3)(C1-C3) dialkylamino(C3)alkoxyl.

129. In some embodiments, the compound is a compound of Embodiment Group 109, or a pharmaceutically acceptable salt thereof, in which R1 is substituted with (C2-C3)(C1-C2)dialkylamino(C2-C3)alkoxyl, (C2-C3)(C1-C2)dialkylamino(C2)alkoxyl, or (C2-C3)(C1-C2)dialkylamino(C3)alkoxyl.

130. In some embodiments, the compound is a compound of Embodiment Group 109, or a pharmaceutically acceptable salt thereof, in which R1 is substituted with (C2-C3)(C2-C3)dialkylamino(C2-C3)alkoxyl, (C2-C3)(C2-C3)dialkylamino(C2)alkoxyl, or (C2-C3)(C2-C3)dialkylamino(C3)alkoxyl.

131. In some embodiments, the compound is a compound of Embodiment Group 109, or a pharmaceutically acceptable salt thereof, in which R1 is substituted with (C2-C3)(C1)dialkylamino(C2-C3)alkoxyl, (C2-C3)(C1)dialkylamino(C2)alkoxyl, or (C2-C3)(C1)dialkylamino(C3)alkoxyl.

132. In some embodiments, the compound is a compound of Embodiment Group 109, or a pharmaceutically acceptable salt thereof, in which R1 is substituted with (C2-C3)(C2)dialkylamino(C2-C3)alkoxyl, (C2-C3)(C2)dialkylamino(C2)alkoxyl, or (C2-C3)(C2)dialkylamino(C3)alkoxyl.

133. In some embodiments, the compound is a compound of Embodiment Group 109, or a pharmaceutically acceptable salt thereof, in which R1 is substituted with (C2-C3)(C3)dialkylamino(C2-C3)alkoxyl, (C2-C3)(C3)dialkylamino(C2)alkoxyl, or (C2-C3)(C3)dialkylamino(C3)alkoxyl.

134. In some embodiments, the compound is a compound of Embodiment Group 109, or a pharmaceutically acceptable salt thereof, in which R1 is substituted with (C1)(C1-C3)dialkylamino(C2-C3)alkoxyl, (C1)(C1-C3)dialkylamino(C2)alkoxyl, or (C1)(C1-C3)dialkylamino(C3)alkoxyl.

135. In some embodiments, the compound is a compound of Embodiment Group 109, or a pharmaceutically acceptable salt thereof, in which R1 is substituted with (C1)(C1-C2)dialkylamino(C2-C3)alkoxyl, (C1)(C1-C2)dialkylamino(C2)alkoxyl, or (C1)(C1-C2)dialkylamino(C3)alkoxyl.

136. In some embodiments, the compound is a compound of Embodiment Group 109, or a pharmaceutically acceptable salt thereof, in which R1 is substituted with (C1)(C2-C3)dialkylamino(C2-C3)alkoxyl, (C1)(C2-C3)dialkylamino(C2)alkoxyl, or (C1)(C2-C3)dialkylamino(C3)alkoxyl.

137. In some embodiments, the compound is a compound of Embodiment Group 109, or a pharmaceutically acceptable salt thereof, in which R1 is substituted with (C1)(C1)dialkylamino(C2-C3)alkoxyl, (C1)(C1)dialkylamino(C2)alkoxyl, or (C1)(C1)dialkylamino(C3)alkoxyl.

138. In some embodiments, the compound is a compound of Embodiment Group 109, or a pharmaceutically acceptable salt thereof, in which R1 is substituted with (C1)(C2)dialkylamino(C2-C3)alkoxyl, (C1)(C2)dialkylamino(C2)alkoxyl, or (C1)(C2)dialkylamino(C3)alkoxyl.

139. In some embodiments, the compound is a compound of Embodiment Group 109, or a pharmaceutically acceptable salt thereof, in which R1 is substituted with (C1)(C3)dialkylamino(C2-C3)alkoxyl, (C1)(C3)dialkylamino(C2)alkoxyl, or (C1)(C3)dialkylamino(C3)alkoxyl.

140. In some embodiments, the compound is a compound of Embodiment Group 109, or a pharmaceutically acceptable salt thereof, in which R1 is substituted with (C2)(C1-C3)dialkylamino(C2-C3)alkoxyl, (C2)(C1-C3)dialkylamino(C2)alkoxyl, or (C2)(C1-C3)dialkylamino(C3)alkoxyl.

141. In some embodiments, the compound is a compound of Embodiment Group 109, or a pharmaceutically acceptable salt thereof, in which R1 is substituted with (C2)(C1-C2)dialkylamino(C2-C3)alkoxyl, (C2)(C1-C2)dialkylamino(C2)alkoxyl, or (C2)(C1-C2)dialkylamino(C3)alkoxyl.

142. In some embodiments, the compound is a compound of Embodiment Group 109, or a pharmaceutically acceptable salt thereof, in which R1 is substituted with (C2)(C2-C3)dialkylamino(C2-C3)alkoxyl, (C2)(C2-C3)dialkylamino(C2)alkoxyl, or (C2)(C2-C3)dialkylamino(C3)alkoxyl.

143. In some embodiments, the compound is a compound of Embodiment Group 109, or a pharmaceutically acceptable salt thereof, in which R1 is substituted with (C2)(C1)dialkylamino(C2-C3)alkoxyl, (C2)(C1)dialkylamino(C2)alkoxyl, or (C2)(C1)dialkylamino(C3)alkoxyl.

144. In some embodiments, the compound is a compound of Embodiment Group 109, or a pharmaceutically acceptable salt thereof, in which R1 is substituted with (C2)(C2)dialkylamino(C2-C3)alkoxyl, (C2)(C2)dialkylamino(C2)alkoxyl, or (C2)(C2)dialkylamino(C3)alkoxyl.

145. In some embodiments, the compound is a compound of Embodiment Group 109, or a pharmaceutically acceptable salt thereof, in which R1 is substituted with (C2)(C3)dialkylamino(C2-C3)alkoxyl, (C2)(C3)dialkylamino(C2)alkoxyl, or (C2)(C3)dialkylamino(C3)alkoxyl.

146. In some embodiments, the compound is a compound of Embodiment Group 109, or a pharmaceutically acceptable salt thereof, in which R1 is substituted with (C3)(C1-C3)dialkylamino(C2-C3)alkoxyl, (C3)(C1-C3)dialkylamino(C2)alkoxyl, or (C3)(C1-C3)dialkylamino(C3)alkoxyl.

147. In some embodiments, the compound is a compound of Embodiment Group 109, or a pharmaceutically acceptable salt thereof, in which R1 is substituted with (C3)(C1-C2)dialkylamino(C2-C3)alkoxyl, (C3)(C1-C2)dialkylamino(C2)alkoxyl, or (C3)(C1-C2)dialkylamino(C3)alkoxyl.

148. In some embodiments, the compound is a compound of Embodiment Group 109, or a pharmaceutically acceptable salt thereof, in which R1 is substituted with (C3)(C2-C3)dialkylamino(C2-C3)alkoxyl, (C3)(C2-C3)dialkylamino(C2)alkoxyl, or (C3)(C2-C3)dialkylamino(C3)alkoxyl.

149. In some embodiments, the compound is a compound of Embodiment Group 109, or a pharmaceutically acceptable salt thereof, in which R1 is substituted with (C3)(C1)dialkylamino(C2-C3)alkoxyl, (C3)(C1)dialkylamino(C2)alkoxyl, or (C3)(C1)dialkylamino(C3)alkoxyl.

150. In some embodiments, the compound is a compound of Embodiment Group 109, or a pharmaceutically acceptable salt thereof, in which R1 is substituted with (C3)(C2)dialkylamino(C2-C3)alkoxyl, (C3)(C2)dialkylamino(C2)alkoxyl, or (C3)(C2)dialkylamino(C3)alkoxyl.

151. In some embodiments, the compound is a compound of Embodiment Group 109, or a pharmaceutically acceptable salt thereof, in which R1 is substituted with (C3)(C3)dialkylamino(C2-C3)alkoxyl, (C3)(C3)dialkylamino(C2)alkoxyl, or (C3)(C3)dialkylamino(C3)alkoxyl.

152. In some embodiments, the compound is a compound of Embodiment Group 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, or 151, or a pharmaceutically acceptable salt thereof, in which the (C1-C3)dialkylamino(C2-C3) alkoxyl is directly linked to R1.

153. In some embodiments, the compound is a compound of Embodiment Group 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, or 151, or a pharmaceutically acceptable salt thereof, in which the (C1-C3)dialkylamino(C2-C3) alkoxyl is linked to R1 through a carbonyl.

154. In some embodiments, the compound is a compound of Embodiment Group, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, or 153, or a pharmaceutically acceptable salt thereof, in which R1 is substituted with (C1-C3)alkylamino(C2-C3)alkylamino, optionally linked to R1 through a carbonyl group.

155. In some embodiments, the compound is a compound of Embodiment Group 154, or a pharmaceutically acceptable salt thereof, in which R1 is substituted with (C1-C3) alkylamino(C2-C3)alkylamino, (C1-C3)alkylamino(C2) alkylamino, or (C1-C3)alkylamino(C3)alkylamino.

156. In some embodiments, the compound is a compound of Embodiment Group 154, or a pharmaceutically acceptable salt thereof, in which R1 is substituted with (C1-C2) alkylamino(C2-C3)alkylamino, (C1-C2)alkylamino(C2) alkylamino, or (C1-C2)alkylamino(C3)alkylamino.

157. In some embodiments, the compound is a compound of Embodiment Group 154, or a pharmaceutically acceptable salt thereof, in which R1 is substituted with (C2-C3) alkylamino(C2-C3)alkylamino, (C2-C3)alkylamino(C2) alkylamino, or (C2-C3)alkylamino(C3)alkylamino.

158. In some embodiments, the compound is a compound of Embodiment Group 154, or a pharmaceutically acceptable salt thereof, in which R1 is substituted with (C1) alkylamino(C2-C3)alkylamino, (C1)alkylamino(C2)alkylamino, or (C1)alkylamino(C3)alkylamino.

159. In some embodiments, the compound is a compound of Embodiment Group 154, or a pharmaceutically acceptable salt thereof, in which R1 is substituted with (C2) alkylamino(C2-C3)alkylamino, (C2)alkylamino(C2)alkylamino, or (C2)alkylamino(C3)alkylamino.

160. In some embodiments, the compound is a compound of Embodiment Group 154, or a pharmaceutically acceptable salt thereof, in which R1 is substituted with (C3) alkylamino(C2-C3)alkylamino, (C3)alkylamino(C2)alkylamino, or (C3)alkylamino(C3)alkylamino.

161. In some embodiments, the compound is a compound of Embodiment Group 154, 155, 156, 167, 158, 159, or 160, or a pharmaceutically acceptable salt thereof, in which the (C1-C3)alkylamino(C2-C3)alkylamino is directly linked to R1.

162. In some embodiments, the compound is a compound of Embodiment Group 154, 155, 156, 167, 158, 159, or 160, or a pharmaceutically acceptable salt thereof, in which the (C1-C3)alkylamino(C2-C3)alkylamino is linked to R1 through a carbonyl.

163. In some embodiments, the compound is a compound of Embodiment Group, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, or 162, or a pharmaceutically acceptable salt thereof, in which R1 is substituted with (C1-C3)dialkylamino(C2-C3)alkylamino, optionally linked to R1 through a carbonyl group.

164. In some embodiments, the compound is a compound of Embodiment Group 163, or a pharmaceutically acceptable salt thereof, in which R1 is substituted with (C1-C3) dialkylamino(C2-C3)alkylamino, (C1-C3)dialkylamino (C2)alkylamino, (C1-C3)dialkylamino(C3)alkylamino, (C1-C3)dialkylamino(C2-C3)alkylamino, (C1)dialkylamino(C2-C3)alkylamino, (C2)dialkylamino(C2-C3) alkylamino, (C3)dialkylamino(C2-C3)alkylamino, (C1-C3)dialkylamino(C2)alkylamino, (C1)dialkylamino(C2-) alkylamino, (C2)dialkylamino(C2)alkylamino, (C3) dialkylamino(C2)alkylamino, (C1-C3)dialkylamino(C3) alkylamino, (C1)dialkylamino(C3)alkylamino, (C2) dialkylamino(C3)alkylamino, or (C3)dialkylamino(C3) alkylamino.

165. In some embodiments, the compound is a compound of Embodiment Group 163, or a pharmaceutically acceptable salt thereof, in which R1 is substituted with (C1) (C1-C3)dialkylamino(C2-C3)alkylamino, (C1)(C1-C3) dialkylamino(C2)alkylamino, (C1)(C1-C3)dialkylamino (C3)alkylamino, (C1)(C1-C3)dialkylamino(C2-C3) alkylamino, (C1)(C1)dialkylamino(C2-C3)alkylamino, (C1)(C2)dialkylamino(C2-C3)alkylamino, (C1)(C3)dialkylamino(C2-C3)alkylamino, (C1)(C1-C3)dialkylamino(C2)alkylamino, (C1)(C1)dialkylamino(C2-)alkylamino, (C1)(C2)dialkylamino(C2)alkylamino, (C1)(C3) dialkylamino(C2)alkylamino, (C1)(C1-C3)dialkylamino (C3)alkylamino, (C1)(C1)dialkylamino(C3)alkylamino, (C1)(C2)dialkylamino(C3)alkylamino, or (C1)(C3)dialkylamino(C3)alkylamino.

166. In some embodiments, the compound is a compound of Embodiment Group 163, or a pharmaceutically acceptable salt thereof, in which R1 is substituted with (C2) (C1-C3)dialkylamino(C2-C3)alkylamino, (C2)(C1-C3) dialkylamino(C2)alkylamino, (C2)(C1-C3)dialkylamino (C3)alkylamino, (C2)(C1-C3)dialkylamino(C2-C3) alkylamino, (C2)(C1)dialkylamino(C2-C3)alkylamino, (C2)(C2)dialkylamino(C2-C3)alkylamino, (C2)(C3)dialkylamino(C2-C3)alkylamino, (C2)(C1-C3)dialkylamino(C2)alkylamino, (C2)(C1)dialkylamino(C2-)alkylamino, (C2)(C2)dialkylamino(C2)alkylamino, (C2)(C3) dialkylamino(C2)alkylamino, (C2)(C1-C3)dialkylamino (C3)alkylamino, (C2)(C1)dialkylamino(C3)alkylamino, (C2)(C2)dialkylamino(C3)alkylamino, or (C2)(C3)dialkylamino(C3)alkylamino.

167. In some embodiments, the compound is a compound of Embodiment Group 163, or a pharmaceutically acceptable salt thereof, in which R1 is substituted with (C3)(C1-C3)dialkylamino(C2-C3)alkylamino, (C3)(C1-C3)dialkylamino(C2)alkylamino, (C3)(C1-C3)dialkylamino(C3)alkylamino, (C3)(C1-C3)dialkylamino(C2-C3)alkylamino, (C3)(C1)dialkylamino(C2-C3)alkylamino, (C3)(C2)dialkylamino(C2-C3)alkylamino, (C3)(C3)dialkylamino(C2-C3)alkylamino, (C3)(C1-C3)dialkylamino(C2)alkylamino, (C3)(C1)dialkylamino(C2-)alkylamino, (C3)(C2)dialkylamino(C2)alkylamino, (C3)(C3)dialkylamino(C2)alkylamino, (C3)(C1-C3)dialkylamino(C3)alkylamino, (C3)(C1)dialkylamino(C3)alkylamino, (C3)(C2)dialkylamino(C3)alkylamino, or (C3)(C3)dialkylamino(C3)alkylamino.

168. In some embodiments, the compound is a compound of Embodiment Group 163, or a pharmaceutically acceptable salt thereof, in which R1 is substituted with (C1-C3)(C1-C3)dialkylamino(C2-C3)alkylamino, (C1-C3)(C1-C3)dialkylamino(C2)alkylamino, (C1-C3)(C1-C3)dialkylamino(C3)alkylamino, (C1-C3)(C1-C3)dialkylamino(C2-C3)alkylamino, (C1-C3)(C1)dialkylamino(C2-C3)alkylamino, (C1-C3)(C2)dialkylamino(C2-C3)alkylamino, (C1-C3)(C3)dialkylamino(C2-C3)alkylamino, (C1-C3)(C1-C3)dialkylamino(C2)alkylamino, (C1-C3)(C1)dialkylamino(C2-)alkylamino, (C1-C3)(C2)dialkylamino(C2)alkylamino, (C1-C3)(C3)dialkylamino(C2)alkylamino, (C1-C3)(C1-C3)dialkylamino(C3)alkylamino, (C1-C3)(C1)dialkylamino(C3)alkylamino, (C1-C3)(C2)dialkylamino(C3)alkylamino, or (C1-C3)(C3)dialkylamino(C3)alkylamino.

169. In some embodiments, the compound is a compound of Embodiment Group 163, or a pharmaceutically acceptable salt thereof, in which R1 is substituted with (C2-C3)(C1-C3)dialkylamino(C2-C3)alkylamino, (C2-C3)(C1-C3)dialkylamino(C2)alkylamino, (C2-C3)(C1-C3)dialkylamino(C3)alkylamino, (C2-C3)(C1-C3)dialkylamino(C2-C3)alkylamino, (C2-C3)(C1)dialkylamino(C2-C3)alkylamino, (C2-C3)(C2)dialkylamino(C2-C3)alkylamino, (C2-C3)(C3)dialkylamino(C2-C3)alkylamino, (C2-C3)(C1-C3)dialkylamino(C2)alkylamino, (C2-C3)(C1)dialkylamino(C2-)alkylamino, (C2-C3)(C2)dialkylamino(C2)alkylamino, (C2-C3)(C3)dialkylamino(C2)alkylamino, (C2-C3)(C1-C3)dialkylamino(C3)alkylamino, (C2-C3)(C1)dialkylamino(C3)alkylamino, (C2-C3)(C2)dialkylamino(C3)alkylamino, or (C2-C3)(C3)dialkylamino(C3)alkylamino.

170. In some embodiments, the compound is a compound of Embodiment Group 163, or a pharmaceutically acceptable salt thereof, in which R1 is substituted with (C1-C2)(C1-C3)dialkylamino(C2-C3)alkylamino, (C1-C2)(C1-C3)dialkylamino(C2)alkylamino, (C1-C2)(C1-C3)dialkylamino(C3)alkylamino, (C1-C2)(C1-C3)dialkylamino(C2-C3)alkylamino, (C1-C2)(C1)dialkylamino(C2-C3)alkylamino, (C1-C2)(C2)dialkylamino(C2-C3)alkylamino, (C1-C2)(C3)dialkylamino(C2-C3)alkylamino, (C1-C2)(C1-C3)dialkylamino(C2)alkylamino, (C1-C2)(C1)dialkylamino(C2-)alkylamino, (C1-C2)(C2)dialkylamino(C2)alkylamino, (C1-C2)(C3)dialkylamino(C2)alkylamino, (C1-C2)(C1-C3)dialkylamino(C3)alkylamino, (C1-C2)(C1)dialkylamino(C3)alkylamino, (C1-C2)(C2)dialkylamino(C3)alkylamino, or (C1-C2)(C3)dialkylamino(C3)alkylamino.

171. In some embodiments, the compound is a compound of Embodiment Group 163, 164, 165, 166, 167, 168, 169, or 170, or a pharmaceutically acceptable salt thereof, in which the (C1-C3)dialkylamino(C2-C3)alkylamino is directly linked to R1.

172. In some embodiments, the compound is a compound of Embodiment Group 163, 164, 165, 166, 167, 168, 169, or 170, or a pharmaceutically acceptable salt thereof, in which the (C1-C3)dialkylamino(C2-C3)alkylamino is linked to R1 through a carbonyl.

173. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or 172, or a pharmaceutically acceptable salt thereof, in which R1 is substituted with (C1-C3)alkylamino(C2-C3)dialkylamino, optionally linked to R1 through a carbonyl group.

174. In some embodiments, the compound is a compound of Embodiment Group 173, or a pharmaceutically acceptable salt thereof, in which R1 is substituted with (C1-C3)alkylamino(C2-C3)dialkylamino, (C1-C3)alkylamino(C2)dialkylamino, or (C1-C3)alkylamino(C3)dialkylamino.

175. In some embodiments, the compound is a compound of Embodiment Group 173, or a pharmaceutically acceptable salt thereof, in which R1 is substituted with (C1)alkylamino(C2-C3)dialkylamino, (C2)alkylamino(C2-C3)dialkylamino, (C3)alkylamino(C2-C3)dialkylamino, (C1-C3)alkylamino(C2-C3)dialkylamino, (C1-C2)alkylamino(C2-C3)dialkylamino, or (C1-C3)alkylamino(C2-C3)dialkylamino.

176. In some embodiments, the compound is a compound of Embodiment Group 173, or a pharmaceutically acceptable salt thereof, in which R1 is substituted with (C1-C3)alkylamino(C2-C3)(C2-C3)dialkylamino, (C1-C3)alkylamino(C2)(C2-C3)dialkylamino, (C1-C3)alkylamino(C3)(C2-C3)dialkylamino, (C1-C3)alkylamino(C1)(C1)dialkylamino, (C1-C3)alkylamino(C1)(C2)dialkylamino, (C1-C3)alkylamino(C1)(C3)dialkylamino, (C1-C3)alkylamino(C2)(C2)dialkylamino, (C1-C3)alkylamino(C2)(C3)dialkylamino, or (C1-C3)alkylamino(C3)(C3)dialkylamino.

177. In some embodiments, the compound is a compound of Embodiment Group 173, 174, 175, or 176, or a pharmaceutically acceptable salt thereof, in which the (C1-C3)alkylamino(C2-C3)dialkylamino is directly linked to R1.

178. In some embodiments, the compound is a compound of Embodiment Group 173, 174, 175, or 176, or a pharmaceutically acceptable salt thereof, in which the (C1-C3)alkylamino(C2-C3)dialkylamino is linked to R1 through a carbonyl.

179. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, or 178, or a pharmaceutically acceptable salt thereof, in which R1 is substituted with (C1-C3)dialkylamino(C2-C3)dialkylamino, optionally linked to R1 through a carbonyl group.

180. In some embodiments, the compound is a compound of Embodiment Group 179, or a pharmaceutically acceptable salt thereof, in which R1 is substituted with (C1-C3)dialkylamino(C2-C3)dialkylamino, (C1-C3)dialkylamino(C2)dialkylamino, (C1-C3)dialkylamino(C3)dialkylamino, (C1-C3)dialkylamino(C2-C3)(C2-3)dialkylamino, (C1-C3)dialkylamino(C2-C3)(C2)dialkylamino, or (C1-C3)dialkylamino(C2-C3)(3)dialkylamino.

181. In some embodiments, the compound is a compound of Embodiment Group 179, or a pharmaceutically acceptable salt thereof, in which R1 is substituted with (C1)dialkylamino(C2-C3)dialkylamino, (C1)dialkylamino(C2)dialkylamino, (C1)dialkylamino(C3)dialkylamino, (C1)dialkylamino(C2-C3)(C2-3)dialkylamino, (C1)dialkylamino(C2-C3)(C2)dialkylamino, or (C1)dialkylamino(C2-C3)(3)dialkylamino.

182. In some embodiments, the compound is a compound of Embodiment Group 179, or a pharmaceutically acceptable salt thereof, in which R1 is substituted with (C2)dialkylamino(C2-C3)dialkylamino, (C2)dialkylamino(C2)dialkylamino, (C2)dialkylamino(C3)dialkylamino, (C2)dialkylamino(C2-C3)(C2-3)dialkylamino, (C2)dialkylamino(C2-C3)(C2)dialkylamino, or (C2)dialkylamino(C2-C3)(3)dialkylamino.

183. In some embodiments, the compound is a compound of Embodiment Group 179, or a pharmaceutically acceptable salt thereof, in which R1 is substituted with (C3)dialkylamino(C2-C3)dialkylamino, (C3)dialkylamino(C2)dialkylamino, (C3)dialkylamino(C3)dialkylamino, (C3)dialkylamino(C2-C3)(C2-3)dialkylamino, (C3)dialkylamino(C2-C3)(C2)dialkylamino, or (C3)dialkylamino(C2-C3)(3)dialkylamino.

184. In some embodiments, the compound is a compound of Embodiment Group 179, or a pharmaceutically acceptable salt thereof, in which R1 is substituted with (C1-C2)dialkylamino(C2-C3)dialkylamino, (C1-C2)dialkylamino(C2)dialkylamino, (C1-C2)dialkylamino(C3)dialkylamino, (C1-C2)dialkylamino(C2-C3)(C2-3)dialkylamino, (C1-C2)dialkylamino(C2-C3)(C2)dialkylamino, or (C1-C2)dialkylamino(C2-C3)(3)dialkylamino.

185. In some embodiments, the compound is a compound of Embodiment Group 179, or a pharmaceutically acceptable salt thereof, in which R1 is substituted with (C1-C3)dialkylamino(C2-C3)dialkylamino, (C1-C3)dialkylamino(C2)dialkylamino, (C1)dialkylamino(C3)dialkylamino, (C1-C3)dialkylamino(C2-C3)(C2-3)dialkylamino, (C1-C3)dialkylamino(C2-C3)(C2)dialkylamino, or (C1-C3)dialkylamino(C2-C3)(3)dialkylamino.

186. In some embodiments, the compound is a compound of Embodiment Group 179, or a pharmaceutically acceptable salt thereof, in which R1 is substituted with (C2-C3)dialkylamino(C2-C3)dialkylamino, (C2-C3)dialkylamino(C2)dialkylamino, (C2-C3)dialkylamino(C3)dialkylamino, (C2-C3)dialkylamino(C2-C3)(C2-3)dialkylamino, (C2-C3)dialkylamino(C2-C3)(C2)dialkylamino, or (C2-C3)dialkylamino(C2-C3)(3)dialkylamino.

187. 179, or a pharmaceutically acceptable salt thereof, in which R1 is substituted with (C1-C3)(C1-C3)dialkylamino(C2-C3)dialkylamino, (C1-C3)(C1-C3)dialkylamino(C2)dialkylamino, (C1-C3)(C1-C3)dialkylamino(C3)dialkylamino, (C1-C3)(C1-C3)dialkylamino(C2-C3)(C2-3)dialkylamino, (C1-C3)(C1-C3)dialkylamino(C2-C3)(C2)dialkylamino, or (C1-C3)(C1-C3)dialkylamino(C2-C3)(3)dialkylamino.

188. In some embodiments, the compound is a compound of Embodiment Group 179, or a pharmaceutically acceptable salt thereof, in which R1 is substituted with (C1-C3)(C1)dialkylamino(C2-C3)dialkylamino, (C1-C3)(C1)dialkylamino(C2)dialkylamino, (C1-C3)(C1)dialkylamino(C3)dialkylamino, (C1-C3)(C1)dialkylamino(C2-C3)(C2-3)dialkylamino, (C1-C3)(C1)dialkylamino(C2-C3)(C2)dialkylamino, or (C1-C3)(C1)dialkylamino(C2-C3)(3)dialkylamino.

189. In some embodiments, the compound is a compound of Embodiment Group 179, or a pharmaceutically acceptable salt thereof, in which R1 is substituted with (C1-C3)(C2)dialkylamino(C2-C3)dialkylamino, (C1-C3)(C2)dialkylamino(C2)dialkylamino, (C1-C3)(C2)dialkylamino(C3)dialkylamino, (C2)dialkylamino(C2-C3)(C2-3)dialkylamino, (C1-C3)(C2)dialkylamino(C2-C3)(C2)dialkylamino, or (C1-C3)(C2)dialkylamino(C2-C3)(3)dialkylamino.

190. In some embodiments, the compound is a compound of Embodiment Group 179, or a pharmaceutically acceptable salt thereof, in which R1 is substituted with (C1-C3)(C3)dialkylamino(C2-C3)dialkylamino, (C1-C3)(C3)dialkylamino(C2)dialkylamino, (C1-C3)(C3)dialkylamino(C3)dialkylamino, (C1-C3)(C3)dialkylamino(C2-C3)(C2-3)dialkylamino, (C1-C3)(C3)dialkylamino(C2-C3)(C2)dialkylamino, or (C1-C3)(C3)dialkylamino(C2-C3)(3)dialkylamino.

191. In some embodiments, the compound is a compound of Embodiment Group 179, or a pharmaceutically acceptable salt thereof, in which R1 is substituted with (C1-C3)(C1-C2)dialkylamino(C2-C3)dialkylamino, (C1-C3)(C1-C2)dialkylamino(C2)dialkylamino, (C1-C3)(C1-C2)dialkylamino(C3)dialkylamino, (C1-C3)(C1-C2)dialkylamino(C2-C3)(C2-3)dialkylamino, (C1-C3)(C1-C2)dialkylamino(C2-C3)(C2)dialkylamino, or (C1-C3)(C1-C2)dialkylamino(C2-C3)(3)dialkylamino.

192. In some embodiments, the compound is a compound of Embodiment Group 179, or a pharmaceutically acceptable salt thereof, in which R1 is substituted with (C1-C3)(C1-C3)dialkylamino(C2-C3)dialkylamino, (C1-C3)(C1-C3)dialkylamino(C2)dialkylamino, (C1-C3)(C1)dialkylamino(C3)dialkylamino, (C1-C3)(C1-C3)dialkylamino(C2-C3)(C2-3)dialkylamino, (C1-C3)(C1-C3)dialkylamino(C2-C3)(C2)dialkylamino, or (C1-C3)(C1-C3)dialkylamino(C2-C3)(3)dialkylamino.

193. In some embodiments, the compound is a compound of Embodiment Group 179, or a pharmaceutically acceptable salt thereof, in which R1 is substituted with (C1-C3)(C2-C3)dialkylamino(C2-C3)dialkylamino, (C1-C3)(C2-C3)dialkylamino(C2)dialkylamino, (C1-C3)(C2-C3)dialkylamino(C3)dialkylamino, (C1-C3)(C2-C3)dialkylamino(C2-C3)(C2-3)dialkylamino, (C1-C3)(C2-C3)dialkylamino(C2-C3)(C2)dialkylamino, or (C1-C3)(C2-C3)dialkylamino(C2-C3)(3)dialkylamino.

194. In some embodiments, the compound is a compound of Embodiment Group 179, or a pharmaceutically acceptable salt thereof, in which R1 is substituted with (C2-C3)(C1-C3)dialkylamino(C2-C3)dialkylamino, (C2-C3)(C1-C3)dialkylamino(C2)dialkylamino, (C2-C3)(C1-C3)dialkylamino(C3)dialkylamino, (C2-C3)(C1-C3)dialkylamino(C2-C3)(C2-3)dialkylamino, (C2-C3)(C1-C3)dialkylamino(C2-C3)(C2)dialkylamino, or (C2-C3)(C1-C3)dialkylamino(C2-C3)(3)dialkylamino.

195. In some embodiments, the compound is a compound of Embodiment Group 179, or a pharmaceutically acceptable salt thereof, in which R1 is substituted with (C2-C3)(C1)dialkylamino(C2-C3)dialkylamino, (C2-C3)(C1)dialkylamino(C2)dialkylamino, (C2-C3)(C1)dialkylamino(C3)dialkylamino, (C2-C3)(C1)dialkylamino(C2-C3)(C2-3)dialkylamino, (C2-C3)(C1)dialkylamino(C2-C3)(C2)dialkylamino, or (C2-C3)(C1)dialkylamino(C2-C3)(3)dialkylamino.

196. In some embodiments, the compound is a compound of Embodiment Group 179, or a pharmaceutically acceptable salt thereof, in which R1 is substituted with (C2-C3)(C2)dialkylamino(C2-C3)dialkylamino, (C2-C3)(C2)dialkylamino(C2)dialkylamino, (C2-C3)(C2)dialkylamino(C3)dialkylamino, (C2)dialkylamino(C2-C3)(C2-3)dialkylamino, (C2-C3)(C2)dialkylamino(C2-C3)(C2)dialkylamino, or (C2-C3)(C2)dialkylamino(C2-C3)(3)dialkylamino.

197. In some embodiments, the compound is a compound of Embodiment Group 179, or a pharmaceutically acceptable salt thereof, in which R1 is substituted with (C1-C3)(C3)dialkylamino(C2-C3)dialkylamino, (C2-C3)(C3)dialkylamino(C2)dialkylamino, (C2-C3)(C3)dialkylamino(C3)dialkylamino, (C2-C3)(C3)dialkylamino(C2-C3)(C2-3)dialkylamino, (C2-C3)(C3)dialkylamino(C2-C3)(C2)dialkylamino, or (C2-C3)(C3)dialkylamino(C2-C3)(3)dialkylamino.

198. In some embodiments, the compound is a compound of Embodiment Group 179, or a pharmaceutically acceptable salt thereof, in which R1 is substituted with (C1-C3)(C1-C2)dialkylamino(C2-C3)dialkylamino, (C2-C3)(C1-C2)dialkylamino(C2)dialkylamino, (C2-C3)(C1-C2)dialkylamino(C3)dialkylamino, (C2-C3)(C1-C2)dialkylamino(C2-C3)(C2-3)dialkylamino, (C2-C3)(C1-C2)dialkylamino(C2-C3)(C2)dialkylamino, or (C2-C3)(C1-C2)dialkylamino(C2-C3)(3)dialkylamino.

199. In some embodiments, the compound is a compound of Embodiment Group 179, or a pharmaceutically acceptable salt thereof, in which R1 is substituted with (C1-C3)(C1-C3)dialkylamino(C2-C3)dialkylamino, (C2-C3)(C1-C3)dialkylamino(C2)dialkylamino, (C2-C3)(C1)dialkylamino(C3)dialkylamino, (C2-C3)(C1-C3)dialkylamino(C2-C3)(C2-3)dialkylamino, (C2-C3)(C1-C3)dialkylamino(C2-C3)(C2)dialkylamino, or (C2-C3)(C1-C3)dialkylamino(C2-C3)(3)dialkylamino.

200. In some embodiments, the compound is a compound of Embodiment Group 179, or a pharmaceutically acceptable salt thereof, in which R1 is substituted with (C1-C3)(C2-C3)dialkylamino(C2-C3)dialkylamino, (C2-C3)(C2-C3)dialkylamino(C2)dialkylamino, (C2-C3)(C2-C3)dialkylamino(C3)dialkylamino, (C2-C3)(C2-C3)dialkylamino(C2-C3)(C2-3)dialkylamino, (C2-C3)(C2-C3)dialkylamino(C2-C3)(C2)dialkylamino, or (C2-C3)(C2-C3)dialkylamino(C2-C3)(3)dialkylamino.

201. In some embodiments, the compound is a compound of Embodiment Group 179, or a pharmaceutically acceptable salt thereof, in which R1 is substituted with (C1-C2)(C1-C2)dialkylamino(C2-C3)dialkylamino, (C1-C2)(C1-C3)dialkylamino(C2)dialkylamino, (C1-C2)(C1-C3)dialkylamino(C3)dialkylamino, (C1-C2)(C1-C3)dialkylamino(C2-C3)(C2-3)dialkylamino, (C1-C2)(C1-C3)dialkylamino(C2-C3)(C2)dialkylamino, or (C1-C2)(C1-C3)dialkylamino(C2-C3)(3)dialkylamino.

202. In some embodiments, the compound is a compound of Embodiment Group 179, or a pharmaceutically acceptable salt thereof, in which R1 is substituted with (C1-C2)(C1)dialkylamino(C2-C3)dialkylamino, (C1-C2)(C1)dialkylamino(C2)dialkylamino, (C1-C2)(C1)dialkylamino(C3)dialkylamino, (C1-C2)(C1)dialkylamino(C2-C3)(C2-3)dialkylamino, (C1-C2)(C1)dialkylamino(C2-C3)(C2)dialkylamino, or (C1-C2)(C1)dialkylamino(C2-C3)(3)dialkylamino.

203. In some embodiments, the compound is a compound of Embodiment Group 179, or a pharmaceutically acceptable salt thereof, in which R1 is substituted with (C1-C2)(C2)dialkylamino(C2-C3)dialkylamino, (C1-C2)(C2)dialkylamino(C2)dialkylamino, (C1-C2)(C2)dialkylamino(C3)dialkylamino, (C2)dialkylamino(C2-C3)(C2-3)dialkylamino, (C1-C2)(C2)dialkylamino(C2-C3)(C2)dialkylamino, or (C1-C2)(C2)dialkylamino(C2-C3)(3)dialkylamino.

204. In some embodiments, the compound is a compound of Embodiment Group 179, or a pharmaceutically acceptable salt thereof, in which R1 is substituted with (C1-C3)(C3)dialkylamino(C2-C3)dialkylamino, (C1-C2)(C3)dialkylamino(C2)dialkylamino, (C1-C2)(C3)dialkylamino(C3)dialkylamino, (C1-C2)(C3)dialkylamino(C2-C3)(C2-3)dialkylamino, (C1-C2)(C3)dialkylamino(C2-C3)(C2)dialkylamino, or (C1-C2)(C3)dialkylamino(C2-C3)(3)dialkylamino.

205. In some embodiments, the compound is a compound of Embodiment Group 179, or a pharmaceutically acceptable salt thereof, in which R1 is substituted with (C1-C3)(C1-C2)dialkylamino(C2-C3)dialkylamino, (C1-C2)(C1-C2)dialkylamino(C2)dialkylamino, (C1-C2)(C1-C2)dialkylamino(C3)dialkylamino, (C1-C2)(C1-C2)dialkylamino(C2-C3)(C2-3)dialkylamino, (C1-C2)(C1-C2)dialkylamino(C2-C3)(C2)dialkylamino, or (C1-C2)(C1-C2)dialkylamino(C2-C3)(3)dialkylamino.

206. In some embodiments, the compound is a compound of Embodiment Group 179, or a pharmaceutically acceptable salt thereof, in which R1 is substituted with (C1-C3)(C1-C3)dialkylamino(C2-C3)dialkylamino, (C1-C2)(C1-C3)dialkylamino(C2)dialkylamino, (C1-C2)(C1)dialkylamino(C3)dialkylamino, (C1-C2)(C1-C3)dialkylamino(C2-C3)(C2-3)dialkylamino, (C1-C2)(C1-C3)dialkylamino(C2-C3)(C2)dialkylamino, or (C1-C2)(C1-C3)dialkylamino(C2-C3)(3)dialkylamino.

207. In some embodiments, the compound is a compound of Embodiment Group 179, or a pharmaceutically acceptable salt thereof, in which R1 is substituted with (C1-C3)(C2-C3)dialkylamino(C2-C3)dialkylamino, (C1-C2)(C2-C3)dialkylamino(C2)dialkylamino, (C1-C2)(C2-C3)dialkylamino(C3)dialkylamino, (C1-C2)(C2-C3)dialkylamino(C2-C3)(C2-3)dialkylamino, (C1-C2)(C2-C3)dialkylamino(C2-C3)(C2)dialkylamino, or (C1-C2)(C2-C3)dialkylamino(C2-C3)(3)dialkylamino.

208. In some embodiments, the compound is a compound of Embodiment Group 179, or a pharmaceutically acceptable salt thereof, in which R1 is substituted with (C1-C2)(C1-C3)dialkylamino(C2-C3)dialkylamino, (C1-C2)(C1-C3)dialkylamino(C2)dialkylamino, (C1-C2)(C1-C3)dialkylamino(C3)dialkylamino, (C1-C2)(C1-C3)dialkylamino(C2-C3)(C2-3)dialkylamino, (C1-C2)(C1-

C3)dialkylamino(C2-C3)(C2)dialkylamino, or (C1-C2)(C1-C3)dialkylamino(C2-C3)(3)dialkylamino.
209. In some embodiments, the compound is a compound of Embodiment Group 179, or a pharmaceutically acceptable salt thereof, in which R1 is substituted with (C1-C2)(C1)dialkylamino(C2-C3)dialkylamino, (C1-C2)(C1)dialkylamino(C2)dialkylamino, (C1-C2)(C1)dialkylamino(C3)dialkylamino, (C1-C2)(C1)dialkylamino(C2-C3)(C2-3)dialkylamino, (C1-C2)(C1)dialkylamino(C2-C3)(C2)dialkylamino, or (C1-C2)(C1)dialkylamino(C2-C3)(3)dialkylamino.
210. In some embodiments, the compound is a compound of Embodiment Group 179, or a pharmaceutically acceptable salt thereof, in which R1 is substituted with (C1-C2)(C2)dialkylamino(C2-C3)dialkylamino, (C1-C2)(C2)dialkylamino(C2)dialkylamino, (C1-C2)(C2)dialkylamino(C3)dialkylamino, (C2)dialkylamino(C2-C3)(C2-3)dialkylamino, (C1-C2)(C2)dialkylamino(C2-C3)(C2)dialkylamino, or (C1-C2)(C2)dialkylamino(C2-C3)(3)dialkylamino.
211. In some embodiments, the compound is a compound of Embodiment Group 179, or a pharmaceutically acceptable salt thereof, in which R1 is substituted with (C1-C2)(C3)dialkylamino(C2-C3)dialkylamino, (C1-C2)(C3)dialkylamino(C2)dialkylamino, (C1-C2)(C3)dialkylamino(C3)dialkylamino, (C1-C2)(C3)dialkylamino(C2-C3)(C2-3)dialkylamino, (C1-C2)(C3)dialkylamino(C2-C3)(C2)dialkylamino, or (C1-C2)(C3)dialkylamino(C2-C3)(3)dialkylamino.
212. In some embodiments, the compound is a compound of Embodiment Group 179, or a pharmaceutically acceptable salt thereof, in which R1 is substituted with (C1-C2)(C1-C2)dialkylamino(C2-C3)dialkylamino, (C1-C2)(C1-C2)dialkylamino(C2)dialkylamino, (C1-C2)(C1-C2)dialkylamino(C3)dialkylamino, (C1-C2)(C1-C2)dialkylamino(C2-C3)(C2-3)dialkylamino, (C1-C2)(C1-C2)dialkylamino(C2-C3)(C2)dialkylamino, or (C1-C2)(C1-C2)dialkylamino(C2-C3)(3)dialkylamino.
213. In some embodiments, the compound is a compound of Embodiment Group 179, or a pharmaceutically acceptable salt thereof, in which R1 is substituted with (C1-C2)(C1-C3)dialkylamino(C2-C3)dialkylamino, (C1-C2)(C1-C3)dialkylamino(C2)dialkylamino, (C1-C2)(C1)dialkylamino(C3)dialkylamino, (C1-C2)(C1-C3)dialkylamino(C2-C3)(C2-3)dialkylamino, (C1-C2)(C1-C3)dialkylamino(C2-C3)(C2)dialkylamino, or (C1-C2)(C1-C3)dialkylamino(C2-C3)(3)dialkylamino.
214. In some embodiments, the compound is a compound of Embodiment Group 179, or a pharmaceutically acceptable salt thereof, in which R1 is substituted with (C1-C2)(C2-C3)dialkylamino(C2-C3)dialkylamino, (C1-C2)(C2-C3)dialkylamino(C2)dialkylamino, (C1-C2)(C2-C3)dialkylamino(C3)dialkylamino, (C1-C2)(C2-C3)dialkylamino(C2-C3)(C2-3)dialkylamino, (C1-C2)(C2-C3)dialkylamino(C2-C3)(C2)dialkylamino, or (C1-C2)(C2-C3)dialkylamino(C2-C3)(3)dialkylamino.
215. v, or a pharmaceutically acceptable salt thereof, in which R1 is substituted with (C1)(C1-C3)dialkylamino(C2-C3)dialkylamino, (C1)(C1-C3)dialkylamino(C2)dialkylamino, (C1)(C1-C3)dialkylamino(C3)dialkylamino, (C1)(C1-C3)dialkylamino(C2-C3)(C2-3)dialkylamino, (C1)(C1-C3)dialkylamino(C2-C3)(C2)dialkylamino, or (C1)(C1-C3)dialkylamino(C2-C3)(3)dialkylamino.
216. In some embodiments, the compound is a compound of Embodiment Group 179, or a pharmaceutically acceptable salt thereof, in which R1 is substituted with (C1)(C1)dialkylamino(C2-C3)dialkylamino, (C1)(C1)dialkylamino(C2)dialkylamino, (C1)(C1)dialkylamino(C3)dialkylamino, (C1)(C1)dialkylamino(C2-C3)(C2-3)dialkylamino, (C1)(C1)dialkylamino(C2-C3)(C2)dialkylamino, or (C1)(C1)dialkylamino(C2-C3)(3)dialkylamino.
217. In some embodiments, the compound is a compound of Embodiment Group 179, or a pharmaceutically acceptable salt thereof, in which R1 is substituted with (C1)(C2)dialkylamino(C2-C3)dialkylamino, (C1)(C2)dialkylamino(C2)dialkylamino, (C1)(C2)dialkylamino(C3)dialkylamino, (C2)dialkylamino(C2-C3)(C2-3)dialkylamino, (C1)(C2)dialkylamino(C2-C3)(C2)dialkylamino, or (C1)(C2)dialkylamino(C2-C3)(3)dialkylamino.
218. In some embodiments, the compound is a compound of Embodiment Group 179, or a pharmaceutically acceptable salt thereof, in which R1 is substituted with (C1)(C3)dialkylamino(C2-C3)dialkylamino, (C1)(C3)dialkylamino(C2)dialkylamino, (C1)(C3)dialkylamino(C3)dialkylamino, (C1)(C3)dialkylamino(C2-C3)(C2-3)dialkylamino, (C1)(C3)dialkylamino(C2-C3)(C2)dialkylamino, or (C1)(C3)dialkylamino(C2-C3)(3)dialkylamino.
219. In some embodiments, the compound is a compound of Embodiment Group 179, or a pharmaceutically acceptable salt thereof, in which R1 is substituted with (C1)(C1-C2)dialkylamino(C2-C3)dialkylamino, (C1)(C1-C2)dialkylamino(C2)dialkylamino, (C1)(C1-C2)dialkylamino(C3)dialkylamino, (C1)(C1-C2)dialkylamino(C2-C3)(C2-3)dialkylamino, (C1)(C1-C2)dialkylamino(C2-C3)(C2)dialkylamino, or (C1)(C1-C2)dialkylamino(C2-C3)(3)dialkylamino.
220. In some embodiments, the compound is a compound of Embodiment Group 179, or a pharmaceutically acceptable salt thereof, in which R1 is substituted with (C1)(C1-C3)dialkylamino(C2-C3)dialkylamino, (C1)(C1-C3)dialkylamino(C2)dialkylamino, (C1)(C1)dialkylamino(C3)dialkylamino, (C1)(C1-C3)dialkylamino(C2-C3)(C2-3)dialkylamino, (C1)(C1-C3)dialkylamino(C2-C3)(C2)dialkylamino, or (C1)(C1-C3)dialkylamino(C2-C3)(3)dialkylamino.
221. In some embodiments, the compound is a compound of Embodiment Group 179, or a pharmaceutically acceptable salt thereof, in which R1 is substituted with (C1)(C2-C3)dialkylamino(C2-C3)dialkylamino, (C1)(C2-C3)dialkylamino(C2)dialkylamino, (C1)(C2-C3)dialkylamino(C3)dialkylamino, (C1)(C2-C3)dialkylamino(C2-C3)(C2-3)dialkylamino, (C1)(C2-C3)dialkylamino(C2-C3)(C2)dialkylamino, or (C1)(C2-C3)dialkylamino(C2-C3)(3)dialkylamino.
222. 179, or a pharmaceutically acceptable salt thereof, in which R1 is substituted with (C2)(C1-C3)dialkylamino(C2-C3)dialkylamino, (C2)(C1-C3)dialkylamino(C2)dialkylamino, (C2)(C1-C3)dialkylamino(C3)dialkylamino, (C2)(C1-C3)dialkylamino(C2-C3)(C2-3)dialkylamino, (C2)(C1-C3)dialkylamino(C2-C3)(C2)dialkylamino, or (C2)(C1-C3)dialkylamino(C2-C3)(3)dialkylamino.
223. In some embodiments, the compound is a compound of Embodiment Group 179, or a pharmaceutically acceptable salt thereof, in which R1 is substituted with (C2)(C1)dialkylamino(C2-C3)dialkylamino, (C2)(C1)dialkylamino(C2)dialkylamino, (C2)(C1)dialkylamino(C3)dialkylamino, (C2)(C1)dialkylamino(C2-C3)(C2-3)dialkylamino, (C2)(C1)dialkylamino(C2-C3)(C2)dialkylamino, or (C2)(C1)dialkylamino(C2-C3)(3)dialkylamino.

224. In some embodiments, the compound is a compound of Embodiment Group 179, or a pharmaceutically acceptable salt thereof, in which R1 is substituted with (C2)(C2)dialkylamino(C2-C3)dialkylamino, (C2)(C2)dialkylamino(C2)dialkylamino, (C2)(C2)dialkylamino(C3)dialkylamino, (C2)(C2)dialkylamino(C2-C3)(C2-3)dialkylamino, (C2)(C2)dialkylamino(C2-C3)(C2)dialkylamino, or (C2)(C2)dialkylamino(C2-C3)(3)dialkylamino.

225. In some embodiments, the compound is a compound of Embodiment Group 179, or a pharmaceutically acceptable salt thereof, in which R1 is substituted with (C2)(C3)dialkylamino(C2-C3)dialkylamino, (C2)(C3)dialkylamino(C2)dialkylamino, (C2)(C3)dialkylamino(C3)dialkylamino, (C2)(C3)dialkylamino(C2-C3)(C2-3)dialkylamino, (C2)(C3)dialkylamino(C2-C3)(C2)dialkylamino, or (C2)(C3)dialkylamino(C2-C3)(3)dialkylamino.

226. In some embodiments, the compound is a compound of Embodiment Group 179, or a pharmaceutically acceptable salt thereof, in which R1 is substituted with (C2)(C1-C2)dialkylamino(C2-C3)dialkylamino, (C2)(C1-C2)dialkylamino(C2)dialkylamino, (C2)(C1-C2)dialkylamino(C3)dialkylamino, (C2)(C1-C2)dialkylamino(C2-C3)(C2-3)dialkylamino, (C2)(C1-C2)dialkylamino(C2-C3)(C2)dialkylamino, or (C2)(C1-C2)dialkylamino(C2-C3)(3)dialkylamino.

227. In some embodiments, the compound is a compound of Embodiment Group 179, or a pharmaceutically acceptable salt thereof, in which R1 is substituted with (C2)(C1-C3)dialkylamino(C2-C3)dialkylamino, (C2)(C1-C3)dialkylamino(C2)dialkylamino, (C2)(C1)dialkylamino(C3)dialkylamino, (C2)(C1-C3)dialkylamino(C2-C3)(C2-3)dialkylamino, (C2)(C1-C3)dialkylamino(C2-C3)(C2)dialkylamino, or (C2)(C1-C3)dialkylamino(C2-C3)(3)dialkylamino.

228. In some embodiments, the compound is a compound of Embodiment Group 179, or a pharmaceutically acceptable salt thereof, in which R1 is substituted with (C2)(C2-C3)dialkylamino(C2-C3)dialkylamino, (C2)(C2-C3)dialkylamino(C2)dialkylamino, (C2)(C2-C3)dialkylamino(C3)dialkylamino, (C2)(C2-C3)dialkylamino(C2-C3)(C2-3)dialkylamino, (C2)(C2-C3)dialkylamino(C2-C3)(C2)dialkylamino, or (C2)(C2-C3)dialkylamino(C2-C3)(3)dialkylamino.

229. 179, or a pharmaceutically acceptable salt thereof, in which R1 is substituted with (C3)(C1-C3)dialkylamino(C2-C3)dialkylamino, (C3)(C1-C3)dialkylamino(C2)dialkylamino, (C3)(C1-C3)dialkylamino(C3)dialkylamino, (C3)(C1-C3)dialkylamino(C2-C3)(C2-3)dialkylamino, (C3)(C1-C3)dialkylamino(C2-C3)(C2)dialkylamino, or (C3)(C1-C3)dialkylamino(C2-C3)(3)dialkylamino.

230. In some embodiments, the compound is a compound of Embodiment Group 179, or a pharmaceutically acceptable salt thereof, in which R1 is substituted with (C3)(C1)dialkylamino(C2-C3)dialkylamino, (C3)(C1)dialkylamino(C2)dialkylamino, (C3)(C1)dialkylamino(C3)dialkylamino, (C3)(C1)dialkylamino(C2-C3)(C2-3)dialkylamino, (C3)(C1)dialkylamino(C2-C3)(C2)dialkylamino, or (C3)(C1)dialkylamino(C2-C3)(3)dialkylamino.

231. In some embodiments, the compound is a compound of Embodiment Group 179, or a pharmaceutically acceptable salt thereof, in which R1 is substituted with (C3)(C2)dialkylamino(C2-C3)dialkylamino, (C3)(C2)dialkylamino(C2)dialkylamino, (C3)(C2)dialkylamino(C3)dialkylamino, (C3)(C2)dialkylamino(C2-C3)(C2-3)dialkylamino, (C3)(C2)dialkylamino(C2-C3)(C2)dialkylamino, or (C3)(C2)dialkylamino(C2-C3)(3)dialkylamino, 232. In some embodiments, the compound is a compound of Embodiment Group 179, or a pharmaceutically acceptable salt thereof, in which R1 is substituted with (C3)(C3)dialkylamino(C2-C3)dialkylamino, (C3)(C3)dialkylamino(C2)dialkylamino, (C3)(C3)dialkylamino(C3)dialkylamino, (C3)(C3)dialkylamino(C2-C3)(C2-3)dialkylamino, (C3)(C3)dialkylamino(C2-C3)(C2)dialkylamino, or (C3)(C3)dialkylamino(C2-C3)(3)dialkylamino, 233. In some embodiments, the compound is a compound of Embodiment Group 179, or a pharmaceutically acceptable salt thereof, in which R1 is substituted with (C3)(C1-C2)dialkylamino(C2-C3)dialkylamino, (C3)(C1-C2)dialkylamino(C2)dialkylamino, (C3)(C1-C2)dialkylamino(C3)dialkylamino, (C3)(C1-C2)dialkylamino(C2-C3)(C2-3)dialkylamino, (C3)(C1-C2)dialkylamino(C2-C3)(C2)dialkylamino, or (C3)(C1-C2)dialkylamino(C2-C3)(3)dialkylamino.

234. In some embodiments, the compound is a compound of Embodiment Group 179, or a pharmaceutically acceptable salt thereof, in which R1 is substituted with (C3)(C1-C3)dialkylamino(C2-C3)dialkylamino, (C3)(C1-C3)dialkylamino(C2)dialkylamino, (C3)(C1)dialkylamino(C3)dialkylamino, (C3)(C1-C3)dialkylamino(C2-C3)(C2-3)dialkylamino, (C3)(C1-C3)dialkylamino(C2-C3)(C2)dialkylamino, or (C3)(C1-C3)dialkylamino(C2-C3)(3)dialkylamino.

235. In some embodiments, the compound is a compound of Embodiment Group 179, or a pharmaceutically acceptable salt thereof, in which R1 is substituted with (C3)(C2-C3)dialkylamino(C2-C3)dialkylamino, (C3)(C2-C3)dialkylamino(C2)dialkylamino, (C3)(C2-C3)dialkylamino(C3)dialkylamino, (C3)(C2-C3)dialkylamino(C2-C3)(C2-3)dialkylamino, (C3)(C2-C3)dialkylamino(C2-C3)(C2)dialkylamino, or (C3)(C2-C3)dialkylamino(C2-C3)(3)dialkylamino.

236. In some embodiments, the compound is a compound of Embodiment Group 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, or 235, or a pharmaceutically acceptable salt thereof, in which the (C1-C3)dialkylamino(C2-C3)dialkylamino is directly linked to R1.

237. In some embodiments, the compound is a compound of Embodiment Group 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, or 235, or a pharmaceutically acceptable salt thereof, in which the (C1-C3)dialkylamino(C2-C3)dialkylamino is linked to R1 through a carbonyl.

238. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, or 237, or a pharmaceutically acceptable salt thereof, in which R1 is substituted with (C1-C3)alkoxyl(C2-C3)alkylamino, optionally linked to R1 through a carbonyl group.

239. In some embodiments, the compound is a compound of Embodiment Group 238, or a pharmaceutically acceptable salt thereof, in which R1 is substituted with (C1-C3)alkoxyl(C2-C3)alkylamino, (C1-C3)alkoxyl(C2)alkylamino, or (C1-C3)alkoxyl(C3)alkylamino.

240. In some embodiments, the compound is a compound of Embodiment Group 238, or a pharmaceutically acceptable salt thereof, in which R1 is substituted with (C1-C2)alkoxyl(C2-C3)alkylamino, (C1-C2)alkoxyl(C2)alkylamino, or (C1-C2)alkoxyl(C3)alkylamino.

241. In some embodiments, the compound is a compound of Embodiment Group 238, or a pharmaceutically acceptable salt thereof, in which R1 is substituted with (C2-C3)alkoxyl(C2-C3)alkylamino, (C2-C3)alkoxyl(C2)alkylamino, or (C2-C3)alkoxyl(C3)alkylamino.

242. In some embodiments, the compound is a compound of Embodiment Group 238, or a pharmaceutically acceptable salt thereof, in which R1 is substituted with (C1)alkoxyl(C2-C3)alkylamino, (C1)alkoxyl(C2)alkylamino, or (C1)alkoxyl(C3)alkylamino.

243. In some embodiments, the compound is a compound of Embodiment Group 238, or a pharmaceutically acceptable salt thereof, in which R1 is substituted with (C2)alkoxyl(C2-C3)alkylamino, (C2)alkoxyl(C2)alkylamino, or (C2)alkoxyl(C3)alkylamino.

244. In some embodiments, the compound is a compound of Embodiment Group 238, or a pharmaceutically acceptable salt thereof, in which R1 is substituted with (C3)alkoxyl(C2-C3)alkylamino, (C3)alkoxyl(C3)alkylamino, or (C3)alkoxyl(C3)alkylamino.

245. In some embodiments, the compound is a compound of Embodiment Group 238, 239, 240, 241, 242, 243, or 244, or a pharmaceutically acceptable salt thereof, in which the (C1-C3)alkoxyl(C2-C3)alkylamino is directly linked to R1.

246. In some embodiments, the compound is a compound of Embodiment Group 238, 239, 240, 241, 242, 243, or 244, or a pharmaceutically acceptable salt thereof, in which the (C1-C3)alkoxyl(C2-C3)alkylamino is linked to R1 through a carbonyl.

247. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, or 246, or a pharmaceutically acceptable salt thereof, in which R1 is substituted with (C1-C3)alkoxyl(C2-C3)dialkylamino, optionally linked to R1 through a carbonyl group.

248. In some embodiments, the compound is a compound of Embodiment Group 247, or a pharmaceutically acceptable salt thereof, in which R1 is substituted with (C1-C3)alkoxyl(C2-C3)dialkylamino, (C1-C3)alkoxyl(C2)dialkylamino, or (C1-C3)alkoxyl(C3)dialkylamino.

249. In some embodiments, the compound is a compound of Embodiment Group 247, or a pharmaceutically acceptable salt thereof, in which R1 is substituted with (C1-C2)alkoxyl(C2-C3)dialkylamino, (C1-C2)alkoxyl(C2)dialkylamino, or (C1-C2)alkoxyl(C3)dialkylamino.

250. In some embodiments, the compound is a compound of Embodiment Group 247, or a pharmaceutically acceptable salt thereof, in which R1 is substituted with (C2-C3)alkoxyl(C2-C3)dialkylamino, (C2-C3)alkoxyl(C2)dialkylamino, or (C2-C3)alkoxyl(C3)dialkylamino.

251. In some embodiments, the compound is a compound of Embodiment Group 247, or a pharmaceutically acceptable salt thereof, in which R1 is substituted with (C1)alkoxyl(C2-C3)dialkylamino, (C1)alkoxyl(C2)dialkylamino, or (C1)alkoxyl(C3)dialkylamino.

252. In some embodiments, the compound is a compound of Embodiment Group 247, or a pharmaceutically acceptable salt thereof, in which R1 is substituted with (C2)alkoxyl(C2-C3)dialkylamino, (C2)alkoxyl(C2)dialkylamino, or (C2)alkoxyl(C3)dialkylamino.

253. In some embodiments, the compound is a compound of Embodiment Group 247, or a pharmaceutically acceptable salt thereof, in which R1 is substituted with (C3)alkoxyl(C2-C3)dialkylamino, (C3)alkoxyl(C2)dialkylamino, or (C3)alkoxyl(C3)dialkylamino.

254. In some embodiments, the compound is a compound of Embodiment Group 247, or a pharmaceutically acceptable salt thereof, in which R1 is substituted with (C1-C3)alkoxyl(C2-C3) (C2-C3)dialkylamino, (C1-C3)alkoxyl(C2) (C2-C3)dialkylamino, or (C1-C3)alkoxyl(C3) (C2-C3)dialkylamino.

255. In some embodiments, the compound is a compound of Embodiment Group 247, or a pharmaceutically acceptable salt thereof, in which R1 is substituted with (C1-C2)alkoxyl(C2-C3) (C2-C3)dialkylamino, (C1-C2)alkoxyl(C2)(C2-C3)dialkylamino, or (C1-C2)alkoxyl(C3) (C2-C3)dialkylamino.

256. In some embodiments, the compound is a compound of Embodiment Group 247, or a pharmaceutically acceptable salt thereof, in which R1 is substituted with (C2-C3)alkoxyl(C2-C3)(C2-C3)dialkylamino, (C2-C3)alkoxyl(C2)(C2-C3)dialkylamino, or (C2-C3)alkoxyl(C3)(C2-C3)dialkylamino.

257. In some embodiments, the compound is a compound of Embodiment Group 247, or a pharmaceutically acceptable salt thereof, in which R1 is substituted with (C1)alkoxyl(C2-C3)(C2-C3)dialkylamino, (C1)alkoxyl(C2) (C2-C3)dialkylamino, or (C1)alkoxyl(C3)(C2-C3)dialkylamino.

258. In some embodiments, the compound is a compound of Embodiment Group 247, or a pharmaceutically acceptable salt thereof, in which R1 is substituted with (C2)

alkoxyl(C2-C3)(C2-C3)dialkylamino, (C2)alkoxyl(C2) (C2-C3)dialkylamino, or (C2)alkoxyl(C3)(C2-C3) dialkylamino.
259. In some embodiments, the compound is a compound of Embodiment Group 247, or a pharmaceutically acceptable salt thereof, in which R1 is substituted with (C3) alkoxyl(C2-C3)(C2-C3)dialkylamino, (C3)alkoxyl(C2) (C2-C3)dialkylamino, or (C3)alkoxyl(C3)(C2-C3) dialkylamino.
260. In some embodiments, the compound is a compound of Embodiment Group 247, or a pharmaceutically acceptable salt thereof, in which R1 is substituted with (C1-C3) alkoxyl(C2-C3) (C2)dialkylamino, (C1-C3)alkoxyl(C2) (C2)dialkylamino, or (C1-C3)alkoxyl(C3) (C2)dialkylamino.
261. In some embodiments, the compound is a compound of Embodiment Group 247, or a pharmaceutically acceptable salt thereof, in which R1 is substituted with (C1-C2) alkoxyl(C2-C3) (C2)dialkylamino, (C1-C2)alkoxyl(C2) (C2)dialkylamino, or (C1-C2)alkoxyl(C3) (C2) dialkylamino.
262. In some embodiments, the compound is a compound of Embodiment Group 247, or a pharmaceutically acceptable salt thereof, in which R1 is substituted with (C2-C3) alkoxyl(C2-C3)(C2)dialkylamino, (C2-C3)alkoxyl(C2) (C2)dialkylamino, or (C2-C3)alkoxyl(C3)(C2) dialkylamino.
263. In some embodiments, the compound is a compound of Embodiment Group 247, or a pharmaceutically acceptable salt thereof, in which R1 is substituted with (C1) alkoxyl(C2-C3)(C2)dialkylamino, (C1)alkoxyl(C2)(C2) dialkylamino, or (C1)alkoxyl(C3)(C2)dialkylamino.
264. In some embodiments, the compound is a compound of Embodiment Group 247, or a pharmaceutically acceptable salt thereof, in which R1 is substituted with (C2) alkoxyl(C2-C3)(C2)dialkylamino, (C2)alkoxyl(C2)(C2) dialkylamino, or (C2)alkoxyl(C3)(C2)dialkylamino.
265. In some embodiments, the compound is a compound of Embodiment Group 247, or a pharmaceutically acceptable salt thereof, in which R1 is substituted with (C3) alkoxyl(C2-C3)(C2)dialkylamino, (C3)alkoxyl(C2)(C2) dialkylamino, or (C3)alkoxyl(C3)(C2)dialkylamino.
266. In some embodiments, the compound is a compound of Embodiment Group 247, or a pharmaceutically acceptable salt thereof, in which R1 is substituted with (C1-C3) alkoxyl(C2-C3) (C3)dialkylamino, (C1-C3)alkoxyl(C2) (C3)dialkylamino, or (C1-C3)alkoxyl(C3) (C3)dialkylamino.
267. In some embodiments, the compound is a compound of Embodiment Group 247, or a pharmaceutically acceptable salt thereof, in which R1 is substituted with (C1-C2) alkoxyl(C2-C3) (C3)dialkylamino, (C1-C2)alkoxyl(C2) (C3)dialkylamino, or (C1-C2)alkoxyl(C3) (C3) dialkylamino.
268. In some embodiments, the compound is a compound of Embodiment Group 247, or a pharmaceutically acceptable salt thereof, in which R1 is substituted with (C2-C3) alkoxyl(C2-C3)(C3)dialkylamino, (C2-C3)alkoxyl(C2) (C3)dialkylamino, or (C2-C3)alkoxyl(C3)(C3) dialkylamino.
269. In some embodiments, the compound is a compound of Embodiment Group 247, or a pharmaceutically acceptable salt thereof, in which R1 is substituted with (C1) alkoxyl(C2-C3)(C3)dialkylamino, (C1)alkoxyl(C2)(C3) dialkylamino, or (C1)alkoxyl(C3)(C3)dialkylamino.
270. In some embodiments, the compound is a compound of Embodiment Group 247, or a pharmaceutically acceptable salt thereof, in which R1 is substituted with (C2) alkoxyl(C2-C3)(C3)dialkylamino, (C2)alkoxyl(C2)(C3) dialkylamino, or (C2)alkoxyl(C3)(C3)dialkylamino.
271. In some embodiments, the compound is a compound of Embodiment Group 247, or a pharmaceutically acceptable salt thereof, in which R1 is substituted with (C3) alkoxyl(C2-C3)(C3)dialkylamino, (C3)alkoxyl(C2)(C3) dialkylamino, or (C3)alkoxyl(C3)(C3)dialkylamino.
272. In some embodiments, the compound is a compound of Embodiment Group 247, 248, 249, 250, 251, 252, 253, 254, 255, 256, 257, 258, 259, 260, 261, 262, 263, 264, 265, 266, 267, 268, 269, or 270, or a pharmaceutically acceptable salt thereof, in which the (C1-C3)alkoxyl(C2-C3)dialkylamino is directly linked to R1.
273. In some embodiments, the compound is a compound of Embodiment Group 247, 248, 249, 250, 251, 252, 253, 254, 255, 256, 257, 258, 259, 260, 261, 262, 263, 264, 265, 266, 267, 268, 269, or 270, or a pharmaceutically acceptable salt thereof, in which the (C1-C3)alkoxyl(C2-C3)dialkylamino is linked to R1 through a carbonyl.
274. In some embodiments, the compound is a compound of Embodiment Group 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, or 273, or a pharmaceutically acceptable salt thereof, in which R1 is substituted with a three- to six-member heterocyclic ring containing 1 or 2 heteroatoms selected from O, N, and S and which independently (1) optionally is substituted with (C1-C3)alkyl, (C1-C3)hydroxylalkyl, (C1-C3)alkoxyl(C1-C3)alkyl, (C1-C3)alkylamino(C1-C3)alkyl and (2) optionally is linked to R1 through a carbonyl group.
275. In some embodiments, the compound is a compound of Embodiment Group 275, or a pharmaceutically acceptable salt thereof, in which the three- to six-member heterocyclic contains 1 heteroatom.
276. In some embodiments, the compound is a compound of Embodiment Group 275, or a pharmaceutically acceptable salt thereof, in which the three- to six-member heterocyclic contains 2 heteroatoms.
277. In some embodiments, the compound is a compound of Embodiment Group 275 or 276, or a pharmaceutically acceptable salt thereof, in which the three- to six-member heterocyclic ring contains 0.
278. In some embodiments, the compound is a compound of Embodiment Group 275, 276, or 277, or a pharmaceutically acceptable salt thereof, in which the three- to six-member heterocyclic ring contains N.

279. In some embodiments, the compound is a compound of Embodiment Group 275, 276, 277, or 278, or a pharmaceutically acceptable salt thereof, in which the three- to six-member heterocyclic ring contains S.

280. In some embodiments, the compound is a compound of Embodiment Group 275, 276, 277, 278, or 279, or a pharmaceutically acceptable salt thereof, in which R1 is substituted with a three-member heterocyclic ring.

281. In some embodiments, the compound is a compound of Embodiment Group 280, or a pharmaceutically acceptable salt thereof, in which the three-member heterocyclic ring is selected from the group consisting of aziridine, azirine, oxirane, oxirene, thiirane, thiirene, diazirine, oxaziridine, and dioxirane.

282. In some embodiments, the compound is a compound of Embodiment Group 275, 276, 277, 278, or 279, or a pharmaceutically acceptable salt thereof, in which R1 is substituted with a four-member heterocyclic ring.

283. In some embodiments, the compound is a compound of Embodiment Group 282, or a pharmaceutically acceptable salt thereof, in which the four-member heterocyclic ring is selected from the group consisting of azetidine, azete, oxetane, oxete, thietane, thiete, diazetidine, dioxetane, dioxete, dithietane, and dithiete.

284. In some embodiments, the compound is a compound of Embodiment Group 275, 276, 277, 278, or 279, or a pharmaceutically acceptable salt thereof, in which R1 is substituted with a five-member heterocyclic ring.

285. In some embodiments, the compound is a compound of Embodiment Group 284, or a pharmaceutically acceptable salt thereof, in which the five-member heterocyclic ring is selected from the group consisting of pyrrolidine, pyrrole, tetrahydrofuran, furan, thiolane, thiophene, borolane, borole, phospholane, phosphole, arsolane, arsole, stibolane, stibole, bismolane, bismole, silolane, silole, stannolane, stannole, imidazolidine, pyrazolidine, imidazole (imidazoline), pyrazole (pyrazoline), oxazolidine, isoxazolidine, oxazole (oxazoline), isoxazole, thiazolidine, isothiazolidine, thiazole (thiazoline), isothiazole, dioxolane, and dithiolane.

286. In some embodiments, the compound is a compound of Embodiment Group 275, 276, 277, 278, or 279, or a pharmaceutically acceptable salt thereof, in which R1 is substituted with a six-member heterocyclic ring.

287. In some embodiments, the compound is a compound of Embodiment Group 286, or a pharmaceutically acceptable salt thereof, in which the six-member heterocyclic ring is selected from the group consisting of piperidine, pyridine, oxane, pyran, thiane, thiopyran, salinane, siline, germinane, germine, stanninane, stannine, borinane, borinine, phosphinane, phosphinine, arsinane, arsinine, piperazine, diazine, morpholine, oxazine, thiomorpholine, thiazine, dioxane, dioxine, dithiane, and dithiine.

288. In some embodiments, the compound is a compound of Embodiment Group 275, 276, 277, 278, 279, 280, 281, 282, 283, 284, 285, 286, or 287, or a pharmaceutically acceptable salt thereof, in which the three- to six-member heterocyclic ring is unsubstituted.

289. In some embodiments, the compound is a compound of Embodiment Group 275, 276, 277, 278, 279, 280, 281, 282, 283, 284, 285, 286, or 287, or a pharmaceutically acceptable salt thereof, in which the three- to six-member heterocyclic ring is substituted with (C1-C3)alkyl.

290. In some embodiments, the compound is a compound of Embodiment Group 289, or a pharmaceutically acceptable salt thereof, in which the three- to six-member heterocyclic ring is substituted with (C1-C3)alkyl, (C1-C2)alkyl, (C2-C3)alkyl, (C1)alkyl, (C2)alkyl, or (C3)alkyl.

291. In some embodiments, the compound is a compound of Embodiment Group 275, 276, 277, 278, 279, 280, 281, 282, 283, 284, 285, 286, 287, 288, 289, or 290, or a pharmaceutically acceptable salt thereof, in which the three- to six-member heterocyclic ring is substituted with hydroxyl(C1-C3)alkyl.

292. In some embodiments, the compound is a compound of Embodiment Group 291, or a pharmaceutically acceptable salt thereof, in which the three- to six-member heterocyclic ring is substituted with hydroxyl (C1-C3)alkyl, hydroxyl (C1-C2)alkyl, hydroxyl (C2-C3)alkyl, hydroxyl (C1)alkyl, hydroxyl (C2)alkyl, or hydroxyl (C3)alkyl.

293. In some embodiments, the compound is a compound of Embodiment Group 275, 276, 277, 278, 279, 280, 281, 282, 283, 284, 285, 286, 287, 288, 289, 290, 291, or 292, or a pharmaceutically acceptable salt thereof, in which the three- to six-member heterocyclic ring is substituted with (C1-C3)alkoxyl.

294. In some embodiments, the compound is a compound of Embodiment Group 293, or a pharmaceutically acceptable salt thereof, in which the three- to six-member heterocyclic ring is substituted with (C1-C3)alkoxyl, (C1-C2)alkoxyl, (C2-C3)alkoxyl, (C1)alkoxyl, (C2)alkoxyl, or (C3)alkoxyl.

295. In some embodiments, the compound is a compound of Embodiment Group 275, 276, 277, 278, 279, 280, 281, 282, 283, 284, 285, 286, 287, 288, 289, 290, 291, 292, 293, or 294, or a pharmaceutically acceptable salt thereof, in which the three- to six-member heterocyclic ring is substituted with (C1-C3)alkylamino(C1-C3)alkyl.

296. In some embodiments, the compound is a compound of Embodiment Group 295, or a pharmaceutically acceptable salt thereof, in which the three- to six-member heterocyclic ring is substituted with (C1-C3)alkylamino (C1-C3)alkyl, (C1-C3)alkylamino(C1-C2)alkyl, (C1-C3)alkylamino(C2-C3)alkyl, (C1-C3)alkylamino(C1)alkyl, (C1-C3)alkylamino(C2)alkyl, or (C1-C3)alkylamino(C3)alkyl.

297. In some embodiments, the compound is a compound of Embodiment Group 296, or a pharmaceutically acceptable salt thereof, in which the three- to six-member heterocyclic ring is substituted with (C1-C2)alkylamino (C1-C3)alkyl, (C2-C3)alkylamino(C1-C2)alkyl, (C1)alkylamino(C2-C3)alkyl, (C2)alkylamino(C1)alkyl, or (C3)alkylamino(C2)alkyl.

298. In some embodiments, the compound is a compound of Embodiment Group 275, 276, 277, 278, 279, 280, 281, 282, 283, 284, 285, 286, 287, 288, 289, 290, 291, 292, 293, 294, 295, 296, or 297, or a pharmaceutically acceptable salt thereof, in which the three- to six-member heterocyclic ring is directly linked to R1.

299. In some embodiments, the compound is a compound of Embodiment Group 275, 276, 277, 278, 279, 280, 281, 282, 283, 284, 285, 286, 287, 288, 289, 290, 291, 292, 293, 294, 295, 296, or 297, or a pharmaceutically acceptable salt thereof, in which the three- to six-member heterocyclic ring is linked to R1 through a carbonyl.

300. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, or a pharmaceutically acceptable salt thereof, in which R2 is H.

301. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, or a pharmaceutically acceptable salt thereof, in which R2 is C1-C6 alkyl, optionally substituted with 1, 2, or 3 groups selected from hydroxyl, methoxyl, ethoxyl, methylamino, N,N-dimethyl amino, ethylamino, N,N-diethylamino, and methylsulfanyl.

302. In some embodiments, the compound is a compound of Embodiment Group 301, or a pharmaceutically acceptable salt thereof, in which R2 is C1-C6 alkyl, C1-05 alkyl, C1-C4 alkyl, C1-C3 alkyl, C1-C2 alkyl, C2-C6 alkyl, C2-C5 alkyl, C2-C4 alkyl, C2-C3 alkyl, C3-C6 alkyl, C3-C5 alkyl, C3-C4 alkyl, C4-C6 alkyl, C4-C5 alkyl, C1 alkyl, C2 alkyl, C3 alkyl, C4 alkyl, C5 alkyl, or C6 alkyl.

303. In some embodiments, the compound is a compound of Embodiment Group 301 or 302, or a pharmaceutically acceptable salt thereof, in which R2 is unsubstituted.

304. In some embodiments, the compound is a compound of Embodiment Group 301 or 302, or a pharmaceutically acceptable salt thereof, in which R2 is substituted with 1, 2, or 3 groups selected from hydroxyl, methoxyl, ethoxyl, methylamino, N,N-dimethyl amino, ethylamino, N,N-diethylamino, and methylsulfanyl.

305. In some embodiments, the compound is a compound of Embodiment Group 304, or a pharmaceutically acceptable salt thereof, in which R2 is substituted with 1 group.

306. In some embodiments, the compound is a compound of Embodiment Group 304, or a pharmaceutically acceptable salt thereof, in which R2 is substituted with 2 groups.

307. In some embodiments, the compound is a compound of Embodiment Group 304, or a pharmaceutically acceptable salt thereof, in which R2 is substituted with 3 groups.

308. In some embodiments, the compound is a compound of Embodiment Group 304, 305, 306, or 307, or a pharmaceutically acceptable salt thereof, in which R2 is substituted with hydroxyl.

309. In some embodiments, the compound is a compound of Embodiment Group 304, 305, 306, 307, or 308, or a pharmaceutically acceptable salt thereof, in which R2 is substituted with methoxyl.

310. In some embodiments, the compound is a compound of Embodiment Group 304, 305, 306, 307, 308, or 309, or a pharmaceutically acceptable salt thereof, in which R2 is substituted with ethoxyl.

311. In some embodiments, the compound is a compound of Embodiment Group 304, 305, 306, 307, 308, 309, or 310, or a pharmaceutically acceptable salt thereof, in which R2 is substituted with methylamino.

312. In some embodiments, the compound is a compound of Embodiment Group 304, 305, 306, 307, 308, 309, 310, or 311, or a pharmaceutically acceptable salt thereof, in which R2 is substituted with N,N-dimethyl amino.

313. In some embodiments, the compound is a compound of Embodiment Group 304, 305, 306, 307, 308, 309, 310, 311, or 312, or a pharmaceutically acceptable salt thereof, in which R2 is substituted with ethylamino.

314. In some embodiments, the compound is a compound of Embodiment Group 304, 305, 306, 307, 308, 309, 310, 311, 312, or 313, or a pharmaceutically acceptable salt thereof, in which R2 is substituted with N,N-diethylamino.

315. In some embodiments, the compound is a compound of Embodiment Group 304, 305, 306, 307, 308, 309, 310, 311, 312, 313, or 314, or a pharmaceutically acceptable salt thereof, in which R2 is substituted with methylsulfanyl.

316. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 319, 320, 321, 322, 323, 324, 325, 309, 310, 311, 312, 313, 314, or 315, or a pharmaceutically acceptable salt thereof, in which R2 is a three- to six-member carbon cyclic ring, optionally substituted with 1, 2, or 3 groups selected from hydroxyl, methoxyl, ethoxyl, methylamino, N,N-dimethyl amino, ethylamino, N,N-diethylamino, and methylsulfanyl.

317. In some embodiments, the compound is a compound of Embodiment Group 316, or a pharmaceutically acceptable salt thereof, in which R2 is cyclopropyl, cyclobutyl, cyclopentyl, cyclohexyl, or cycloheptyl.

318. In some embodiments, the compound is a compound of Embodiment Group 316 or 317, or a pharmaceutically acceptable salt thereof, in which R2 is unsubstituted.

319. In some embodiments, the compound is a compound of Embodiment Group 316 or 317, or a pharmaceutically acceptable salt thereof, in which R2 is substituted with 1, 2, or 3 groups selected from hydroxyl, methoxyl, ethoxyl, methylamino, N,N-dimethyl amino, ethylamino, N,N-diethylamino, and methylsulfanyl.

320. In some embodiments, the compound is a compound of Embodiment Group 319, or a pharmaceutically acceptable salt thereof, in which R2 is substituted with 1 group.

321. In some embodiments, the compound is a compound of Embodiment Group 319, or a pharmaceutically acceptable salt thereof, in which R2 is substituted with 2 groups.

322. In some embodiments, the compound is a compound of Embodiment Group 319, or a pharmaceutically acceptable salt thereof, in which R2 is substituted with 3 groups.

323. In some embodiments, the compound is a compound of Embodiment Group 319, 320, 321, or 311, or a pharmaceutically acceptable salt thereof, in which R2 is substituted with hydroxyl.

324. In some embodiments, the compound is a compound of Embodiment Group 319, 320, 321, 322, or 323, or a pharmaceutically acceptable salt thereof, in which R2 is substituted with methoxyl.

325. In some embodiments, the compound is a compound of Embodiment Group 319, 320, 321, 322, 323, or 324, or a pharmaceutically acceptable salt thereof, in which R2 is substituted with ethoxyl.

326. In some embodiments, the compound is a compound of Embodiment Group 319, 320, 321, 322, 323, 324, or 325, or a pharmaceutically acceptable salt thereof, in which R2 is substituted with methylamino.

327. In some embodiments, the compound is a compound of Embodiment Group 319, 320, 321, 322, 323, 324, 325, or 326, or a pharmaceutically acceptable salt thereof, in which R2 is substituted with N,N-dimethyl amino.

328. In some embodiments, the compound is a compound of Embodiment Group 319, 320, 321, 322, 323, 324, 325, 326, or 327, or a pharmaceutically acceptable salt thereof, in which R2 is substituted with ethylamino.

329. In some embodiments, the compound is a compound of Embodiment Group 319, 320, 321, 322, 323, 324, 325, 326, 327, or 328, or a pharmaceutically acceptable salt thereof, in which R2 is substituted with N,N-diethylamino.

330. In some embodiments, the compound is a compound of Embodiment Group 319, 320, 321, 322, 323, 324, 325, 326, 327, 328, or 329, or a pharmaceutically acceptable salt thereof, in which R2 is substituted with methylsulfanyl.

331. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 331, 332, 333, 334, 335, 319, 320, 321, 322, 323, 324, 325, 326, 327, 328, 329, or 330, or a pharmaceutically acceptable salt thereof, in which R2 is a three- to six-member heterocyclic ring, optionally substituted with 1, 2, or 3 groups selected from hydroxyl, C1-C3 alkyl, methoxyl, ethoxyl, methylamino, N,N-dimethylamino, ethylamino, N,N-diethylamino, and methylsulfanyl.

332. In some embodiments, the compound is a compound of Embodiment Group 331, or a pharmaceutically acceptable salt thereof, in which R2 is selected from the group consisting of aziridine, azirine, oxirane, oxirene, thiirane, thiirene, diazirine, oxaziridine, dioxirane, azetidine, azete, oxetane, oxete, thietane, thiete, diazetidine, dioxetane, dioxete, dithietane, dithiete, pyrrolidine, pyrrole, tetrahydrofuran, furan, thiolane, thiophene, borolane, borole, phospholane, phosphole, arsolane, arsole, stibolane, stibole, bismolane, bismole, silolane, silole, stannolane, stannole, imidazolidine, pyrazolidine, imidazole (imidazoline), pyrazole (pyrazoline), oxazolidine, isoxazolidine, oxazole (oxazoline), isoxazole, thiazolidine, isothiazolidine, thiazole (thiazoline), isothiazole, dioxolane, dithiolane, piperidine, pyridine, oxane, pyran, thiane, thiopyran, salinane, siline, germinane, germine, stanninane, stannine, borinane, borinine, phosphinane, phosphinine, arsinane, arsinine, piperazine, diazine, morpholine, oxazine, thiomorpholine, thiazine, dioxane, dioxine, dithiane, and dithiine.

333. In some embodiments, the compound is a compound of Embodiment Group 331 or 332, or a pharmaceutically acceptable salt thereof, in which R2 is unsubstituted.

334. In some embodiments, the compound is a compound of Embodiment Group 331 or 332, or a pharmaceutically acceptable salt thereof, in which R2 is substituted with 1 group.

335. In some embodiments, the compound is a compound of Embodiment Group 331 or 332, or a pharmaceutically acceptable salt thereof, in which R2 is substituted with 2 groups.

336. In some embodiments, the compound is a compound of Embodiment Group 331 or 332, or a pharmaceutically acceptable salt thereof, in which R2 is substituted with 3 groups.
337. In some embodiments, the compound is a compound of Embodiment Group 331, 332, 333, 334, 335, or 336, or a pharmaceutically acceptable salt thereof, in which R2 is substituted with hydroxyl.
338. In some embodiments, the compound is a compound of Embodiment Group 331, 332, 333, 334, 335, 336, or 337, or a pharmaceutically acceptable salt thereof, in which R2 is substituted with methoxyl.
339. In some embodiments, the compound is a compound of Embodiment Group 331, 332, 333, 334, 335, 336, 337, or 338, or a pharmaceutically acceptable salt thereof, in which R2 is substituted with ethoxyl.
340. In some embodiments, the compound is a compound of Embodiment Group 331, 332, 333, 334, 335, 336, 337, 338, or 339, or a pharmaceutically acceptable salt thereof, in which R2 is substituted with methylamino.
341. In some embodiments, the compound is a compound of Embodiment Group 331, 332, 333, 334, 335, 336, 337, 338, 339, or 340, or a pharmaceutically acceptable salt thereof, in which R2 is substituted with N,N-dimethyl amino.
342. In some embodiments, the compound is a compound of Embodiment Group 331, 332, 333, 334, 335, 336, 337, 338, 339, 340, or 341, or a pharmaceutically acceptable salt thereof, in which R2 is substituted with ethylamino.
343. In some embodiments, the compound is a compound of Embodiment Group 331, 332, 333, 334, 335, 336, 337, 338, 339, 340, 341, or 342, or a pharmaceutically acceptable salt thereof, in which R2 is substituted with N,N-diethylamino.
344. In some embodiments, the compound is a compound of Embodiment Group 331, 332, 333, 334, 335, 336, 337, 338, 339, 340, 341, 342, or 343, or a pharmaceutically acceptable salt thereof, in which R2 is substituted with methylsulfanyl.
345. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 331, 332, 333, 334, 335, 319, 320, 321, 322, 323, 324, 325, 326, 327, 328, 329, or 330, or a pharmaceutically acceptable salt thereof, in which R2 is phenyl, optionally substituted with 1, 2, or 3 groups selected from hydroxyl, methoxyl, ethoxyl, methylamino, N,N-dimethylamino, ethylamino, N,N-diethylamino, and methylsulfanyl.
346. In some embodiments, the compound is a compound of Embodiment Group 345, or a pharmaceutically acceptable salt thereof, in which R2 is unsubstituted.
347. In some embodiments, the compound is a compound of Embodiment Group 345, or a pharmaceutically acceptable salt thereof, in which R2 is substituted with 1 group.
348. In some embodiments, the compound is a compound of Embodiment Group 345, or a pharmaceutically acceptable salt thereof, in which R2 is substituted with 2 groups.
349. In some embodiments, the compound is a compound of Embodiment Group 345, or a pharmaceutically acceptable salt thereof, in which R2 is substituted with 3 groups.
350. In some embodiments, the compound is a compound of Embodiment Group 345, 346, 347, 348, or 349, or a pharmaceutically acceptable salt thereof, in which R2 is substituted with hydroxyl.
351. In some embodiments, the compound is a compound of Embodiment Group 345, 346, 347, 348, 349, or 350, or a pharmaceutically acceptable salt thereof, in which R2 is substituted with methoxyl.
352. In some embodiments, the compound is a compound of Embodiment Group 345, 346, 347, 348, 349, 350, or 351, or a pharmaceutically acceptable salt thereof, in which R2 is substituted with ethoxyl.
353. In some embodiments, the compound is a compound of Embodiment Group 345, 346, 347, 348, 349, 350, 351, or 352, or a pharmaceutically acceptable salt thereof, in which R2 is substituted with methylamino.
354. In some embodiments, the compound is a compound of Embodiment Group 345, 346, 347, 348, 349, 350, 351, 352, or 353, or a pharmaceutically acceptable salt thereof, in which R2 is substituted with N,N-dimethyl amino.
355. In some embodiments, the compound is a compound of Embodiment Group 345, 346, 347, 348, 349, 350, 351, 352, 353, or 354, or a pharmaceutically acceptable salt thereof, in which R2 is substituted with ethylamino.
356. In some embodiments, the compound is a compound of Embodiment Group 345, 346, 347, 348, 349, 350, 351, 352, 353, 354, or 355, or a pharmaceutically acceptable salt thereof, in which R2 is substituted with N,N-diethylamino.
357. In some embodiments, the compound is a compound of Embodiment Group 345, 346, 347, 348, 349, 350, 351, 352, 353, 354, 355, or 356, or a pharmaceutically acceptable salt thereof, in which R2 is substituted with methylsulfanyl.
358. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 331, 332, 333, 334, 335, 319, 320, 321, 322, 323, 324, 325, 326, 327, 328, 329, or 330, or a pharmaceutically acceptable salt thereof, in which R2 is heteroaryl, optionally substituted with 1, 2, or 3 groups selected from hydroxyl, methoxyl, ethoxyl, methylamino, N,N-dimethylamino, ethylamino, N,N-diethylamino, and methylsulfanyl.

359. In some embodiments, the compound is a compound of Embodiment Group 358, or a pharmaceutically acceptable salt thereof, in which R2 is selected from the group consisting of pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, furanyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

360. In some embodiments, the compound is a compound of Embodiment Group 358 or 359, or a pharmaceutically acceptable salt thereof, in which R2 is unsubstituted.

361. In some embodiments, the compound is a compound of Embodiment Group 358 or 359, or a pharmaceutically acceptable salt thereof, in which R2 is substituted with 1 group.

362. In some embodiments, the compound is a compound of Embodiment Group 358 or 359, or a pharmaceutically acceptable salt thereof, in which R2 is substituted with 2 groups.

363. In some embodiments, the compound is a compound of Embodiment Group 358 or 359, or a pharmaceutically acceptable salt thereof, in which R2 is substituted with 3 groups.

364. In some embodiments, the compound is a compound of Group 358, 359, 360, 361, 362, or 363, or a pharmaceutically acceptable salt thereof, in which R2 is substituted with hydroxyl.

365. In some embodiments, the compound is a compound of Embodiment Group 358, 359, 360, 361, 362, 363, or 364, or a pharmaceutically acceptable salt thereof, in which R2 is substituted with methoxyl.

366. In some embodiments, the compound is a compound of Embodiment Group 358, 359, 360, 361, 362, 363, 364, or 365, or a pharmaceutically acceptable salt thereof, in which R2 is substituted with ethoxyl.

367. In some embodiments, the compound is a compound of Embodiment Group 358, 359, 360, 361, 362, 363, 364, 365, or 366, or a pharmaceutically acceptable salt thereof, in which R2 is substituted with methylamino.

368. In some embodiments, the compound is a compound of Embodiment Group 358, 359, 360, 361, 362, 363, 364, 365, or 367, or a pharmaceutically acceptable salt thereof, in which R2 is substituted with N,N-dimethyl amino.

369. In some embodiments, the compound is a compound of Embodiment Group 358, 359, 360, 361, 362, 363, 364, 365, 367, or 368, or a pharmaceutically acceptable salt thereof, in which R2 is substituted with ethylamino.

370. In some embodiments, the compound is a compound of Embodiment Group 358, 359, 360, 361, 362, 363, 364, 365, 367, 368, or 369, or a pharmaceutically acceptable salt thereof, in which R2 is substituted with N,N-diethylamino.

371. In some embodiments, the compound is a compound of Embodiment Group 358, 359, 360, 361, 362, 363, 364, 365, 367, 368, 369, or 370, or a pharmaceutically acceptable salt thereof, in which R2 is substituted with methylsulfanyl.

372. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is halogen.

373. In some embodiments, the compound is a compound of Embodiment Group 372, or a pharmaceutically acceptable salt thereof, in which R3 is F.

374. In some embodiments, the compound is a compound of Embodiment Group 372, or a pharmaceutically acceptable salt thereof, in which R3 is Br.

375. In some embodiments, the compound is a compound of Embodiment Group 372, or a pharmaceutically acceptable salt thereof, in which R3 is Cl.

376. In some embodiments, the compound is a compound of Embodiment Group 372, or a pharmaceutically acceptable salt thereof, in which R3 is I.

377. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is C1-C6 alkyl.

378. In some embodiments, the compound is a compound of Embodiment Group 377, or a pharmaceutically acceptable salt thereof, in which R3 is C1-C6 alkyl, C1-05 alkyl, C1-C4 alkyl, C1-C3 alkyl, C1-C2 alkyl, C2-C6 alkyl, C2-C5 alkyl, C2-C4 alkyl, C2-C3 alkyl, C3-C6 alkyl, C3-C5 alkyl, C3-C4 alkyl, C4-C6 alkyl, C4-C5 alkyl, C1 alkyl, C2 alkyl, C3 alkyl, C4 alkyl, C5 alkyl, or C6 alkyl.

379. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is C1-C6 hydroxylalkyl.

380. In some embodiments, the compound is a compound of Embodiment Group 379, or a pharmaceutically acceptable salt thereof, in which R3 is C1-C6 hydroxylalkyl, C1-05 hydroxylalkyl, C1-C4 hydroxylalkyl, C1-C3 hydroxylalkyl, C1-C2 hydroxylalkyl, C2-C6 hydroxylalkyl, C2-C5 hydroxylalkyl, C2-C4 hydroxylalkyl, C2-C3 hydroxylalkyl, C3-C6 hydroxylalkyl, C3-C5 hydroxylalkyl, C3-C4 hydroxylalkyl, C4-C6 hydroxylalkyl, C4-C5 hydroxylalkyl, C1 hydroxylalkyl, C2 hydroxylalkyl, C3 hydroxylalkyl, C4 hydroxylalkyl, C5 hydroxylalkyl, or C6 hydroxylalkyl.

381. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is C1-C6 alkylcarbonyl.

382. In some embodiments, the compound is a compound of Embodiment Group 381, or a pharmaceutically acceptable salt thereof, in which R3 is C1-C6 alkylcarbonyl, C1-05 alkylcarbonyl, C1-C4 alkylcarbonyl, C1-C3 alkylcarbonyl, C1-C2 alkylcarbonyl, C2-C6 alkylcarbonyl, C2-C5 alkylcarbonyl, C2-C4 alkylcarbonyl, C2-C3 alkylcarbonyl, C3-C6 alkylcarbonyl, C3-C5 alkylcarbonyl, C3-C4 alkylcarbonyl, C4-C6 alkylcarbonyl, C4-C5 alkylcarbonyl, C1 alkylcarbonyl, C2 alkylcarbonyl, C3 alkylcarbonyl, C4 alkylcarbonyl, C5 alkylcarbonyl, or C6 alkylcarbonyl.

383. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is C1-C6 perfluoroalkyl.

384. In some embodiments, the compound is a compound of Embodiment Group 383, or a pharmaceutically acceptable salt thereof, in which R3 is C1-C6 perfluoroalkyl, C1-05 perfluoroalkyl, C1-C4 perfluoroalkyl, C1-C3 perfluoroalkyl, C1-C2 perfluoroalkyl, C2-C6 perfluoroalkyl, C2-05 perfluoroalkyl, C2-C4 perfluoroalkyl, C2-C3 perfluoroalkyl, C3-C6 perfluoroalkyl, C3-05 perfluoroalkyl, C3-C4 perfluoroalkyl, C4-C6 perfluoroalkyl, C4-05 perfluoroalkyl, C1 perfluoroalkyl, C2 perfluoroalkyl, C3 perfluoroalkyl, C4 perfluoroalkyl, C5 perfluoroalkyl, or C6 perfluoroalkyl.

385. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is C3-C6 cycloalkyl.

386. In some embodiments, the compound is a compound of Embodiment Group 385, or a pharmaceutically acceptable salt thereof, in which R3 is cyclopropyl, cyclobutyl, cyclopentyl, or cyclohexyl.

387. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is C2-C6 alkenyl, optionally substituted with 1, 2, or 3 substituents selected from the group consisting of C1-C3 alkoxyl, C1-C3 alkoxylcarbonyl, and trifluoromethyl.

388. In some embodiments, the compound is a compound of Embodiment Group 387, or a pharmaceutically acceptable salt thereof, in which R3 is C2-C6 alkenyl, C2-C5 alkenyl, C2-C4 alkenyl, C2-C3 alkenyl, C3-C6 alkenyl, C3-C5 alkenyl, C3-C4 alkenyl, C4-C6 alkenyl, C4-C5 alkenyl, C2 alkenyl, C3 alkenyl, C4 alkenyl, C5 alkenyl, or C6 alkenyl.

389. In some embodiments, the compound is a compound of Embodiment Group 387 or 388, or a pharmaceutically acceptable salt thereof, in which R3 is unsubstituted.

390. In some embodiments, the compound is a compound of Embodiment Group 387 or 388, or a pharmaceutically acceptable salt thereof, in which R3 is substituted with 1 substituent.

391. In some embodiments, the compound is a compound of Embodiment Group 387 or 388, or a pharmaceutically acceptable salt thereof, in which R3 is substituted with 2 substitutents.

392. In some embodiments, the compound is a compound of Embodiment Group 387 or 388, or a pharmaceutically acceptable salt thereof, in which R3 is substituted with 3 substitutents.

393. In some embodiments, the compound is a compound of Embodiment Group 390, 391, or 392, or a pharmaceutically acceptable salt thereof, in which R3 is substituted with C1-C3 alkoxyl.
394. In some embodiments, the compound is a compound of Embodiment Group 393, or a pharmaceutically acceptable salt thereof, in which R3 is substituted with C1-C3 alkoxyl, C1 alkoxyl, C2 alkoxyl, C3 alkoxyl, C1-C2 alkoxyl, or C2-C3 alkoxyl.
395. In some embodiments, the compound is a compound of Embodiment Group 390, 391, 392, 393, or 394, or a pharmaceutically acceptable salt thereof, in which R3 is substituted with C1-C3 alkoxylcarbonyl.
396. In some embodiments, the compound is a compound of Embodiment Group 395, or a pharmaceutically acceptable salt thereof, in which R3 is substituted with C1-C3 alkoxylcarbonyl, C1 alkoxylcarbonyl, C2 alkoxylcarbonyl, C3 alkoxylcarbonyl, C1-C2 alkoxylcarbonyl, or C2-C3 alkoxylcarbonyl.
397. In some embodiments, the compound is a compound of Embodiment Group 390, 391, 392, 393, 394, 395, or 396, or a pharmaceutically acceptable salt thereof, in which R3 is substituted with trifluoromethyl.
398. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is C2-C6 alkynyl, optionally substituted with 1, 2, or 3 substituents selected from the group consisting of C1-C3 alkoxyl, hydroxyl, C-1C6 alkyl, and trifluoromethyl.
399. In some embodiments, the compound is a compound of Embodiment Group 398, or a pharmaceutically acceptable salt thereof, in which R3 is C2-C6 alkynyl, C2-C5 alkynyl, C2-C4 alkynyl, C2-C3 alkynyl, C3-C6 alkynyl, C3-C5 alkynyl, C3-C4 alkynyl, C4-C6 alkynyl, C4-C5 alkynyl, C2 alkynyl, C3 alkynyl, C4 alkynyl, C5 alkynyl, or C6 alkynyl.
400. In some embodiments, the compound is a compound of Embodiment Group 398 or 399, or a pharmaceutically acceptable salt thereof, in which R3 is unsubstituted.
401. In some embodiments, the compound is a compound of Embodiment Group 398 or 399, or a pharmaceutically acceptable salt thereof, in which R3 is substituted with 1 substituent.
402. In some embodiments, the compound is a compound of Embodiment Group 398 or 399, or a pharmaceutically acceptable salt thereof, in which R3 is substituted with 2 substitutents.
403. In some embodiments, the compound is a compound of Embodiment Group 398 or 399, or a pharmaceutically acceptable salt thereof, in which R3 is substituted with 3 substitutents.
404. In some embodiments, the compound is a compound of Embodiment Group 401, 402, or 403, or a pharmaceutically acceptable salt thereof, in which R3 is substituted with C1-C3 alkoxyl.
405. In some embodiments, the compound is a compound of Embodiment Group 404, or a pharmaceutically acceptable salt thereof, in which R3 is substituted with C1-C3 alkoxyl, C1 alkoxyl, C2 alkoxyl, C3 alkoxyl, C1-C2 alkoxyl, or C2-C3 alkoxyl.
406. In some embodiments, the compound is a compound of Embodiment Group 401, 402, 403, 404, or 405, or a pharmaceutically acceptable salt thereof, in which R3 is substituted with hydroxyl.
407. In some embodiments, the compound is a compound of Embodiment Group 401, 402, 403, 404, 405, or 406, or a pharmaceutically acceptable salt thereof, in which R3 is substituted with C1-C6 alkyl.
408. In some embodiments, the compound is a compound of Embodiment Group 407, or a pharmaceutically acceptable salt thereof, in which R3 is substituted with C1-C6 alkyl, C1-05 alkyl, C1-C4 alkyl, C1-C3 alkyl, C1-C2 alkyl, C2-C6 alkyl, C2-C5 alkyl, C2-C4 alkyl, C2-C3 alkyl, C3-C6 alkyl, C3-C5 alkyl, C3-C4 alkyl, C4-C6 alkyl, C4-C5 alkyl, C1 alkyl, C2 alkyl, C3 alkyl, C4 alkyl, C5 alkyl, or C6 alkyl.
409. In some embodiments, the compound is a compound of Embodiment Group 401, 402, 403, 404, 405, 406, 407, or 408, or a pharmaceutically acceptable salt thereof, in which R3 is substituted with trifluoromethyl.
410. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is phenyl, optionally substituted with 1, 2, or 3 substituents selected from the group consisting of halogen, C1-C3 alkoxyl, and trifluoromethyl.

411. In some embodiments, the compound is a compound of Embodiment Group 410, or a pharmaceutically acceptable salt thereof, in which R3 is unsubstituted.

412. In some embodiments, the compound is a compound of Embodiment Group 410, or a pharmaceutically acceptable salt thereof, in which R3 is substituted with 1 substituent.

413. In some embodiments, the compound is a compound of Embodiment Group 410, or a pharmaceutically acceptable salt thereof, in which R3 is substituted with 2 substitutents.

414. In some embodiments, the compound is a compound of Embodiment Group 410, or a pharmaceutically acceptable salt thereof, in which R3 is substituted with 3 substitutents.

415. In some embodiments, the compound is a compound of Embodiment Group 412, 413, or 414, or a pharmaceutically acceptable salt thereof, in which R3 is substituted with halogen.

416. In some embodiments, the compound is a compound of Embodiment Group 415, or a pharmaceutically acceptable salt thereof, in which R3 is substituted with F.

417. In some embodiments, the compound is a compound of Embodiment Group 415 or 416, or a pharmaceutically acceptable salt thereof, in which R3 is substituted with Br.

418. In some embodiments, the compound is a compound of Embodiment Group 415, 416, or 417, or a pharmaceutically acceptable salt thereof, in which R3 is substituted with Cl.

419. In some embodiments, the compound is a compound of Embodiment Group 415, 416, 417, or 418, or a pharmaceutically acceptable salt thereof, in which R3 is substituted with I.

420. In some embodiments, the compound is a compound of Embodiment Group 412, 413, 414, 415, 416, 417, 418, or 419, or a pharmaceutically acceptable salt thereof, in which R3 is substituted with C1-C3 alkoxyl.

421. In some embodiments, the compound is a compound of Embodiment Group 420, or a pharmaceutically acceptable salt thereof, in which R3 is substituted with C1-C3 alkoxyl, C1 alkoxyl, C2 alkoxyl, C3 alkoxyl, C1-C2 alkoxyl, or C2-C3 alkoxyl.

422. In some embodiments, the compound is a compound of Embodiment Group 412, 413, 414, 415, 416, 417, 418, 419, 420, or 421, or a pharmaceutically acceptable salt thereof, in which R3 is substituted with trifluoromethyl.

423. In some embodiments, the compound is a compound of Embodiment Group 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, or 371, or a pharmaceutically acceptable salt thereof, in which R3 is a 5- or 6-member heteroaryl, optionally substituted with 1, 2, or 3 substituents independently selected from the group consisting of halogen, C1-C3 alkoxyl, and trifluoromethyl.

424. In some embodiments, the compound is a compound of Embodiment Group 423, or a pharmaceutically acceptable salt thereof, in which R3 is a 5-member heteroaryl.

425. In some embodiments, the compound is a compound of Embodiment Group 424, or a pharmaceutically acceptable salt thereof, in which the 5-member heteroaryl is selected from the group consisting of pyrrolidine, imidazolidine, pyrazolidine, oxazolidine, isoxazolidine, thiazolidine, isothiazolidine, thiolane, borolane, phospholane, arsolane, stibolane, bismolane, silolane, stannolane, dioxolane, dithiolane, pyrrole, imidazole, pyrazole, oxazole, isoxazole, thiazole, isothiazole, triazole, furazan, oxadiazole, thiadiazole, dithiadiazole, tetrazole, thiophene, borole, phosphole, arsole, stibole, bismole, silole, and stannole.

426. In some embodiments, the compound is a compound of Embodiment Group 423, or a pharmaceutically acceptable salt thereof, in which R3 is a 6-member heteroaryl.

427. In some embodiments, the compound is a compound of Embodiment Group 426, or a pharmaceutically acceptable salt thereof, in which the 6-member heteroaryl is selected from the group consisting of piperidine, piperazine, morpholine, thiomorpholine, thiane, silinane, germinane, stanninane, borinane, phosphinane, arsinane dioxane, dithiane, trioxane, pyridine, diazine, oxazine, thiazine, triazine, tetrazine, thiopyran, saline, germine, stannine, bornine, phosphine, arsinine, dioxine, and dithiine.

428. In some embodiments, the compound is a compound of Embodiment Group 423, 424, 425, or 426, or a pharmaceutically acceptable salt thereof, in which R3 is unsubstituted.

429. In some embodiments, the compound is a compound of Embodiment Group 423, 424, 425, or 426, or a pharmaceutically acceptable salt thereof, in which R3 is substituted with 1 substituent.

430. In some embodiments, the compound is a compound of Embodiment Group 423, 424, 425, or 426, or a pharmaceutically acceptable salt thereof, in which R3 is substituted with 2 substitutents.

431. In some embodiments, the compound is a compound of Embodiment Group 423, 424, 425, or 426, or a pharmaceutically acceptable salt thereof, in which R3 is substituted with 3 substitutents.
432. In some embodiments, the compound is a compound of Embodiment Group 429, 430, or 431, or a pharmaceutically acceptable salt thereof, in which R3 is substituted with halogen.
433. In some embodiments, the compound is a compound of Embodiment Group 432, or a pharmaceutically acceptable salt thereof, in which R3 is substituted with F.
434. In some embodiments, the compound is a compound of Embodiment Group 432 or 433, or a pharmaceutically acceptable salt thereof, in which R3 is substituted with Br.
435. In some embodiments, the compound is a compound of Embodiment Group 432, 433, or 434, or a pharmaceutically acceptable salt thereof, in which R3 is substituted with Cl.
436. In some embodiments, the compound is a compound of Embodiment Group 432, 433, 434, or 435, or a pharmaceutically acceptable salt thereof, in which R3 is substituted with I.
437. In some embodiments, the compound is a compound of Embodiment Group 429, 430, 431, 432, 433, 434, 435, or 436, or a pharmaceutically acceptable salt thereof, in which R3 is substituted with C1-C3 alkoxyl.
438. In some embodiments, the compound is a compound of Embodiment Group 437, or a pharmaceutically acceptable salt thereof, in which R3 is substituted with C1-C3 alkoxyl, C1 alkoxyl, C2 alkoxyl, C3 alkoxyl, C1-C2 alkoxyl, or C2-C3 alkoxyl.
439. In some embodiments, the compound is a compound of Embodiment Group 429, 430, 431, 432, 433, 434, 435, 436, 437, or 438, or a pharmaceutically acceptable salt thereof, in which R3 is substituted with trifluoromethyl.
440. In some embodiments, the compound is a compound selected from the group consisting of compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152 set forth in Table 1, below, or a pharmaceutically acceptable salt thereof.
441. With respect to each of embodiment groups 1-440 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440) there are embodiments that include the corresponding solvates or a subset of such solvates, for example monohydrates.
442. Compounds, or pharmaceutically acceptable salts thereof, of Embodiment Groups 1-441 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, or 441) or combinations thereof, are useful in therapeutic methods disclosed below.
443. In some embodiments, compounds or pharmaceutically acceptable salts of compound 86, 87, 88, 89, 90, and 91, or any combination thereof, are useful in therapeutic methods disclosed below.
444. In some embodiments, one or more compounds of Embodiment Groups 442 and 443 are used in combination in therapeutic methods disclosed below.

TABLE 1

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 1 | 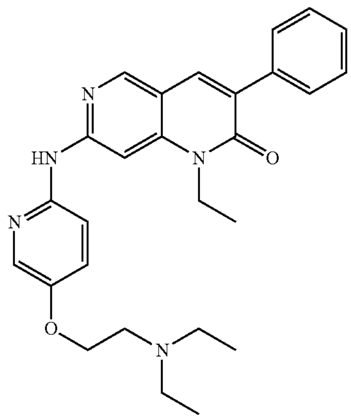 | <0.1 | 0.1-1 | 0.1-1 | <1 | 1-10 |
| 2 | 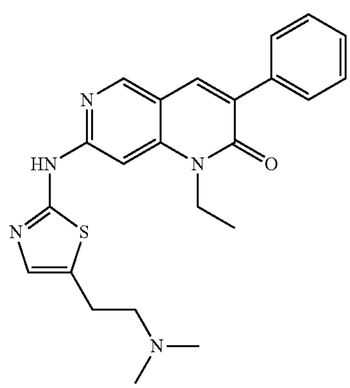 [SMILES: CCn1c(=O)c(-c2ccccc2)cc2cnc(Nc3ncc(CCN(C)C)s3)cc21] | >5 | >5 | 1-5 | 1-10 | 1-10 |
| 3 | 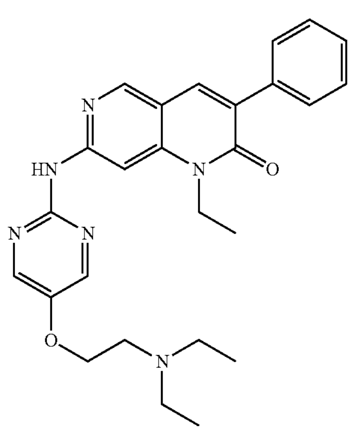 [SMILES: CCN(CC)CCOc1cnc(Nc2cc3c(cn2)cc(-c2ccccc2)c(=O)n3CC)nc1] | 1-5 | 1-5 | >5 | 1-10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 4 | 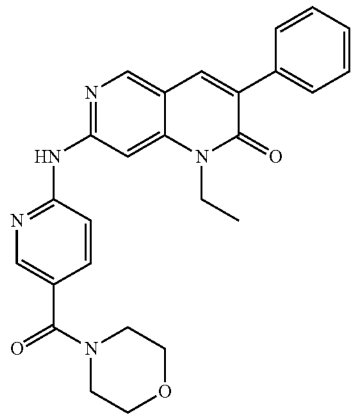 [SMILES: CCn1c(=O)c(-c2ccccc2)cc2cnc(Nc3ccc(C(=O)N4CCOCC4)cn3)cc21] | >5 | 0.1-1 | <0.1 | 1-10 | <1 |
| 5 | 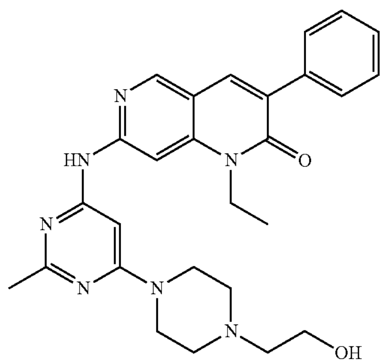 [SMILES: CCn1c(=O)c(-c2ccccc2)cc2cnc(Nc3cc(N4CCN(CCO)CC4)nc(C)n3)cc21] | 0.1-1 | 1-5 | 0.1-1 | 1-10 | >10 |
| 6 | 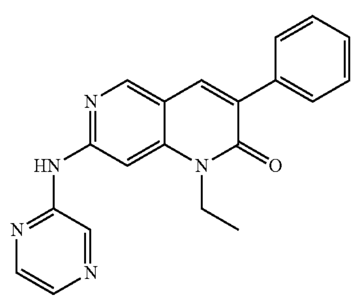 [SMILES: CCn1c(=O)c(-c2ccccc2)cc2cnc(Nc3cnccn3)cc21] | 1-5 | 1-5 | 0.1-1 | >10 | >10 |
| 7 | 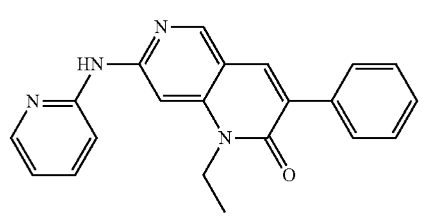 [SMILES: CCn1c(=O)c(-c2ccccc2)cc2cnc(Nc3ccccn3)cc21] | 0.1-1 | 0.1-1 | 1-5 | 1-10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 8 | 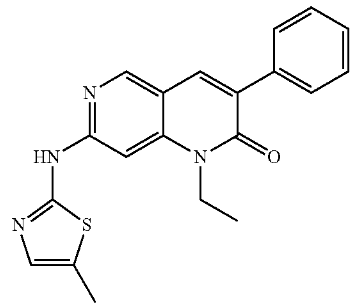 [SMILES: CCn1c(=O)c(-c2ccccc2)cc2cnc(Nc3ncc(C)s3)cc21] | 1-5 | 1-5 | 0.1-1 | >10 | >10 |
| 9 | 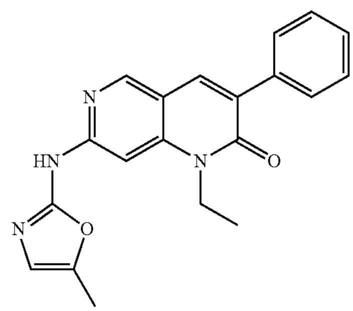 [SMILES: CCn1c(=O)c(-c2ccccc2)cc2cnc(Nc3ncc(C)o3)cc21] | 1-5 | >5 | >5 | 1-10 | >10 |
| 10 | 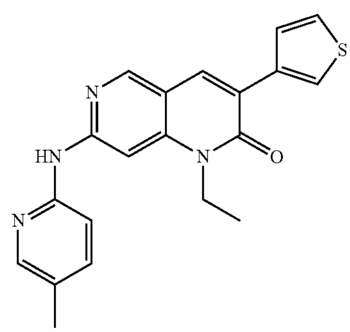 [SMILES: CCn1c(=O)c(-c2ccsc2)cc2cnc(Nc3ccc(C)cn3)cc21] | 1-5 | >5 | >5 | >10 | >10 |
| 11 | 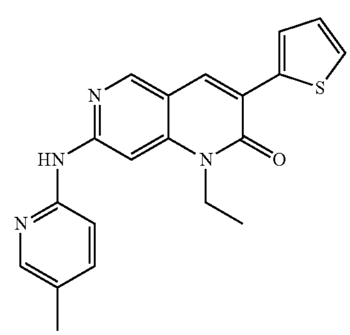 [SMILES: CCn1c(=O)c(-c2cccs2)cc2cnc(Nc3ccc(C)cn3)cc21] | 0.1-1 | >5 | >5 | >10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
| --- | --- | --- | --- | --- | --- | --- |
| 12 | 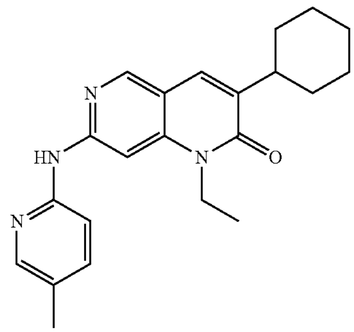 [SMILES: CCn1c(=O)c(C2CCCCC2)cc2cnc(Nc3ccc(C)cn3)cc21] | >5 | >5 | >5 | >10 | >10 |
| 13 | 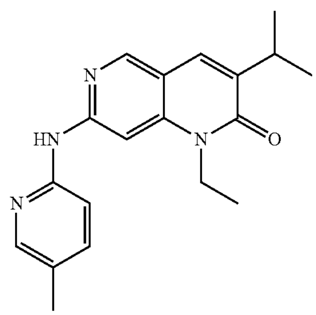 [SMILES: CCn1c(=O)c(C(C)C)cc2cnc(Nc3ccc(C)cn3)cc21] | 1-5 | >5 | >5 | 1-10 | 1-10 |
| 14 | 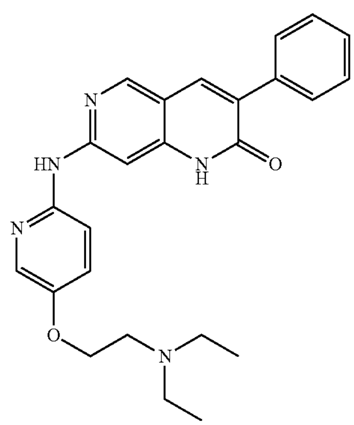 [SMILES: CCN(CC)CCOc1ccc(Nc2cc3[nH]c(=O)c(-c4ccccc4)cc3cn2)nc1] | <0.1 | 0.1-1 | 0.1-1 | 1-10 | >10 |
| 15 | 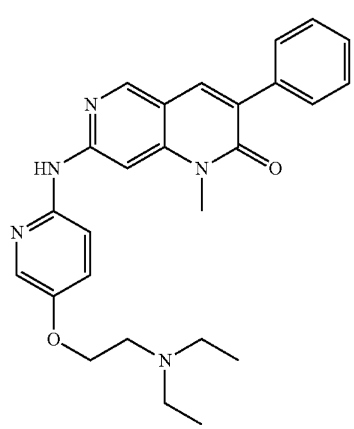 [SMILES: CCN(CC)CCOc1ccc(Nc2cc3c(cn2)cc(-c2ccccc2)c(=O)n3C)nc1] | <0.1 | <0.1 | 0.1-1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 16 | 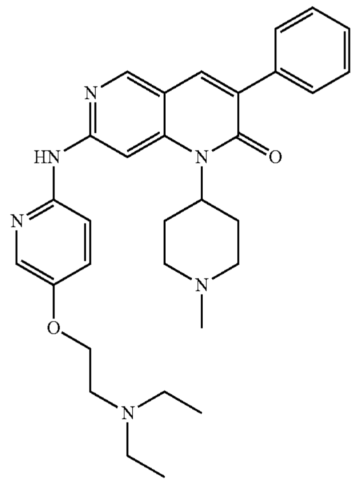 [SMILES: CCN(CC)CCOc1ccc(Nc2cc3c(cn2)cc(-c2ccccc2)c(=O)n3C2CCN(C)CC2)nc1] | 0.1-1 | <0.1 | 0.1-1 | <1 | 1-10 |
| 17 | 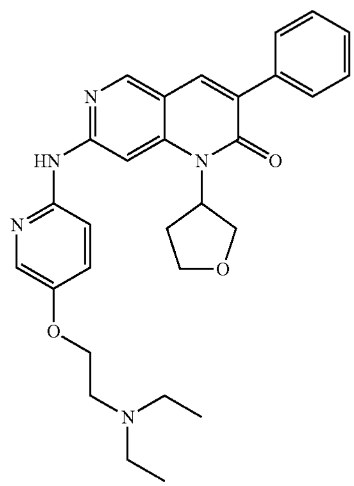 [SMILES: CCN(CC)CCOc1ccc(Nc2cc3c(cn2)cc(-c2ccccc2)c(=O)n3C2CCOC2)nc1] | 1-5 | 0.1-1 | 0.1-1 | <1 | 1-10 |
| 18 | 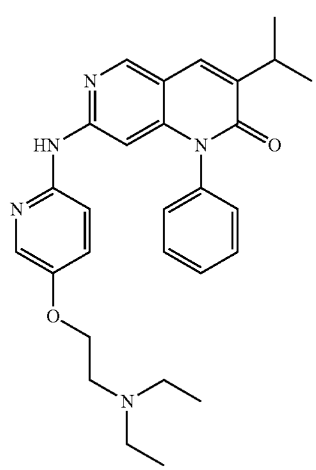 [SMILES: CCN(CC)CCOc1ccc(Nc2cc3c(cn2)cc(C(C)C)c(=O)n3-c2ccccc2)nc1] | 0.1-1 | 0.1-1 | 0.1-1 | <1 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 19 | 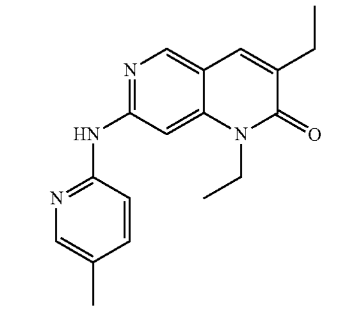 [SMILES: CCc1cc2cnc(Nc3ccc(C)cn3)cc2n(CC)c1=O] | 0.1-1 | >5 | >5 | 1-10 | 1-10 |
| 20 | 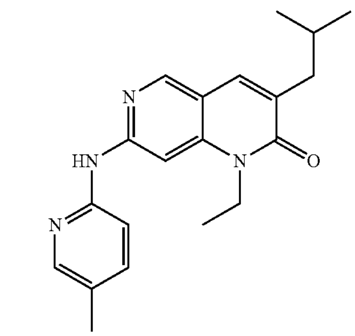 [SMILES: CCn1c(=O)c(CC(C)C)cc2cnc(Nc3ccc(C)cn3)cc21] | 0.1-1 | >5 | >5 | >10 | >10 |
| 21 | 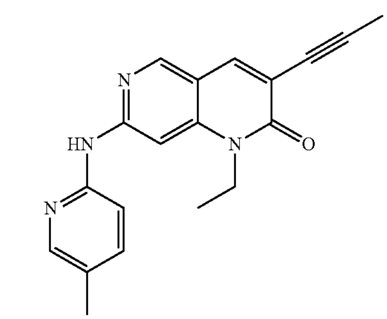 [SMILES: CC#Cc1cc2cnc(Nc3ccc(C)cn3)cc2n(CC)c1=O] | >5 | 0.1-1 | >5 | 1-10 | 1-10 |
| 22 | 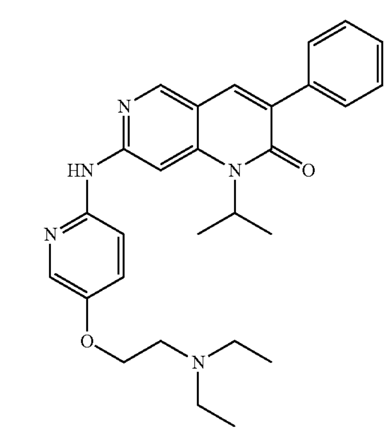 [SMILES: CCN(CC)CCOc1ccc(Nc2cc3c(cn2)cc(-c2ccccc2)c(=O)n3C(C)C)nc1] | <0.1 | 0.1-1 | 0.1-1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 23 | 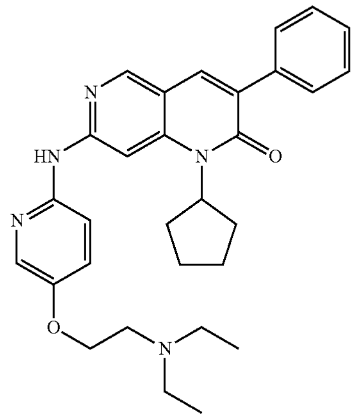 [SMILES: CCN(CC)CCOc1ccc(Nc2cc3c(cn2)cc(-c2ccccc2)c(=O)n3C2CCCC2)nc1] | <0.1 | 0.1-1 | 0.1-1 | <1 | 1-10 |
| 24 | 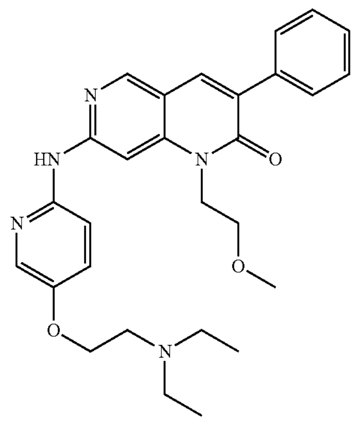 [SMILES: CCN(CC)CCOc1ccc(Nc2cc3c(cn2)cc(-c2ccccc2)c(=O)n3CCOC)nc1] | <0.1 | <0.1 | <0.1 | <1 | 1-10 |
| 25 | 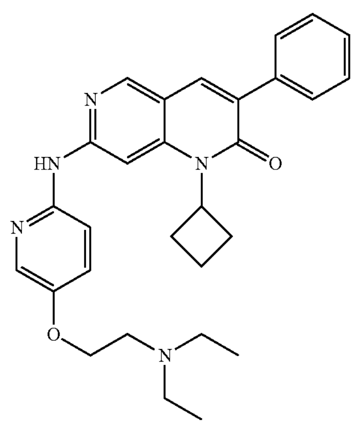 [SMILES: CCN(CC)CCOc1ccc(Nc2cc3c(cn2)cc(-c2ccccc2)c(=O)n3C2CCC2)nc1] | <0.1 | 1-5 | 1-5 | <1 | 1-10 |
| 26 | 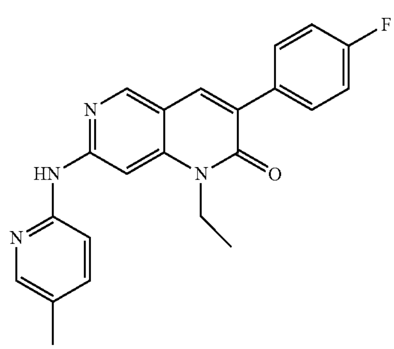 [SMILES: CCn1c(=O)c(-c2ccc(F)cc2)cc2cnc(Nc3ccc(C)cn3)cc21] | >5 | >5 | >5 | >10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 27 | 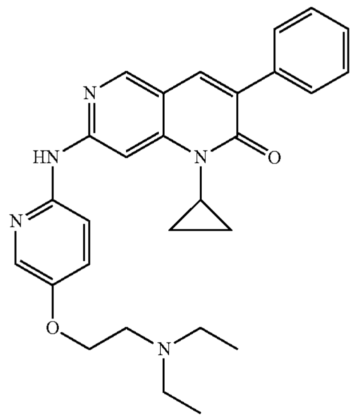 [SMILES: CCN(CC)CCOc1ccc(Nc2cc3c(cn2)cc(-c2ccccc2)c(=O)n3C2CC2)nc1] | <0.1 | 0.1-1 | 0.1-1 | <1 | 1-10 |
| 28 | 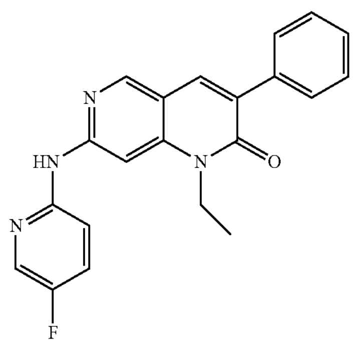 [SMILES: CCn1c(=O)c(-c2ccccc2)cc2cnc(Nc3ccc(F)cn3)cc21] | >5 | >5 | >5 | 1-10 | 1-10 |
| 29 | 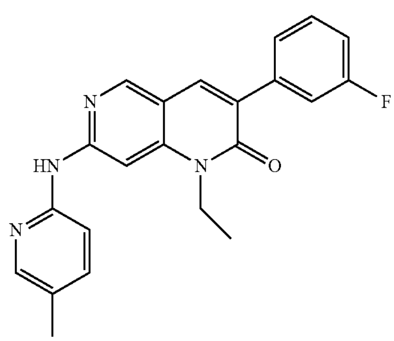 [SMILES: CCn1c(=O)c(-c2cccc(F)c2)cc2cnc(Nc3ccc(C)cn3)cc21] | >5 | >5 | >5 | >10 | >10 |
| 30 | 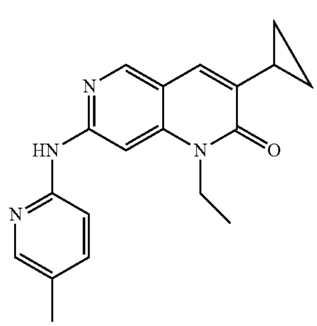 [SMILES: CCn1c(=O)c(C2CC2)cc2cnc(Nc3ccc(C)cn3)cc21] | >5 | 0.1-1 | 1-5 | 1-10 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 31 | 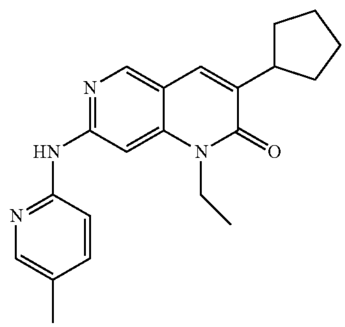 [SMILES: CCn1c(=O)c(C2CCCC2)cc2cnc(Nc3ccc(C)cn3)cc21] | >5 | 0.1-1 | >5 | >10 | 1-10 |
| 32 | 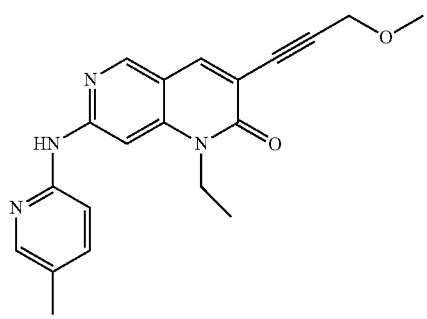 [SMILES: CCn1c(=O)c(C#CCOC)cc2cnc(Nc3ccc(C)cn3)cc21] | >5 | 1-5 | >5 | >10 | >10 |
| 33 | 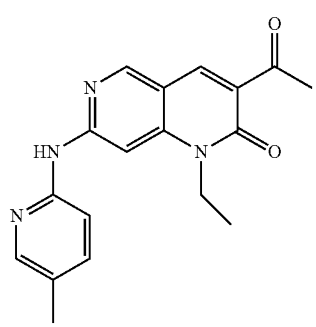 [SMILES: CCn1c(=O)c(C(C)=O)cc2cnc(Nc3ccc(C)cn3)cc21] | >5 | 1-5 | >5 | >10 | >10 |
| 34 | 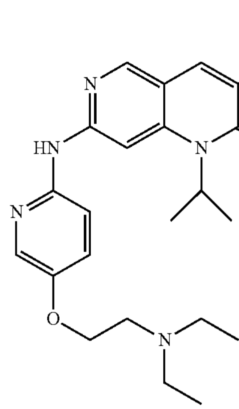 | 0.1-1 | <0.1 | <0.1 | 1-10 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 35 | 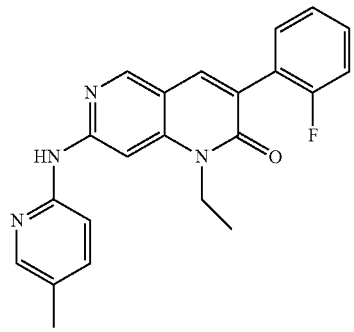 [SMILES: CCn1c(=O)c(-c2ccccc2F)cc2cnc(Nc3ccc(C)cn3)cc21] | 0.1-1 | 0.1-1 | <0.1 | <1 | >10 |
| 36 | 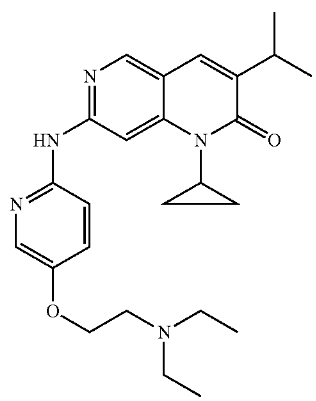 [SMILES: CCN(CC)CCOc1ccc(Nc2cc3c(cn2)cc(C(C)C)c(=O)n3C2CC2)nc1] | 0.1-1 | 0.1-1 | 0.1-1 | 1-10 | >10 |
| 37 | 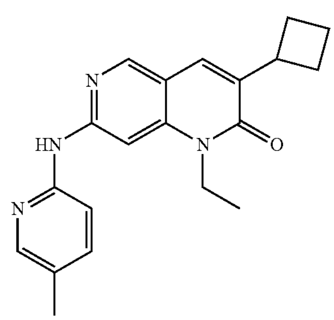 [SMILES: CCn1c(=O)c(C2CCC2)cc2cnc(Nc3ccc(C)cn3)cc21] | 0.1-1 | >5 | 1-5 | >10 | >10 |
| 38 | 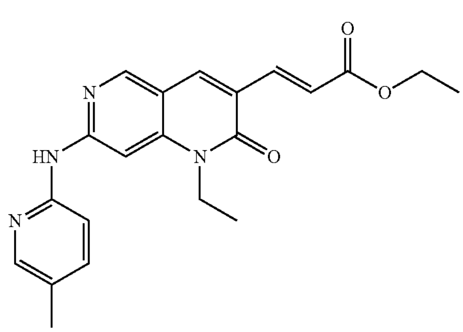 [SMILES: CCOC(=O)/C=C/c1cc2cnc(Nc3ccc(C)cn3)cc2n(CC)c1=O] | >5 | >5 | >5 | >10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 39 | 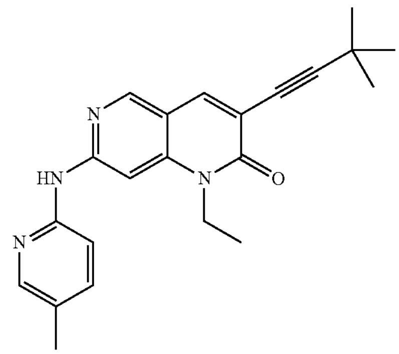 [SMILES: CCn1c(=O)c(C#CC(C)(C)C)cc2cnc(Nc3ccc(C)cn3)cc21] | >5 | 0.1-1 | >5 | 1-10 | 1-10 |
| 40 | 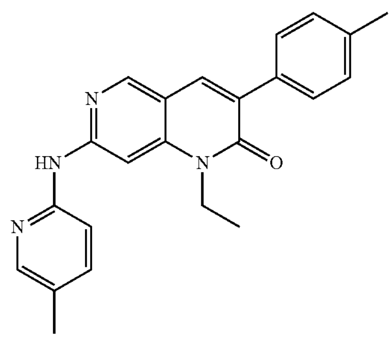 [SMILES: CCn1c(=O)c(-c2ccc(C)cc2)cc2cnc(Nc3ccc(C)cn3)cc21] | >5 | 0.1-1 | >5 | >10 | >10 |
| 41 | 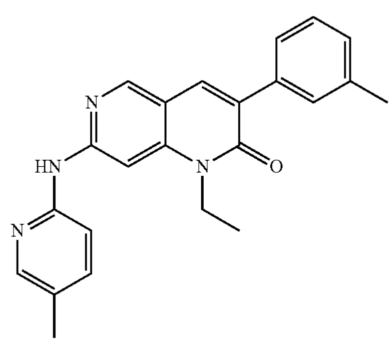 [SMILES: CCn1c(=O)c(-c2cccc(C)c2)cc2cnc(Nc3ccc(C)cn3)cc21] | >5 | >5 | 1-5 | >10 | >10 |
| 42 | 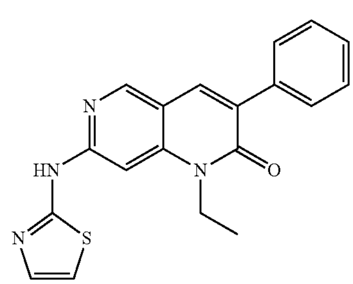 [SMILES: CCn1c(=O)c(-c2ccccc2)cc2cnc(Nc3nccs3)cc21] | 1-5 | 1-5 | >5 | <1 | <1 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
| --- | --- | --- | --- | --- | --- | --- |
| 43 | 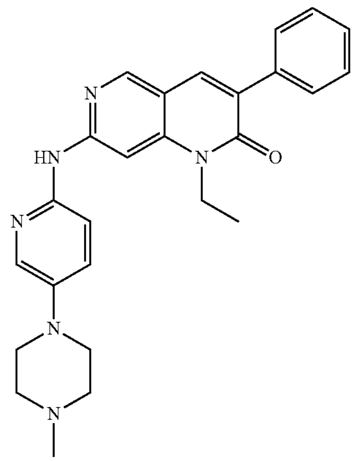 [SMILES: CCn1c(=O)c(-c2ccccc2)cc2cnc(Nc3ccc(N4CCN(C)CC4)cn3)cc21] | 0.1-1 | <0.1 | <0.1 | <1 | 1-10 |
| 44 | 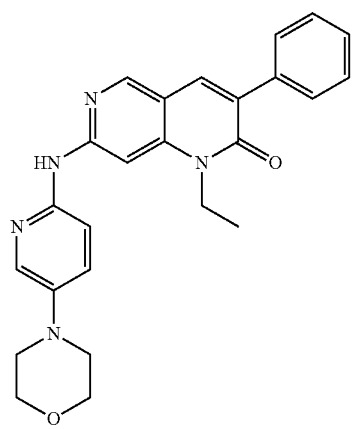 [SMILES: CCn1c(=O)c(-c2ccccc2)cc2cnc(Nc3ccc(N4CCOCC4)cn3)cc21] | >5 | 0.1-1 | 0.1-1 | <1 | 1-10 |
| 45 | 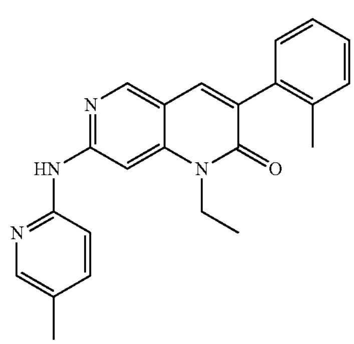 [SMILES: CCn1c(=O)c(-c2ccccc2C)cc2cnc(Nc3ccc(C)cn3)cc21] | 0.1-1 | 0.1-1 | 0.1-1 | >10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 46 | 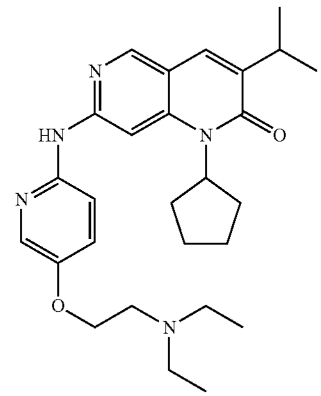 [SMILES: CCN(CC)CCOc1ccc(Nc2cc3c(cn2)cc(C(C)C)c(=O)n3C2CCCC2)nc1] | 0.1-1 | 0.1-1 | 0.1-1 | <1 | 1-10 |
| 47 | 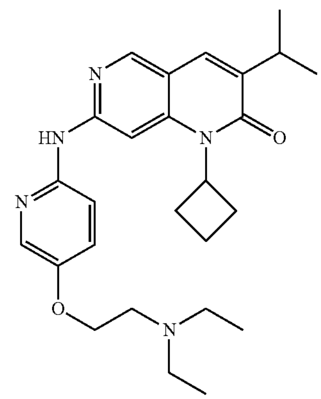 [SMILES: CCN(CC)CCOc1ccc(Nc2cc3c(cn2)cc(C(C)C)c(=O)n3C2CCC2)nc1] | 0.1-1 | <0.1 | <0.1 | <1 | 1-10 |
| 48 | 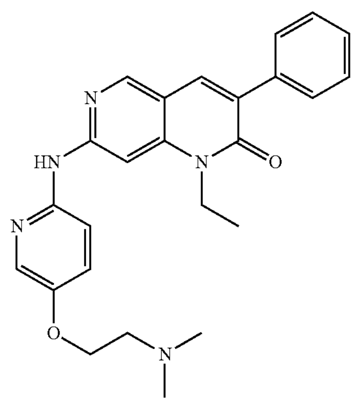 [SMILES: CCn1c(=O)c(-c2ccccc2)cc2cnc(Nc3ccc(OCCN(C)C)cn3)cc21] | 1-5 | 1-5 | 0.1-1 | 1-10 | >10 |
| 49 | 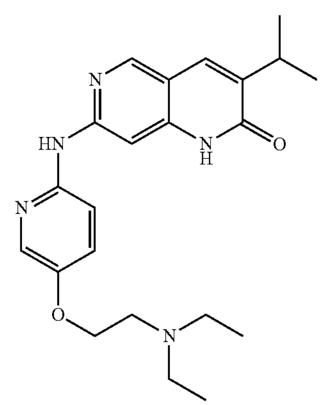 [SMILES: CCN(CC)CCOc1ccc(Nc2cc3[nH]c(=O)c(C(C)C)cc3cn2)nc1] | 1-5 | 0.1-1 | 0.1-1 | 1-10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 50 | 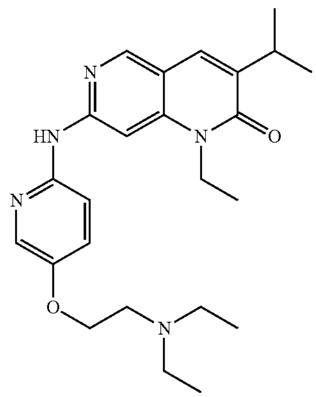 [SMILES: CCN(CC)CCOc1ccc(Nc2cc3c(cn2)cc(C(C)C)c(=O)n3CC)nc1] | 1-5 | 0.1-1 | 0.1-1 | 1-10 | >10 |
| 51 | 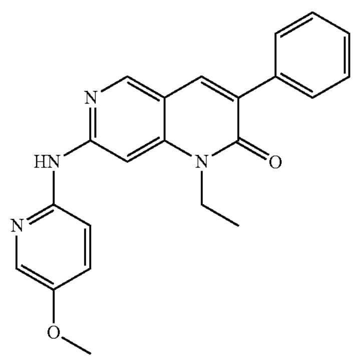 [SMILES: CCn1c(=O)c(-c2ccccc2)cc2cnc(Nc3ccc(OC)cn3)cc21] | 1-5 | 0.1-1 | 0.1-1 | 1-10 | >10 |
| 52 | 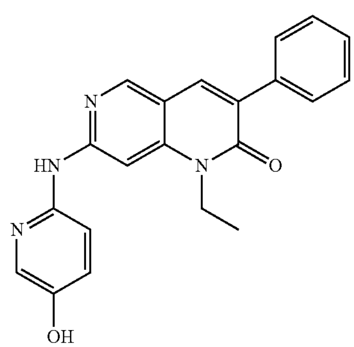 [SMILES: CCn1c(=O)c(-c2ccccc2)cc2cnc(Nc3ccc(O)cn3)cc21] | 0.1-1 | <0.1 | 0.1-1 | 1-10 | >10 |
| 53 | 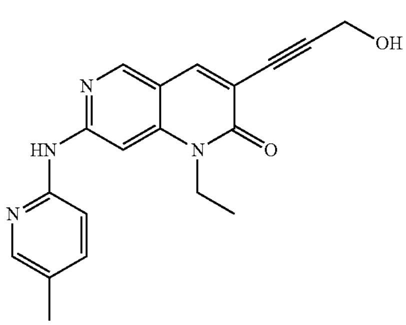 [SMILES: CCn1c(=O)c(C#CCO)cc2cnc(Nc3ccc(C)cn3)cc21] | >5 | 0.1-1 | 1-5 | 1-10 | 1-10 |

TABLE 1-continued

| Compound | Structure | BTK IC$_{50}$ (µM) | Src IC$_{50}$ (µM) | Lyn IC$_{50}$ (µM) | DoHH2 EC$_{50}$ (µM) | Ramos EC$_{50}$ (µM) |
|---|---|---|---|---|---|---|
| 54 | 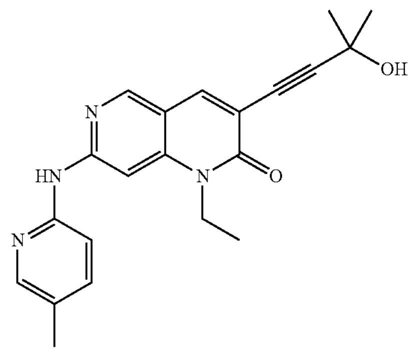 [SMILES: CCn1c(=O)c(C#CC(C)(C)O)cc2cnc(Nc3ccc(C)cn3)cc21] | 1-5 | 0.1-1 | 0.1-1 | 1-10 | >10 |
| 55 | 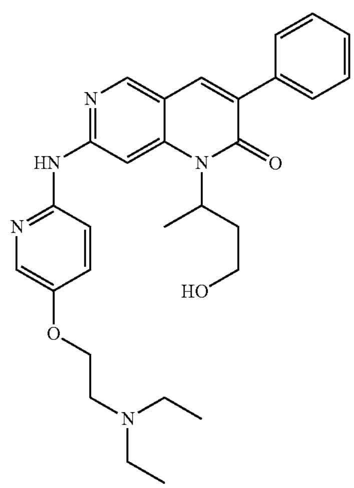 [SMILES: CCN(CC)CCOc1ccc(Nc2cc3c(cn2)cc(-c2ccccc2)c(=O)n3C(C)CCO)nc1] | 0.1-1 | <0.1 | <0.1 | <1 | 1-10 |
| 56 | 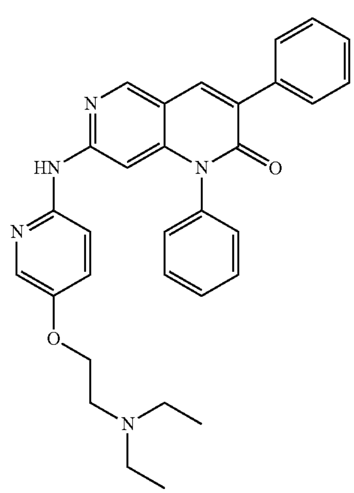 [SMILES: CCN(CC)CCOc1ccc(Nc2cc3c(cn2)cc(-c2ccccc2)c(=O)n3-c2ccccc2)nc1] | 0.1-1 | 0.1-1 | 0.1-1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 57 | 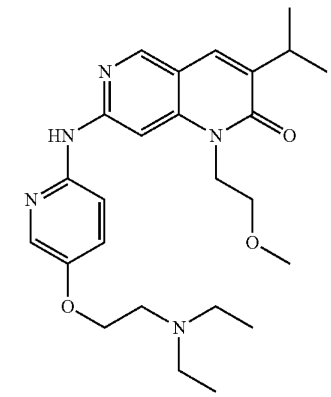 [SMILES: CCN(CC)CCOc1ccc(Nc2cc3c(cn2)cc(C(C)C)c(=O)n3CCOC)nc1] | 1-5 | 0.1-1 | >5 | 1-10 | >10 |
| 58 | 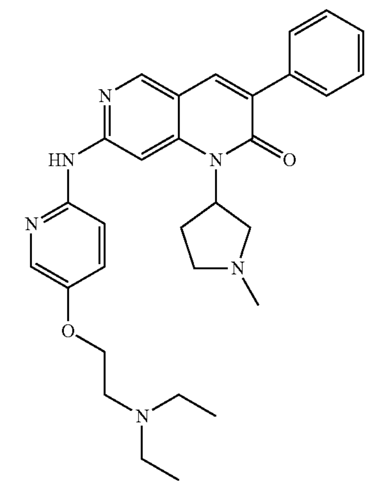 [SMILES: CCN(CC)CCOc1ccc(Nc2cc3c(cn2)cc(-c2ccccc2)c(=O)n3C2CCN(C)C2)nc1] | 1-5 | 0.1-1 | 0.1-1 | 1-10 | >10 |
| 59 | 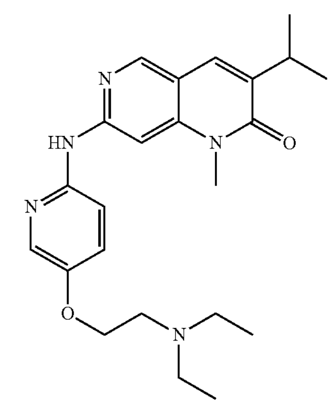 [SMILES: CCN(CC)CCOc1ccc(Nc2cc3c(cn2)cc(C(C)C)c(=O)n3C)nc1] | 1-5 | 0.1-1 | >5 | 1-10 | >10 |
| 60 | 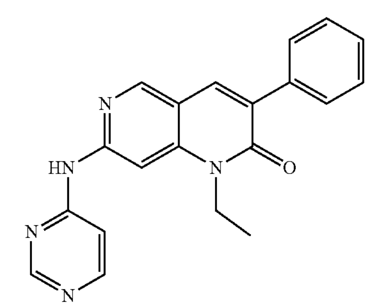 [SMILES: CCn1c(=O)c(-c2ccccc2)cc2cnc(Nc3ccncn3)cc21] | 0.1-1 | 0.1-1 | 1-5 | 1-10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 61 | 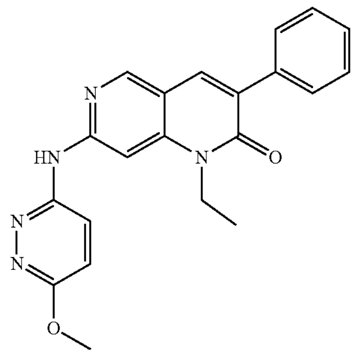 [SMILES: CCn1c(=O)c(-c2ccccc2)cc2cnc(Nc3ccc(OC)nn3)cc21] | 1-5 | 0.1-1 | 1-5 | <1 | 1-10 |
| 62 | 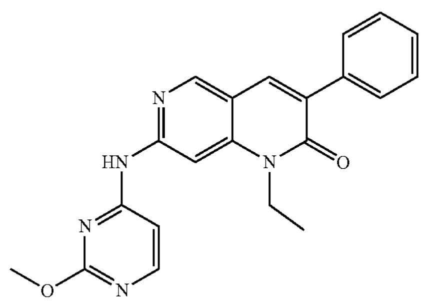 [SMILES: CCn1c(=O)c(-c2ccccc2)cc2cnc(Nc3ccnc(OC)n3)cc21] | 1-5 | 0.1-1 | 1-5 | <1 | 1-10 |
| 63 | 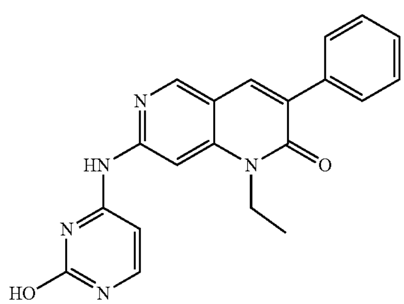 [SMILES: CCn1c(=O)c(-c2ccccc2)cc2cnc(Nc3ccnc(O)n3)cc21] | 1-5 | <0.1 | 0.1-1 | 1-10 | 1-10 |
| 64 | 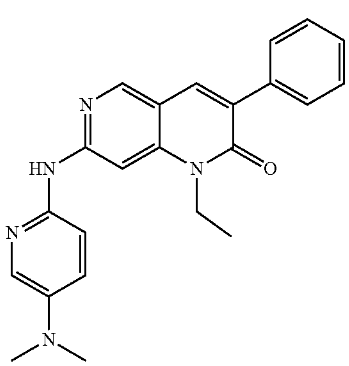 [SMILES: CCn1c(=O)c(-c2ccccc2)cc2cnc(Nc3ccc(N(C)C)cn3)cc21] | 1-5 | 0.1-1 | 0.1-1 | <1 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 65 | 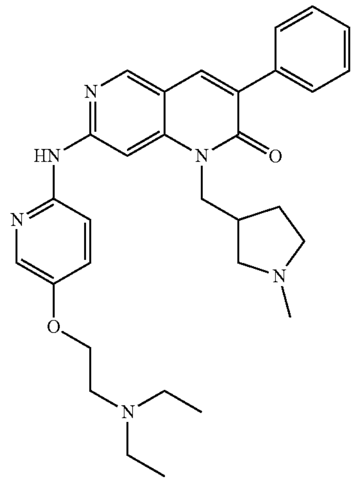 [SMILES: CCN(CC)CCOc1ccc(Nc2cc3c(cn2)cc(-c2ccccc2)c(=O)n3CC2CCN(C)C2)nc1] | >5 | 0.1-1 | 1-5 | <1 | >10 |
| 66 | 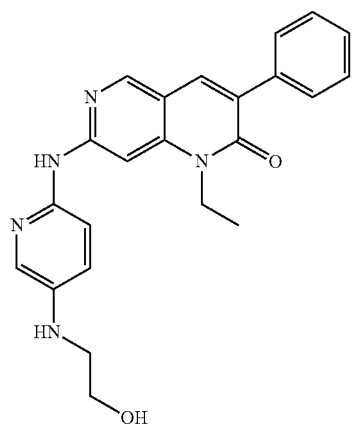 [SMILES: CCn1c(=O)c(-c2ccccc2)cc2cnc(Nc3ccc(NCCO)cn3)cc21] | 0.1-1 | <0.1 | <0.1 | <1 | 1-10 |
| 67 | 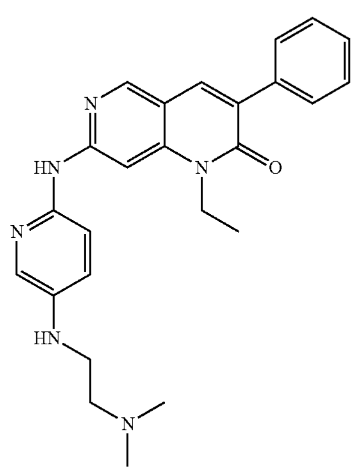 [SMILES: CCn1c(=O)c(-c2ccccc2)cc2cnc(Nc3ccc(NCCN(C)C)cn3)cc21] | 0.1-1 | 1-5 | <0.1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 68 | 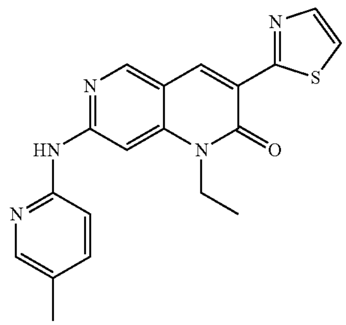 [SMILES: CCn1c(=O)c(-c2nccs2)cc2cnc(Nc3ccc(C)cn3)cc21] | >5 | >5 | 1-5 | 1-10 | >10 |
| 69 | 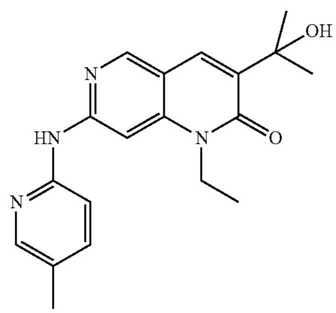 [SMILES: CCn1c(=O)c(C(C)(C)O)cc2cnc(Nc3ccc(C)cn3)cc21] | >5 | <0.1 | >5 | >10 | >10 |
| 70 | 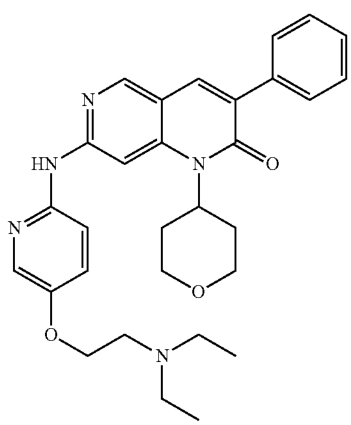 [SMILES: CCN(CC)CCOc1ccc(Nc2cc3c(cn2)cc(-c2ccccc2)c(=O)n3C2CCOCC2)nc1] | 0.1-1 | 0.1-1 | 0.1-1 | <1 | >10 |
| 71 | 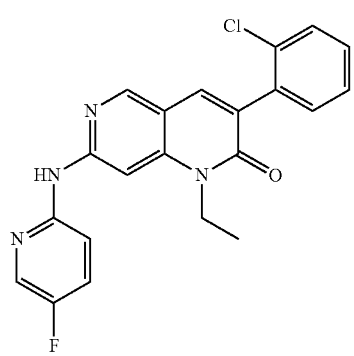 [SMILES: CCn1c(=O)c(-c2ccccc2Cl)cc2cnc(Nc3ccc(F)cn3)cc21] | 1-5 | <0.1 | 0.1-1 | 1-10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 72 | 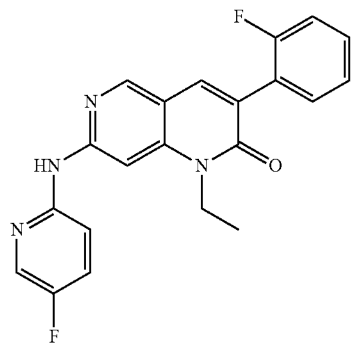 [SMILES: CCn1c(=O)c(-c2ccccc2F)cc2cnc(Nc3ccc(F)cn3)cc21] | 1-5 | 1-5 | 0.1-1 | 1-10 | >10 |
| 73 | 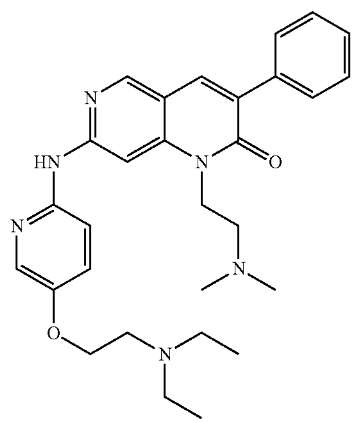 [SMILES: CCN(CC)CCOc1ccc(Nc2cc3c(cn2)cc(-c2ccccc2)c(=O)n3CCN(C)C)nc1] | 0.1-1 | 0.1-1 | 0.1-1 | <1 | 1-10 |
| 74 | 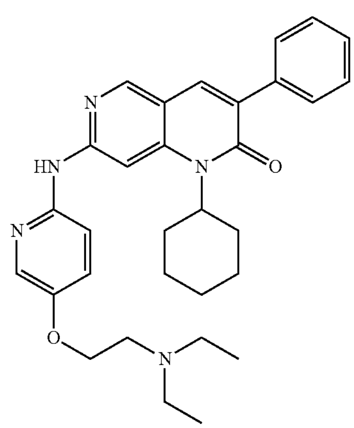 [SMILES: CCN(CC)CCOc1ccc(Nc2cc3c(cn2)cc(-c2ccccc2)c(=O)n3C2CCCCC2)nc1] | >5 | <0.1 | 1-5 | 1-10 | 1-10 |
| 75 | 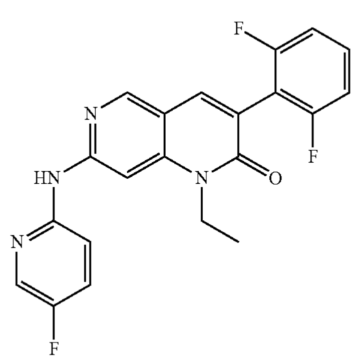 [SMILES: CCn1c(=O)c(-c2c(F)cccc2F)cc2cnc(Nc3ccc(F)cn3)cc21] | <0.1 | 0.1-1 | <0.1 | <1 | 1-10 |

TABLE 1-continued

| Compound | Structure | BTK IC$_{50}$ (µM) | Src IC$_{50}$ (µM) | Lyn IC$_{50}$ (µM) | DoHH2 EC$_{50}$ (µM) | Ramos EC$_{50}$ (µM) |
|---|---|---|---|---|---|---|
| 76 | 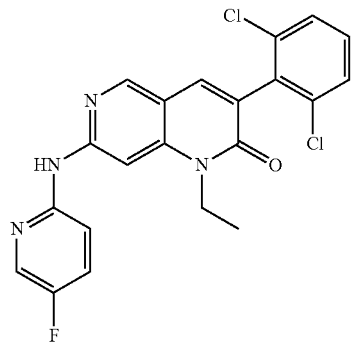 [SMILES: CCn1c(=O)c(-c2c(Cl)cccc2Cl)cc2cnc(Nc3ccc(F)cn3)cc21] | 0.1-1 | <0.1 | <0.1 | <1 | >10 |
| 77 | 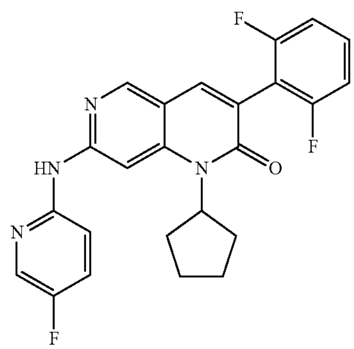 [SMILES: O=c1c(-c2c(F)cccc2F)cc2cnc(Nc3ccc(F)cn3)cc2n1C1CCCC1] | 0.1-1 | <0.1 | <0.1 | <1 | >10 |
| 78 | 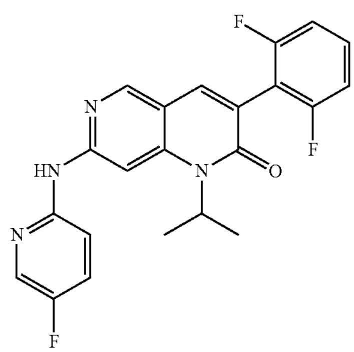 [SMILES: CC(C)n1c(=O)c(-c2c(F)cccc2F)cc2cnc(Nc3ccc(F)cn3)cc21] | 0.1-1 | >5 | >5 | <1 | >10 |
| 79 | 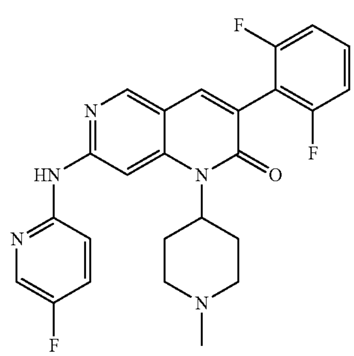 [SMILES: CN1CCC(n2c(=O)c(-c3c(F)cccc3F)cc3cnc(Nc4ccc(F)cn4)cc32)CC1] | 0.1-1 | 2.577 | <0.1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 80 | 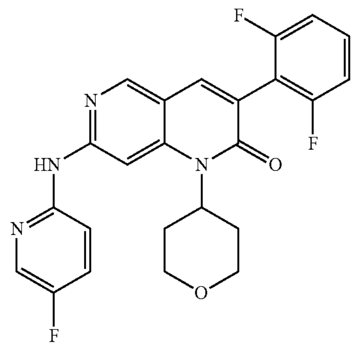 [SMILES: O=c1c(-c2c(F)cccc2F)cc2cnc(Nc3ccc(F)cn3)cc2n1C1CCOCC1] | 0.1-1 | >5 | <0.1 | <1 | >10 |
| 81 | 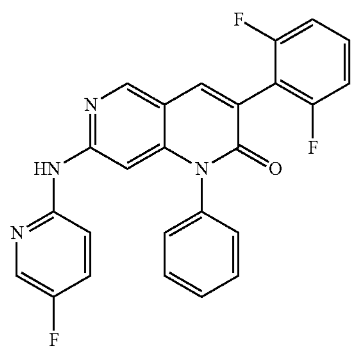 [SMILES: O=c1c(-c2c(F)cccc2F)cc2cnc(Nc3ccc(F)cn3)cc2n1-c1ccccc1] | 0.1-1 | <0.1 | <0.1 | 1-10 | >10 |
| 82 | 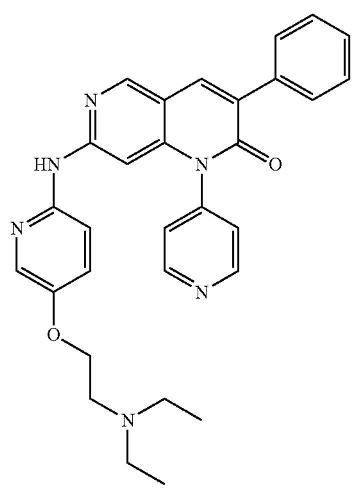 | 0.1-1 | <0.1 | <0.1 | <1 | >10 |
| 83 | 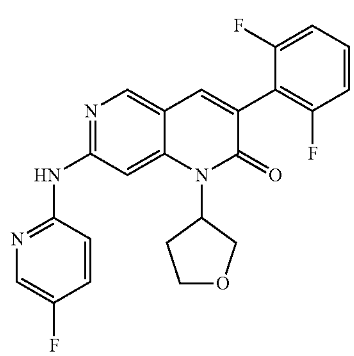 | 0.1-1 | <0.1 | <0.1 | <1 | 1-10 |

TABLE 1-continued

| Compound | Structure | BTK IC$_{50}$ (µM) | Src IC$_{50}$ (µM) | Lyn IC$_{50}$ (µM) | DoHH2 EC$_{50}$ (µM) | Ramos EC$_{50}$ (µM) |
|---|---|---|---|---|---|---|
| 84 | 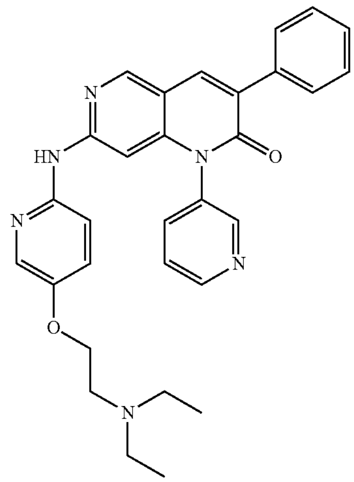 [SMILES: CCN(CC)CCOc1ccc(Nc2cc3c(cn2)cc(-c2ccccc2)c(=O)n3-c2cccnc2)nc1] | 0.1-1 | 0.1-1 | 1-5 | 1-10 | >10 |
| 85 | 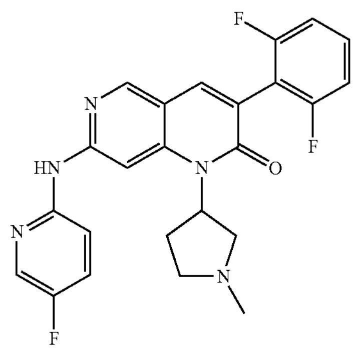 [SMILES: CN1CCC(n2c(=O)c(-c3c(F)cccc3F)cc3cnc(Nc4ccc(F)cn4)cc32)C1] | 1-5 | 1-5 | 1-5 | 1-10 | >10 |
| 86 | 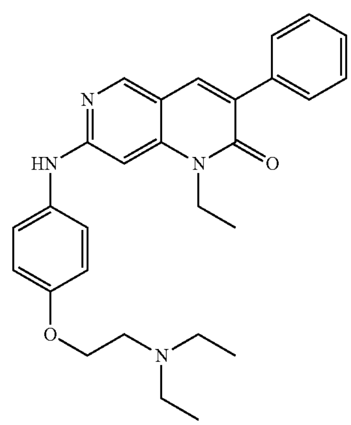 [SMILES: CCN(CC)CCOc1ccc(Nc2cc3c(cn2)cc(-c2ccccc2)c(=O)n3CC)cc1] | 0.1-1 | 1 | <0.1 | 1-10 | >10 |
| 87 | 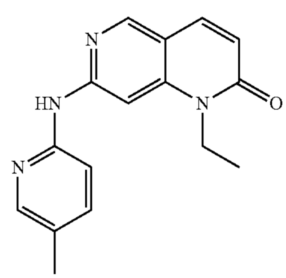 [SMILES: CCn1c(=O)ccc2cnc(Nc3ccc(C)cn3)cc21] | 1-5 | >5 | >5 | 1-10 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 88 | 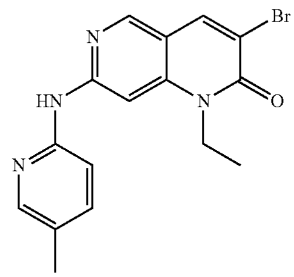 [SMILES: CCn1c(=O)c(Br)cc2cnc(Nc3ccc(C)cn3)cc21] | 0.1-1 | <0.1 | >5 | <1 | <1 |
| 89 | 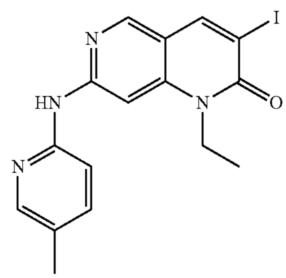 [SMILES: CCn1c(=O)c(I)cc2cnc(Nc3ccc(C)cn3)cc21] | >5 | >5 | >5 | <1 | <1 |
| 90 | 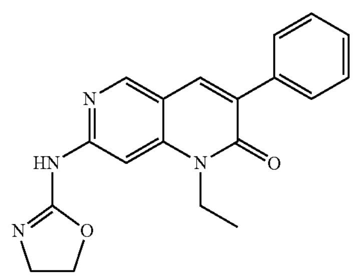 [SMILES: CCn1c(=O)c(-c2ccccc2)cc2cnc(NC3=NCCO3)cc21] | >5 | | | >10 | >10 |
| 91 | 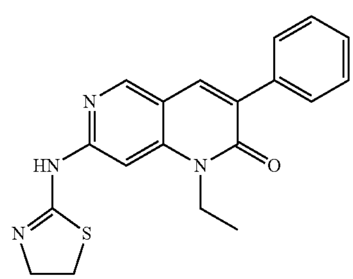 [SMILES: CCn1c(=O)c(-c2ccccc2)cc2cnc(NC3=NCCS3)cc21] | >5 | | | >10 | >10 |
| 92 | 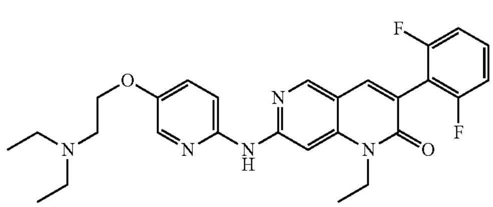 [SMILES: CCN(CC)CCOc1ccc(Nc2cc3c(cn2)cc(-c2c(F)cccc2F)c(=O)n3CC)nc1] | <0.1 | <0.1 | <0.1 | <1 | 1-10 |
| 93 | 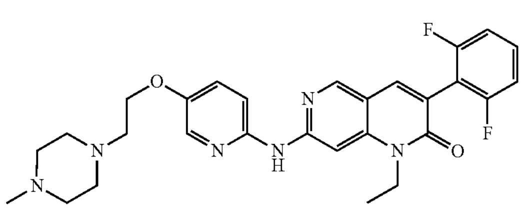 [SMILES: CCn1c(=O)c(-c2c(F)cccc2F)cc2cnc(Nc3ccc(OCCN4CCN(C)CC4)cn3)cc21] | <0.1 | <0.1 | <0.1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 94 | 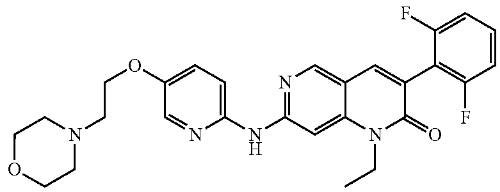 [SMILES: CCn1c(=O)c(-c2c(F)cccc2F)cc2cnc(Nc3ccc(OCCN4CCOCC4)cn3)cc21] | <0.1 | <0.1 | <0.1 | <1 | 1-10 |
| 95 | 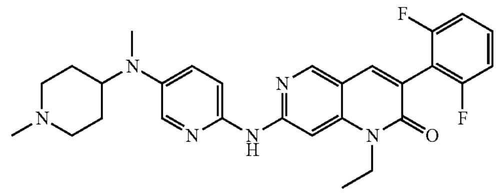 [SMILES: CCn1c(=O)c(-c2c(F)cccc2F)cc2cnc(Nc3ccc(N(C)C4CCN(C)CC4)cn3)cc21] | <0.1 | <0.1 | <0.1 | <1 | 1-10 |
| 96 | 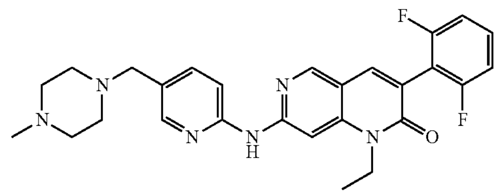 [SMILES: CCn1c(=O)c(-c2c(F)cccc2F)cc2cnc(Nc3ccc(CN4CCN(C)CC4)cn3)cc21] | 0.1-1 | <0.1 | <0.1 | <1 | 1-10 |
| 97 | 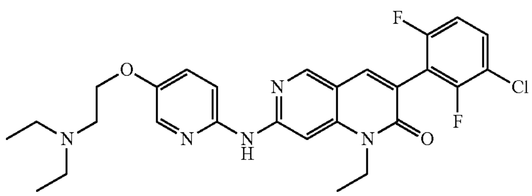 [SMILES: CCN(CC)CCOc1ccc(Nc2cc3c(cn2)cc(-c2c(F)ccc(Cl)c2F)c(=O)n3CC)nc1] | 0.1-1 | <0.1 | <0.1 | <1 | 1-10 |
| 98 | 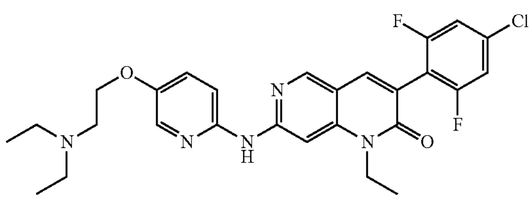 [SMILES: CCN(CC)CCOc1ccc(Nc2cc3c(cn2)cc(-c2c(F)cc(Cl)cc2F)c(=O)n3CC)nc1] | <0.1 | <0.1 | 0.1-1 | 1-10 | 1-10 |
| 99 | 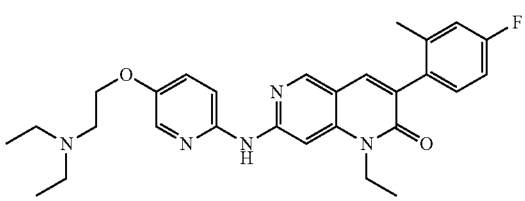 [SMILES: CCN(CC)CCOc1ccc(Nc2cc3c(cn2)cc(-c2ccc(F)cc2C)c(=O)n3CC)nc1] | <0.1 | <0.1 | <0.1 | <1 | 1-10 |
| 100 | 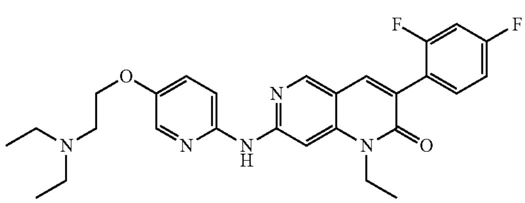 [SMILES: CCN(CC)CCOc1ccc(Nc2cc3c(cn2)cc(-c2ccc(F)cc2F)c(=O)n3CC)nc1] | <0.1 | <0.1 | <0.1 | <1 | 1-10 |
| 101 | 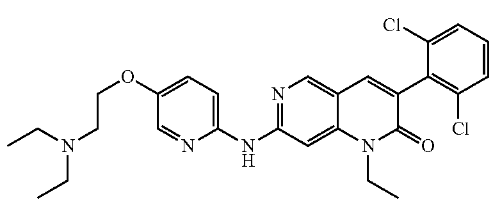 | <0.1 | <0.1 | <0.1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 102 | 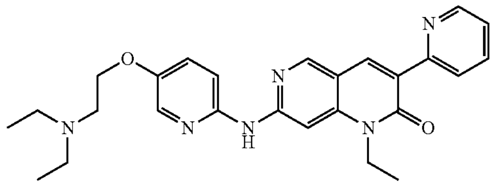 [SMILES: CCN(CC)CCOc1ccc(Nc2cc3c(cn2)cc(-c2ccccn2)c(=O)n3CC)nc1] | >5 | 0.1-1 | 0.1-1 | 1-10 | >10 |
| 103 | 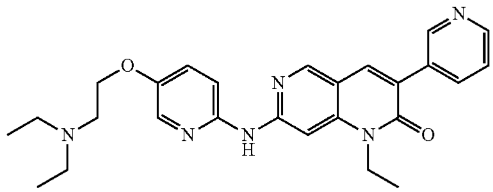 [SMILES: CCN(CC)CCOc1ccc(Nc2cc3c(cn2)cc(-c2cccnc2)c(=O)n3CC)nc1] | >5 | <0.1 | 0.1-1 | 1-10 | >10 |
| 104 | 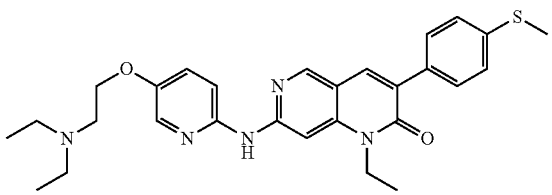 [SMILES: CCN(CC)CCOc1ccc(Nc2cc3c(cn2)cc(-c2ccc(SC)cc2)c(=O)n3CC)nc1] | >5 | 0.1-1 | 0.1-1 | 1-10 | 1-10 |
| 105 | 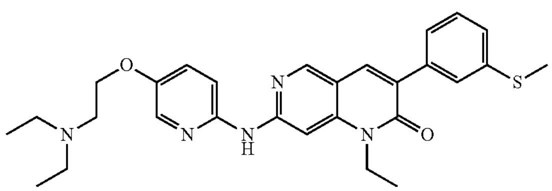 [SMILES: CCN(CC)CCOc1ccc(Nc2cc3c(cn2)cc(-c2cccc(SC)c2)c(=O)n3CC)nc1] | 1-5 | <0.1 | 0.1-1 | 1-10 | 1-10 |
| 106 | 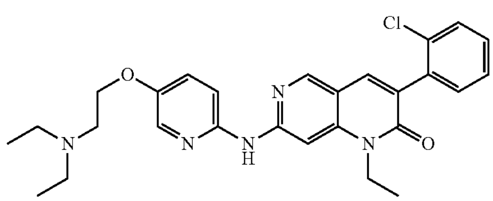 [SMILES: CCN(CC)CCOc1ccc(Nc2cc3c(cn2)cc(-c2ccccc2Cl)c(=O)n3CC)nc1] | <0.1 | >5 | 0.1-1 | <1 | >10 |
| 107 | 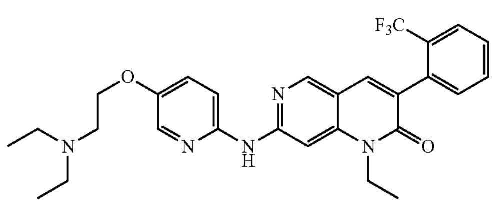 [SMILES: CCN(CC)CCOc1ccc(Nc2cc3c(cn2)cc(-c2ccccc2C(F)(F)F)c(=O)n3CC)nc1] | <0.1 | <0.1 | 0.1-1 | <1 | >10 |
| 108 | 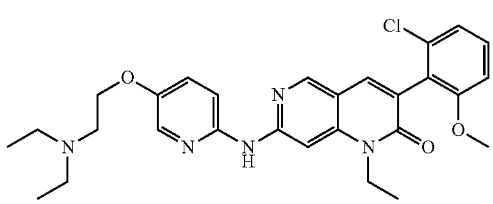 [SMILES: CCN(CC)CCOc1ccc(Nc2cc3c(cn2)cc(-c2c(Cl)cccc2OC)c(=O)n3CC)nc1] | <0.1 | <0.1 | <0.1 | <1 | >10 |
| 109 | 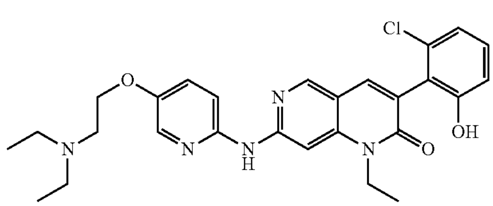 [SMILES: CCN(CC)CCOc1ccc(Nc2cc3c(cn2)cc(-c2c(O)cccc2Cl)c(=O)n3CC)nc1] | <0.1 | <0.1 | <0.1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 110 | 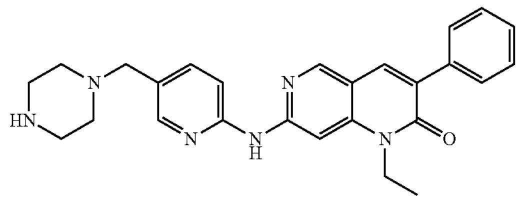 [SMILES: CCn1c(=O)c(-c2ccccc2)cc2cnc(Nc3ccc(CN4CCNCC4)cn3)cc21] | <0.1 | 0.1-1 | 0.1-1 | <1 | 1-10 |
| 111 | 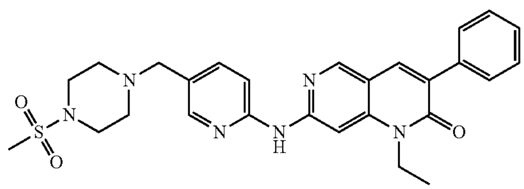 [SMILES: CCn1c(=O)c(-c2ccccc2)cc2cnc(Nc3ccc(CN4CCN(S(C)(=O)=O)CC4)cn3)cc21] | <0.1 | 0.1-1 | 0.1-1 | <1 | 1-10 |
| 112 | 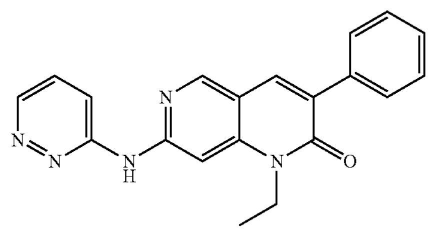 [SMILES: CCn1c(=O)c(-c2ccccc2)cc2cnc(Nc3cccnn3)cc21] | 1-5 | >5 | >5 | >10 | >10 |
| 113 | 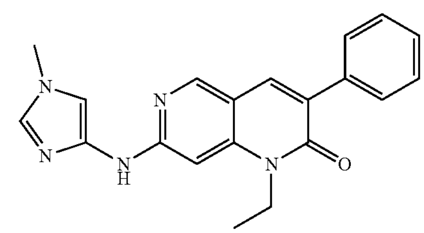 [SMILES: CCn1c(=O)c(-c2ccccc2)cc2cnc(Nc3cn(C)cn3)cc21] | 1-5 | 0.1-1 | 0.1-1 | >10 | >10 |
| 114 | 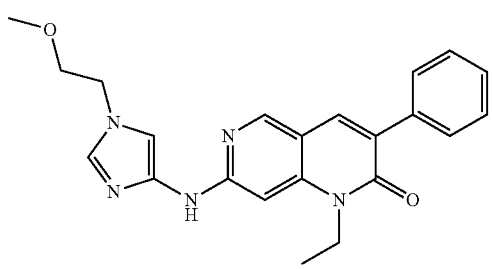 [SMILES: CCn1c(=O)c(-c2ccccc2)cc2cnc(Nc3cn(CCOC)cn3)cc21] | <0.1 | 0.1-1 | 1-5 | 1-10 | >10 |
| 115 | 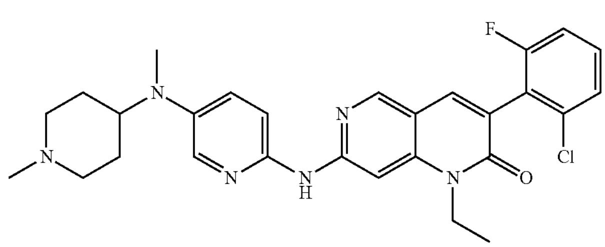 [SMILES: CCn1c(=O)c(-c2c(F)cccc2Cl)cc2cnc(Nc3ccc(N(C)C4CCN(C)CC4)cn3)cc21] | <0.1 | <0.1 | <0.1 | <1 | 1-10 |
| 117 | 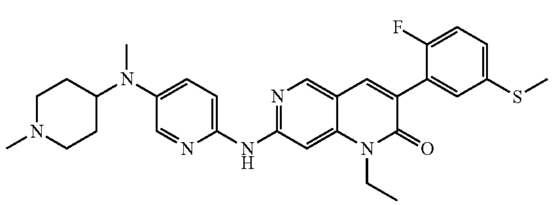 | <0.1 | 0.1-1 | <0.1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
| --- | --- | --- | --- | --- | --- | --- |
| 117 | 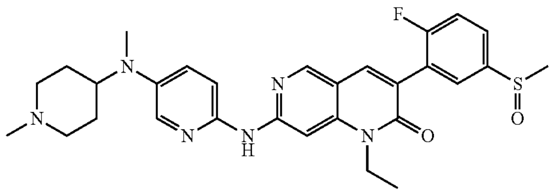 | 0.1-1 | 0.1-1 | <0.1 | 1-10 | >10 |
| 118 | 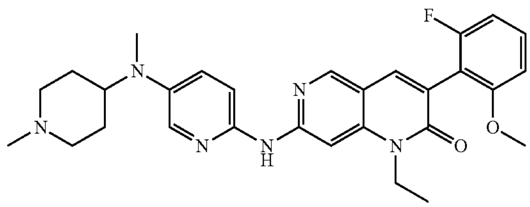 | <0.1 | <0.1 | <0.1 | <1 | 1-10 |
| 119 | 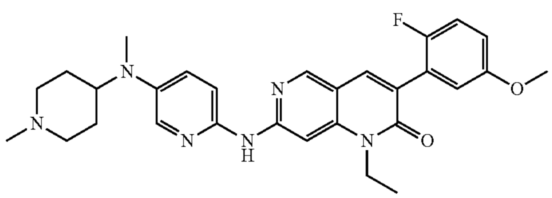 | 0.1-1 | <0.1 | <0.1 | <1 | 1-10 |
| 120 | 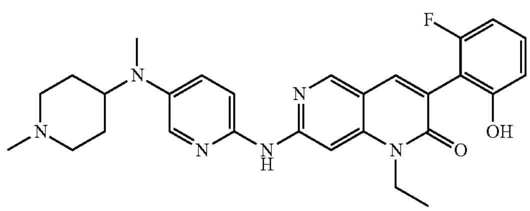 | <0.1 | <0.1 | <0.1 | <1 | 1-10 |
| 121 | 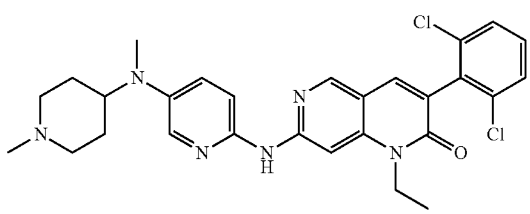 | <0.1 | <0.1 | <0.1 | <1 | 1-10 |
| 122 | 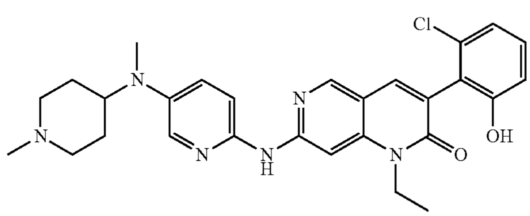 [SMILES: CCn1c(=O)c(-c2c(O)cccc2F)cc2cnc(Nc3ccc(N(C)C4CCN(C)CC4)cn3)cc21] | <0.1 | <0.1 | <0.1 | <1 | 1-10 |
| 123 | 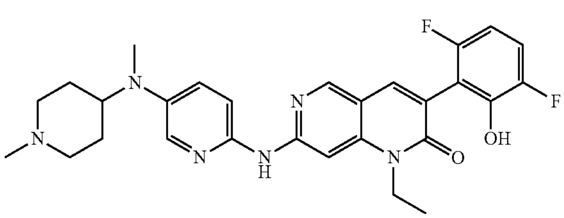 [SMILES: CCn1c(=O)c(-c2c(F)ccc(F)c2O)cc2cnc(Nc3ccc(N(C)C4CCN(C)CC4)cn3)cc21] | <0.1 | <0.1 | <0.1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 124 | 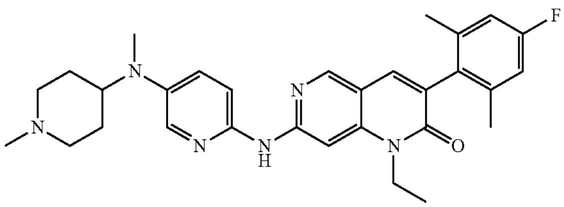 [SMILES: CCn1c(=O)c(-c2c(C)cc(F)cc2C)cc2cnc(Nc3ccc(N(C)C4CCN(C)CC4)cn3)cc21] | <0.1 | <0.1 | <0.1 | <1 | >10 |
| 125 | 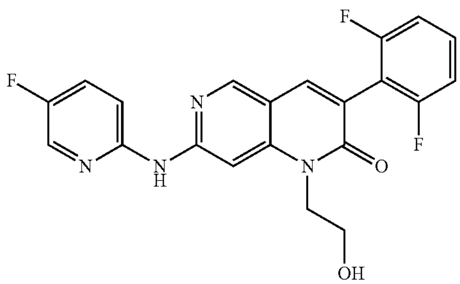 [SMILES: O=c1c(-c2c(F)cccc2F)cc2cnc(Nc3ccc(F)cn3)cc2n1CCO] | 0.1-1 | 0.1-1 | 0.1-1 | <1 | >10 |
| 126 | 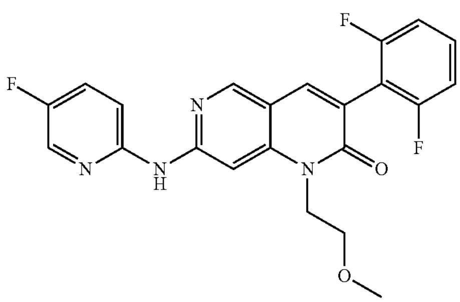 [SMILES: COCCn1c(=O)c(-c2c(F)cccc2F)cc2cnc(Nc3ccc(F)cn3)cc21] | 0.1-1 | 1-5 | >5 | 1-10 | >10 |
| 127 | 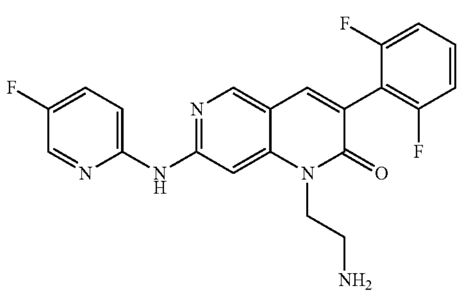 [SMILES: NCCn1c(=O)c(-c2c(F)cccc2F)cc2cnc(Nc3ccc(F)cn3)cc21] | <0.1 | 0.1-1 | 0.1-1 | 1-10 | >10 |
| 128 | 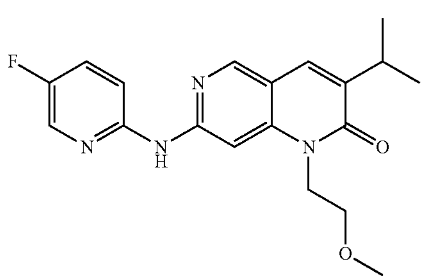 [SMILES: COCCn1c(=O)c(C(C)C)cc2cnc(Nc3ccc(F)cn3)cc21] | 1-5 | 1-5 | 1-5 | 1-10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 129 | 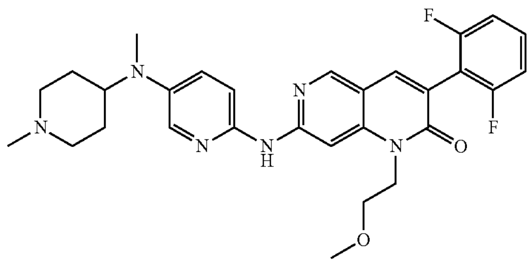 [SMILES: COCCn1c(=O)c(-c2c(F)cccc2F)cc2cnc(Nc3ccc(N(C)C4CCN(C)CC4)cn3)cc21] | <0.1 | <0.1 | <0.1 | <1 | 1-10 |
| 130 | 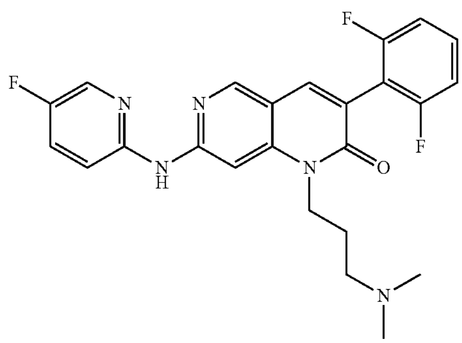 [SMILES: CN(C)CCCn1c(=O)c(-c2c(F)cccc2F)cc2cnc(Nc3ccc(F)cn3)cc21] | <0.1 | <0.1 | <0.1 | <1 | 1-10 |
| 131 | 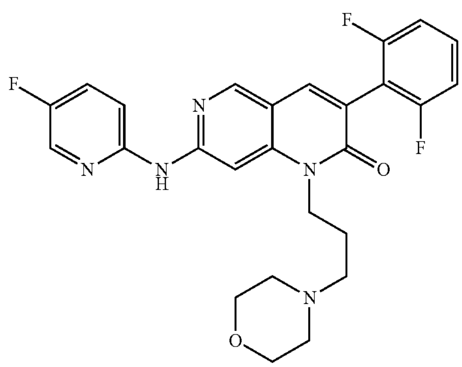 [SMILES: O=c1c(-c2c(F)cccc2F)cc2cnc(Nc3ccc(F)cn3)cc2n1CCCN1CCOCC1] | 0.1-1 | <0.1 | <0.1 | <1 | >10 |
| 132 | 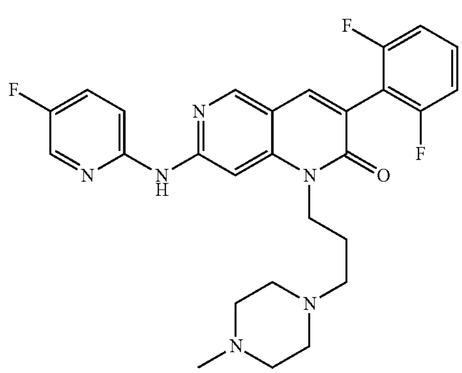 [SMILES: CN1CCN(CCCn2c(=O)c(-c3c(F)cccc3F)cc3cnc(Nc4ccc(F)cn4)cc32)CC1] | <0.1 | <0.1 | <0.1 | <1 | >10 |

TABLE 1-continued

| Compound | Structure | BTK IC$_{50}$ (µM) | Src IC$_{50}$ (µM) | Lyn IC$_{50}$ (µM) | DoHH2 EC$_{50}$ (µM) | Ramos EC$_{50}$ (µM) |
|---|---|---|---|---|---|---|
| 133 | 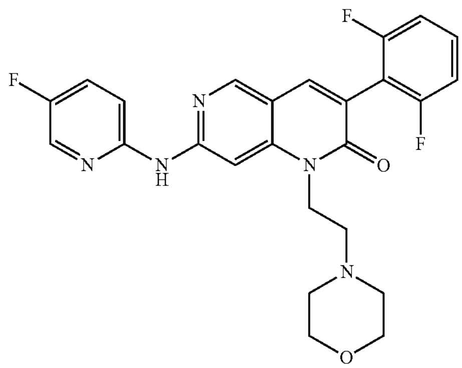 [SMILES: O=c1c(-c2c(F)cccc2F)cc2cnc(Nc3ccc(F)cn3)cc2n1CCN1CCOCC1] | <0.1 | <0.1 | <0.1 | <1 | >10 |
| 134 | 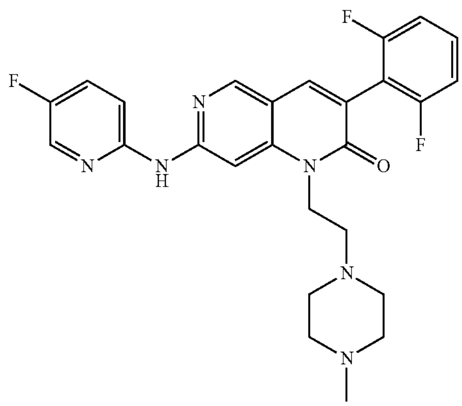 [SMILES: CN1CCN(CCn2c(=O)c(-c3c(F)cccc3F)cc3cnc(Nc4ccc(F)cn4)cc32)CC1] | <0.1 | <0.1 | <0.1 | <1 | 1-10 |
| 135 | 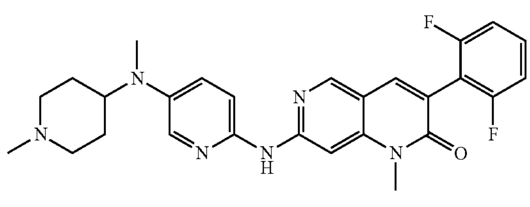 [SMILES: CN1CCC(N(C)c2ccc(Nc3cc4c(cn3)cc(-c3c(F)cccc3F)c(=O)n4C)nc2)CC1] | <0.1 | <0.1 | <0.1 | <1 | 1-10 |
| 136 | 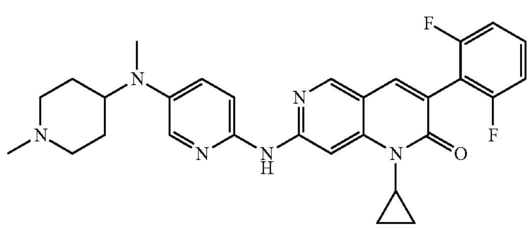 [SMILES: CN1CCC(N(C)c2ccc(Nc3cc4c(cn3)cc(-c3c(F)cccc3F)c(=O)n4C3CC3)nc2)CC1] | <0.1 | <0.1 | <0.1 | <1 | 1-10 |
| 137 | 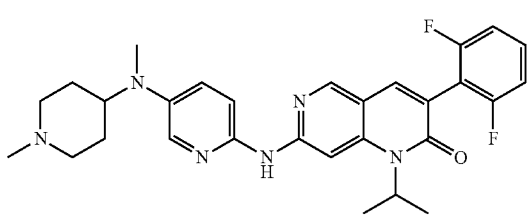 [SMILES: CC(C)n1c(=O)c(-c2c(F)cccc2F)cc2cnc(Nc3ccc(N(C)C4CCN(C)CC4)cn3)cc21] | <0.1 | <0.1 | <0.1 | <1 | 1-10 |

TABLE 1-continued
| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 138 | 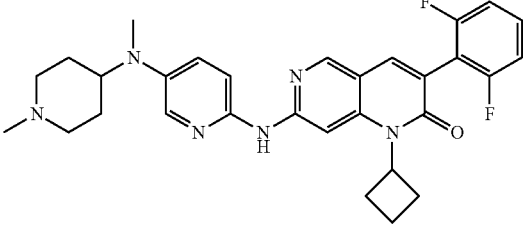 | <0.1 | <0.1 | <0.1 | <1 | 1-10 |
| 139 | 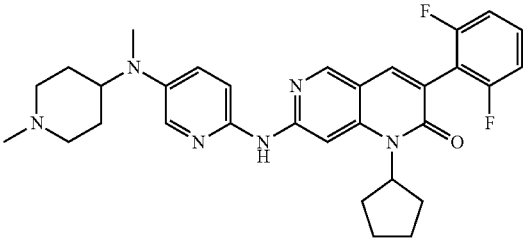 [SMILES: CN1CCC(N(C)c2ccc(Nc3cc4c(cn3)cc(-c3c(F)cccc3F)c(=O)n4C3CCCC3)nc2)CC1] | <0.1 | <0.1 | <0.1 | <1 | 1-10 |
| 140 | 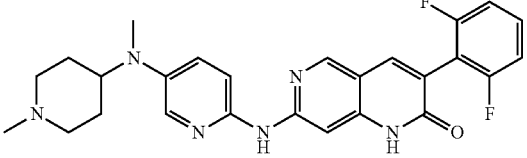 | <0.1 | <0.1 | <0.1 | <1 | 1-10 |
| 141 | 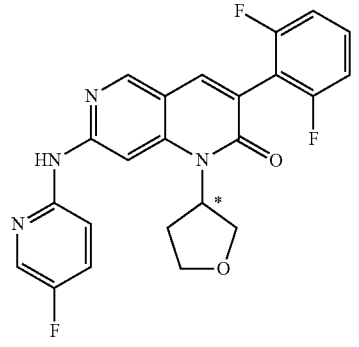 [SMILES: O=c1c(-c2c(F)cccc2F)cc2cnc(Nc3ccc(F)cn3)cc2n1C1CCOC1] | <0.1 | <0.1 | 0.1-1 | <1 | 1-10 |
| 142 | 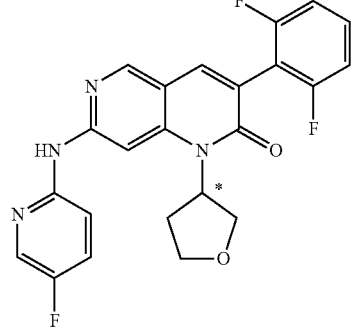 | <0.1 | <0.1 | <0.1 | <1 | 1-10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 143 | 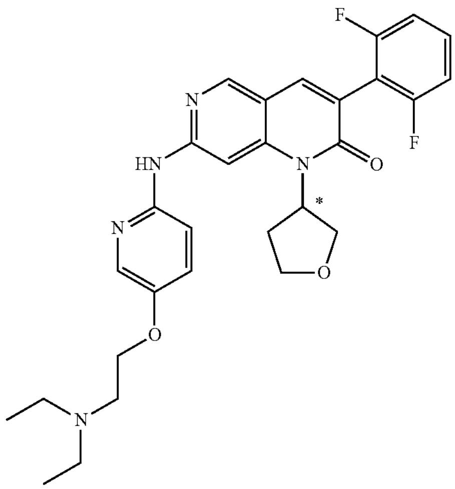 [SMILES: CCN(CC)CCOc1ccc(Nc2cc3c(cn2)cc(-c2c(F)cccc2F)c(=O)n3C2CCOC2)nc1] | <0.1 | <0.1 | <0.1 | <1 | >10 |
| 144 | 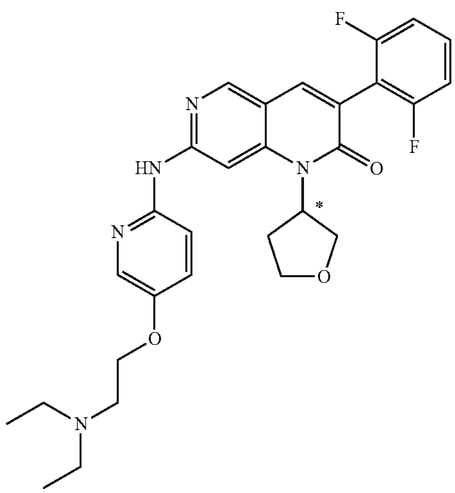 [SMILES: CCN(CC)CCOc1ccc(Nc2cc3c(cn2)cc(-c2c(F)cccc2F)c(=O)n3C2CCOC2)nc1] | <0.1 | <0.1 | <0.1 | <1 | 1-10 |
| 145 | 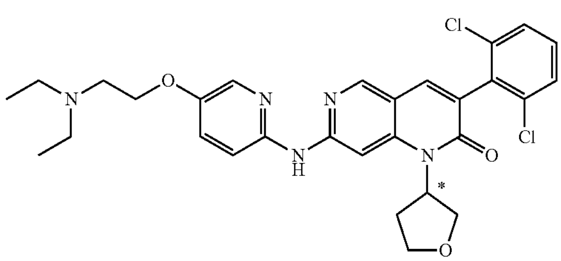 [SMILES: CCN(CC)CCOc1ccc(Nc2cc3c(cn2)cc(-c2c(Cl)cccc2Cl)c(=O)n3C2CCOC2)nc1] | <0.1 | <0.1 | <0.1 | <1 | 1-10 |
| 146 | 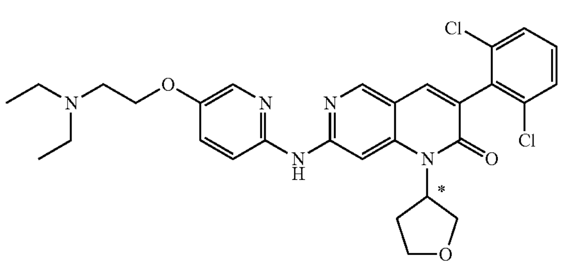 [SMILES: CCN(CC)CCOc1ccc(Nc2cc3c(cn2)cc(-c2c(Cl)cccc2Cl)c(=O)n3C2CCOC2)nc1] | <0.1 | <0.1 | <0.1 | <1 | 1-10 |

TABLE 1-continued
| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 147 | 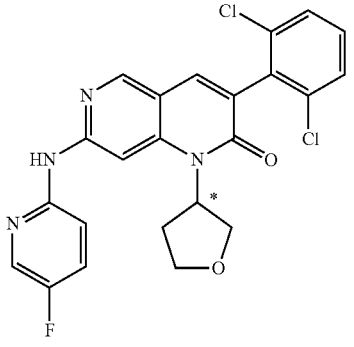 | <0.1 | <0.1 | <0.1 | <1 | >10 |
| 148 | 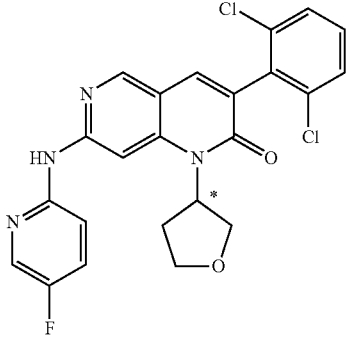 [SMILES: O=c1c(-c2c(Cl)cccc2Cl)cc2cnc(Nc3ccc(F)cn3)cc2n1C1CCOC1] | <0.1 | <0.1 | <0.1 | <1 | >10 |
| 149 | 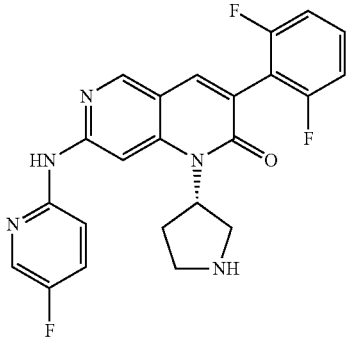 [SMILES: O=c1c(-c2c(F)cccc2F)cc2cnc(Nc3ccc(F)cn3)cc2n1[C@H]1CCNC1] | 0.1-1 | 1-5 | >5 | 1-10 | >10 |
| 150 | 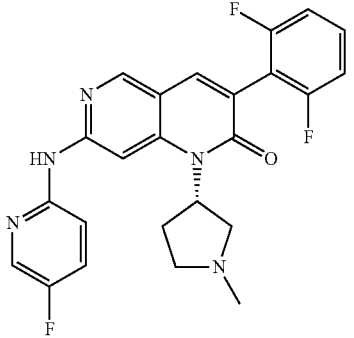 [SMILES: CN1CC[C@H](n2c(=O)c(-c3c(F)cccc3F)cc3cnc(Nc4ccc(F)cn4)cc32)C1] | <0.1 | 0.1-1 | 0.1-1 | 1-10 | >10 |

TABLE 1-continued

| Compound | Structure | BTK IC$_{50}$ (μM) | Src IC$_{50}$ (μM) | Lyn IC$_{50}$ (μM) | DoHH2 EC$_{50}$ (μM) | Ramos EC$_{50}$ (μM) |
|---|---|---|---|---|---|---|
| 151 | 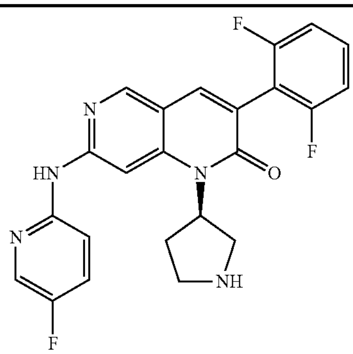 | 1-5 | 0.1-1 | 0.1-1 | 1-10 | >10 |
| 152 | 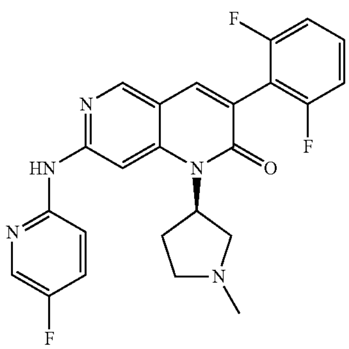 [SMILES: CN1CC[C@@H](n2c(=O)c(-c3c(F)cccc3F)cc3cnc(Nc4ccc(F)cn4)cc32)C1] | 0.1-1 | 0.1-1 | 0.1-1 | <1 | >10 |

Some compounds disclosed herein are potentially internal salts or zwitterions, because under physiological conditions a deprotonated acidic moiety in the compound, such as a carboxyl group, can be anionic, and this electronic charge might then be balanced off internally against the cationic charge of a protonated or alkylated basic moiety, such as a quaternary nitrogen atom.

Compounds disclosed herein may have asymmetric centers, chiral axes, chiral planes, etc., and may occur as racemates, racemic mixtures, stereoisomers, E/Z isomers, enantiomers, or diastereomers; each is within the scope of this disclosure.

For compounds disclosed herein which can exist as tautomers, both tautomeric forms are encompassed, even though only one tautomeric structure is depicted, as well as mixtures thereof.

Compounds disclosed herein may also exist as solvates (e.g., monohydrates, dihydrates, or alcoholates). Solvates of compounds disclosed herein are encompassed in this disclosure.

Salts

Salts of compounds described above can be used in the disclosed methods. If a compound has, for example, at least one basic center, it can form an acid addition salt. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1-C4)alkyl or arylsulfonic acids which are unsubstituted or substituted, for example by halogen, for example methyl- or p-toluene-sulfonic acid. Corresponding acid addition salts can also be formed having, if desired, an additionally present basic center. Compounds having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts can furthermore be formed. Salts which are unsuitable for pharmaceutical uses but which can be employed, for example, for the isolation or purification of free compounds or their pharmaceutically acceptable salts, are also included. In some embodiments salts of compounds which contain a basic group include monohydrochloride, hydrogensulfate, methanesulfonate, phosphate or nitrate. In some embodiments salts of compounds which contain an acid group include sodium, potassium and magnesium salts and pharmaceutically acceptable organic amines.

In some embodiments the salts are pharmaceutically acceptable (e.g., non-toxic, physiologically acceptable) salts. Pharmaceutically acceptable salts retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound in its free acid or base form with a suitable organic or inorganic base or acid, respectively, and isolating the salt thus formed during subsequent purification.

Prodrugs

This disclosure also provides prodrugs which are metabolized to active compounds after administration. For example, compounds disclosed herein can be modified, for example, with alkyl or acyl groups, sugars, or oligopeptides and which are rapidly cleaved in vivo to release the active compounds.

Derivatives of the corresponding aromatic alcohols can serve as prodrugs for aromatic aldehydes because alcohols and aldehydes are metabolically interconvertible, according to the following general scheme:

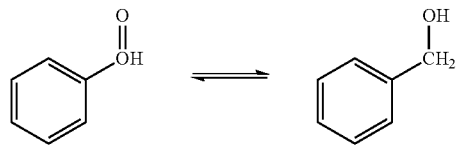

Scheline, 1972, *Xenobiotica*, 2, 227-36.

Examples of prodrugs of aldehydes, ketones, alcohols and other functional groups are described in Wermuth et al., 1996, *Designing Prodrugs and Bioprecursors I: Carrier Prodrugs. In The Practice of Medicinal Chemistry*, pp. 672-696; and in Wermuth, 1996, "Preparation of Water-Soluble Compounds by Covalent Attachment of Solubilizing Moieties," in Wermuth, ed., *The Practice of Medicinal Chemistry*, pp. 756-776. Other general aldehyde derivatives and alcohol derivatives that can perform prodrug functions as well as methods for their preparation are described in Cheronis et al., 1965, *Semimicro Qualitative Organic Analysis*, New York: Interscience, pp. 465-518.

Pharmaceutical Compositions

For convenience, "active agent" as used in the following descriptions of "Pharmaceutical Composition" and "Therapeutic Methods" encompasses compounds disclosed above; pharmaceutically acceptable salts of the disclosed compounds; mixtures of racemates, stereoisomers, E/Z isomers, enantiomers, and/or diastereomers; purified preparations of an individual racemate, stereoisomer, E/Z isomer, enantiomer, and/or diasteriomer; a solvate of a disclosed compound; and a prodrug of a disclosed compound.

Pharmaceutical compositions typically comprise at least one active agent mixed with a carrier, diluted with a diluent, and/or enclosed or encapsulated by an ingestible carrier in the form of a capsule, sachet, cachet, paper, or other container or by a disposable container such as an ampoule. A carrier or diluent can be a solid, semi-solid or liquid material. Some examples of diluents or carriers which can be employed in the disclosed pharmaceutical compositions are lactose, dextrose, sucrose, sorbitol, mannitol, propylene glycol, liquid paraffin, white soft paraffin, kaolin, microcrystalline cellulose, calcium silicate, silica polyvinylpyrrolidone, cetostearyl alcohol, starch, gum acacia, calcium phosphate, cocoa butter, oil of theobroma, arachis oil, alginates, tragacanth, gelatin, methyl cellulose, polyoxyethylene sorbitan monolaurate, ethyl lactate, propylhydroxybenzoate, sorbitan trioleate, sorbitan sesquioleate, and oleyl alcohol.

Pharmaceutical compositions can be manufactured by methods well known in the art, including conventional mixing, dissolving, granulating, dragee-making, levigating, emulsifying, encapsulating, entrapping, or lyophilizing processes.

For injection, an active agent can be formulated in aqueous solutions, preferably in physiologically compatible buffers such as acetate, Hanks's solution, Ringer's solution, or physiological saline buffer. Preferably the solutions are sterile and non-pyrogenic. For transmucosal administration, penetrants appropriate to the barrier to be permeated are used in the formulation. Such penetrants are generally known in the art.

For oral administration, an active agent can be combined with pharmaceutically acceptable carriers which enable the active agent to be formulated as tablets, pills, dragees, capsules, liquids, gels, syrups, slurries, suspensions and the like. Fillers can be used, such as gelatin, sugars (e.g., lactose, sucrose, mannitol, or sorbitol); cellulose preparations (e.g., maize starch, wheat starch, rice starch, potato starch, gum tragacanth, methyl cellulose, hydroxypropylmethyl-cellulose, sodium carboxymethylcellulose); and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agent doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, an active agent can be dissolved or suspended in suitable liquids, such as fatty oils, liquid paraffin, or liquid polyethylene glycols. In addition, stabilizers can be added. All formulations for oral administration preferably are in dosages suitable for such administration.

For buccal administration, the compositions can take the form of tablets or lozenges formulated in conventional manner.

For administration by inhalation, pharmaceutical compositions can be delivered in the form of an aerosol sprays from pressurized packs or a nebulizer, with the use of a suitable propellant, e.g., dichlorodifluoromethane, trichlorofluoromethane, dichlorotetrafluoroethane, carbon dioxide, or other suitable gas. If desired, a valve can be used to deliver a metered amount. Capsules and cartridges of e.g., gelatin for use in an inhaler or insufflator, can be formulated containing a powder mix of an active agent and a suitable powder base such as lactose or starch.

An active agent can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical compositions for parenteral administration include aqueous solutions of an active agent. Additionally, suspensions of an active agent can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of an active agent to allow for the preparation of highly concentrated solutions.

Alternatively, the active ingredient can be in powder form for constitution with a suitable vehicle, e.g., sterile pyrogen-free water, before use.

An active agent can also be formulated in rectal compositions such as suppositories or retention enemas, e.g., containing conventional suppository bases such as cocoa butter or other glycerides.

In addition to the compositions described previously, an active agent can also be formulated as a depot preparation. Such long acting compositions can be administered by implantation (for example subcutaneously or intramuscularly) or by intramuscular injection. Thus, for example, an active agent can be formulated with suitable polymeric or hydrophobic materials (for example as an emulsion in an acceptable oil) or ion exchange resins, or as sparingly soluble derivatives, for example, as a sparingly soluble salt.

A pharmaceutical compositions also can comprise suitable solid or gel phase carriers or excipients. Examples of such carriers or excipients include but are not limited to, calcium carbonate, calcium phosphate, various sugars, starches, cellulose derivatives, gelatin, and polymers such as polyethylene glycols.

In addition to the common dosage forms set out above, active agents disclosed herein can also be administered by controlled release means and/or delivery devices including ALZET® osmotic pumps which are available from Alza Corporation. Suitable delivery devices are described in U.S. Pat. Nos. 3,845,770; 3,916,899; 3,536,809; 3,598,123; 3,944,064 and 4,008,719.

Methods of Inhibition

The amino naphthyridinones can be used in methods of inhibiting kinase activity, signal transduction, and generation of downstream signal mediators. Kinases that can be inhibited include BTK, SRC, and LYN as well as those kinases for which inhibitory activity is described in Example 57. The method of inhibition can be for single kinase or for the simultaneous inhibition of two, three, or more of such kinases. Similarly other downstream biochemical activities can be inhibited indirectly as described above, including PLC-γ activity (as in Examples 82) and PI3K activity, as well as inhibition of the generation of the products of such reactions (such as phosphorylated kinases as in Example 83, or PI3). Further methods of inhibition include the inhibition of immunologic function (such as inhibition of degranulation as in Example 86 or antibody secretion) cellular proliferation (as through the induction of cell cycle arrest as in Example 80), cellular survival (as through the inductioin of apoptosis as in Example 81) or tumor growth (as demonstrated in Example 85). Such methods of inhibition can be applied as therapeutic methods and uses.

Such methods of inhibition involve contacting the kinase(s) with an amino naphthyridinones which can be provided in the form of a salt, solvate, or prodrug, any of which may be a component of a pharmaceutical composition. The contacting may take place in a cell-free system, e.g. a cell lysates or a system constituted of purified or partially purified components; in a cell; in vitro; or in a patient. Choice of appropriate compounds and concentrations for any particular purpose can be guided by such data as contained in Tables 1 and 2, as well as the Examples in general.

Therapeutic Methods and Uses

The amino naphthyridinone compounds can be administered to a human or veterinary patient, either alone or in pharmaceutical compositions where they are mixed with suitable carriers or excipient(s) at doses to treat or ameliorate any disease or disorder associated with the activation of the inhibited kinases such as those herein described. BTK inhibitors developed for humans are known to be effective against spontaneous lymphomas, so veterinary applications in mammals are also contemplated. Such conditions include blood-related cancers (e.g., lymphomas and leukemias) allergic, inflammatory and autoimmune disorders. Reduction of intracellular kinase activity also is useful to suppress the immune system of transplant patients prior to, during, and/or after transplant. Certain solid tumors, for example those in which BMX and/or SRC are activated, can also be treated. For each embodiment comprising an amino naphthyridinone or group of amino naphthyridinones there are corresponding methods of treatment and uses.

Throughout this specification the advantages of inhibiting particular combinations of kinases are described. The compounds can thus be used in the treatment of diseases generally associated with the expression or activation of such a combination of kinases and a patient can be selected for treatment on that basis. Alternatively, a patient may be selected for treatment because such a combination of kinases is determined to be expressed or activated in their tissue associated with the disease state (for example a tumor or pathologically active lymphocytes or granulocytes such as basophils or mast cells). The foregoing notwithstanding in alternative embodiments the compound is used to treat a disease or disorder on the basis of the expression or activation of a single kinase that it inhibits, such expression or activation being either generally known or individually determined.

Several of the amino naphthyridinone compounds show activity in inhibiting the proliferation of the drug-resistant cell line Ramos. Thus in some embodiments they are used to treat patients with cancers that are or have become resistant to dasatinib [or other drugs with to which Ramos is resistant]. In various aspects of these embodiments the amino thryridinone has an $EC_{50}$ measured as inhibition of Ramos proliferation of <10, <5, <3, <2, <1, <0.5, <0.2, or <0.1 µM. For example Compounds 1, 2, 4, 13, 15-17, 19, 21-25, 27, 28, 30, 31, 34, 39, 42-44, 46, 47, 53, 55, 56, 61-63, 66, 67, 73-75, 79, 83, 87, 88-89, 92-101, 104-105, 109-111, 115-116, 118-123, 129-130, 134-142, and, 144-146 each have $EC_{50}$ measured as inhibition of Ramos proliferation of <10 and Compounds 4, 42, 88, and 89 each have $EC_{50}$ measured as inhibition of Ramos proliferation of <1.

Other embodiments provide methods of treatment involving administration of effective doses of a compound that inhibits signaling through either or both the PLC-γ and PI3 kinase arms of the signaling network to a patient in need thereof. In various embodiments the patient in need thereof has a tumor that expresses a targeted kinase disposed in one, the other, or both of these pathways.

In some embodiments the patient has a B cell malignancy, for example, the tumor is a myeloma or B cell derived leukemia or lymphoma, or a mast cell malignancy, for example, a mastocytoma, and an amino naphthyridinone is used to treat the condition. In one aspect of these embodiments the tumor cells express BTK. These cells can express a basal or elevated level of BTK activity. In some embodiments patients can be selected for treatment on the basis of having BTK expression, a basal level of activity, or an elevated level of activity. In another aspect of these embodiments the tumor cells express LYN. These cells can express a basal or elevated level of LYN activity. In some embodiments patients can be selected for treatment on the basis of having LYN expression, a basal level of activity, or an elevated level of activity. In yet another aspect of these embodiments the tumor cells express SRC. These cells can express a basal or elevated level of SRC activity. In some embodiments patients can be selected for treatment on the basis of having SRC expression, a basal level of activity, or an elevated level of activity.

In alternative embodiments the tumor is a solid tumor, that is, a carcinoma or sarcoma. BTK activation can be associated with pancreatic and colon cancer, clear cell renal cell carcinoma, and thyroid tumors. LYN activation can be associated with pancreatic, prostate, breast, ovarian, and colon cancer, sarcoma, and Ewing's glioblastoma. SRC activation can be associated with prostate, breast, lung and colon cancer, glioma, melanoma, thyroid tumors and sarcoma, including osteosarcoma. HCK has been associated with thyroid tumors and clear cell renal cell carcinoma. Similarly other solid tumors not necessarily expressing BTK but expressing BMX are the object of further embodiments related to the treatment of cancers including, for example, breast cancer, bladder cancer, glioblastoma, prostate cancer, small-cell lung cancer, and hepatocellular cancer.

In further embodiments the patient in need thereof has a B cell-related pathology for example a B cell lymphoma, a B cell leukemia, a B cell-based autoimmune disorder, and the like.

Lymphomas are malignant growths of B or T cells in the lymphatic system, including Hodgkin's lymphoma and non-Hodgkin's lymphoma. Non-Hodgkin's lymphomas include cutaneous T cell lymphomas (e.g., Sezary syndrome and Mycosis fungoides), diffuse large cell lymphoma, HTLV-1 associated T cell lymphoma, nodal peripheral T cell lymphoma, extranodal peripheral T cell lymphoma, central nervous system lymphoma, and AIDS-related lymphoma.

Leukemias include acute and chronic types of both lymphocytic and myelogenous leukemia (e.g, acute lymphocytic or lymphoblastic leukemia, acute myelogenous leukemia, acute myeloid leukemia, chronic myelogenous leukemia, chronic lymphocytic leukemia, T cell prolymphocytic leukemia, adult T cell leukemia, and hairy cell leukemia).

Allergic hypersensitivity disorders include allergic rhinitis, dermatitis, anaphylactic reaction, and passive cutaneous anaphylaxis. Inflammatory disorders include synovitis, inflammatory bowel disease, and ulcerative colitis. Autoimmune disorders include systemic lupus erythematosus, anti-phospholipid antibody syndrome, multiple sclerosis, ulcerative colitis, Crohn's disease, rheumatoid arthritis, asthma, Hashimoto's thyroiditis, Reiter's syndrome, Sjögren's syndrome, Guillain-Barré syndrome, myasthenia gravis, large vessel vasculitis, medium vessel vasculitis, polyarteritis nodosa, pemphigus vulgaris, scleroderma, Goodpasture's syndrome, glomerulonephritis, primary biliary cirrhosis, Grave's disease, membranous nephropathy, autoimmune hepatitis, celiac sprue, Addison's disease, polymyositis, dermatomyositis, monoclonal gammopathy, Factor VIII deficiency, cryoglobulinemia, peripheral neuropathy, IgM polyneuropathy, chronic neuropathy, autoimmune hemolytic anemia, autoimmune thrombocytopenic purpura, pernicious anemia, ankylosing spondylitis, vasculitis, inflammatory bowel disease, and type I diabetes mellitus. The autoimmune disease may involve a secretory cell, such as a T lymphocyte, B lymphocyte, Mast cell, or dendritic cell. Compounds of the invention also can be used to treat patients who undergo protein replacement therapies and who develop antibodies to the replacement.

Routes of Administration

Pharmaceutical preparations of the invention can be administered locally or systemically. Suitable routes of administration include oral, pulmonary, rectal, transmucosal, intestinal, parenteral (including intramuscular, subcutaneous, intramedullary routes), intranodal, intrathecal, direct intraventricular, intravenous, intraperitoneal, intranasal, intraocular, transdermal, topical, and vaginal routes. As described in more detail above, dosage forms include, but are not limited to, tablets, troches, dispersions, suspensions, suppositories, solutions, capsules, creams, patches, minipumps and the like. Targeted delivery systems also can be used (for example, a liposome coated with target-specific antibody).

Dosage

A pharmaceutical composition of the invention comprises at least one active ingredient in a therapeutically effective amount. A "therapeutically effective dose" is the amount of an active agent which, when administered to a patient, results in a measurable improvement in a characteristic of the disease being treated (e.g., improved laboratory values, retarded development of a symptom, reduced severity of a symptom, improved levels of a biological marker such as CD25a or IL2). The improvement can be evident after a single administration of the therapeutically effective dose. More usually multiple administrations are utilized in order to achieve or maintain optimal effect. In preferred embodiments frequency of administration can range from twice a month to once a week to one or more times a day, for example 1-4 times a day. In alternative embodiments administration can be by time-release formulations, or extended or continuous infusions. The frequency of administration can be selected to achieve a systemic or local concentration at or above some predetermined level for a period of time. The period of time can be all or a substantial portion of the interval between administrations or comprise the period of time-release or infusion. In some embodiments, the treatment schedule can require that a concentration of the compound be maintained for a period of time (e.g., several days or a week) and then allowed to decay by ceasing administration for a period of time (e.g., 2, 3, 4, 5, or more days up to 1, 2, or 3 weeks).

Determination of therapeutically effective amounts is well within the capability of those skilled in the art. A therapeutically effective dose initially can be estimated from in vitro enzyme assays, cell culture assays and/or animal models. For example, a dose can be formulated in an animal model to achieve a circulating concentration range that includes the $IC_{50}$ as determined in an in vitro enzyme assay or in a cell culture (i.e., the concentration of the test compound which achieves a half-maximal inhibition of SFK or BTK activity). Similarly, a dose can be formulated to achieve a blood concentration that includes the $EC_{50}$ as determined in, for example, a cell proliferation assay in cell culture or a tumor growth assay in an animal model. Such information can be used to more accurately determine useful doses in humans.

Appropriate animal models for the relevant diseases are known in the art. See, e.g., *Exp Hematol.* 34, 284-88, 2006 (aggressive systemic mastocytosis and mast cell leukemia); *Leuk. Lymphoma.* 47, 521-29, 2006 (acute myeloid leukemia); *Leuk. Lymphoma.* 7, 79-86, 1992 (disseminated human B-lineage acute lymphoblastic leukemia and non-Hodgkins lymphoma); *J. Virol.* 79, 9449-57, 2006 (adult T-cell leukemia); *Neoplasia* 7, 984-91, 2005 (lymphoma); *Oligonucleotides* 15, 85-93, 005 (lymphoma); *Transfus. Apher. Sci.* 32, 197-203, 2005 (cutaneous T cell lymphoma); *Nature* 17, 254-56, 1991 (follicular lymphoma and diffuse large cell lymphoma); *Cell. Mol. Immunol.* 2, 461-65, 2005 (myasthenia gravis); *Proc. Natl. Acad. Sci. USA* 102, 11823-28, 2005 (type I diabetes); *Arthritis Rheum.* 50, 3250-59, 2004 (lupus erythymatosus); *Clin. Exp. Immunol.* 99, 294-302, 1995 (Grave's disease); *J. Clin. Invest.* 116, 905-15, 2006 (multiple sclerosis); *Pharmacol Res.* e-published Feb. 1, 2006 (ulcerative colitis); *J. Pathol.* e-published Mar. 21, 2006 (Crohn's disease); *J. Clin. Invest.* 116, 961-973, 2006 (rheumatoid arthritis); *Endocrinol.* 147, 754-61, 2006 (asthma); *Exp Mol Pathol.* 77, 161-67, 2004 (Hashimoto's thyroiditis); *J. Rheumatol. Suppl.* 11, 114-17, 1983 (Reiter's syndrome); *Rheumatol.* 32, 1071-75, 2005 (Sjögren's syndrome); *Brain Pathol.* 12, 420-29, 2002 (Guillain-Barré syndrome); *J. Clin. Invest.* 110, 955-63, 2002 (vessel vasculitis); *Vet. Pathol.* 32, 337-45, 1995 (polyarteritis nodosa); *Immunol. Invest.* 3, 47-61, 2006 (pemphigus vulgaris); *Arch. Dermatol. Res.* 297, 333-44, 2006 (scleroderma); *J. Exp. Med.* 191, 899-906, 2000 (Goodpasture's syndrome); *J. Vet. Med. Sci.* 68, 65-68, 2006 (glomerulonephritis); *Liver Int.* 25, 595-603, 2005 (primary biliary cirrhosis); *Clin. Exp. Immunol.* 99, 294-302, 1995 (Grave's disease); *J. Clin. Invest.* 91, 1507-15, 1993 (membranous nephropathy); *J. Immunol.* 169, 4889-96, 2002 (autoimmune hepatitis); *Isr. J. Med. Sci.* 15, 348-55, 1979 (celiac sprue); *Surgery* 128, 999-1006, 2000 (Addison's disease); *J. Neuroimmunol.* 98, 130-35, 1999 (polymyositis); *Am. J. Pathol.* 120, 323-25, 1985 (dermatomyositis); *Bone* 20, 515-20, 1997 (monoclonal gammopathy); *Haemophilia* 11, 227-32, 2005 (Factor VIII deficiency); *Proc. Natl. Acad. Sci. USA* 94, 233-36, 1997 (cryoglobulinemia); *Pain* 110, 56-63, 2004 (peripheral neuropathy); *Ann. Neurol.* 49, 712-20, 2001 (IgM polyneuropathy); *J. Neurosci. Res.* 44, 58-65, 1996 (chronic neuropathy); *Eur. J. Immunol.* 32, 1147-56, 2002 (autoimmune hemolytic anemia); *Haematologica* 88, 679-87, 2003 (autoimmune thrombocytopenic purpura); *Curr. Top. Microbiol. Immunol.* 293, 153-77, 2005 (pernicious anemia); *J. Immunol.* 175, 2475-83, 2005 (ankylosing spondylitis); *Inflamm. Res.* 53, 72-77, 2004 (vasculitis); *Vet. Pathol.* 43, 2-14, 2006 (inflammatory bowel disease); and *J. Biol. Chem.* 276,-13821, 2001 (anti-phospholipid antibody syndrome).

$LD_{50}$ (the dose lethal to 50% of the population) and the $ED_{50}$ (the dose therapeutically effective in 50% of the population) can be determined by standard pharmaceutical procedures in cell cultures and/or experimental animals. Data obtained from cell culture assays or animal studies can be used to determine initial human doses. As is known in the art, the dosage may vary depending upon the dosage form and route of administration used.

As is well known, the FDA guidance document "Guidance for Industry and Reviewers Estimating the Safe Starting Dose in Clinical Trials for Therapeutics in Adult Healthy Volunteers" (HFA-305) provides an equation for use in calculating a human equivalent dose (HED) based on in vivo animal studies. Based on the studies described in Example 85, below, the human equivalent dose ranges between 1.5 mg/kg and 8 mg/kg, with some compounds showing considerable efficacy at lower or higher doses than those estimated by the HED. Thus, human dosages for systemic administration can range from, e.g., 1.5 mg/kg to 3 mg/kg; 2 mg/kg to 4 mg/kg; 5 mg/kg to 7 mg/kg; and 4 mg/kg to 8 mg/kg. The amount of composition administered will, of course, be dependent on the subject being treated, on the subject's weight, the severity of the disorder, the manner of administration and the judgment of the prescribing physician.

Embodiment Groups

445. In some embodiments, compounds, or pharmaceutically acceptable salts, solvates, or prodrugs thereof, of Embodiment Groups 1-441 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, or 441) or any combination thereof, are used to treat a B cell malignancy or are used in the preparation of a medicament to treat a B cell malignancy.

446. In some embodiments, compounds or pharmaceutically acceptable salts of compound 86, 87, 88, 89, 90, and 91, or any combination thereof, are used to treat a B cell malignancy or are used in the preparation of a medicament to treat a B cell malignancy.

447. In some embodiments of Embodiment Groups 445 and 446, the B cell malignancy is a myeloma, a B cell derived leukemia or lymphoma, or a mast cell malignancy.
448. In some embodiments of Embodiment Group 447, the B cell malignancy is a mastocytoma.
449. In some embodiments of Embodiment Groups 445, 446, 447, or 448, cells of the malignancy express BTK.
450. In some embodiments of Embodiment Groups 445, 446, 447, 448, or 449, cells of the malignancy express LYN
451. In some embodiments of Embodiment Groups 445, 446, 447, 448, 449, or 450, cells of the malignancy express SRC.
452. In some embodiments, compounds, or pharmaceutically acceptable salts thereof, of Embodiment Groups 1-441 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, or 441) or any combination thereof, are used to treat a solid tumor or are used in the preparation of a medicament to treat a solid tumor.
453. In some embodiments, compounds or pharmaceutically acceptable salts of compound 86, 87, 88, 89, 90, and 91, or any combination thereof, are used to treat a solid tumor or are used in the preparation of a medicament to treat a solid tumor.
454. In some embodiments of Embodiment Groups 452 and 453, the solid tumor is a carcinoma or sarcoma.
455. In some embodiments of Embodiment Group 454, the solid tumor is selected from the group consisting of a pancreatic cancer, a colon cancer, a clear cell renal cell carcinoma, and a thyroid tumor.
456. In some embodiments of Embodiment Group 454, the solid tumor is selected from the group consisting of a pancreatic tumor, a prostate tumor, a breast tumor, an ovarian tumor, a colon tumor, a sarcoma, and Ewing's glioblastoma.
457. In some embodiments of Embodiment Group 454, the solid tumor is selected from the group consisting of a prostate tumor, a breast tumor, a lung tumor, a colon tumor, a glioma, a melanoma, a thyroid tumor, a sarcoma, and an osteosarcoma.
458. In some embodiments of Embodiment Group 454, the solid tumor is selected from the group consisting of a thyroid tumor and a clear cell renal cell carcinoma.
459. In some embodiments, compounds, or pharmaceutically acceptable salts thereof, of Embodiment Groups 1-441 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, or 441) or any combination thereof, are used to treat a B cell-related pathology or are used in the preparation of a medicament to treat a B cell-related pathology.
460. In some embodiments, compounds or pharmaceutically acceptable salts of compound 86, 87, 88, 89, 90, and 91, or any combination thereof, are used to treat a B cell-related pathology or are used in the preparation of a medicament to treat a B cell-related pathology.
461. In some embodiments of Embodiment Groups 459 or 460, the B cell-related pathology is a B cell lymphoma, a B cell leukemia, or a B cell-based autoimmune disorder.
462. In some embodiments, compounds, or pharmaceutically acceptable salts thereof, of Embodiment Groups 1-441 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, or 441) or any combination thereof, are used to treat a lymphoma or are used in the preparation of a medicament to treat a lymphoma.

463. In some embodiments, compounds or pharmaceutically acceptable salts of compound 86, 87, 88, 89, 90, and 91, or any combination thereof, are used to treat a lymphoma or are used in the preparation of a medicament to treat a lymphoma.

464. In some embodiments of Embodiment Group 463, the lymphoma is selected from the group consisting of Hodgkin's lymphoma and non-Hodgkin's lymphoma. Non-Hodgkin's lymphomas include cutaneous T cell lymphomas (e.g., Sezary syndrome and Mycosis fungoides), diffuse large cell lymphoma, HTLV-1 associated T cell lymphoma, nodal peripheral T cell lymphoma, extranodal peripheral T cell lymphoma, central nervous system lymphoma, and AIDS-related lymphoma.

465. In some embodiments, compounds, or pharmaceutically acceptable salts thereof, of Embodiment Groups 1-441 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, or 441) or any combination thereof, are used to treat a leukemia or are used in the preparation of a medicament to treat a leukemia.

466. In some embodiments, compounds or pharmaceutically acceptable salts of compound 86, 87, 88, 89, 90, and 91, or any combination thereof, are used to treat a leukemia or are used in the preparation of a medicament to treat a leukemia.

467. In some embodiments of Embodiment Groups 465 or 466, the leukemia is selected from the group consisting of acute lymphocytic or lymphoblastic leukemia, acute myelogenous leukemia, acute myeloid leukemia, chronic myelogenous leukemia, chronic lymphocytic leukemia, T cell prolymphocytic leukemia, adult T cell leukemia, and hairy cell leukemia.

468. In some embodiments, compounds, or pharmaceutically acceptable salts thereof, of Embodiment Groups 1-441 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, or 441) or any combination thereof, are used to treat an autoimmune disorder or are used in the preparation of a medicament to treat an autoimmune disorder.

469. In some embodiments, compounds or pharmaceutically acceptable salts of compound 86, 87, 88, 89, 90, and 91, or any combination thereof, are used to treat an autoimmune disorder or are used in the preparation of a medicament to treat an autoimmune disorder.

470. In some embodiments of Embodiment Group 468 or 469, the autoimmune disorder is selected from the group consisting of systemic lupus erythematosus, anti-phospholipid antibody syndrome, multiple sclerosis, ulcerative colitis, Crohn's disease, rheumatoid arthritis, asthma, Hashimoto's thyroiditis, Reiter's syndrome, Sjögren's syndrome, Guillain-Barré syndrome, myasthenia gravis, large vessel vasculitis, medium vessel vasculitis, polyarteritis nodosa, pemphigus vulgaris, scleroderma, Goodpasture's syndrome, glomerulonephritis, primary biliary cirrhosis, Grave's disease, membranous nephropathy, autoimmune hepatitis, celiac sprue, Addison's disease, polymyositis, dermatomyositis, monoclonal gammopathy, Factor VIII deficiency, cryoglobulinemia, peripheral neuropathy, IgM polyneuropathy, chronic neuropathy, autoimmune hemolytic anemia, autoimmune thrombocytopenic purpura, pernicious anemia, ankylosing spondylitis, vasculitis, inflammatory bowel disease, and type I diabetes mellitus.

471. In some embodiments of Embodiment Group 468 or 469, the autoimmune disorder involves a secretory cell, such as a T lymphocyte, B lymphocyte, Mast cell, or dendritic cell.

472. In some embodiments of Embodiment Group 468 or 469, the autoimmune disorder is an antibody response developed in response to a protein replacement therapy.

In some embodiments, compounds, or pharmaceutically acceptable salts thereof, of Embodiment Groups 1-441 (i.e., Embodiment Groups 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, or 441) or any combination thereof, are used to treat allergic, immune, or inflammatory diseases, such as systemic lupus erythematosus (SLE), rheumatoid arthritis (RA), synovitis, and immune hypersensitivity responses (e.g., allergic rhinitis, dermatitis, anaphylactic reaction, and passive cutaneous anaphylaxis).

All patents, patent applications, and references cited in this disclosure are expressly incorporated herein by reference. A more complete understanding of this disclosure can be obtained by reference to the following specific Examples, which are provided for purposes of illustration only and are not intended to limit the scope of the invention.

EXAMPLE 1

General Method

All commercially available reagents were used as received unless otherwise stated. Anhydrous solvents were pre-treated with a 3A MS column. Solvent mixtures are given as volume to volume ratios. Chemical shifts (δ) are reported in parts-per-million (ppm) relative to the residual solvent signals. Coupling constants (J-values) are expressed in Hz.

For Compound 1 through 91: Chromatographic purifications were done via flash chromatography column using 100~200 mesh silica gel. NMR spectra were recorded on a Bruker Avance spectrometer, 400 MHz for $^1$H NMR and 100 MHz for $^{13}$C NMR. LCMS were taken on a quadrupole Mass Spectrometer on a Shimadzu LCMS 2010 (Column: sepax ODS 50×2.0 mm, 5 um) or an Agilent 1200 HPLC, 1956 MSD (Column: Shim-pack XR-ODS 30×3.0 mm, 2.2 um) operating in ES (+) ionization mode.

For Compounds 92 through 152: chromatographic purifications were done via flash chromatography column using 100-200 mesh 40 A silica gel. Reactions were monitored by TLC on DC Kieselgel 60 $F_{254}$ plates coated with 60$F_{254}$ silica gel containing a fluorescent indicator. Spot visualization was achieved using UV light. Microwave-assisted reactions were performed on a Biotage Initiator. Hydrogenation reactions were performed on a standard Parr hydrogenation apparatus. NMR spectra were recorded on a Mercury Plus console operating at 400 MHz for $^1$H NMR and using an IDPFG probe.

HPLC was performed on a Waters Acquity UPLC or a Waters Alliance 2695 HPLC both equipped with PDA detectors. The columns used were Acquity BEH C18, 100× 2.1 mm, 1.7 μm (for mobile phases consisting of 0.025%

TFA in water and 0.025% TFA in acetonitrile with varying ratios) or X-bridge C18, 100×4.6 mm, 5 μm (for mobile phases consisting of 0.01M ammonium bicarbonate and acetonitrile in varying ratios).

Preparative HPLC purifications were performed on an Agilent 1200 series Semi Prep with DAD detector or a Waters Prep with PDA detector or a Gilson Prep HPLC with Dual wavelength detector. The columns used were C18 stationary phase with dimensions of 250×30 mm and 150× 20 mm with 5 μm and 10 μm particle size. The mobile phases used were 0.1% formic acid in acetonitrile or 0.01M ammonium bicarbonate in acetonitrile or 0.01M ammonium acetate in acetonitrile in varying ratios.

Chiral preparative HPLC purifications were performed on a Gilson Prep HPLC with dual wavelength detector. The columns used were Chiralpak-AD-H (250×30 mm), Chiralpak-IC (250×30 mm) or Chiralcel OJ-H (250×30 mm). The mobile phases used were a combination of hexane and ethanol with different additives such as TFA or DEA based on solubility and separation.

LCMS was performed on a Waters Quattro Micro Triple Quad with PDA detector or an Agilent 1200 series Ion Trap mass spectrometer operating in ES (+) or ES (−) ionization mode. The columns used were Acquity BEH C18 50×2.1 mm, 1.7 μm (for mobile phases consisting of 0.025% TFA in water and 0.025% TFA in acetonitrile with varying ratios) or X-bridge C18, 150×4.6 mm, 3.5 μm (for mobile phases consisting of 0.01M ammonium bicarbonate and acetonitrile in varying ratios).

EXAMPLE 2

Synthesis of Compound 1

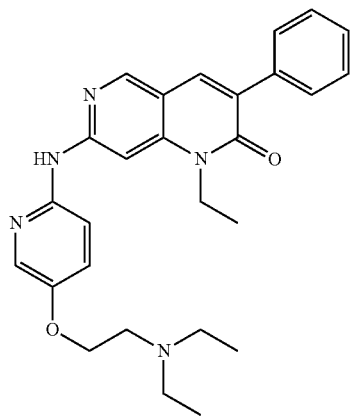

Compound 1

Compound 1, 7-[5-(2-Diethylamino-ethoxy)-pyridin-2-ylamino]-1-ethyl-3-phenyl-1H-[1,6]naphthyridin-2-one was synthesized as shown in Scheme 1 as a general procedure:

Scheme 1

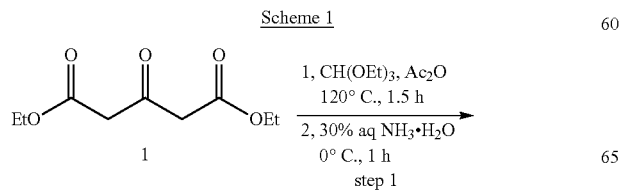

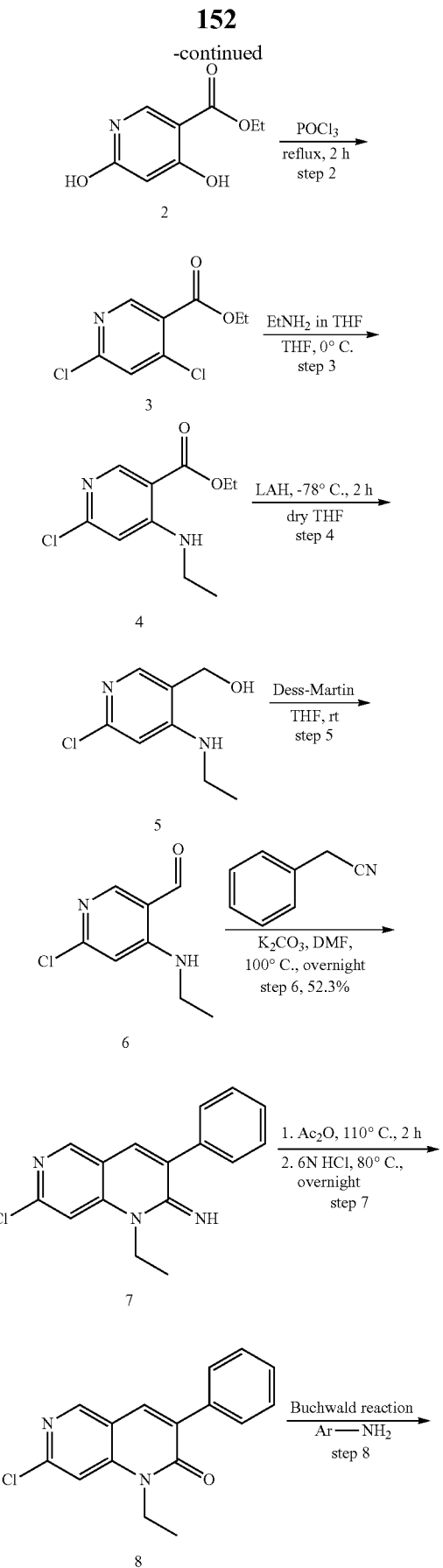

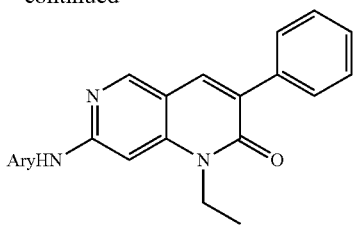

A mixture of scheme 1 compound 1 (50.0 g, 247.5 mmol), triethyl orthofomate (40.3 g, 272.3 mmol) and acetic anhydride (50.5 g, 495.0 mmol) was heated at 120° C. for 1.5h with vigorous stirring. The dark yellow solution was cooled in an ice bath, and mixed with ammonia (20 mL, 30% water solution). The resulting mixture was stirred at 0° C. for 1 h. A yellow solid formed in the mixture. After the mixture was acidified with 2N HCl to pH=5, a white solid formed. The mixture was filtered, washed with water and air dried to give scheme 1 compound 2 (10.0 g, yield: 22.0%) as a white solid. $^1$H NMR (400 MHz, MeOD): δ 8.16 (s, 1H, ArH), 5.79 (s, 1H, ArH), 4.38 (q, J=7.2 Hz, 2H, $CH_2$), 1.37 (t, J=7.2 Hz, 3H, $CH_3$).

A mixture of scheme 1 compound 2 (8.01 g, 43.7 mmol) and $POCl_3$ (70 mL, 751.1 mmol) was stirred at 110° C. for 2 h. TLC showed the starting material was consumed completely. After cooling down, most of $POCl_3$ was removed under vacuum. The residue was mixed with ice-water, and neutralized with sodium carbonate solution. The resulting mixture was extracted with ethyl acetate. The organic layer was washed with brine and dried over anhydrous $Na_2SO_4$, concentrated to give scheme 1 compound 3 (8.7 g) as a brown solid which was used in the next step immediately without further purification.

To a solution of scheme 1 compound 3 (7.5 g, 31.1 mmol) in THF (40 mL) was added $EtNH_2$ in THF (64 mL, 170.4 mmol) at 0° C. The mixture was stirred at 0° C. for 30 min and warmed to room temperature after stirring for 2 h. TLC showed the starting material was consumed completely. After the solvent was removed, scheme 1 compound 4 was obtained (7.58 g) as a yellow solid, which was used in the next step immediately without further purification. $^1$H NMR (400 MHz, $CDCl_3$): δ 8.64 (s, 1H, ArH), 8.05 (brs, 1H, NH), 6.51 (s, 1H, ArH), 4.32 (q, J=7.2 Hz, 2H, $CH_2$), 3.25-3.18 (m, 2H, $CH_2$), 1.38 (t, J=7.2 Hz, 3H, $CH_3$), 1.30 (t, J=7.2 Hz, 3H, $CH_3$).

Scheme 1 compound 4 (6.6 g, 28.8 mmol) was dissolved in THF (50 mL) and cooled to −78° C. To this solution, $LiAlH_4$ (2.3 g, 60.4 mmol) in THF (60 mL) was added drop-wise. The resulting mixture was stirred at −78° C. for 3 h, then warmed up to room temperature. TLC showed the starting material was consumed completely. Small amount of MeOH/ethyl acetate (1/1) mixture was added slowly to the reaction mixture to quench the excess $LiAlH_4$. The reaction mixture was filtered and the solid was washed with ethyl acetate. The combined filtrate was concentrated to give the crude product which was purified by silica gel chromatography (PE/EA=10/1 to 5/1) to give scheme 1 compound 5 (4.5 g, yield: 83.7%) as a pale yellow solid.

Scheme 1 compound 5 (4.3 g, 23.0 mmol) was dissolved in THF (80 mL). To this mixture was added Dess-Martin periodinane (14.6 g, 34.5 mmol) at 0° C. The resulting mixture was stirred at room temperature for 5 h. TLC showed the reaction was completely. The reaction mixture was quenched with aq. $Na_2S_2O_3$ and extracted with ethyl acetate. The organic layer was dried over anhydrous $Na_2SO_4$ and concentrated to give a crude residue that was purified by silica gel chromatography (PE/EA=10/1) to give scheme 1 compound 6 (3.7 g, yield: 87.0%) as a pale yellow solid.

Scheme 1 compound 6 (3.7 g, 20.0 mmol), phenyl-acetonitrile (2.3 g, 20.0 mmol) and $K_2CO_3$ (8.3 g, 60.0 mmol) were mixed in anhydrous DMF (100 mL). The mixture was stirred at 100° C. overnight. TLC showed the starting material was consumed completely; the mixture was quenched with $H_2O$ and extracted with ethyl acetate. The organic layer was washed with half-saturated brine, and dried over anhydrous $Na_2SO_4$. It was then concentrated to give the crude residue that was purified by silica gel chromatography (PE/EA=10/1) to give scheme 1 compound 7 (3.0 g, yield: 52.8%) as a brown oil. $^1$H NMR (400 MHz, $CDCl_3$): δ 8.25 (s, 1H, CH), 7.50-7.40 (m, 6H, ArH), 7.09 (s, 1H, ArH), 7.00 (s, 1H, NH), 4.30 (q, J=7.2 Hz, 2H, $CH_2$), 1.36 (t, J=7.2 Hz, 3H, $CH_3$).

Scheme 1 compound 7 (2.7 g, 9.5 mmol) was dissolved in acetic anhydride (30 mL) and heated at 120° C. for 2 h. TLC showed the starting material was consumed completely. The solvent was removed under vacuum and the remaining residue was mixed with 6N HCl (30 mL). The mixture was stirred at 80° C. for 1 h; it was then cooled to 0° C. To this mixture was added 1N NaOH dropwisely until a solid precipitated out. The solid was filtered and washed with water, dried in vacuum to give scheme 1 compound 8 (2.0 g, yield: 74.0%) as a white solid. $^1$H NMR (400 MHz, $CDCl_3$): δ 8.61 (s, 1H, CH), 7.81 (s, 1H, ArH), 7.69-7.67 (m, 2H, ArH) 7.47-7.40 (m, 2H, ArH), 7.27-7.24 (m, 1H, ArH), 4.32 (q, J=7.2 Hz, 2H, $CH_2$), 1.42-1.38 (t, J=7.2 Hz, 3H, $CH_3$).

The aryl amine for compound 1 was synthesized as shown in Scheme 2.

Scheme 2

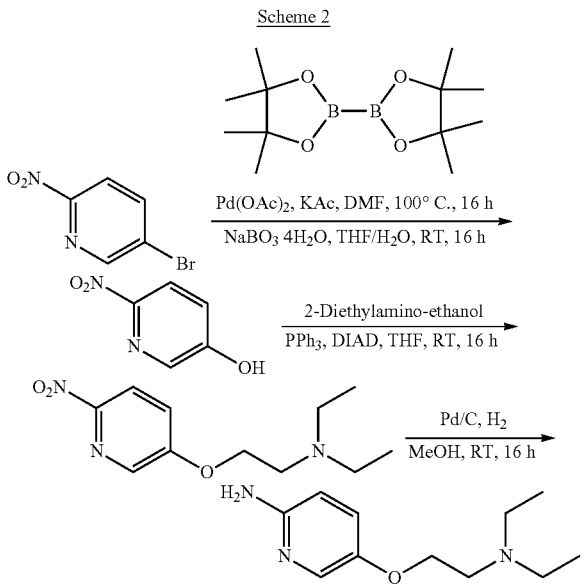

A suspension of 5-bromo-2-nitro-pyridine (10.0 g, 49 mmol), Boric acid ester (13.7 g, 54 mmol), $Pd(OAc)_2$ (121 mg, 0.54 mmol) and KOAc (14.4 g, 147 mmol) in DMF (180 mL) was heated to 100° C. for 16 h. After the solvent was removed under vacuum, the remaining residue was mixed with EtOAc (600 mL). The EtOAc solution was washed with water (100 mL), brine (100 mL), and dried over $Na_2SO_4$. It was concentrated to a residue that was mixed with $NaBO_3 4H_2O$ (19.0 g, 125 mmol), THF (180 mL) and $H_2O$ (180 mL). The resulting mixture was stirred at room temperature for 16 h. The aqueous phase was separated with the organic phase, and washed with EtOAc (100 mL×2). The combined organic solution was then concentrated to give 6-nitro-pyridin-3-ol (1.5 g, 21.8%) as a yellow solid.

To a solution of 6-Nitro-pyridin-3-ol (1.5 g, 10.7 mmol), PPh₃ (4.24 g, 16.1 mmol) and 2-Diethylamino-ethanol (1.25 g, 10.7 mmol) in THF (100 mL) was added DIAD (3.25 g, 16.1 mmol) dropwise at ° C. over 0.5 h. The mixture was stirred at RT for 16 h. The solvent was removed to give a residue that was then purified by column chromatography procedure on silica gel to give diethyl-[2-(6-nitro-pyridin-3-yloxy)-ethyl]-amine (0.45 g, 17.6%) as a yellow solid. $^1$H NMR (400 MHz, CDCl₃): δ 8.29 (d, J=8.8 Hz, 2H, ArH), 7.45-7.42 (dd, J=8.8 Hz, 2.8 Hz, 1H, ArH), 4.23 (t, J=5.8 Hz, 2H, CH₂), 2.95 (t, J=5.8 Hz, 2H, CH₂), 2.69 (q, J=6.8 Hz, 4H, 2CH₂), 1.09 (t, J=6.8 Hz, 6H, 2CH₃).

A suspension of diethyl-[2-(6-nitro-pyridin-3-yloxy)-ethyl]-amine (450 mg, 1.88 mmol) and Pd/C in MeOH (50 mL) was hydrogenated under H₂ at RT for 16 h. The reaction mixture was filtered and the filtrate was concentrated to give 5-(2-diethylamino-ethoxy)-pyridin-2-ylamine amine 02 (300 mg, 76.3%) as a crude red oil. $^1$H NMR (400 MHz, DMSO): δ 7.63 (d, J=2.8 Hz, 1H, ArH), 7.12-7.09 (dd, J=8.4 Hz, 2.4 Hz, 1H, ArH), 6.41 (d, J=8.8 Hz, 1H, ArH), 5.44 (br, 2H, NH), 3.91 (t, J=6.2 Hz, 2H, CH₂), 2.71 (t, J=6.2 Hz, 2H, CH₂), 2.54 (q, J=7.2 Hz, 4H, 2CH₂), 0.96 (t, J=7.2 Hz, 6H, 2CH₃).

Scheme 1 compound 8 (200.0 mg, 0.7 mmol) in Scheme 1 and 5-(2-diethylamino-ethoxy)-pyridin-2-ylamine in Scheme 2 (167.4 mg, 0.8 mmol) were dissolved in anhydrous dioxane (10 mL). To this mixture was added t-BuONa (201.8 mg, 2.1 mmol), X-PHOS (66.7 mg, 0.14 mmol), Pd₂(dba)₃ (64.1 mg, 0.07 mmol) under nitrogen atmosphere. The reaction mixture was stirred at 80° C. under nitrogen atmosphere overnight. After TLC showed the starting material was consumed completely, the mixture was quenched with water and extracted with ethyl acetate. The organic layer was washed with brine and dried over anhydrous Na₂SO₄, filtered, concentrated to give a residue which was purified by silica gel chromatography (DCM/MeOH=200/1 to 80/1) to give Compound 1(35.3 mg, yield: 11.0%) as a pale yellow solid. $^1$H NMR (400 MHz, CDCl₃): δ 8.49 (s, 1H, CH), 8.06 (s, 1H, ArH), 7.94 (s, 1H, ArH), 7.75-7.71 (m, 3H, ArH), 7.48-7.38 (m, 2H, ArH) 7.36-7.28 (m, 1H, ArH), 7.18 (d, J=8.0 Hz, 1H, ArH), 4.30 (q, J=7.2 Hz, 2H, CH₂), 4.15 (s, 2H, CH₂), 2.95 (s, 2H, CH₂), 2.76 (s, 4H, CH₂), 1.45 (t, J=7.2 Hz, 3H, CH₃), 1.07 (s, 6H, 2CH₃).

EXAMPLE 3

Synthesis of Compound 2

Compound 2

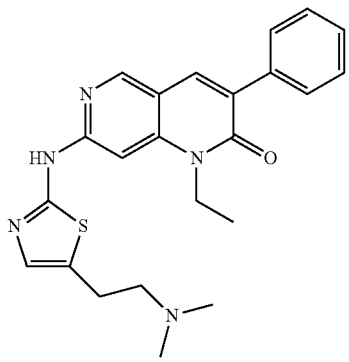

Compound 2, 7-[5-(2-Dimethylamino-ethyl)-thiazol-2-ylamino]-1-ethyl-3-phenyl-1H-[1,6]naphthyridin-2-one was synthesized in a similar manner to compound 1 using 5-(2-dimethylamino-ethyl)-thiazol-2-ylamine as the coupling reagent, which was synthesized as shown in Scheme 3.

Scheme 3

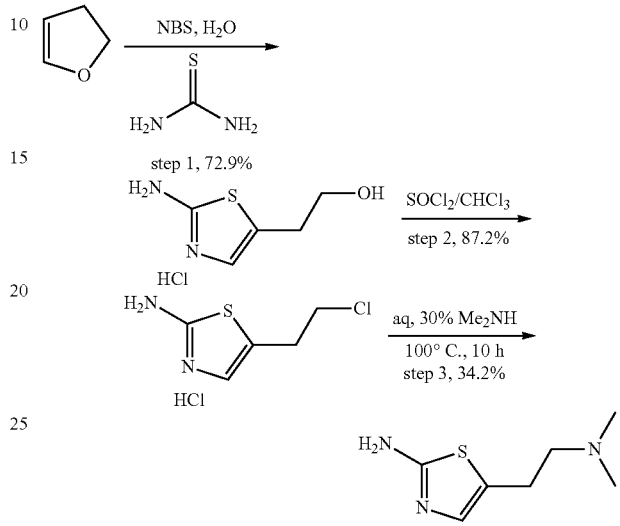

To an ice cold suspension of NBS (126.2 g, 0.713 mol) in H₂O (400 ml) was added 2,3-dihydro-furan dropwise (50 g, 0.713 mol). The resulting solution was stirred at 0° C. for 1 h. Thiourea (54 g, 0.713 mol) was added and the solution was heated to 100° C. for 16 h. After cooling to RT, the aqueous phase was basified with concentrated NH₄Cl to pH=10-11, extracted with EtOAc (200 mL×6). The combined extracts were washed with brine, dried over Na₂SO₄, concentrated to give 2-(2-amino-thiazol-5-yl)-ethanol (60 g, yield 60%) as an oil.

To a solution of 2-(2-amino-thiazol-5-yl)-ethanol (10 g, 0.064 mol) in CHCl₃ (60 mL) was added SOCl₂ (50 mL) dropwise at 0° C. over 0.5 h and heated to 60° C. for 3 h, the solvent then was removed in vacuum to give the crude product 5-(2-chloro-ethyl)-thiazol-2-ylamine (12 g, yield: 89.5%) as an oil.

A mixture of 5-(2-chloro-ethyl)-thiazol-2-ylamine (6 g, 36.2 mmol) in aq. 30% Me₂NH (50 mL) was heated to 100° C. for 10 h. the reaction mixture was then extracted with EtOAc (200 mL×4). The combined extracts was washed with brine, dried over Na₂SO₄, and concentrated to give 5-(2-dimethylamino-ethyl)-thiazol-2-ylamine (2.6 g, yield: 41%). $^1$H NMR (400 MHz, D₂O) δ 6.74 (s, 1H, ArH), 2.79 J=7.6 Hz, 2H, CH₂), 2.55 (t, J=7.6 Hz, 2H, CH₂), 2.21 (s, 6H, 2CH₃).

Scheme 1 compound 8 (200.0 mg, 0.7 mmol) and 5-(2-dimethylamino-ethyl)-thiazol-2-ylamine (136.9 mg, 0.8 mmol) was dissolved in anhydrous dioxane (10 mL). To this mixture was added Na₂CO₃ (222.6 mg, 2.1 mmol), Xantphos (161.8 mg, 0.28 mmol), Pd₂(dba)₃ (128.1 mg, 0.14 mmol) under nitrogen atmosphere. The reaction vessel was sealed and heated in microwave at 130° C. for 3 h. TLC showed the starting material was consumed completely; the mixture was quenched with water and extracted with ethyl acetate. The organic layer was washed with brine and dried over anhydrous Na₂SO₄, filtered, concentrated to give a residue which was purified by silica gel chromatography (DCM/MeOH=200/1 to 100/1) to give Compound 2 (36.7 mg, yield: 12.5%) as a yellow solid. $^1$H NMR (400 MHz, CDCl$_3$): δ 9.83 (brs, 1H, NH), 8.61 (s, 1H, CH), 7.78 (s, 1H, ArH), 7.72-7.70 (d, J=8.0 Hz, 2H, ArH), 7.48-7.31 (m, 3H, ArH), 7.20 (s, 1H, ArH) 6.94 (s, 1H, CH), 4.36 (q, J=7.2 Hz, 2H, CH$_2$), 2.98 (t, J=7.2 Hz, 2H, CH$_2$), 2.65 (t, J=7.2 Hz, 2H, CH$_2$), 2.35 (s, 6H, 2CH$_3$), 1.44 (t, J=7.2 Hz, 3H, CH$_3$).

EXAMPLE 4

Synthesis of Compound 3

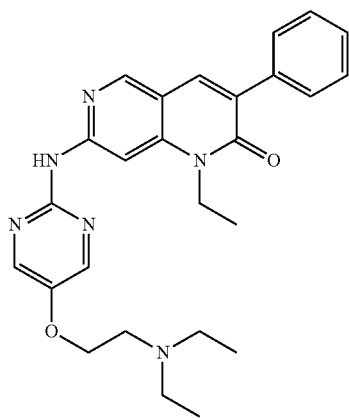

Compound 3

Compound 3, 7-[5-(2-Diethylamino-ethoxy)-pyrimidin-2-ylamino]-1-ethyl-3-phenyl-1H-[1,6]naphthyridin-2-one was synthesized in a similar manner to Compound 1 using 5-(2-diethylamino-ethoxy)-pyrimidin-2-ylamine as the coupling reagent, which was synthesized as shown in Scheme 4.

Scheme 4

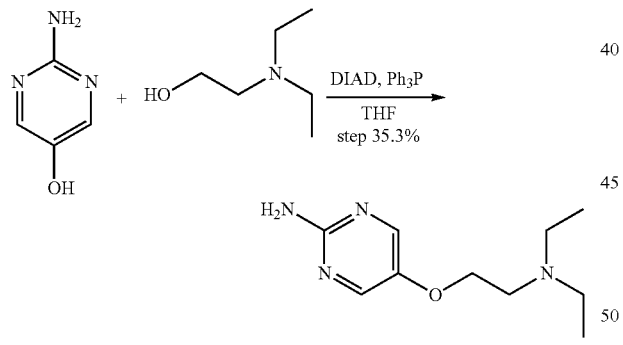

To a suspension of 2-amino-pyrimidin-5-ol (200 mg, 1.8 mmol), 2-diethylamino-ethanol (316 mg, 2.69 mmol) and PPh$_3$ (708 mg, 2.7 mmol) in THF (3 ml) was added dropwise of DIAD (546 mg, 2.7 mmol) at 0° C. under nitrogen atmosphere. The reaction mixture was stirred at room temperature overnight. TLC showed the reaction was completed. The solvent was evaporated in vacuum and the residue was purified by silica gel chromatography (DCM/MeOH=20:1) to afford 5-(2-diethylamino-ethoxy)-pyrimidin-2-ylamine (200 mg, 35.3% yield) as a pale solid.

Scheme 1 compound 8 (200.0 mg, 0.7 mmol) and 5-(2-diethylamino-ethoxy)-pyrimidin-2-ylamine (168.2 mg, 0.8 mmol) was dissolved in anhydrous dioxane (10 mL). To this solution was added t-BuONa (201.8 mg, 2.1 mmol), X-PHOS (66.7 mg, 0.14 mmol), Pd$_2$(dba)$_3$ (64.1 mg, 0.07 mmol) under nitrogen atmosphere. The mixture was stirred at 80° C. under nitrogen atmosphere overnight. TLC showed the starting material was consumed completely; the mixture was quenched with water and extracted with ethyl acetate. The organic layer was washed with brine and dried over anhydrous Na$_2$SO$_4$, filtered, concentrated to give a residue which was purified by silica gel chromatography (DCM/MeOH=200/1 to 100/1) to give Compound 3 (22.6 mg, yield: 7.0%) as a yellow solid. $^1$H NMR (TH03607-043-1B, 400 MHz, CDCl$_3$): δ 8.46 (s, 1H, CH), 8.43 (s, 1H, ArH), 8.24 (s, 2H, ArH), 8.07 (s, 1H, NH), 7.69 (s, 1H, ArH), 7.64 (d, J=7.2 Hz, 2H, ArH), 7.38-7.29 (m, 3H, ArH), 4.36 (q, J=7.2 Hz, 2H, CH$_2$), 4.07 (t, J=7.2 Hz, 2H, CH$_2$), 2.84 (t, J=7.2 Hz, 2H, CH$_2$), 2.59 (q, J=7.2 Hz, 4H, CH$_2$), 1.39 (t, J=7.2 Hz, 3H, CH$_3$), 1.02 (t, J=7.2 Hz, 6H, 2CH$_3$).

EXAMPLE 5

Synthesis of Compound 4

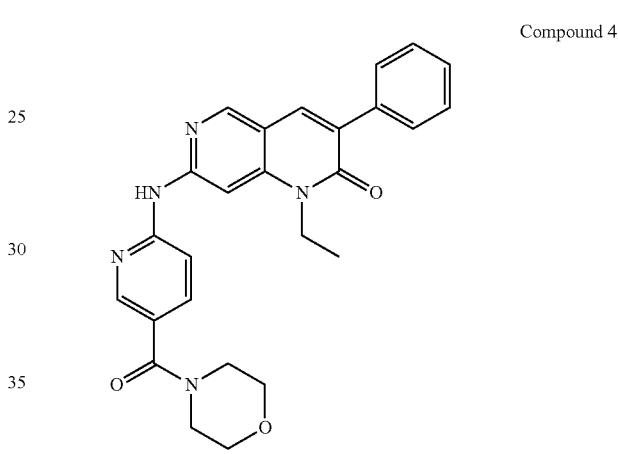

Compound 4

Compound 4, 1-Ethyl-7-[5-(morpholine-4-carbonyl)-pyridin-2-ylamino]-3-phenyl-1H-[1,6]naphthyridin-2-one was synthesized in a similar manner to Compound 1 using (6-Amino-pyridin-3-yl)-morpholin-4-yl-methanone as the coupling reagent, which was synthesized as in Scheme 5.

Scheme 5

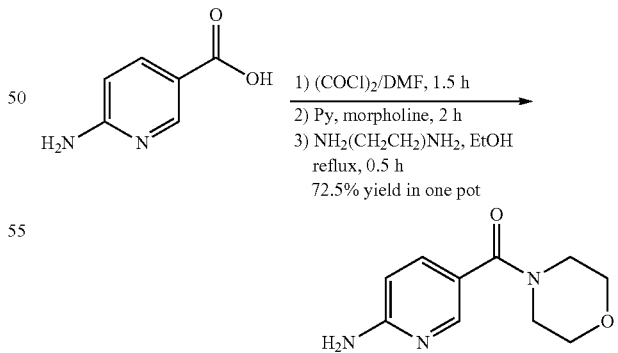

1) (COCl)$_2$/DMF, 1.5 h
2) Py, morpholine, 2 h
3) NH$_2$(CH$_2$CH$_2$)NH$_2$, EtOH reflux, 0.5 h
72.5% yield in one pot (COCl)$_2$ (7.63 g, 60.1 mmol) was added dropwise to a solution of DMF (4.54 g, 62.1 mmol) in DCM (60 mL) below 5° C. in a flask. The reaction mixture was stirred at 0~5° C. for 1 h. 6-Amino-nicotinic acid (4.14 g, 29.9 mmol) was added in one portion to the flask. The reaction mixture was stirred at RT for 1.5 h. Pyridine (7.35 g, 36 mmol) was then added dropwise at 0° C., and stirred for 0.5 h. Morpholine (2.61 g, 30 mmol) was added dropwise to the above reaction mixture at 0° C., and then stirred at RT for 2 h. The reaction mixture was concentrated. The residue was dissolved in EtOH (75 mL), NH$_2$(CH$_2$)$_2$NH$_2$ (8.1 g, 134.7 mmol) was added. The reaction mixture was refluxed for 0.5 h. The reaction mixture was concentrated, purified by silica gel chromatography (PE/EA=2/1) to give (6-amino-pyridin-3-yl)-morpholin-4-yl-methanone (4.5 g, yield: 72.5%) as a white solid. $^1$H NMR (400 MHz, CDCl$_3$): δ 8.01 (s, 1H, ArH), 7.43 (d, J=8.4 Hz, 1H, ArH), 6.42 (d, J=8.4 Hz, 1H, ArH), 6.37 (s, 2H, NH$_2$), 3.59-3.57 (m, 4H, 2CH$_2$), 3.50-3.47 (m, 4H, 2CH$_2$).

Scheme 1 compound 8 (200.0 mg, 0.706 mmol) and (6-amino-pyridin-3-yl)-morpholin-4-yl-methanone (176.0 mg, 1.2 mmol) was dissolved in anhydrous dioxane (8 mL). To this solution was added t-BuONa (202.4 mg, 2.1 mmol), X-PHOS (66.4 mg, 0.139 mmol), Pd(dba)$_2$ (40.0 mg, 0.069 mmol) under nitrogen atmosphere. The mixture was stirred at 80° C. under nitrogen atmosphere overnight. TLC showed the starting material was consumed completely. The reaction mixture was concentrated, the residue was purified by prep-HPLC to give Compound 4 (120 mg, yield: 37.2%) as a yellow solid.

$^1$H NMR (400 MHz, CDCl$_3$): δ 8.52 (s, 1H, ArH), 8.45 (s, 1H, NH), 8.09 (s, 1H, ArH) 7.76-7.69 (m, 5H, ArH), 7.46-7.37 (m, 3H, ArH), 7.27-7.25 (m, 1H, ArH), 4.39 (q, J=7.2 Hz, 2H, CH$_2$), 3.90-3.51 (m, 8H, 4CH$_2$), 1.44 (t, J=7.2 Hz, 3H, CH$_3$).

EXAMPLE 6

Synthesis of Compound 5

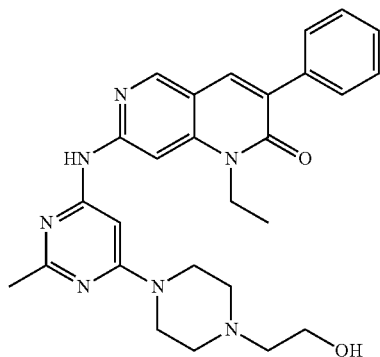

Compound 5

Compound 5, 1-Ethyl-7-{6-[4-(2-hydroxy-ethyl)-piperazin-1-yl]-2-methyl-pyrimidin-4-ylamino}-3-phenyl-1H-[1,6]naphthyridin-2-one was synthesized in a similar manner to Compound 1 using 2-[4-(6-amino-2-methyl-pyrimidin-4-yl)-piperazin-1-yl]-ethanol as the coupling reagent, which was prepared as in scheme 6

Scheme 6

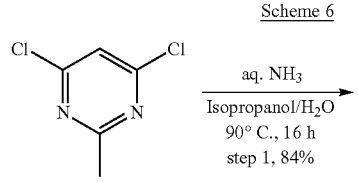

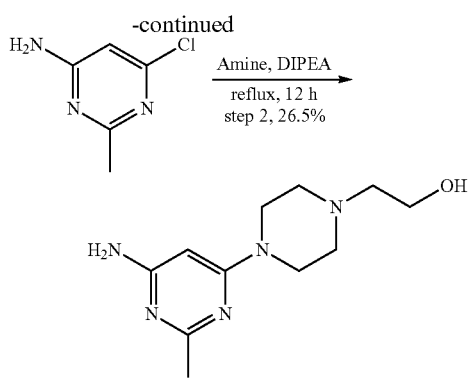

4,6-Dichloro-2-methyl-pyrimidine (5.0 g, 30.6 mmol) was added to a mixture of Isopropanol/NH$_3$.H$_2$O (40 mL/10 mL). The reaction mixture was heated to 90° C. for 18 h. After cooled to RT, the precipitate was collected by filtration, washed with H$_2$O (10 mL×3) and dried. 6-Chloro-2-methyl-pyrimidin-4-ylamine (1.5 g, yield: 33.9%) was obtained as a white solid.

6-Chloro-2-methyl-pyrimidin-4-ylamine (500 mg, 3.49 mmol), 2-piperazinyl-ethanol (500 mg, 3.84 mmol) and DIPEA (541 mg, 4.19 mmol) were added to Dioxane (5 mL). The reaction mixture was refluxed for 12 h. TLC showed the reaction was completed. The reaction mixture was concentrated. The residue was washed with MeCN, recrystallized from MeOH to yield 2-[4-(6-amino-2-methyl-pyrimidin-4-yl)-piperazin-1-yl]-ethanol (220 mg, yield: 26.5%) as a white solid. $^1$H NMR (400 MHz, MeOD): δ 5.61 (s, 1H, ArH), 3.74 (t, J=6.0 Hz, 2H, OCH$_2$), 3.64-3.61 (m, 4H, 2CH$_2$), 2.67-2.62 (m, 6H, 3CH$_2$), 2.31 (s, 3H, ArCH$_3$).

Scheme 1 compound 8 (180.0 mg, 0.636 mmol) and 2-[4-(6-amino-2-methyl-pyrimidin-4-yl)-piperazin-1-yl]-ethanol (180.0 mg, 0.763 mmol) were dissolved in anhydrous dioxane (8 mL) in a flask. To this flask were added t-BuONa (183.0 mg, 1.908 mmol), X-PHOS (60.6 mg, 0.127 mmol), Pd(dba)$_2$ (36.6 mg, 0.0636 mmol) under nitrogen atmosphere. The mixture was stirred at 80° C. under nitrogen atmosphere overnight. TLC showed the starting material was consumed completely. The reaction mixture was concentrated, the residue was purified by prep-HPLC to give Compound 5 (90.0 mg, yield: 29.0%) as a white solid. $^1$H NMR (400 MHz, CDCl$_3$+MeOD+D$_2$O): δ 8.43 (s, 1H, CH), 7.97 (s, 1H, ArH), 7.61-7.25 (m, 5H, ArH), 6.44 (s, 1H, ArH), 4.30 (q, J=7.2 Hz, 2H, CH$_2$), 3.65-3.59 (m, 6H, 3CH$_2$), 2.56-2.53 (m, 6H, 3CH$_2$), 2.41 (s, 3H, CH$_3$), 1.38 (t, J=7.2 Hz, 3H, CH$_3$).

EXAMPLE 7

Synthesis of Compound 6

Compound 6

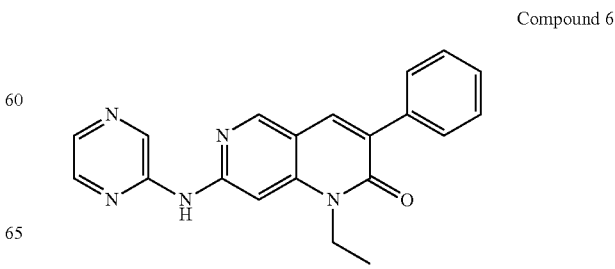

Compound 6, 1-Ethyl-3-phenyl-7-(pyrazin-2-ylamino)-1H-[1,6]naphthyridin-2-one. This compound was synthesized in a similar manner to Compound 1 using pyrazin-2-ylamine as the coupling reagent. $^1$H NMR (CDCl$_3$, 400 MHz): δ 8.60 (s, 1H, ArH), 8.54 (s, 1H, ArH), 8.26 (s, 1H, ArH), 8.16 (d, J=14.4 Hz, 2H, ArH), 7.87 (s, 1H, NH), 7.77 (s, 1H, ArH), 7.70 (dd, J$^1$=1.2 Hz, J$^2$=4.8 Hz, 2H, ArH), 7.46-7.40 (dd, J$^1$=6.8 Hz, J$^2$=18.4 Hz, 2H, ArH), 7.38 (d, J=6.0 Hz, 1H, ArH), 4.40 (q, J=6.8 Hz, 2H, CH$_2$), 1.45 (t, J=7.2 Hz, 3H, CH$_3$).

EXAMPLE 8

Synthesis of Compound 7

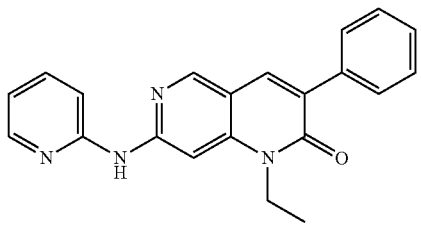

Compound 7

Compound 7, 1-Ethyl-3-phenyl-7-(pyridin-2-ylamino)-1H-[1,6]naphthyridin-2-one. This compound was synthesized in a similar manner to Compound 1 using 2-aminopyridine as the coupling reagent. $^1$H NMR (CDCl$_3$, 400 MHz): δ 8.49 (s, 1H, ArH), 8.34 (d, J=4.4 Hz, 1H, ArH), 8.18 (s, 1H, ArH), 7.74 (s, 1H, ArH), 7.70 (d, J=7.2 Hz, 1H, ArH), 7.63 (t, J=7.2 Hz, 1H, ArH), 7.56 (br, 1H, NH), 7.43 (t, J=7.2 Hz, 2H, ArH), 7.38 (t, J=6.8 Hz, 1H, ArH), 7.14 (d, J=8.4 Hz, 1H, ArH), 6.91 (t, J=6.0 Hz, 1H, ArH), 4.39 (q, J=7.2 Hz, 2H, CH$_2$), 1.44 (t, J=7.2 Hz, 3H, CH$_3$)

EXAMPLE 9

Synthesis of Compound 8

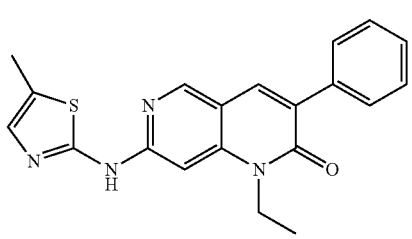

Compound 8

Compound 8, 1-Ethyl-7-(5-methyl-thiazol-2-ylamino)-3-phenyl-1H-[1,6]naphthyridin-2-one. This compound was synthesized in a similar manner to Compound 1 using 5-methyl-thiazol-2-ylamine as the coupling reagent. $^1$H NMR (DMSO, 400 MHz): δ 8.71 (s, 1H, ArH), 8.08 (s, 1H, NH), 7.71 (d, J=7.6 Hz, 2H, 2ArH), 7.45-7.37 (m, 3H, 3ArH), 7.06 (d, J=5.2 Hz, 2H, 2ArH), 4.20 (q, J=7.2 Hz, 2H, CH$_2$), 2.36 (s, 3H, ArCH$_3$), 1.1.28 (t, J=7.2 Hz, 3H, CH$_3$). MS [ESI, MH$^+$]:=363.2.

EXAMPLE 10

Synthesis of Compound 9

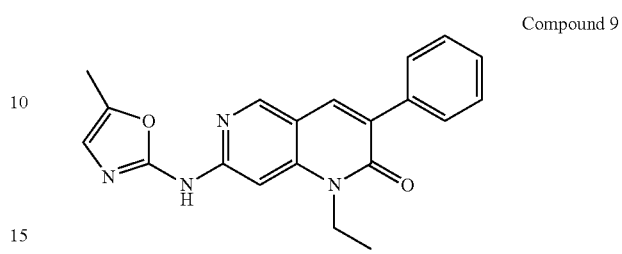

Compound 9

Compound 9, 1-Ethyl-7-(5-methyl-oxazol-2-ylamino)-3-phenyl-1H-[1,6]naphthyridin-2-one. This compound was synthesized in a similar manner to Compound 1 using 5-methyl-oxazol-2-ylamine as the coupling reagent. $^1$H NMR (DMSO, 400 MHz): δ 8.50 (s, 1H, ArH), 8.21 (br, 1H, NH), 7.75-7.68 (m, 3H, 3ArH), 7.45-7.37 (m, 3H, 3ArH), 6.62 (s, 1H, ArH), 4.42 (q, J=7.2 Hz, 2H, CH$_2$), 2.32 (s, 3H, ArCH$_3$), 1.44 (t, J=7.2 Hz, 3H, CH$_3$)

EXAMPLE 11

Synthesis of Compounds 10-13

Compound 10-13 were synthesized as shown in Scheme 7. It started with the intermediate compound 6 as shown in scheme 1. There are two general methods A and B to perform the first step as described below. Method A was used for Compounds 10 and 11; method B was used for Compounds 12 and 13. The last step uses a same procedure as described for Compound 1.

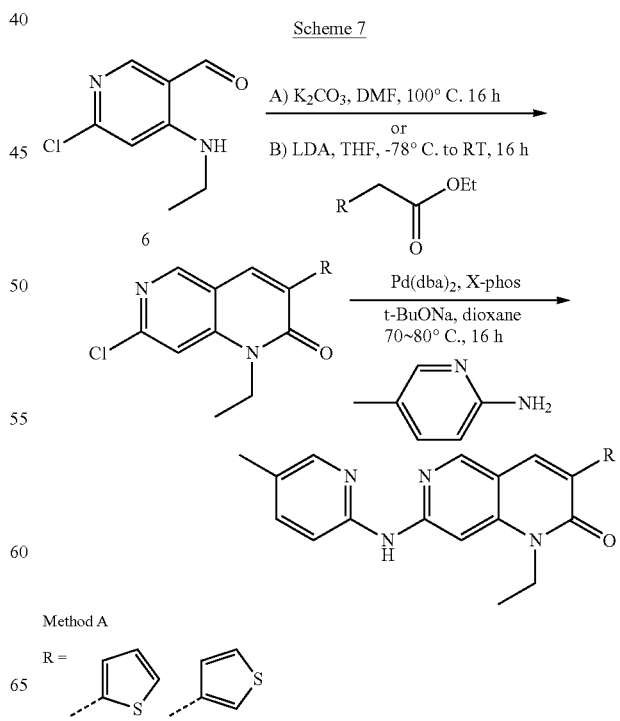

Scheme 7

Method B

R = 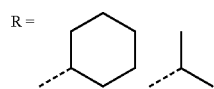

Method A Scheme 1 compound 6 (1 eq) was dissolved in anhydrous DMF and added Thiophen-2-yl-acetic acid ethyl ester (1.1 eq) and $K_2CO_3$ (3.0 eq). The mixture was stirred at 100° C. overnight. TLC showed the starting material was consumed completely. The reaction mixture was diluted with $H_2O$ and extracted with EtOAc. The organic layer was washed with brine and dried over anhydrous $Na_2SO_4$, concentrated to give crude residue which was purified by silica gel chromatography to give intermediate 7-Chloro-1-ethyl-3-thiophen-2-yl-1H-[1,6]naphthyridin-2-one as yellow solid.

Method B Scheme 1 compound 6 (2.2 eq) was dissolved in anhydrous THF, cooled to −78° C. LDA (2.2 eq) was added dropwise. The mixture was then stirred at −78° C. for 1 h. The solution of cyclohexyl-acetic acid ethyl ester (1.0 eq) in THF was added dropwise at −78° C. The resulting reaction mixture was warmed slowly to RT and stirred for 16 h. The reaction was quenched with saturated $NH_4Cl$ and extracted with EtOAc. The organic layer was washed with brine, dried over anhydrous $Na_2SO_4$, concentrated to give crude residue which was purified by silica gel chromatography to give 7-Chloro-3-cyclohexyl-1-ethyl-1H-[1,6]naphthyridin-2-one as a yellow solid.

The final products Compounds 10-13 were synthesized using same coupling procedure as described for Compound 1.

Compound 10

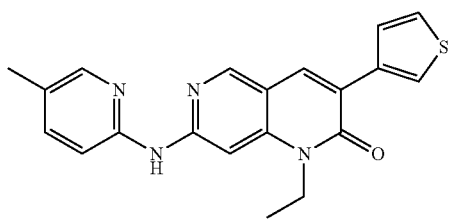

Compound 10, 1-Ethyl-7-(5-methyl-pyridin-2-ylamino)-3-thiophen-3-yl-1H-[1,6]naphthyridin-2-one: $^1$H NMR (CDCl$_3$, 400 MHz): δ 8.49 (s, 1H, ArH), 8.18-8.16 (m 2H, ArH), 8.11 (s, 1H, ArH), 7.89 (s, 1H, ArH), 7.55-7.54 (dd, J=1.2 Hz, J$^2$=5.2 Hz 1H, ArH), 7.47-7.45 (m, 2H, ArH and NH), 7.37-7.35 (dd, J$^1$=3.2 Hz, J$^2$=5.2 Hz, 1H, ArH), 7.07-7.06 (d, J=7.2 Hz, 1H, ArH), 4.42-4.36 (q, J=7.2 Hz, 2H, CH$_2$), 2.30 (s, 3H, ArCH$_3$), 1.45-1.41 (t, J=7.2 Hz, 3H, CH$_3$). MS [ESI, MH$^+$]:=363.1.

Compound 11

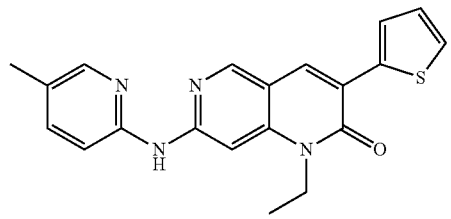

Compound 11, 1-Ethyl-7-(5-methyl-pyridin-2-ylamino)-3-thiophen-2-yl-1H-[1,6]naphthyridin-2-one: $^1$H NMR (CDCl$_3$, 400 MHz): δ 8.52 (s, 1H, ArH), 8.15 (s, 2H, ArH), 8.04 (s, 1H, ArH), 7.71-7.70 (dd, J$^1$=1.2 Hz, J$^2$=4.0 Hz 1H, ArH), 7.48-7.46 (d, J=8.0 Hz, 2H, ArH), 7.42-7.40 (dd, J$^1$=0.8 Hz, J$^2$=5.2 Hz, 1H, ArH), 7.13-7.11 (dd, J$^1$=4.0 Hz, J$^2$=1.2 Hz, 1H, ArH), 7.07 (brs, 1H, NH), 4.45-4.39 (q, J=7.2 Hz, 2H, CH$_2$), 2.30 (s, 3H, ArCH$_3$), 1.46-1.43 (t, J=7.2 Hz, 3H, CH$_3$); MS [ESI, MH$^+$]:=363.1.

Compound 12

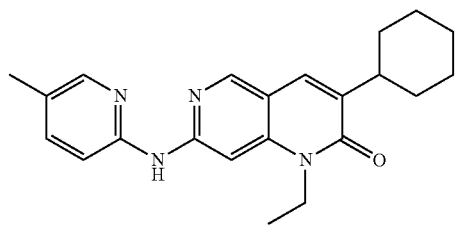

Compound 12, 3-Cyclohexyl-1-ethyl-7-(5-methyl-pyridin-2-ylamino)-1H-[1,6]naphthyridin-2-one: $^1$H NMR (CDCl$_3$, 400 MHz): δ 8.38 (s, 1H, ArH), 8.15 (s, 1H, ArH), 7.99 (s, 1H, ArH), 7.44 (d, J=2.4 Hz, 2H, ArH), 7.42 (s, 1H, NH), 7.05 (d, J=8.4 Hz, 1H, ArH), 4.33-4.28 (q, J=7.2 Hz, 2H, CH$_2$), 2.94-2.88 (m, 1H, CH), 2.28 (s, 3H, ArCH$_3$), 1.94 (q, J=12 Hz, 2H, CH$_2$), 1.85-1.75 (m, 3H, CH$_3$), 1.52-1.48 (m, 2H, CH$_2$), 1.38 (t, J=7.2 Hz, 3H, CH$_3$), 1.32-1.26 (m, 3H, CH$_3$), MS [ESI, MH$^+$]:=363.3.

Compound 13

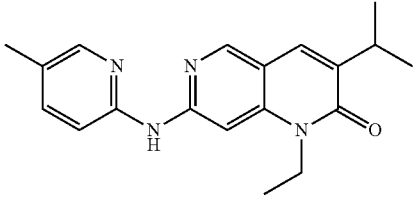

Compound 13, 1-Ethyl-3-isopropyl-7-(5-methyl-pyridin-2-ylamino)-1H-[1,6]naphthyridin-2-one: $^1$H NMR (CDCl$_3$, 400 MHz): δ 8.39 (s, 1H, ArH), 8.14 (dd, J'=0.8 Hz, J$^2$=1.6 Hz, 1H, ArH 1H, ArH), 7.44-7.38(m, ,3H, ArH), 7.047 (d, J=8.4 Hz, 1H, ArH), ArH), 4.37-4.31 (q, J=7.2 Hz, 2H, CH$_2$), 3.31-3.24 (m, 1H, CH),2.28 (s, 3H, ArCH$_3$),1.38(t, J=7.2 Hz, 3H, CH$_3$), 1.24(d, J=0.8 Hz, 3H, CH$_3$),1.22(d, J=7.2 Hz, 3H, CH$_3$), MS [ESI, MH$^+$]:=323.2.

EXAMPLE 12

Synthesis of Compounds 14 and 15

Compounds 14 and 15 were synthesized as shown in Scheme 8

Scheme 8

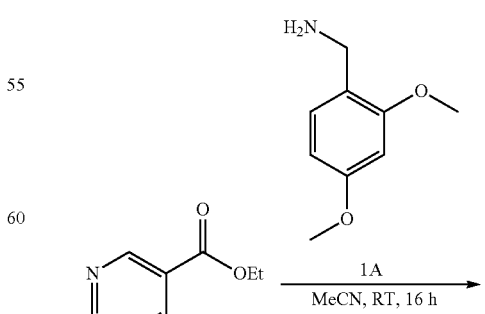

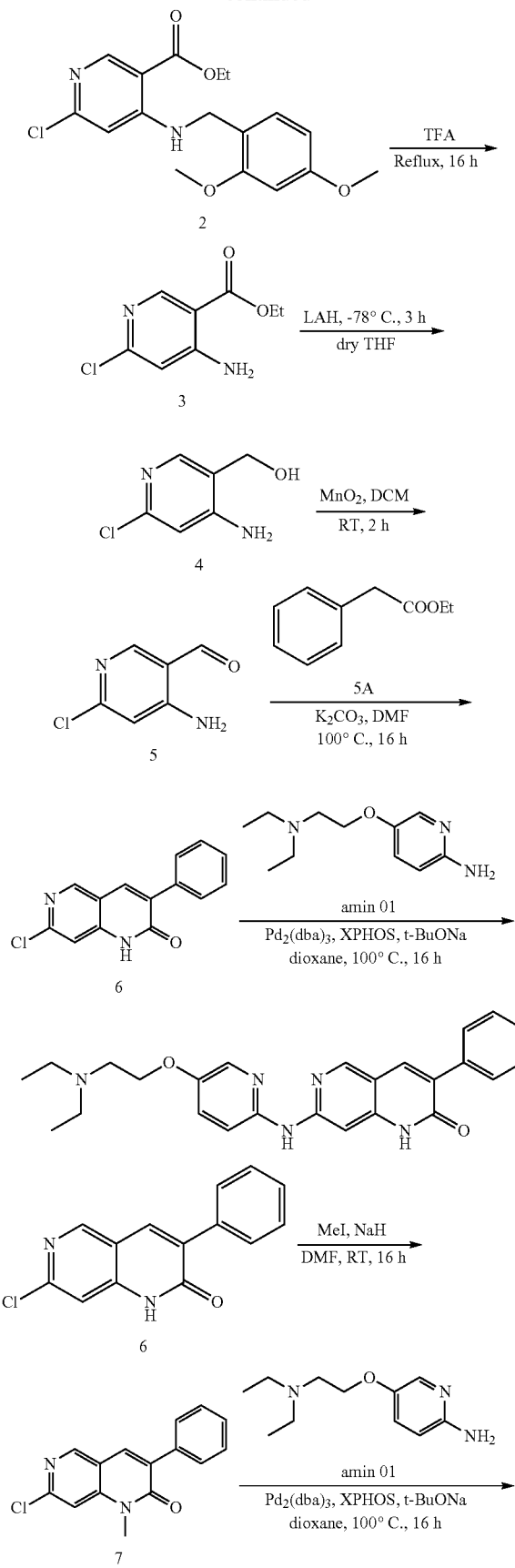

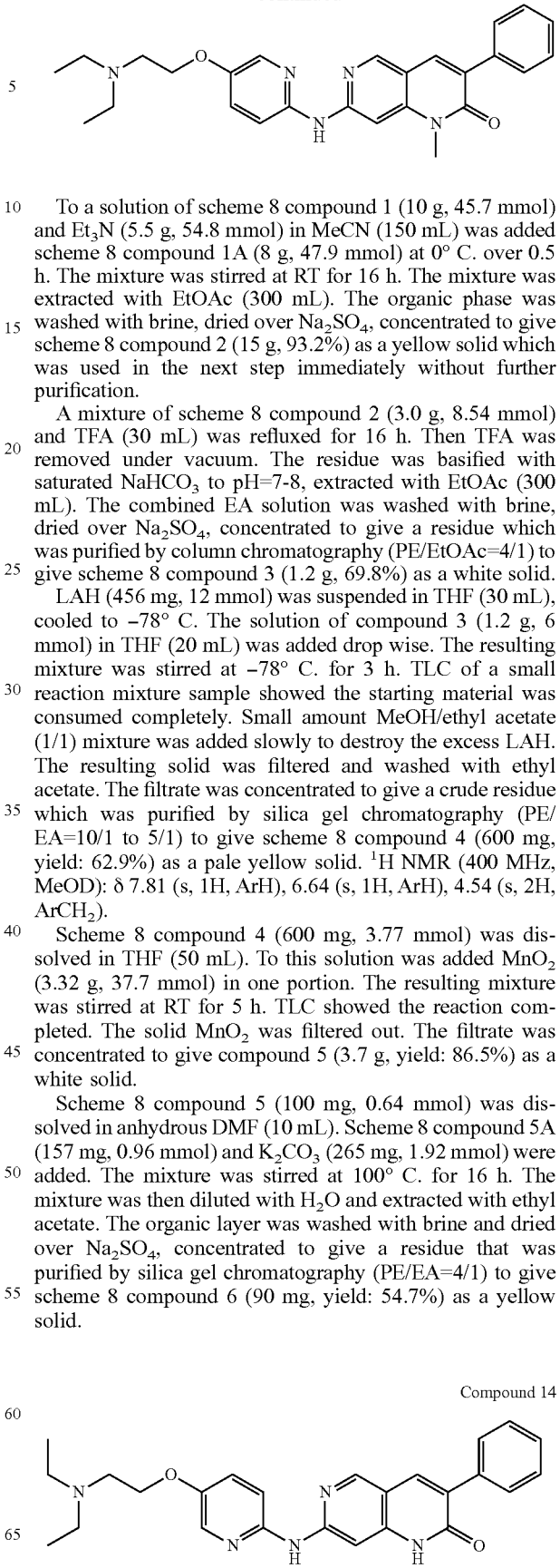

To a solution of scheme 8 compound 1 (10 g, 45.7 mmol) and Et$_3$N (5.5 g, 54.8 mmol) in MeCN (150 mL) was added scheme 8 compound 1A (8 g, 47.9 mmol) at 0° C. over 0.5 h. The mixture was stirred at RT for 16 h. The mixture was extracted with EtOAc (300 mL). The organic phase was washed with brine, dried over Na$_2$SO$_4$, concentrated to give scheme 8 compound 2 (15 g, 93.2%) as a yellow solid which was used in the next step immediately without further purification.

A mixture of scheme 8 compound 2 (3.0 g, 8.54 mmol) and TFA (30 mL) was refluxed for 16 h. Then TFA was removed under vacuum. The residue was basified with saturated NaHCO$_3$ to pH=7-8, extracted with EtOAc (300 mL). The combined EA solution was washed with brine, dried over Na$_2$SO$_4$, concentrated to give a residue which was purified by column chromatography (PE/EtOAc=4/1) to give scheme 8 compound 3 (1.2 g, 69.8%) as a white solid.

LAH (456 mg, 12 mmol) was suspended in THF (30 mL), cooled to −78° C. The solution of compound 3 (1.2 g, 6 mmol) in THF (20 mL) was added drop wise. The resulting mixture was stirred at −78° C. for 3 h. TLC of a small reaction mixture sample showed the starting material was consumed completely. Small amount MeOH/ethyl acetate (1/1) mixture was added slowly to destroy the excess LAH. The resulting solid was filtered and washed with ethyl acetate. The filtrate was concentrated to give a crude residue which was purified by silica gel chromatography (PE/EA=10/1 to 5/1) to give scheme 8 compound 4 (600 mg, yield: 62.9%) as a pale yellow solid. $^1$H NMR (400 MHz, MeOD): δ 7.81 (s, 1H, ArH), 6.64 (s, 1H, ArH), 4.54 (s, 2H, ArCH$_2$).

Scheme 8 compound 4 (600 mg, 3.77 mmol) was dissolved in THF (50 mL). To this solution was added MnO$_2$ (3.32 g, 37.7 mmol) in one portion. The resulting mixture was stirred at RT for 5 h. TLC showed the reaction completed. The solid MnO$_2$ was filtered out. The filtrate was concentrated to give compound 5 (3.7 g, yield: 86.5%) as a white solid.

Scheme 8 compound 5 (100 mg, 0.64 mmol) was dissolved in anhydrous DMF (10 mL). Scheme 8 compound 5A (157 mg, 0.96 mmol) and K$_2$CO$_3$ (265 mg, 1.92 mmol) were added. The mixture was stirred at 100° C. for 16 h. The mixture was then diluted with H$_2$O and extracted with ethyl acetate. The organic layer was washed with brine and dried over Na$_2$SO$_4$, concentrated to give a residue that was purified by silica gel chromatography (PE/EA=4/1) to give scheme 8 compound 6 (90 mg, yield: 54.7%) as a yellow solid.

Compound 14: 7-[5-(2-Diethylamino-ethoxy)-pyridin-2-ylamino]-3-phenyl-1H-[1,6]naphthyridin-2-one Scheme 8 compound 6 (90 mg, 0.35 mmol) and Amine 01 (81 mg, 0.39 mmol) was dissolved in anhydrous dioxane (5 mL). t-BuONa (67 mg, 0.7 mmol), X-PHOS (33 mg, 0.07 mmol), Pd$_2$(dba)$_3$ (32 mg, 0.035 mmol) were added. The mixture was stirred at 100° C. under nitrogen atmosphere for 16 h. The mixture was diluted with water and extracted with EtOAc. The organic layer was washed with brine, and dried over Na$_2$SO$_4$, concentrated to give a residue that was purified by column chromatography to give 7-[5-(2-Diethylamino-ethoxy)-pyridin-2-ylamino]-3-phenyl-1H-[1,6]naphthyridin-2-one (25.2 mg, yield: 16.8%) as a yellow solid. $^1$H NMR (400 MHz, DMSO): δ 11.88 (s, 1H, NH), 9.76 (s, 1H, NH), 8.57 (s, 1H, ArH), 8.02 (s, 1H, ArH), 7.96 (d, J=2.4 Hz, 1H, ArH), 7.74-7.70 (m, 3H, ArH), 7.45-7.34 (m, 5H, ArH), 4.07-4.03 (t, J=6.2 Hz, 2H, CH$_2$), 2.77-2.74 (t, J=6.2 Hz, 2H, CH$_2$), 2.50-2.49 (t, J=9.0 Hz, 4H, CH$_2$), 0.98-0.95 (t, J=9.0 Hz, 6H, 2CH$_3$), MS [ESI, MH$^+$]: 430.2.

To a suspension of NaH (37 mg, 0.93 mmol) in DMF (1 mL) was added the solution of Scheme 8 compound 6 (200 mg, 0.78 mmol) in DMF (4 mL) at 0° C. over 30 min. Then MeI (133 mg, 0.93 mmol) was added. The mixture was stirred at RT for 16 h, then diluted with water, extracted with EtOAc, washed with brine, dried over Na$_2$SO$_4$, concentrated to give compound 7 (200 mg, 94.8%) as yellow solid.

Compound 15

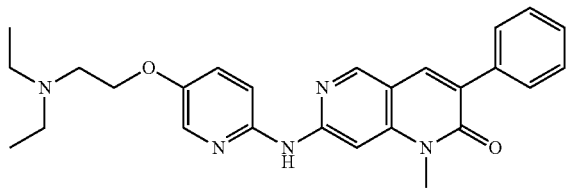

Compound 15, 7-[5-(2-Diethylamino-ethoxy)-pyridin-2-ylamino]-1-methyl-3-phenyl-1H-[1,6]naphthyridin-2-one Scheme 8 compound 7 (200 mg, 0.74 mmol) and Amine 01 (170 mg, 0.81 mmol) was dissolved in anhydrous dioxane (10 mL). t-BuONa (142 mg, 1.48 mmol), X-PHOS (71 mg, 0.148 mmol), Pd$_2$(dba)$_3$ (68 mg, 0.074 mmol) were added. The mixture was stirred at 100° C. under nitrogen atmosphere for 16 h. The mixture was diluted with water and extracted with EtOAc. The organic layer was washed with brine, and dried over Na$_2$SO$_4$, concentrated to give the residue, purified by column chromatography to give 7-[5-(2-Diethylamino-ethoxy)-pyridin-2-ylamino]-1-methyl-3-phenyl-1H-[1,6]naphthyridin-2-one (109.6 mg, yield: 33.3%) as a yellow solid.

$^1$H NMR (400 MHz, CDCl$_3$): δ 8.46 (s, 1H, NH), 8.06-8.05 (d, J=3.2 Hz, 1H, ArH), 7.86 (s, 1H, ArH), 7.73 (s, 1H, ArH), 7.69-7.67 (t, J=8.4 Hz, 2H, ArH), 7.57 (s, 1H, ArH), 7.45-7.38 (m, 2H, ArH), 7.30-7.27 (m, 2H, ArH), 7.19-7.16 (d, J=8.8 Hz 1H, ArH), 4.18 (s, 2H, CH$_2$), 3.73 (s, 3H, NCH$_3$), 2.98 (s, 2H, CH$_2$), 2.77-2.76 (d, J=4.8 Hz, 4H, CH$_2$), 1.17-1.13 (t, J=7.0 Hz, 6H, 2CH$_3$), MS [ESI, MH$^+$]: 444.3.

EXAMPLE 13

Synthesis of Compound 28

Compound 28

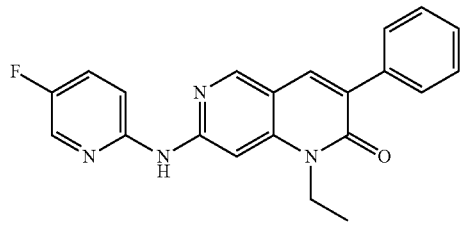

Compound 28, 1-Ethyl-7-(5-fluoro-pyridin-2-ylamino)-3-phenyl-1H-[1,6]naphthyridin-2-one: This compound was synthesized in a similar manner to Compound 1 using 5-fluoro-pyridin-2-ylamine as the coupling reagent. $^1$H NMR (CDCl$_3$, 400 MHz): δ 8.48 (s, 1H, ArH), 8.16 (s, 1H, ArH), 8.12 (s, 1H, ArH), 7.71 (s, 1H, ArH), 7.70-7.66 (m, 2H, ArH), 7.50 (br, 1H, NH), 7.49-7.48 (m, 1H, ArH), 7.13-7.09 (m, 3H, ArH), 4.37 (q, J=7.2 Hz, 2H, CH$_2$), 2.30 (s, 3H, ArCH$_3$), 1.43 (t, J=7.2 Hz, 3H, CH$_3$)

EXAMPLE 14

Synthesis of Compound 42

Compound 42

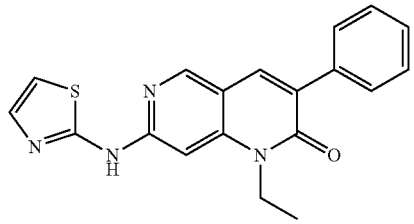

Compound 42, 1-Ethyl-3-phenyl-7-(thiazol-2-ylamino)-1H-[1,6]naphthyridin-2-one: This compound was synthesized in a similar manner to Compound 1 using thiazol-2-ylamine as the coupling reagent. $^1$H NMR (400 MHz, DMSO): δ 11.35 (s, 1H, ArH), 8.73 (s, 1H, ArH), 8.07 (s, 1H, ArH) 7.66 (d, J=7.2 Hz, 2H, ArH), 7.432-7.349 (m, 4H, ArH), 7.056 (t, J=10.8 Hz, 2H, ArH), 4.173 (d, J=6.4 Hz, 2H, CH$_2$), 1.263 (q, J=7.2 Hz, 3H, CH$_3$).

EXAMPLE 15

Synthesis of Compound 43

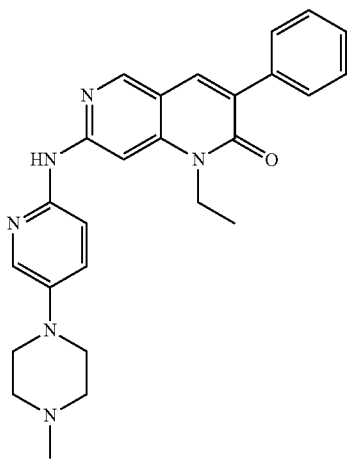

Compound 43

Compound 43, 1-Ethyl-7-[5-(4-methyl-piperazin-1-yl)-pyridin-2-ylamino]-3-phenyl-1H-[1,6]naphthyridin-2-one: $^1$H NMR (400 MHz, CDCl$_3$): δ 8.491 (s, 1H, ArH), 8.06 (s, 1H, ArH), 7.967 (s, 1H, ArH) 7.73 (t, J=7.2 Hz, 3H, ArH), 7.612 (s, 1H, ArH), 7.450 (t, J=7.2 Hz, 2H, ArH), 7.396-7.285 (m, 2H, ArH), 7.150 (t, J=8.8 Hz, 1H, ArH), 4.411-4.360 (m, 2H, CH$_2$), 3.215 (t, J=4.8 Hz, 4H, 2CH$_2$), 2.637 (t, J=4.8 Hz, 4H, 2CH$_2$) 2.398 (s, 3H, CH$_3$), 1.449(t, J=7.2 Hz, 3H, CH$_3$). This compound was synthesized in a similar manner to Compound 1 using 5-(4-methyl-piperazin-1-yl)-pyridin-2-ylamine as the coupling reagent, which was prepared as in Scheme 9.

Scheme 9

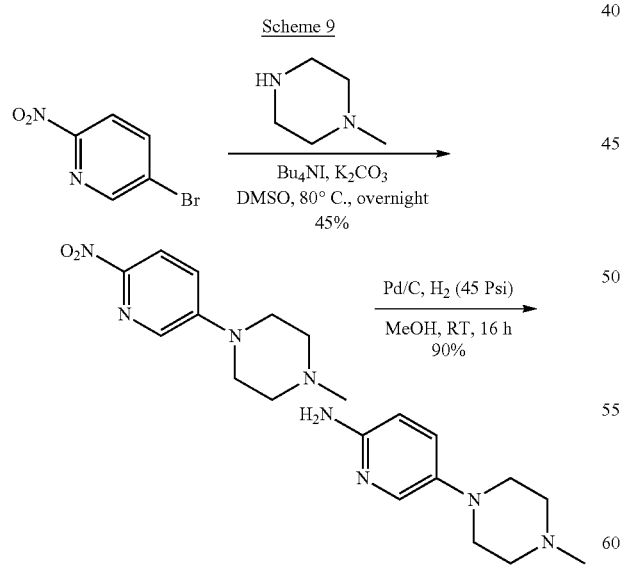

5-Bromo-2-nitro-pyridine (4.06 g, 20.0 mmol), 1-Methyl-piperazine (2.21 g, 22.1 mmol), K$_2$CO$_3$ (3.1 g, 22.1 mmol), Bu$_4$N$^+$ I$^-$ (371 mg, 1.004 mmol) were mixed in DMSO (50 mL). The mixture was stirred at 80° C. overnight. TLC showed the starting material was consumed completely; water was added and extracted with DCM. The organic layer was washed with water and brine, dried over anhydrous Na$_2$SO$_4$. It was then concentrated to give the crude product 1-methyl-4-(6-nitro-pyridin-3-yl)-piperazine (2.0 g, 45%) which was used in the next step directly.

A suspension of 1-methyl-4-(6-nitro-pyridin-3-yl)-piperazine (2 g, 9 mmol) and wet Pd/C (0.5 g) in MeOH (200 mL) was hydrogenated under H$_2$ (45 Psi) at RT for 16 h. The reaction mixture was filtered and the filtrate was concentrated to give 5-(4-methyl-piperazin-1-yl)-pyridin-2-ylamine (1.5 g, 86.7%) as a black solid.

EXAMPLE 16

Synthesis of Compound 44

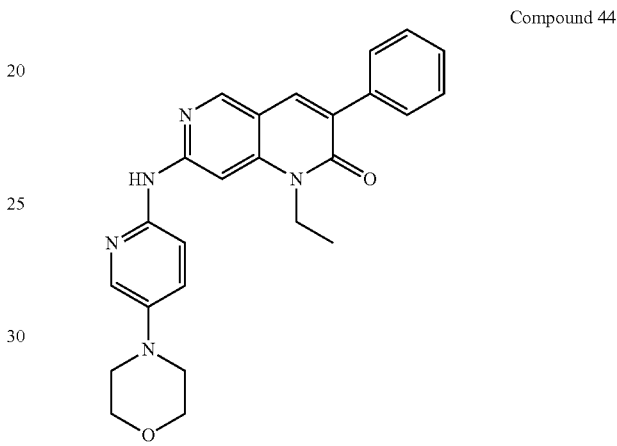

Compound 44

Compound 44, 1-Ethyl-7-(5-morpholin-4-yl-pyridin-2-ylamino)-3-phenyl-1H-[1,6]naphthyridin-2-one: This compound was synthesized in a similar manner to Compound 1 using 5-morpholin-4-yl-pyridin-2-ylamine as the coupling reagent, which was prepared in a similar manner to in scheme 9 using morpholine instead of 1-methyl-piperazine. $^1$H NMR (400 MHz, CDCl$_3$): δ 8.49 (s, 1H, ArH), 8.005 (d, J=2.8 Hz, 1H, ArH), 7.928 (s, 1H, ArH) 7.718-7.677 (m, 3H, ArH), 7.491 (brs, 1H, NH), 7.437-4.400 (m, 2H, ArH), 7.370-7.286 (m, 2H, ArH), 7.151 (d, J=8.8 Hz, 1H, ArH), 4.367 (q, J=5.6 Hz, 2H, CH$_2$), 3.884 (t, J=4.8 Hz, 4H, 2CH$_2$), 3.206-3.120(m, 4H, 2CH$_2$) 1.421 (t, J=7.2 Hz 3H, CH$_3$).

EXAMPLE 17

Synthesis of Compound 48

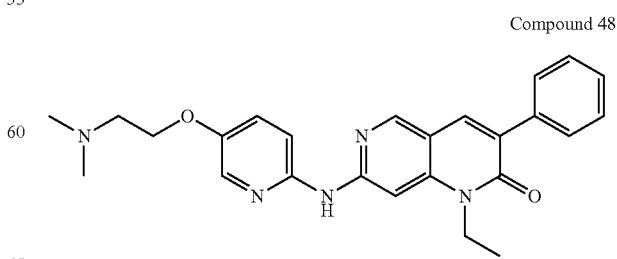

Compound 48

Compound 48, 7-[5-(2-Dimethylamino-ethoxy)-pyridin-2-ylamino]-1-ethyl-3-phenyl-1H-[1,6]naphthyridin-2-one:

This compound was synthesized in a similar manner to Compound 1 using 5-(2-dimethylamino-ethoxy)-pyridin-2-ylamine as the coupling reagent. ¹H NMR (CDCl₃, 400 MHz): δ 8.47 (s, 1H, ArH), 8.05 (s, 1H, ArH), 7.90 (s, 1H, ArH), 7.72-7.68 (m, 3H, 3ArH), 7.57 (s, 1H, NH), 7.37-7.28 (m, 4H, 4ArH), 4.36 (d, J=7.6 Hz, 2H, CH₂), 4.11 (t, J=4.8 Hz, 2H, CH₂), 2.77 (d, J=5.2 Hz, 2H, CH₂), 2.36 (s, 6H, 2CH₃), 1.43 (m, 3H, CH₃)

EXAMPLE 18

Synthesis of Compound 51

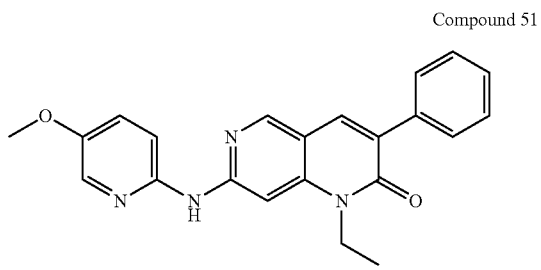 [SMILES: CCn1c(=O)c(-c2ccccc2)cc2cnc(Nc3ccc(OC)cn3)cc21]

Compound 51

Compound 51, 1-Ethyl-7-(5-methoxy-pyridin-2-ylamino)-3-phenyl-1H-[1,6]naphthayridin-2-one: This compound was synthesized in a similar manner to Compound 1 using 5-methoxy-pyridin-2-ylamine as the coupling reagent. ¹H NMR (CDCl₃, 400 MHz): δ 8.47 (s, 1H, ArH), 8.04 (d, J=2.4 Hz, 1H, ArH), 7.92 (s, 1H, ArH), 7.53 (br, 1H, NH), 7.38-7.34 (m, 2H, 2ArH), 7.28 (d, J=2.4 Hz, 1H, ArH), 7.19 (d, J=8.8 Hz 1H, ArH), 4.38 (q, J=7.2 Hz, 2H, CH₂), 3.87 (s, 3H, OCH₃), 1.45 (t, J=7.2 Hz, 3H, CH₃)

EXAMPLE 19

Synthesis of Compound 52

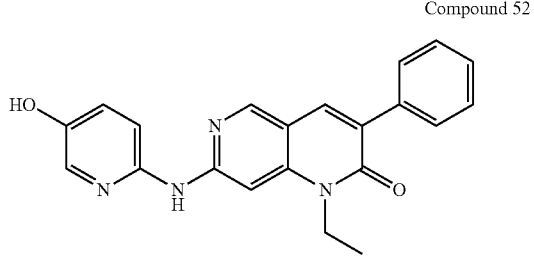 [SMILES: CCn1c(=O)c(-c2ccccc2)cc2cnc(Nc3ccc(O)cn3)cc21]

Compound 52

Compound 52, 1-Ethyl-7-(5-hydroxy-pyridin-2-ylamino)-3-phenyl-1H-[1,6]naphthyridin-2-one This compound was synthesized in a similar manner to Compound 1 using 6-amino-pyridin-3-ol as the coupling reagent. ¹H NMR (DMSO, 400 MHz): δ 9.72 (s, 1H, OH), 9.39 (s, 1H, NH), 8.59 (s, 1H, ArH), 8.01 (s, 1H, ArH), 7.88-7.85 (m, 2H, 2ArH), 7.68-7.66 (m, 2H, 2ArH), 7.49-7.39 (m, 4H, 4ArH), 7.18 (d, J=2.8 Hz 1H, ArH), 4.21 (q, J=7.2 Hz, 2H, CH₂), 1.29 (t, J=7.2 Hz, 3H, CH₃).

EXAMPLE 20

Synthesis of Compound 60

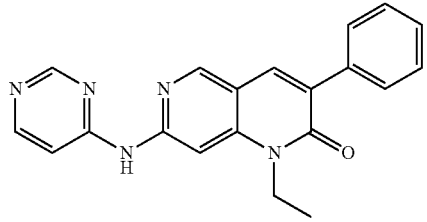 [SMILES: CCn1c(=O)c(-c2ccccc2)cc2cnc(Nc3ccnc(OC)n3)cc21]

Compound 60

Compound 60, 1-Ethyl-3-phenyl-7-(pyrimidin-4-ylamino)-1H-[1,6]naphthyridin-2-one: This compound was synthesized in a similar manner to Compound 1 using pyrimidin-4-ylamine as the coupling reagent. ¹H NMR (DMSO, 400 MHz): δ 10.55 (s, 1H, NH), 8.85 (s, 1H, ArH), 8.80 (s, 1H, ArH), 8.53 (d, J=6 Hz, 1H, ArH), 8.17 (s, 1H, ArH), 8.08 (s, 1H, ArH), 7.76 (d, J=7.2 Hz, 2H, 2ArH), 7.52-7.44 (m, 3H, 3ArH), 4.32 (t, J=7.0 Hz, 2H, CH₂), 1.38 (t, J=6.8 Hz, 3H, CH₃).

EXAMPLE 21

Synthesis of Compound 61

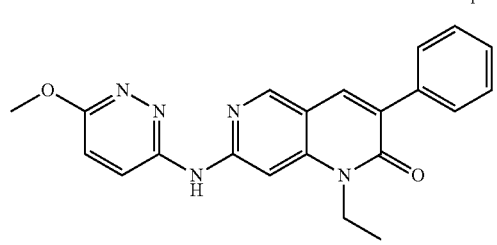

Compound 61

Compound 61, 1-Ethyl-7-(6-methoxy-pyridazin-3-ylamino)-3-phenyl-1H-[1,6]naphthyridin-2-one: This compound was synthesized in a similar manner to Compound 1 using 6-methoxy-pyridazin-3-ylamine as the coupling reagent. ¹H NMR (DMSO, 400 MHz): δ 10.15 (s, 1H, NH), 8.64(s, 1H, ArH), 8.03 (d, J=9.2 Hz, 2H, 2ArH), 7.85 (d, J=9.6 Hz, 1H, ArH), 7.72 (d, J=4.2 Hz, 1H, ArH), 7.69-7.61 (m, 3H, 3ArH), 7.18(d, J=9.2 Hz, 1H, ArH), 4.22 (q, J=6.8 Hz, 2H, CH₂), 3.97 (s, 3H, CH₃), 1.29 (t, J=7.2 Hz, 3H, CH₃).

EXAMPLE 22

Synthesis of Compound 62

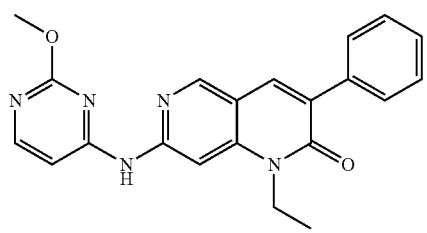

Compound 62, 1-Ethyl-7-(2-methoxy-pyrimidin-4-ylamino)-3-phenyl-1H-[1,6]naphthyridin-2-one: This compound was synthesized in a similar manner to Compound 1 using 2-methoxy-pyrimidin-4-ylamine as the coupling reagent. $^1$H NMR (DMSO, 400 MHz): δ 10.48 (s, 1H, NH), 8.70(s, 1H, ArH), 8.21 (t, J=7.2 Hz, 2H, 2ArH), 8.07 (s, 1H, ArH), 7.68 (t, J=4.2 Hz, 2H, 2ArH), 7.43-7.33 (m, 3H, 3ArH), 7.08 (d, J=5.6 Hz, 1H, ArH), 4.23 (q, J=6.4 Hz, 2H, CH$_2$), 3.94 (s, 3H, CH$_3$), 1.27 (t, J=7.0 Hz, 3H, CH$_3$).

EXAMPLE 23

Synthesis of Compound 63

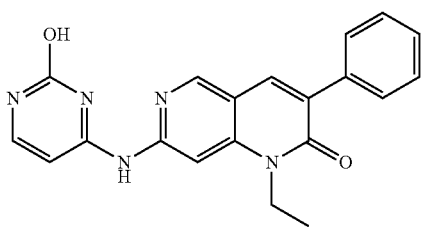 [SMILES: CCn1c(=O)c(-c2ccccc2)cc2cnc(Nc3ccnc(O)n3)cc21]

Compound 63, 1-Ethyl-7-(2-hydroxy-pyrimidin-4-ylamino)-3-phenyl-1H-[1,6]naphthyridin-2-one: This compound was synthesized in a similar manner to Compound 1 using 2-hydroxy-pyrimidin-4-ylamine as the coupling reagent. $^1$H NMR (DMSO, 400 MHz): δ 11.02 (s, 1H, NH), 10.44 (s, 1H, OH), 8.69 (s, 1H, ArH), 8.64 (br, 1H, ArH), 8.08 (s, 1H, ArH), 7.68 (t, J=4.2 Hz, 2H, 2ArH), 7.59 (d, J=6.8 Hz, 1H, ArH), 7.43-7.7.33 (m, 3H, 3ArH), 6.31 (d, J=4.8 Hz, 1H, ArH), 4.22 (d, J=6.8 Hz, 2H, CH$_2$), 1.29 (t, J=7.0 Hz, 3H, CH$_3$)

EXAMPLE 24

Synthesis of Compound 64

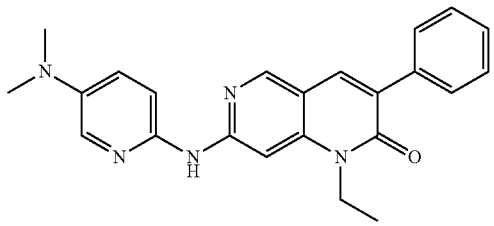 [SMILES: CCn1c(=O)c(-c2ccccc2)cc2cnc(Nc3ccc(N(C)C)cn3)cc21]

Compound 64, 7-(5-Dimethylamino-pyridin-2-ylamino)-1-ethyl-3-phenyl-1H-[1,6]naphthyridin-2-one: This compound was synthesized in a similar manner to Compound 1 using 5-dimethylamino-2-pyridinylamine as the coupling reagent, which was prepared in a similar manner to in scheme 9. $^1$H NMR (400 MHz, CDCl$_3$): δ 8.481 (s, 1H, ArH), 7.917 (d, J=2.8 Hz, 1H, ArH), 7.866 (s, 1H, ArH), 7.732(t, J=3.8 Hz, 3H, ArH), 7.604(brs, 1H, NH), 7.450 (t, J=7.2 Hz, 2H, ArH), 7.376(t, J=7.2 Hz, 1H, CH), 7.204-7.140 (m, 2H, ArH), 4.381 (q, J=7.2 Hz, 2H, CH$_2$), 2.982 (s, 6H, 2CH$_3$), 1.446(t, J=7.2 Hz, 3H, CH$_3$).

EXAMPLE 25

Synthesis of Compound 66

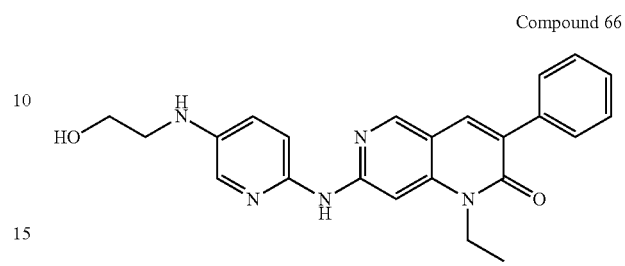

Compound 66

Compound 66, 1-Ethyl-7-[5-(2-hydroxy-ethylamino)-pyridin-2-ylamino]-3-phenyl-1H-[1,6]naphthyridin-2-one: This compound was synthesized in a similar manner to Compound 1 using 5-[2-(tert-Butyl-dimethyl-silanyloxy)-ethoxy]-pyridin-2-ylamine as the coupling reagent which was prepared as in scheme 10.

Scheme 10

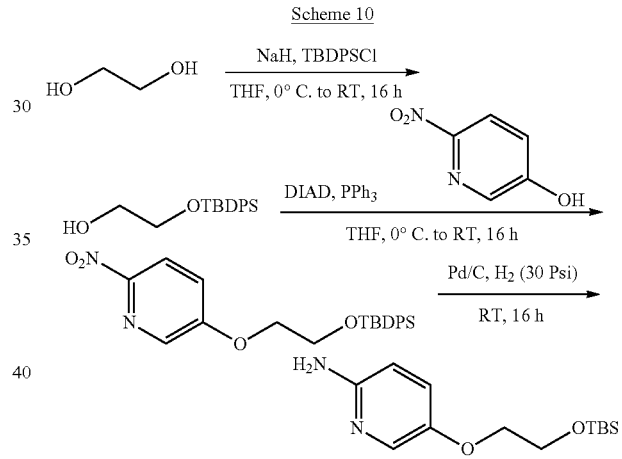

To a suspension of NaH (7.76 g, 0.194 mol) in THF (250 mL) was added ethane-1,2-diol (10 g, 0.162 mol) dropwise at 0° C. for 0.5 h. The mixture was stirred at 0° C. for 1 h, then added TBDPSCl (44 g, 0.194 mol) dropwise at 0° C. over 0.5 h. The mixture was warmed to RT and stirred at RT for 16 h. the mixture was poured into ice water, and then extracted with EtOAc, washed with water and brine, dried over Na$_2$SO$_4$, concentrated to give 2-(tert-Butyl-diphenyl-silanyloxy)-ethanol (40 g, 83.3%) as yellow oil.

To a solution of 2-(tert-Butyl-diphenyl-silanyloxy)-ethanol (1.8 g, 5.98 mmol), PPh$_3$ (1.88 g, 7.18 mmol) and 6-Nitro-pyridin-3-ol (0.84 g, 5.98 mmol) in THF (100 mL) was added DIAD (1.45 g, 7.18 mmol) dropwise at 0° C. over 0.5 h. The mixture was stirred at RT for 16 h. The solvent was removed to give the residue, and then purified by column chromatography on silica gel to give 5-[2-(tert-Butyl-diphenyl-silanyloxy)-ethoxy]-2-nitro-pyridine (1.8 g, 71.1%) as a yellow oil.

To a suspension of 5[2-(tert-Butyl-diphenyl-silanyloxy)-ethoxy]-2-nitro-pyridine (1.8 g, 3.57 mmol) and Pd/C (360 mg) in MeOH (100 mL) was hydrogenated under H$_2$ at RT for 16 h. The reaction mixture was filtered off and the filtrate was concentrated to give 5-[2-(tert-Butyl-dimethyl-silanyloxy)-ethoxy]-pyridin-2-ylamine (1.0 g, 59.9%) as a brown oil.

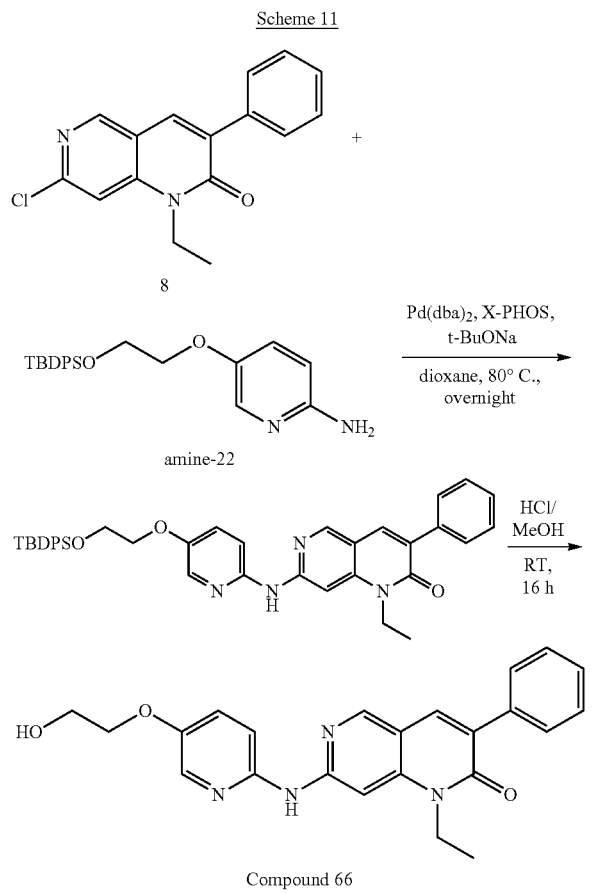

Scheme 11

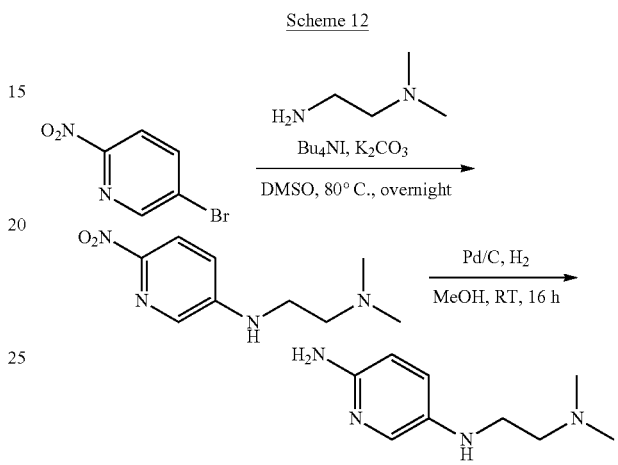

Scheme 12

5-Bromo-2-nitro-Pyridine (10 g, 50 mmol), amine (5 g, 55 mmol), K$_2$CO$_3$ (7.6 g, 55 mmol), Bu$_4$N$^+$I$^-$ (920 mg, 2.5 mmol) were mixed in DMSO (100 mL). The mixture was stirred at 80° C. overnight. TLC showed the starting material was consumed completely; water was added and extracted with DCM. The organic layer was washed with water and brine, dried over anhydrous Na$_2$SO$_4$. It was then concentrated to give the crude product (1.5 g, yield: 14.3%) which was used in the next step directly. A suspension of above crude product (1.5 g, 7.14 mmol) and Pd/C in MeOH (100 mL) was hydrogenated under H$_2$ at RT for 16 h. The reaction mixture was filtered and the filtrate was concentrated to give N5-(2-Dimethylamino-ethyl)-pyridine-2,5-diamine (1.3 g, 100%) as a black solid.

Compound 66 was synthesized in a similar manner to Compound 1 using 5-[2-(tert-Butyl-dimethyl-silanyloxy)-ethoxy]-pyridin-2-ylamine as the coupling reagent and after a n acid treatment step as in scheme 11. $^1$H NMR (CD$_3$OD, 400 MHz): δ 8.75 (s, 1H, NH), 8.08-8.06 (m, 2H, 2ArH), 7.83 (dd, J$^1$=2.4 Hz, J$^2$=9.2 Hz, 1H, CH$_2$),, 7.69 (d, J=3.2 Hz, 2H, 2ArH), 7.46-7.40 (m, 3H, 3ArH), 7.29-7.27 (d, J=9.2 Hz, 1H, ArH), 7.08 (s, 1H, ArH), 4.36 (q, J=7.2 Hz, 2H, CH$_2$), 4.17 (t, J=4.4 Hz, 2H, CH$_2$), 3.91 (t, J=4.6 Hz, 2H, CH$_2$), 1.40 (t, J=7.2 Hz, 3H, CH$_3$)

EXAMPLE 26

Synthesis of Compound 67 one: This compound was synthesized in a similar manner to Compound 1 using (Amine-23) as the coupling reagent, which was prepared as described below in scheme 12. $^1$H NMR (400 MHz, CDCl$_3$): δ 8.472(s, 1H, ArH), 7.840 (d, J=3.6 Hz, 2H, ArH), 7.730 (t, J=5.8 Hz, 3H, ArH), 7.449(t, J=7.6 Hz, 2H, ArH), 7.375(t, J=7.6 Hz, 2H, ArH), 7.110-7.053(m, 2H, NH and ArH), 4.373(q, J=7.2 Hz, 3H, NH and CH$_2$), 3.219 (t, J=5.4 Hz, 2H, CH$_2$), 2.667 (t, J=5.8 Hz, 2H, CH$_2$), 2.342 (s, 6H, 2CH$_3$), 1.438 (t, J=7.2 Hz, 3H, CH$_3$).

EXAMPLE 27

Synthesis of Compounds 26, 29, 32, 33, 35, 38-41, 45, 53, 54, 68, and 69

Compounds 26, 29, 32, 33, 35, 38-41, 45, 53, 54, 68, and 69

These compounds were synthesized as shown in Scheme 13. It started with the intermediate scheme 13 compound 6 as shown in Scheme 1.

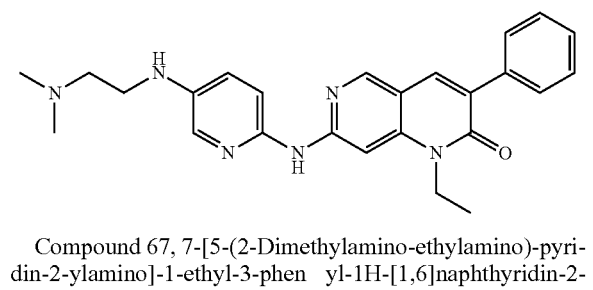

Compound 67, 7-[5-(2-Dimethylamino-ethylamino)-pyridin-2-ylamino]-1-ethyl-3-phen yl-1H-[1,6]naphthyridin-2-

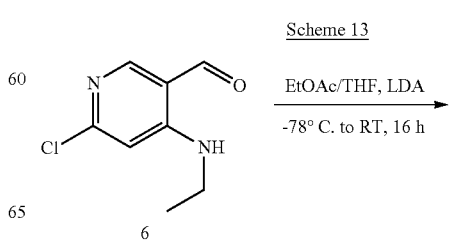

Scheme 13

6

EXAMPLE 28

Synthesis of Compound 21

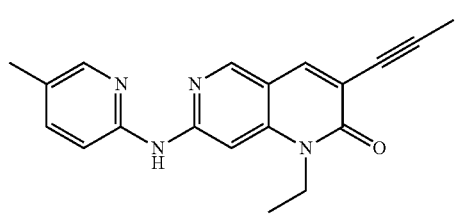

Compound 21

Compound 21 was synthesized showed as Scheme 14:

Scheme 14

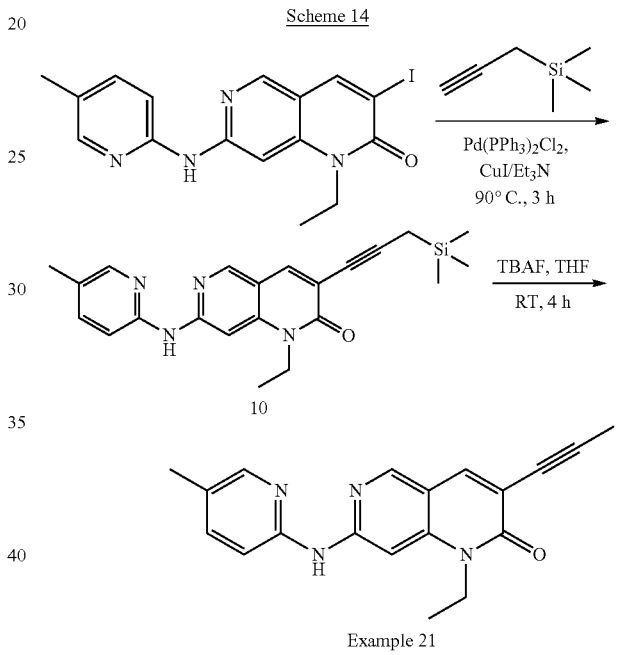

Example 21

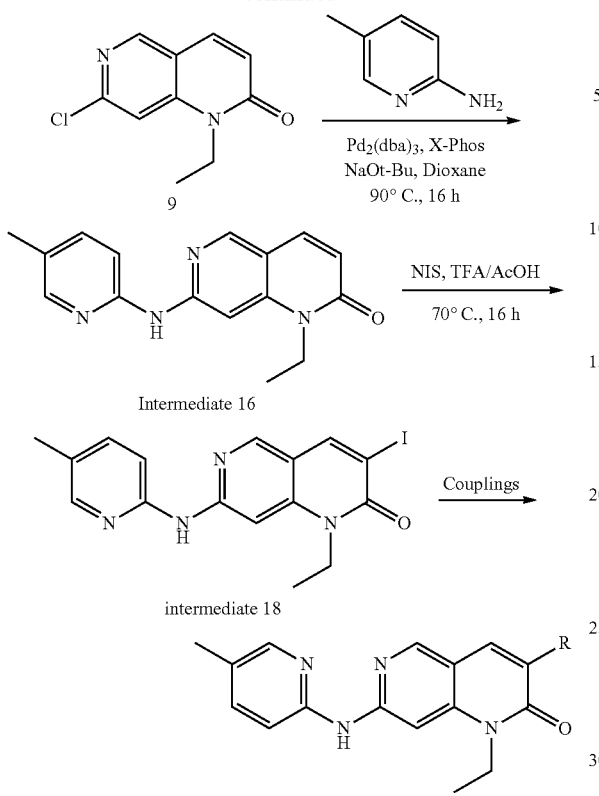

Scheme 13 compound 9 (1.9 g, 9.13 mmol), amine (1.2 g, 11.11 mmol), Pd$_2$(dba)$_3$ (834 mg, 0.911 mmol), NaOt-Bu (1.75 g, 18.23 mmol) and X-Phos (868 mg, 1.85 mmol) were mixed together, degassed with N$_2$. Dioxane (90 mL) was added, then the reaction mixture was degassed with N$_2$ for 3 times and heated to 90° C. for 16 h. After cooling to RT, the reaction mixture was diluted with DCM, filtered through Celite Pad. The filtrate was washed with water, concentrated. The crude product was purified by silica gel chromatography (DCM:MeOH=40:1) to give intermediate 16 1-Ethyl-7-(5-methyl-pyridin-2-ylamino)-1H-[1,6]naphthyridin-2-one (1.9 g, 74.3%) as a white solid.

$^1$H NMR (CDCl$_3$, 400 MHz): δ 8.40 (s, 1H, ArH), 8.15 (d, J=1.2 Hz, 1H, Ar), 8.08 (s, 1H, ArH), 7.59 (br, 1H, NH), 7.58 (d, J=9.2 Hz 1H, ArH), 7.44 (dd, J$^1$=2.4 Hz, J$^2$=8.4 Hz 1H, ArH), 6.49 (d, J=9.2 Hz 1H, ArH), 4.29 (q, J=7.2 Hz, 2H, CH$_2$).3H, ArCH$_3$), 2.29 (s, 3H, CH$_3$) 1.38 (t, J=7.2 Hz, 3H, CH$_3$).

1-Ethyl-7-(5-methyl-pyridin-2-ylamino)-1H-[1,6]naphthyridin-2-one (9 g, 32.1 mmol) was added to AcOH (150 mL). TFA (10.97 g, 96.3 mmol) was added dropwise. Then the reaction mixture was stirred at RT for 20 min. NIS (15.91 g, 70.7 mmol) was added. The reaction mixture was heated to 70° C. for 16 h under N$_2$. The reaction mixture was concentrated. The residue was dissolved in DCM/MeOH (10:1), washed with sat. Na$_2$SO$_3$. The organic layer was concentrated. The residue was triturated with DCM, afforded intermediate 18 (7.2 g, 55.2%) as a yellow solid. $^1$H NMR (CDCl$_3$, 400 MHz): δ 8.36 (s, 1H, ArH), 8.26 (s, 1H, =CH), 8.15 (br, 2H, ArH), 7.45 (d, J=8.4 Hz 1H), 6.99 (d, J=8.4 Hz 1H, ArH), 4.36 (q, J=7.2 Hz, 2H, CH$_2$), 2.29 (s, 3H, ArCH$_3$), 1.40 (t, J=7.2 Hz, 3H, CH$_3$).

Intermediate 18 (150 mg, 0.369 mmol), Trimethyl-prop-2-ynyl-silane (62 mg, 0.554 mmol), Pd(PPh$_3$)$_2$Cl$_2$ (25.8 mg, 0.0367 mmol) and CuI (13.8 mg, 0.0724 mmol) were added to Et$_3$N (6 mL). The reaction mixture was degassed with N$_2$. and heated to 90° C. for 3 h. After cooling to RT, the reaction mixture was diluted with DCM, filtered through Celite Pad. The filtrate was washed with water, concentrated. The crude product was purified by silica gel chromatography (DCM:MeOH=100:1) to give compound 10 (100 mg, 69.4%) as yellow solid.

Scheme 14 compound 10 (100 mg, 0.256 mmol) was dissolved in THF (3 mL), cooled by ice-bath. The solution of TBAF (67 mg, 0.256 mmol) in THF (0.5 mL) was added dropwise. Then the reaction mixture was stirred at RT for 4 h. The reaction mixture was diluted with H$_2$O, extracted with DCM. The combined organic layers was concentrated. The crude product was purified by Prep-HPLC to give Compound 21 (24 mg, 29.4%) as yellow solid.

$^1$H NMR (CDCl$_3$, 400 MHz): δ 8.36 (s, 1H, ArH), 8.14 (s, 1H, ArH), 8.08 (s, 1H, ArH), 7.73 (s, 1H, ArH), 7.47 (br, 1H, NH), 7.45 (d, J=8.4 Hz, 1H, ArH), 7.04 (d, J=8.4 Hz, 1H, ArH), 4.31 (q, J=7.2 Hz, 2H, CH$_2$), 2.12 (s, 3H, CH$_3$), 1.38 (t, J=7.2 Hz, 3H, CH$_3$).

Compound 26

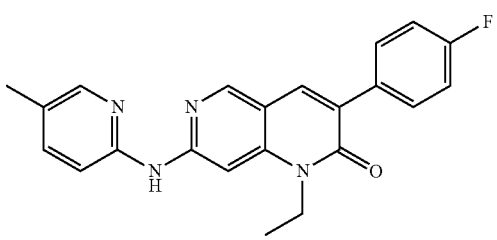

Intermediate 18 (207.4 mg, 0.511 mmol), 4-fluorophenylboronic acid (85.6 mg, 0.611 mmol), Pd(PPh$_3$)$_4$ (59.3 mg, 0.051 mmol) and Na$_2$CO$_3$ (161.7 mg, 1.525 mmol) were added to Dioxane/H$_2$O (4 mL/1 mL). The reaction mixture was degassed with N$_2$, and heated to 90° C. for 16 h. After cooling to RT, the reaction mixture was diluted with DCM, filtered through a celite pad. The filtrate was washed with water, concentrated. The crude product was purified by silica gel chromatography (DCM:MeOH=100:1) to give Compound 26 (45 mg, 23.5%) as a white solid. $^1$H NMR (CDCl$_3$, 400 MHz): δ 8.48 (s, 1H, ArH), 8.16 (s, 1H, ArH), 8.12 (s, 1H, ArH), 7.71 (s, 1H, ArH), 7.70-7.66 (m, 2H, ArH), 7.50 (br, 1H, NH), 7.49-7.48 (m, 1H, ArH), 7.13-7.09 (m, 3H, ArH), 4.37 (q, J=7.2 Hz, 2H, CH$_2$), 2.30 (s, 3H, ArCH$_3$), 1.43 (t, J=7.2 Hz, 3H, CH$_3$).

Compounds 29, 35, 40, 41, and 45 were synthesized in a similar manner to Compound 26 using corresponding boronic acids as coupling reagents.

Compound 29

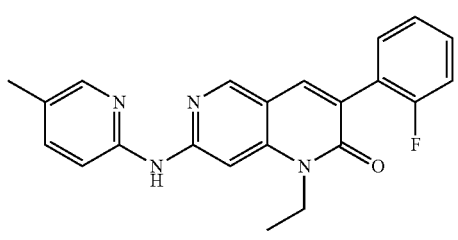

Compound 29: 1-ethyl-3-(3-fluorophenyl)-7-(5-methylpyridin-2-ylamino)-1,6-naphthyridin-2(1H)-one: $^1$H NMR (CDCl$_3$, 400 MHz): δ 8.48 (s, 1H, ArH), 8.18 (s, 1H, ArH), 8.13 (s, 1H, ArH), 7.75 (s, 1H, ArH), 7.49-7.47 (m, 4H, ArH), 7.40-7.35 (m, 1H, ArH), 7.05-7.03 (m, 2H, ArH), 4.37 (q, J=7.2 Hz, 2H, CH$_2$), 2.30 (s, 3H, ArCH$_3$), 1.43 (t, J=7.2 Hz, 3H, CH$_3$).

Compound 35

Compound 35: 1-ethyl-3-(2-fluorophenyl)-7-(5-methylpyridin-2-ylamino)-1,6-naphthyridin-2(1H)-one: $^1$H NMR (400 MHz, DMSO): δ 9.97 (s, 1H, ArH), 8.63 (s, 1H, ArH), 8.13 (d, J=7.6 Hz, 2H, ArH), 7.98 (s, 1H, CH), 7.56-7.29 (m, 4H, NH and ArH), 7.27 (t, J=7.6 Hz, 2H, ArH), 7.22(d, J=6.8 Hz, 2H, CH$_2$), 2.24 (s, 3H, CH$_3$), 1.31 (t, J=7.2 Hz, 3H, CH$_3$).

Compound 40

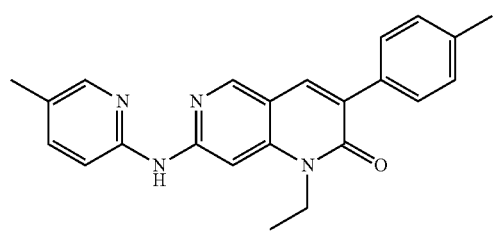

Compound 40: 1-ethyl-7-(5-methylpyridin-2-ylamino)-3-p-tolyl-1,6-naphthyridin-2(1H)-one: $^1$H NMR (400 MHz, DMSO): δ 8.49(s, 1H, ArH), 8.18(s, 1H, ArH), 8.10(s, 1H, ArH), 7.73(s, 1H, ArH), 7.62(d, J=8 Hz, 2H, ArH), 7.50(t, J=4 Hz, 1H, CH), 7.27(t, J=6.0 Hz, 3H, ArH), 7.11(d, J=6.4 Hz, 1H, ArH), 4.42-4.31(m, 2H, CH$_2$), 2.41 (s, 3H, CH$_3$), 2.32 (s, 3H, CH$_3$) 1.45(t, J=7.2 Hz, 3H, CH$_3$).

Compound 41

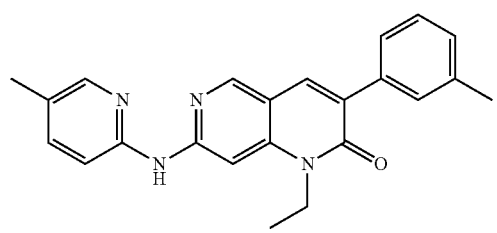

Compound 41: 1-ethyl-7-(5-methylpyridin-2-ylamino)-3-m-tolyl-1,6-naphthyridin-2(1H)-one: $^1$H NMR (CDCl$_3$, 400 MHz): δ 8.47 (s, 1H, ArH), 8.17 (s, 1H, ArH), 8.09 (s, 1H, ArH), 7.72 (s, 1H, ArH), 7.53-7.44 (m, 3H, 2ArH and NH), 7.19 (d, J=7.6 Hz, 1H, ArH), 7.07 (d, J=8.4 Hz, 1H, ArH), 4.38 (q, J=7.2 Hz, 2H, CH$_2$), 2.41 (s, 3H, CH$_3$), 2.30 (s, 3H, CH$_3$), 1.43 (t, J=7.2 Hz, 3H, CH$_3$).

Compound 45

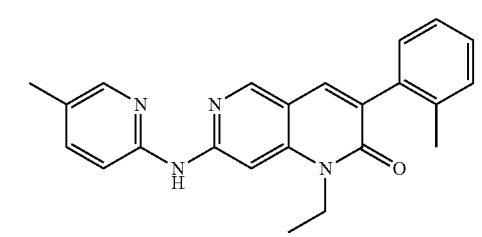

Compound 45: 1-ethyl-7-(5-methylpyridin-2-ylamino)-3-o-tolyl-1,6-naphthyridin-2(1H)-one: $^1$H NMR (400 MHz, CDCl$_3$): δ 8.466 (s, 1H, ArH), 8.202 (s, 1H, ArH), 8.142 (s, 1H, ArH) 7.591 (s, 1H, ArH), 7.495 (d, J=6 Hz, 2H, ArH), 7.277 (d, J=6 Hz 4H, ArH), 7.102 (brs, 1H, NH), 4.404 (q, J=7.2 Hz, 2H, CH$_2$), 2.333 (s, 3H, CH$_3$), 2.280 (s, 3H, CH$_3$), 1.453(t, J=7.2 Hz, 3H, CH$_3$).

Compound 32, 39, 53, 54 were synthesized in a similar manner to scheme 14 compound 10.

Compound 32

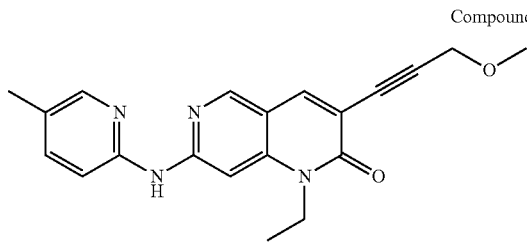

Intermediate 18 (200 mg, 0.493 mmol), 3-Methoxy-propyne (70 mg, 0.985 mmol), Pd(PPh$_3$)$_2$Cl$_2$ (34.6 mg, 0.0493 mmol) and CuI (18.8 mg, 0.0986 mmol) were added to Et$_3$N (6 mL). The reaction mixture was degassed with N$_2$. and heated to 90° C. for 16 h. After cooling to RT, the reaction mixture was diluted with DCM, filtered through Celite Pad. The filtrate was washed with water, concentrated. The crude product was purified by Prep-HPLC to give Compound 32 (20 mg, 11.6%) as yellow solid. $^1$H NMR (CDCl$_3$, 400 MHz): δ 8.39 (s, 1H, ArH), 8.17 (s, 1H, ArH), 8.14 (s, 1H, ArH), 7.83 (s, 1H, ArH), 7.47-7.45 (m, 2H, ArH), 4.39 (s, 2H, CH$_2$O), 4.32 (q, J=6.8 Hz, 2H, CH$_2$), 3.48 (s, 3H, OCH$_3$), 2.30 (s, 3H, CH$_3$), 1.40 (t, J=6.8 Hz, 3H, CH$_3$).

Compound 39

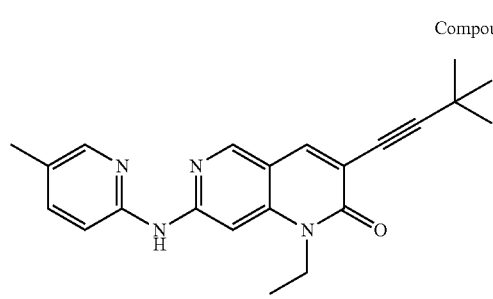

Intermediate 18 (100 mg, 0.25 mmol); 3,3-Dimethyl-but-1-yne (205 mg, 2.5 mmol), Pd(PPh$_3$)$_2$Cl$_2$ (17.5 mg, 0.025 mmol) and CuI (9.5 mg, 0.05 mmol) were added to Et$_3$N (3 mL). The reaction mixture was purged with N$_2$. and charged MW at 80° C. for 1 h. After cooling to RT, the reaction mixture was diluted with DCM, filtered through Celite Pad. The filtrate was washed with water, concentrated. The crude product was purified by Prep-HPLC to give Compound 39 (60 mg, 66.7%) as yellow solid. $^1$H NMR (CDCl$_3$, 400 MHz): δ 8.36 (s, 1H, ArH), 8.15 (s, 1H, ArH), 8.06 (s, 1H, ArH), 7.74 (s, 1H, ArH), 7.57 (br, 1H, NH), 7.45 (q, J=8.4 Hz, 1H, ArH), 7.04 (q, J=8.4 Hz, 1H, ArH), 4.30 (q, J=7.2 Hz, 2H, CH$_2$), 1.40-1.35 (m, 12H).

Compound 53

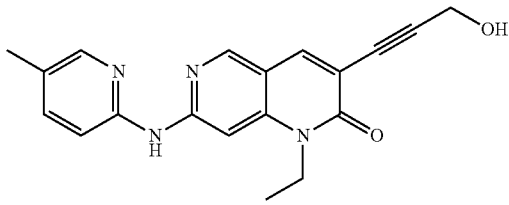

Intermediate 18 (200 mg, 0.5 mmol), prop-2-yn-1-ol (280 mg, 5 mmol) and Phenol (14 mg, 0.05 mmol) was dissolved in dioxane/Et$_3$N. To this mixture was added CuI (20 mg, 0.1 mmol), Pd(PPh$_3$)$_2$Cl$_2$ (36 mg, 0.05 mmol) under nitrogen atmosphere. The reaction vessel was sealed and heated in microwave at 85° C. for 1.5 h. After TLC showed the starting material was consumed completely, the mixture was filtered and diluted in DCM, the organic layer was washed with brine and dried over anhydrous Na$_2$SO$_4$, filtered, concentrated to give a residue which was purified by prep-HPLC to give Compound 53 (42 mg, yield: 25%) as a yellow solid. $^1$H NMR (400 MHz, CDCl$_3$): δ 8.394 (s, 1H, ArH), 8.147 (s, 1H, ArH), 8.110 (s, 1H, ArH) 7.811 (s, 1H, ArH), 7.492 (q, J=2 Hz, 1H, ArH), 7.065 (d, J=2 Hz, 1H, NH), 4.547 (s, 2H, CH$_2$), 4.319 (q, J=7.2 Hz, 2H, CH$_2$), 2.308 (s, 3H, CH$_3$), 2.171 (brs, 1H, OH), 1.393(t, J=7.2 Hz, 3H, CH$_3$).

Compound 54

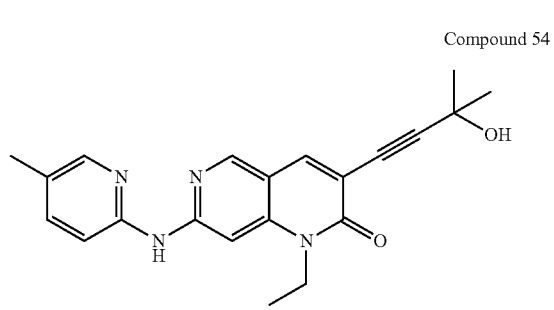 [SMILES: CCn1c(=O)c(C#CC(C)(C)O)cc2cnc(Nc3ccc(C)cn3)cc21]

Intermediate 18 (300 mg, 0.5 mmol), 2-Methyl-but-3-yn-2-ol (631 mg, 7.5 mmol) and Phenol (14 mg, 0.05 mmol) was dissolved in dioxane/Et$_3$N. To this mixture was added CuI (30 mg, 0.15 mmol), Pd(PPh$_3$)$_2$Cl$_2$ (54 mg, 0.075 mmol) under nitrogen atmosphere. The reaction vessel was sealed and heated in microwave at 85° C. for 1.5 h. After TLC showed the starting material was consumed completely, the mixture was filtered and diluted in DCM, the organic layer was washed with brine and dried over anhydrous Na$_2$SO$_4$, filtered, concentrated to give a residue which was purified by prep-HPLC to give Compound 54 (85 mg, yield: 31%) as a yellow solid. $^1$H NMR (400 MHz, CDCl$_3$): δ 8.379 (s, 1H, ArH), 8.146 (s, 1H, ArH), 8.088 (s, 1H, ArH) 7.782(s, 1H, ArH), 7.470 (q, J=2 Hz, 1H, ArH), 7.068 (brs, 1H, NH), 4.307 (q, J=7.2 Hz, 2H, CH$_2$), 2.504 (brs, 1H, OH), 2.301 (s, 3H, CH$_3$), 1.695 (s, 6H, 2CH$_3$), 1.388(t, J=7.2 Hz, 3H, CH$_3$).

Compound 33

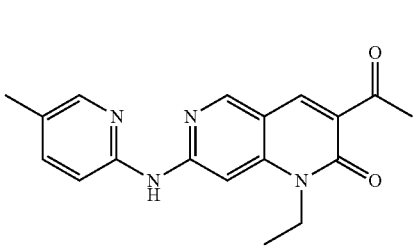

Compound 33 was synthesized showed as Scheme 15:

Scheme 15

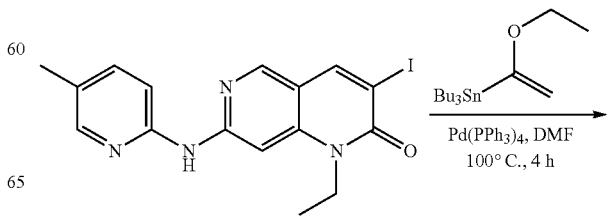

-continued

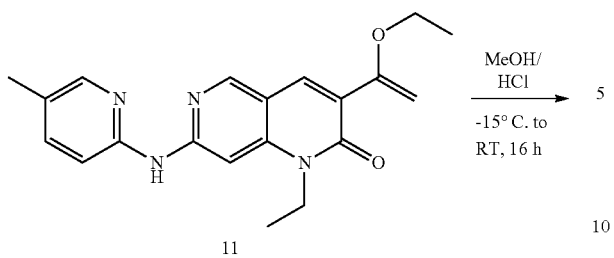

11

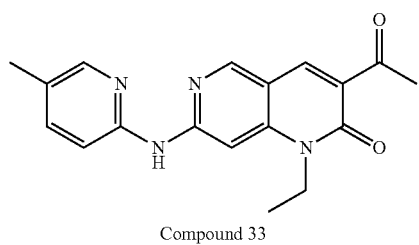

Compound 33

Intermediate 18 (300 mg, 0.739 mmol), the Tin reagent as in the scheme (533.6 mg, 1.478 mmol) and Pd(PPh$_3$)$_4$ (85.5 mg, 0.074 mmol) were added to DMF (6 mL). The reaction mixture was purged with N$_2$. and heated at 100° C. for 4 h. After cooling to RT, the reaction mixture was diluted with DCM, filtered through Celite Pad. The filtrate was washed with water, concentrated. The crude product was purified by flash column to give scheme 15 compound 11 (200 mg, 77.3%) as yellow solid.

Scheme 15 compound 11 (200 mg, 0.571 mmol) was added to cool MeOH/HCl (5 mL). The reaction mixture was stirred at RT for 16 h. Then the reaction mixture was concentrated, purified by prep-HPLC to give Compound 33 (50 mg, 27.1%) as light yellow solid. $^1$H NMR (CDCl$_3$, 400 MHz): δ 8.56 (s, 1H, ArH), 8.40 (s, 1H, ArH), 8.18 (s, 1H, ArH), 8.17 (s, 1H, ArH), 7.53 (br, 1H, NH), 7.47 (d, J=8.4 Hz, 1H, ArH), 7.02 (d, J=8.4 Hz, 1H, ArH), 4.33 (q, J=6.8 Hz, 2H, CH$_2$), 2.74 (s, 3H, ArCH$_3$), 2.31 (s, 3H, COCH$_3$), 1.41 (t, J=6.8 Hz, 3H, CH$_3$).

Compound 38

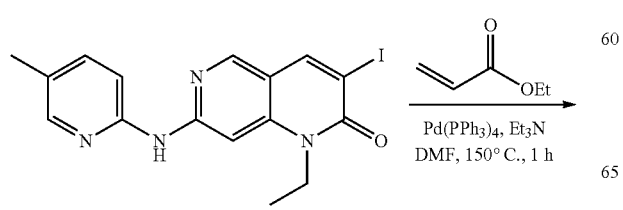

Scheme 16

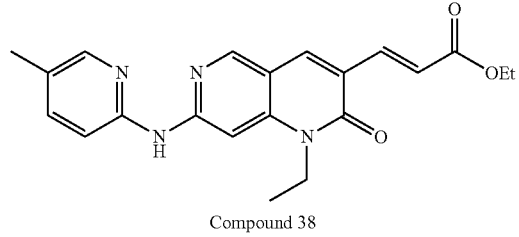

Compound 38

Intermediate 18 (200 mg, 0.493 mmol), Acrylic acid ethyl ester (74 mg, 0.739 mmol), E$_3$N (150 mg, 1.479 mmol) and Pd(PPh$_3$)$_4$ (28 mg, 0.0246 mmol) were added to DMF (3 mL). The reaction mixture was purged with N$_2$. and charged in MW at 150° C. for 1 h. After cooling to RT, the reaction mixture was diluted with DCM, filtered through Celite Pad. The filtrate was washed with water, concentrated. The crude product was purified by Prep-HPLC to give example 38 (50 mg, 26.8%) as yellow solid. $^1$H NMR (CDCl$_3$, 400 MHz): δ 8.47 (s, 1H, ArH), 8.17 (s, 1H, ArH), 8.13 (s, 1H, ArH), 7.81 (s, 1H, ArH), 7.72 (d, J=16.0 Hz 1H, =CH), 7.64 (s, 1H, ArH), 7.46 (d, J=8.4 Hz, 1H, ArH), 7.03-6.99 (m, 2H, ArH), 4.33 (q, J=7.2 Hz, 2H, CH$_2$), 4.24 (q, J=7.2 Hz, 2H, CH$_2$), 2.29 (s, 3H, CH$_3$), 1.39 (t, J=7.2 Hz, 3H, CH$_3$), 1.31 (t, J=7.2 Hz, 3H, CH$_3$).

Compound 68

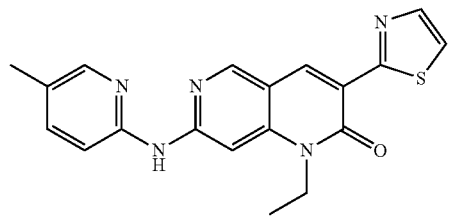

Compound 68 was synthesized as shown in Scheme 17:

Scheme 17

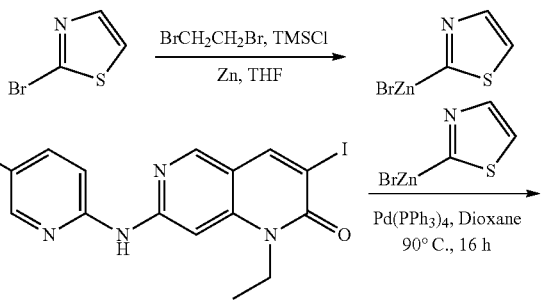

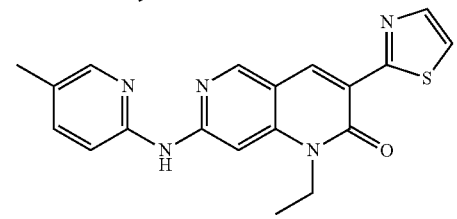

Zn dust (1.95 g, 30 mmol) was added to THF (5 mL) in a round bottom flask. To this flask, BrCH$_2$CH$_2$Br (507.6 mg, 2.7 mmol) was added. The reaction mixture was heated by hot gun until the evolution of ethylene gas was done for twice. TMSCl (130.8 mg, 1.2 mmol) was then added. Then the solution of 2-Bromo-thiazole (1.64 g, 10 mmol) in THF (5 mL) was added dropwise. After the addition, the reaction mixture was stirred at rt for 2 h. The fresh prepared bromozinc thiazole reagent was used as a solution (1 M) directly.

Intermediate 18 (50 mg, 0.125 mmol) and Pd(PPh$_3$)$_4$ (14.4 mg, 0.0125 mmol) were added to Dioxane (1.5 mL). The solution of the bromo-zinc thiazole reagent (1 M, 025 mL) was added dropwise. The reaction mixture was then heated to 90° C. for 16 h. After cooling to RT, the reaction mixture was diluted with DCM, filtered through a celite pad. The filtrate was washed with water, concentrated. The crude product was purified by Prep-HPLC to give Compound 68 (20 mg, 44.7%) as a yellow solid.

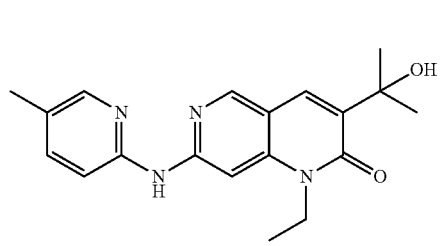

Compound 69

Scheme 18

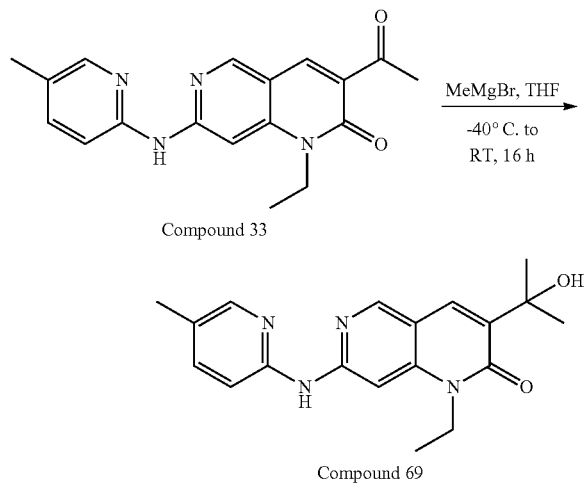

Compound 33

Compound 69

Compound 33 (74 mg, 0.23 mmol) was dissolved in dry THF (3 mL), cooled to −40° C. MeMgBr (3M, 0.16 mL, 0.46 mmol) was added dropwise. Then the reaction mixture was warmed slowly to RT and stirred for 16 h. The reaction was quenched with sat NH$_4$Cl, extracted with EtOAc. The combined EtOAc was dried, concentrated. The crude product was purified by prep-TLC to give Compound 69 (20 mg, 25.8%) as white solid. $^1$H NMR (CDCl$_3$, 400 MHz): δ 8.46 (s, 1H, ArH), 8.14 (br, 2H, ArH), 7.59 (s, 1H, ArH), 7.47 (d, J=8.4 Hz 1H, ArH), 7.07 (d, J=8.4 Hz 1H, ArH), 5.55 (br, 1H, OH), 4.34 (q, J=7.2 Hz, 2H, CH$_2$), 2.30 (s, 3H, CH$_3$), 1.63 (s, 6H, 2CH$_3$), 1.41 (t, J=7.2 Hz, 3H, CH$_3$).

Example 29

Synthesis of Compounds 10-13, 19, 20, 30, 31, and 37

Compounds 10-13, 19, 20, 30, 31, and 37. These compounds were synthesized as shown in Scheme 19. It started with the intermediate compound 6 as shown in scheme 1. There are two general methods A and B to perform the first step as described below. Method A was used for Compounds 10 and 11; method B was used for Compounds 12 and 13. The last step uses a same procedure as described for Compound 1.

Scheme 19

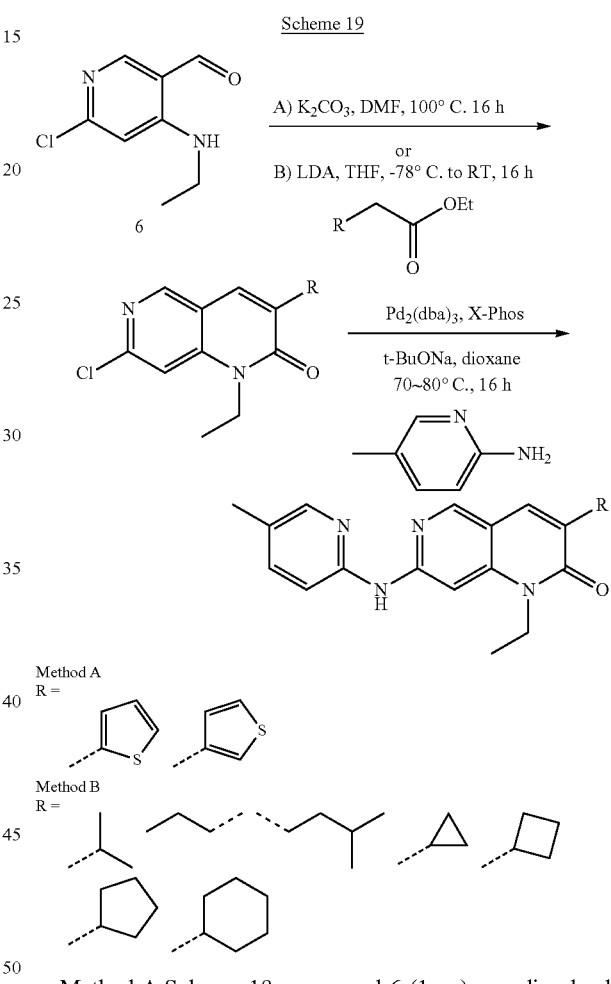

Method A Scheme 19 compound 6 (1 eq) was dissolved in anhydrous DMF and added Thiophen-2-yl-acetic acid ethyl ester (1.1 eq) and K$_2$CO$_3$ (3.0 eq). The mixture was stirred at 100° C. overnight. TLC showed the starting material was consumed completely. The reaction mixture was diluted with H$_2$O and extracted with EtOAc. The organic layer was washed with brine and dried over anhydrous Na$_2$SO$_4$, concentrated to give crude residue which was purified by silica gel chromatography to give intermediate 7-Chloro-1-ethyl-3-thiophen-2-yl-1H-[1,6]naphthyridin-2-one as yellow solid.

Method B Scheme 19 compound 6 (2.2 eq) was dissolved in anhydrous THF, cooled to −78° C. LDA (2.2 eq) was added dropwise. The mixture was then stirred at −78° C. for 1 h. The solution of cyclohexyl-acetic acid ethyl ester (1.0 eq) in THF was added dropwise at −78° C. The resulting reaction mixture was warmed slowly to RT and stirred for 16 h. The reaction was quenched with saturated NH$_4$Cl and extracted with EtOAc. The organic layer was washed with brine, dried over anhydrous Na$_2$SO$_4$, concentrated to give crude residue which was purified by silica gel chromatography to give 7-Chloro-3-cyclohexyl-1-ethyl-1H-[1,6]naphthyridin-2-one as a yellow solid.

The final products Compounds 10-13 were synthesized using same coupling procedure as described for Compound 1.

Compound 10

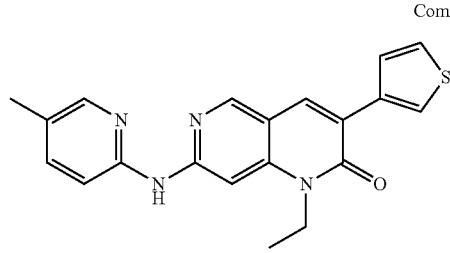

Compound 10, 1-Ethyl-7-(5-methyl-pyridin-2-ylamino)-3-thiophen-3-yl-1H-[1,6]naphthyridin-2-one: $^1$H NMR (CDCl$_3$, 400 MHz): δ 8.49 (s, 1H, ArH), 8.18-8.16 (m 2H, ArH), 8.11 (s, 1H, ArH), 7.89 (s, 1H, ArH), 7.55-7.54 (dd, I=1.2 Hz, J$^2$=5.2 Hz 1H, ArH), 7.47-7.45 (m, 2H, ArH and NH), 7.37-7.35 (dd, J$^1$=3.2 Hz, J$^2$=5.2 Hz, 1H, ArH), 7.07-7.06 (d, J=7.2 Hz, 1H, ArH), 4.42-4.36 (q, J=7.2 Hz, 2H, CH$_2$), 2.30 (s, 3H, ArCH$_3$), 1.45-1.41 (t, J=7.2 Hz, 3H, CH$_3$). MS [ESI, MH$^+$]:=363.1.

Compound 11

Compound 11, 1-Ethyl-7-(5-methyl-pyridin-2-ylamino)-3-thiophen-2-yl-1H-[1,6]naphthyridin-2-one: $^1$H NMR (CDCl$_3$, 400 MHz): δ 8.52 (s, 1H, ArH), 8.15 (s, 2H, ArH), 8.04 (s, 1H, ArH), 7.71-7.70 (dd, J$^1$=1.2 Hz, J$^2$=4.0 Hz 1H, ArH), 7.48-7.46 (d, J=8.0 Hz, 2H, ArH), 7.42-7.40 (dd, J$^1$=0.8 Hz, J$^2$=5.2 Hz, 1H, ArH), 7.13-7.11 (dd, J$^1$=4.0 Hz, J$^2$=1.2 Hz, 1H, ArH), 7.07 (brs, 1H, NH), 4.45-4.39 (q, J=7.2 Hz, 2H, CH$_2$), 2.30 (s, 3H, ArCH$_3$), 1.46-1.43 (t, J=7.2 Hz, 3H, CH$_3$); MS [ESI, MH$^+$]:=363.1.

Compound 12

Compound 12, 3-Cyclohexyl-1-ethyl-7-(5-methyl-pyridin-2-ylamino)-1H-[1,6]naphthyridin-2-one: $^1$H NMR (CDCl$_3$, 400 MHz): δ 8.38 (s, 1H, ArH), 8.15 (s, 1H, ArH), 7.99 (s, 1H, ArH), 7.44 (d, J=2.4 Hz, 2H, ArH), 7.42 (s, 1H, NH), 7.05 (d, J=8.4 Hz, 1H, ArH), 4.33-4.28 (q, J=7.2 Hz, 2H, CH$_2$), 2.94-2.88 (m, 1H, CH), 2.28 (s, 3H, ArCH$_3$), 1.94 (q, J=12 Hz, 2H, CH$_2$), 1.85-1.75(m, 3H, CH$_3$), 1.52-1.48 (m, 2H, CH$_2$), 1.38(t, J=7.2 Hz, 3H, CH$_3$), 1.32-1.26(m, 3H, CH$_3$), MS [ESI, MH$^+$]:=363.3.

Compound 13

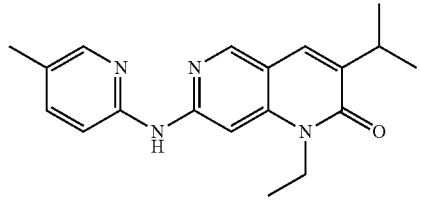

Compound 13, 1-Ethyl-3-isopropyl-7-(5-methyl-pyridin-2-ylamino)-1H-[1,6]naphthyridin-2-one: $^1$H NMR (CDCl$_3$, 400 MHz): δ 8.39 (s, 1H, ArH), 8.14 (dd, J'=0.8 Hz, J$^2$=1.6 Hz, 1H, ArH 1H, ArH), 7.44-7.38(m, 3H, ArH), 7.047 (d, J=8.4 Hz, 1H, ArH), ArH), 4.37-4.31 (q, J=7.2 Hz, 2H, CH$_2$), 3.31-3.24 (m, 1H, CH), 2.28 (s, 3H, ArCH$_3$), 1.38(t, J=7.2 Hz, 3H, CH$_3$), 1.24(d, J=6.8 Hz, 3H, CH$_3$), 1.22(d, J=7.2 Hz, 3H, CH$_3$), MS [ESI, MH$^+$]:=323.2.

Compound 19

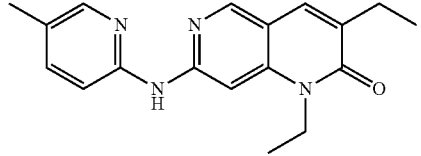

Compound 19, 1,3-Diethyl-7-(5-methyl-pyridin-2-ylamino)-1H-[1,6]naphthyridin-2-one: $^1$H NMR (CDCl$_3$, 400 MHz): δ 8.37 (s, 1H, ArH), 8.12 (s, 1H, ArH), 7.99 (s, 1H, ArH), 7.51-7.40 (m, 3H, 2ArH, NH), 7.13-6.97 (m, 1H, ArH), 4.30(q, J=7.2 Hz, 2H, CH$_2$), 2.64-2.58 (m, 2H, CH$_2$), 2.26 (s, 3H, CH$_3$), 1.36 (t, J=7.2 Hz, 3H, CH$_3$), 1.23 (t, J=7.4 Hz, 3H, CH$_3$). MS [ESI, MH$^+$]=309.2.

Compound 20

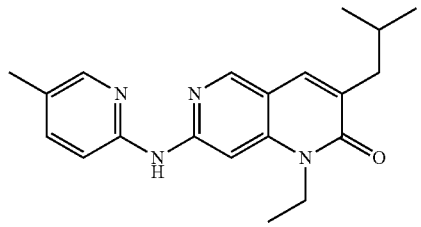

Compound 20, 1-Ethyl-3-isobutyl-7-(5-methyl-pyridin-2-ylamino)-1H-[1,6]naphthyridin-2-one: $^1$H NMR (CDCl$_3$, 400 MHz): δ 8.38 (s, 1H, ArH), 8.14(s, 1H, ArH), 8.00 (s, 1H, ArH), 7.54 (br, 1H, NH), 7.45-7.42 (dd, J$^1$=2.0 Hz, J$^2$=2.0 Hz, 2H, ArH), 7.39 (s, 1H, ArH), 7.06 (d, J=8.4 Hz 1H, ArH), 4.30 (q, J=7.2 Hz, 2H, CH$_2$), 2.45 (d, J=6.8 Hz, 2H, CH$_2$), 2.28 (s, 3H, CH$_3$), 2.06-1.99(m, 1H, CH), 1.37 (t, J=7.2 Hz, 3H, CH$_3$), 0.94 (d, J=6.4 Hz, 6H, 2CH$_3$). MS [ESI, MH$^+$]=337.2.

Compound 30

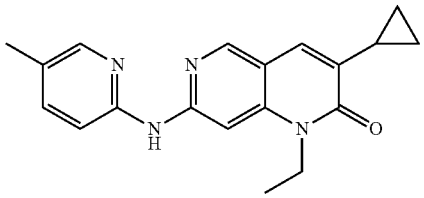

Compound 30, 3-Cyclopropyl-1-ethyl-7-(5-methyl-pyridin-2-ylamino)-1H-[1,6]naphthaayridin-2-one: ¹H NMR (CDCl₃, 400 MHz): δ 8.34 (s, 1H, ArH), 8.14 (t, J=8 Hz, 1H, ArH), 8.00 (s, 1H, ArH), 7.57 (br, 1H, NH), 7.44-7.42 (dd, J¹=2.4 Hz, J²=2.4 Hz, 1H, ArH), 7.25 (s, 1H, ArH), 7.12 (s, 1H, ArH), 7.06 (d, J=8.4 Hz, 1H, ArH), 4.33 (q, J=7.2 Hz, 2H, CH₂), 2.28 (s, 3H, CH₃), 2.29-2.17 (m, 1H, CH), 1.39 (t, J=7.0 Hz, 3H, CH₃), 1.01-09.6 (m, 2H, CH₂), 0.69-0.66 (m, 2H, CH₂). MS [ESI, MH⁺]=321.2.

Compound 31

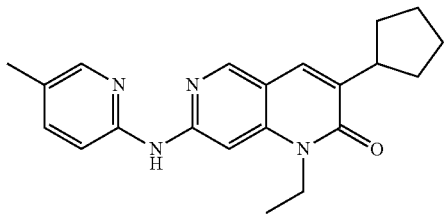

Compound 31, 3-Cyclopentyl-1-ethyl-7-(5-methyl-pyridin-2-ylamino)-1H-[1,6]naphthayridin-2-one: ¹H NMR (CDCl₃, 400 MHz): δ 8.38(s, 1H, ArH), 8.19(s, 1H, ArH), 8.00 (s, 1H, ArH), 7.45 (q, J=8 Hz, 2H, ArH), 7.09 (br, 1H, ArH), 4.43-4.22 (m, 2H, CH₂), 3.31-3.22 (m, 1H, CH), 2.29 (s, 3H, CH₃), 2.12-2.05 (m, 2H, CH₂), 2.81-1.72(m, 6H, 3CH₂), 1.70 (t, J=7.2 Hz, 3H, CH₃).

Compound 37

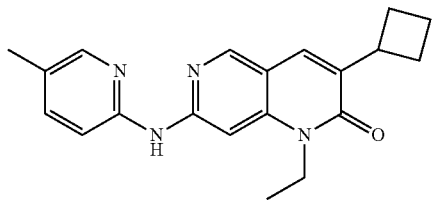

Compound 37, 3-Cyclobutyl-1-ethyl-7-(5-methyl-pyridin-2-ylamino)-1H-[1,6]naphthyridin-2-one: ¹H NMR (CDCl₃, 400 MHz): δ 8.42(s, 1H, ArH), 8.16(d, J=8 Hz, 1H, ArH), 7.99 (s, 1H, ArH), 7.82 (br, 1H, NH), 7.45-7.42 (dd, J¹=2.0 Hz, J²=2.8 Hz, 2H, ArH), 7.06 (d, J=8.4 Hz, 1H, ArH), 4.29(q, J=7.2 Hz, 2H, CH₂), 3.68 (q, J=7.2 Hz, 1H, CH), 2.41 (s, 2H, CH₂), 2.41(s, 3H, CH₃), 2.28-2.02(m, 3H, CH₃), 1.86-1.82 (m, 1H, CH), 1.37 (t, J=7.2 Hz, 3H, CH₃).MS [ESI, MH⁺]=335.2.

Example 30

Synthesis of Compound 24

Compound 24

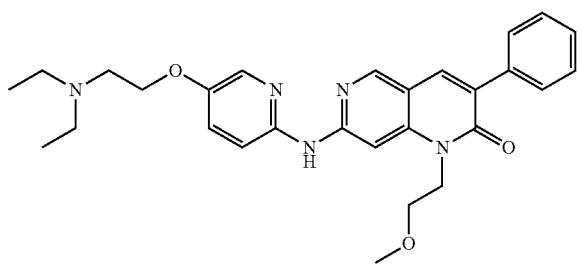

Compound 24, 7-(5-(2-(diethylamino)ethoxy)pyridin-2-ylamino)-1-(2-methoxyethyl)-3-phenyl-1,6-naphthyridin-2 (1H)-one: This compound was synthesized in a similar manner to Compound 15 showed in Scheme 8 using BrCH₂CH₂OMe as alkylation reagent instead of methyl iodide. ¹H NMR (CDCl₃, 400 MHz): δ 8.47 (s, 1H, ArH), 8.03 (s 1H, ArH), 7.86 (s, 1H, ArH), 7.74 (s, 1H, ArH), 7.69 (d, J=7.6 Hz, 1H, ArH), 7.50 (br, 1H, NH), 7.44-7.41 (m 2H, 2ArH), 7.38-734 (m, 1H, ArH), 7.29 (s, 2H, 2ArH), 4.09 (t, J=6.0 Hz, 2H, CH₂), 4.16 (s, 2H, CH₂), 3.81 (t, J=6.0 Hz 2H, CH₂), 3.41 (s, 3H, OCH₃) 2.97 (s, 2H, CH₂), 2.81-2.75 (q, J=7.2 Hz, 4H, 2CH₂), 1.14 (t, 6H, 2CH₃). MS [ESI, MH⁺]:=488.3.

Example 31

Synthesis of Compounds 22, 23, 25, 27, 70, 73, and 74

Compounds 22, 23, 25, 27, 70, 73, and 74 were synthesized as shown in Scheme 20 as a general scheme.

Scheme 20

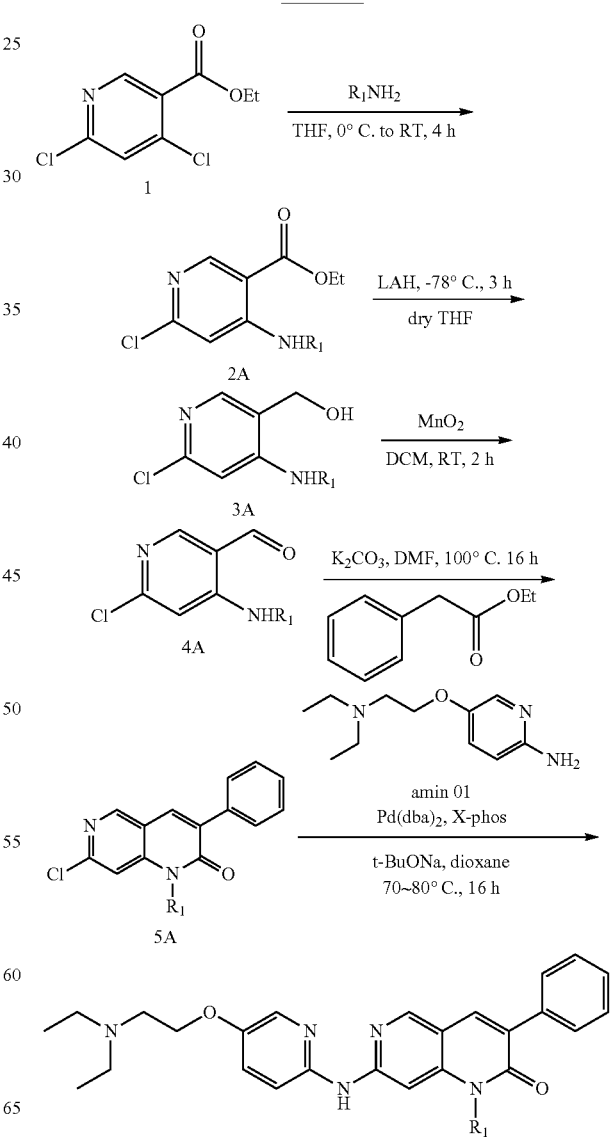

R₁ =

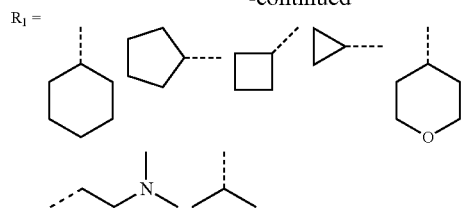

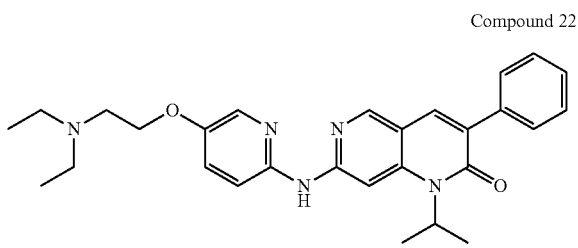 [SMILES: CCN(CC)CCOc1ccc(Nc2cc3c(cn2)cc(-c2ccccc2)c(=O)n3C(C)C)nc1]

Compound 22

Compound 22, 7-(5-(2-(diethylamino)ethoxy)pyridin-2-ylamino)-1-isopropyl-3-phenyl-1,6-naphthyridin-2(1H)-one was synthesized as shown in scheme 21.

Scheme 21

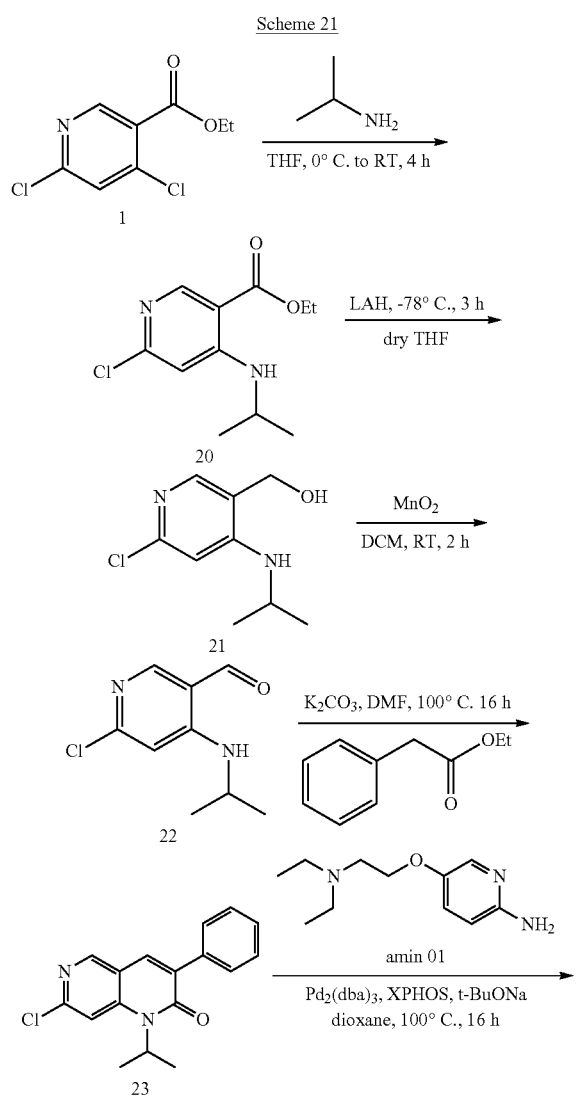

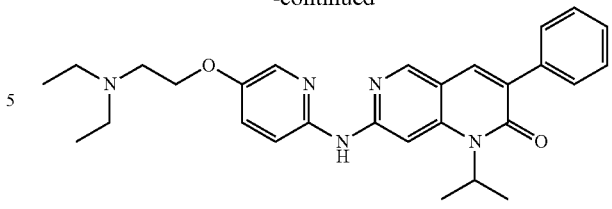

As in scheme 21, to a solution of scheme 21 compound 1 (1.5 g, 6.8 mmol) in THF (50 mL) was added i-PrNH₂ (2.01 g, 34.0 mmol). The resulting mixture was stirred at RT for 16 h. The mixture was diluted with water, extracted with EtOAc, washed with brine, dried over Na₂SO₄, concentrated to give a residue that was purified by column chromatography on silica gel to give scheme 21 compound 20 (1.0 g, 60.6%) as a white solid.

Scheme 21 compound 20 (1.0 g, 4.12 mmol) was dissolved in THF (30 mL) and cooled to −78° C. The solution was added drop-wise a solution of LAH (313 mg, 8.24 mmol) in THF (20 mL). The mixture was stirred at −78° C. for 3 h, then allowed to warm up to room temperature. TLC showed the starting material was consumed completely. Small amount MeOH/ethyl acetate (1/1) mixture was added slowly to quench the excess LAH. A solid formed and it was filtered and washed with ethyl acetate. The filtrate was concentrated to give a crude residue as yellow solid which was used next step directly.

Scheme 21 compound 21 (0.9 g, 4.48 mmol) was dissolved in DCM (50 mL). To this mixture was added MnO₂ (3.95 g, 44.8 mmol). The resulting mixture was stirred at room temperature for 5 h. TLC showed the reaction was completely. The inorganic by-product of MnO₂ was filtered off, and the filtrate was concentrated to give compound 22 (0.82 g, yield: 98.9%) as a white solid.

Scheme 1 compound 22 (0.82 g, 4.13 mmol) was dissolved in anhydrous DMF. To this solution was added the ester as shown in the scheme (0.81 g, 4.96 mmol) and K₂CO₃ (17.1 g, 12.39 mmol). The resulting mixture was stirred at 100° C. overnight. It was then quenched with H₂O and extracted with EtOAc. The organic layer was washed with half-saturated NaCl aq. and dried over anhydrous Na₂SO₄, concentrated to give a crude residue which was purified by silica gel chromatography to give scheme 1 compound 23 (110 mg, 8.9%) as a yellow solid.

Scheme 1 compound 23 (104 mg, 0.35 mmol) and Amine 01 (81 mg, 0.39 mmol) was dissolved in anhydrous dioxane (5 mL) in a round bottom flask. To this flask was added t-BuONa (67 mg, 0.7 mmol), X-PHOS (33 mg, 0.07 mmol), Pd₂(dba)₃ (32 mg, 0.035 mmol) under nitrogen atmosphere. The resulting mixture was stirred at 100° C. under nitrogen atmosphere for 16 h. It was then quenched with water and extracted with EtOAc. The organic layer was washed with brine, and dried over Na₂SO₄, concentrated to give a residue that was purified by column chromatography to give Compound 22 (30 mg, yield: 18.1%) as a yellow solid. ¹H NMR (MeOD, 400 MHz): δ 8.55 (br, 1H, ArH), 8.52 (br, 1H, ArH), 8.48 (br, 1H, ArH), 8.37 (m, 1H, ArH), 8.10 (d, J=6.8 Hz, 1H, ArH), 7.62 (d, J=7.2 Hz, 1H, ArH), 7.43-7.33 (m, 5H, ArH), 3.44 (s, 2H, CH₂), 3.20 (q, J=7.2 Hz, 4H, 2CH₂), 1.70 (d, J=6.8 Hz, 6H, 2CH₃), 1.33 (t, J=7.4 Hz, 6H, 2CH₃). MS [ESI, MH⁺]=472.3.

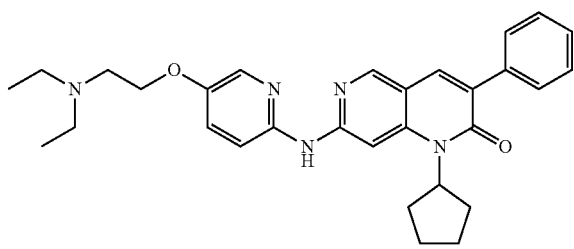

Compound 23

Compound 23, 1-cyclopentyl-7-(5-(2-(diethylamino)ethoxy)pyridin-2-ylamino)-3-phenyl-1,6-naphthyridin-2(1H)-one: This compound was synthesized in a similar manner to Compound 22 using cyclopentanamine instead of iso-propylamine. ¹H NMR (CDCl₃, 400 MHz): δ 8.45 (s, 1H, ArH), 8.14 (s 1H, ArH), 8.00 (d, J=2.8 Hz, 1H, ArH), 767 (d, J=5.6 Hz, 3H, 3ArH), 7.44-7.40 (m, 3H, 2ArH and NH), 7.30-7.26 (m, 2H, 2ArH), 7.04 (d, J=8.8 Hz, 1H, ArH), 5.85-5.80 (m, 1H, NCH), 4.21 (br, 2H, CH₂), 3.02 (br 2H, CH₂), 2.80 (br, 4H, 2CH₂), 2.42-2.35 (m, 2H, CH₂) 2.23-2.20 (m, 2H, CH₂), 2.07-1.98 (m, 2H, CH₂), 1.83-1.78 (m, 2H, CH₂), 1.18 (br, 6H, 2CH₃). MS [ESI, MH⁺]:=498.3.

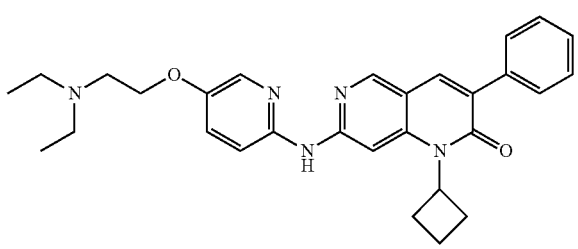

Compound 25

Compound 25, 1-cyclobutyl-7-(5-(2-(diethylamino)ethoxy)pyridin-2-ylamino)-3-phenyl-1,6-naphthyridin-2(1H)-one: This compound was synthesized in a similar manner to Compound 22 using cyclobutanamine instead of iso-propylamine. ¹H NMR (CDCl₃, 400 MHz): δ 8.43 (s, 1H, ArH), 8.19 (s 1H, ArH), 8.04 (d, J=2.8 Hz, 1H, ArH), 7.67-7.65 (m, 3H, 3ArH), 7.44-7.40 (m, 2H, 2ArH), 7.37-7.35 (m, 2H, ArH and NH), 7.29-7.26 (m, 1H, ArH), 7.04 (d, J=9.2 Hz, 1H, ArH), 5.26-5.17 (m, 1H), 4.09 (br, 2H, CH₂), 2.93 (m, 2H, CH₂), 2.81-2.71 (br, 7H, NCH and 3CH₂), 2.00-1.92 (m, 2H, CH₂), 1.12 (br, 6H, 2CH₃). MS [ESI, MH⁺]:=484.3.

Compound 27

Compound 27, 1-cyclopropyl-7-(5-(2-(diethylamino)ethoxy)pyridin-2-ylamino)-3-phenyl-1,6-naphthyridin-2(1H)-one: This compound was synthesized in a similar manner to Compound 22 using cyclopropanamine instead of iso-propylamine.

¹H NMR (CDCl₃, 400 MHz): δ 8.43 (s, 1H, ArH), 8.20 (s 1H, ArH), 8.04 (d, J=2.4 Hz, 1H, ArH), 7.68-7.67 (m, 1H, ArH), 7.58 (br, 1H, NH), 7.43-7.40 (m, 2H, 2ArH), 7.36-7.33 (m, 1H, ArH), 7.31-7.26 (m, 2H, 2ArH), 7.25-7.24 (m, 2H, 2ArH), 4.16 (br, 2H, CH₂), 2.99-2.95 (m, 3H, NCH and CH₂), 2.77 (br, 4H, 2CH₂), 1.40 (m, 2H, CH₂), 1.14 (t, J=6.6 Hz, 6H, 2CH₃), 0.98 (m, 2H, CH₂). MS [ESI, MH⁺]:=470.3.

Compound 70

Compound 70, 7-(5-(2-(diethylamino)ethoxy)pyridin-2-ylamino)-3-phenyl-1-(tetrahydro-2H-pyran-4-yl)-1,6-naphthyridin-2(1H)-one: This compound was synthesized in a similar manner to Compound 22 using tetrahydro-2H-pyran-4-amine instead of iso-propylamine. ¹H NMR (CDCl₃, 400 MHz): δ 8.71 (br, 1H, NH), 8.44 (s, 1H, ArH), 8.07 (d, J=2.4 Hz, 1H, ArH), 7.68-7.65 (m, 3H, 3ArH), 7.51 (s, 1H, ArH), 7.44-7.41 (m, 2H, 2ArH), 7.37-7.35 (m, 1H, ArH), 7.29-7.27 (m, 1H, ArH), 7.00 (d, J=8.8 Hz, 1H, ArH), 5.43 (br, 1H, NCH), 4.21 (dd, J¹=4.0 Hz, J²=11.2 Hz, 1H, CH₂), 4.11 (br, 2H, CH₂), 3.62 (t, J=11.2 Hz, 2H, CH₂), 3.08 (d, J=8.8 Hz, 2H, CH₂), 2.91 (br, 2H, CH₂), 2.69 (br, 4H, 2CH₂), 1.74 (d, J=10.8 Hz, 2H, CH₂), 1.10 (t, J=6.8 Hz, 6H, 2CH₃). MS [ESI, MH⁺]:=514.3.

Compound 73

Compound 73, 7-(5-(2-(diethylamino)ethoxy)pyridin-2-ylamino)-1-(2-(dimethylamino)ethyl)-3-phenyl-1,6-naphthyridin-2(1H)-one: This compound was synthesized in a similar manner to Compound 22 using N1,N1-dimethylethane-1,2-diamine instead of iso-propylamine. ¹H NMR (MeOD, 400 MHz): δ 8.53 (s, 1H, ArH), 8.13 (s, 1H, ArH), 7.99 (d, J=2.4 Hz 1H, ArH), 7.91 (s, 1H, ArH), 7.66 (d, J=3.2 Hz, 2H, ArH), 7.44-7.30 (m, 5H, ArH), 4.45 (t, J=7.8 Hz, 2H, CH₂), 4.15(t, J=5.6 Hz, 2H, CH₂), 2.97-2.94 (m, 2H, CH₂), 2.94-2.76 (m, 6H, 3CH₂), 2.46(s, 6H, 2CH₃), 1.13(t, J=7.2 Hz, 6H, 2CH₃), MS [ESI, MH⁺]=501.4.

Compound 74

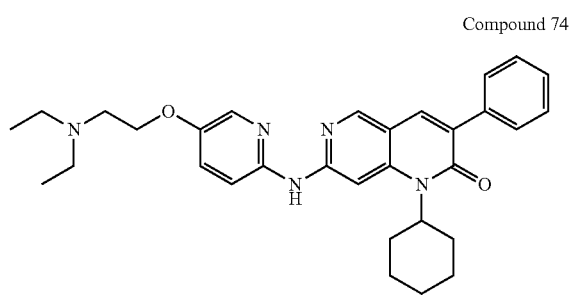 [SMILES: CCN(CC)CCOc1ccc(Nc2cc3c(cn2)cc(-c2ccccc2)c(=O)n3C2CCCCC2)nc1]

Compound 74, 1-cyclohexyl-7-(5-(2-(diethylamino) ethoxy)pyridin-2-ylamino)-3-phenyl-1,6-naphthyridin-2 (1H)-one: This compound was synthesized in a similar manner to Compound 22 using cyclohexanamine instead of iso-propylamine. $^1$H NMR (CDCl$_3$, 400 MHz): δ 8.75 (br, 1H, NH), 8.66 (s, 1H, ArH), 8.01 (s, 1H, ArH), 7.73-7.65 (m, 4H, 4ArH), 7.43-7.33 (m, 4H, 4ArH), 7.08 (br, 1H, ArH), 5.71 (br, 1H, NCH), 4.38 (br, 1H, CH$_2$), 3.20 (br, 2H, CH$_2$), 3.01 (br, 4H, 2CH$_2$), 2.70 (br, 2H, CH$_2$), 2.00 (d, J=12.4 Hz, 2H, CH$_2$), 1.84 (d, J=10.8 Hz, 2H, CH$_2$), 1.51 (br, 2H, CH$_2$), 1.30 (br, 8H, CH$_2$ and 2CH$_3$). MS [ESI, MH$^+$]:=512.3.

Example 32

Synthesis of Compounds 34, 36, 46, and 47

Compounds 34, 36, 46, and 47 were synthesized in a similar manner to Compound 22 with 3-methyl-butyric acid ethyl ester in stead of phenyl-acetic acid ethyl ester. Scheme 22 was shown as a general method.

Scheme 22

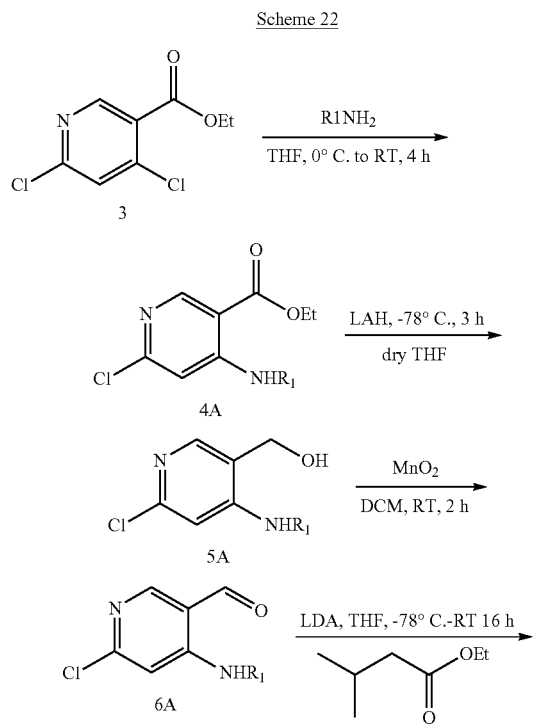

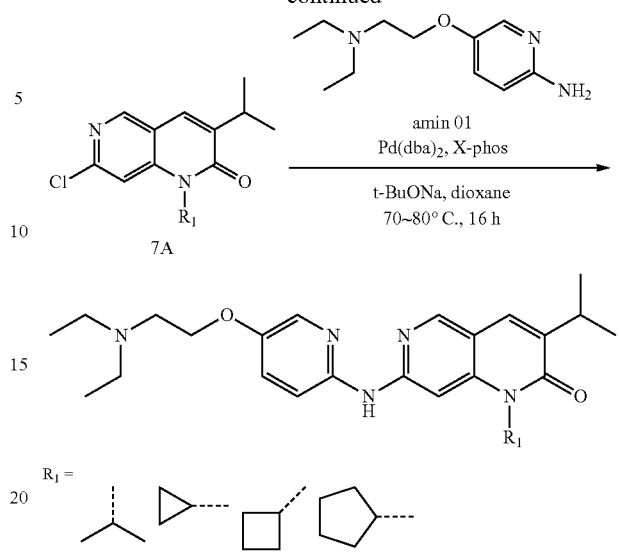

Compound 34

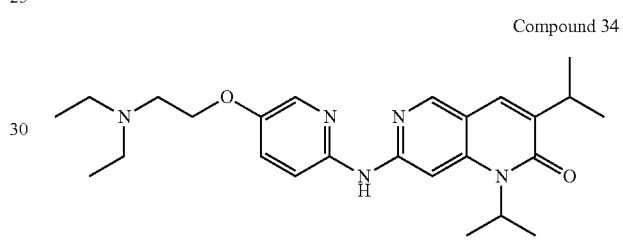

Compound 34, 7-[5-(2-Diethylamino-ethoxy)-pyridin-2-ylamino]-1,3-diisopropyl-1H-[1,6]naphthyridin-2-one: $^1$H NMR (CDCl$_3$, 400 MHz): δ 8.36 (s, 1H, ArH), 8.28 (br, 1H, ArH), 7.57 (br, 7.30 (m, 1H, NH), 1H, 7.36-7.26 (m, 2H, 2ArH), 7.11 (br, 1H, ArH), 5.26-5.17 (m, 1H), 5.56 (br, 1H, NCH), 4.52 (br, 2H, CH$_2$), 3.37 (br, 2H, CH$_2$), 3.24-3.19 (m, 5H, ArCH and 2CH$_2$), 1.68 (d, J=7.8 Hz, 6H, 2CH$_3$), 1.41 (br, 6H, 2CH$_3$) 1.23 (d, J=6.8 Hz, 6H, 2CH$_3$). MS [ESI, MH$^+$]:=438.3.

Compound 36

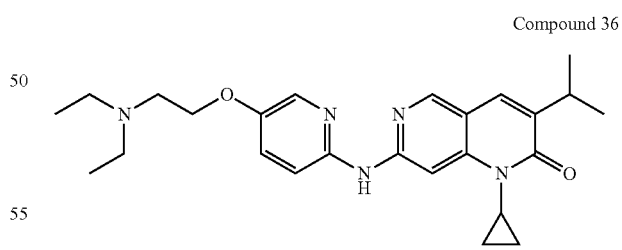

Compound 36, 1-Cyclopropyl-7-[5-(2-diethylamino-ethoxy)-pyridin-2-ylamino]-3-isopropyl-1H-[1,6]naphthyridin-2-one: $^1$H NMR (CDCl$_3$, 400 MHz): δ 8.36 (s, 1H, ArH), 8.28 (br, 1H, ArH), 7.57 (br, 7.30 (m, 1H, NH), 1H, 7.36-7.26 (m, 2H, 2ArH), 7.11 (br, 1H, ArH), 5.26-5.17 (m, 1H), 5.56 (br, 1H, NCH), 4.52 (br, 2H, CH$_2$), 3.37 (br, 2H, CH$_2$), 3.24-3.19 (m, 5H, ArCH and 2CH$_2$), 1.68 (d, J=7.8 Hz, 6H, 2CH$_3$), 1.41 (br, 6H, 2CH$_3$) 1.23 (d, J=6.8 Hz, 6H, 2CH$_3$). MS [ESI, MH$^+$]:=438.3.

Compound 46

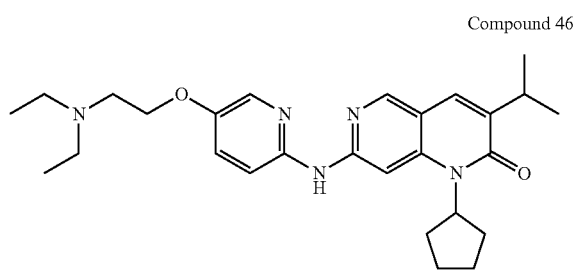 [SMILES: CCN(CC)CCOc1ccc(Nc2cc3c(cn2)cc(C(C)C)c(=O)n3C2CCCC2)nc1]

Compound 46, 1-Cyclopentyl-7-[5-(2-diethylamino-ethoxy)-pyridin-2-ylamino]-3-isopropyl-1H-[1,6]naphthyridin-2-one: $^1$H NMR (MeOD, 400 MHz): δ 8.44(s, 1H, ArH), 8.12(s, 1H, ArH), 7.97(d, J=2.8 Hz, 1H, ArH), 7.60 (s, 1H, ArH), 7.39-7.36 (dd, J$^1$=3.2 Hz, J$^2$=2.8 Hz, 1H, ArH), 7.22 (d, 1H, J=9.2 Hz, ArH), 5.79-5.70 (m, 1H, CH), 4.15 (t, J=5.6 Hz, 2H, CH$_2$), 3.30-3.09 (m, 1H, CH), 2.97 (t, J=5.6 Hz, 2H, CH$_2$), 2.77-2.71 (m, 4H, 2CH$_2$), 2.36-2.21 (m, 2H, CH$_2$), 2.21-2.00 (m, 2H, CH$_2$), 2.00-1.80 (m, 4H, 2CH$_2$), 1.21 (d, J=6.8 Hz, 6H, 2CH$_3$), 1.14 (t, J=7.0 Hz, 6H, 2CH$_3$). MS [ESI, MH$^+$]:=464.3.

Compound 47

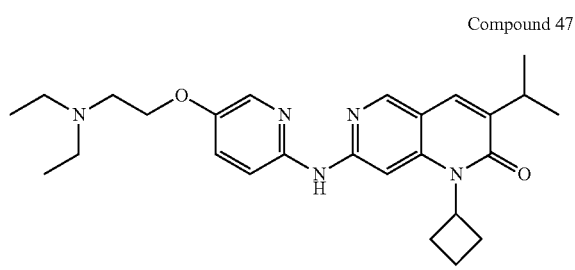 [SMILES: CCN(CC)CCOc1ccc(Nc2cc3c(cn2)cc(C(C)C)c(=O)n3C2CCC2)nc1]

Compound 47, 1-Cyclobutyl-7-[5-(2-diethylamino-ethoxy)-pyridin-2-ylamino]-3-isopropyl-1H-[1,6]naphthyridin-2-one: $^1$H NMR (CDCl$_3$, 400 MHz): δ 8.34(s, 1H, ArH), 8.15(s, 1H, ArH), 8.01 (d, J=2.8 Hz, 1H, ArH), 7.48 (s, 1H, ArH), 7.34 (s, 1H, ArH), 7.23 (s, 1H, ArH) 7.01 (d, J=8.8 Hz, 1H, ArH), 5.31-5.10 (m, 1H, CH), 4.11 (t, J=5.2 Hz, 2H, CH$_2$), 3.22-3.15 (m, 2H, CH$_2$), 2.94-2.72 (m, 8H, 4CH$_2$), 2.03-1.87 (m, 2H, CH$_2$), 1.21 (d, J=6.8 Hz, 6H, 2CH$_3$) 1.10 (t, J=7.0 Hz, 6H, 2CH$_3$). MS [ESI, MH$^+$]:=450.3.

Example 33

Synthesis of Compounds 49, 50, 57, and 59

Compounds 49, 50, 57, and 59 were synthesized as shown in Scheme 23

Scheme 23

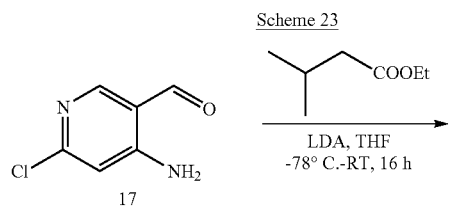

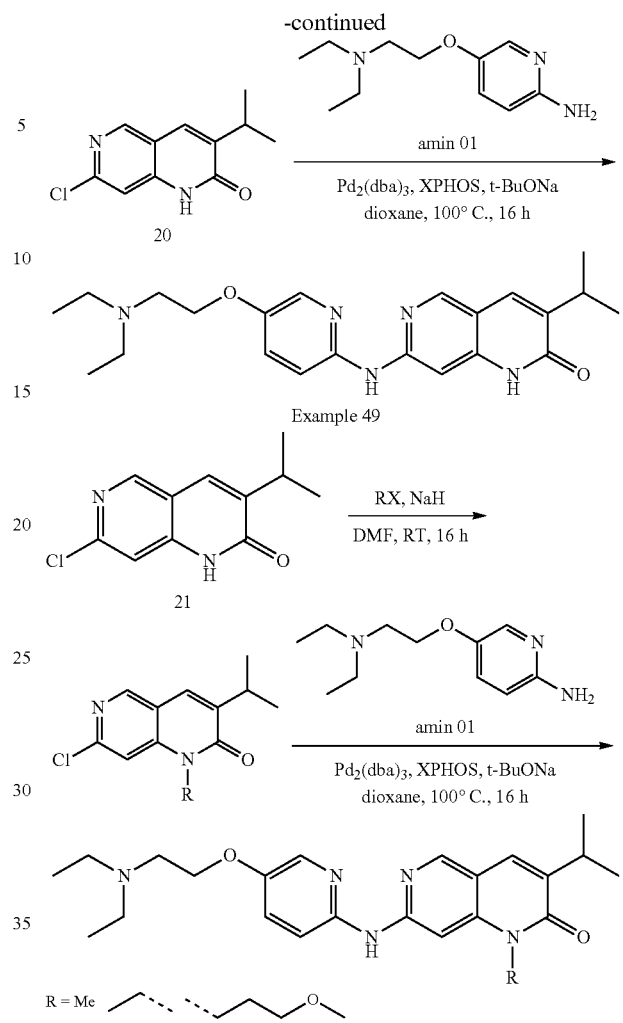

Example 49

R = Me, <span>ethyl-like groups</span>, propyl-methoxy

Compound 49

Compound 49, 7-(5-(2-(diethylamino)ethoxy)pyridin-2-ylamino)-3-isopropyl-1,6-naphthyridin-2(1H)-one:

3-Methyl-butyric acid ethyl ester (166 mg, 1.28 mmol) was dissolved in anhydrous THF (3 mL). The resulting solution was cooled to −78° C., LDA (0.64 mL, 1.28 mmol) was then added into the solution slowly in small portions at a rate that the temperature did not rise above −70° C. The resulting solution was stirred at −78° C. for 1 h. Scheme 23 compound 17 (100 mg, 0.64 mmol) was added into the above solution at −78° C. The reaction mixture was stirred at rt overnight and was quenched with saturated aqueous NH$_4$Cl, extracted with EtOAc (3*10 mL). The organic layer was washed with brine and dried over Na$_2$SO$_4$, concentrated to give a residue that was purified by silica gel column chromatography (PE/EA=20:1) to give scheme 23 compound 20 (95 mg, yield: 66.9%) as a yellow solid.

Scheme 23 compound 20 (78 mg, 0.35 mmol) and Amine 01 (81 mg, 0.39 mmol) was dissolved in anhydrous dioxane (5 mL). To the resulting solution was added t-BuONa (67 mg, 0.7 mmol), X-PHOS (33 mg, 0.07 mmol), Pd$_2$(dba)$_3$ (32 mg, 0.035 mmol) under nitrogen atmosphere. The mixture was stirred at 100° C. under nitrogen atmosphere for 16 h. The mixture was then quenched with water and extracted with EtOAc. The organic layer was washed with brine, and dried over Na$_2$SO$_4$, concentrated to give a residue that was purified by column chromatography to give Compound 49 (32.0 mg, yield: 23.1%) as a yellow solid. $^1$H NMR (DMSO, 400 MHz): δ 11.65 (s, 1H, NH), 9.62 (s, 1H, NH), 8.45 (s, 1H, ArH), 7.93 (d, J=2.8 Hz, 1H, NH), 7.64 (d, J=7.6 Hz, 2H, ArH), 7.44-7.36 (m, 2H, 2ArH), 4.02 (t, J=6.0 Hz, 2H, CH$_2$), 3.03-3.0 (m, 1H, ArCH), 2.74 (t, J=6.0 Hz, 2H, CH$_2$), 2.53 (q, J=7.2 Hz, 4H, 2CH$_2$), 1.15 (d, J=6.8 Hz, 6H, 2CH$_3$), 0.95 (t, J=7.2 Hz, 6H, 2CH$_3$). MS [ESI, MH$^+$]:=363.1.

Compound 50

Compound 50, 7-[5-(2-Diethylamino-ethoxy)-pyridin-2-ylamino]-1-ethyl-3-isopropyl-1H-[1,6]naphthyridin-2-one was synthesized in a similar manner to Compound 49. $^1$H NMR (CDCl$_3$, 400 MHz): δ 8.39 (s, 1H, ArH), 8.00 (s, 1H, ArH), 7.83-7.75 (m, 1H, ArH), 7.72 (s, 1H, NH), 7.40 (s, 1H, ArH), 7.31-7.22 (m, 2H, 2ArH), 4.46 (br, 2H, CH$_2$), 4.31 (t, J=6.8 Hz, 2H, CH$_2$), 3.30-3.22 (m, 3H, ArCH and CH$_2$), 3.11 (br, 4H, CH$_2$), 1.37 (d, J=4.8 Hz, 9H, 3CH$_3$), 1.24 (d, J=6.8 Hz, 6H, 2CH$_3$). MS [ESI, MH$^+$]:=424.3.

Compound 57

Compound 57, 7-[5-(2-Diethylamino-ethoxy)-pyridin-2-ylamino]-3-isopropyl-1-(2-methoxy-ethyl)-1H-[1,6]naphthyridin-2-one in a similar manner to Compound 49. $^1$H NMR (CDCl$_3$, 400 MHz): δ 8.38 (s, 1H, ArH), 7.95 (s, 1H, ArH), 7.78 (s, 1H, CH$_2$), 7.40 (br, 1H, ArH), 7.36 (s, 2H, 2ArH), 4.51 (t, J=4.4 Hz, 2H, CH$_2$), 4.42 (t, J=6.0 Hz, 2H, CH$_2$), 3.75 (t, J=6.0 Hz, 2H, CH$_2$), 3.40 (br, 5H, CH$_2$ and OCH$_3$), 3.21 (t, J=6.4 Hz, 5H, 2CH$_2$ and ArCH), 1.42 (t, J=7.2 Hz, 6H, 2CH$_3$), 1.23 (d, J=7.2 Hz 6H, 2CH$_3$). MS [ESI, MH$^+$]:=454.3.

Compound 59

Compound 59, 7-[5-(2-Diethylamino-ethoxy)-pyridin-2-ylamino]-3-isopropyl-1-methyl-1H-[1,6]naphthyridin-2-one in a similar manner to Compound 49. $^1$H NMR (MeOD, 400 MHz): δ 8.48 (s, 1H, ArH), 8.04 (d, J=2.4 Hz 1H, ArH), 7.85 (s, 1H, ArH), 7.69 (s, 1H, ArH), 7.45-7.39 (m, 2H, 2ArH), 4.18 (t, J=5.6 Hz, 2H, CH$_2$), 3.68(s, 3H, CH$_3$), 3.24-3.13 (m, 1H, CH), 3.00 (t, J=5.4 Hz, 2H, CH$_2$), 2.77(q, J=7.2 Hz, 4H, 2CH$_2$), 1.26 (d, J=6.8 Hz, 6H, 3CH$_2$),1.15 (t, J=7.2 Hz,6H, 3CH$_2$).MS [ESI, MH$^+$]:=304.3.

Example 34

Synthesis of Compounds 71 and 72

Compounds 71 and 72 were synthesized as shown in Scheme 24. The procedure is described for Compound 71 as an example.

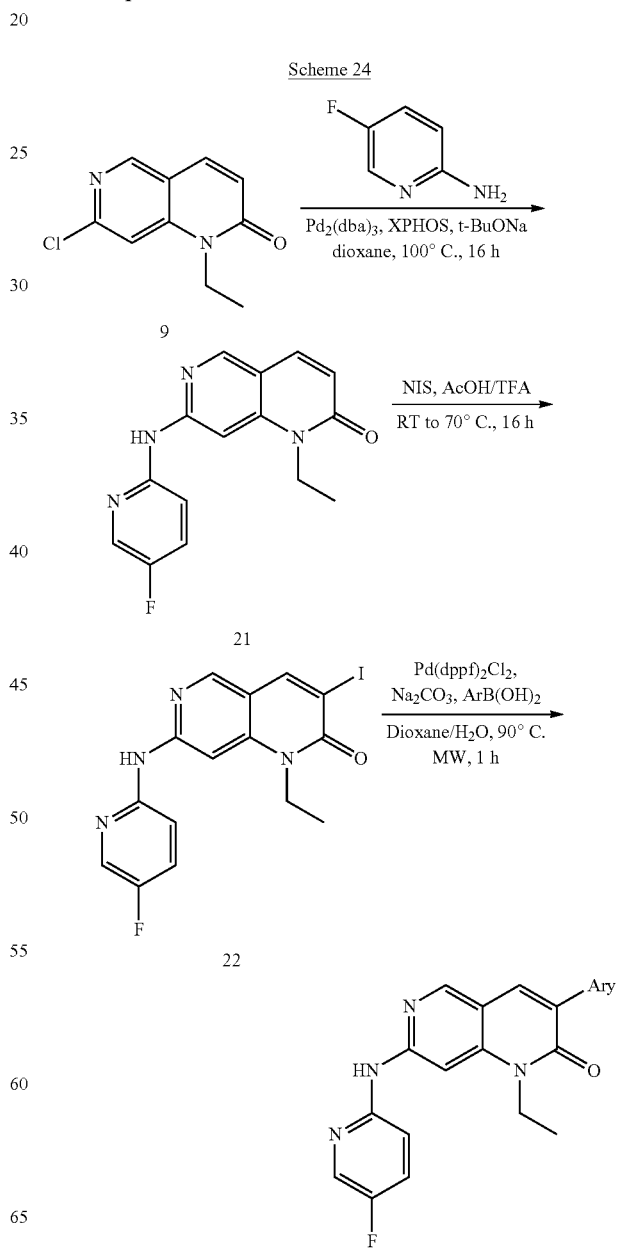

Scheme 24

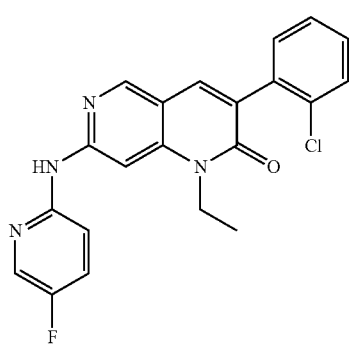

Compound 71

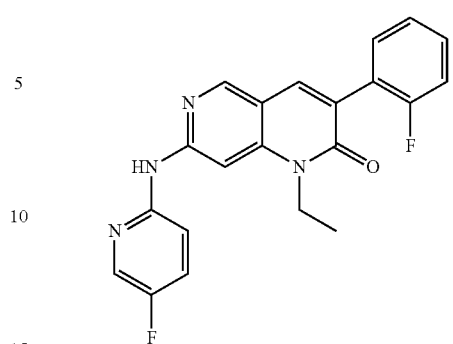

Compound 72

Compound 71: 3-(2-chlorophenyl)-1-ethyl-7-(5-fluoropyridin-2-ylamino)-1,6-naphthyridin-2(1H)-one. Scheme 24 compound 9 (10.55 g, 51 mmol) and amine (6.82 g, 61 mmol) were dissolved in anhydrous dioxane (100 mL) in a flask. To this flask were added t-BuONa (9.8 g, 102 mmol), X-PHOS (4.9 g, 10.2 mmol), Pd(dba)$_2$ (4.7 g, 5.1 mmol) under nitrogen atmosphere. The mixture was stirred at 100° C. under nitrogen atmosphere for 16 h. TLC showed the starting material was consumed completely. The reaction mixture was concentrated, the remaining residue was purified by silica gel column chromatography (DCM/MeOH=20/1) to give scheme 24 compound 21 (11.28 g, yield: 76%) as a white solid. $^1$H NMR (400 MHz, CDCl$_3$): δ 8.422(s, 1H, ArH), 8.179(d, J=2.8 Hz 1H, ArH), 7.923 (t, J=7.6 Hz 1H, ArH), 7.612(t, J=7.4 Hz, 1H, ArH), 7.423-7.374(m, 1H, ArH), 7.270-7.239(m, 1H, CH) 6.530-6.446 (m, 1H, CH), 4.307(q, J=7.2 Hz, 2H, CH2) 1.386(t, J=7.2 Hz, 3H, CH3).

To the solution of scheme 24 compound 21 (3 g, 10.53 mmol) in AcOH (60 ml) was added TFA (3.6 g, 31.59 mmol). The resulting solution was stirred at room temperature for 10 min. A white solid was formed in the mixture. After the mixture was stirred at 70° C. for 20 min, NIS (5.21 g, 23.16 mmol) was added in one portion. The resulting mixture was stirred at 70° C. under nitrogen atmosphere for 16 h. TLC showed the starting material was consumed completely. After the reaction mixture was concentrated, the remaining residue was diluted in DCM. The DCM solution was washed with water and concentrated to a residue that was purified by silica gel column chromatography (DCM/MeOH=20/1) to give scheme 24 compound 22 (3 g, yield: 69%) as a white solid. $^1$H NMR (400 MHz, DMSO): δ 10.111 (s, 1H, ArH), 8.594(s, 1H, ArH), 8.550 (s, 1H, ArH), 8.252(t, J=1.8 Hz, 1H, ArH), 7.885(s, 1H, CH), 7.680-7.656 (m, 2H, NH and ArH), 4.186(q, J=7.2 Hz, 2H, CH2), 1.243(t, J=7.2 Hz, 3H, CH3).

Scheme 24 compound 22 (1 eq) and AryB(OH)$_2$ (1.2 eq) were dissolved in dioxane/H$_2$O. To this mixture was added NaCO$_3$ (3 eq), Pd(dppf)$_2$Cl$_2$ (0.1 eq) under nitrogen atmosphere. The reaction vessel was sealed and heated under microwave at 90° C. for 1 h. After TLC showed the starting material was consumed completely, the mixture was filtered and the filtrate was diluted in DCM. The organic layer was washed with brine and dried over anhydrous Na$_2$SO$_4$, filtered, concentrated to give a residue which was purified by prep-HPLC to give the product as a yellow solid. $^1$H NMR (400 MHz, CDCl$_3$): δ 8.489(s, 1H, ArH), 8.225(d, J=2.8 Hz, 1H, ArH), 7.980 (s, 1H, ArH), 7.837(brs, 1H, NH), 7.694(s, 1H, ArH), 7.516-7.321(m, 6H, ArH), 4.394(m, 2H, CH$_2$), 1.455 (t, J=7.2 Hz, 3H, CH$_3$).

Compound 72: 1-ethyl-3-(2-fluorophenyl)-7-(5-fluoropyridin-2-ylamino)-1,6-naphthyridin-2(1H)-one. $^1$H NMR (400 MHz, CDCl$_3$): δ 8.489 (s, 1H, ArH), 8.225 (d, J=2.8 Hz, 1H, ArH), 7.980 (s, 1H, ArH), 7.837(brs, 1H, NH), 7.694(s, 1H, ArH), 7.516-7.321(m, 6H, ArH), 4.394(m, 2H, CH$_2$), 1.455 (t, J=7.2 Hz, 3H, CH$_3$).

Example 35

Synthesis of Compound 75

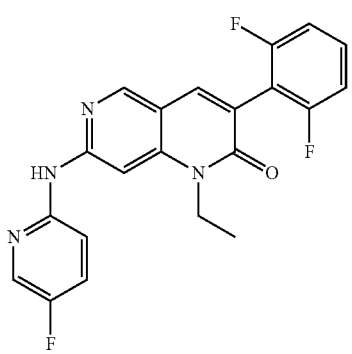

Compound 75

Compound 75, 3-(2,6-difluorophenyl)-1-ethyl-7-((5-fluoropyridin-2-yl)amino)-1,6-naphthyri-din-2 (1H)-one was synthesized as shown in Scheme 25 as a general procedure:

Scheme 25

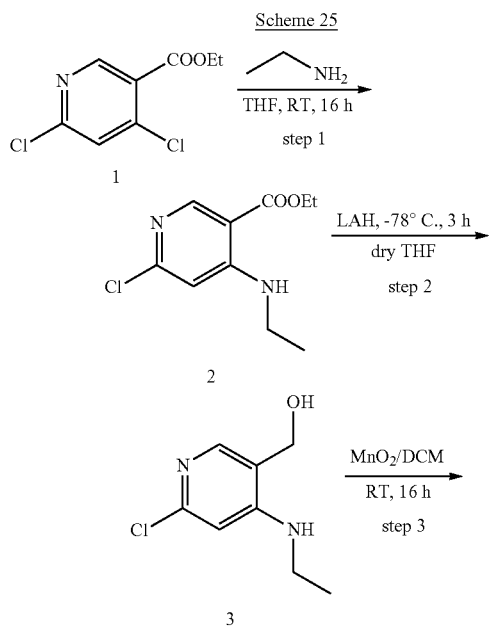

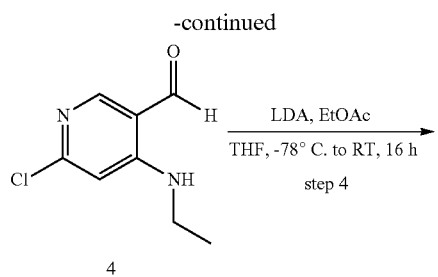

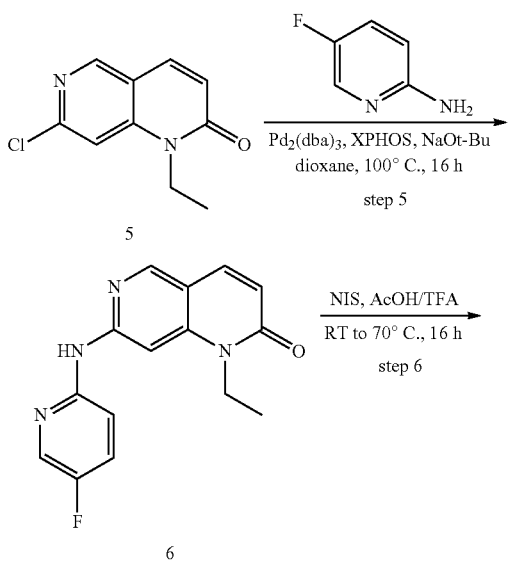

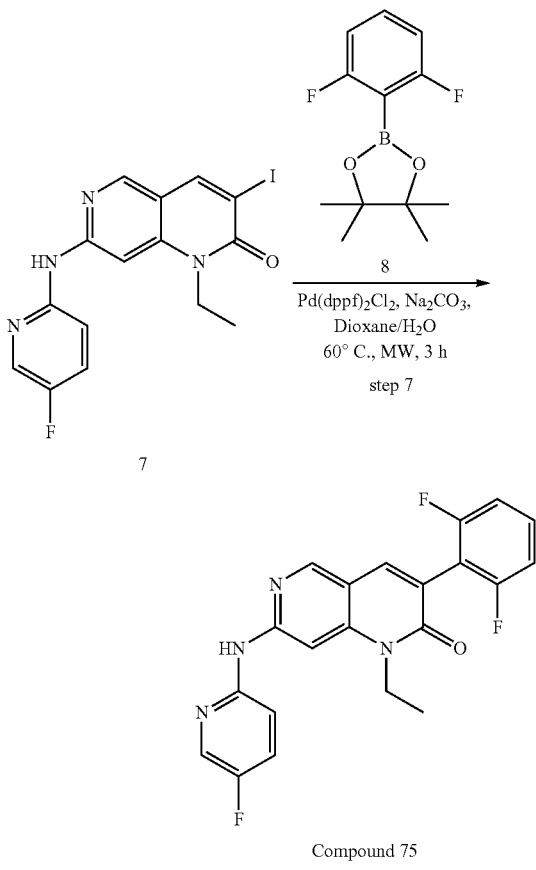

Compound 75

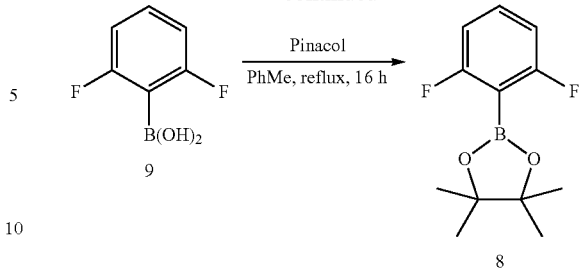

To a solution of scheme 25 compound 1 (25 g, 114 mmol) in THF (100 mL) was added EtNH$_2$ (26 g, 568 mmol) at 0° C. The mixture was stirred at 0° C. for 30 min and warmed to RT and stirred for 16 h. TLC showed the starting material was consumed completely. After the solvent was removed, scheme 25 compound 2 was obtained (25.9 g, yield 99.6%) as yellow solid, which was used in the next step directly without further purification.

LiAlH$_4$ (8.7 g, 228 mmol) was suspended in dry THF (300 mL), cooled to −78° C. The solution of scheme 25 compound 2 (25.9 g, 114 mmol) in THF (200 mL) was added dropwised. The resulting mixture was stirred at −78° C. for 3 h, then warmed to RT. TLC showed the starting material was consumed completely. Small amount of MeOH/ethyl acetate (1/1) mixture was added slowly to the reaction mixture to quench the excess LiAlH$_4$. The reaction mixture was filtered and the solid was washed with ethyl acetate. The combined filtrate was concentrated to give the crude product which was purified by silica gel chromatography (PE/EA=10/1 to 5/1) to give compound 3 (13 g, yield: 62%) as pale yellow solid.

Scheme 25 compound 3 (13 g, 69.67 mmol) was dissolved in DCM (150 mL). MnO$_2$ (68 g, 782.5 mmol) was added as in scheme 80. The resulting mixture was stirred at RT for 16 h. TLC showed the reaction was completely. The reaction mixture was filtered through celite and washed with DCM. The combined filtrate was concentrated to give the crude product which was purified by silica gel chromatography (PE/EA=10/1 to 5/1) to give scheme 25 compound 4 (12 g, yield: 94%) as pale yellow solid.

Anhydrous EtOAC (12.63 g, 143.5 mmol) was dissolved in anhydrous THF (300 mL) and cooled to −78° C. LDA (72 mL, 143.5 mmol) was added dropwise. The resulting mixture was stirred at −78° C. for 30 min. Then the solution of scheme 25 compound 4 (12 g, 65.22 mmol) in THF (100 mL) was added dropwise and the reaction mixture was warmed slowly to RT and stirred for 16 h. The reaction mixture was quenched with sat.NH$_4$Cl at −50° C. Then water was added and extracted with ethyl acetate. The organic layer was washed with brine and dried over Na$_2$SO$_4$, concentrated to give a residue which was purified by silica gel chromatography (DCM/MeOH=20/1) to give compound 5 as in scheme 80 (10.55 g, yield: 76%) as yellow solid. $^1$H NMR (400 MHz, CDCl$_3$): δ 8.57 (d, J=4 Hz, 1H, ArH), 7.72 (d, J=9.6 Hz, 1H, CH), 7.25 (s, 1H, ArH), 6.76-6.73 (m, 1H, CH), 4.27 (q, J=7.2 Hz, 2H, CH2), 1.37 (t, J=7.2 Hz, 3H, CH3). MS [ESI, MH$^+$]:=209.0.

Scheme 25 compound 5 (10.55 g, 51 mmol) and compound 5A (6.82 g, 61 mmol) were dissolved in anhydrous dioxane (100 mL). Then NaOt-Bu (9.8 g, 102 mmol), X-PHOS (4.9 g, 10.2 mmol), and Pd$_2$(dba)$_3$ (4.7 g, 5.1 mmol) were added under nitrogen atmosphere. The mixture was stirred at 100° C. under nitrogen atmosphere for 16 h. TLC showed the starting material was consumed completely. The reaction mixture was concentrated, the residue was purified by silica gel chromatography (DCM/MeOH=20/1) to give scheme 25 compound 6 (11.28 g, yield: 76%) as white solid. $^1$H NMR (400 MHz, CDCl$_3$): δ 8.42 (s, 1H, ArH), 8.18 (d, J=2.8 Hz, 1H, ArH), 7.92 (t, J=7.6 Hz, 1H, ArH), 7.61 (t, J=7.4 Hz, 1H, ArH), 7.42-7.37 (m, 1H, ArH), 7.27-7.24 (m, 1H, CH) 6.53-6.45 (m, 1H, CH), 4.31 (q, J=7.2 Hz, 2H, CH2) 1.39 (t, J=7.2 Hz, 3H, CH3). MS [ESI, MH$^+$]:=284.1.

To the solution of Compound 6 (3 g, 10.53 mmol) in AcOH (60 ml) was added TFA (3.6 g, 31.59 mmol). The resulting solution was stirred at RT for 10 min. During this time, a white precipitate was formed. Then the mixture was stirred at 70° C. for 20 min, NIS (5.21 g, 23.16 mmol) was added in one portion. The mixture was stirred at 70° C. under nitrogen atmosphere for 16 h. TLC showed the starting material was consumed completely. The reaction mixture was concentrated; the residue was dissolved in DCM, washed with water. The DCM layer was concentrated, the residue was purified by silica gel chromatography (DCM/MeOH=20/1) to give scheme 25 compound 6 (3 g, yield: 69%) as white solid. $^1$H NMR (400 MHz, DMSO): δ 10.11 (s, 1H, ArH), 8.59(s, 1H, ArH), 8.55 (s, 1H, ArH), 8.25 (t, J=1.8 Hz, 1H, ArH), 7.89 (s, 1H, CH), 7.68-7.66 (m, 2H, NH and ArH), 4.19 (q, J=7.2 Hz, 2H, CH2), 1.24 (t, J=7.2 Hz, 3H, CH3). MS [ESI, MH$^+$]:=411.0.

Scheme 25 compound 9 (0.7 g, 4.4 mmol) and pinacol (0.52 g, 4.4 mmol) were dissolved in toluene (30 mL) and heated to reflux for 16 h. TLC showed the starting material was consumed completely. The solvent was removed under vacuum to give scheme 25 compound 8 (1.0 g, yield: 95%) as white solid.

Scheme 25 compound 7 (600.0 mg, 1.464 mmol) and scheme 25 compound 8 (526 mg, 2.196 mmol) were dissolved in dioxane/H$_2$O (10 mL/2 mL). To this mixture was added Na$_2$CO$_3$ (464 mg, 4.4 mmol), Pd(dppf)$_2$Cl$_2$ (120 mg, 0.14 mmol) under nitrogen atmosphere. The reaction vessel was sealed and heated in microwave at 60° C. for 3 hours. TLC showed the starting material was consumed completely; the mixture was concentrated in vacuum. The remaining residue was purified by prep-HPLC to give Compound 75 (28.6 mg, yield: 4.93%) as a yellow solid. $^1$H NMR (400 MHz, DMSO): δ 10.21 (s, 1H, ArH), 8.67 (s, 1H, ArH), 8.31 (s, 1H, ArH), 8.08 (s, 1H, ArH), 7.99 (s, 1H, ArH), 7.73(t, J=3.4 Hz, 2H, ArH), 7.56-7.48 (m, 1H, ArH), 7.21(t, J=7.8 Hz, 2H, NH and ArH), 4.24-4.19 (m, 2H, CH$_2$), 1.31 (t, J=6.8 Hz, 3H, CH$_3$).

Example 36

Synthesis of Compound 77

Compound 77

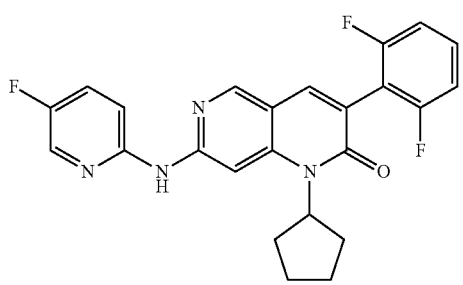

Compound 77: 1-cyclopentyl-3-(2,6-difluorophenyl)-7-((5-fluoropyridin-2-yl)amino)-1,6-naphthyridin-2(1H)-one was synthesized as shown in Scheme 26 as a general procedure. The aldehyde 1 was prepared in a similar manner to Compound 75.

Scheme 26

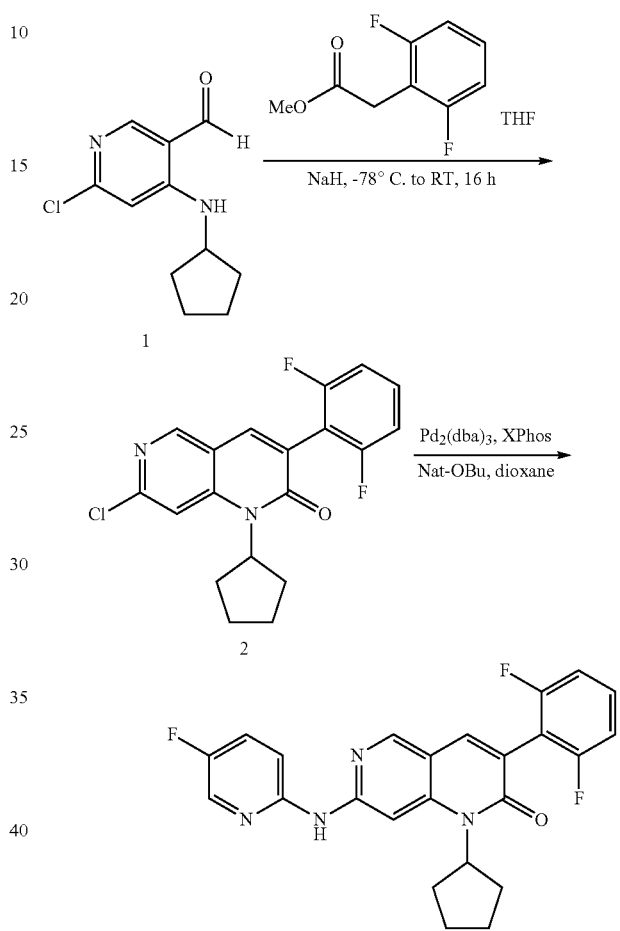

(2,6-Difluoro-phenyl)-acetic acid methyl ester (2.49 g, 13.4 mmol) was dissolved in anhydrous THF, cooled to −78° C. NaH (0.54 g, 13.5 mmol) was then added in one portion. The mixture was stirred at −78° C. for 1 h. The solution of scheme 26 compound 1 (1.5 g, 6.70 mmol) in THF (20 mL) was added dropwise at −78° C. The resulting reaction mixture was warmed slowly to RT and stirred for 16 h. The reaction was quenched with saturated aqueous NH$_4$Cl and extracted with EA. The organic layer was washed with brine, dried over anhydrous Na$_2$SO$_4$, concentrated to give a crude residue which was purified by silica gel column chromatography (PE:EA=10:1) to give compound 2 (0.6 g, yield: 25%) as a yellow solid.

Scheme 26 compound 2 (360 mg, 1.00 mmol) and 5-Fluoro-pyridin-2-ylamine (130 mg, 120 mmol) were dissolved in anhydrous dioxane (15 mL). To this mixture was added NaOt-Bu (200 mg, 0.566 mmol), X-PHOS (100 mg, 0.2 mmol), Pd$_2$(dba)$_3$ (96 mg, 0.11 mmol) under nitrogen atmosphere. The reaction mixture was stirred at 80° C. under nitrogen atmosphere overnight. After TLC showed the starting material was consumed completely, the mixture was quenched with water and extracted with EA. The organic layer was washed with brine and dried over anhydrous Na$_2$SO$_4$, filtered, concentrated to give a residue which was purified by silica gel column chromatography (DCM/MeOH=200/1 to 80/1) to give Compound 77 (100 mg, yield: 22.7%) as a pale yellow solid. $^1$H NMR (CDCl$_3$, 400 MHz): δ 8.45 (s, 1H, ArH), 8.17 (m, 2H, 2ArH), 7.68 (s, 1H, ArH), 7.57 (s, 1H, ArH), 7.43-7.34 (m, 1H, ArH), 7.33-7.26 (m, 1H, ArH), 7.25-7.11 (m, 1H, ArH), 7.10-7.96 (m, 1H, ArH), 5.80-5.30 (m, 1H, CH), 2.41-2.34 (m, 2H, CH$_2$), 2.24-2.08 (m, 2H, CH$_2$), 2.05-1.84 (m, 2H, CH$_2$), 1.83-1.80 (m, 2H, CH$_2$). MS [ESI, MH$^+$]:=437.

Example 37

Synthesis of Compound 78

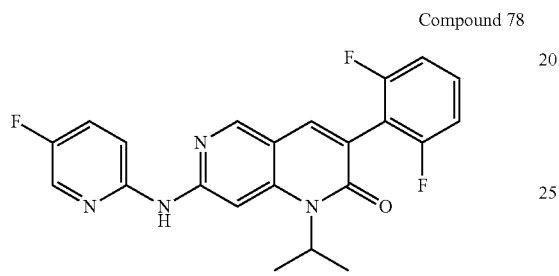

Compound 78

Compound 78: 3-(2,6-difluorophenyl)-7-((5-fluoropyridin-2-yl)amino)-1-isopropyl-1,6-naphthyridin-2(1H)-one was synthesized as shown in Scheme 27 as a general procedure:

Scheme 27

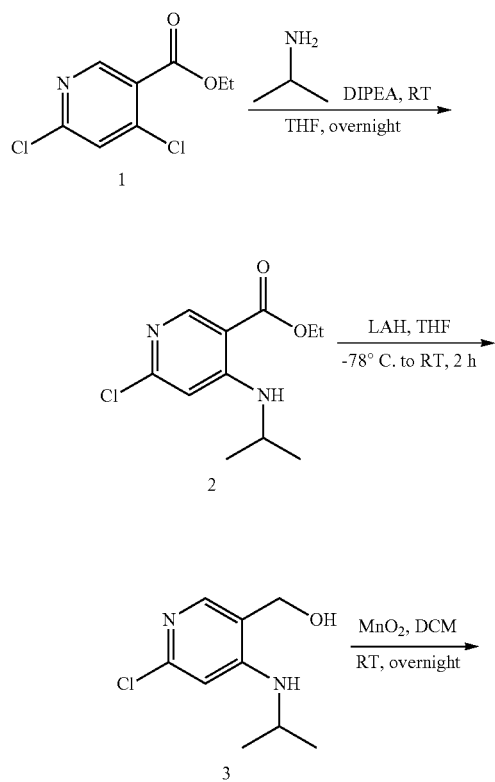

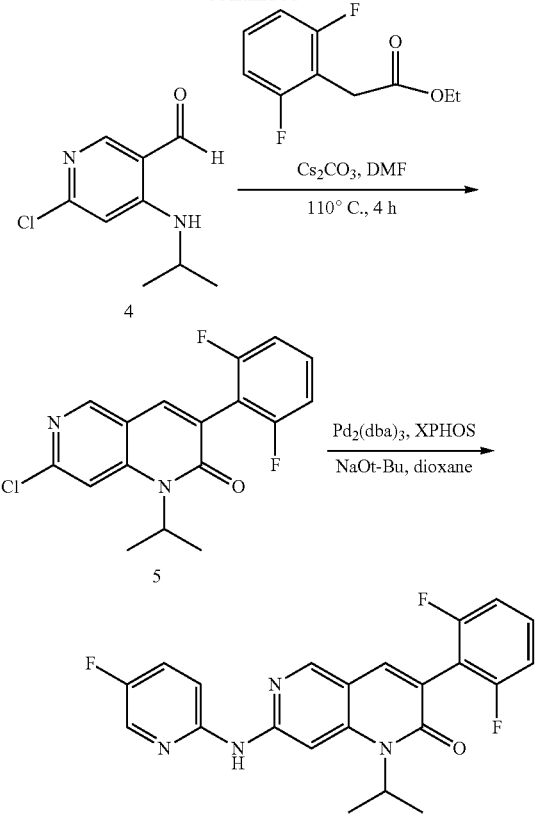

A solution of scheme 27 compound 1 (5 g, 22.7 mmol), isopropylamine (4.03 g, 68.2 mmol) and DIPEA (5.85 g, 45.4 mmol) in THF (166 mL) was stirred at RT overnight. The mixture solvent was evaporated and the residue was dissolved in CH$_2$Cl$_2$ and washed with water three times. Then the combined organic layers were washed with brine, dried over Na$_2$SO$_4$ and concentrated in vacuo to afford scheme 27 compound 2 (4.7 g, 85.4%) as a yellow solid To a suspension of LAH (1.47, 38.8 mmol) in THF (50 mL) under N$_2$ was added dropwise a solution of scheme 27 compound 2 (4.7 g, 19.4 mmol) in THF (64.7 mL) at −78° C. The mixture was stirred at −78° C. and warmed up to room temperature for 3 h. Then the excess LAH was quenched slowly with water at 0° C. The mixture was filtered and the filter cake was washed with THF. The filtrate was concentrated in vacuo to afford scheme 27 compound 3 (4.16 g, crude, 85% purity on NMR) as a yellow white solid.

A suspension of scheme 27 compound 3 (4.16 g, 20.7 mmol) and MnO$_2$ (18 g, 207 mmol) in DCM (169 mL) was stirred at room temperature overnight. The mixture was filtered and washed with DCM. The filtrate was concentrated in vacuo. The crude product was purified by column chromatography (PE:EA=20:1) to afford scheme 27 compound 4 (3 g, 72.8%) as a yellow solid.

A mixture of scheme 27 compound 4 (1.4 g, 7.07 mmol) and (2,6-difluoro-phenyl)-acetic acid ethyl ester (2.63 g, 14.14 mmol), Cs$_2$CO$_3$ (6.9 g, 21.2 mmol), were dissolved in DMF. The reaction mixture was heated to 110° C. and stirred for 4 h. The mixture was evaporated in vacuo, the residue was purified by silica gel column chromatography (DCM/MeOH=100/1 to 10/1) to give the scheme 27 compound 5 (410 mg, 17%) as a yellow solid.

Scheme 27 compound 5 (100.0 mg, 0.3 mmol) and 5-fluoro-pyridin-2-ylamine (40.3 mg, 0.36 mmol) were dissolved in anhydrous dioxane (10 mL). To this mixture was added NaOt-Bu (58 mg, 0.6 mmol), X-PHOS (29 mg, 0.06 mmol), Pd$_2$(dba)$_3$ (28 mg, 0.03 mmol) under nitrogen atmosphere. The reaction mixture was stirred at 100° C. under nitrogen atmosphere overnight. After TLC showed the starting material was consumed completely, the mixture was quenched with water and extracted with ethyl acetate. The organic layer was washed with brine and dried over anhydrous Na$_2$SO$_4$, filtered, concentrated to give a residue which was purified by silica gel column chromatography (DCM/MeOH=200/1 to 80/1) to give Compound 78 (60 mg, yield: 48.8%) as a pale yellow solid. $^1$H NMR (400 MHz, CDCl$_3$): δ 8.39 (s, 1H, ArH), 8.38 (s, 1H, ArH), 8.24 (d, J=3.2 Hz, 1H, ArH), 7.71 (s, 1H, ArH), 7.58 (s, 1H, ArH), 7.46-7.41 (m, 1H, ArH), 7.37 (t, J=4 Hz, 1H, ArH), 7.19-7.17 (m, 1H, ArH), 7.01 (t, J=8 Hz, 2H, ArH), 5.69-5.52 (m, 1H, NH), 1.73 (d, J=6.8 Hz, 6H, 2CH$_3$). MS [ESI, MH$^+$]: 410.1.

Example 38

Synthesis of Compound 79

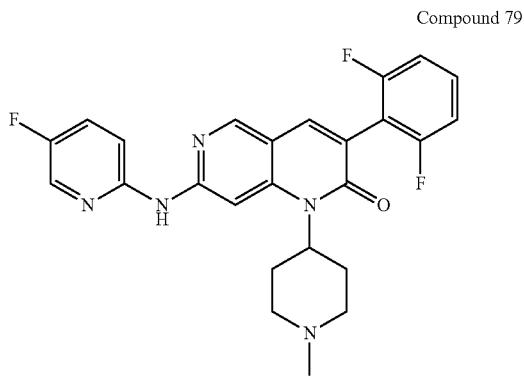 [SMILES: CN1CCC(n2c(=O)c(-c3c(F)cccc3F)cc3cnc(Nc4ccc(F)cn4)cc32)CC1]

Compound 79

Compound 79: 3-(2,6-difluorophenyl)-7-((5-fluoropyridin-2-yl)amino)-1-(1-methylpiperidin-4-yl)-1,6-naphthyridin-2(1H)-one was synthesized as shown in Scheme 28 as a general procedure. The aldehyde 1 was prepared in a similar manner to Compound 75.

Scheme 28

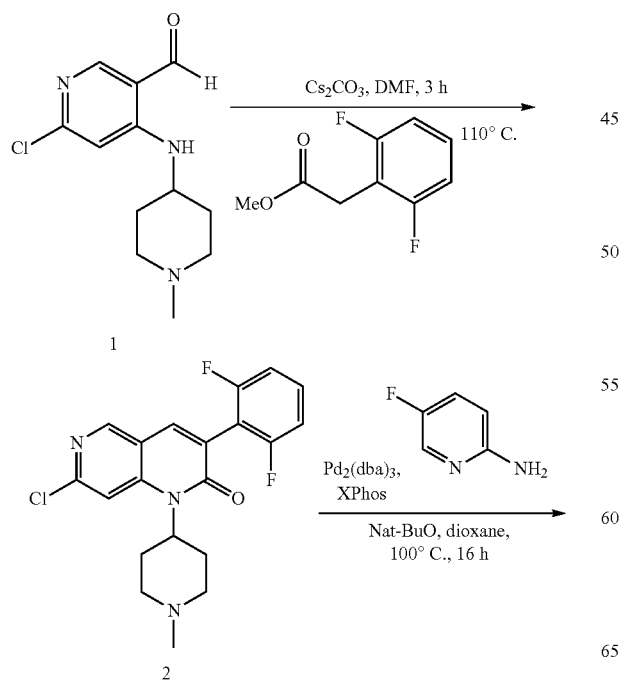

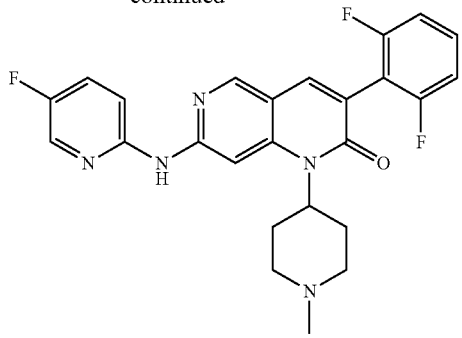

Compound 79

As in the scheme, a solution of scheme 28 compound 1 (1 g, 3.95 mmol), ester (1.47 g, 7.9 mmol) and Cs$_2$CO$_3$ (3.86 g, 11.85 mmol) in DMF (30 mL) under N$_2$ was added and stirred at 110° C. for 4 h. The solvent then was evaporated and the remaining residue was diluted with water and extracted with CH$_2$Cl$_2$. The combined extracts were washed with brine, dried over Na$_2$SO$_4$ and concentrated in vacuo. The crude product was purified by prep-HPLC to afford scheme 28 compound 2 (420 mg, 27.4%) as a brown solid.

A solution of scheme 28 compound 2 (150 mg, 0.384 mmol), 5-fluorine-2-amino-pyridine (51.7 mg, 0.461 mmol), Pd$_2$(dba)$_3$ (35.14 mg, 0.0284 mmol), X-PHOS (36.36 mg, 0.0768 mmol) and NaOt-Bu (73.73 mg, 0.768 mmol) in dioxane (10 mL) under N$_2$ was stirred at 100° C. overnight. The solvent was evaporated and the residue was diluted with saturated NH$_4$Cl and extracted with CH$_2$Cl$_2$. The combined extracts was washed with brine, dried over Na$_2$SO$_4$ and concentrated in vacuo. The crude product was purified by column chromatography (DCM:MeOH=20:1) to afford Compound 79 (147 mg, 82.2%) as a brown solid. $^1$H NMR (400 MHz, CDCl$_3$): δ 8.428 (d, J=6.8 Hz, 2H, 2ArH); 8.21 (s, 1H, ArH); 7.71-7.78 (m, 1H, NH); 7.69 (s, 1H, ArH); 7.29-7.45 (m, 3H, 3ArH); 6.96 (t, J=5.6 Hz, 2H, 2ArH); 5.25-5.47 (m, 1H, N—CH); 3.03-3.12 (m, 4H, 2CH$_2$); 2.41 (s, 3H, CH$_3$); 2.26 (t, J=4 Hz, 2H, CH$_2$); 1.80 (t, J=7.2 Hz, 2H, CH$_2$).

Example 39

Synthesis of Compound 80

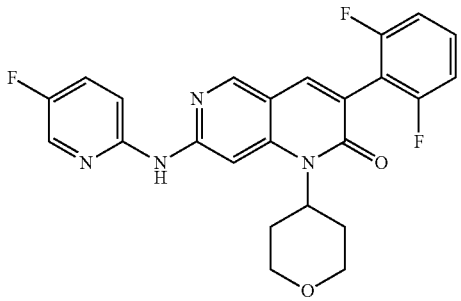

Compound 80

Compound 80: 3-(2,6-difluorophenyl)-7-((5-fluoropyridin-2-yl)amino)-1-(tetrahydro-2H-pyran-4-yl)-1,6-naphthyridin-2(1H)-one was synthesized in a similar manner to Compound 79. $^1$H NMR (CDCl$_3$, 400 MHz): δ 8.78 (br, 1H, NH), 8.46 (s, 1H, ArH), 8.26 (d, J=3.2 Hz, 1H, ArH), 7.71 (s, 1H, ArH), 7.54 (s, 1H, ArH), 7.44-7.30 (m, 2H, 2ArH), 7.09 (dd, 1H, J$^1$=3.6 Hz, J$^2$=9.2 Hz, 1H, ArH), 5.52-5.46 (m, 1H, NCH), 4.23 (dd, J$^1$=4.8 Hz, J$^2$=11.6 Hz, 2H, CH$_2$), 3.64 (t, J=11.0 Hz, 2H, CH$_2$), 3.10-3.00 (m, 2H, 1.77 (d, J=10.0 Hz, 2H, CH$_2$). MS [ESI, MH+]:=453.2.

Example 40

Synthesis of Compound 81

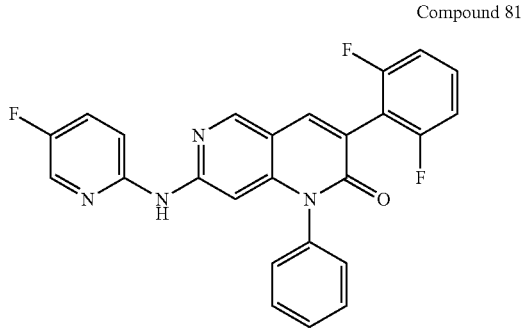 [SMILES: O=c1c(-c2c(F)cccc2F)cc2cnc(Nc3ccc(F)cn3)cc2n1-c1ccccc1]

Compound 81

Compound 81: 3-(2,6-difluorophenyl)-7-((5-fluoropyridin-2-yl)amino)-1-phenyl-1,6-naphthyridin-2(1H)-one was synthesized as shown in Scheme 29:

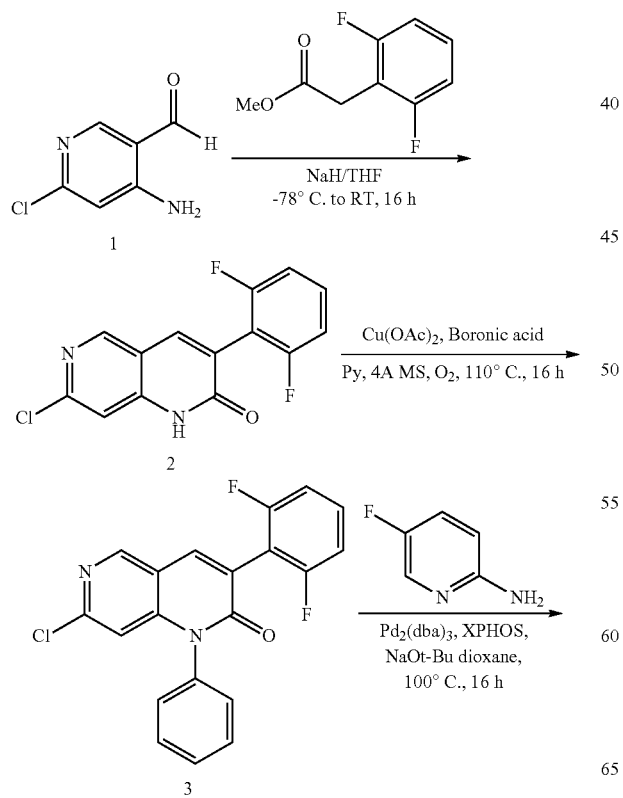

Methyl 2-(2,6-difluorophenyl) acetate (2.85 g, 15.32 mmol) in THF (25 mL) was cooled to −78° C. in a round bottom flask. To the flask, NaH (613 mg, 15.32 mmol) was then added in one portion. The resulting mixture was stirred for 30 min. A solution of scheme 29 compound 1 (798 mg, 5.10 mmol) in THF (8 mL) was then added dropwise into the flask. The reaction mixture was warmed slowly to RT and stirred for another 16 h. The reaction was quenched with saturated aqueous NH$_4$Cl. The reaction mixture was extracted with DCM multiple times. The combined DCM was dried over Na$_2$SO$_4$, concentrated to give a residue which was purified by silica gel column chromatography (PE/EA=4/1) to give scheme 29 compound 2 (800 mg, yield: 53%) as a white solid.

As in the scheme, scheme 29 compound 2 (847 mg, 2.90 mmol), the boronic acid (1.06 g, 8.7 mmol), Cu(OAc)$_2$ (1.05 g, 5.80 mmol) and 4 A MS (3.4 g) were added to pyridine (30 mL) in a flask. The reaction mixture was heated to 110° C. for 16 h. The reaction mixture was then concentrated; and the remaining residue was purified by silica gel column chromatography (DCM/MeOH=10/1) to give compound 3 (165 mg, yield: 15.4%) as a white solid.

Scheme 29 compound 3 (165 mg, 0.448 mmol), the amine (60.2 mg, 0.537 mmol), NaOt-Bu (86 mg, 0.896 mmol), X-PHOS (42.7 mg, 0.0896 mmol) and Pd$_2$(dba)$_3$ (41 mg, 0.0448 mmol) were added to dry dioxane (5 mL) under nitrogen atmosphere. The mixture was heated to 90° C. for 16 h under N$_2$. The reaction was quenched with water and extracted with EtOAc. The organic layer was washed with brine and dried over Na$_2$SO$_4$, concentrated to give a residue that was purified by a silica gel column chromatography (DCM/MeOH=20/1) to give Compound 81 (100 mg, yield: 50.3%) as a yellow solid.

$^1$H NMR (CDCl$_3$, 400 MHz): δ 8.51 (s, 1H, ArH), 7.87-7.85 (m, 2H, 2ArH), 7.62-7.54 (m, 3H, 3ArH), 7.48 (s, 1H, ArH), 7.40-7.30 (m, 5H, 5ArH), 6.99-6.95 (m, 2H, 2ArH), 6.89 (s, 1H, ArH). MS [ESI, MH$^+$]:=445.1.

Example 41

Synthesis of Compound 82

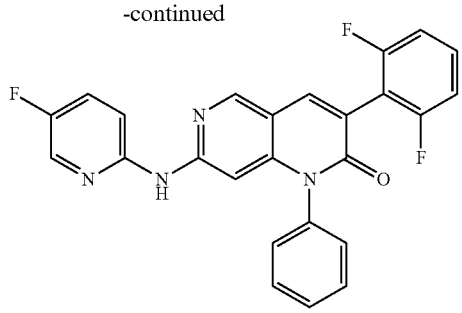

Compound 81

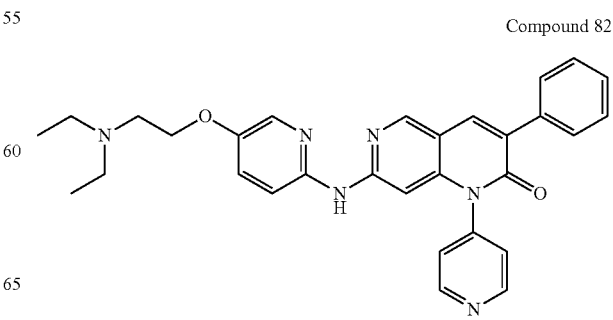

Compound 82

Compound 82: 7-[5-(2-Diethylamino-ethoxy)-pyridin-2-ylamino]-3-phenyl-1-pyridin-4-yl-1H-[1,6]naphthyridin-2-one was synthesized as shown in Scheme 30:

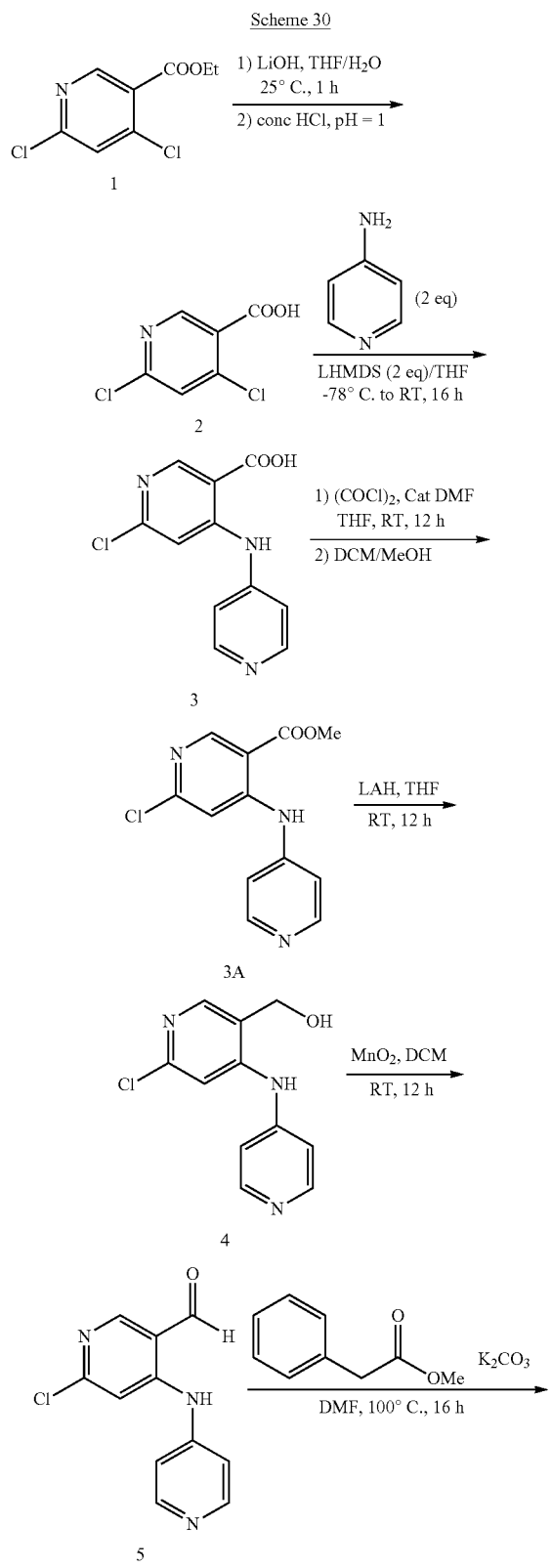

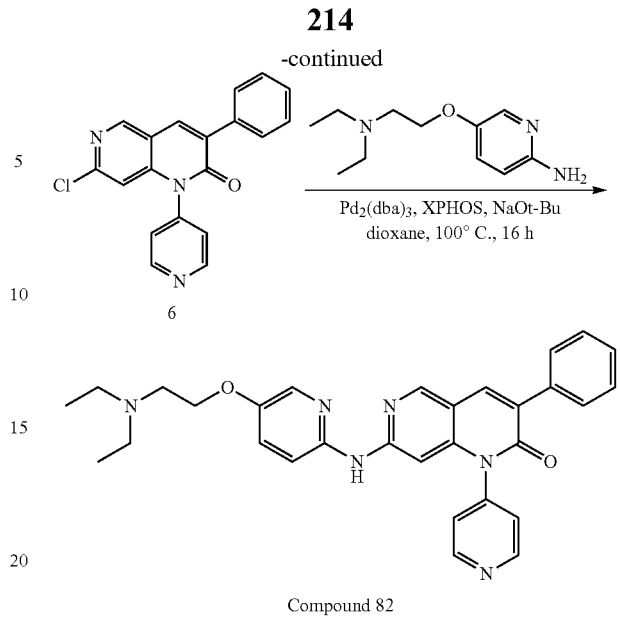

Compound 82

Scheme 30 compound 1 and LiOH were dissolved in THF/H$_2$O, the reaction mixture was stirred at RT for 1 h, conc HCl was added until PH=5-6, The resulting mixture was stirred for 30 min at RT, some light red solid precipitated, the mixture was filtered and filter cake was washed with (DCM/MeOH=2:1) to give the scheme 30 compound 2 (4.2 g, yield 96.3%) as a red solid.

To the solution of 4-aminopyridine (103 mg, 1.1 mmol) in THF (10 mL) was added LHMDS over a period of 15 min at −78° C., It was stirred for another 30 min, then a solution of scheme 30 compound 2 in THF (10 mL) was added dropwise. After complete addition, the mixture was gradually allowed to warm RT and the reaction mixture was stirred for 12 h, the mixture was mixed with water and HCl until PH=5-6, the resulting mixture was filtered and the filter cake was washed with MeOH to give the scheme 30 compound 3 (98 mg, yield: 77%) as a red solid. $^1$H NMR (400 MHz, CDCl$_3$): δ 11.29-11.26 (m, 1H, NH), 8.75 (s, 1H, ArH), 8.50 (d, J=6 Hz, 2H, ArH) 7.4 (t, J=6.2 Hz, 3H, ArH).

To the solution of scheme 30 compound 3 (0.83 g, 3.35 mmol) in THF (100 mL) was added DMF (1 mL) and (COCl)$_2$ (0.65 g, 5.05 mmol) at RT, the reaction mixture was stirred for another 12 h, the reaction mixture was evaporated in vacuo and the remaining residue was dissolved in MeOH and stirred for 20 min, the mixture was then evaporated, the remaining residue was purified by silica gel column chromatography (DCM/MeOH=100/1 to 10/1) to give scheme 30 compound 3A (1.4 g, yield: 79.5%) as a white solid. $^1$H NMR (400 MHz, MeOD): δ 9.0 (s, 1H, NH), 8.54 (d, J=6.8 Hz, 2H, ArH), 7.82 (s, 1H, ArH) 7.71 (d, J=3.2 Hz, 2H, ArH), 4.0 (s, 3H, CH$_3$).

Scheme 30 compound 3A (0.7 g, 2.66 mmol) was dissolved in THF (80 mL) and cooled to −78° C., To this mixture, LAH (202.5 mg, 5.33 mmol) in THF (20 mL) was added dropwise. The resulting mixture was stirred for 12 h at RT. The excess LAH was quenched with water. The reaction mixture was filtered and the filtrate was evaporated, the remaining residue was purified by silica gel column chromatography (DCM/MeOH=100/1 to 10/1) to give scheme 30 compound 4 (770 mg, yield: 61.6%) as a yellow solid.

To a solution of scheme 30 compound 4 (720 mg, 3.1 mmol) in DCM (180 mL) was added MnO₂ (3.3 g, 37 mmol), the reaction mixture was stirred at RT for 12 h; it was then filtered and the filtrate was concentrated in vacuo; the remaining residue was purified by a silica gel column chromatography (DCM/MeOH=100/1 to 10/1) to give compound 5 (701.7 mg, yield: 98.3%) as a yellow solid.

Scheme 30 compound 5 (725 mg, 3.11 mmol) and phenylacetic acid ethyl ester (1.021 g, 6.22 mmol), K₂CO₃ (1.3 g, 9.33 mmol) were dissolved in DMF (150 mL), the reaction mixture was heated to 90° C. and stirred for 16 h. After cooled to RT, the mixture was concentrated in vacuo, the remaining residue was dissolved in EtOAC and washed with brine and dried with anhydrous sodium sulfate, filtered and evaporated to yield a residue that was purified by silica gel column chromatography (PE/EA=10/1 to 1/1) to give scheme 30 compound 6 (792 mg, yield: 76.5%) as a yellow solid.

Scheme 30 compound 6 (300 mg, 0.9 mmol) and Amine 01 (207 mg, 1 mmol) was dissolved in anhydrous dioxane (10 mL). To the dioxane solution were added NaOt-Bu (173 mg, 1.8 mmol), X-PHOS (86 mg, 0.18 mmol), Pd₂(dba)₃ (83 mg, 0.09 mmol) under nitrogen atmosphere. The resulting mixture was stirred at 100° C. under nitrogen atmosphere for 16 h. The mixture was quenched with water and extracted with EtOAc. The organic layer was washed with brine, and dried over Na₂SO₄, concentrated to give a residue which was purified by column chromatography (DCM/MeOH=50/1 to 3/1) to give Compound 82 (233.8 mg, yield: 51.3%) as a yellow solid. ¹H NMR (400 MHz, CDCl₃): δ 8.93-8.91 (m, 2H, NH and ArH), 8.53 (s, 1H, ArH), 7.88 (s, 1H, ArH), 7.74-7.71 (m, 3H, ArH), 7.45-7.41 (m, 2H, ArH), 738-7.37 (m, 3H, ArH), 7.26 (t, J=5.4 Hz, 1H, ArH), 7.20-7.17 (m, 2H, CH and ArH), 7.04 (d, J=4.4 Hz, 1H, ArH), 4.01 (t, J=6.2 Hz, 2H, CH₂), 2.85 (t, J=6 Hz, 2H, CH₂), 2.66-2.61 (m, 4H, 2CH₂), 1.07 (t, J=7.2 Hz, 6H, 2CH₃).

Example 42

Synthesis of Compound 83

Compound 83

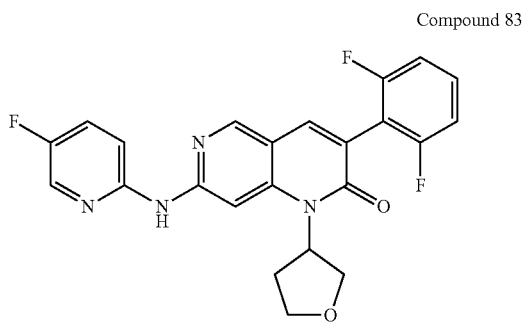 [SMILES: O=c1c(-c2c(F)cccc2F)cc2cnc(Nc3ccc(F)cn3)cc2n1C1CCOC1]

Compound 83: 3-(2,6-difluorophenyl)-7-((5-fluoropyridin-2-yl)amino)-1-(tetrahydrofuran-3-yl)-1,6-naphthyridin-2(1H)-one was synthesized as shown in Scheme 31. The aldehyde 1 was prepared in a similar manner to Compound 75.

Scheme 31

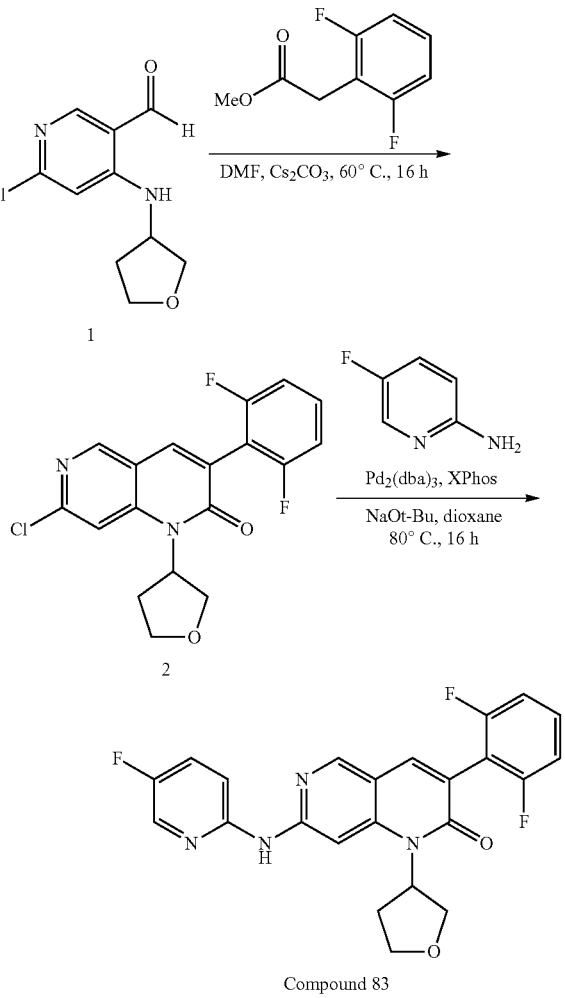

Compound 83

Scheme 31 compound 1 (800 mg, 3.54 mmol) was dissolved in anhydrous DMF. To this DMF solution, methyl 2-(2,6-difluorophenyl) acetate (989 mg, 5.31 mmol) and Cs₂CO₃ (3.45 g, 10.62 mmol) were added. The resulting mixture was stirred at 60° C. for 16 h. The mixture was then quenched with H₂O and extracted with EA. The organic layer was washed with saturated NaCl, dried over anhydrous Na₂SO₄, concentrated to give a crude residue which was purified by silica gel column chromatography (DCM/MeOH=10:1) to give scheme 31 compound 2 (300 mg, 23.4%) as a yellow solid.

Scheme 31 compound 2 (200 mg, 0.55 mmol) and 5-fluorine-2-amino-pyridine (74.2 mg, 0.66 mmol) was dissolved in anhydrous dioxane (5 mL) was added NaOt-Bu (104.5 mg, 1.10 mmol), X-PHOS (52.4 mg, 0.11 mmol), Pd₂(dba)₃ (50 mg, 0.055 mmol) under nitrogen atmosphere. The mixture was stirred at 80° C. under nitrogen atmosphere for 16 h. The mixture was quenched with water and extracted with EA. The organic layer was washed with brine, and dried over Na₂SO₄, concentrated to give a residue which was purified by column chromatography (DCM/MeOH=10:1) to give Compound 83 (98.4 mg, yield 40.8%) as a yellow solid. ¹H NMR (CDCl₃, 400 MHz): δ 8.48 (s, 1H, NH), 8.20 (d, J=2.8 Hz, 1H, ArH), 8.03 (s, 1H, ArH), 7.69-7.68 (m, 2H, 2ArH), 7.48-7.31 (m, 3H, 3ArH), 7.01-6.97 (m, 2H, 2ArH), 6.35-6.32 (m, 1H, NCH), 4.51-4.46 (m, 1H, CH), 4.25-4.21 (m, 1H, CH), 4.06-4.01 (m, 1H, CH), 3.89-3.83 (m, 1H, CH), 2.53-2.48 (m, 1H, CH), 2.37-2.33 (m, 1H, CH). MS [ESI, MH+]:=439.2.

Example 43

Synthesis of Compound 84

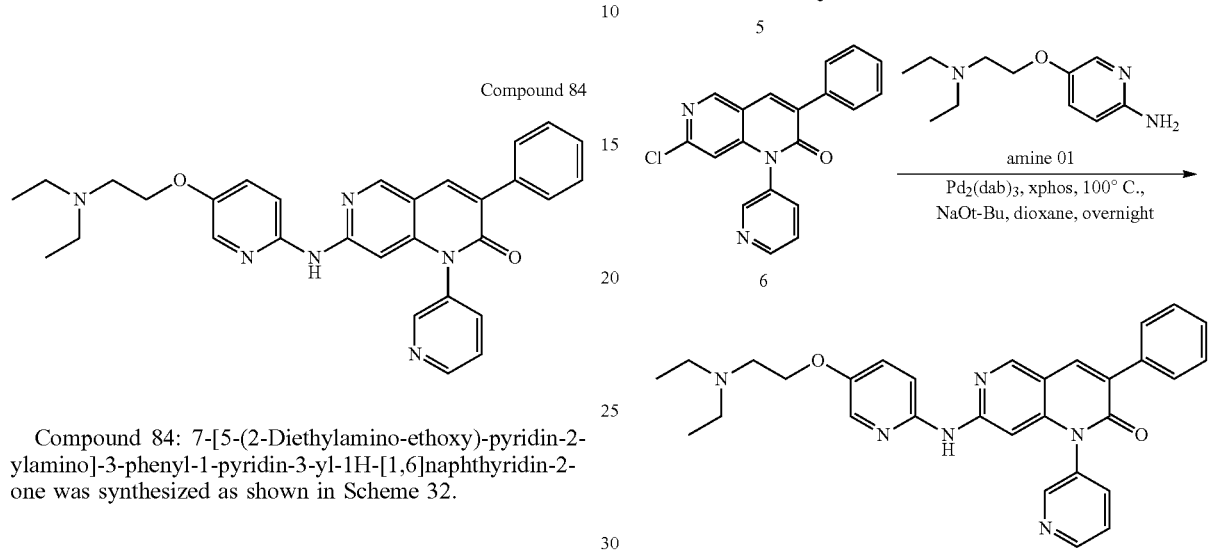

Compound 84

Compound 84: 7-[5-(2-Diethylamino-ethoxy)-pyridin-2-ylamino]-3-phenyl-1-pyridin-3-yl-1H-[1,6]naphthyridin-2-one was synthesized as shown in Scheme 32.

Scheme 32

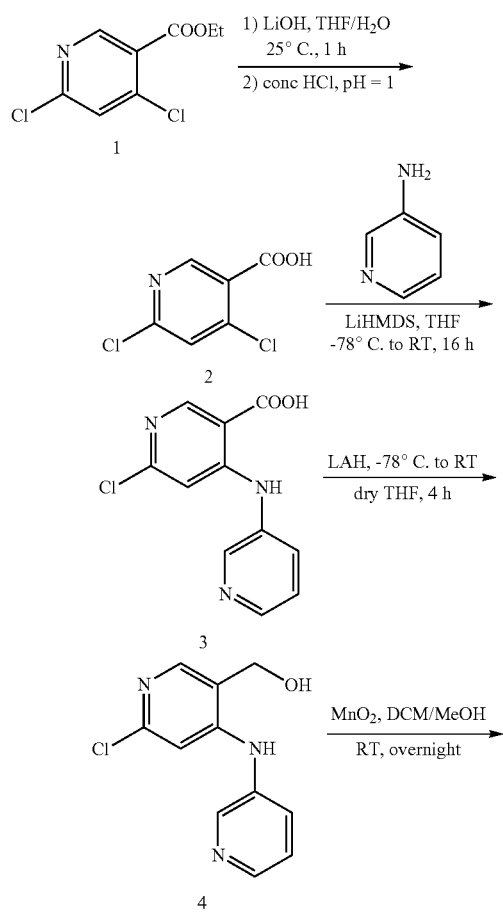

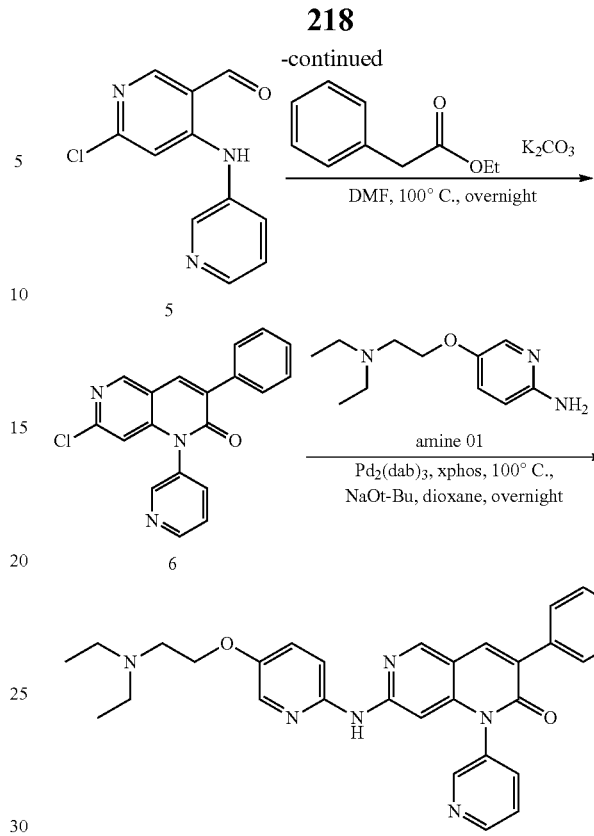

To a solution of scheme 32 compound 1 (8 g, 36.34 mmol), LiOH.H$_2$O (3.84 g, 90.85 mmol) in THF/H$_2$O (160 mL:80 mL) was added and stirred at 25° C. for 1 h. The solvent was evaporated and the residue was acidified with 1 M HCl and extracted with EA. The combined extracts were washed with brine, dried over Na$_2$SO$_4$ and concentrated in vacuo to afford scheme 32 compound 2 (6.3 g, 90.2%) as a white solid.

A solution of LiHMDS (99 mL, 99 mmol) in THF was added dropwise to a stirred solution of 2-amino pyridine (6.17 g, 65.62 mmol) in THF (99.32 mL) at −78° C. The mixture was stirred at −78° C. for 30 min. A solution of scheme 32 compound 2 (6 g, 31.25 mmol) was then added dropwise to the above mixture at −78° C. After addition, the resulting mixture was stirred at −78° C. and warmed up to room temperature overnight, and then quenched with 1M HCl. The solvent was evaporated and the remaining residue was diluted with water and the pH of the solution was adjusted to 4-5. The formed precipitate was filtered and washed with MeOH and TBME to afford scheme 32 compound 3 (7 g, 89.7%) as a grey solid.

A suspension of compound 3 (7 g, 28 mmol) and LAH (2.1 g, 56 mmol) in THF (100 mL) was added and stirred at −78° C. for 4 h. It was then allowed to warm up to room temperature. The mixture was quenched with water at about −20° C. and filtered. The filter cake was washed with THF and the filtrate was concentrated in vacuo to afford scheme 32 compound 4 (5.1 g, 77.2%) as a yellow solid.

A suspension of scheme 32 compound 4 (5 g, 21.18 mmol) and MnO$_2$ (22.1 g, 254.2 mmol) in DCM/MeOH (200 mL:20 mL) was stirred at room temperature overnight. The mixture was filtered and the filter cake was washed with DCM. The filtrate was concentrated in vacuo to yield the crude product that was washed with n-pentane to afford scheme 32 compound 5 (3.8 g, 77.5%) as a yellow solid.

A solution of scheme 32 compound 5 (500 mg, 2.14 mmol), the ester (702 mg, 4.28 mmol) and K₂CO₃ (886 mg, 6.42 mmol) in DMF (10 mL) was stirred at 100° C. overnight. The mixture was diluted with water and extracted with EA. The combined extracts were washed with brine, dried with Na₂SO₄ and concentrated in vacuo to afford scheme 32 compound 6 (500 mg, 70.1%) as a brown solid.

A solution of scheme 32 compound 6 (200 mg, 0.599 mmol), amine 01 (137.9 mg, 0.659 mmol), Pd₂(dba)₃ (54.8 mg, 0.0599 mmol), X-PHOS (57.14 mg, 0.1198 mmol) and NaOt-Bu (115 mg, 1.198 mmol) in dioxane (8 mL) was degassed, and then stirred at 100° C. overnight. The mixture was diluted with water and extracted with EA. The combined extracts were washed with brine, dried with Na₂SO₄ and concentrated in vacuum to yield a crude that was purification by column chromatography (DCM:MeOH=20:1) to afford Compound 84 (50 mg, 16.5%) as a yellow solid. ¹H NMR (400 MHz, CDCl₃): δ 8.82 (d, J=2 Hz, 1H, ArH); 8.66 (d, J=2 Hz, 1H, ArH); 8.53 (s, 1H, ArH); 7.89 (s, 1H, ArH); 7.72-7.75 (m, 4H, ArH); 7.57-7.60 (m, 1H, ArH); 7.35-7.45 (m, 3H, ArH); 7.29 (s, 1H, ArH); 7.18-7.21 (m, 1H, ArH); 7.11 (d, J=4.4 Hz, 1H, ArH); 7.06 (s, 1H, NH); 4.05 (s, 2H, CH₂); 2.89 (s, 2H, CH₂); 2.68 (s, 4H, CH₂); 1.10 (t, 6H, CH₃).

Example 44

Synthesis of Compound 85

Compound 85: 3-(2,6-difluorophenyl)-7-((5-fluoropyridin-2-yl)amino)-1-(1-methylpyrrolidin-3-yl)-1,6-naphthyridin-2(1H)-one was synthesized as shown in Scheme 33.

Scheme 33

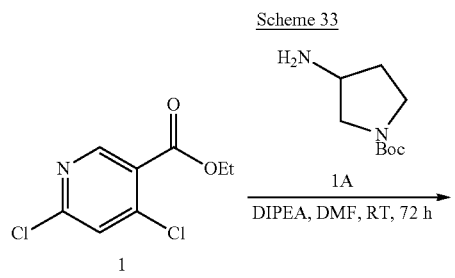

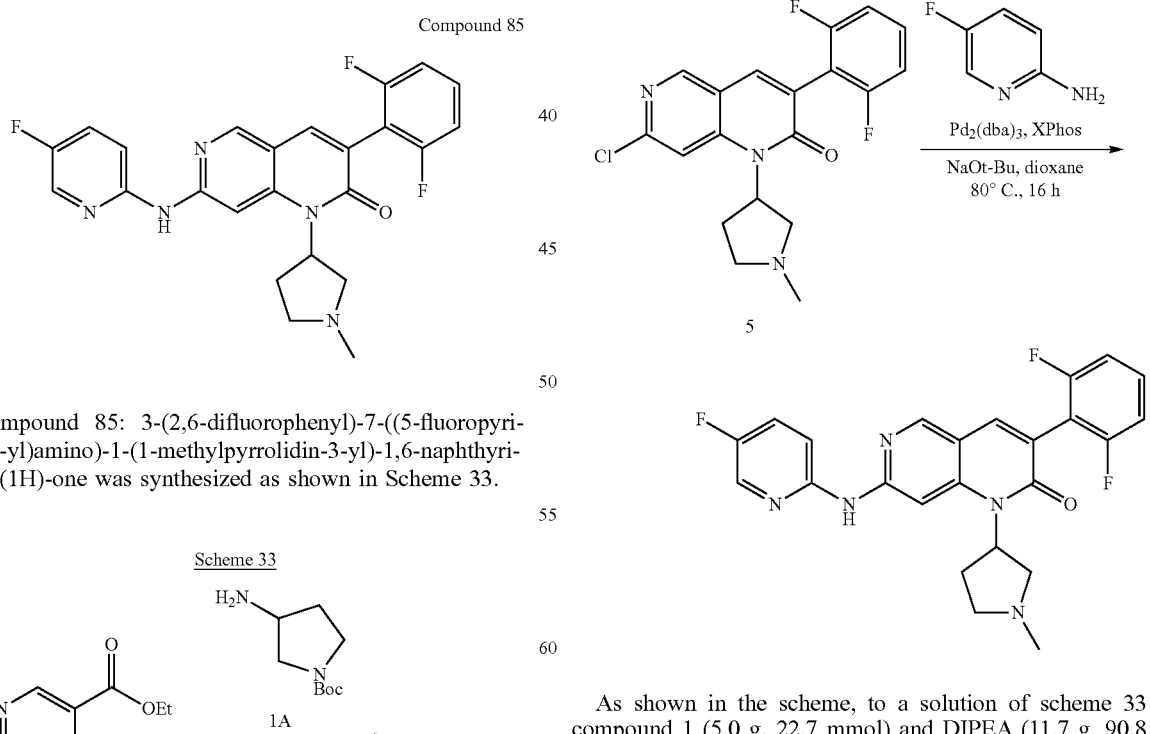

As shown in the scheme, to a solution of scheme 33 compound 1 (5.0 g, 22.7 mmol) and DIPEA (11.7 g, 90.8 mmol) in DMF (50 mL) was added scheme 33 compound 1A (5.1 g, 27.3 mmol) at RT. The mixture was stirred at RT for 72 h. The mixture was diluted with water, extracted with EA. The organic phase was washed with brine, dried over Na₂SO₄, concentrated to the crude product which was purified by column chromatography (PE/EA=10:1) to give scheme 33 compound 2 (4.0 g, 47.8%) as a white solid.

To a suspension of LAH (1.06 g, 28.0 mmol) in THF (50 mL) was added scheme 33 compound 2 (5.2 g, 14.0 mmol) in THF (50 mL) dropwise at −78° C. The mixture was stirred at −78° C. for 30 min, then warmed up to RT and stirred at RT for 1 h. The reaction mixture was quenched with MeOH/EA (1/1) mixture at 0° C. The solid was filtered and washed with EA. The filtrate was concentrated to give a crude residue as a yellow solid which was used for next step directly.

Scheme 33 compound 3 (4.0 g, 16.6 mmol) was mixed with MnO₂ (14.6 g, 166 mmol) in DCM (150 mL). The mixture was stirred at RT for 16 h. The MnO₂ was filtered off, and the filtrate was concentrated to give the residue which was purified by column chromatography (DCM/MeOH=15:1) and prep-HPLC to give scheme 33 compound 4 (400 mg, yield: 10.1%) as a brown solid.

Scheme 33 compound 4 (400 mg, 1.67 mmol) was dissolved in anhydrous DMF (20 mL). To this DMF solution was added methyl 2-(2,6-difluorophenyl) acetate (623 mg, 3.34 mmol) and Cs₂CO₃ (1.63 g, 5.02 mmol). The resulting mixture was stirred at 60° C. for 16 h. The mixture was quenched with H₂O and extracted with EA. The organic layer was washed with saturated aqueous NaCl, dried over anhydrous Na₂SO₄, concentrated to give a crude residue which was purified by silica gel column chromatography and prep-HPLC to give scheme 33 compound 5 (150 mg, 24.0%) as a brown solid.

Scheme 33 compound 5 (150 mg, 0.40 mmol) and 5-fluorine-2-amino-pyridine (53.8 mg, 0.48 mmol) was dissolved in anhydrous dioxane (5 mL). To this solution were added NaOt-Bu (76 mg, 0.80 mmol), X-PHOS (38.1 mg, 0.08 mmol), Pd₂(dba)₃ (36.6 mg, 0.04 mmol) under nitrogen atmosphere. The resulting mixture was stirred at 80° C. under nitrogen atmosphere for 16 h. The mixture was quenched with water and extracted with EA. The organic layer was washed with brine, dried over Na₂SO₄, concentrated to give a residue which was purified by column chromatography (DCM/MeOH=10:1) to give Compound 85 (30 mg, yield: 16.7%) as a yellow solid. ¹H NMR (CDCl₃, 400 MHz): δ 8.39 (s, 1H, NH), 8.28 (s, 2H, 2ArH), 7.69 (s, 1H, ArH), 7.54 (s 1H, ArH), 7.36-7.25 (m, 2H, 2ArH), 7.01-6.97 (m, 2H, 2ArH), 5.92 (br, 1H, NCH), 3.87 (br, 1H, CH), 3.67 (br, 1H, CH₂), 3.54 (br, 1H, CH), 2.89 (s, 3H, NCH₃), 2.73 (s, 1H, CH), 2.59-2.58 (d, J=4.4 Hz, 1H, CH). MS [ESI, MH+]:=452.2.

Example 45

Synthesis of Compound 65

Compound 65: 7-((5-(2-(diethylamino)ethoxy)pyridin-2-yl)amino)-1-((1-methylpyrrolidin-3-yl)methyl)-3-phenyl-1,6-naphthyridin-2(1H)-one was synthesized as shown in Scheme 34.

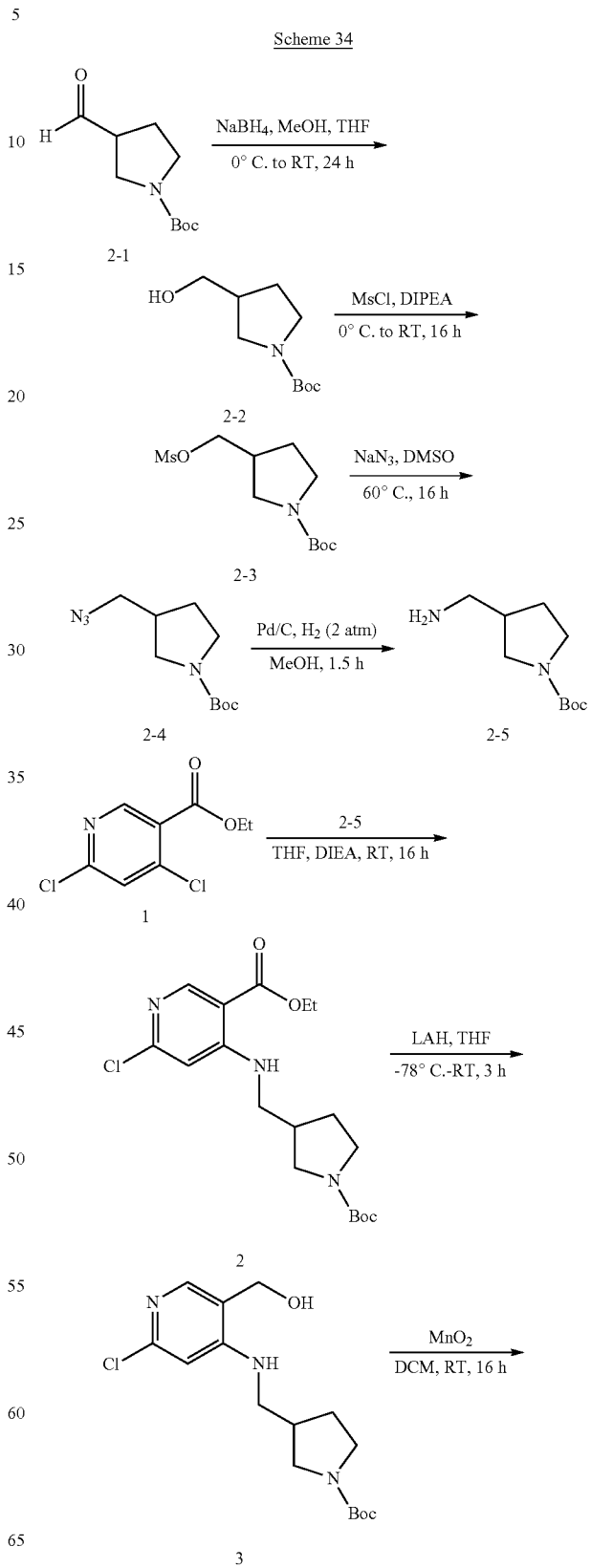

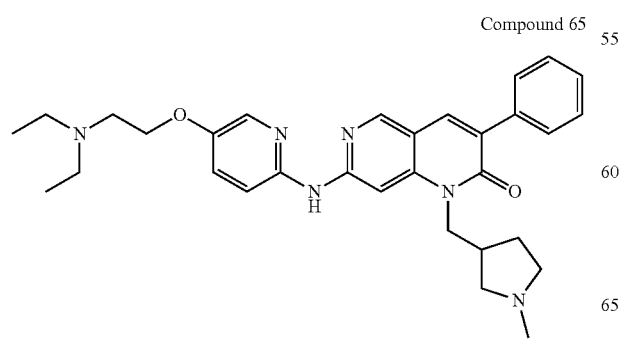

Compound 65

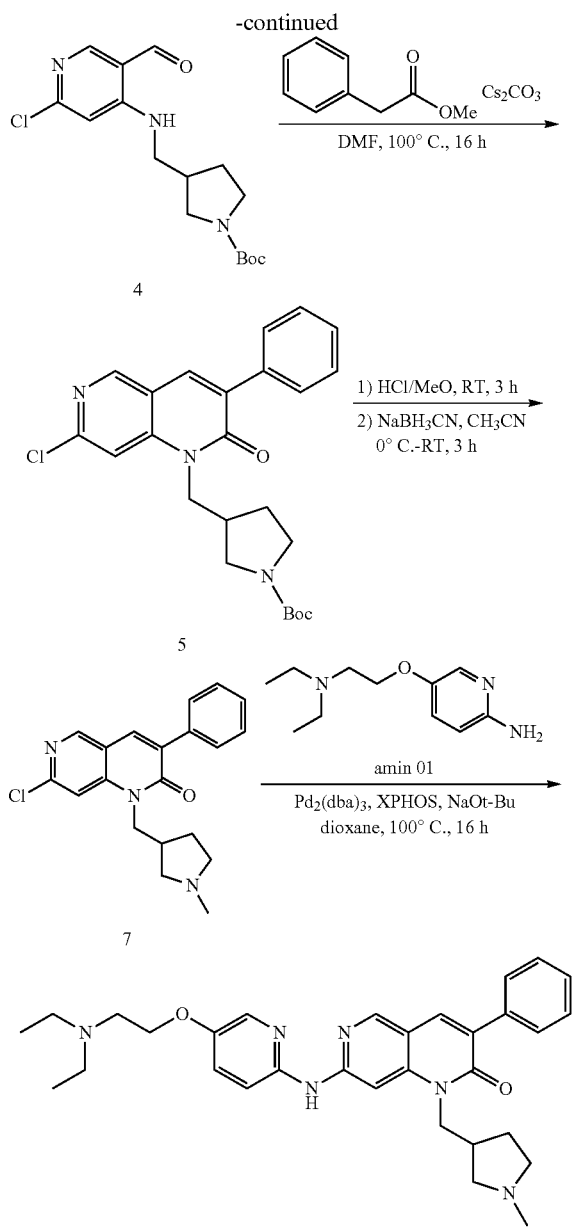

The synthesis started with preparing amine 2-5. To a solution of scheme 34 compound 2-1 (4 g, 0.02 mol) in THF/MeOH (16 mL/16 mL) at 0° C. was added NaBH₄ (2.56 g, 0.08 mol) in several portions. After the addition, the reaction mixture was diluted with EA, quenched with sat Na₂CO₃ and stirred for 15 min. The aqueous layers was extracted with EA (30 mL), dried over Na₂SO₄, concentrated to give a crude residue (3.9 g, 97.7%) which was used in the next step immediately without further purification.

To a solution of scheme 34 compound 2-2 (6.14 g, 0.031 mol) and Et₃N (10.4 g, 0.102 mol) in DCM (20 mL) was added MsCl (11.8 g, 0.102 mol) at 0° C. After stirring for 30 min, H₂O was added. The aqueous layer was extracted with EA (30 mL), dried with Na₂SO₄, and concentrated to give a residue which was purified by silica gel column chromatography (PE:EA=5/1) to give scheme 34 compound 2-3 (5.5 g, yield: 64.7%) as a pale yellow solid. ¹H NMR (CDCl₃, 400 MHz): δ 4.20-4.10 (m, 2H, CH₂), 3.54-3.12 (m, 4H, 2CH₂), 3.00 (s, 3H, CH₃), 2.60 (br, 1H, CH), 2.59-1.44 (m, 1H, CH), 1.43 (s, 9H, 3CH₃)

A stirred suspension of scheme 34 compound 2-3 (6.1 g, 21.9 mmol) and sodium azide (5.7 g, 87.7 mmol) in DMSO (200 mL) was heated at 60° C. overnight. The reaction mixture was cooled to RT, poured into water and extracted with EA. The combined organics were washed with brine, dried over Na₂SO₄ and concentrated to give a residue which was purified by silica gel column chromatography (PE:EA=10/1) to give scheme 34 compound 2-4 (5 g, yield: 96%) as a pale yellow solid.

A stirred suspension of scheme 34 compound 2-4 and 10% Pd/C (5 g, 21 mmol) in MeOH (80 mL) was stirred under H₂ (2 atm) at RT for 1.5 h. The reaction mixture was diluted with EA and filtered through a short column of celite. The celite column was rinsed with additional portions of EA and the combine organics fractions were dried over Na₂SO₄ and concentrated in vacuo to afford scheme 34 2-5 (3.4 g, yield: 80.2%) which was used in the next step immediately without further purification.

To a solution of scheme 34 1 (3.74 g, 17 mmol) in THF (80 mL) was added amine 2-5 (3.4 g, 17 mmol) and DIPEA (4.4 g, 34 mmol). The mixture was stirred at RT for 16 h. TLC showed the starting material was consumed completely. After the solvent was removed, the mixture was extracted with EA (100 mL), washed with water and brine, dried over Na₂SO₄, concentrated to give the crude product which was purified by silica gel chromatography (PE/EA=10/1 to 5/1) to give scheme 34 2 (1 g, yield: 15.4%) as a pale yellow solid.

The solution of scheme 34 compound 2 (1 g, 2.61 mmol)) in THF (20 mL) was added dropwise to a suspension of LAH (0.12 g, 3.39 mmol) in THF (20 mL) at −78° C. during a period of 30 min. The resulting mixture was stirred at −78° C. for 30 min, then warmed up to RT for 2 h. TLC showed the starting material was consumed completely. Small amount of MeOH/EA (1/1) mixture was added slowly to the reaction mixture to quench the excess LAH. The reaction mixture was filtered and the solid was washed with EA. The combined filtrate was concentrated to give the crude product (1 g) which was used in the next step immediately without further purification.

MnO₂ (2.6 g, 29.7 mmol) and scheme 34 compound 3 (1 g, 2.97 mmol) was mixed in DCM (25 mL). The mixture was stirred at RT for 5 h. TLC showed the reaction was completely. The MnO₂ was filtered off and the filtrate was concentrated to give scheme 34 4 (500 mg, yield: 50.5%) as a yellow solid which was used in the next step immediately without further purification.

scheme 34 compound 4 (0.45 g, 1.33 mmol) was dissolved in anhydrous DMF along with scheme 34 compound 6 (0.40 g, 2.66 mmol) and Cs₂CO₃ (0.86 g, 2.66 mmol). The mixture was stirred at 100° C. overnight. TLC showed the starting material was consumed completely. The mixture was quenched with H₂O and extracted with EA. The organic layer was washed with saturated aqueous NaCl, dried over anhydrous Na₂SO₄ and concentrated to give a crude residue which was purified by silica gel chromatography (PE:EA=5:1) to give compound 5 (0.32 g, 55.2%) as a yellow solid. ¹H NMR (MeOD, 400 MHz): δ 8.55 (s, 1H, ArH), 7.75 (s, 1H, ArH), 7.59 (d, J=7.2 Hz 1H, ArH), 7.38-7.36 (m, 3H, ArH), 7.13 (s, 1H, ArH), 4.51-4.17 (m, 2H, CH₂), 4.16-4.08 (m, 2H, CH₂), 4.07-4.02 (m, 2H, CH₂), 3.55-3.46 (m, 1H, CH), 3.32-3.22 (m, 1H, CH), 3.20-3.16 (m, 1H, CH), 3.05 (s, 9H, 3CH₃). MS [ESI, MH⁺]:=440.2.

The solution of scheme 34 compound 5 (0.32 g, 0.73 mmol) in saturated HCl in MeOH (30 mL) was stirred at RT for 3 h. The pH of the solution was adjusted to around 9 by adding saturated aqueous NaHCO₃. The aqueous layer was extracted with DCM thoroughly. The combined organic layer was dried over MgSO$_4$, filtered and concentrated to give the crude product (0.2 g, 80%) which was used in the next step immediately without further purification.

A stirred and cooled (0° C.) solution of CH$_3$CN (15 mL) containing the crude product (0.2 g, 0.59 mmol) and 37% HCHO (6 mL) was treated with NaBH$_3$CN (64 mg, 1.12 mmol) in one portion. After being allowed to stir for 1 h at 0° C., the reaction mixture was warmed to RT and stirred for additional 2 h. The mixture was mixed with H$_2$O and extracted with DCM. The organic layer was washed with half-saturated aqueous NaCl, dried over anhydrous Na$_2$SO$_4$ and concentrated to give a crude residue (0.12 g, 48%) which was used in the next step immediately without further purification.

Scheme 34 compound 7 (100 mg, 0.283 mmol) and Amine 01 in (77 mg, 0.368 mmol) were dissolved in anhydrous dioxane (10 mL). To this mixture was added NaOt-Bu (54 mg, 0.566 mmol), X-PHOS (27 mg, 0.0566 mmol), Pd$_2$(dba)$_3$ (26 mg, 0.028 mmol) under nitrogen atmosphere. The reaction mixture was stirred at 80° C. under nitrogen atmosphere overnight. After TLC showed the starting material was consumed completely, the mixture was quenched with water and extracted with EA. The organic layer was washed with brine and dried over anhydrous Na$_2$SO$_4$, filtered and concentrated to give a residue which was purified by silica gel chromatography (DCM/MeOH=10/1 to 1/1) to give Compound 65 (35.3 mg, yield: 11.0%) as a pale yellow solid. $^1$H NMR (CD$_3$OD, 400 MHz): δ 8.37 (s, 1H, ArH), 7.98 (s, 1H, ArH), 7.91 (s, 1H, ArH), 7.72 (s, 1H, ArH), 7.72 (s, 1H, ArH), 7.58 (dd, J$^1$=8.0 Hz, J$^2$=7.2 Hz, 2H, 2ArH), 7.36-7.24 (m, 5H, 5ArH), 4.29-4.26(m, 1H, CH), 4.24-4.17 (m, 1H, CH), 4.05 (t, J=6.0 Hz, 2H, CH$_2$), 2.87-2.71(m, 11H, 11 CH), 2.69 (s, 3H, CH$_3$), 2.68 (s, 1H, CH), 2.32 (s, 1H, CH), 1.08 (t, J=7.2 Hz, 6H, 2CH$_3$). MS [ESI, MH$^+$]:=527.3.

Example 46

Synthesis of Compound 76

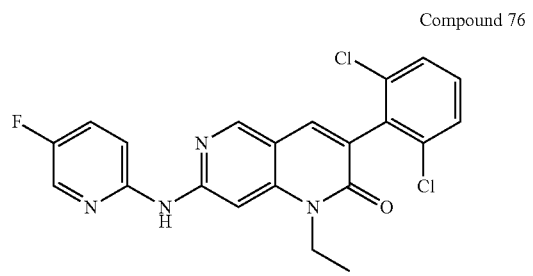 [SMILES: CCn1c(=O)c(-c2c(Cl)cccc2Cl)cc2cnc(Nc3ccc(F)cn3)cc21]

Compound 76

Compound 76: 3-(2,6-dichlorophenyl)-1-ethyl-7-((5-fluoropyridin-2-yl)amino)-1,6-naphthyridin-2(1H)-one was synthesized as shown in Scheme 35.

Scheme 35

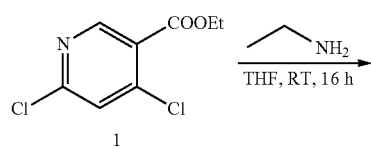

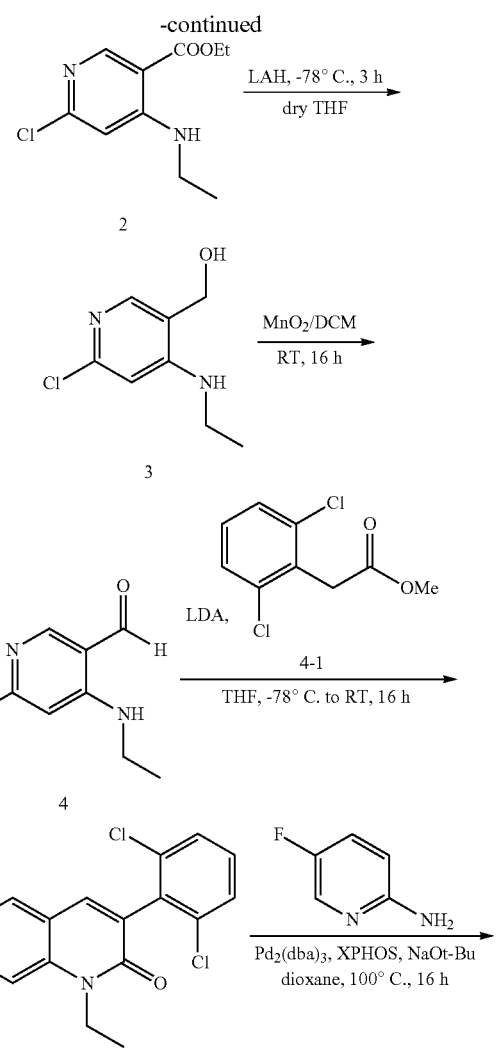

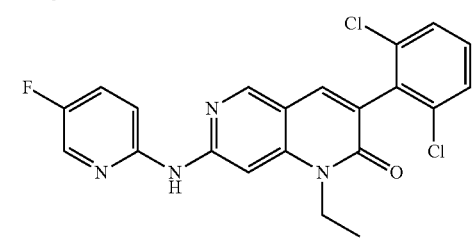

As shown in scheme 35, scheme 35 compound 4 was prepared in the same manner showed before. The solution of 4,6-dichloro-nicotinic acid ethyl ester (2.86 g, 13.04 mmol) in THF (25 mL) was cooled to −78° C. in a flask. LDA (2 M, 7 mL, 13.92 mmol) was added dropwised into the flask. After the addition, the reaction mixture was stirred for another 30 min at −78° C. The solution of scheme 35 compound 4 (800 mg, 4.35 mmol) in THF (8 mL) was added dropwise into the flask slowly to maintain the reaction temperature below −60° C. After the addition, the reaction mixture was allowed to warm to ambient temperature and was stirred overnight. The reaction mixture was quenched with saturated aqueous NH$_4$Cl, and extracted with DCM. The combined DCM was dried over anhydrous Na$_2$SO$_4$ and concentrated to give a crude residue that was purified by silica gel column chromatography (PE/EA=10/1) to give scheme 35 compound 5 (160 mg, yield: 10.4%) as a white solid.

scheme 35 compound 5 (160.0 mg, 0.455 mmol), Amine (61.1 mg, 0.545 mmol), Pd$_2$(dba)$_3$ (41.6 mg, 0.0455 mmol), X-PHOS (43.4 mg, 0.091 mmol) and NaOt-Bu (87.4 mg, 0.91 mmol) were added to dry Dioxane (5 mL). The reaction mixture was degassed with N$_2$ for 3 times and heated to 100° C. for 16 h. After cooling to rt, the reaction mixture was diluted with H$_2$O (20 mL), extracted with DCM (15 mL×3). The combined DCM was washed with brine and concentrated to give a residue that was purified by silica gel column chromatography (DCM/MeOH=100/1) to give Compound 76 (100 mg, yield: 48.5%) as a white solid. $^1$H NMR (d$^6$-DMSO, 400 MHz): δ 10.17 (s, 1H, NH), 8.65 (s, 1H, ArH), 8.30-8.29 (m, 1H, ArH), 7.98 (s, 1H, ArH), 7.94 (s, 1H, ArH), 7.72-7.70 (m, 2H, 2ArH), 7.59 (s, 1H, ArH), 7.57 (s, 1H, ArH), 7.46-7.44 (m, 1H, ArH), 4.22 (q, J=7.2 Hz, 2H, CH$_2$), 1.29 (t, J=7.2 Hz, 3H, CH$_3$). MS [ESI, MH$^+$]:=429.1.

Example 47

Synthesis of Compound 16

Compound 16

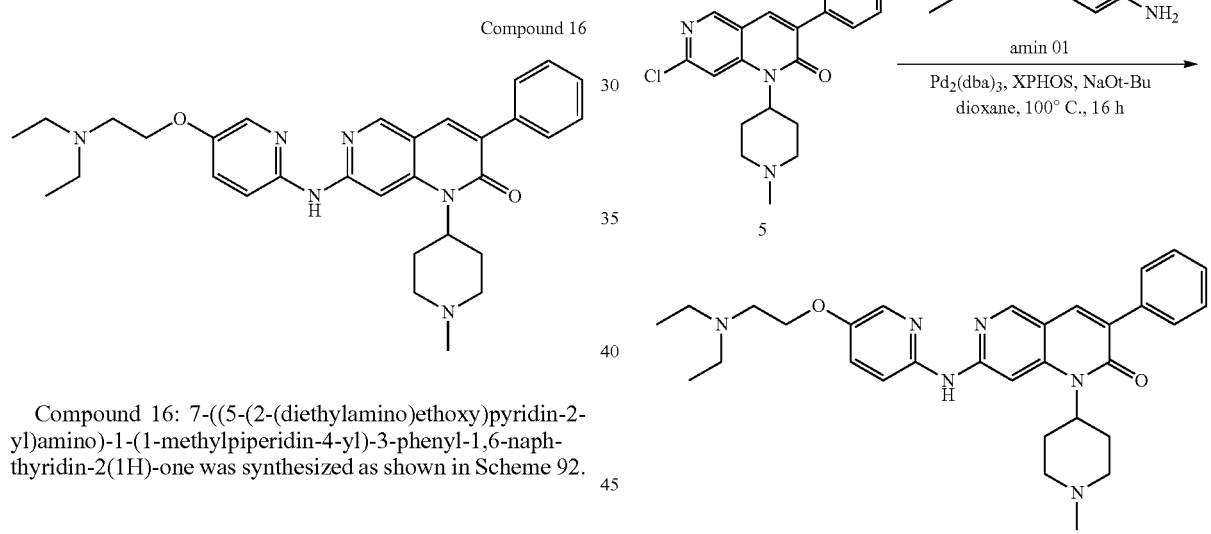

Compound 16: 7-((5-(2-(diethylamino)ethoxy)pyridin-2-yl)amino)-1-(1-methylpiperidin-4-yl)-3-phenyl-1,6-naphthyridin-2(1H)-one was synthesized as shown in Scheme 92.

Scheme 36

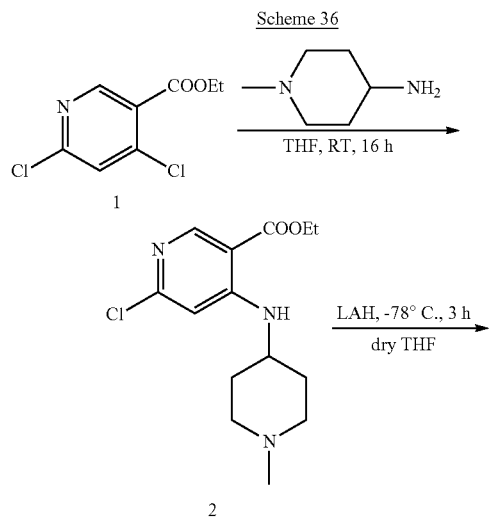

To a solution of scheme 36 compound 1 (3.3 g, 15 mmol) in THF (80 mL) was added 1-methyl-piperidin-4-ylamine (2.9 g, 25 mmol) and Et$_3$N (4.0 g, 39.6 mmol). The mixture was stirred at RT for 16 h. TLC showed the starting material was consumed completely. After the solvent was removed, the remaining residue was extracted with EA (120 mL). The organics were washed with water and brine, dried over Na$_2$SO$_4$ and concentrated to give a crude product which was purified by silica gel column chromatography (PE/EA=10/1 to 5/1) to give scheme 36 compound 2 (2 g, yield: 44.9%) as a pale yellow solid.

A solution of scheme 36 compound 2 (2 g, 6.73 mmol) in THF (10 mL) was added drop-wise to a suspension of LAH (0.38 g, 10 mmol) in THF (10 mL) at −78° C. during a period of 30 min. The resulting mixture was stirred at −78° C. for 30 min, then warmed up to RT for 3 h. TLC showed the starting material was consumed completely. Small amount of MeOH/EA (1/1) mixture was added slowly to the reaction mixture to quench the excess LAH. The reaction mixture was filtered and the solid was washed with EA. The combined filtrate was concentrated to give the crude product scheme 36 compound 3 (1 g, 58.8%) which was used in the next step immediately without further purification.

Scheme 36 compound 3 (1 g, 3.92 mmol) and MnO$_2$ (4 g, 46.0 mmol) were mixed in DCM (100 mL) in a flask. The mixture was stirred at RT for 16 h. TLC showed the reaction was completely. The MnO$_2$ was filtered off and the filtrate was concentrated to give scheme 36 compound 4 (0.6 g, yield: 60.6%) as a yellow solid which was used in the next step immediately without further purification.

Scheme 36 compound 4 (0.40 g, 1.58 mmol) was dissolved in anhydrous DMF (10 mL) along with scheme 36 compound 6 (0.47 g, 3.16 mmol) and Cs$_2$CO$_3$ (1.02 g, 3.14 mmol). The mixture was stirred at 100° C. overnight. TLC showed the starting material was consumed completely. The mixture was quenched with H$_2$O and extracted with EA. The organic layer was washed with saturated aqueous NaCl, dried over anhydrous Na$_2$SO$_4$ and concentrated to give a crude residue which was purified by silica gel column chromatography (PE/EA=5:1) yielding scheme 36 compound 5 (100 mg, 17.9%) as a yellow solid.

Scheme 36 compound 5 (100 mg, 0.283 mmol) and Amine 01 (88 mg, 0.425 mmol) were dissolved in anhydrous dioxane (6 mL). To this mixture was added NaOt-Bu (54 mg, 0.566 mmol), X-PHOS (27 mg, 0.0566 mmol), Pd$_2$(dba)$_3$ (26 mg, 0.028 mmol) under nitrogen atmosphere. The reaction mixture was stirred at 80° C. under nitrogen atmosphere overnight. After TLC showed the starting material was consumed completely, the mixture was quenched with water and extracted with EA. The organic layer was washed with brine and dried over anhydrous Na$_2$SO$_4$, filtered and concentrated to give a residue which was purified by prep-HPLC to give Compound 16 (70 mg, yield: 46.9%) as a pale yellow solid. $^1$H NMR (CDCl$_3$, 400 MHz): δ 8.35 (s, 1H, ArH), 8.06 (br, 1H, NH), 7.86 (s, 1H, ArH), 7.67-7.65 (dd, J$^1$=2.8 Hz, J$^2$=0.8 Hz, 3H, ArH), 7.64-7.39 (m, 3H, ArH), 7.36-7.34 (m, 1H, ArH), 7.33-7.21 (m, 2H, ArH), 4.09 (t, J=6.2 Hz, 2H, 2CH$_2$), 3.06-3.00 (m, 4H, 2CH$_2$), 2.89 (t, J=6.0 Hz, 2H, CH$_2$), 3.41 (q, J=7.2 Hz, 4H, 2CH$_2$), 2.37 (s, 3H, CH$_3$), 2.20 (t, J=10.8 Hz, 2H, CH$_2$), 1.14 (d, J=10.8 Hz, 2H, CH$_2$), 1.08 (t, J=7.0 Hz, 6H, 2CH$_3$). MS [ESI, MH$^+$]:=527.

Example 48

Synthesis of Compound 17

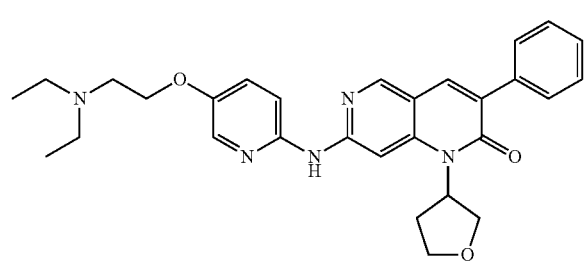

Compound 17

Compound 17: 7-((5-(2-(diethylamino)ethoxy)pyridin-2-yl)amino)-3-phenyl-1-(tetrahydrofuran-3-yl)-1,6-naphthyridin-2(1H)-one was synthesized in the similar manner to Compound 16 using tetrahydro-furan-3-ylamine instead of 1-methyl-piperidin-4-ylamine. $^1$HNMR (CDCl$_3$, 400 MHz): δ 8.49 (s, 1H, ArH), 8.03 (d, J=12.4 Hz, 2H, ArH), 7.83 (br, 1H, NH), 7.70-7.65 (m, 2H, 2ArH), 7.46-7.7.28 (m, 7H, ArH), 6.34 (br, 1H, CH), 4.52-4.49 (m, 1H, CH), 4.24 (t, J=7.0 Hz, 3H, CH$_3$), 4.06 (t, J=9.6 Hz, 1H, CH), 3.93-3.66 (m, 1H, CH), 3.04 (s, 2H, CH$_2$), 2.82 (d, J=7.2 Hz, 4H, 2CH$_2$), 2.57-2.37 (m, 1H, CH), 2.57-2.37 (m, 1H, CH), 1.19 (t, J=6.8 Hz, 6H, 2CH$_3$). MS [ESI, MH$^+$]:=500.2.

Example 49

Synthesis of Compound 58

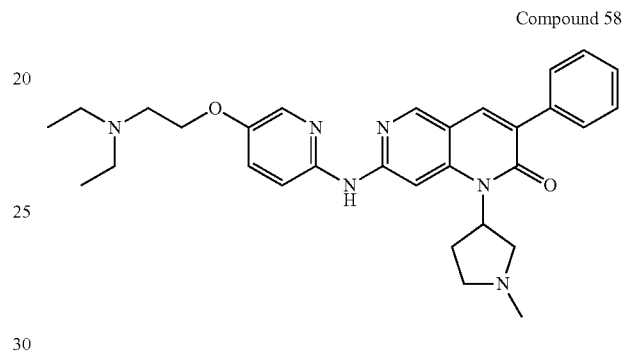

Compound 58

Compound 58: 7-((5-(2-(diethylamino)ethoxy)pyridin-2-yl)amino)-1-(1-methylpyrrolidin-3-yl)-3-phenyl-1,6-naphthyridin-2(1H)-one was synthesized in the similar manner to Compound 16 using 1-methyl-pyrrolidin-3-ylamine instead of 1-methyl-piperidin-4-ylamine. $^1$H NMR (400 MHz, CDCl$_3$): δ 8.47 (s, 1H, ArH); 8.24 (s, 1H, ArH); 8.03 (d, J=1.4 Hz, 1H, ArH); 7.73 (d, J=4.6 Hz, 1H, ArH); 7.64-7.67 (m, 3H, ArH); 7.35-7.44 (m, 4H, ArH); 7.29 (d, J=3.0 Hz, 1H, ArH); 6.25 (br, 1H, CH); 4.09 (t, J=6.2 Hz, 2H, CH$_2$); 3.18-3.26 (m, 2H, CH$_2$); 2.89 (t, J=6.2 Hz, CH$_2$); 2.63-2.69 (q, J=10.6 Hz, 5H, CH$_2$); 2.53(br, 1H, CH$_2$); 2.43 (s, 4H, CH$_3$, CH$_2$); 2.28 (br 1H, CH$_2$); 1.09 (t, J=7.2 Hz, 6H, CH$_3$).

Example 50

Synthesis of Compound 55

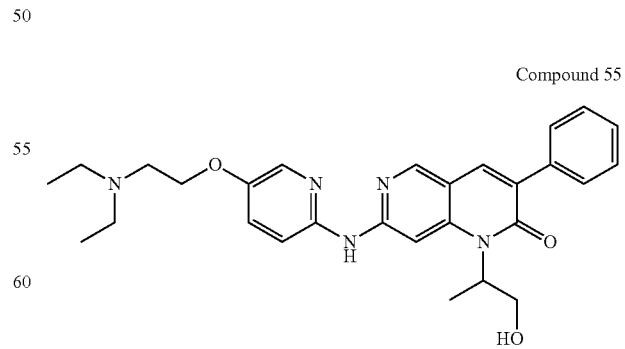

Compound 55

Compound 55: 7-((5-(2-(diethylamino)ethoxy)pyridin-2-yl)amino)-1-(1-hydroxypropan-2-yl)-3-phenyl-1,6-naphthyridin-2(1H)-one was synthesized as shown in Scheme 37.

Scheme 37

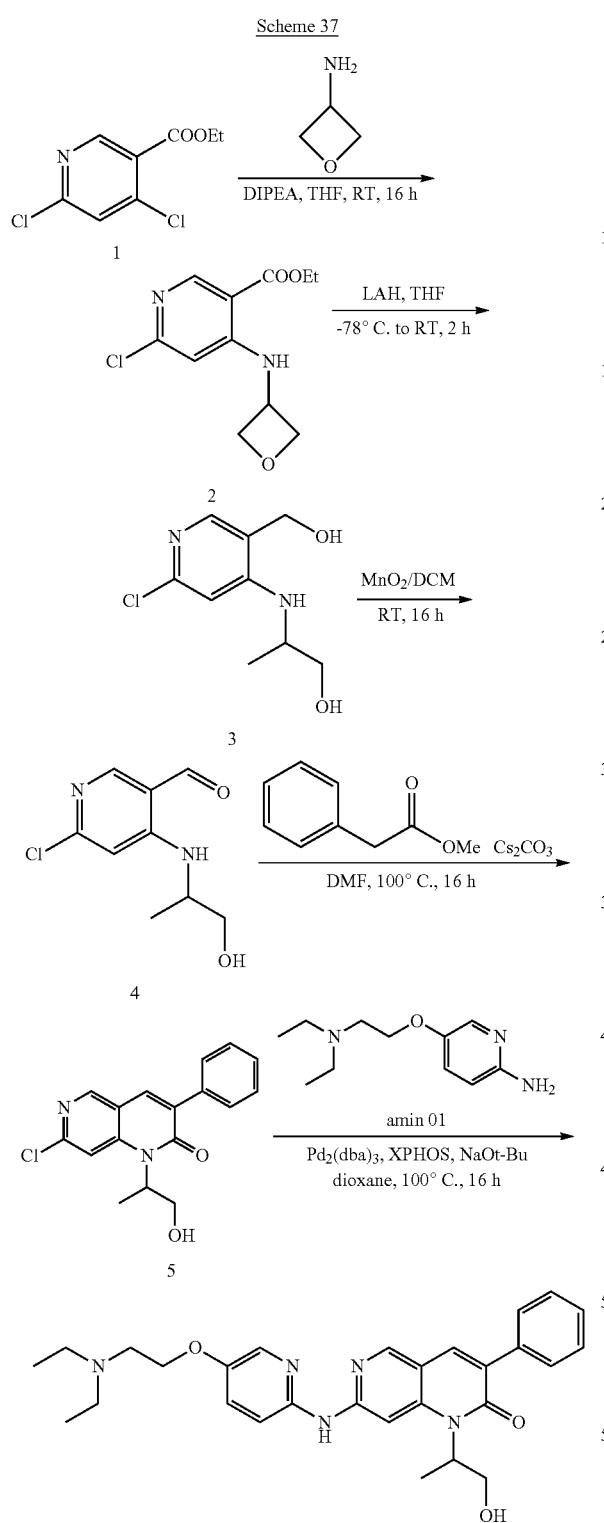

To a solution of scheme 37 compound 1 (2 g, 9.09 mmol) in THF (60 mL) was added amine (3.3 g, 45.2 mmol) and Et₃N (4.5 g, 44.5 mmol). The mixture was stirred at RT for 16 h. TLC showed the starting material was consumed completely. After the solvent was removed, the mixture was extracted with EA (100 mL), washed with water and brine, dried over Na₂SO₄, concentrated to give a crude product which was purified by silica gel column chromatography (PE/EA=10/1 to 5/1) to give scheme 37 compound 2 (2 g, yield: 86.2%) as a pale yellow solid.

The solution of scheme 37 compound 2 (2 g, 7.01 mmol) in THF (10 mL) was added drop-wise to a suspension of LAH (0.42 g, 11 mol) in THF (10 mL) at −78° C. during a period of 30 min. The resulting mixture was stirred at −78° C. for 30 min, then warmed up to RT for 1 h. TLC showed the starting material was consumed completely. Small amount of MeOH/EA (1/1) mixture was added slowly to the reaction mixture to quench the excess LAH. The reaction mixture was filtered and the solid was washed with EA. The combined filtrate was concentrated to give the crude product scheme 37 compound 3 (3 g) which was used in the next step immediately without further purification.

Scheme 37 compound 3 (3 g, 13.9 mmol) was dissolved in DCM (100 mL) along with MnO₂ (12.2 g, 140 m mol). The mixture was stirred at RT for 16 h. TLC showed the reaction was completed. The MnO₂ by-product was filtered off and the filtrate was concentrated to give scheme 37 compound 4 (2 g, yield: 67.8%) as a yellow solid which was used in the next step immediately without further purification.

Scheme 37 compound 4 (2 g, 9.30 mmol) was dissolved in anhydrous DMF (50 mL) along with scheme 37 compound 6 (3.1 g, 20.6 mmol) and Cs₂CO₃ (6.04 g, 18.5 mmol). The mixture was stirred at 100° C. overnight. TLC showed the starting material was consumed completely. The mixture was quenched with H₂O and extracted with EA. The organic layer was washed with saturated aqueous NaCl, dried over anhydrous Na₂SO₄ and concentrated to give a crude residue which was purified by silica gel column chromatography to give scheme 37 compound 5 (0.35 g, yield: 12%) as a yellow solid.

Scheme 37 compound 5 (330 mg, 1.05 mmol) and Amine 01 (280 mg, 134 mmol) were dissolved in anhydrous dioxane (20 mL). To this mixture was added NaOt-Bu (200 mg, 0.566 mmol), X-PHOS (100 mg, 0.2 mmol), Pd₂(dba)₃ (96 mg, 0.11 mmol) under nitrogen atmosphere. The reaction mixture was stirred at 80° C. under nitrogen atmosphere overnight. After TLC showed the starting material was consumed completely, the mixture was quenched with water and extracted with EA. The organic layer was washed with brine and dried over anhydrous Na₂SO₄, filtered and concentrated to give a residue which was purified by silica gel chromatography (DCM/MeOH=200/1 to 80/1) to give Compound 2 (50 mg, yield: 9.8%) as a pale yellow solid. ¹H NMR (CDCl₃, 400 MHz): δ 8.45 (s, 1H, ArH), 8.13 (br, 1H, NH), 8.12 (d, J=2.4 Hz, 1H, ArH), 8.04 (d, J=2.8 Hz, 1H, ArH), 7.75 (s, 1H, ArH), 7.69-7.64 (m, 3H, ArH), 7.46-7.42 (m, 2H, ArH), 7.69-7.36 (m, 1H, ArH), 7.28-7.27 (m, 1H, ArH), 7.14 (br, 1H, ArH), 4.33 (s, 1H, CH), 4.30-4.28 (br, 1H, OH), 4.13-4.07 (m, 3H, 3CH), 2.94 (t, J=6.0 Hz, 2H, CH₂), 2.54 (q, J=6.8 Hz, 4H, 2CH₂), 1.65 (d, J=7.2 Hz, 3H, CH₃), 1.12 (t, J=7.2 Hz, 6H, 2CH₃). MS [ESI, MH⁺]:=488.

Example 51

Synthesis of Compound 56

Compound 56

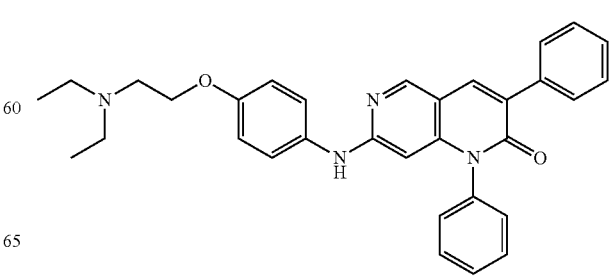

Compound 56: 7-((5-(2-(diethylamino)ethoxy)pyridin-2-yl)amino)-1-(1-methylpyrrolidin-3-yl)-3-phenyl-1,6-naphthyridin-2(1H)-one was synthesized as shown in Scheme 38.

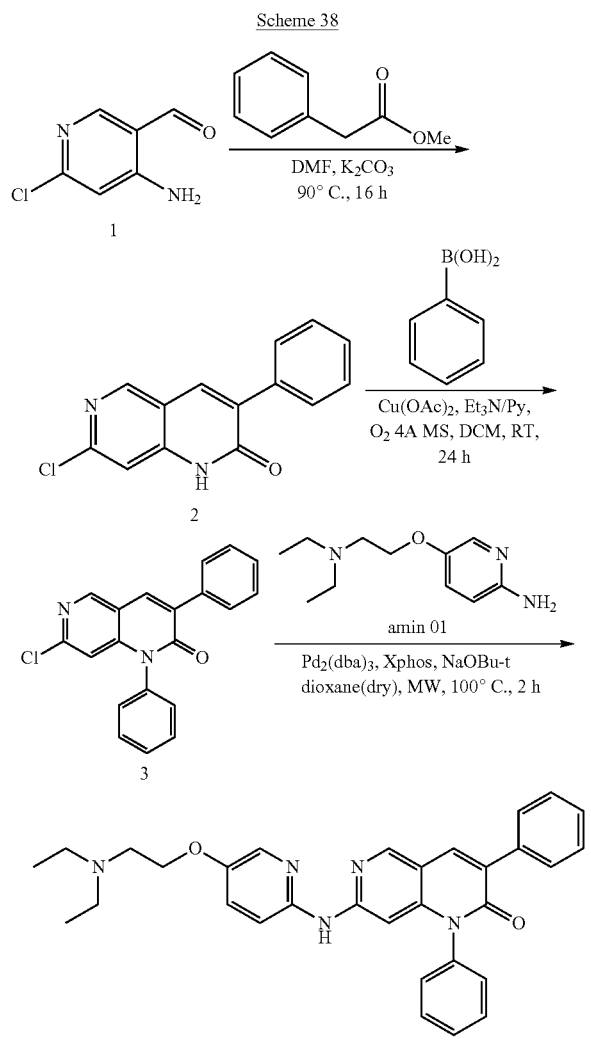

Scheme 38 compound 1 in Scheme 94 was synthesized according to the procedure as for Compound 18.

Scheme 38 compound 1 (100 mg, 0.64 mmol) was dissolved in anhydrous DMF (100 mL) along with phenylacetic acid methyl ester (157 mg, 0.96 mmol) and K₂CO₃ (265 mg, 1.92 mmol). The mixture was stirred at 100° C. for 16 h. It was then quenched with H₂O and extracted with ethyl acetate. The organic layer was washed with brine and dried over Na₂SO₄, concentrated to give a residue that was purified by silica gel column chromatography (PE/EA=4/1) to give scheme 38 compound 2 (90 mg, yield: 54.7%) as a yellow solid.

To a solution of scheme 38 compound 2 (1 g, 3.9 mmol) and the boronic acid (1.43 g, 11.69 mmol) was added Cu(OAC)₂ (1.8 g, 9.7 mmol), Et₃N (2.4 mL), pyridine (1.6 mL), and 4 A molecular sieve. The reaction mixture was heated between 25° C. to 30° C. and stirred for 24 h. The mixture was then evaporated in vacuo and the remaining residue was purified by silica gel column chromatography (PE/EA=10/1 to 1/1) to give scheme 38 compound 7 (1 g, 77.2%) as a yellow solid.

Scheme 38 compound 3 (300 mg, 0.90 mmol) and Amine 01 (208 mg, 0.99 mmol) were dissolved in anhydrous dioxane (5 mL). To this dioxane solution were added NaOt-Bu (173 mg, 1.80 mmol), X-PHOS (86 mg, 0.18 mmol), Pd₂(dba)₃ (82.4 mg, 0.09 mmol) under nitrogen atmosphere. The mixture was sealed and heated under microwave at 100° C. for 2 h. The reaction mixture was then quenched with water and extracted with EtOAc. The organic layer was washed with brine, dried over Na₂SO₄ and concentrated to give a residue which was purified by prep-HPLC to give Compound 56 (203 mg, yield: 52%) as a yellow solid. $^1$H NMR (400 MHz, CDCl₃): δ 8.54 (s, 1H, NH), 7.90 (s, 1H, ArH), 7.79-7.75 (m, 3H, ArH), 7.65 (t, J=7.4 Hz, 2H, ArH), 7.57 (t, J=7.2 Hz, 1H, ArH), 7.44 (t, J=7.4 Hz, 2H, ArH), 7.39-7.36 (m, 3H, NH and ArH), 7.32 (s, 1H, ArH), 7.24 (d, J=8 Hz, 1H ArH), 7.20 (t, J=4.6 Hz, 1H, ArH), 6.89 (s, 1H, CH), 4.07 (s, 1H, CH₂), 2.9 (s, 2H, CH₂), 2.7 (s, 4H, 2CH₂), 1.12 (t, J=7 Hz, 6H, 2CH₃). MS [ESI, MH⁺]: 505.2.

Example 52

Synthesis of Compound 18

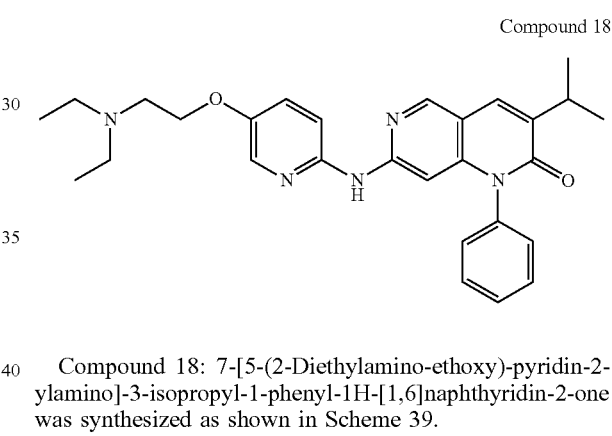

Compound 18: 7-[5-(2-Diethylamino-ethoxy)-pyridin-2-ylamino]-3-isopropyl-1-phenyl-1H-[1,6]naphthyridin-2-one was synthesized as shown in Scheme 39.

Scheme 39

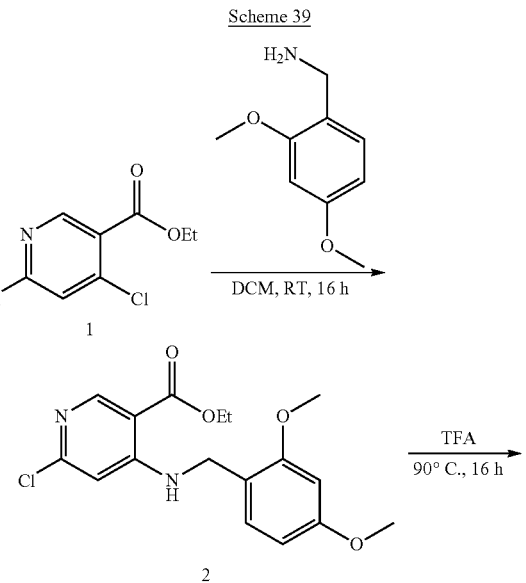

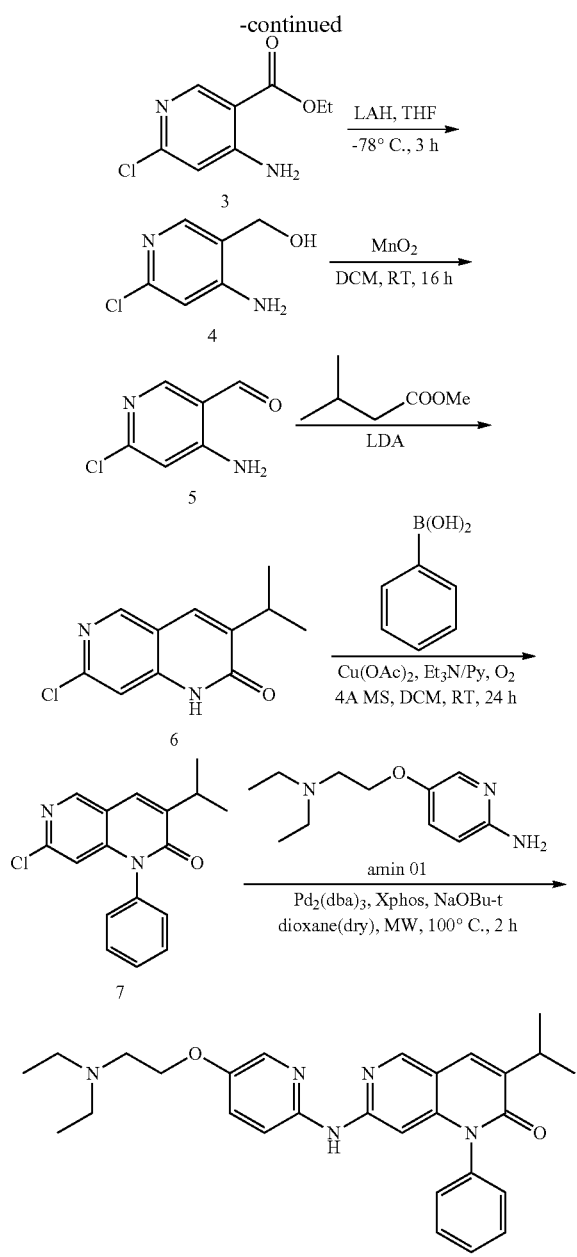

As in scheme 39, to a solution of scheme 39 compound 1 (10 g, 45.7 mmol) and Et₃N (5.5 g, 54.8 mmol) in MeCN (150 mL) was added 2,4-Dimethoxy-benzylamine (8 g, 47.9 mmol) at 0° C. over 0.5 h. The mixture was stirred at RT for 16 h. The mixture was then extracted with EtOAc (300 mL), washed with water and brine, dried over Na₂SO₄, concentrated to give scheme 39 compound 2 (15 g, 93.2%) as a yellow solid, which was used in the next step immediately without further purification.

A mixture of scheme 39 compound 2 and TFA was heated to reflux for 16 h. After the solvent was removed to give a residue that was neutralized with saturated NaHCO₃ to PH=7-8, extracted with EtOAc (300 mL), washed with water and brine, dried over Na₂SO₄, and concentrated to give a residue that was purified by column chromatography (PE/EtOAc=4/1) to give scheme 39 compound 3 (1.2 g, 69.8%) as a white solid.

LAH (456 mg, 12.0 mmol) was suspended in THF (20 mL), cooled to −78° C. in a flask. The solution of scheme 39 compound 3 (1.2 g 6.0 mmol) in THF (30 mL) was added dropwise into the flask. The resulting mixture was stirred at −78° C. for 3 h. After the reaction mixture warming up to RT, TLC showed the starting material was consumed completely. Small amount MeOH/ethyl acetate (1/1) mixture was added slowly to destroy the excess LAH. The formed solid was filtered and washed with ethyl acetate, the filtrate was concentrated to give a crude residue which was purified by silica gel column chromatography (PE/EA=10/1 to 5/1) to give scheme 39 compound 4 (600 mg, yield: 62.9%) as a pale yellow solid.

Scheme 38 compound 4 (600 mg, 3.77 mmol) was dissolved in DCM (50 mL) along with MnO₂ (3.32 g, 37.7 mmol). The mixture was stirred at RT for 5 h. TLC showed the reaction was completely. The MnO₂ by-product was filtered off and the filtrate was concentrated to give scheme 39 compound 5 (3.7 g, yield: 86.5%) as a white solid.

Scheme compound 5 (100 mg, 0.64 mmol) was dissolved in anhydrous DMF (100 mL) along with scheme 39 compound 5A (157 mg, 0.96 mmol) and K₂CO₃ (265 mg, 1.92 mmol). The mixture was stirred at 100° C. for 16 h. The mixture was then quenched with H₂O and extracted with ethyl acetate. The organic layer was washed with brine and dried over Na₂SO₄, concentrated to give a residue that was purified by silica gel column chromatography (PE/EA=4/1) to give scheme 39 compound 6 (90 mg, yield: 54.7%) as a yellow solid.

To a THF solution of scheme 39 compound 6 (370 mg, 1.66 mmol) and benzene boronic acid (305 mg, 2.5 mmol) was added Cu(OAC)₂ (604 mg, 3.32 mmol), Et₃N (0.46 mL), pyridine (0.27 mL), and 4 A molecular sieve. The reaction mixture was heated between 25° C. to 30° C. and stirred for 24 h. The mixture was then evaporated in vacuo, and the remaining residue was purified by silica gel column chromatography (PE/EA=10/1 to 1/1) to give scheme 39 compound 7 (348 mg, yield: 70.2%) as a yellow solid.

Scheme 38 compound 7 (248 mg, 0.83 mmol) and Amine 01 (192 mg, 0.913 mmol) was dissolved in anhydrous dioxane (5 mL) in a microwave heating tube. To this tube were added NaOt-Bu (160 mg, 1.66 mmol), X-PHOS (80 mg, 0.166 mmol), Pd₂(dba)₃ (76 mg, 0.083 mmol) under nitrogen atmosphere. The tube was sealed and heated under microwave at 100° C. for 2 h. The mixture was then quenched with water and extracted with EtOAc. The organic layer was washed with brine, dried over Na₂SO₄ and concentrated to give a residue that was purified by prep-HPLC to give Compound 18 (203 mg, yield: 52%) as a yellow solid. ¹H NMR (400 MHz, CDCl₃): δ 8.42 (s, 1H, ArH), 7.72 (s, 1H, ArH), 7.71-7.58 (m, 2H, ArH), 7.53 (t, J=7.2 Hz, 2H, ArH), 7.29 (d, J=7.6 Hz, 2H, ArH), 7.25 (t, J=6.2 Hz, 1H, ArH), 7.18-7.13 (m, 2H, CH and ArH), 6.77 (s, 1H, ArH), 4.05 (s, 2H, CH₂), 3.27-3.20 (m, 1H, CH), 2.88 (s, 2H, CH₂), 2.68(s, 4H, 2CH₂), 1.28 (d, J=6.8 Hz, 6H, 2CH₃), 1.10 (t, J=6.2 Hz, 6H, 2CH₃). MS [ESI, MH⁺]: 471.3.

Example 53

Synthesis of Compound 92

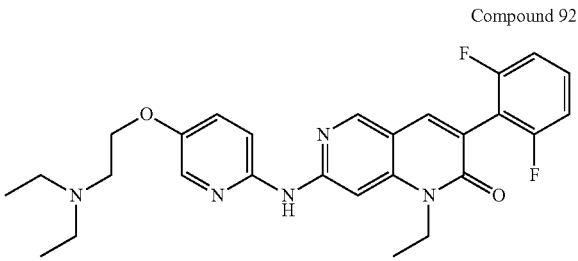 [SMILES: CCN(CC)CCOc1ccc(Nc2cc3c(cn2)cc(-c2c(F)cccc2F)c(=O)n3CC)nc1]

Compound 92

Compound 92, 7-((5-(2-(diethylamino)ethoxy)pyridin-2-yl)amino)-3-(2,6-difluorophenyl)-1-ethyl-1,6-naphthyridin-2(1H)-one was synthesized following the general procedure depicted in Scheme 40 using 5-(2-diethylaminoethoxy)-pyridin-2-ylamine in the final cross-coupling reaction. The preparation of Scheme 40 aldehyde 1 was described in Scheme 1 (compound 6) and the preparation of 5-(2-diethylaminoethoxy)-pyridin-2-ylamine was described in Scheme 2.

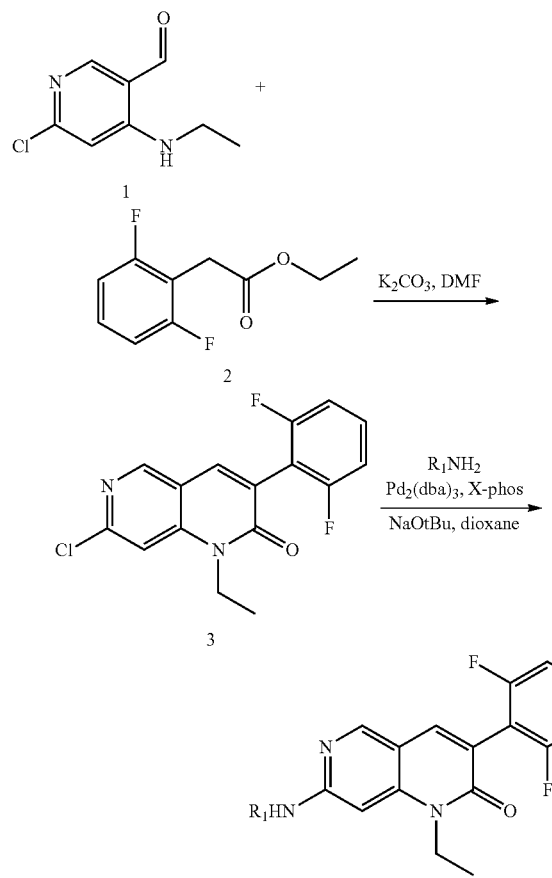

A mixture of Scheme 40 compound 1 (4.5 g, 24.45 mmol), Scheme 40 compound 2 (7.3 g, 36.70 mmol) and K$_2$CO$_3$ (10.2 g, 73.35 mmol) in dry DMF (100 mL) was heated to 100° C. under nitrogen atmosphere for 48 h. After TLC showed the starting material was completely consumed, the reaction mixture was cooled to RT and diluted with EtOAc (100 mL), washed with water (2×30 mL) and brine (20 mL) then dried over Na$_2$SO$_4$ and concentrated. The resulting residue was purified by flash chromatography on silica gel (eluting with petroleum ether/EtOAc 100/0 gradually increasing to 70/30) to give Scheme 40 compound 3 (3.0 g, 38%) as a light yellow solid. $^1$H NMR (400 MHz, DMSO-d$_6$): δ 8.81 (s, 1H), 8.28 (s, 1H), 7.79 (s, 1H), 7.61-7.46 (m, 1H), 7.24 (t, J=8.0 Hz, 2H), 4.29 (m, 2H), 1.22 (t, J=7.0 Hz, 5H). MS [ESI, MH$^+$]=321.02.

Scheme 40 compound 3 (200 mg, 0.625 mmol) and 5-(2-diethylaminoethoxy)-pyridin-2-ylamine (156 mg, 0.748 mmol) were dissolved in anhydrous dioxane (10 mL). To this mixture was added tBuONa (180 mg, 1.870 mmol), X-PHOS (72 mg, 0.124 mmol) and Pd$_2$(dba)$_3$ (57 mg, 0.062 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$, filtered and concentrated to give a residue which was purified by flash chromatography on silica gel (eluting with CH$_2$Cl$_2$/MeOH 100/0 gradually increasing to 90/10) to give Compound 92 (75 mg, yield: 24%) as a pale yellow solid. $^1$H NMR (400 MHz, CD$_3$OD): δ 8.56 (d, J=1.4 Hz, 1H), 8.04 (t, J=2.3 Hz, 2H), 7.93 (s, 1H), 7.49-7.36 (m, 3H), 7.06 (t, J=7.8 Hz, 2H), 4.35 (q, J=7.1 Hz, 2H), 4.17 (td, J=5.6, 1.8 Hz, 2H), 2.98 (d, J=5.5 Hz, 2H), 2.73 (m, 4H), 1.40 (q, J=6.6, 6.0 Hz, 3H), 1.13 (td, J=7.2, 1.5 Hz, 6H). MS [ESI, MH$^+$]=494.24.

Synthesis of Compound 96

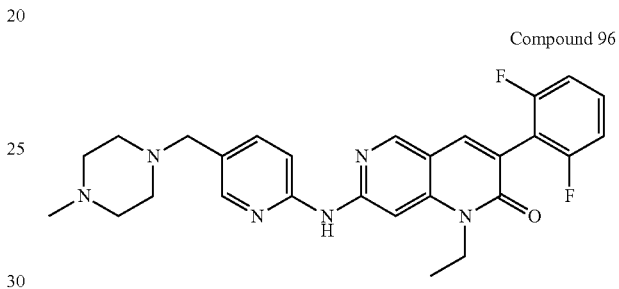

Compound 96

Compound 96, 3-(2,6-difluorophenyl)-1-ethyl-7-((5-((4-methylpiperazin-1-yl)methyl)pyridin-2-yl)amino)-1,6-naphthyridin-2(1H)-one was synthesized in a similar manner as Compound 92 using N$^5$-methyl-N$^5$-(1-methylpiperidin-4-yl)pyridine-2,5-diamine in the cross-coupling step, which was synthesized as shown in Scheme 44.

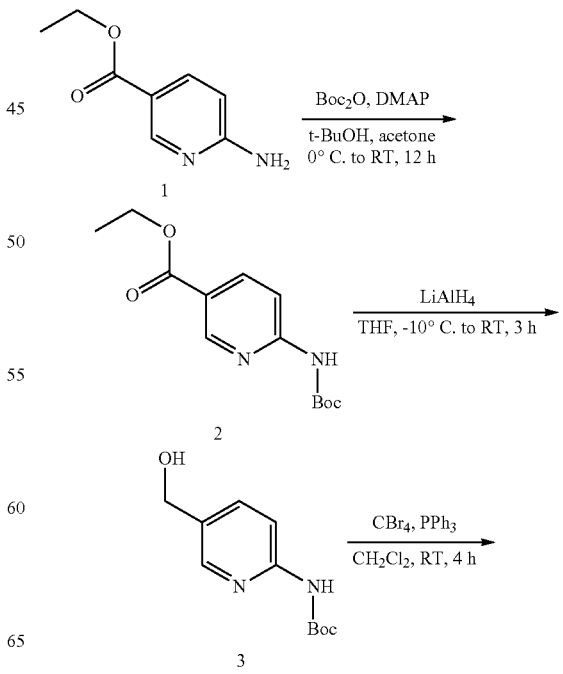

-continued

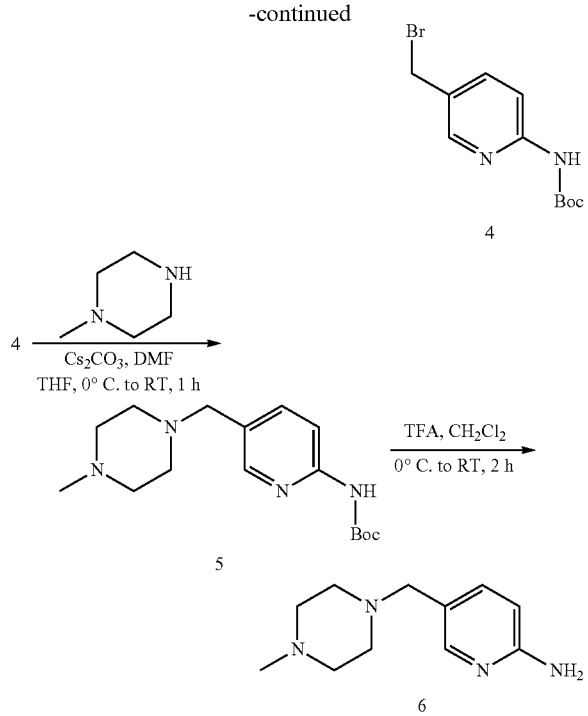

To a cooled (0° C.) solution of Scheme 44 compound 1 (2.0 g, 12.00 mmol) in dry tBuOH (20 mL) and acetone (10 mL) were added DMAP (19 mg, 0.15 mmol) and (Boc)$_2$O (5.2 mL, 24.0 mmol) and the reaction mixture was stirred at RT for 12 h after which time the solvent was evaporated. The residue was diluted with EtOAc (20 mL), washed with water (2×10 mL) and brine (10 mL) then dried over Na$_2$SO$_4$ and concentrated to give a residue which was purified by flash chromatography on silica gel (eluting with petroleum ether/EtOAc 100/0 gradually increasing to 70/30) to give Scheme 44 compound 2 (1.7 g, 45%) as an off-white solid. MS [ESI, MH$^+$]=267.2.

To a cooled (−10° C.) solution of Scheme 44 compound 2 (1.7 g, 6.4 mmol) in dry THF (200 mL) was added LiAlH$_4$ (305 mg, 8.5 mmol) portion wise over a period of 30 min and the reaction mixture was slowly warmed to RT over 3 h. After TLC showed the starting material was completely consumed, the reaction mixture was quenched with saturated ammonium chloride (10 mL), passed through a pad of celite and washed with EtOAc (30 mL). The filtrate was washed with water (2×5 mL) and brine (2×5 mL), dried over Na$_2$SO$_4$ and concentrated to give a residue which was purified by flash chromatography on silica gel (eluting with petroleum ether/EtOAc 100/0 gradually increasing to 60/40) to give Scheme 44 compound 3 (900 mg, 64%) as an off-white solid. MS [ESI, MH$^+$]=225.2.

To a cooled (0° C.) solution of Scheme 44 compound 3 (900 mg, 4.0 mmol) in dry CH$_2$Cl$_2$ (20 mL) were added TPP (1.1 g, 4.2 mmol) and CBr$_4$ (2.2 g, 6.5 mmol) and the reaction mixture was stirred at RT for 4 h. After TLC showed the starting material was completely consumed, the reaction mixture was diluted with CH$_2$Cl$_2$ (20 mL), washed with water (2×10 mL) and brine (10 mL), dried over Na$_2$SO$_4$ and concentrated to give a residue which was purified by flash chromatography on silica gel (eluting with petroleum ether/EtOAc 100/0 gradually increasing to 90/10) to give Scheme 44 compound 4 (800 mg, 72%) as a colorless liquid. MS [ESI, MH$^+$]=287.0.

To a cooled (0° C.) solution of Scheme 44 compound 4 (800 mg, 2.8 mmol) and 1-methylpiperazine (307 mg, 3.0 mmol) in dry DMF (8 mL) was added Cs$_2$CO$_3$ (1.8 g, 5.6 mmol) and the reaction mixture was stirred at RT for 1 h. After TLC showed the starting material was completely consumed, the reaction mixture was diluted with water (20 mL) and extracted with EtOAc (30 mL). The organic layer was washed with water (10 mL) and brine (10 mL) then dried over Na$_2$SO$_4$ and concentrated to give a residue which was purified by flash chromatography on silica gel (eluting with CH$_2$Cl$_2$/MeOH 100/0 gradually increasing to 95/5) to give Scheme 44 compound 5 (600 mg, 70%) as a brown solid. MS [ESI, MH$^+$]=307.2.

To a cooled (0° C.) solution of Scheme 44 compound 5 (600 mg, 1.9 mmol) in dry CH$_2$Cl$_2$ (8 mL) was added TFA (4 mL) and the reaction mixture was stirred at RT for 2 h. The reaction mixture was concentrated under reduced pressure to give Scheme 44 compound 6 (200 mg, 49%) as a brown solid. $^1$H NMR (400 MHz, DMSO-d$_6$): δ 8.09 (s, 2H), 7.85 (dd, J=6.9, 2.6 Hz, 2H), 6.98 (d, J=9.6 Hz, 1H), 3.50 (s, 2H), 2.97 (s, 4H), 2.79 (s, 3H), 2.35 (d, J=13.4 Hz, 4H). MS [ESI, MH$^+$]=207.1.

Scheme 40 compound 3 (200 mg, 0.625 mmol) and Scheme 44 compound 6 (154 mg, 0.750 mmol) were dissolved in anhydrous dioxane (10 mL). To this mixture was added tBuONa (180 mg, 1.870 mmol), X-PHOS (72 mg, 0.124 mmol) and Pd$_2$(dba)$_3$ (57 mg, 0.062 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$, filtered and concentrated to give a residue which was purified by flash chromatography on silica gel (eluting with CH$_2$Cl$_2$/MeOH 100/0 gradually increasing to 90/10) to give Compound 96 (35 mg, yield: 11%) as a yellow solid. $^1$H NMR (400 MHz, CDCl$_3$): δ 8.48 (s, 1H), 8.29-8.23 (m, 2H), 7.74 (s, 1H), 7.63 (dd, J=8.5, 2.3 Hz, 1H), 7.53 (s, 1H), 7.37-7.30 (m, 1H), 7.09 (d, J=8.4 Hz, 1H), 6.99 (t, J=7.8 Hz, 2H), 4.39 (m, 2H), 3.49 (s, 2H), 2.53 (s, 8H), 2.34 (s, 3H), 1.45 (t, J=7.1 Hz, 3H). MS [ESI, MH$^+$]=491.16.

Example 54

Synthesis of Compound 93

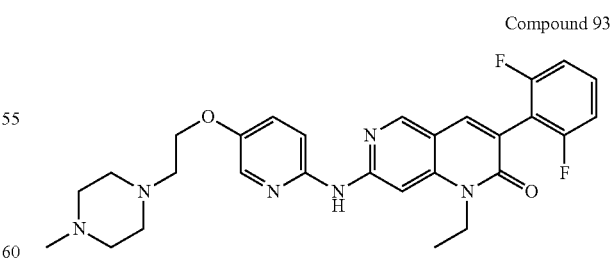

Compound 93

Compound 93, 3-(2,6-difluorophenyl)-1-ethyl-7-((5-(2-(4-methylpiperazin-1-yl)ethoxy)pyridin-2-yl)amino)-1,6-naphthyridin-2(1H)-one was synthesized in a similar manner as Compound 92 using 5-(2-(4-methylpiperazin-1-yl)ethoxy)pyridin-2-amine in the cross-coupling step, which was synthesized as shown in Scheme 41.

Scheme 41

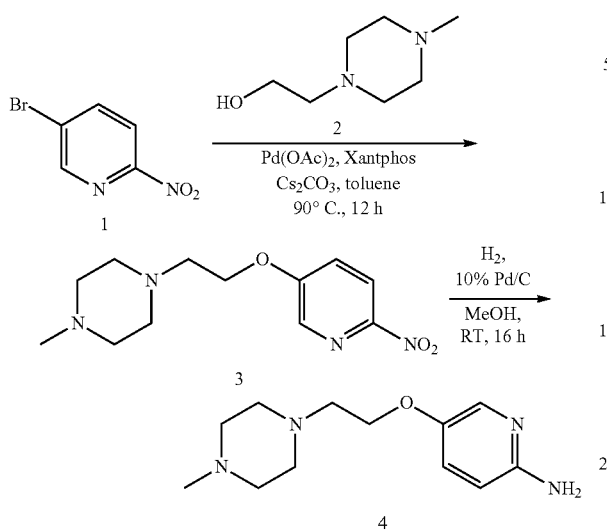

To mixture of Scheme 41 compound 1 (2.00 g, 9.80 mmol), Scheme 41 compound 2 (1.41 g, 9.85 mmol), $Cs_2CO_3$ (9.60 g, 29.55 mmol) and Xantphos (569 mg, 0.98 mmol) in dry toluene (20 mL) was added $Pd(OAc)_2$ (221 mg, 0.98 mmol) and the reaction mixture was heated to 90° C. for 12 h. After TLC showed the starting material was completely consumed, the reaction mixture was cooled to RT, passed through a pad of celite and washed with EtOAc. The filtrate was washed with water and brine, dried over $Na_2SO_4$ and concentrated to give a residue which was purified by flash chromatography on silica gel (eluting with $CH_2Cl_2$/MeOH 100/0 gradually increasing to 95/5) to give Scheme 41 compound 3 (1.10 g, 33%) as a pale yellow solid. MS [ESI, $MH^+$]=267.13.

Scheme 41 Compound 3 (1.0 g, 3.75 mmol) in MeOH (10 mL) was treated with 10% Pd/C (100 mg) and kept under $H_2$ atmosphere (balloon pressure) at RT for 16 h. After TLC showed the starting material was completely consumed, the mixture was passed through a pad of celite. The filtrate was evaporated to give a residue which was purified by flash chromatography on silica gel (eluting with $CH_2Cl_2$/MeOH 100/0 gradually increasing to 90/10) to give Scheme 41 Compound 4 (800 mg, 90%) as a dark solid. $^1$H NMR (400 MHz, DMSO-$d_6$): δ 7.63 (d, J=3.0 Hz, 1H), 7.11 (dd, J=9.0, 3.1 Hz, 1H), 6.40 (d, J=8.8 Hz, 1H), 5.47 (s, 2H), 3.96 (t, J=5.8 Hz, 2H), 2.62 (t, J=5.8 Hz, 2H), 2.51-2.28 (m, 8H), 2.20 (s, 3H). MS [ESI, $MH^+$]=237.3.

Scheme 40 compound 3 (200 mg, 0.625 mmol) and Scheme 41 compound 4 (177 mg, 0.748 mmol) were dissolved in anhydrous dioxane (10 mL). To this mixture was added tBuONa (180 mg, 1.870 mmol), X-PHOS (72 mg, 0.124 mmol) and $Pd_2(dba)_3$ (57 mg, 0.062 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$, filtered and concentrated to give a residue which was purified by flash chromatography on silica gel (eluting with $CH_2Cl_2$/MeOH 100/0 gradually increasing to 90/10) to give Compound 93 (80 mg, yield: 25%) as a pale yellow solid. $^1$H NMR (400 MHz, $CD_3OD$): δ 8.56 (s, 1H), 8.05 (d, J=3.7 Hz, 2H), 7.93 (s, 1H), 7.48-7.37 (m, 2H), 7.06 (t, J=7.8 Hz, 2H), 4.35 (m, 2H), 4.20 (t, J=5.4 Hz, 2H), 2.85 (t, J=5.4 Hz, 2H), 2.62 (s, 8H), 2.32 (s, 3H), 1.40 (t, J=7.1 Hz, 3H). MS [ESI, $MH^+$]=521.32.

Example 55

Synthesis of Compound 94

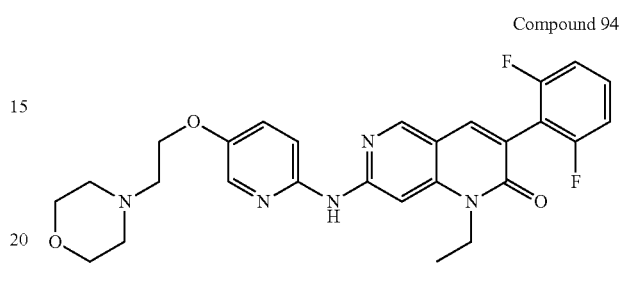

Compound 94

Compound 94, 3-(2,6-difluorophenyl)-1-ethyl-7-((5-(2-morpholinoethoxy)pyridin-2-yl)amino)-1,6-naphthyridin-2 (1H)-one was synthesized in a similar manner as Compound 92 using 5-(2-morpholinoethoxy)pyridin-2-amine in the cross-coupling step, which was synthesized as shown in Scheme 42.

Scheme 42

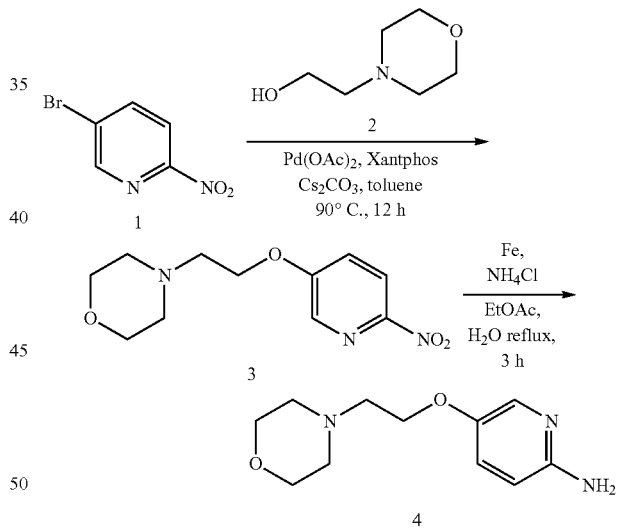

To a mixture of Scheme 42 compound 1 (3.0 g, 14.77 mmol), Scheme 42 compound 2 (1.9 g, 14.77 mmol), $Cs_2CO_3$ (14.4 g, 44.30 mmol) and Xantphos (853 mg, 1.47 mmol) in dry toluene (30 mL) was added $Pd(OAc)_2$ (332 mg, 1.47 mmol) and the reaction mixture was heated to 90° C. for 12 h. After TLC showed the starting material was completely consumed, the reaction mixture was passed through a pad of celite and washed with EtOAc. The filtrate was washed with water and brine, dried over $Na_2SO_4$ and concentrated to give a residue which was purified by flash chromatography on silica gel (eluting with $CH_2Cl_2$/MeOH 100/0 gradually increasing to 90/10) to give Scheme 42 compound 3 (2.0 g, 55%) as a pale yellow solid. MS [ESI, $MH^+$]=254.10.

A mixture of Scheme 42 Compound 3 (2.00 g, 7.0 mmol), iron (1.76 g, 31.6 mmol) and NH₄Cl (4.25 g, 79.0 mmol) in EtOAc/H₂O (40 mL; 1:1) was heated to 80° C. for 3 h. After TLC showed the starting material was completely consumed, the reaction mixture was passed through a pad of celite and washed with EtOAc. The filtrate was concentrated to give a residue which was purified by flash chromatography on silica gel (eluting with CH₂Cl₂/MeOH 100/0 gradually increasing to 80/20) to give Scheme 42 Compound 4 (1.47 g, 83%) as a dark solid. ¹H NMR (400 MHz, DMSO-d₆): δ 7.64 (d, J=3.0 Hz, 1H), 7.11 (dd, J=8.9, 3.1 Hz, 1H), 6.40 (d, J=8.9 Hz, 1H), 5.47 (s, 2H), 3.98 (t, J=5.8 Hz, 2H), 3.57 (t, J=4.5 Hz, 4H), 2.62 (t, J=5.8 Hz, 2H), 2.44 (t, J=4.5 Hz, 4H). MS [ESI, MH⁺]=224.13.

Scheme 40 compound 3 (100 mg, 0.312 mmol) and Scheme 42 compound 4 (83 mg, 0.375 mmol) were dissolved in anhydrous dioxane (5 mL). To this mixture was added tBuONa (90 mg, 0.937 mmol), X-PHOS (36 mg, 0.062 mmol) and Pd₂(dba)₃ (28 mg, 0.031 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na₂SO₄ then filtered and concentrated to give a residue which was purified by flash chromatography on silica gel (eluting with CH₂Cl₂/MeOH 100/0 gradually increasing to 90/10) to give Compound 94 (40 mg, yield: 25%) as a yellow solid. ¹H NMR (400 MHz, CD₃OD): δ 8.56 (s, 1H), 8.07-8.00 (m, 2H), 7.93 (s, 1H), 7.49-7.37 (m, 3H), 7.06 (dd, J=9.0, 6.7 Hz, 2H), 4.35 (m, 2H), 4.20 (t, J=5.4 Hz, 2H), 3.73 (t, J=4.7 Hz, 4H), 2.83 (t, J=5.4 Hz, 2H), 2.62 (t, J=4.6 Hz, 4H), 1.40 (t, J=7.1 Hz, 3H). MS [ESI, MH⁺]=508.23.

Example 56

Synthesis of Compound 95

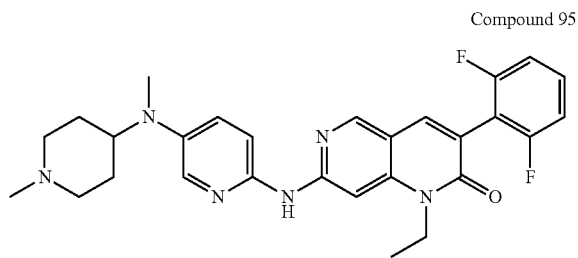 [SMILES: CCn1c(=O)c(-c2c(F)cccc2F)cc2cnc(Nc3ccc(N(C)C4CCN(C)CC4)cn3)cc21]

Compound 95

Compound 95, 3-(2,6-difluorophenyl)-1-ethyl-7-((5-(methyl(1-methylpiperidin-4-yl)amino)pyridin-2-yl)amino)-1,6-naphthyridin-2(1H)-one was synthesized in a similar manner as Compound 92 using N⁵-methyl-N⁵-(1-methylpiperidin-4-yl)pyridine-2,5-diamine in the cross-coupling step, which was synthesized as shown in Scheme 43.

Scheme 43

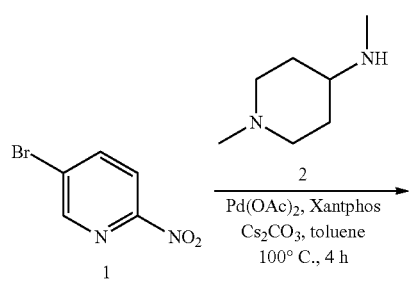

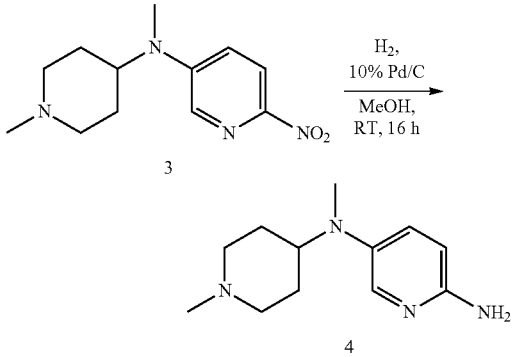

To a mixture of Scheme 43 compound 1 (1.0 g, 4.90 mmol), Scheme 43 compound 2 (630 mg, 4.90 mmol), Cs₂CO₃ (4.8 g, 14.80 mmol) and Xantphos (286 mg, 0.49 mmol) in dry toluene (10 mL) was added Pd(OAc)₂ (111 mg, 0.49 mmol) and the reaction mixture was heated to 100° C. for 4 h. After TLC showed the starting material was completely consumed, the reaction mixture was cooled to RT, passed through a pad of celite and washed with EtOAc. The filtrate was washed with water and brine, dried over Na₂SO₄ and concentrated to give a residue which was purified by flash chromatography on silica gel (eluting with CH₂Cl₂/MeOH 100/0 gradually increasing to 95/5) to give Scheme 43 compound 3 (1.0 g, 83%) as a yellow solid. MS [ESI, MH⁺]=251.15.

Scheme 43 compound 3 (1.0 g, 4.0 mmol) in MeOH (20 mL) was treated with 10% Pd/C (100 mg) and kept under H₂ atmosphere (balloon pressure) at RT for 16h. After TLC showed the starting material was completely consumed, the reaction mixture was passed through a pad of celite. The filtrate was evaporated to give a residue which was purified by flash chromatography on silica gel (eluting with CH₂Cl₂/MeOH 100/0 gradually increasing to 90/10) to give Scheme 43 Compound 4 (700 mg, 62%) as a dark brown solid. ¹H NMR (400 MHz, DMSO-d₆): δ 7.56 (d, J=2.9 Hz, 1H), 7.12 (dd, J=8.8, 2.9 Hz, 1H), 6.38 (d, J=8.8 Hz, 1H), 5.34 (s, 2H), 3.04 (tt, J=10.4, 5.9 Hz, 1H), 2.78 (d, J=10.9 Hz, 2H), 2.56 (s, 3H), 2.14 (s, 3H), 1.89 (m, 2H), 1.53 (td, J=10.5, 9.9, 3.7 Hz, 4H). MS [ESI, MH⁺]=221.16.

Scheme 40 compound 3 (200 mg, 0.625 mmol) and Scheme 43 compound 4 (131 mg, 0.748 mmol) were dissolved in anhydrous dioxane (10 mL). To this mixture was added tBuONa (180 mg, 1.870 mmol), X-PHOS (72 mg, 0.124 mmol) and Pd₂(dba)₃ (57 mg, 0.062 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na₂SO₄, filtered and concentrated to give a residue which was purified by flash chromatography on silica gel (eluting with CH₂Cl₂/MeOH 100/0 gradually increasing to 90/10) to give Compound 95 (55 mg, yield: 17%) as a yellow solid. ¹H NMR (400 MHz, DMSO-d₆): δ 9.80 (s, 1H), 8.59 (d, J=3.0 Hz, 1H), 8.00 (d, J=12.1 Hz, 2H), 7.90 (d, J=3.0 Hz, 1H), 7.55-7.42 (m, 2H), 7.35 (dd, J=9.2, 3.1 Hz, 1H), 7.20 (t, J=7.8 Hz, 2H), 4.20 (m, 2H), 3.53-3.43 (m, 1H), 2.83 (d, J=11.0 Hz, 2H), 2.71 (s, 3H), 2.18 (s, 3H), 2.01 (t, J=11.1 Hz, 2H), 1.71 (m, 2H), 1.57 (d, J=12.0 Hz, 2H), 1.30 (t, J=7.0 Hz, 4H). MS [ESI, MH⁺]=505.26.

Synthesis of Compound 115

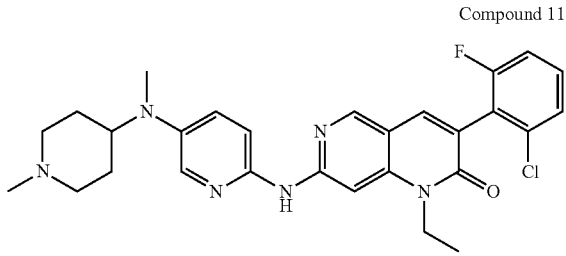

Compound 115

Compound 115, 3-(2-chloro-6-fluorophenyl)-1-ethyl-7-((5-(methyl(1-methylpiperidin-4-yl)amino)pyridin-2-yl)amino)-1,6-naphthyridin-2(1H)-one was synthesized in a similar manner as Compound 95 using ethyl 2-(2-chloro-6-fluorophenyl)acetate in the naphthyridinone formation step.

To a cooled (0° C.) solution of 2-(2-chloro-6-fluorophenyl)acetic acid (5.0 g, 26.60 mmol) in dry EtOH (50 mL) was added $H_2SO_4$ (5 mL) dropwise and the reaction mixture was stirred at 90° C. for 16 h. After TLC showed the starting material was completely consumed, the reaction mixture was concentrated, neutralized with aqueous $NaHCO_3$ then extracted with EtOAc (100 mL). The organic layer was washed with water (20 mL) and brine (20 mL) then dried over $Na_2SO_4$ and concentrated to give a residue which was purified by flash chromatography on silica gel (eluting with petroleum ether/EtOAc 100/0 gradually increasing to 85/15) to give ethyl 2-(2-chloro-6-fluorophenyl)acetate (5.5 g, 95%) as a colorless liquid. MS [ESI, $MH^+$]=217.9.

A mixture of 6-chloro-4-(ethyl amino) nicotinaldehyde (Scheme 1 compound 6) (400 mg, 2.17 mmol), ethyl 2-(2-chloro-6-fluorophenyl)acetate (652 mg, 3.26 mmol) and $K_2CO_3$ (900 mg, 6.50 mmol) in dry DMF (5 mL) was heated to 100° C. under nitrogen atmosphere for 16 h. After TLC showed the starting material was completely consumed, the reaction mixture was cooled to RT, diluted with EtOAc (100 mL), washed with water (2×30 mL) and brine (20 mL) then dried over $Na_2SO_4$ and concentrated to give a residue which was purified by flash chromatography on silica gel (eluting with petroleum ether/EtOAc 100/0 gradually increasing to 80/20) to give 7-chloro-3-(2-chloro-6-fluorophenyl)-1-ethyl-1,6-naphthyridin-2(1H)-one (140 mg, 19%) as a brown solid. $^1$H NMR (400 MHz, $CDCl_3$): δ 8.61 (s, 1H), 7.78 (s, 1H), 7.38-7.26 (m, 3H), 7.11 (m, 1H), 4.32 (m, 2H), 1.40 (t, J=7.2 Hz, 3H). MS [ESI, $MH^+$]=337.6

7-Chloro-3-(2-chloro-6-fluorophenyl)-1-ethyl-1,6-naphthyridin-2(1H)-one (200 mg, 0.59 mmol) and $N^5$-methyl-$N^5$-(1-methylpiperidin-4-yl)pyridine-2,5-diamine (Scheme 43 compound 4) (196 mg, 0.89 mmol) were dissolved in anhydrous dioxane (10 mL). To this mixture was added tBuONa (171 mg, 1.78 mmol), X-PHOS (69 mg, 0.12 mmol) and $Pd_2(dba)_3$ (54 mg, 0.06 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL) and dried over anhydrous $Na_2SO_4$ then filtered and concentrated to give a residue which was purified by flash chromatography on silica gel (eluting with $CH_2Cl_2$/MeOH 100/0 gradually increasing to 90/10) to give Compound 115 (40 mg, yield: 11%) as a yellow solid. $^1$H NMR (400 MHz, $CDCl_3$): δ 8.44 (s, 1H), 7.95 (d, J=3.1 Hz, 1H), 7.89 (s, 1H), 7.65 (s, 1H), 7.36-7.27 (m, 3H), 7.25-7.18 (m, 1H), 7.15-7.04 (m, 2H), 4.36 (m, 2H), 3.46 (t, J=12.3 Hz, 1H), 2.99 (s, 2H), 2.81 (s, 3H), 2.33 (s, 3H), 2.09 (s, 2H), 1.88 (s, 2H), 1.76 (d, J=11.9 Hz, 2H), 1.43 (t, J=7.0 Hz, 3H). MS [ESI, $MH^+$]=521.32.

Example 57

Synthesis of Compound 97

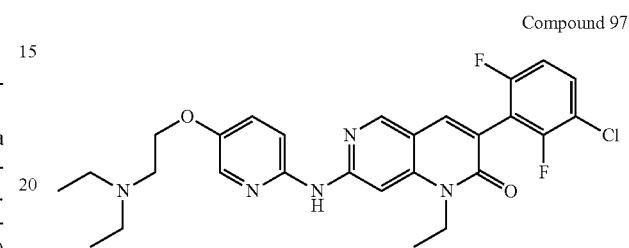

Compound 97

Compound 97, 3-(3-chloro-2,6-difluorophenyl)-7-((5-(2-(diethylamino)ethoxy)pyridin-2-yl)amino)-1-ethyl-1,6-naphthyridin-2(1H)-one was synthesized following the general procedure shown in Scheme 45 using ethyl 2-(3-chloro-2,6-difluorophenyl)acetate in the naphthyridinone formation step.

Scheme 45

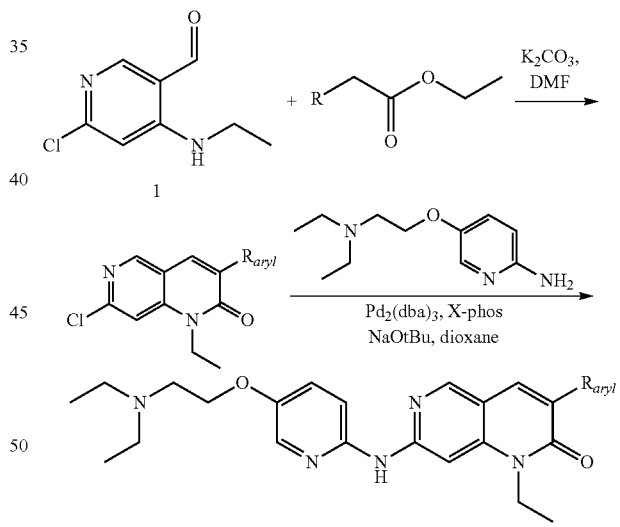

A mixture of 6-chloro-4-(ethyl amino) nicotinaldehyde (Scheme 1 compound 6) (707 mg, 3.84 mmol), ethyl 2-(3-chloro-2,6-difluorophenyl)acetate (Scheme 46 compound 6) (600 mg, 2.56 mmol) and $K_2CO_3$ (1.06 g, 7.69 mmol) in dry DMF (6 mL) was heated to 100° C. under nitrogen atmosphere for 48 h. After TLC showed the starting material was completely consumed, the reaction mixture was cooled to RT, diluted with EtOAc (100 mL), washed with water (2×30 mL) and brine (20 mL) then dried over $Na_2SO_4$ and concentrated to give a residue which was purified by flash chromatography on silica gel (eluting with petroleum ether/EtOAc 100/0 gradually increasing to 70/30) to give 7-chloro-3-(3-chloro-2,6-difluorophenyl)-1-ethyl-1,6-naphthyridin-2(1H)-one (470 mg, 52%) as a white solid. $^1$H NMR (400 MHz, DMSO-$d_6$): δ 8.81 (s, 1H), 8.36 (s, 1H), 7.96-7.66 (m, 2H), 7.34 (td, J=8.9, 1.7 Hz, 1H), 4.30 (m, 2H), 1.22 (t, J=7.0 Hz, 3H). MS [ESI, MH$^+$]=355.3

7-Chloro-3-(3-chloro-2,6-difluorophenyl)-1-ethyl-1,6-naphthyridin-2(1H)-one (250 mg, 0.71 mmol) and 5-(2-diethylaminoethoxy)-pyridin-2-ylamine (Scheme 2 compound 4) (177 mg, 0.84 mmol) were dissolved in anhydrous dioxane (10 mL). To this mixture was added tBuONa (203 mg, 2.11 mmol), X-PHOS (81 mg, 0.14 mmol) and Pd$_2$(dba)$_3$ (64 mg, 0.07 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$, filtered and concentrated to give a residue which was purified by flash chromatography on silica gel (eluting with CH$_2$Cl$_2$/MeOH 100/0 gradually increasing to 90/10) to give Compound 97 (100 mg, yield: 27%) as an off-white solid. $^1$H NMR (400 MHz, CD$_3$OD): δ 8.57 (s, 1H), 8.05 (d, J=2.4 Hz, 2H), 7.98 (s, 1H), 7.56 (m, 1H), 7.48-7.36 (m, 2H), 7.15-7.06 (m, 1H), 4.36 (m, 2H), 4.17 (t, J=5.6 Hz, 2H), 2.97 (t, J=5.5 Hz, 2H), 2.74 (m, 4H), 1.40 (m, 3H), 1.13 (t, J=7.2 Hz, 6H). MS [ESI, MH$^+$]=528.24.

The preparation of Scheme 45 intermediate 1 was described in Scheme 1 while ethyl 2-(3-chloro-2,6-difluorophenyl)acetate was prepared as shown in Scheme 46.

Scheme 46

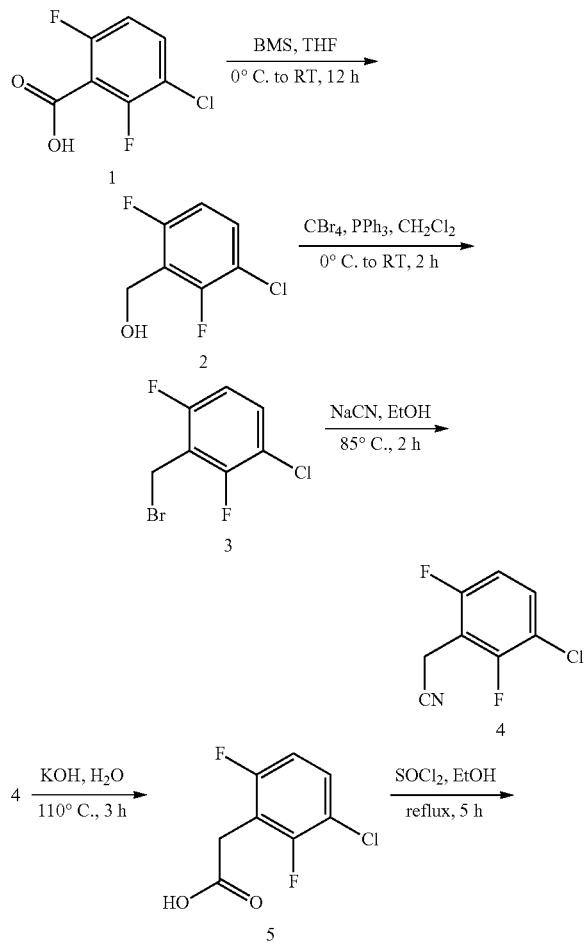

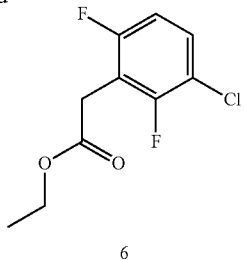

To a cooled (0° C.) solution of Scheme 46 compound 1 (3.0 g, 15.6 mmol) in dry THF (30 mL) was added BH$_3$.DMS (3.7 mL, 39.1 mmol) and the reaction mixture was stirred at RT for 12 h. After TLC showed the starting material was completely consumed, the reaction mixture was diluted with ice water (30 mL) and extracted with EtOAc (2×50 mL). The organic layer was washed with brine (20 mL), dried over Na$_2$SO$_4$ and concentrated to give a residue which was purified by flash chromatography on silica gel (eluting with petroleum ether/EtOAc 100/0 gradually increasing to 80/20) to give Scheme 46 compound 2 (2.7 g, 97%) as a colorless liquid. MS [ESI, MH$^+$]=179.0.

To a cooled (0° C.) solution of Scheme 46 compound 2 (2.7 g, 15.16 mmol) in dry CH$_2$Cl$_2$ (27 mL) was added PPh$_3$ (6.3 g, 24.26 mmol) and CBr$_4$ (8.04 g, 24.26 mmol) and the reaction mixture was stirred at RT for 2 h. After TLC showed the starting material was completely consumed, the reaction mixture was concentrated under reduced pressure to give a residue which was purified by flash chromatography on silica gel (eluting with petroleum ether/EtOAc 100/0 gradually increasing to 90/10) to give Scheme 46 compound 3 (2.8 g, 77%) as a colorless liquid. MS [ESI, MH$^+$]=240.0.

To a solution of Scheme 46 compound 3 (2.8 g, 11.60 mmol) in dry EtOH (28 mL) was added NaCN (613 mg, 12.78 mmol) and the reaction mixture was stirred at 85° C. for 2 h. After TLC showed the starting material was completely consumed, the reaction mixture was concentrated. The resulting crude compound was diluted with ice water (30 mL) and extracted with EtOAc (2×50 mL). The organic layer was washed with brine (20 mL), dried over Na$_2$SO$_4$ and concentrated to get Scheme 46 compound 4 (1.4 g, 64.5%, crude) as a dark brown liquid which was used without further purification. MS [ESI, MH$^+$]=188.0.

To a solution of Scheme 46 compound 4 (1.4 g, 7.48 mmol) in water (14 mL) was added KOH (838 mg, 14.97 mmol) and the reaction mixture was stirred at 110° C. for 3 h. After TLC showed the starting material was completely consumed, the reaction mixture was washed with CH$_2$Cl$_2$ (20 mL) to remove impurities, neutralized with 2N HCl (down to pH 2) and extracted with EtOAc (2×50 mL). The organic phase was dried over Na$_2$SO$_4$ and concentrated to give Scheme 46 compound 5 (760 mg, 50%) as an off-white solid. MS [ESI, (M-H)$^-$]=205.7.

To a cooled (0° C.) solution of Scheme 46 compound 5 (700 mg, 3.4 mmol) in dry EtOH (10 mL) was added SOCl$_2$ (3 eq.) dropwise and the reaction mixture was stirred at 90° C. for 5 h. The reaction mixture was then concentrated, neutralized with aqueous NaHCO$_3$ and extracted with EtOAc (100 mL). The organic layer was washed with water (20 mL) and brine (20 mL), dried over Na$_2$SO$_4$ and concentrated to give a residue which was purified by flash chromatography on silica gel (eluting with petroleum ether/EtOAc 100/0 gradually increasing to 50/50) to give Scheme 46 compound 6 (680 mg, 85.5%) as a colorless liquid. $^1$H NMR (400 MHz, DMSO-d$_6$): δ 7.66-7.56 (m, 1H), 7.25-7.13 (m, 1H), 4.10 (qd, J=7.2, 1.6 Hz, 2H), 3.78 (d, J=2.0 Hz, 2H), 1.17 (td, J=7.2, 1.5 Hz, 3H). MS [ESI, MH$^+$]=235.4.

Synthesis of Compound 98

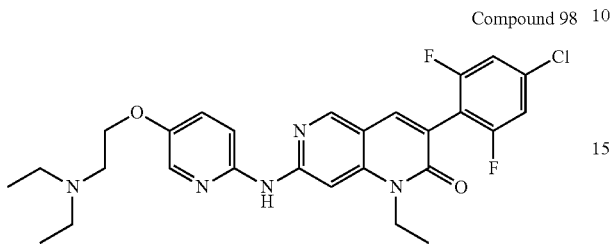

Compound 98

Compound 98, 3-(4-chloro-2,6-difluorophenyl)-7-((5-(2-(diethylamino)ethoxy)pyridin-2-yl)amino)-1-ethyl-1,6-naphthyridin-2(1H)-one was synthesized in a similar manner as Compound 97 using ethyl 2-(4-chloro-2,6-difluorophenyl)acetate in the naphthyridinone formation step.

A mixture of 6-chloro-4-(ethyl amino) nicotinaldehyde (Scheme 1 compound 6) (600 mg, 3.26 mmol), ethyl 2-(4-chloro-2,6-difluorophenyl)acetate (930 mg, 3.97 mmol) and K$_2$CO$_3$ (1.35 g, 9.78 mmol) in dry DMF (6 mL) was heated to 100° C. under nitrogen atmosphere for 48 h. After TLC showed the starting material was completely consumed, the reaction mixture was cooled to RT and diluted with EtOAc (100 mL), washed with water (2 x 30 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give 7-chloro-3-(4-chloro-2,6-difluorophenyl)-1-ethyl-1,6-naphthyridin-2(1H)-one (500 mg, 43%) as a light yellow solid. MS [ESI, MH$^+$]=355.0.

7-Chloro-3-(4-chloro-2,6-difluorophenyl)-1-ethyl-1,6-naphthyridin-2(1H)-one (150 mg, 0.42 mmol) and 5-(2-diethylaminoethoxy)-pyridin-2-ylamine (Scheme 2 compound 4) (133 mg, 0.63 mmol) were dissolved in anhydrous dioxane (10 mL). To this mixture was added tBuONa (122 mg, 1.27 mmol), X-PHOS (49 mg, 0.08 mmol) and Pd$_2$(dba)$_3$ (39 mg, 0.04 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$, filtered and concentrated to give a residue which was purified by flash chromatography on silica gel (eluting with CH$_2$Cl$_2$/MeOH 100/0 gradually increasing to 90/10) to give Compound 98 (63 mg, yield: 28%) as a yellow solid. $^1$H NMR (400 MHz, CD$_3$OD): δ 8.58 (s, 1H), 8.06 (d, J=3.6 Hz, 2H), 7.92 (s, 1H), 7.48-7.39 (m, 2H), 7.35 (td, J=8.8, 4.6 Hz, 1H), 7.23 (dd, J=8.4, 4.3 Hz, 1H), 4.36 (q, J=7.1 Hz, 2H), 4.18 (t, J=5.6 Hz, 2H), 2.98 (s, 2H), 2.74 (d, J=8.0 Hz, 4H), 1.41 (t, J=7.0 Hz, 3H), 1.13 (t, J=7.1 Hz, 6H). MS [ESI, MH$^+$]=528.18.

Ethyl 2-(4-chloro-2,6-difluorophenyl)acetate was prepared from 2-(4-chloro-2,6-difluorophenyl) acetic acid in a manner similar to Scheme 46 compound 6. MS [ESI, MH$^+$]=235.4.

Synthesis of Compound 99

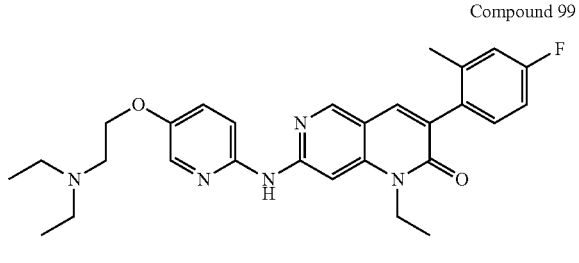 [SMILES: CCN(CC)CCOc1ccc(Nc2cc3c(cn2)cc(-c2ccc(F)cc2C)c(=O)n3CC)nc1]

Compound 99

Compound 99, 7-((5-(2-(diethylamino)ethoxy)pyridin-2-yl)amino)-1-ethyl-3-(4-fluoro-2-methyl phenyl)-1,6-naphthyridin-2(1H)-one was synthesized in a similar manner as Compound 97 using ethyl 2-(4-fluoro-2-methylphenyl)acetate in the naphthyridinone formation step.

A mixture of 6-chloro-4-(ethyl amino) nicotinaldehyde (Scheme 1 compound 6) (500 mg, 2.55 mmol), ethyl 2-(4-fluoro-2-methylphenyl)acetate (704 mg, 3.82 mmol) and K$_2$CO$_3$ (1.05 g, 7.65 mmol) in dry DMF (6 mL) was heated to 100° C. under nitrogen atmosphere for 48 h. After TLC showed the starting material was completely consumed, the reaction mixture was cooled to RT and diluted with EtOAc (100 mL), washed with water (2×30 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give 7-chloro-1-ethyl-3-(4-fluoro-2-methylphenyl)-1,6-naphthyridin-2(1H)-one (400 mg, 50%) as a light yellow solid. $^1$H NMR (400 MHz, CDCl$_3$): δ 8.59 (s, 1H), 7.66 (s, 1H), 7.27 (d, J=4.2 Hz, 1H), 7.19 (dd, J=8.4, 5.7 Hz, 1H), 6.97 (ddt, J=16.7, 8.4, 4.2 Hz, 2H), 4.31 (q, J=7.1 Hz, 2H), 2.23 (s, 3H), 1.39 (t, J=7.1 Hz, 3H). MS [ESI, MH$^+$]=317.4

7-Chloro-1-ethyl-3-(4-fluoro-2-methylphenyl)-1,6-naphthyridin-2(1H)-one (250 mg, 0.79 mmol) and 5-(2-diethylaminoethoxy)-pyridin-2-ylamine (Scheme 2 compound 4) (198 mg, 0.95 mmol) were dissolved in anhydrous dioxane (10 mL). To this mixture was added tBuONa (228 mg, 2.37 mmol), X-PHOS (92 mg, 0.16 mmol) and Pd$_2$(dba)$_3$ (75 mg, 0.08 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$, filtered and concentrated to give a residue which was purified by flash chromatography on silica gel (eluting with CH$_2$Cl$_2$/MeOH 100/0 gradually increasing to 90/10) to give Compound 99 (40 mg, yield: 10%) as a yellow solid. $^1$H NMR (400 MHz, CD$_3$OD): δ 8.54 (s, 1H), 8.06-7.99 (m, 2H), 7.76 (s, 1H), 7.47-7.38 (m, 2H), 7.22 (dd, J=8.4, 5.9 Hz, 1H), 7.06-6.90 (m, 2H), 4.35 (q, J=7.1 Hz, 2H), 4.18 (t, J=5.6 Hz, 2H), 3.00 (t, J=5.9 Hz, 2H), 2.76 (m, 4H), 1.38 (m, 3H), 1.14 (t, J=7.2 Hz, 6H). MS [ESI, MH$^+$]=490.25.

Ethyl 2-(4-fluoro-2-methylphenyl)acetate was prepared from 2-(4-fluoro-2-methylphenyl)acetic acid in a manner similar to Scheme 46 compound 6. MS [ESI, MH$^+$]=197.07.

251
Synthesis of Compound 100

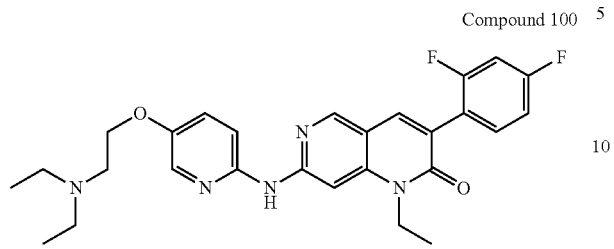

Compound 100

Compound 100, 7-((5-(2-(diethylamino)ethoxy)pyridin-2-yl)amino)-3-(2,4-difluorophenyl)-1-ethyl-1,6-naphthyridin-2(1H)-one was synthesized in a similar manner as Compound 97 using ethyl 2-(2,4-difluorophenyl)acetate in the naphthyridinone formation step.

A mixture of 6-chloro-4-(ethyl amino) nicotinaldehyde (Scheme 1 compound 6) (662 mg, 3.6 mmol), ethyl-2-(2,4-difluorophenyl)acetate (600 mg, 3.0 mmol) and $K_2CO_3$ (1.24 g, 9.0 mmol) in dry DMF (20 mL) was heated to 100° C. under nitrogen atmosphere for 48 h. After TLC showed the starting material was completely consumed, the reaction mixture was cooled to RT, diluted with EtOAc (100 mL), washed with water (2×30 mL) and brine (20 mL) then dried over $Na_2SO_4$ and concentrated to give a residue which was purified by flash chromatography on silica gel (eluting with petroleum ether/EtOAc 100/0 gradually increasing to 70/30) to give 7-chloro-3-(2,4-difluorophenyl)-1-ethyl-1,6-naphthyridin-2(1H)-one (850 mg, 81%) as a light yellow solid. $^1$H NMR (400 MHz, DMSO-$d_6$): δ 8.80 (s, 1H), 8.18 (s, 1H), 7.77 (s, 1H), 7.58 (m, 1H), 7.38 (m, 1H), 7.21 (m, 1H), 4.29 (m, 2H), 1.22 (t, J=7.0 Hz, 3H). MS [ESI, MH$^+$]=321.06.

7-Chloro-3-(2,4-difluorophenyl)-1-ethyl-1,6-naphthyridin-2(1H)-one (200 mg, 0.625 mmol) and 5-(2-diethylaminoethoxy)-pyridin-2-ylamine (Scheme 2 compound 4) (156 mg, 0.750 mmol) were dissolved in anhydrous dioxane (10 mL). To this mixture was added tBuONa (180 mg, 1.870 mmol), X-PHOS (72 mg, 0.124 mmol) and Pd$_2$(dba)$_3$ (57 mg, 0.062 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$, filtered and concentrated to give a residue which was purified by flash chromatography on silica gel (eluting with CH$_2$Cl$_2$/MeOH 100/0 gradually increasing to 90/10) to give Compound 100 (35 mg, yield: 11%) as a yellow solid. $^1$H NMR (400 MHz, CDCl$_3$): δ 8.46 (s, 1H), 8.05 (d, J=3.0 Hz, 1H), 7.97 (s, 1H), 7.72 (s, 1H), 7.54 (td, J=8.3, 6.6 Hz, 1H), 7.38 (s, 1H), 7.29 (dd, J=9.4, 3.5 Hz, 1H), 7.14 (d, J=8.9 Hz, 1H), 7.00-6.86 (m, 2H), 4.36 (m, 2H), 4.12 (s, 2H), 2.92 (s, 2H), 2.69 (s, 4H), 1.43 (t, J=7.1 Hz, 3H), 1.11 (t, J=7.2 Hz, 6H). MS [ESI, MH$^+$]=494.22.

Ethyl 2-(2,4-difluorophenyl)acetate was prepared from 2-(2,4-difluorophenyl)acetic acid in a manner similar to Scheme 46 compound 6. MS [ESI, MH$^+$]=201.07.

252
Synthesis of Compound 101

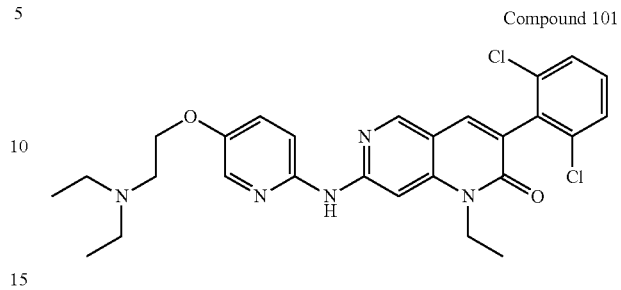

Compound 101

Compound 101, 3-(2,6-dichlorophenyl)-7-((5-(2-(diethylamino)ethoxy)pyridin-2-yl)amino)-1-ethyl-1,6-naphthyridin-2(1H)-one was synthesized in a similar manner as Compound 97 using ethyl 2-(2,6-dichlorophenyl)acetate in the naphthyridinone formation step.

A mixture of 6-chloro-4-(ethyl amino) nicotinaldehyde (Scheme 1 compound 6) (2.0 g, 10.9 mmol), ethyl 2-(2,6-dichlorophenyl)acetate (3.0 g, 13.0 mmol) and $K_2CO_3$ (7.5 g, 54.3 mmol) in dry DMF (15 mL) was heated to 100° C. under nitrogen atmosphere for 12 h. After TLC showed the starting material was completely consumed, the reaction mixture was cooled to RT, diluted with EtOAc (100 mL), washed with water (2×30 mL) and brine (20 mL) then dried over $Na_2SO_4$ and concentrated to give a residue which was purified by flash chromatography on silica gel (eluting with petroleum ether/EtOAc 100/0 gradually increasing to 80/20) to give 7-chloro-3-(2,6-dichlorophenyl)-1-ethyl-1,6-naphthyridin-2(1H)-one (700 mg, 23%) as an off-white solid. $^1$H NMR (400 MHz, DMSO-$d_6$): δ 8.81 (s, 1H), 8.17 (s, 1H), 7.82 (s, 1H), 7.70-7.57 (m, 2H), 7.50 (dd, J=8.8, 7.4 Hz, 1H), 4.30 (m, 2H), 1.21 (t, J=7.0 Hz, 3H). MS [ESI, MH$^+$]=353.00.

7-Chloro-3-(2,6-dichlorophenyl)-1-ethyl-1,6-naphthyridin-2(1H)-one (250 mg, 0.710 mmol) and 5-(2-diethylaminoethoxy)-pyridin-2-ylamine (Scheme 2 compound 4) (178 mg, 0.852 mmol) were dissolved in anhydrous dioxane (10 mL). To this mixture was added tBuONa (204 mg, 2.130 mmol), X-PHOS (82 mg, 0.140 mmol) and Pd$_2$(dba)$_3$ (65 mg, 0.071 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$, filtered and concentrated to give a residue which was purified by flash chromatography on silica gel (eluting with CH$_2$Cl$_2$/MeOH 100/0 gradually increasing to 90/10) to give Compound 101 (40 mg, yield: 11%) as a yellow solid. $^1$H NMR (400 MHz, CD$_3$OD): δ 8.57 (s, 1H), 8.05 (d, J=2.5 Hz, 2H), 7.81 (s, 1H), 7.53-7.32 (m, 5H), 4.36 (m, 2H), 4.17 (t, J=5.6 Hz, 2H), 2.97 (t, J=5.7 Hz, 2H), 2.73 (m, 4H), 1.40 (t, J=7.1 Hz, 3H), 1.13 (t, J=7.2 Hz, 6H). MS [ESI, MH$^+$]=526.21.

Ethyl 2-(2,6-dichlorophenyl)acetate was prepared from 2-(2,6-dichlorophenyl)acetic acid in a manner similar to Scheme 46 compound 6. MS [ESI, MH$^+$]=233.01.

Synthesis of Compound 102

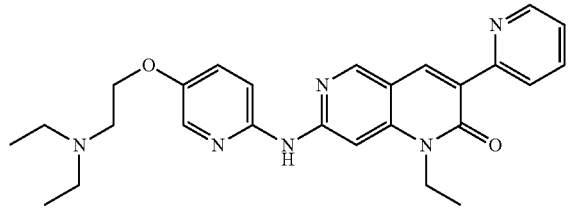

Compound 102

Compound 102, 7-((5-(2-(diethylamino)ethoxy)pyridin-2-yl)amino)-1-ethyl-3-(pyridin-2-yl)-1,6-naphthyridin-2(1H)-one was synthesized in a similar manner as Compound 97 using ethyl 2-(pyridin-2-yl)acetate in the naphthyridinone formation step.

A mixture of 6-chloro-4-(ethyl amino) nicotinaldehyde (Scheme 1 compound 6) (1.0 g, 5.45 mmol), ethyl 2-(pyridin-2-yl)acetate (600 mg, 3.63 mmol) and $K_2CO_3$ (1.5 g, 10.9 mmol) in dry DMF (6 mL) was heated to 100° C. under nitrogen atmosphere for 48 h. After TLC showed the starting material was completely consumed, the reaction mixture was cooled to RT, diluted with EtOAc (3×30 mL), washed with water (2×10 mL) and brine (10 mL) then dried over $Na_2SO_4$ and concentrated to give a residue which was purified by flash chromatography on silica gel (eluting with petroleum ether/EtOAc 100/0 gradually increasing to 80/20) to give 7-chloro-1-ethyl-3-(pyridin-2-yl)-1,6-naphthyridin-2(1H)-one (600 mg, 63%) as a light yellow solid. $^1$H NMR (400 MHz, CDCl$_3$): δ 8.78-8.63 (m, 3H), 8.42 (dt, J=8.1, 1.1 Hz, 1H), 7.80 (m, 1H), 7.32 (m, 1H), 4.36 (m, 2H), 1.42 (t, J=7.1 Hz, 3H). MS [ESI, MH$^+$]=286.0.

7-Chloro-1-ethyl-3-(pyridin-2-yl)-1,6-naphthyridin-2(1H)-one (250 mg, 0.877 mmol) and 5-(2-diethylamino ethoxy)-pyridin-2-ylamine (Scheme 2 compound 4) (219 mg, 1.052 mmol) were dissolved in anhydrous dioxane (10 mL). To this mixture was added tBuONa (252 mg, 2.630 mmol), X-PHOS (50 mg, 0.086 mmol) and Pd$_2$(dba)$_3$ (40 mg, 0.043 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over Na$_2$SO$_4$, filtered and concentrated to give a residue which was purified by flash chromatography on silica gel (eluting with CH$_2$Cl$_2$/MeOH 100/0 gradually increasing to 90/10) to give Compound 102 (35 mg, yield: 9%) as a yellow solid. $^1$H NMR (400 MHz, CD$_3$OD): δ 8.86 (s, 1H), 8.59 (s, 1H), 8.51 (d, J=4.7 Hz, 1H), 8.18 (d, J=7.9 Hz, 1H), 8.11-8.02 (m, 2H), 8.00 (s, 1H), 7.50 (dd, J=8.1, 4.9 Hz, 1H), 7.42 (d, J=4.4 Hz, 2H), 4.36 (m, 2H), 4.22 (t, J=5.4 Hz, 2H), 3.12 (t, J=5.3 Hz, 2H), 2.88 (m, 4H), 1.41 (t, J=7.0 Hz, 3H), 1.19 (t, J=7.2 Hz, 6H). MS [ESI, MH$^+$]=459.17.

Synthesis of Compound 103

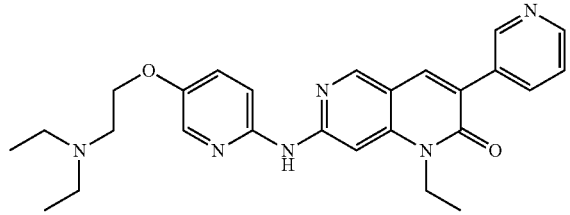

Compound 103

Compound 103, 7-((5-(2-(diethylamino)ethoxy)pyridin-2-yl)amino)-1-ethyl-3-(pyridin-3-yl)-1,6-naphthyridin-2(1H)-one was synthesized in a similar manner as Compound 97 using ethyl 2-(pyridin-3-yl)acetate in the naphthyridinone formation step.

A mixture of 6-chloro-4-(ethyl amino) nicotinaldehyde (Scheme 1 compound 6) (1.0 g, 5.45 mmol), ethyl 2-(pyridin-3-yl) acetate (600 mg, 3.63 mmol) and $K_2CO_3$ (1.5 g, 10.9 mmol) in dry DMF (6 mL) was heated to 100° C. under nitrogen atmosphere for 48 h. After TLC showed the starting material was completely consumed, the reaction mixture was cooled to RT, diluted with EtOAc (3×30 mL), washed with water (2×10 mL) and brine (10 mL) then dried over Na$_2$SO$_4$ and concentrated to give a residue which was purified by flash chromatography on silica gel (eluting with petroleum ether/EtOAc 100/0 gradually increasing to 80/20) to give 7-chloro-1-ethyl-3-(pyridin-3-yl)-1,6-naphthyridin-2(1H)-one (600 mg, 63%) as a light yellow solid. $^1$H NMR (400 MHz, CDCl$_3$): δ 8.86 (d, J=2.4 Hz, 1H), 8.71-8.54 (m, 2H), 8.12 (dt, J=7.8, 2.1 Hz, 1H), 7.88 (s, 1H), 7.40 (dd, J=7.9, 4.8 Hz, 1H), 7.27 (s, 1H), 4.34 (m, 2H), 1.42 (t, J=7.1 Hz, 3H). MS [ESI, MH$^+$]=286.0.

7-Chloro-1-ethyl-3-(pyridin-3-yl)-1,6-naphthyridin-2(1H)-one (250 mg, 0.877 mmol) and 5-(2-diethylamino ethoxy)-pyridin-2-ylamine (Scheme 2 compound 4) (219 mg, 1.052 mmol) were dissolved in anhydrous dioxane (10 mL). To this mixture was added tBuONa (252 mg, 2.630 mmol), X-PHOS (101 mg, 0.175 mmol) and Pd$_2$(dba)$_3$ (80 mg, 0.087 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over Na$_2$SO$_4$, filtered and concentrated to give a residue which was purified by flash chromatography on silica gel (eluting with CH$_2$Cl$_2$/MeOH 100/0 gradually increasing to 90/10) to give Compound 103 (35 mg, yield: 9%) as a yellow solid. $^1$H NMR (400 MHz, CD$_3$OD): δ 8.66-8.60 (m, 2H), 8.40 (s, 1H), 8.17 (d, J=8.1 Hz, 1H), 8.10 (d, J=2.8 Hz, 1H), 8.02 (s, 1H), 7.88 (td, J=7.8, 1.9 Hz, 1H), 7.52-7.34 (m, 3H), 4.44-4.26 (m, 4H), 3.40 (s, 2H), 3.15 (m, 4H), 1.42 (t, J=7.1 Hz, 3H), 1.30 (t, J=7.2 Hz, 6H). MS [ESI, MH$^+$]=459.17.

Synthesis of Compound 104

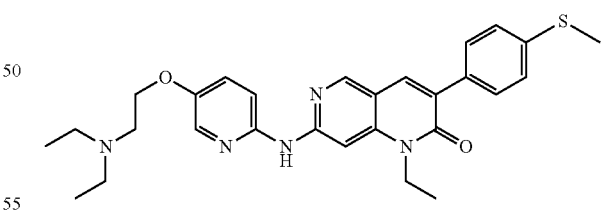

Compound 104

Compound 104, 7-((5-(2-(diethylamino)ethoxy)pyridin-2-yl)amino)-1-ethyl-3-(4-(methylthio)phenyl)-1,6-naphthyridin-2(1H)-one was synthesized in a similar manner as Compound 97 using ethyl 2-(4-(methylthio)phenyl)acetate in the naphthyridinone formation step.

A mixture of 6-chloro-4-(ethyl amino) nicotinaldehyde (Scheme 1 compound 6) (500 mg, 2.71 mmol), ethyl 2-(4-(methylthio)-phenyl)acetate (856 mg, 4.07 mmol) and $K_2CO_3$ (1.12 g, 8.13 mmol) in dry DMF (10 mL) was heated to 100° C. under nitrogen atmosphere for 24 h. After TLC showed the starting material was completely consumed, the reaction mixture was cooled to RT, diluted with EtOAc (100 mL), washed with water (2×30 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give 7-chloro-1-ethyl-3-(4-(methylthio)phenyl)-1,6-naphthyridin-2(1H)-one (300 mg, 33%) as a pale brown solid. $^1$H NMR (400 MHz, DMSO-d$_6$): δ 8.79 (s, 1H), 8.21 (s, 1H), 7.74-7.64 (m, 3H), 7.37-7.28 (m, 2H), 4.30 (m, 2H), 2.52 (s, 3H), 1.23 (t, J=7.0 Hz, 3H). MS [ESI, MH$^+$]=331.02.

7-Chloro-1-ethyl-3-(4-(methylthio)-phenyl)-1,6-naphthyridin-2(1H)-one (200 mg, 0.606 mmol) and 5-(2-diethylaminoethoxy)-pyridin-2-ylamine (Scheme 2 compound 4) (152 mg, 0.727 mmol) were dissolved in anhydrous dioxane (10 mL). To this mixture was added Cs$_2$CO$_3$ (591 mg, 1.818 mmol), X-PHOS (35 mg, 0.060 mmol) and Pd$_2$(dba)$_3$ (28 mg, 0.030 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 104 (80 mg, yield: 26%) as a yellow solid. $^1$H NMR (400 MHz, CD$_3$OD): δ 8.54 (s, 1H), 8.03 (d, J=2.7 Hz, 1H), 7.96 (s, 1H), 7.92 (d, J=1.7 Hz, 1H), 7.61 (d, J=8.0 Hz, 2H), 7.44-7.37 (m, 2H), 7.30 (d, J=8.1 Hz, 2H), 4.34 (m, 2H), 4.22-4.13 (m, 2H), 3.04 (m, 2H), 2.81 (m, 4H), 2.51 (s, 3H), 1.39 (t, J=7.0 Hz, 3H), 1.20-1.10 (m, 6H). MS [ESI, MH$^+$]=504.19.

Ethyl 2-(4-(methylthio)phenyl)acetate was prepared from 2-(4-(methylthio)phenyl)acetic acid in a manner similar to Scheme 46 compound 6. MS [ESI, MH$^+$]=211.0.

80/20) to give 7-chloro-1-ethyl-3-(3-(methylthio)phenyl)-1,6-naphthyridin-2(1H)-one (550 mg, 61%) as a yellow solid. $^1$H NMR (400 MHz, CDCl$_3$): δ 8.62 (s, 1H), 7.82 (s, 1H), 7.58 (t, J=1.9 Hz, 1H), 7.45 (dt, J=7.5, 1.4 Hz, 1H), 7.37 (t, J=7.7 Hz, 1H), 7.31 (dt, J=8.0, 1.5 Hz, 1H), 7.25 (s, 1H), 4.32 (m, 2H), 2.52 (s, 3H), 1.40 (t, J=7.1 Hz, 3H). MS [ESI, MH$^+$]=331.02.

7-Chloro-1-ethyl-3-(3-(methylthio)-phenyl)-1,6-naphthyridin-2(1H)-one (250 mg, 0.757 mmol) and 5-(2-diethylaminoethoxy)-pyridin-2-ylamine (Scheme 3 compound 4) (190 mg, 0.900 mmol) were dissolved in anhydrous dioxane (10 mL). To this mixture was added tBuONa (218 mg, 2.270 mmol), X-PHOS (87.6 mg, 0.151 mmol) and Pd$_2$(dba)$_3$ (69 mg, 0.075 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 105 (55 mg, yield: 15%) as a yellow solid. $^1$H NMR (400 MHz, CD$_3$OD): δ 8.57 (s, 1H), 8.03 (d, J=2.8 Hz, 1H), 7.97 (d, J=10.8 Hz, 2H), 7.58 (t, J=1.9 Hz, 1H), 7.47-7.38 (m, 3H), 7.35 (t, J=7.7 Hz, 1H), 7.28-7.22 (m, 1H), 4.36 (m, 2H), 4.18 (t, J=5.5 Hz, 2H), 3.00 (t, J=5.7 Hz, 2H), 2.76 (m, 4H), 2.52 (s, 3H), 1.40 (t, J=7.0 Hz, 3H), 1.14 (t, J=7.1 Hz, 6H). MS [ESI, MH$^+$]=504.19.

Ethyl 2-(3-(methylthio)-phenyl)-acetate was prepared from 2-(3-(methylthio)phenyl)acetic acid in a manner similar to Scheme 46 compound 6. MS [ESI, MH$^+$]=211.0.

Synthesis of Compound 106

Synthesis of Compound 105

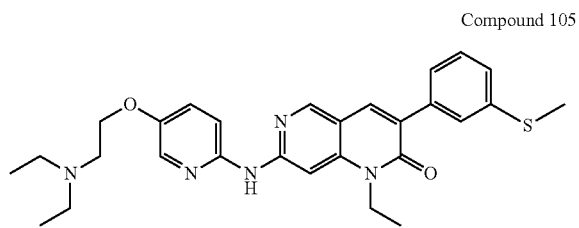 [SMILES: CCN(CC)CCOc1ccc(Nc2cc3c(cn2)cc(-c2cccc(SC)c2)c(=O)n3CC)nc1]

Compound 105

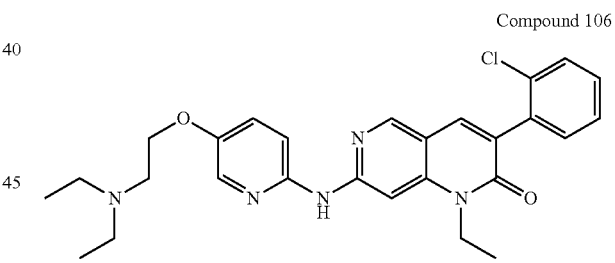

Compound 106

Compound 105, 7-((5-(2-(diethylamino)ethoxy)pyridin-2-yl)amino)-1-ethyl-3-(3-(methylthio)phenyl)-1,6-naphthyridin-2(1H)-one was synthesized in a similar manner as Compound 97 using ethyl 2-(3-(methylthio)phenyl)acetate in the naphthyridinone formation step.

A mixture of 6-chloro-4-(ethyl amino) nicotinaldehyde (Scheme 1 compound 6) (500 mg, 2.71 mmol), ethyl 2-(3-(methylthio)-phenyl)acetate (856 mg, 4.07 mmol) and K$_2$CO$_3$ (1.12 g, 8.95 mmol) in dry DMF (10 mL) was heated to 100° C. under nitrogen atmosphere for 48 h. After TLC showed the starting material was completely consumed, the reaction mixture was cooled to RT, diluted with EtOAc (100 mL), washed with water (2×30 mL) and brine (20 mL) then dried over Na$_2$SO$_4$ and concentrated to give a residue which was purified by flash chromatography on silica gel (eluting with petroleum ether/EtOAc 100/0 gradually increasing to Compound 106, 3-(2-chlorophenyl)-7-((5-(2-(diethylamino)-ethoxy)pyridin-2-yl)amino)-1-ethyl-1,6-naphthyridin-2(1H)-one was synthesized in a similar manner as Compound 97 using ethyl 2-(2-chlorophenyl) acetate in the naphthyridinone formation step.

A mixture of 6-chloro-4-(ethyl amino) nicotinaldehyde (Scheme 1 compound 6) (620 mg, 3.36 mmol), ethyl 2-(2-chlorophenyl)-acetate (800 mg, 4.04 mmol) and K$_2$CO$_3$ (1.39 g, 10.08 mmol) in dry DMF (10 mL) was heated to 100° C. under nitrogen atmosphere for 48 h. After TLC showed the starting material was completely consumed, the reaction mixture was cooled to RT, diluted with EtOAc (100 mL), washed with water (2×30 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give 7-chloro-3-(2-chlorophenyl)-1-ethyl-1,6-naphthyridin-2(1H)-one (1.10 g, 85%) as an off-white solid.

$^1$H NMR (400 MHz, DMSO-d$_6$): δ 8.79 (s, 1H), 8.10 (s, 1H), 7.77 (s, 1H), 7.50 (d, J=44.7 Hz, 4H), 4.29 (m, 2H), 1.22 (t, J=6.7 Hz, 3H). MS [ESI, MH$^+$]=319.04.

7-Chloro-3-(2-chlorophenyl)-1-ethyl-1,6-naphthyridin-2 (1H)-one (250 mg, 0.786 mmol) and 5-(2-diethyl aminoethoxy)-pyridin-2-ylamine (Scheme 2 compound 4) (249 mg, 1.170 mmol) were dissolved in anhydrous dioxane (10 mL). To this mixture was added tBuONa (226 mg, 2.350 mmol), X-PHOS (90 mg, 0.157 mmol) and Pd$_2$(dba)$_3$ (71 mg, 0.078 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 106 (120 mg, yield: 31%) as a light yellow solid. $^1$H NMR (400 MHz, CD$_3$OD): δ 8.55 (s, 1H), 8.08-7.96 (m, 2H), 7.82 (s, 1H), 7.52-7.47 (m, 1H), 7.47-7.36 (m, 5H), 4.35 (m, 2H), 4.18 (t, J=5.5 Hz, 2H), 2.98 (t, J=5.8 Hz, 2H), 2.75 (m, 4H), 1.40 (t, J=7.0 Hz, 3H), 1.13 (t, J=7.2 Hz, 6H). MS [ESI, MH$^+$]=492.20.

Ethyl 2-(2-chlorophenyl)acetate was prepared from 2-(2-chlorophenyl)acetic acid in a manner similar to Scheme 46 compound 6. MS [ESI, MH$^+$]=200.01.

Synthesis of Compound 107

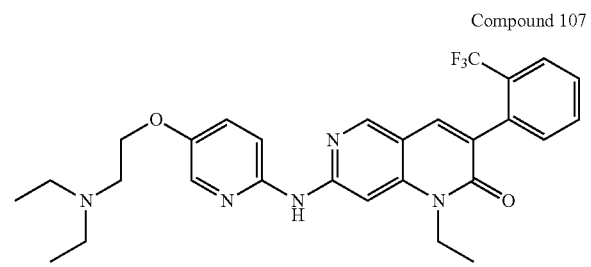 [SMILES: CCN(CC)CCOc1ccc(Nc2cc3c(cn2)cc(-c2ccccc2C(F)(F)F)c(=O)n3CC)nc1]

Compound 107

Compound 107, 7-((5-(2-(diethylamino)ethoxy)pyridin-2-yl)amino)-1-ethyl-3-(2-(trifluoromethyl)phenyl)-1,6-naphthyridin-2(1H)-one was synthesized in a similar manner as Compound 97 using ethyl 2-(2-(trifluoromethyl) phenyl)acetate in the naphthyridinone formation step.

A mixture of 6-chloro-4-(ethyl amino) nicotinaldehyde (Scheme 1 compound 6) (1.21 g, 5.21 mmol), 2-(2-(trifluoromethyl)-phenyl)acetate (800 mg, 4.34 mmol) and K$_2$CO$_3$ (1.80 g, 13.02 mmol) in dry DMF (10 mL) was heated to 100° C. under nitrogen atmosphere for 48 h. After TLC showed the starting material was completely consumed, the reaction mixture was cooled to RT, diluted with EtOAc (100 mL), washed with water (2×30 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give 7-chloro-1-ethyl-3-(2-(trifluoromethyl)phenyl)-1,6-naphthyridin-2(1H)-one (1.00 g, 50%) as a yellow solid. $^1$H NMR (400 MHz, CDCl$_3$): δ 8.58 (s, 1H), 7.78 (d, J=7.8 Hz, 1H), 7.67 (s, 1H), 7.62 (t, J=7.6 Hz, 1H), 7.55 (t, J=7.7 Hz, 1H), 7.38 (d, J=7.5 Hz, 1H), 7.28 (s, 1H), 4.30 (m, 2H), 1.38 (t, J=7.1 Hz, 3H). MS [ESI, MH$^+$]=353.0.

7-Chloro-1-ethyl-3-(2-(trifluoromethyl)-phenyl)-1,6-naphthyridin-2(1H)-one (250 mg, 0.708 mmol) and 5-(2-diethylaminoethoxy)-pyridin-2-ylamine (Scheme 2 compound 4) (177 mg, 0.850 mmol) were dissolved in anhydrous dioxane (10 mL). To this mixture was added tBuONa (204 mg, 2.120 mmol), X-PHOS (82 mg, 0.140 mmol) and Pd$_2$(dba)$_3$ (65 mg, 0.071 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 107 (50 mg, yield: 11%) as a light yellow solid. $^1$H NMR (400 MHz, dmso): δ 9.92 (s, 1H), 8.60 (s, 1H), 8.08-7.94 (m, 2H), 7.85-7.79 (m, 2H), 7.72 (t, J=7.6 Hz, 1H), 7.61 (dd, J=26.1, 8.4 Hz, 2H), 7.50-7.37 (m, 2H), 4.28-4.13 (m, 2H), 4.08 (t, J=6.1 Hz, 2H), 2.80 (s, 2H), 2.68-2.53 (m, 4H), 1.28 (t, J=7.0 Hz, 3H), 0.99 (t, J=7.1 Hz, 6H). MS [ESI, MH$^+$]=526.14.

Ethyl 2-(2-(trifluoromethyl)phenyl)acetate was prepared from 2-(2-(trifluoromethyl)phenyl) acetic acid in a manner similar to Scheme 46 compound 6. MS [ESI, MH$^+$]=233.07.

Example 58

Synthesis of Compound 108

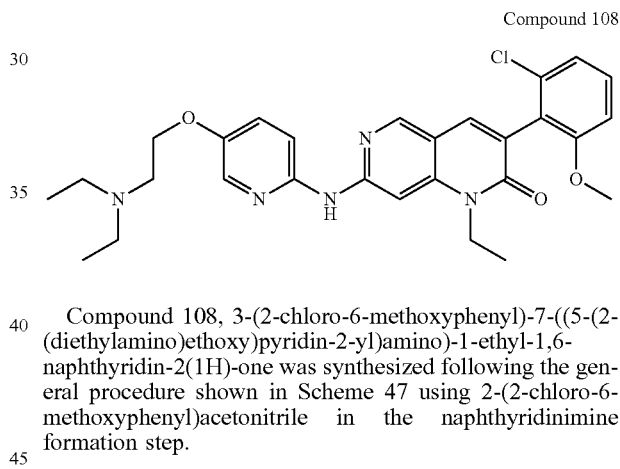

Compound 108

Compound 108, 3-(2-chloro-6-methoxyphenyl)-7-((5-(2-(diethylamino)ethoxy)pyridin-2-yl)amino)-1-ethyl-1,6-naphthyridin-2(1H)-one was synthesized following the general procedure shown in Scheme 47 using 2-(2-chloro-6-methoxyphenyl)acetonitrile in the naphthyridinimine formation step.

Scheme 47

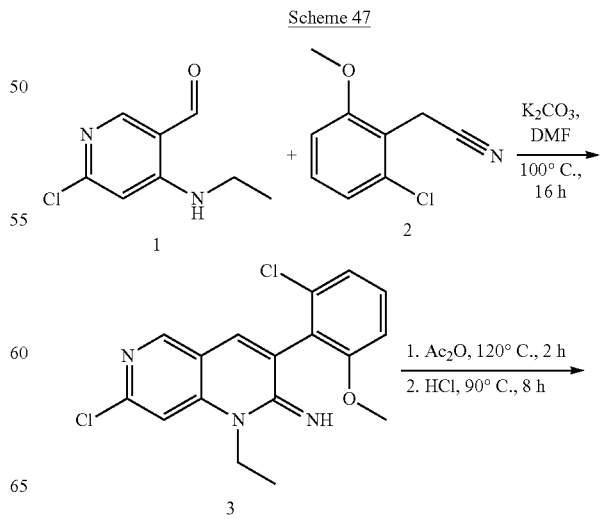

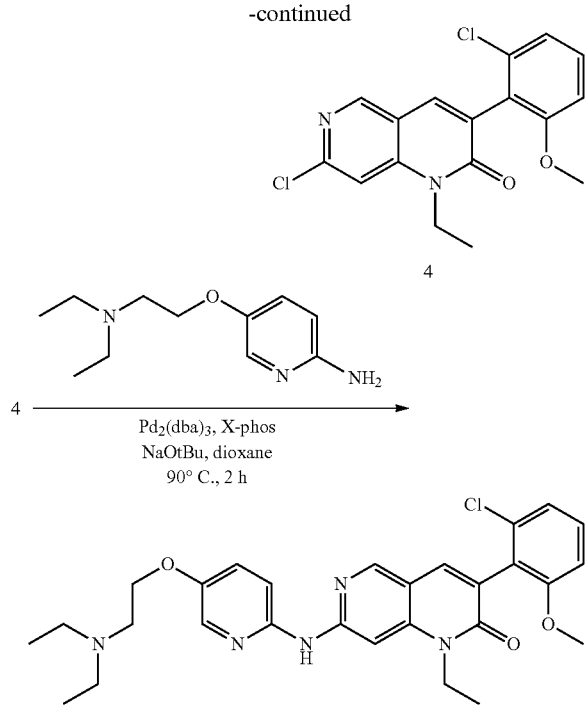

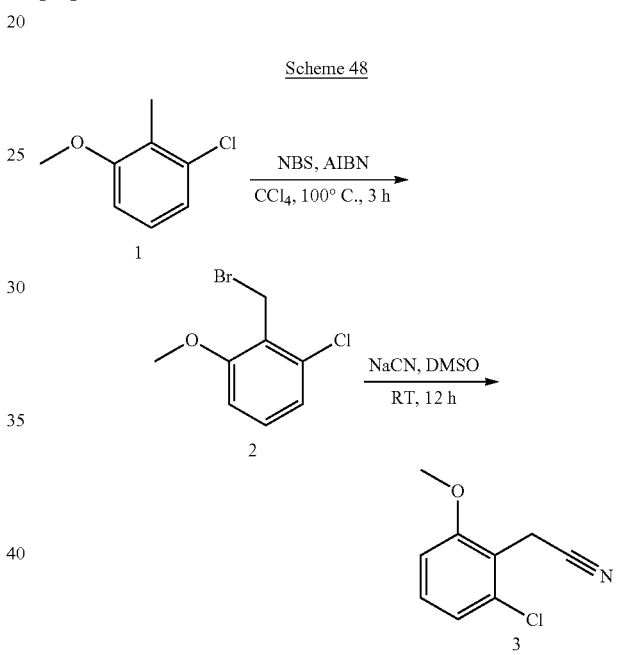

Scheme 48

A mixture of 6-chloro-4-(ethyl amino) nicotinaldehyde (Scheme 1 compound 6) (2.0 g, 10.86 mmol), 2-(2-chloro-6-methoxyphenyl)-acetonitrile (Scheme 47 compound 2) (2.5 g, 14.13 mmol) and $K_2CO_3$ (4.5 g, 32.60 mmol) in dry DMF (15 mL) was heated to 100° C. under nitrogen atmosphere for 16 h. After TLC showed the starting material was completely consumed, the reaction mixture was cooled to RT, diluted with EtOAc (100 mL), washed with water (2×30 mL) and brine (20 mL) then dried over $Na_2SO_4$ and concentrated to give a residue which was purified by flash chromatography on silica gel (eluting with petroleum ether/EtOAc 100/0 gradually increasing to 50/50) to give Scheme 47 compound 3 (1.0 g, 26%) as a brown solid. $^1$H NMR (400 MHz, DMSO-$d_6$): δ 8.43 (s, 1H), 7.50 (t, J=8.3 Hz, 1H), 7.40 (d, J=16.7 Hz, 2H), 7.20 (dd, J=18.5, 8.2 Hz, 2H), 4.27 (m, 2H), 3.75 (s, 3H), 1.19 (t, J=6.9 Hz, 3H). MS [ESI, MH$^+$]=348.02.

A solution of Scheme 47 compound 3 (1.0 g, 2.88 mmol) in $Ac_2O$ (10 mL) was stirred at 120° C. for 2 h. The reaction mixture was cooled to RT and concentrated under reduced pressure to give a crude compound which was dissolved in 6N aqueous HCl (10 mL) and stirred at 90° C. for 8 h. After TLC showed the starting material was completely consumed, the reaction mixture was neutralized with saturated aqueous $NaHCO_3$ (up to pH 3) and extracted with EtOAc (50 mL). The organic layer was washed with water (20 mL) and brine (10 mL), dried over $Na_2SO_4$ and concentrated to give a residue which was purified by flash chromatography on silica gel (eluting with petroleum ether/EtOAc 100/0 gradually increasing to 80/20) to give Scheme 47 compound 4 (800 mg, 80%) as a brown solid. MS [ESI, MH$^+$]=350.04.

Scheme 47 compound 4 (300 mg, 0.860 mmol) and 5-(2-diethylaminoethoxy)-pyridin-2-ylamine (Scheme 2 compound 4) (234 mg, 1.120 mmol) were dissolved in anhydrous dioxane (10 mL). To this mixture was added tBuONa (248 mg, 2.580 mmol), X-PHOS (99 mg, 0.172 mmol) and $Pd_2(dba)_3$ (79 mg, 0.086 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$ then filtered and concentrated to give a residue which was purified by flash chromatography on silica gel (eluting with $CH_2Cl_2$/MeOH 100/0 gradually increasing to 90/10) to give Compound 108 (35 mg, yield: 11%) as a yellow solid. $^1$H NMR (400 MHz, $CD_3OD$): δ 8.55 (s, 1H), 8.13 (t, J=1.9 Hz, 1H), 7.99 (s, 1H), 7.73 (s, 1H), 7.50 (d, J=1.9 Hz, 2H), 7.36 (t, J=8.3 Hz, 1H), 7.11 (d, J=8.1 Hz, 1H), 7.03 (d, J=8.4 Hz, 1H), 4.42 (t, J=4.9 Hz, 2H), 4.38-4.31 (m, 2H), 3.77 (s, 3H), 3.64 (t, J=4.8 Hz, 2H), 3.36 (m, 4H), 1.59-1.16 (m, 9H). MS [ESI, MH$^+$]=522.26.

The preparation of Scheme 47 intermediate 1 was described in Scheme 1 while Scheme 47 intermediate 2 was prepared as shown in Scheme 48.

A mixture of Scheme 48 compound 1 (20.0 g, 128.0 mmol), N-bromo succinimide (26.1 g, 146.0 mmol) and AIBN (210 mg, 1.3 mmol) in dry $CCl_4$ (200 mL) was heated to 100° C. under nitrogen atmosphere for 3 h. After TLC showed the starting material was completely consumed, the reaction mixture was cooled to RT and filtered through a pad of celite. The filtrate was dried over $Na_2SO_4$ and concentrated to give a residue which was purified by flash chromatography on silica gel (eluting with petroleum ether/EtOAc 100/0 gradually increasing to 80/20) to give Scheme 48 compound 2 (20 g, 66%) as a brown liquid. MS [ESI, MH$^+$]=234.94.

To a solution of Scheme 48 compound 2 (50 g, 212.7 mmol) in dry DMSO (500 mL) was added NaCN (22 g, 446.0 mmol) and the reaction mixture was stirred at RT for 12 h. After TLC showed the starting material was completely consumed, the mixture was quenched with water (200 mL) and extracted with ethyl acetate (2×100 mL). The organic layer was washed with brine (10 mL), dried over $Na_2SO_4$ filtered and concentrated to give a residue which was purified by flash chromatography on silica gel (eluting with petroleum ether/EtOAc 100/0 gradually increasing to 70/30) to give Scheme 48 compound 3 (20 g, 66%) as a brown solid. ¹H NMR (400 MHz, CDCl₃): δ 7.29-7.20 (m, 1H), 7.04 (dd, J=8.1, 1.1 Hz, 1H), 6.83 (dd, J=8.4, 1.1 Hz, 1H), 3.90 (s, 3H), 3.85 (s, 2H). MS [ESI, MH⁺]=182.03.

Example 59

Synthesis of Compound 109

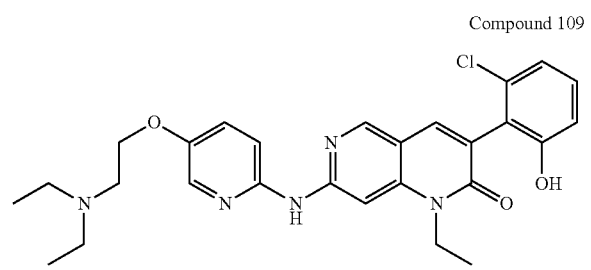 [SMILES: CCN(CC)CCOc1ccc(Nc2cc3c(cn2)cc(-c2c(O)cccc2Cl)c(=O)n3CC)nc1]

Compound 109

Compound 109, 3-(2-chloro-6-hydroxyphenyl)-7-((5-(2-(diethylamino)ethoxy)pyridin-2-yl)amino)-1-ethyl-1,6-naphthyridin-2(1H)-one was prepared following Scheme 49.

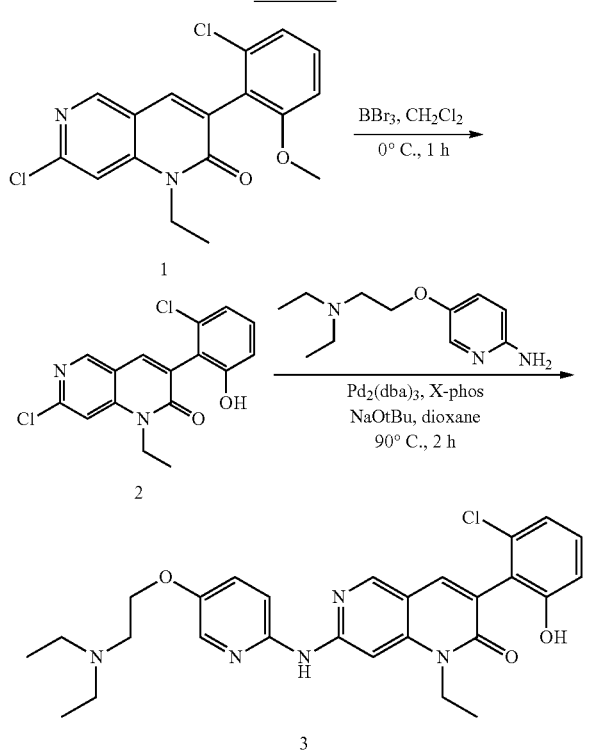

Scheme 49

The preparation of Scheme 49 intermediate 1 is described in Scheme 47.

To a cooled (0° C.) solution of Scheme 49 compound 1 (6 g, 17.24 mmol) in dry CH₂Cl₂ (60 mL) was added BBr₃ (5 mL, 34.40 mmol) dropwise and the reaction mixture was stirred at 0° C. for 1 h. After TLC showed the starting material was completely consumed, the reaction mixture was diluted with water (30 mL) and extracted with CH₂Cl₂ (100 mL). The organic layer was washed with water (20 mL) and brine (20 mL) then dried over Na₂SO₄ and concentrated to give a residue which was purified by flash chromatography on silica gel (eluting with petroleum ether/EtOAc 100/0 gradually increasing to 70/30) to give Scheme 49 compound 2 (5 g, 87%) as a yellow solid. ¹H NMR (400 MHz, DMSO-d₆): δ 9.90 (s, 1H), 8.77 (s, 1H), 7.98 (s, 1H), 7.75 (s, 1H), 7.24 (t, J=8.1 Hz, 1H), 6.98 (d, J=7.9 Hz, 1H), 6.90 (d, J=8.3 Hz, 1H), 4.28 (m, 2H), 1.21 (t, J=7.1 Hz, 4H). MS [ESI, MH⁺]=335.03.

Scheme 49 compound 2 (300 mg, 0.898 mmol) and 5-(2-diethylaminoethoxy)-pyridin-2-ylamine (Scheme 2 compound 4) (280 mg, 1.340 mmol) were dissolved in anhydrous dioxane (10 mL). To this mixture was added tBuONa (260 mg, 2.690 mmol), X-PHOS (100 mg, 0.179 mmol) and Pd₂(dba)₃ (80 mg, 0.089 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na₂SO₄ then filtered and concentrated to give a residue which was purified by flash chromatography on silica gel (eluting with CH₂Cl₂/MeOH 100/0 gradually increasing to 90/10) to give Compound 109 (35 mg, yield: 11%) as a yellow solid. ¹H NMR (400 MHz, CD₃OD): δ 8.52 (s, 1H), 8.05 (d, J=2.8 Hz, 1H), 8.01 (s, 1H), 7.73 (s, 1H), 7.48-7.36 (m, 2H), 7.17 (t, J=8.1 Hz, 1H), 6.97 (dd, J=8.0, 1.1 Hz, 1H), 6.84 (dd, J=8.1, 1.1 Hz, 1H), 4.35 (m, 2H), 4.20 (t, J=5.5 Hz, 2H), 3.04 (t, J=5.6 Hz, 2H), 2.80 (m, 4H), 1.40 (t, J=7.1 Hz, 3H), 1.15 (t, J=7.2 Hz, 6H). MS [ESI, MH⁺]=508.22.

Synthesis of Compound 122

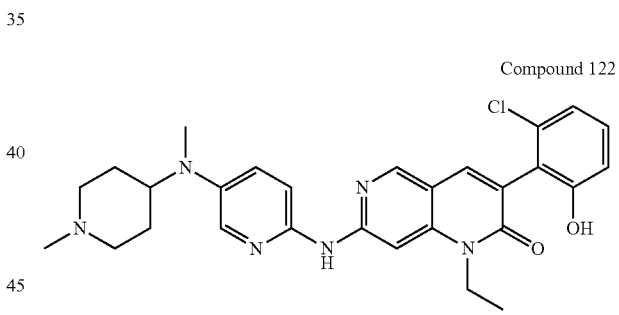

Compound 122

Compound 122, 3-(2-chloro-6-hydroxyphenyl)-1-ethyl-7-((5-(methyl(1-methylpiperidin-4-yl)amino)pyridin-2-yl)amino)-1,6-naphthyridin-2(1H)-one was synthesized in a similar manner as Compound 109 using Scheme 49 compound 2 and N⁵-methyl-N⁵-(1-methylpiperidin-4-yl)pyridine-2,5-diamine in the cross-coupling step.

Scheme 49 compound 2 (290 mg, 0.86 mmol) and N⁵-methyl-N⁵-(1-methylpiperidin-4-yl)pyridine-2,5-diamine (Scheme 43 compound 4) (230 mg, 1.04 mmol) were dissolved in anhydrous dioxane (8 mL). To this mixture was added tBuONa (250 mg, 2.60 mmol), X-PHOS (100 mg, 0.17 mmol) and Pd₂(dba)₃ (79 mg, 0.09 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na₂SO₄ then filtered and concentrated to give a residue which was purified by flash chromatography on silica gel (eluting with CH₂Cl₂/MeOH 100/0 gradually increasing to 90/10) to give Compound 122 (50 mg, yield: 11%) as a yellow solid. ¹H NMR (300 MHz, CD₃OD): δ 8.49 (s, 1H), 7.96 (dd, J=2.6, 1.1 Hz, 1H), 7.85 (s, 1H), 7.71 (s, 1H), 7.47-7.34 (m, 2H), 7.17 (t, J=8.1 Hz, 1H), 6.97 (dd, J=8.1, 1.1 Hz, 1H), 6.84 (dd, J=8.2, 1.1 Hz, 1H), 4.41-4.11 (m, 2H), 3.60 (d, J=5.0 Hz, 1H), 3.13 (d, J=11.8 Hz, 2H), 2.81 (s, 3H), 2.46 (s, 5H), 1.98-1.68 (m, 4H), 1.39 (t, J=7.0 Hz, 3H). MS [ESI, MH⁺]=519.21.

Example 60

Synthesis of Compound 110

Compound 110

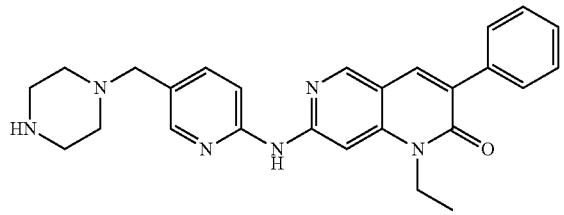

Compound 110, 1-ethyl-3-phenyl-7-((5-(piperazin-1-yl-methyl)pyridin-2-yl)amino)-1,6-naphthyridin-2(1H)-one was prepared from 7-chloro-1-ethyl-3-phenyl-1,6-naphthyridin-2(1H)-one (Scheme 1 compound 8) using 5-(piperazin-1-ylmethyl)pyridin-2-amine in the final cross-coupling step described in Scheme 40.

Scheme 1 compound 8 (500 mg, 1.760 mmol) and 5-(piperazin-1-ylmethyl)pyridin-2-amine (Scheme 50 compound 7) (960 mg, 2.290 mmol) were dissolved in anhydrous dioxane (20 mL). To this mixture was added tBuONa (840 mg, 8.800 mmol), X-PHOS (203 mg, 0.352 mmol) and Pd₂(dba)₃ (161 mg, 0.176 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL) and dried over Na₂SO₄ then filtered and concentrated to give a residue which was purified by flash chromatography on silica gel (eluting with CH₂Cl₂/MeOH 100/0 gradually increasing to 90/10) to give Compound 110 (250 mg, yield: 32%) as a yellow solid. ¹H NMR (400 MHz, DMSO-d₆): δ 10.08 (s, 1H), 8.67 (s, 1H), 8.23-8.13 (m, 2H), 8.07 (s, 1H), 7.69 (d, J=7.6 Hz, 2H), 7.64 (dd, J=8.5, 2.2 Hz, 1H), 7.56 (d, J=8.5 Hz, 1H), 7.44 (t, J=7.5 Hz, 2H), 7.37 (t, J=7.2 Hz, 1H), 4.25 (m, 2H), 3.45 (s, 2H), 2.90 (t, J=4.8 Hz, 4H), 2.44 (s, 4H), 1.32 (t, J=7.0 Hz, 3H). MS [ESI, MH⁺]=439.30.

5-(piperazin-1-ylmethyl)pyridin-2-amine was synthesized as the di-TFA salt as shown in Scheme 50

Scheme 50

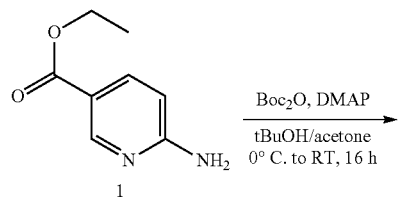

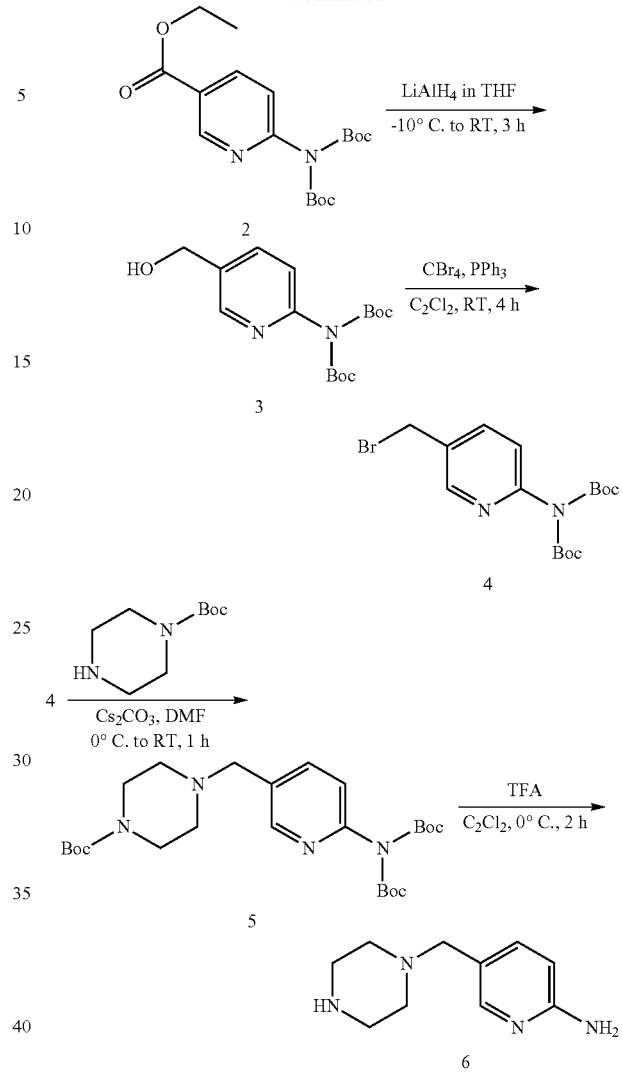

To a cooled (0° C.) solution of Scheme 50 compound 1 (6.5 g, 39.15 mmol) in dry tBuOH (70 mL) and acetone (20 mL) were added DMAP (62 mg, 0.50 mmol) and (Boc)₂O (25.6 g, 117.60 mmol) and the reaction mixture was stirred at RT for 16 h. After TLC showed the starting material was completely consumed, the reaction mixture was concentrated, diluted with EtOAc (20 mL), washed with water (2×10 mL) and brine (10 mL) then dried over Na₂SO₄ and concentrated to give a residue which was purified by flash chromatography on silica gel (eluting with petroleum ether/EtOAc 100/0 gradually increasing to 70/30) to give Scheme 50 compound 2 (10 g, 71%) as an off-white solid. MS [ESI, MH⁺]=367.18.

To a cooled (−10° C.) solution of Scheme 50 compound 2 (10.0 g, 27.3 mmol) in dry THF (100 mL) was added LiAlH₄ (1.7 g, 50.0 mmol) portionwise over a period of 30 min. The reaction mixture was slowly warmed to RT and stirred for 3 h. After TLC showed the starting material was completely consumed, the reaction mixture was quenched with saturated ammonium chloride solution (10 mL) and passed through a pad of celite then washed with EtOAc (2×30 mL). The filtrate was washed with water (2×5 mL) and brine (2×5 mL) then dried over Na₂SO₄ and concentrated to give a residue which was purified by flash chromatography on silica gel (eluting with petroleum ether/ EtOAc 100/0 gradually increasing to 60/40) to give Scheme 50 compound 3 (3.8 g, 634%) as an off-white solid. MS [ESI, MH$^+$]=325.15.

To a cooled (0° C.) solution of Scheme 50 compound 3 (3.8 g, 11.76 mmol) in dry CH$_2$Cl$_2$ (40 mL) were added TPP (3.3 g, 12.67 mmol) and CBr$_4$ (6.5 g, 19.82 mmol) and the reaction mixture was stirred at RT for 4 h. After TLC showed the starting material was completely consumed, the reaction mixture was diluted with CH$_2$Cl$_2$ (20 mL), washed with water (2×10 mL) and brine (10 mL) then dried over Na$_2$SO$_4$ and concentrated to give a residue which was purified by flash chromatography on silica gel (eluting with petroleum ether/EtOAc 100/0 gradually increasing to 90/20) to give Scheme 50 compound 4 (800 mg, 72%) as a colorless liquid. MS [ESI, MH$^+$]=387.02.

To a cooled (0° C.) solution of Scheme 50 compound 4 (300 mg, 0.778 mmol) and tent-butyl piperazine-1-carboxylate (158 mg, 0.854 mmol) in dry DMF (8 mL) was added Cs$_2$CO$_3$ (605 mg, 1.550 mmol) and the reaction mixture was stirred at RT for 1 h. After TLC showed the starting material was completely consumed, the reaction mixture was diluted with water (20 mL) and extracted with EtOAc (30 mL). The organic layer was washed with water (10 mL) and brine (10 mL) then dried over Na$_2$SO$_4$ and concentrated to give Scheme 50 compound 5 (280 mg, 73%) as a brown solid. MS [ESI, MH$^+$]=493.5.

To a cooled (0° C.) solution of Scheme 50 compound 5 (280 mg, 0.57 mmol) in dry CH$_2$Cl$_2$ (3 mL) was added TFA (2 mL) and the reaction mixture was stirred at RT for 2 h. After TLC showed the starting material was completely consumed, the reaction mixture was concentrated under reduced pressure to give Scheme 50 compound 6 (200 mg, semi-pure) as a brown solid. $^1$H NMR (400 MHz, DMSO-d$_6$): δ 8.90 (s, 2H), 7.99 (s, 1H), 7.87 (s, 1H), 7.80 (dd, J=8.7, 2.1 Hz, 1H), 6.92 (d, J=9.0 Hz, 1H), 3.42 (s, 2H), 3.09 (t, J=5.1 Hz, 4H), 2.58 (s, 4H). MS [ESI, MH$^+$]=193.0.

Example 61

Synthesis of Compound 111

Compound 111

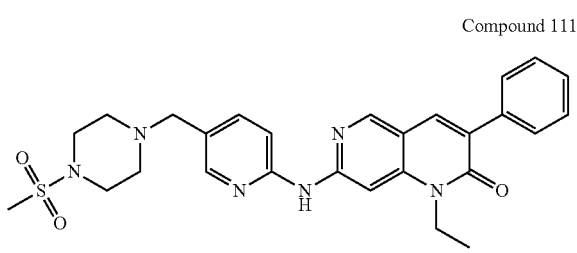 [SMILES: CCn1c(=O)c(-c2ccccc2)cc2cnc(Nc3ccc(CN4CCN(S(C)(=O)=O)CC4)cn3)cc21]

Compound 111, 1-ethyl-7-((5-((4-(methylsulfonyl)piperazin-1-yl)methyl)pyridin-2-yl)amino)-3-phenyl-1,6-naphthyridin-2(1H)-one was synthesized as shown in Scheme 51.

Scheme 51

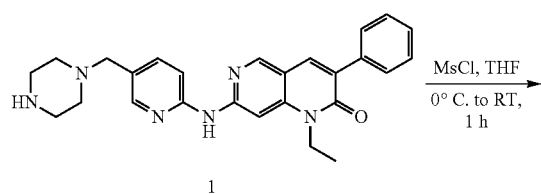

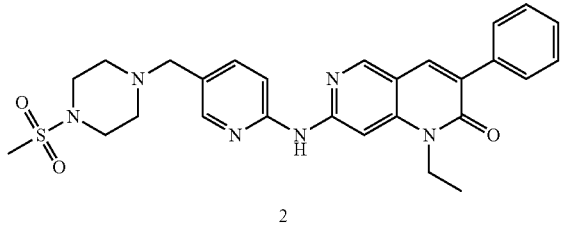

The preparation of Scheme 51 intermediate 1 is described in the preparation of Compound 110.

To a cooled (0° C.) stirred solution of Compound 110 (120 mg, 0.272 mmol) in dry THF (3 mL) was added methane sulfonyl chloride (31 mg, 0.272 mmol) dropwise and the reaction mixture was stirred at RT for 1 h. After TLC showed the starting material was completely consumed, the reaction mixture was diluted with water (30 mL) and extracted with EtOAc (10 mL). The organic layer was washed with water (5 mL) and brine (5 mL) then dried over Na$_2$SO$_4$ and concentrated to give a residue which was purified by flash chromatography on silica gel (eluting with CH$_2$Cl$_2$/MeOH 100/0 gradually increasing to 90/10) to give Compound 111 (40 mg, yield: 28%) as a yellow solid. $^1$H NMR (400 MHz, CDCl$_3$): δ 8.50 (s, 1H), 8.25 (d, J=2.3 Hz, 1H), 8.16 (s, 1H), 7.75 (s, 1H), 7.73-7.66 (m, 2H), 7.61 (dd, J=8.6, 2.3 Hz, 1H), 7.51 (d, J=12.3 Hz, 1H), 7.46-7.41 (m, 2H), 7.40-7.34 (m, 1H), 7.14 (d, J=8.4 Hz, 1H), 4.40 (m, 2H), 3.53 (s, 2H), 3.26 (t, J=4.8 Hz, 4H), 2.79 (s, 3H), 2.59 (t, J=4.9 Hz, 4H), 1.45 (t, J=7.1 Hz, 3H). MS [ESI, MH$^+$]=519.17.

Synthesis of Compound 112

Compound 112

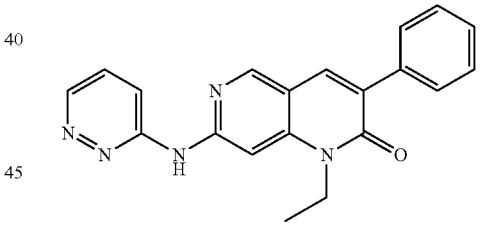

Compound 112, 1-ethyl-3-phenyl-7-(pyridazin-3-ylamino)-1,6-naphthyridin-2(1H)-one was synthesized in a similar manner as Compound 110 using pyridazin-3-amine in the cross-coupling step.

Scheme 1 compound 8 (200 mg, 0.70 mmol) and pyridazin-3-amine (100 mg, 1.05 mmol) were dissolved in anhydrous dioxane (20 mL). To this mixture was added tBuONa (133 mg, 2.11 mmol), X-PHOS (81 mg, 0.14 mmol) and Pd$_2$(dba)$_3$ (64 mg, 0.07 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over Na$_2$SO$_4$ then filtered and concentrated to give a residue which was purified by flash chromatography on silica gel (eluting with CH$_2$Cl$_2$/MeOH 100/0 gradually increasing to 90/10) to give Compound 112 (80 mg, yield: 33%) as a pale yellow solid. $^1$H NMR (400 MHz, DMSO-d$_6$): δ 10.41 (s, 1H), 8.82 (d, J=4.6 Hz, 1H), 8.71 (s, 1H), 8.11 (s, 1H), 8.01 (d, J=10.1 Hz, 2H), 7.70 (d, J=7.4 Hz, 2H), 7.60 (dd, J=9.0, 4.5 Hz, 1H), 7.41 (m, 3H), 4.25 (m, 2H), 1.32 (t, J=7.1 Hz, 3H). MS [ESI, MH$^+$]=344.12.

Synthesis of Compound 113

Compound 113

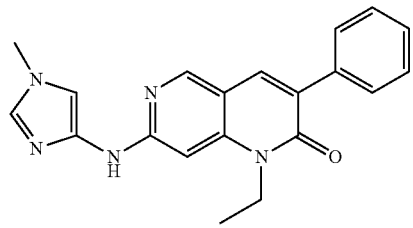

Compound 113, 1-ethyl-7-((1-methyl-1H-imidazol-4-yl) amino)-3-phenyl-1,6-naphthyridin-2(1H)-one was synthesized in a similar manner as Compound 110 using 1-methyl-1H-imidazol-4-amine in the cross-coupling step.

Scheme 1 compound 8 (500 mg, 1.76 mmol) and 1-methyl-1H-imidazol-4-amine (205 mg, 2.110 mmol) were dissolved in anhydrous dioxane (10 mL). To this mixture was added tBuONa (507 mg, 5.280 mmol), X-PHOS (203 mg, 0.352 mmol) and Pd$_2$(dba)$_3$ (161 mg, 0.176 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over Na$_2$SO$_4$ then filtered and concentrated to give a residue which was purified by flash chromatography on silica gel (eluting with CH$_2$Cl$_2$/MeOH 100/0 gradually increasing to 95/05) to give Compound 113 (80 mg, yield: 13%) as a pale yellow solid. $^1$H NMR (400 MHz, DMSO-d$_6$): δ 9.48 (s, 1H), 8.57 (s, 1H), 7.99 (s, 1H), 7.71-7.59 (m, 2H), 7.46-7.38 (m, 3H), 7.37-7.30 (m, 1H), 7.24 (s, 1H), 6.95 (s, 1H), 4.14 (m, 2H), 3.65 (s, 3H), 1.25 (t, J=6.9 Hz, 3H). MS [ESI, MH$^+$]=346.16.

Synthesis of Compound 114

Compound 114

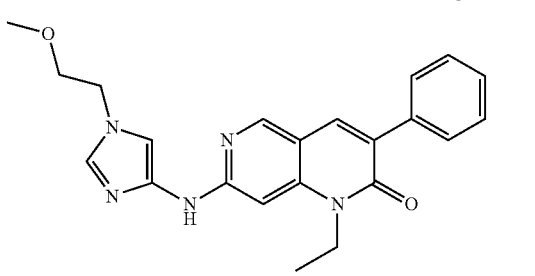

Compound 114, 1-ethyl-7-((1-(2-methoxyethyl)-1H-imidazol-4-yl)amino)-3-phenyl-1,6-naphthyridin-2(1H)-one was synthesized in a similar manner as Compound 110 using 1-(2-methoxyethyl)-1H-imidazol-4-amine in the cross-coupling step, which was prepared according to Scheme 52.

Scheme 1 compound 8 (500 mg, 1.76 mmol) and 1-(2-methoxyethyl)-1H-imidazol-4-amine (992 mg, 7.040 mmol) were dissolved in anhydrous dioxane (10 mL). To this mixture was added tBuONa (507 mg, 5.280 mmol), X-PHOS (203 mg, 0.352 mmol) and Pd$_2$(dba)$_3$ (161 mg, 0.176 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over Na$_2$SO$_4$ then filtered and concentrated to give a residue which was purified by flash chromatography on silica gel (eluting with CH$_2$Cl$_2$/MeOH 100/0 gradually increasing to 95/5) to give Compound 114 (80 mg, yield: 13%) as a pale yellow solid. $^1$H NMR (400 MHz, CDCl$_3$): δ 8.47 (s, 1H), 7.73-7.65 (m, 3H), 7.48-7.31 (m, 4H), 7.26 (s, 4H), 7.19 (d, J=1.5 Hz, 1H), 6.65 (s, 1H), 4.28 (m, 2H), 4.11 (t, J=5.1 Hz, 2H), 3.70 (t, J=5.1 Hz, 2H), 3.39 (s, 3H), 1.37 (t, J=7.1 Hz, 3H). MS [ESI, MH$^+$]=390.22.

Scheme 52

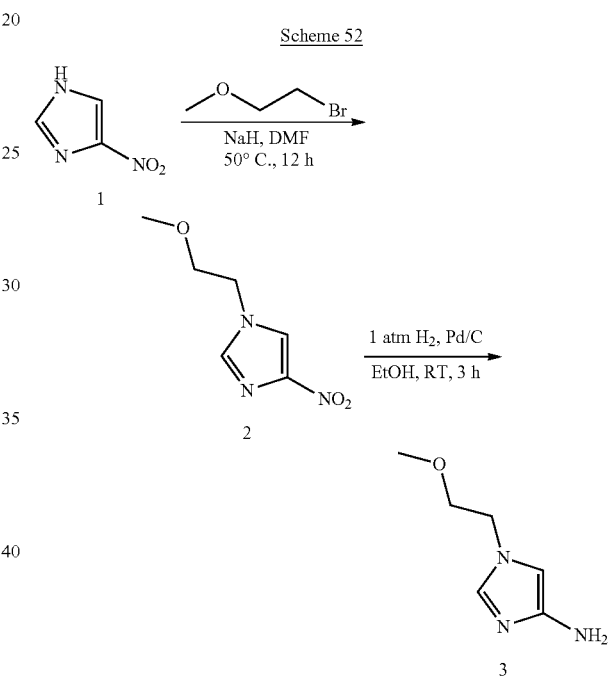

To a stirred solution of Scheme 52 compound 1 (1.00 g, 8.84 mmol) in dry DMF (5 mL) was added NaH (254 mg, 10.61 mmol, 50-60% in oil) portion wise, followed after 15 min of stirring by 1-bromo-2-methoxyethane (1.23 g, 8.84 mmol). The reaction mixture was stirred at 50° C. for 12 h. After TLC showed the starting material was completely consumed, the reaction mixture was diluted with water (30 mL) and extracted with EtOAc (10 mL). The organic layer was washed with water (5 mL) and brine (5 mL) then dried over Na$_2$SO$_4$ and concentrated to give a residue which was purified by flash chromatography on silica gel (eluting with CH$_2$Cl$_2$/MeOH 100/0 gradually increasing to 95/5) to give Scheme 52 compound 2 (800 mg, 53%) as a yellow solid. MS [ESI, MH$^+$]=172.07.

Scheme 52 compound 2 (500 mg, 2.92 mmol) in MeOH (20 mL) was treated with 10% Pd/C (70 mg) and kept under H$_2$ atmosphere (balloon pressure) at RT for 3 h. After TLC showed the starting material was completely consumed, the reaction mixture was passed through a pad of celite. The filtrate was evaporated under reduced pressure to give a residue which was purified by flash chromatography on silica gel (eluting with CH$_2$Cl$_2$/MeOH 100/0 gradually increasing to 90/10) to give Scheme 52 compound 3 (300 mg, 73%) as a dark solid. $^1$H NMR (400 MHz, DMSO-$d_6$): δ 7.09 (d, J=1.5 Hz, 1H), 6.15 (d, J=1.6 Hz, 1H), 4.08 (s, 2H), 3.91 (t, J=5.2 Hz, 2H), 3.51 (t, J=5.2 Hz, 2H), 3.23 (s, 3H). MS [ESI, MH$^+$]=142.05.

Example 62

Synthesis of Compound 116

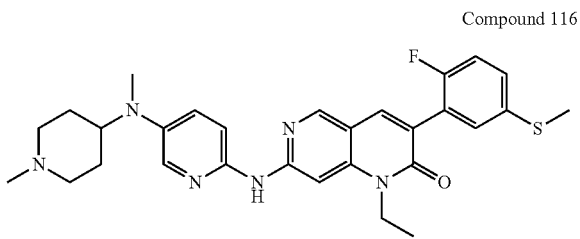

Compound 116

Compound 116, 1-ethyl-3-(2-fluoro-5-(methylthio)phenyl)-7-((5-(methyl(1-methylpiperidin-4-yl)amino)pyridin-2-yl)amino)-1,6-naphthyridin-2(1H)-one was synthesized following the general procedure shown in Scheme 53 using 2-(2-fluoro-5-(methylthio)phenyl)acetonitrile in the naphthyridinimine formation step.

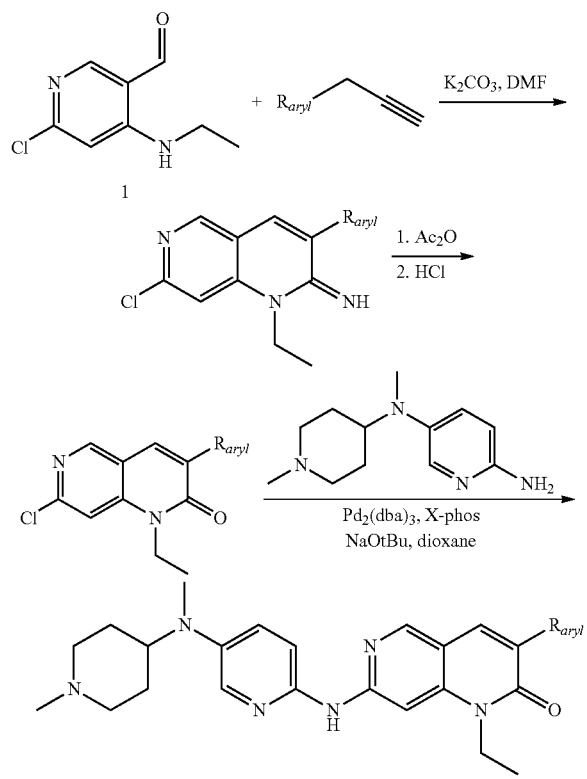

Scheme 53

A mixture of 6-chloro-4-(ethylamino)nicotinaldehyde (Scheme 1 compound 6) (1.8 g, 9.78 mmol), 2-(2-fluoro-5-(methylthio)phenyl)acetonitrile (2.1 g, 11.73 mmol) and K$_2$CO$_3$ (4.0 g, 29.34 mmol) in dry DMF (20 mL) was heated to 100° C. under nitrogen atmosphere for 16 h. After TLC showed the starting material was completely consumed, the reaction mixture was cooled to RT, diluted with EtOAc (100 mL), washed with water (2×30 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give 7-chloro-1-ethyl-3-(2-fluoro-5-(methylthio)phenyl)-1,6-naphthyridin-2(1H)-imine (2.0 g, 61%) as a brown solid. $^1$H NMR (400 MHz, DMSO-$d_6$): δ 8.49 (s, 1H), 7.72-7.58 (m, 1H), 7.50 (s, 1H), 7.47-7.39 (m, 1H), 7.37-7.28 (m, 2H), 4.30 (m, 2H), 2.52 (s, 3H), 1.20 (m, 5H). MS [ESI, MH$^+$]=348.5.

A solution of 7-chloro-1-ethyl-3-(2-fluoro-5-(methylthio)phenyl)-1,6-naphthyridin-2(1H)-imine (3.0 g, 8.64 mmol) in Ac$_2$O (30 mL) was stirred at 120° C. for 2 h. The reaction mixture was cooled to RT and concentrated under reduced pressure to give a crude compound which was dissolved in 6N aqueous HCl (30 mL) and stirred at 90° C. for 8 h. After TLC showed the starting material was completely consumed, the reaction mixture was neutralized with saturated aqueous NaHCO$_3$ (up to pH 3) and extracted with EtOAc (50 mL). The organic layer was washed with water (20 mL) and brine (10 mL), dried over Na$_2$SO$_4$ then concentrated to give a residue which was purified by flash chromatography on silica gel (eluting with petroleum ether/EtOAc 100/0 gradually increasing to 80/20) to give 7-chloro-1-ethyl-3-(2-fluoro-5-(methylthio)phenyl)-1,6-naphthyridin-2(1H)-one (1.8 g, 60%) as an off-white solid. MS [ESI, MH$^+$]=349.05.

7-Chloro-1-ethyl-3-(2-fluoro-5-(methylthio)phenyl)-1,6-naphthyridin-2(1H)-one (300 mg, 0.86 mmol) and N$^5$-methyl-N$^5$-(1-methylpiperidin-4-yl)pyridine-2,5-diamine (Scheme 43 compound 4) (220 mg, 1.29 mmol) were dissolved in anhydrous dioxane (10 mL). To this mixture was added tBuONa (248 mg, 2.50 mmol), X-PHOS (99 mg, 0.17 mmol) and Pd$_2$(dba)$_3$ (79 mg, 0.09 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 116 (150 mg, yield: 33%) as a yellow solid. $^1$H NMR (400 MHz, DMSO-$d_6$): δ 9.73 (s, 1H), 8.58 (s, 1H), 7.96 (d, J=6.9 Hz, 2H), 7.89 (d, J=3.0 Hz, 1H), 7.48 (d, J=9.0 Hz, 1H), 7.35 (m, 3H), 7.24 (t, J=9.2 Hz, 1H), 4.20 (q, J=7.0 Hz, 2H), 3.48 (tt, J=11.6, 3.8 Hz, 1H), 2.83 (d, J=10.9 Hz, 2H), 2.71 (s, 3H), 2.17 (s, 3H), 2.06-1.90 (m, 2H), 1.71 (m, 2H), 1.58 (d, J=11.6 Hz, 2H), 1.30 (t, J=7.0 Hz, 3H). MS [ESI, MH$^+$]=533.28.

2-(2-Fluoro-5-(methylthio)phenyl)acetonitrile was synthesized following Scheme 54.

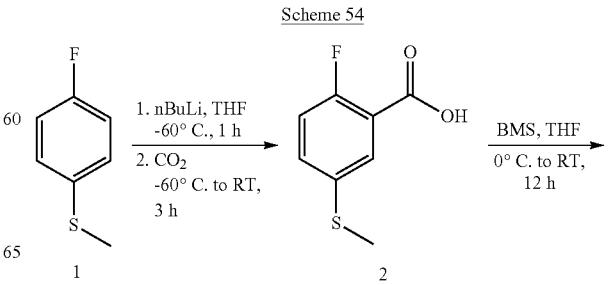

Scheme 54

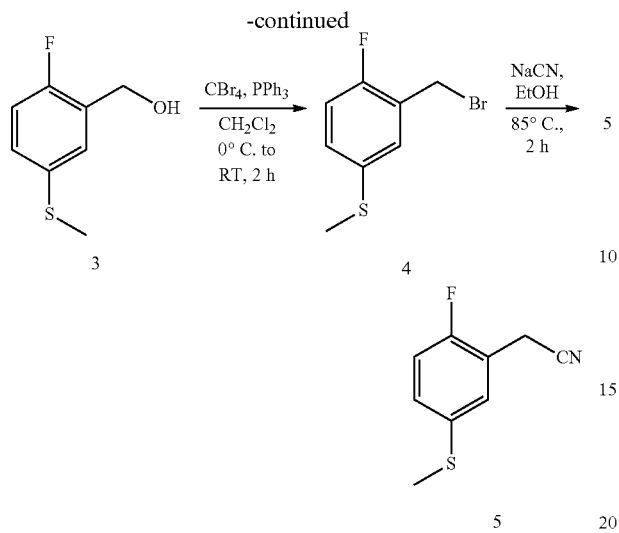

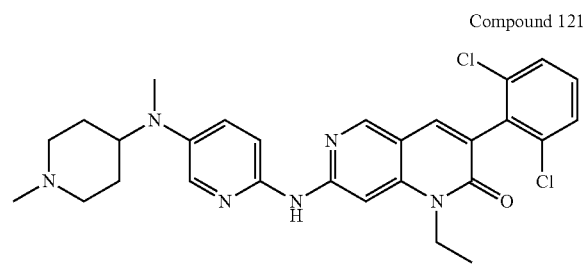 [SMILES: CCn1c(=O)c(-c2c(Cl)cccc2Cl)cc2cnc(Nc3ccc(N(C)C4CCN(C)CC4)cn3)cc21]

Compound 121

To a cooled (−60° C.) solution of Scheme 54 compound 1 (5.0 g, 35.66 mmol) in dry THF (50 mL) was added nBuLi (21.9 mL, 35.66 mmol, 1.6 M in THF) dropwise. The reaction mixture was stirred at −60° C. for 1 h after which time $CO_2$ gas was passed through while the solution was allowed to warm to RT and stirred for 3 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$ then filtered and concentrated to give a residue which was purified by flash chromatography on silica gel (eluting with petroleum ether/EtOAc 100/0 gradually increasing to 80/20) to give Scheme 54 compound 2 (5 g, 76%) as an off-white solid. MS [ESI, (M-H)$^-$]=185.3.

To a cooled (0° C.) solution of Scheme 54 compound 2 (5 g, 26.80 mmol) in dry THF (50 mL) was added $BH_3$.DMS (33.5 mL, 67.20 mmol) and the reaction mixture was stirred at RT for 12 h. After TLC showed the starting material was completely consumed, the reaction mixture was diluted with ice water (30 mL) and extracted with EtOAc (2×50 mL). The organic layer was washed with brine (20 mL), dried over $Na_2SO_4$ then concentrated to give a residue which was purified by flash chromatography on silica gel (eluting with petroleum ether/EtOAc 100/0 gradually increasing to 80/20) to give Scheme 54 compound 3 (3.4 g, 86%) as a colorless liquid. MS [ESI, MH$^+$]=173.04.

To a cooled (0° C.) stirred solution of Scheme 54 compound 3 (3.5 g, 20.34 mmol) in dry $CH_2Cl_2$ (35 mL) was added $PPh_3$ (8.0 g, 30.52 mmol) and $CBr_4$ (10.0 g, 30.52 mmol) and the reaction mixture was stirred at RT for 2 h. After TLC showed the starting material was completely consumed, the reaction mixture was concentrated under reduced pressure to give a residue which was purified by flash chromatography on silica gel (eluting with petroleum ether/EtOAc 100/0 gradually increasing to 90/10) to give Scheme 54 compound 4 (4 g, 85%) as a colorless liquid. MS [ESI, MH$^+$]=235.0.

To a solution of Scheme 54 compound 4 (4.0 g, 17.02 mmol) in dry EtOH (40 mL) was added NaCN (898 mg, 18.72 mmol) and the reaction mixture was stirred at 85° C. for 2 h. After TLC showed the starting material was completely consumed, the reaction mixture was concentrated to give a crude compound which was diluted with ice water (30 mL) and extracted with EtOAc (2×50 mL). The organic layer was washed with brine (20 mL) then dried over $Na_2SO_4$ and concentrated to give Scheme 54 compound 5 (2 g, 77%) as a colorless liquid. $^1$H NMR (400 MHz, CDCl$_3$): δ 7.37-7.29 (m, 1H), 7.25-7.18 (m, 1H), 7.04 (t, J=9.0 Hz, 1H), 3.75 (s, 2H), 2.49 (d, J=1.2 Hz, 3H). MS [ESI, (M-H)$^-$]=180.0.

Synthesis of Compound 121

Compound 121, 3-(2,6-dichlorophenyl)-1-ethyl-7-((5-(methyl(1-methylpiperidin-4-yl)amino)pyridin-2-yl)amino)-1,6-naphthyridin-2(1H)-one was synthesized in a similar manner as Compound 116 using 2-(2,6-dichlorophenyl)acetonitrile in the naphthyridinimine formation step.

A mixture of 6-chloro-4-(ethyl amino) nicotinaldehyde (Scheme 1 compound 6) (1.20 g, 6.52 mmol), 2-(2,6-dichlorophenyl)acetonitrile (1.57 g, 8.47 mmol) and $K_2CO_3$ (2.70 g, 19.56 mmol) in dry DMF (12 mL) was heated to 100° C. under nitrogen atmosphere for 16 h. After TLC showed the starting material was completely consumed, the reaction mixture was cooled to RT, diluted with EtOAc (100 mL), washed with water (2×30 mL) and brine (20 mL) then dried over $Na_2SO_4$ and concentrated to give a residue which was purified by flash chromatography on silica gel (eluting with petroleum ether/EtOAc 100/0 gradually increasing to 70/30) to give 7-chloro-3-(2,6-dichlorophenyl)-1-ethyl-1,6-naphthyridin-2(1H)-imine (1.5 g, 45%) as a black gummy solid. $^1$H NMR (400 MHz, DMSO-d$_6$): δ 8.45 (d, J=4.7 Hz, 1H), 7.66 (d, J=8.1 Hz, 2H), 7.56 (t, J=7.2 Hz, 1H), 7.50 (s, 1H), 7.45 (s, 1H), 6.85 (d, J=10.0 Hz, 1H), 4.30 (s, 2H), 1.22-1.16 (m, 3H). MS [ESI, MH$^+$]=352.05.

A solution of 7-chloro-3-(2,6-dichlorophenyl)-1-ethyl-1,6-naphthyridin-2(1H)-imine (1.5 g, 4.27 mmol) in $Ac_2O$ (15 mL) was stirred at 120° C. for 2 h. The reaction mixture was cooled to RT and concentrated under reduced pressure to give a crude compound which was dissolved in 6N aqueous HCl (15 mL) and stirred at 90° C. for 8 h. After TLC showed the starting material was completely consumed, the reaction mixture was neutralized with saturated aqueous $NaHCO_3$ (up to pH 3) and extracted with EtOAc (50 mL). The organic layer was washed with water (20 mL) and brine (10 mL) then dried over $Na_2SO_4$ and concentrated to give a residue which was purified by flash chromatography on silica gel (eluting with petroleum ether/EtOAc 100/0 gradually increasing to 80/20) to give 7-chloro-3-(2,6-dichlorophenyl)-1-ethyl-1,6-naphthyridin-2(1H)-one (800 mg, 53%) as pale yellow solid. MS [ESI, MH$^+$]=353.05.

7-Chloro-3-(2,6-dichlorophenyl)-1-ethyl-1,6-naphthyridin-2(1H)-one (300 mg, 0.86 mmol) and $N^5$-methyl-$N^5$-(1-methylpiperidin-4-yl)pyridine-2,5-diamine (Scheme 43 compound 4) (225 mg, 1.02 mmol) were dissolved in anhydrous dioxane (8 mL). To this mixture was added tBuONa (245 mg, 2.50 mmol), X-PHOS (98 mg, 0.09 mmol) and Pd$_2$(dba)$_3$ (78 mg, 0.09 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$ then filtered and concentrated to give a residue which was purified by flash chromatography on silica gel (eluting with $CH_2Cl_2$/MeOH 100/0 gradually increasing to 90/10) to give Compound 121 (39 mg, yield: 9%) as a yellow solid. $^1$H NMR (400 MHz, DMSO-$d_6$): δ 9.78 (s, 1H), 8.58 (s, 1H), 7.99 (s, 1H), 7.92-7.82 (m, 2H), 7.58 (d, J=8.1 Hz, 2H), 7.52-7.41 (m, 2H), 7.34 (dd, J=9.1, 3.0 Hz, 1H), 4.20 (m, 2H), 3.48 (m, 1H), 2.82 (d, J=10.9 Hz, 2H), 2.71 (s, 3H), 2.17 (s, 3H), 1.99 (dd, J=12.6, 10.1 Hz, 2H), 1.81-1.59 (m, 2H), 1.57 (d, J=11.3 Hz, 2H), 1.29 (t, J=7.0 Hz, 3H). MS [ESI, MH$^+$]=537.21.

Example 63

Synthesis of Compound 117

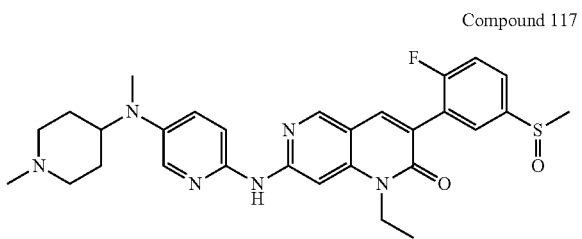

Compound 117

Compound 117, 1-ethyl-3-(2-fluoro-5-(methylsulfinyl)phenyl)-7-((5-(methyl(1-methylpiperidin-4-yl)amino)pyridin-2-yl)amino)-1,6-naphthyridin-2(1H)-one was synthesized following Scheme 55.

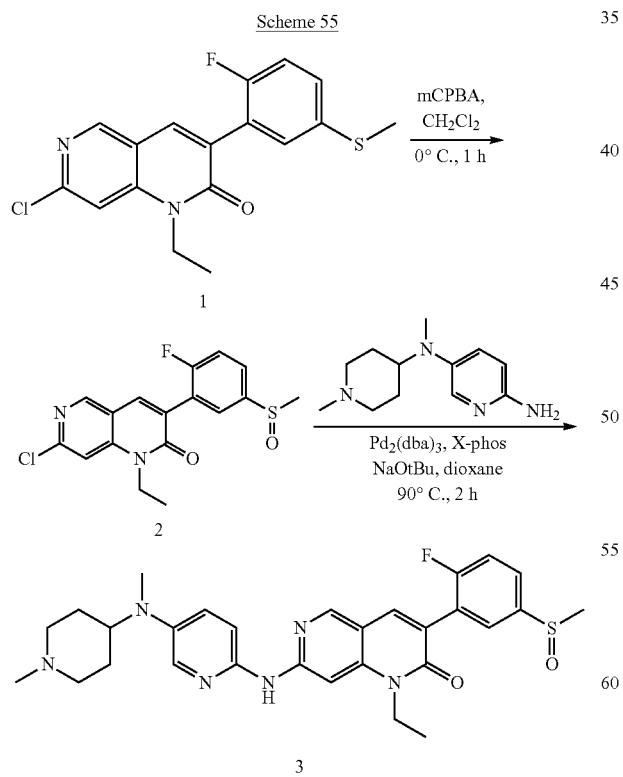

Scheme 55

The preparation of Scheme 55 intermediate 1 is described in the preparation of Compound 116 (Scheme 53 compound 4).

To a cooled (0° C.) solution of Scheme 55 compound 1 (500 mg, 1.43 mmol) in dry $CH_2Cl_2$ (5 mL) was added mCPBA (247 mg, 1.44 mmol) and the reaction mixture was stirred at 0° C. for 1 h. After TLC showed the starting material was completely consumed, the reaction mixture was diluted with ice water (10 mL) and extracted with EtOAc (2×50 mL). The organic layer was washed with saturated aqueous $NaHCO_3$ (10 mL) and brine (10 mL) then dried over $Na_2SO_4$ and concentrated to give a residue which was purified by flash chromatography on silica gel (eluting with petroleum ether/EtOAc 100/0 gradually increasing to 80/20) to give Scheme 55 compound 2 (340 mg, 65%) as an off-white solid. MS [ESI, MH$^+$]=365.4.

Scheme 55 compound 2 (250 mg, 0.686 mmol) and N$^5$-methyl-N$^5$-(1-methylpiperidin-4-yl)pyridine-2,5-diamine (Scheme 43 compound 4) (226 mg, 1.03 mmol) were dissolved in anhydrous dioxane (10 mL). To this mixture was added tBuONa (197 mg, 0.14 mmol), X-PHOS (79 mg, 0.14 mmol) and Pd$_2$(dba)$_3$ (62 mg, 0.07 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$ then filtered and concentrated to give a residue which was purified by flash chromatography on silica gel (eluting with $CH_2Cl_2$/MeOH 100/0 gradually increasing to 90/10) to give Compound 117 (70 mg, yield: 18%) as a pale yellow solid. $^1$H NMR (400 MHz, DMSO-$d_6$): δ 9.76 (s, 1H), 8.60 (s, 1H), 8.05 (s, 1H), 7.96 (s, 1H), 7.90 (d, J=3.1 Hz, 1H), 7.83 (dd, J=6.7, 2.4 Hz, 1H), 7.76 (m, 1H), 7.57-7.43 (m, 2H), 7.34 (dd, J=9.2, 3.1 Hz, 1H), 4.21 (m, 2H), 3.49 (m, 1H), 2.91-2.76 (m, 5H), 2.72 (s, 3H), 2.18 (s, 3H), 2.02 (dd, J=12.6, 9.7 Hz, 2H), 1.70 (m, 2H), 1.58 (d, J=12.7 Hz, 2H), 1.31 (t, J=7.0 Hz, 3H). MS [ESI, MH$^+$]=549.15.

Example 64

Synthesis of Compound 118

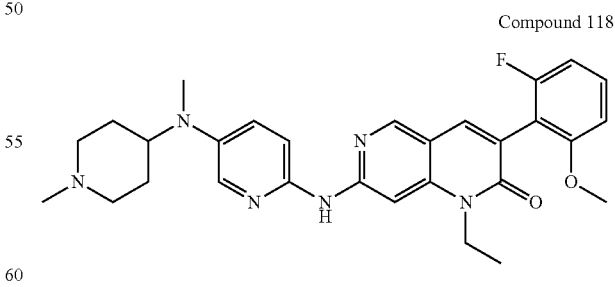

Compound 118

Compound 118, 1-ethyl-3-(2-fluoro-6-methoxyphenyl)-7-((5-(methyl(1-methylpiperidin-4-yl)amino)pyridin-2-yl)amino)-1,6-naphthyridin-2(1H)-one was synthesized in a similar manner as Compound 116 using 2-(2-fluoro-6-methoxyphenyl)acetonitrile in the naphthyridinimine formation step. This nitrile was prepared as shown in Scheme 56.

Scheme 56

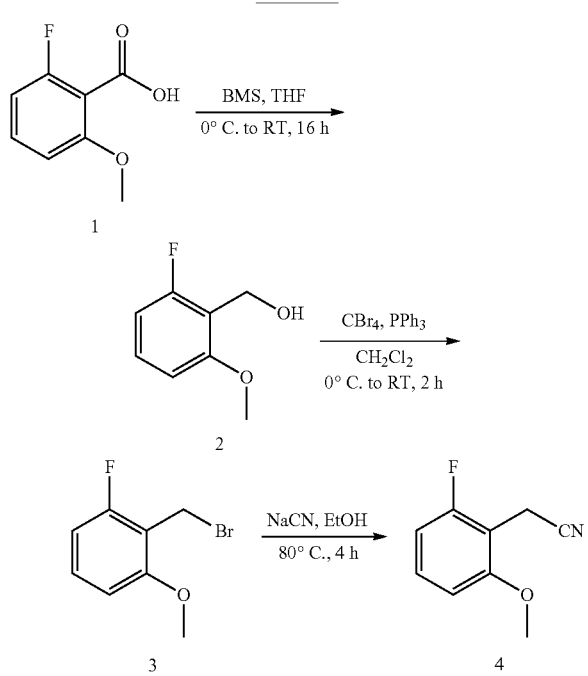

To a cooled (0° C.) stirred solution of Scheme 56 compound 1 (8.0 g, 47.66 mmol) in dry THF (80 mL) was added BH$_3$.DMS (8.9 mL, 117.65 mmol) and the reaction mixture was stirred at RT for 16 h. After TLC showed the starting material was completely consumed, the reaction mixture was diluted with ice water (30 mL) and extracted with EtOAc (2×50 mL). The organic layer was washed with brine (20 mL), dried over Na$_2$SO$_4$ and concentrated to give a residue which was purified by flash chromatography on silica gel (eluting with petroleum ether/EtOAc 100/0 gradually increasing to 80/20) to give Scheme 56 compound 2 (7.0 g, 95%) as a colorless liquid. MS [ESI, MH$^+$]=157.05.

To a cooled (0° C.) stirred solution of Scheme 56 compound 2 (7.0 g, 44.87 mmol) in dry CH$_2$Cl$_2$ (70 mL) was added PPh$_3$ (11.0 g, 44.87 mmol) and CBr$_4$ (25.0 g, 76.27 mmol) and the reaction mixture was stirred at RT for 2 h. After TLC showed the starting material was completely consumed, the reaction mixture was concentrated under reduced pressure to give a residue which was purified by flash chromatography on silica gel (eluting with petroleum ether/EtOAc 100/0 gradually increasing to 90/10) to give Scheme 56 compound 3 (5.7 g, 58%) as a colorless liquid. MS [ESI, MH$^+$]=218.98.

To a solution of Scheme 56 compound 3 (5.7 g, 26.15 mmol) in dry EtOH (70 mL) was added NaCN (1.4 g, 28.76 mmol) and the reaction mixture was stirred at 80° C. for 4 h. After TLC showed the starting material was completely consumed, the reaction mixture was concentrated to give a crude compound which was diluted with ice water (30 mL) and extracted with EtOAc (2×50 mL). The organic layer was washed with brine (20 mL), dried over Na$_2$SO$_4$ and concentrated to give a residue which was purified by column chromatography (eluting with petroleum ether/EtOAc 100/0 gradually increasing to 60/40) to give Scheme 56 compound 4 (2.0 g, 46%) as a colorless liquid. MS [ESI, MH$^+$]=166.06.

A mixture of 6-chloro-4-(ethyl amino) nicotinaldehyde (Scheme 1 compound 6) (1.7 g, 9.32 mmol), Scheme 56 compound 4 (2.0 g, 12.11 mmol) and K$_2$CO$_3$ (3.8 g, 27.96 mmol) in dry DMF (10 mL) was heated to 100° C. under nitrogen atmosphere for 16 h. After TLC showed the starting material was completely consumed, the reaction mixture was cooled to RT, diluted with EtOAc (2×50 mL), washed with water (2×20 mL) and brine (10 mL) then dried over Na$_2$SO$_4$ and concentrated to give a residue which was purified by flash chromatography on silica gel (eluting with petroleum ether/EtOAc 100/0 gradually increasing to 60/40) to give 7-chloro-1-ethyl-3-(2-fluoro-6-methoxyphenyl)-1,6-naphthyridin-2(1H)-imine (800 mg, 26%) as a yellow solid. $^1$H NMR (400 MHz, DMSO-d$_6$): δ 8.41 (s, 1H), 7.51 (q, J=8.0 Hz, 1H), 7.41 (d, J=10.6 Hz, 2H), 7.07-6.92 (m, 2H), 4.26 (m, 2H), 3.77 (d, J=2.4 Hz, 3H), 1.22-1.16 (m, 3H). MS [ESI, MH$^+$]=332.09.

A solution of 7-chloro-1-ethyl-3-(2-fluoro-6-methoxyphenyl)-1,6-naphthyridin-2(1H)-imine (800 mg, 2.41 mmol) in Ac$_2$O (10 mL) was stirred at 120° C. for 2 h after which time the reaction mixture was cooled to RT and concentrated under reduced pressure. The resulting crude compound was dissolved in 6N aqueous HCl (10 mL) and stirred at 90° C. for 8 h. After TLC showed the starting material was completely consumed, the reaction mixture was neutralized with saturated aqueous NaHCO$_3$ (up to pH 3) and extracted with EtOAc (50 mL). The organic layer was washed with water (20 mL) and brine (10 mL) then dried over Na$_2$SO$_4$ and concentrated to give a residue which was purified by flash chromatography on silica gel (eluting with petroleum ether/EtOAc 100/0 gradually increasing to 80/20) to give 7-chloro-1-ethyl-3-(2-fluoro-6-methoxyphenyl)-1,6-naphthyridin-2(1H)-one (500 mg, 62%) as a pale yellow solid. MS [ESI, MH$^+$]=333.3.

7-Chloro-1-ethyl-3-(2-fluoro-6-methoxyphenyl)-1,6-naphthyridin-2(1H)-one (200 mg, 0.60 mmol) and N$^5$-methyl-N$^5$-(1-methylpiperidin-4-yl)pyridine-2,5-diamine (Scheme 43 compound 4) (198 mg, 0.90 mmol) were dissolved in anhydrous dioxane (10 mL). To this mixture was added tBuONa (173 mg, 1.80 mmol), X-PHOS (69 mg, 0.12 mmol) and Pd$_2$(dba)$_3$ (55 mg, 0.06 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 118 (60 mg, yield: 19%) as a yellow solid. $^1$H NMR (400 MHz, CDCl$_3$): δ 8.41 (s, 1H), 7.95 (d, J=3.0 Hz, 1H), 7.84 (s, 1H), 7.63 (s, 1H), 7.31 (dd, J=8.8, 6.7 Hz, 1H), 7.21 (t, J=5.4 Hz, 2H), 7.11 (d, J=8.9 Hz, 1H), 6.87-6.72 (m, 2H), 4.42-4.25 (m, 2H), 3.80 (s, 3H), 3.45 (m, 1H), 2.98 (d, J=11.0 Hz, 2H), 2.80 (s, 3H), 2.32 (s, 3H), 2.07 (t, J=11.4 Hz, 2H), 1.86 (m, 2H), 1.75 (d, J=11.6 Hz, 2H), 1.42 (t, J=7.1 Hz, 3H). MS [ESI, MH$^+$]=517.29.

Example 65

Synthesis of Compound 119

Compound 119

Compound 119, 1-ethyl-3-(2-fluoro-5-methoxyphenyl)-7-((5-(methyl(1-methylpiperidin-4-yl)amino)pyridin-2-yl)amino)-1,6-naphthyridin-2(1H)-one was synthesized in a similar manner as Compound 116 using 2-(2-fluoro-5-methoxyphenyl)acetonitrile in the naphthyridinimine formation step. This nitrile was prepared as shown in Scheme 57.

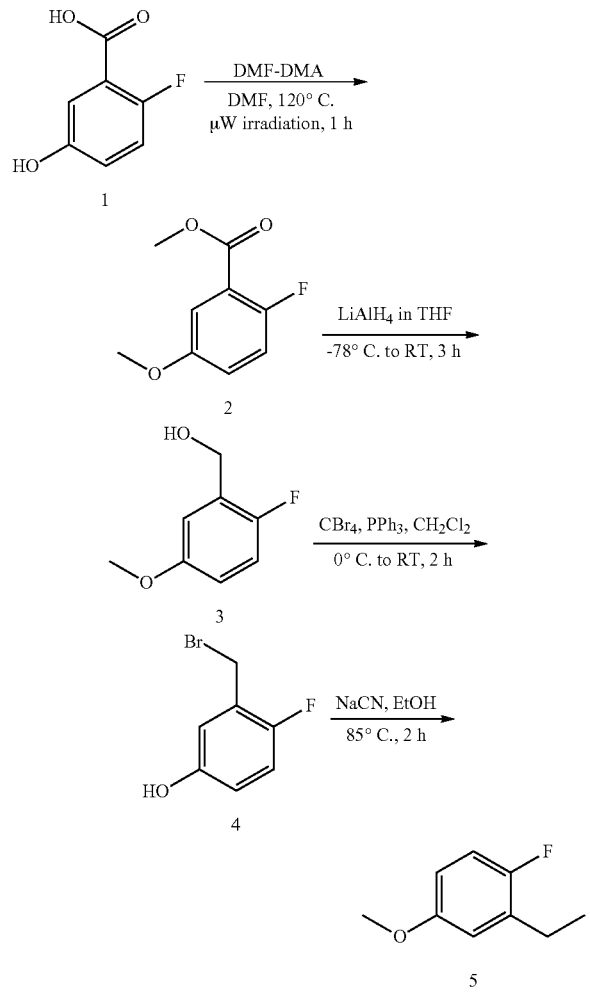

To a solution of Scheme 57 compound 1 (1.2 g, 7.05 mmol) in dry DMF (8 mL) was added DMF.DMA (1.6 g, 14.11 mmol) and the reaction mixture was stirred under microwave at 120° C. for 1 h. After TLC showed the starting material was completely consumed, the reaction mixture was diluted with ice water (30 mL) and extracted with EtOAc (2×20 mL). The organic layer was washed with brine (10 mL), dried over Na$_2$SO$_4$ and concentrated to give a residue which was purified by flash chromatography on silica gel (eluting with petroleum ether/EtOAc 100/0 gradually increasing to 90/10) to give Scheme 57 compound 2 (2.0 g, 83%) as a colorless liquid. MS [ESI, MH$^+$]=185.06.

To a cooled (−78° C.) solution of Scheme 57 compound 2 (10.0 g, 27.3 mmol) in dry THF (100 mL) was added LiAlH$_4$ (11.0 mL, 22.0 mmol, 2M in THF) portion wise over a period of 30 min and the reaction mixture was slowly warmed to RT and stirred for 3 h. After TLC showed the starting material was completely consumed, the reaction mixture was quenched with saturated ammonium chloride (10 mL), passed through a pad of celite and washed with EtOAc (2×30 mL). The filtrate was then washed with water (2×5 mL) and brine (2×5 mL), dried over Na$_2$SO$_4$ and concentrated to give a residue which was purified by flash chromatography on silica gel (eluting with petroleum ether/EtOAc 100/0 gradually increasing to 60/40) to give Scheme 57 compound 3 (1.5 g, 88%) as an off-white solid. MS [ESI, MH$^+$]=157.0

To a cooled (0° C.) solution of Scheme 57 compound 3 (1.5 g, 9.60 mmol) in dry CH$_2$Cl$_2$ (15 mL) was added PPh$_3$ (3.7 g, 14.42 mmol) and CBr$_4$ (4.7 g, 14.42 mmol) and the reaction mixture was stirred at RT for 2 h. After TLC showed the starting material was completely consumed, the reaction mixture was concentrated under reduced pressure to give a residue which was purified by flash chromatography on silica gel (eluting with petroleum ether/EtOAc 100/0 gradually increasing to 90/10) to give Scheme 57 compound 4 (1.5 g, 83%) as a colorless liquid. MS [ESI, MH$^+$]=218.98.

To a solution of Scheme 57 compound 4 (1.5 g, 6.84 mmol) in dry EtOH (15 mL) was added NaCN (362 mg, 7.53 mmol) and the reaction mixture was stirred at 85° C. for 2 h. After TLC showed the starting material was completely consumed, the reaction mixture was concentrated to give a crude compound which was diluted with ice water (30 mL) and extracted with EtOAc (2×50 mL). The organic layer was washed with brine (20 mL) then dried over Na$_2$SO$_4$ and concentrated to give a residue which was purified by flash chromatography on silica gel (petroleum ether/EtOAc 100/0 gradually increasing to 70/30) to give Scheme 57 compound 5 (1 g, 90%) as a colorless liquid. $^1$H NMR (400 MHz, DMSO-d$_6$): δ 7.21 (t, J=9.2 Hz, 1H), 7.01 (dd, J=6.1, 3.1 Hz, 1H), 6.94 (m, 1H), 4.01 (s, 2H), 3.75 (s, 3H). MS [ESI, MH$^+$]=166.06.

A mixture of 6-chloro-4-(ethyl amino) nicotinaldehyde (Scheme 1 compound 6) (800 mg, 4.34 mmol), Scheme 57 compound 5 (1.0 g, 6.52 mmol) and K$_2$CO$_3$ (1.7 g, 13.04 mmol) in dry DMF (8 mL) was heated to 100° C. under nitrogen atmosphere for 16 h. After TLC showed the starting material was completely consumed, the reaction mixture was cooled to RT, diluted with EtOAc (100 mL), washed with water (2×30 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give 7-chloro-1-ethyl-3-(2-fluoro-5-methoxyphenyl)-1,6-naphthyridin-2(1H)-imine (1.0 g, 71%) as a brown solid. $^1$H NMR (400 MHz, DMSO-d$_6$): δ 8.46 (s, 1H), 7.54 (s, 1H), 7.44 (s, 1H), 7.30 (t, J=9.1 Hz, 1H), 7.08 (dt, J=9.1, 3.7 Hz, 1H), 6.99 (dd, J=5.8, 3.2 Hz, 2H), 4.29 (q, J=7.0 Hz, 2H), 3.78 (s, 3H), 1.19 (dt, J=9.3, 6.9 Hz, 3H). MS [ESI, MH$^+$]=332.09

A solution of 7-chloro-1-ethyl-3-(2-fluoro-5-methoxyphenyl)-1,6-naphthyridin-2(1H)-imine (1.0 g, 3.02 mmol) in Ac$_2$O (10 mL) was stirred at 120° C. for 2 h. The reaction mixture was cooled to RT and concentrated under reduced pressure to give a crude compound which was dissolved in 6N aqueous HCl (10 mL) and stirred at 90° C. for 8 h. After TLC showed the starting material was completely consumed, the reaction mixture was neutralized with saturated aqueous NaHCO$_3$ (up to pH 3) and extracted with EtOAc (50 mL). The organic layer was washed with water (20 mL) and brine (10 mL) then dried over Na$_2$SO$_4$ and concentrated to give a residue which was purified by flash chromatography on silica gel (eluting with petroleum ether/EtOAc 100/0 gradually increasing to 80/20) to give 7-chloro-1-ethyl-3-

(2-fluoro-5-methoxyphenyl)-1,6-naphthyridin-2(1H)-one (500 mg, 50%) as a light brown solid. MS [ESI, MH+]=333.6.

7-Chloro-1-ethyl-3-(2-fluoro-5-methoxyphenyl)-1,6-naphthyridin-2(1H)-one (250 mg, 0.75 mmol) and N5-methyl-N5-(1-methylpiperidin-4-yl)pyridine-2,5-diamine (Scheme 43 compound 4) (248 mg, 1.12 mmol) were dissolved in anhydrous dioxane (10 mL). To this mixture was added tBuONa (217 mg, 2.25 mmol), X-PHOS (87 mg, 0.15 mmol) and Pd$_2$(dba)$_3$ (68 mg, 0.07 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 119 (70 mg, yield: 16%) as a yellow solid. $^1$H NMR (400 MHz, DMSO-d$_6$): δ 9.74 (s, 1H), 8.58 (s, 1H), 7.95 (d, J=4.9 Hz, 2H), 7.89 (d, J=3.0 Hz, 1H), 7.48 (d, J=9.1 Hz, 1H), 7.34 (dd, J=9.2, 3.1 Hz, 1H), 7.18 (t, J=9.3 Hz, 1H), 7.03 (dd, J=5.9, 3.2 Hz, 1H), 6.96 (m, 1H), 4.20 (m, 2H), 3.77 (s, 3H), 3.48 (m, 1H), 2.84 (d, J=10.9 Hz, 2H), 2.71 (s, 3H), 2.18 (s, 3H), 2.01 (t, J=11.4 Hz, 2H), 1.71 (m, 2H), 1.58 (t, J=7.2 Hz, 2H), 1.29 (t, J=7.0 Hz, 3H). MS [ESI, MH+]=517.16.

Example 66

Synthesis of Compound 120

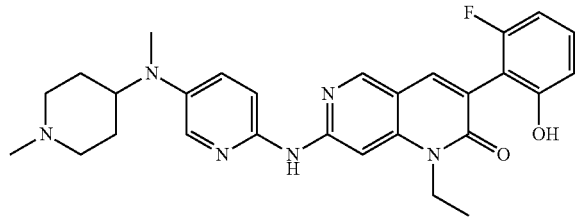

Compound 120

Compound 120, 1-ethyl-3-(2-fluoro-6-hydroxyphenyl)-7-((5-(methyl(1-methylpiperidin-4-yl)amino)pyridin-2-yl)amino)-1,6-naphthyridin-2(1H)-one was synthesized as described in Scheme 58.

Scheme 58

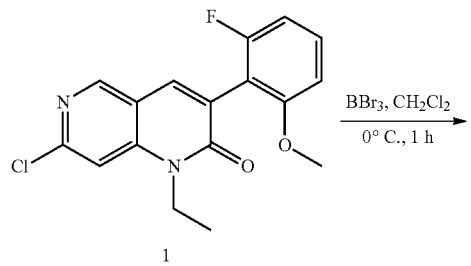

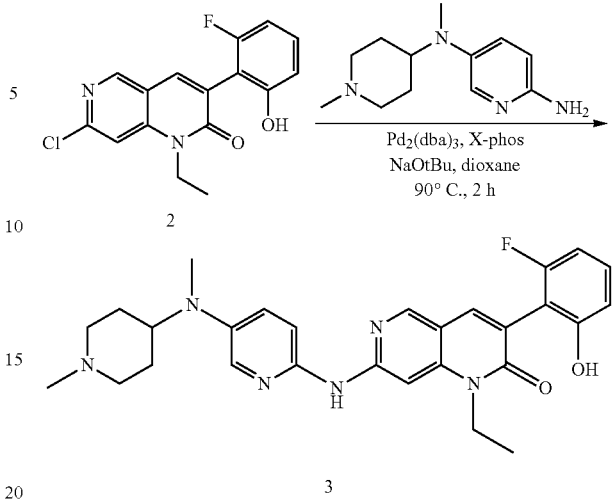

The preparation of Scheme 58 intermediate 1 is described in the preparation of Compound 118.

To a cooled (0° C.) stirred solution of Scheme 58 compound 1 (300 mg, 0.90 mmol) in dry CH$_2$Cl$_2$ (5 mL) was added BBr$_3$ (677 mg, 2.71 mmol) dropwise and the reaction mixture was stirred at 0° C. for 1 h. After TLC showed the starting material was completely consumed, the reaction mixture was diluted with water (10 mL) and extracted with CH$_2$Cl$_2$ (30 mL). The organic layer was washed with water (10 mL) and brine (10 mL) then dried over Na$_2$SO$_4$ and concentrated to give a residue which was purified by flash chromatography on silica gel (eluting with petroleum ether/EtOAc 100/0 gradually increasing to 70/30) to give Scheme 58 compound 2 (200 mg, 69%) as a yellow solid. $^1$H NMR (400 MHz, DMSO-d$_6$): δ 9.94 (s, 1H), 8.77 (s, 1H), 8.05 (s, 1H), 7.74 (s, 1H), 7.24 (m, 1H), 6.82-6.56 (m, 2H), 4.27 (m, 2H), 1.21 (t, J=7.0 Hz, 3H). MS [ESI, MH+]=319.06.

Scheme 58 compound 2 (200 mg, 0.628 mmol) and N5-methyl-N5-(1-methylpiperidin-4-yl)pyridine-2,5-diamine (Scheme 43 compound 4) (207 mg, 0.943 mmol) were dissolved in anhydrous dioxane (10 mL). To this mixture was added tBuONa (181 mg, 1.880 mmol), X-PHOS (72 mg, 0.125 mmol) and Pd$_2$(dba)$_3$ (57 mg, 0.063 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 120 (37 mg, yield: 11%) as a yellow solid. $^1$H NMR (400 MHz, CD$_3$OD): δ 8.52 (s, 1H), 7.99 (d, J=3.0 Hz, 1H), 7.89 (s, 1H), 7.82 (s, 1H), 7.50-7.32 (m, 2H), 7.20 (m, 1H), 6.81-6.57 (m, 2H), 4.34 (m, 2H), 3.73 (d, J=9.6 Hz, 1H), 3.36 (s, 2H), 2.82 (s, 5H), 2.67 (s, 3H), 2.11-1.76 (m, 4H), 1.40 (t, J=7.1 Hz, 3H). MS [ESI, MH+]=503.25.

Example 67

Synthesis of Compound 123

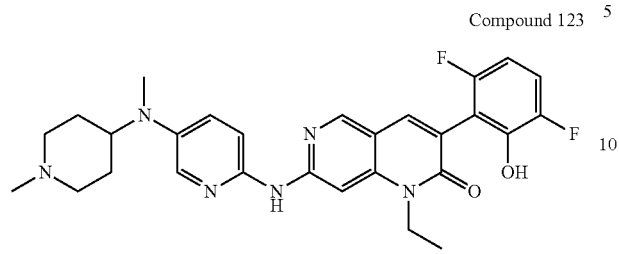

Compound 123

Compound 123, 3-(3,6-difluoro-2-hydroxyphenyl)-1-ethyl-7-((5-(methyl(1-methylpiperidin-4-yl)amino)pyridin-2-yl)amino)-1,6-naphthyridin-2(1H)-one was synthesized in a similar manner as Compound 116 using 2-(3,6-difluoro-2-methoxyphenyl)acetonitrile in the naphthyridinimine formation step. The preparation of this nitrile as well as the unmasking of the hydroxyl groups is shown in Scheme 59.

Scheme 59

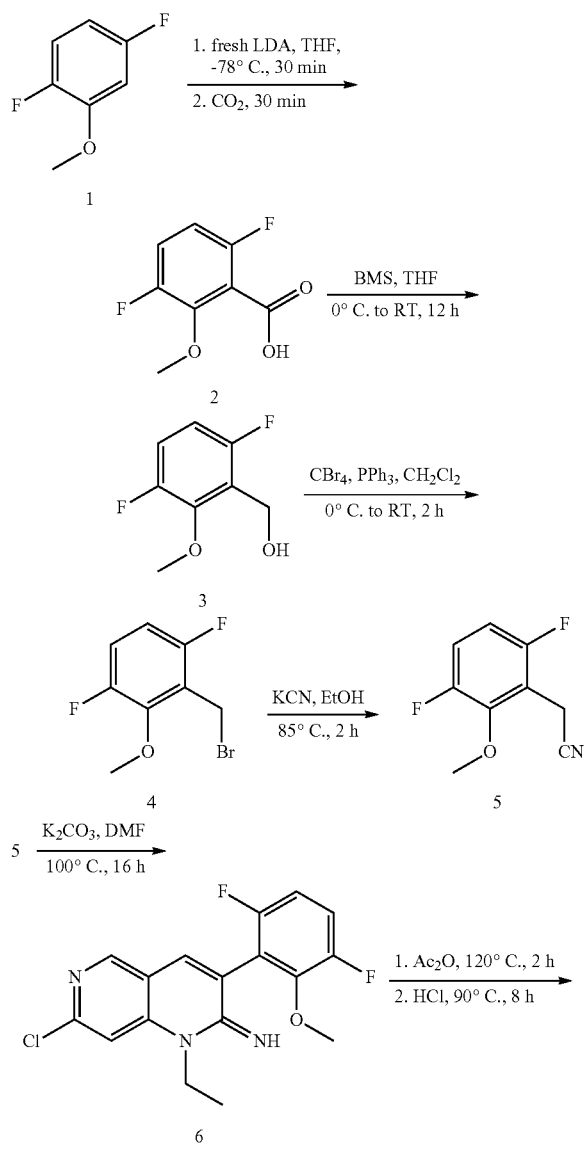

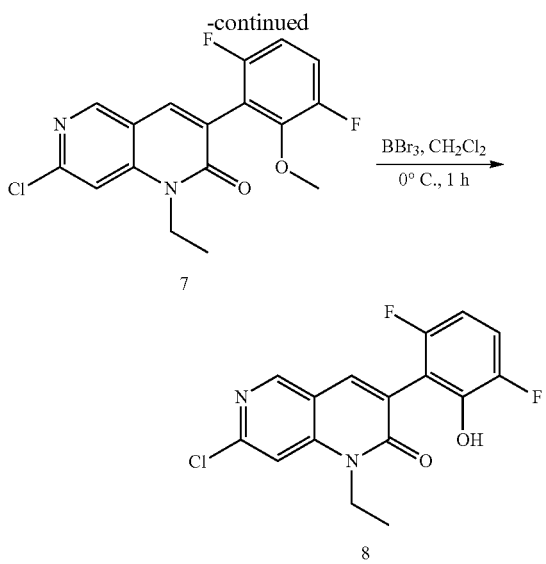

Freshly prepared LDA made from n-BuLi (24.0 mL, 38.19 mmol, 1.6 M in hexanes) and di-isopropyl amine (6.9 mL, 48.60 mmol) in THF (25 mL) at −78° C. was added dropwise over a period of 30 min to a cooled (−78° C.) solution of Scheme 59 compound 1 (5.0 g, 34.72 mmol) in dry THF (25 mL). Following 30 min of stirring at −78° C., $CO_2$ gas was bubbled through the reaction mixture for 30 min while maintaining the temperature. After TLC showed the starting material was completely consumed, the reaction mixture was quenched with 2% aqueous sulfuric acid (down to pH 4) and extracted with EtOAc (100 mL). The organic layer was washed with brine (2×15 mL) then dried over $Na_2SO_4$ and concentrated to give a residue which was purified by flash chromatography on silica gel (eluting with petroleum ether/EtOAc 100/0 gradually increasing to 30/70) to give Scheme 59 compound 2 (3.0 g, 46%) as an off-white solid. MS [ESI, MH$^+$]=187.04.

To a cooled (0° C.) stirred solution of Scheme 59 compound 2 (5.0 g, 26.59 mmol) in dry THF (50 mL) was added $BH_3$.DMS (15.4 mL, 159 mmol) and the reaction mixture was stirred at RT for 12 h. After TLC showed the starting material was completely consumed, the reaction mixture was diluted with ice water (30 mL) and extracted with EtOAc (2×50 mL). The organic layer was washed with brine (20 mL) then dried over $Na_2SO_4$ and concentrated to give a residue which was purified by flash chromatography on silica gel (eluting with petroleum ether/EtOAc 100/0 gradually increasing to 80/20) to give Scheme 59 compound 3 (4.0 g, 87%) as an off-white solid. MS [ESI, MH$^+$]=175.04.

To a cooled (0° C.) stirred solution of Scheme 59 compound 3 (2.0 g, 11.49 mmol) in dry $CH_2Cl_2$ (20 mL) was added $PPh_3$ (3.0 g, 11.49 mmol) and $CBr_4$ (5.7 g, 17.24 mmol) and the reaction mixture was stirred at RT for 2 h. After TLC showed the starting material was completely consumed, the reaction mixture was concentrated under reduced pressure to give a residue which was purified by flash chromatography on silica gel (eluting with petroleum ether/EtOAc 100/0 gradually increasing to 90/10) to give Scheme 59 compound 4 (1.5 g, 55%) as a brown liquid. MS [ESI, MH$^+$]=236.97.

To a solution of Scheme 59 compound 4 (3.0 g, 12.6 mmol) in dry EtOH (30 mL) was added NaCN (668 mg, 13.9 mmol) and the reaction mixture was stirred at 85° C. for 2 h. After TLC showed the starting material was completely consumed, the reaction mixture was concentrated to give a crude compound which was diluted with ice water (30 mL) and extracted with EtOAc (2×50 mL). The organic layer was washed with brine (20 mL) then dried over Na$_2$SO$_4$ and concentrated to give Scheme 59 compound 5 (1.8 g, 78%) as a colorless liquid. $^1$H NMR (400 MHz, CDCl$_3$): δ 7.07 (m, 1H), 6.78 (m, 1H), 4.09 (d, J=2.8 Hz, 3H), 3.70 (d, J=1.3 Hz, 2H). MS [ESI, MH$^+$]=184.04.

A mixture of 6-chloro-4-(ethylamino) nicotinaldehyde (Scheme 1 compound 6) (800 mg, 4.34 mmol), Scheme 59 compound 5 (1.19 g, 6.52 mmol) and K$_2$CO$_3$ (1.79 g, 13.04 mmol) in dry DMF (10 mL) was heated to 100° C. under nitrogen atmosphere for 16 h. After TLC showed the starting material was completely consumed, the reaction mixture was cooled to RT, diluted with EtOAc (100 mL), washed with water (2×30 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give Scheme 59 compound 6 (1.0 g, 55%) as a brown solid. MS [ESI, MH$^+$]=350.4.

A solution of Scheme 59 compound 6 (1.0 g, 2.86 mmol) in Ac$_2$O (10 mL) was stirred at 120° C. for 2 h. The reaction mixture was cooled to RT and concentrated under reduced pressure to give a crude compound which was dissolved in 6N aqueous HCl (10 mL) and stirred at 90° C. for 8 h. After TLC showed the starting material was completely consumed, the reaction mixture was neutralized with saturated aqueous NaHCO$_3$ (up to pH 3) and extracted with EtOAc (50 mL). The organic layer was washed with water (20 mL) and brine (10 mL) then dried over Na$_2$SO$_4$ and concentrated to give a residue which was purified by flash chromatography on silica gel (eluting with petroleum ether/EtOAc 100/0 gradually increasing to 80/20) to give Scheme 59 compound 7 (800 mg, 80%) as a yellow solid. MS [ESI, MH$^+$]=351.06.

To a cooled (0° C.) solution of Scheme 59 compound 7 (800 mg, 2.28 mmol) in dry CH$_2$Cl$_2$ (10 mL) was added BBr$_3$ (6.85 mL, 6.75 mmol) dropwise and the reaction mixture was stirred at 0° C. for 1 h. After TLC showed the starting material was completely consumed, the reaction mixture was diluted with water (30 mL) and extracted with CH$_2$Cl$_2$ (100 mL). The organic layer was washed with water (20 mL) and brine (20 mL) then dried over Na$_2$SO$_4$ and concentrated to give a residue which was purified by flash chromatography on silica gel (eluting with petroleum ether/EtOAc 100/0 gradually increasing to 70/30) to give Scheme 59 compound 8 (600 g, 78%) as a yellow solid. $^1$H NMR (400 MHz, DMSO-d$_6$): δ 10.12 (s, 1H), 8.78 (s, 1H), 8.11 (s, 1H), 7.77 (s, 1H), 7.32-7.22 (m, 1H), 6.76 (m, 1H), 4.28 (m, 2H), 1.19 (m, 3). MS [ESI, MH$^+$]=337.02.

Scheme 59 compound 8 (250 mg, 0.74 mmol) and N$^5$-methyl-N$^5$-(1-methylpiperidin-4-yl)pyridine-2,5-diamine (Scheme 43 compound 4) (196 mg, 0.89 mmol) were dissolved in anhydrous dioxane (10 mL). To this mixture was added tBuONa (214 mg, 2.22 mmol), X-PHOS (86 mg, 0.15 mmol) and Pd$_2$(dba)$_3$ (68 mg, 0.07 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 123 (60 mg, yield: 15%) as a yellow solid. $^1$H NMR (400 MHz, CDCl$_3$): δ 8.55 (s, 1H), 8.12 (s, 1H), 7.96 (d, J=3.4 Hz, 2H), 7.39 (s, 1H), 7.22 (dd, J=9.0, 3.1 Hz, 2H), 7.12-6.98 (m, 2H), 6.69 (s, 1H), 4.46 (s, 2H), 3.47 (t, J=11.5 Hz, 1H), 2.98 (d, J=11.2 Hz, 2H), 2.82 (s, 3H), 2.32 (s, 3H), 2.07 (t, J=11.4 Hz, 2H), 1.93-1.79 (m, 2H), 1.75 (d, J=12.2 Hz, 2H), 1.49 (d, J=7.3 Hz, 3H). MS [ESI, MH$^+$]=521.25.

Synthesis of Compound 124

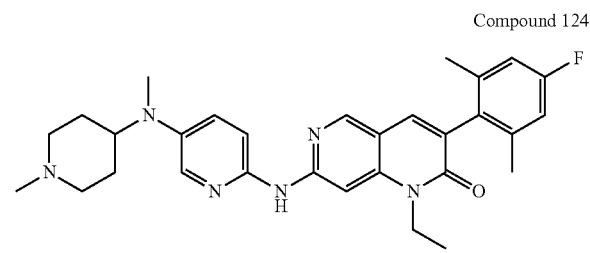 [SMILES: CCn1c(=O)c(-c2c(C)cc(F)cc2C)cc2cnc(Nc3ccc(N(C)C4CCN(C)CC4)cn3)cc21]

Compound 124

Compound 124, 1-ethyl-3-(4-fluoro-2,6-dimethylphenyl)-7-((5-(methyl(1-methylpiperidin-4-yl)amino)pyridin-2-yl)amino)-1,6-naphthyridin-2(1H)-one was synthesized in a similar manner as Compound 116 using 2-(4-fluoro-2,6-dimethylphenyl)acetonitrile in the naphthyridinimine formation step. This nitrile was prepared as shown in Scheme 60.

Scheme 60

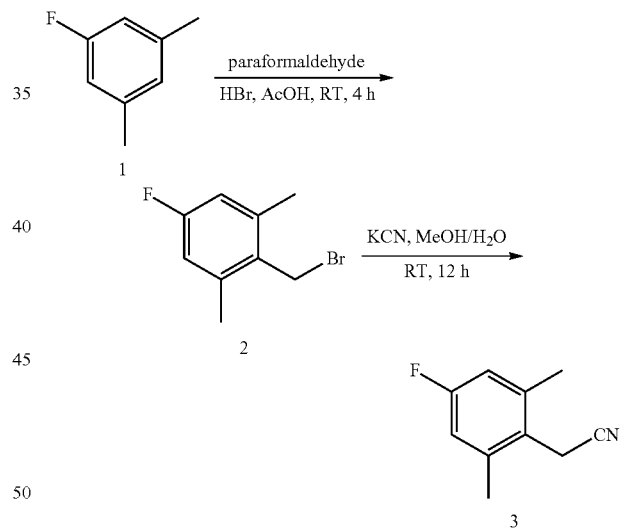

A mixture of Scheme 60 compound 1 (5.0 g, 40.32 mmol), paraformaldehyde (15.0 g) and HBr (33% in acetic acid, 35 mL) in acetic acid (25 mL) was stirred at RT for 4 h. After TLC showed the starting material was completely consumed, the reaction mixture was diluted with water (30 mL) and extracted with petroleum ether (2×40 mL) then dried over Na$_2$SO$_4$, filtered and concentrated under reduced pressure to give a residue which was purified by flash chromatography on silica gel (eluting with petroleum ether/EtOAc 100/0 gradually increasing to 90/10) to give Scheme 60 compound 2 (3.0 g, 34%) as an off-white solid. MS [ESI, MH$^+$]=217.99.

To a solution of Scheme 60 compound 2 (3.0 g, 13.38 mmol) in MeOH/water (50 mL, 1:1) was added KCN (1.17 g, 18.05 mmol) and the reaction mixture was stirred at RT for 12 h. After TLC showed the starting material was completely consumed, the reaction mixture was concentrated to give a crude compound which was diluted with ice water (30 mL) and extracted with EtOAc (2×50 mL). The organic layer was washed with brine (20 mL), dried over $Na_2SO_4$ and concentrated to give a residue which was purified by flash chromatography on silica gel (eluting with petroleum ether/EtOAc 100/0 gradually increasing to 90/10) to give Scheme 60 compound 3 (2.0 g, 90%) as an off-white solid. $^1$H NMR (400 MHz, $CDCl_3$): δ 6.80 (d, J=9.1 Hz, 2H), 3.60 (s, 2H), 2.39 (s, 6H). MS [ESI, MH$^+$]=164.01.

A mixture of 6-chloro-4-(ethyl amino) nicotinaldehyde (Scheme 1 compound 6) (1.3 g, 7.95 mmol), Scheme 60 compound 3 (1 g, 5.26 mmol) and $K_2CO_3$ (2.1 g, 15.78 mmol) in dry DMF (10 mL) was heated to 100° C. under nitrogen atmosphere for 16 h. After TLC showed the starting material was completely consumed, the reaction mixture was cooled to RT, diluted with EtOAc (100 mL), washed with water (2×30 mL) and brine (20 mL) then dried over $Na_2SO_4$ and concentrated to give a residue which was purified by flash chromatography on silica gel (eluting with petroleum ether/EtOAc 100/0 gradually increasing to 70/30) to give 7-chloro-1-ethyl-3-(4-fluoro-2,6-dimethylphenyl)-1,6-naphthyridin-2(1H)-imine (900 mg, 60.6%) as a brown solid. $^1$H NMR (400 MHz, $CDCl_3$): δ 8.26 (s, 1H), 8.02 (s, 1H), 7.06 (s, 1H), 6.99 (s, 1H), 6.88 (d, J=9.4 Hz, 1H), 4.32 (m, 2H), 2.13 (s, 6H), 1.36 (t, J=7.2 Hz, 3H). MS [ESI, MH$^+$]=330.10.

A solution of 7-chloro-1-ethyl-3-(4-fluoro-2,6-dimethylphenyl)-1,6-naphthyridin-2(1H)-imine (900 mg, 2.73 mmol) in $Ac_2O$ (9 mL) was stirred at 120° C. for 2 h. The reaction mixture was cooled to RT and concentrated under reduced pressure to give a crude compound which was dissolved in 6N aqueous HCl (9 mL) and stirred at 90° C. for 8 h. After TLC showed the starting material was completely consumed, the reaction mixture was neutralized with saturated aqueous $NaHCO_3$ (up to pH 3) and extracted with EtOAc (50 mL). The organic layer was washed with water (20 mL) and brine (10 mL) then dried over $Na_2SO_4$ and concentrated to give a residue which was purified by flash chromatography on silica gel (eluting with petroleum ether/EtOAc 100/0 gradually increasing to 80/20) to give 7-chloro-1-ethyl-3-(4-fluoro-2,6-dimethylphenyl)-1,6-naphthyridin-2(1H)-one (550 g, 62%) as an off-white solid. MS [ESI, MH$^+$]=331.09.

7-Chloro-1-ethyl-3-(4-fluoro-2,6-dimethylphenyl)-1,6-naphthyridin-2(1H)-one (450 mg, 1.36 mmol) and $N^5$-methyl-$N^5$-(1-methylpiperidin-4-yl)pyridine-2,5-diamine (Scheme 43 compound 4) (390 mg, 1.77 mmol) were dissolved in anhydrous dioxane (10 mL). To this mixture was added tBuONa (391 mg, 4.08 mmol), X-PHOS (157 mg, 0.27 mmol) and $Pd_2(dba)_3$ (125 mg, 0.14 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$ then filtered and concentrated to give a residue which was purified by flash chromatography on silica gel (eluting with $CH_2Cl_2$/MeOH 100/0 gradually increasing to 90/10) to give Compound 124 (80 mg, yield: 12%) as a yellow solid. $^1$H NMR (400 MHz, $CDCl_3$): δ 8.40 (s, 1H), 7.95 (d, J=3.0 Hz, 1H), 7.89 (s, 1H), 7.44 (s, 1H), 7.22 (dd, J=8.9, 3.2 Hz, 1H), 7.09 (d, J=8.9 Hz, 1H), 6.82 (d, J=9.5 Hz, 2H), 4.35 (m, 2H), 3.46 (m, 1H), 2.98 (d, J=10.6 Hz, 2H), 2.81 (s, 3H), 2.32 (s, 3H), 2.13 (s, 6H), 2.07 (t, J=12.2 Hz, 2H), 1.86 (d, J=12.4 Hz, 2H), 1.75 (d, J=12.0 Hz, 2H), 1.41 (t, J=7.1 Hz, 3H). MS [ESI, MH$^+$]=515.25.

Example 68

Synthesis of Compound 125

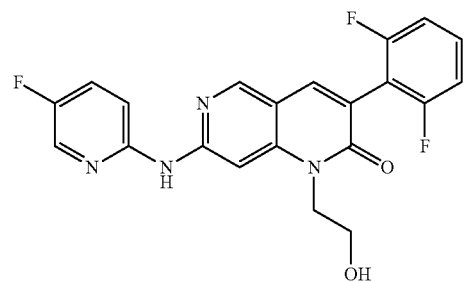

Compound 125

Compound 125, 3-(2,6-difluorophenyl)-7-((5-fluoropyridin-2-yl)amino)-1-(2-hydroxyethyl)-1,6-naphthyridin-2(1H)-one was synthesized as shown in Scheme 61.

Scheme 61

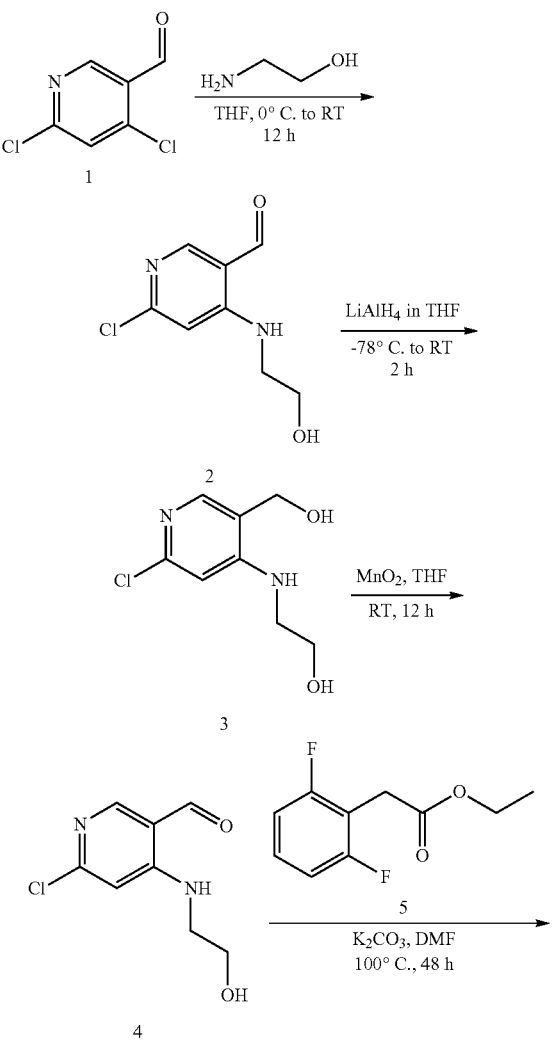

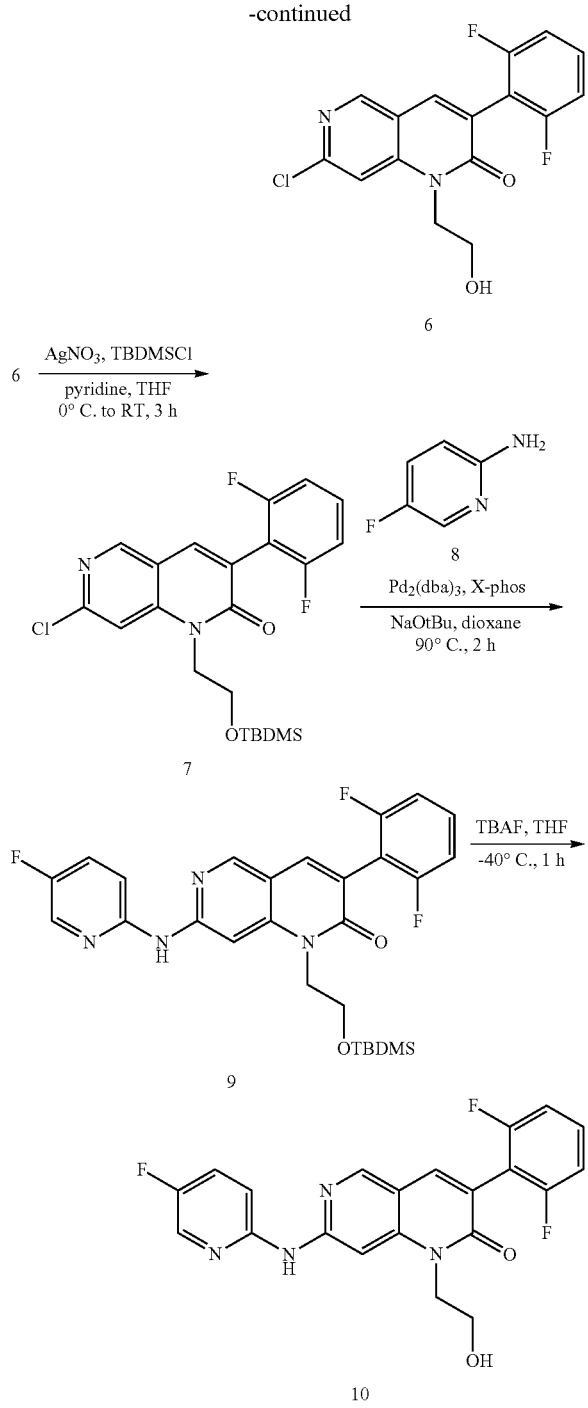

To a cold (0° C.) solution of Scheme 61 compound 1 (30.0 g, 13.69 mmol) in acetonitrile (30 mL) was added ethanolamine (9.6 mL, 164.30 mmol) dropwise and the reaction mixture was stirred at RT for 12 h. After TLC showed the starting material was completely consumed, the reaction mixture was diluted with EtOAc (3×100 mL), washed with water (2×30 mL) and brine (20 mL) then dried over $Na_2SO_4$ and concentrated to give a crude compound which was washed with $CH_2Cl_2$/pentane (60 mL, 1/1) to give Scheme 61 compound 2 (27 g, 80%) as a white solid. MS [ESI, MH$^+$]=245.4.

To a cooled (−78° C.) solution of Scheme 61 compound 2 (5.0 g, 20.49 mmol) in dry THF (50 mL) was added $LiAlH_4$ (20.5 mL, 41 mmol, 2M solution in THF) dropwise over a period of 30 min and the reaction mixture was slowly warmed to 0° C. and stirred for 2 h. After TLC showed the starting material was completely consumed, the reaction mixture was quenched with saturated ammonium chloride (100 mL) and passed through a pad of celite which was washed with EtOAc (100 mL). The filtrate was washed with water (2×30 mL) and brine (2×15 mL) then dried over $Na_2SO_4$ and concentrated to give a residue which was purified by flash chromatography on silica gel (eluting with petroleum ether/EtOAc 100/0 gradually increasing to 50/50) to give Scheme 61 compound 3 (3.5 g, 85%) as an off-white solid. MS [ESI, MH$^+$]=203.1.

To a solution of Scheme 61 compound 3 (22.0 g, 108.9 mmol) in dry THF (70 mL) was added $MnO_2$ (93.7 g, 108.9 mmol) and the reaction mixture was stirred at RT for 12 h. After TLC showed the starting material was completely consumed, the reaction mixture was passed through a pad of celite which was washed with EtOAc (200 mL). The filtrate was dried over $Na_2SO_4$ and concentrated to give Scheme 61 compound 4 (19 g, 87%) as an off-white solid. $^1$H NMR (400 MHz, DMSO-$d_6$): δ 9.87 (s, 1H), 8.75 (t, J=5.5 Hz, 1H), 8.44 (s, 1H), 6.90 (s, 1H), 4.97 (t, J=5.1 Hz, 1H), 3.58 (m, 2H), 3.40-3.34 (m, 2H). MS [ESI, MH$^+$]=201.2.

A mixture of Scheme 61 compound 4 (3.0 g, 15.0 mmol), Scheme 60 compound 5 (4.5 g, 22.5 mmol) and $K_2CO_3$ (6.2 g, 45.0 mmol) in dry DMF (30 mL) was heated to 100° C. under nitrogen atmosphere for 48 h. After TLC showed the starting material was completely consumed, the reaction mixture was cooled to RT, diluted with EtOAc (100 mL), washed with water (2×30 mL) and brine (20 mL) then dried over $Na_2SO_4$ and concentrated to give a crude compound which was purified by flash chromatography on silica gel (eluting with petroleum ether/EtOAc 100/0 gradually increasing to 70/30) to give Scheme 61 compound 6 (2.5 g, 50%) as a white solid. MS [ESI, MH$^+$]=337.05.

To a cooled (0° C.) mixture of Scheme 61 compound 6 (1.0 g, 2.97 mmol), TBDMSCl (896 mg, 5.95 mmol) and $AgNO_2$ (758 mg, 4.46 mmol) in dry THF (10 mL) was added pyridine (0.6 mL, 7.44 mmol) and the reaction mixture was allowed to warm to RT and stirred for 3 h. After TLC showed the starting material was completely consumed, the mixture was quenched with water (30 mL) and extracted with ethyl acetate (2×100 mL). The organic layer was washed with brine (20 mL), dried over anhydrous $Na_2SO_4$ then filtered and concentrated to give a residue which was purified by flash chromatography on silica gel (eluting with petroleum ether/EtOAc 100/0 gradually increasing to 85/15) to give Scheme 61 compound 7 (1.2 g, 92%,) as a white solid. MS [ESI, MH$^+$]=451.6.

Scheme 61 compound 7 (500 mg, 1.11 mmol) and 5-fluoropyridin-2-amine (149 mg, 1.33 mmol) were dissolved in anhydrous dioxane (5 mL). To this mixture was added tBuONa (320 mg, 3.33 mmol), X-PHOS (128 mg, 0.22 mmol) and $Pd_2(dba)_3$ (101 mg, 0.11 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$ then filtered and concentrated to give a residue which was purified by flash chromatography on silica gel (petroleum ether/EtOAc 100/0 gradually increasing to 60/40) to give Scheme 61 compound 9 (300 mg, 51%) as an off-white solid. MS [ESI, MH$^+$]=527.16.

To a cooled (−40° C.) solution of Scheme 61 compound 9 (400 mg, 0.76 mmol) in dry THF (10 mL) was added TBAF (1.14 mL, 1.14 mmol, 1 M in THF) dropwise and the reaction mixture was stirred at −40° C. for 1 h. After TLC showed the starting material was completely consumed, the reaction mixture was diluted with water (30 mL) and extracted with EtOAc (2×30 mL). The organic layer was washed with water (10 mL) and brine (10 mL) then dried over Na$_2$SO$_4$ and concentrated to give a residue which was purified by flash chromatography on silica gel (eluting with CH$_2$Cl$_2$/MeOH=100/0 gradually increasing to 90/10) to give Compound 125 (60 mg, yield: 19%) as a yellow solid. $^1$H NMR (400 MHz, DMSO-d$_6$): δ 10.18 (s, 1H), 8.64 (s, 1H), 8.29 (t, J=1.9 Hz, 1H), 8.06 (d, J=15.5 Hz, 2H), 7.74-7.67 (m, 2H), 7.51 (m, 1H), 7.21 (t, J=7.8 Hz, 2H), 5.03 (t, J=5.4 Hz, 1H), 4.27 (t, J=6.5 Hz, 2H), 3.72 (m, 2H). MS [ESI, MH$^+$]=413.09.

Synthesis of Compound 126

Compound 126

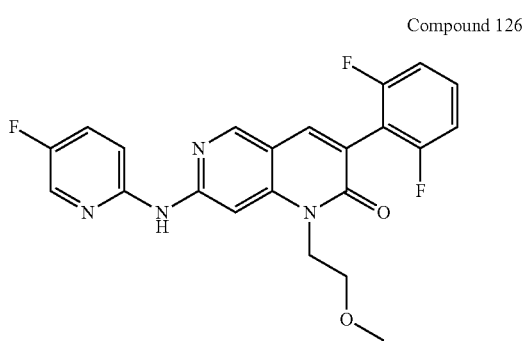 [SMILES: COCCn1c(=O)c(-c2c(F)cccc2F)cc2cnc(Nc3ccc(F)cn3)cc21]

Compound 126, 3-(2,6-difluorophenyl)-7-((5-fluoropyridin-2-yl)amino)-1-(2-methoxyethyl)-1,6-naphthyridin-2(1H)-one was prepared in a manner similar to Compound 125 by masking the hydroxyl group as a methyl ether instead of a silyl ether as depicted in Scheme 62.

Scheme 62

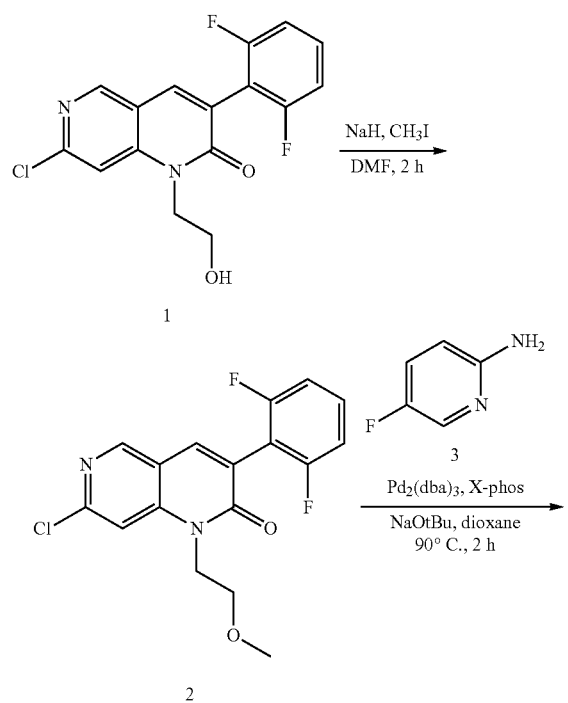

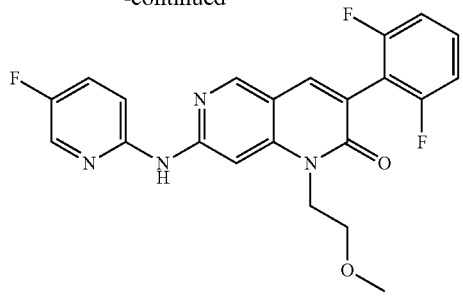

4

A mixture of NaH (88 mg, 2.20 mmol, 50-60% in oil), Scheme 62 compound 1 (300 mg, 0.89 mmol) and MeI (0.22 mL, 3.56 mmol) in dry DMF (5 mL) was stirred at RT under nitrogen atmosphere for 2 h. After TLC showed the starting material was completely consumed, the reaction mixture was quenched with water (10 mL), diluted with EtOAc (30 mL), washed with water (2×10 mL) and brine (10 mL) then dried over Na$_2$SO$_4$, filtered and concentrated to give a residue which was purified by flash chromatography on silica gel (eluting with petroleum ether/EtOAc 100/0 gradually increasing to 80/20) to give Scheme 62 compound 2 (120 mg, 38%) as an off-white solid. MS [ESI, MH$^+$]=351.07.

Scheme 62 compound 2 (400 mg, 1.14 mmol) and 5-fluoropyridin-2-amine (192 mg, 1.71 mmol) were dissolved in anhydrous dioxane (8 mL). To this mixture was added tBuONa (329 mg, 3.42 mmol), X-PHOS (132 mg, 0.23 mmol) and Pd$_2$(dba)$_3$ (104 mg, 0.11 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with petroleum ether/EtOAc 100/0 gradually increasing to 60/40) to give Compound 126 (200 mg, yield: 41%) as an off-white solid. $^1$H NMR (400 MHz, DMSO-d$_6$): δ 10.22 (s, 1H), 8.65 (s, 1H), 8.27 (s, 1H), 8.06 (d, J=25.0 Hz, 2H), 7.71 (d, J=5.8 Hz, 2H), 7.52 (t, J=7.3 Hz, 1H), 7.21 (t, J=7.9 Hz, 2H), 4.37 (t, J=6.0 Hz, 2H), 3.68 (t, J=6.2 Hz, 2H), 3.32 (s, 3H). MS [ESI, MH$^+$]=427.12.

Synthesis of Compound 129

Compound 129

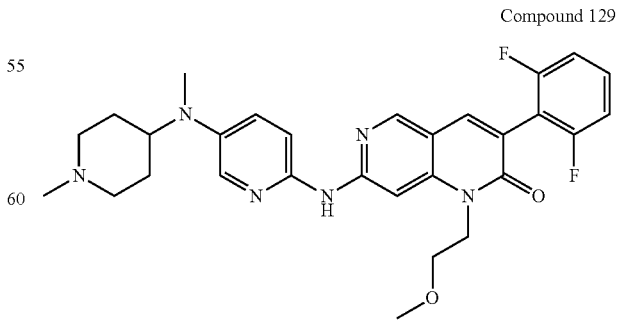

Compound 129, 3-(2,6-difluorophenyl)-1-(2-methoxyethyl)-7-((5-(methyl(1-methylpiperidin-4-yl)amino)pyridin- 2-yl)amino)-1,6-naphthyridin-2(1H)-one was prepared in a manner similar to Compound 126 using N⁵-methyl-N⁵-(1-methylpiperidin-4-yl)pyridine-2,5-diamine in the cross-coupling step.

Scheme 61 compound 2 (170 mg, 0.480 mmol) and N⁵-methyl-N⁵-(1-methylpiperidin-4-yl)pyridine-2,5-diamine (Scheme 43 compound 4) (160 mg, 0.727 mmol) were dissolved in anhydrous dioxane (10 mL). To this mixture was added tBuONa (139 mg, 1.450 mmol), X-PHOS (56 mg, 0.097 mmol) and Pd$_2$(dba)$_3$ (44 mg, 0.048 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH 100/0 gradually increasing to 90/10) to give Compound 129 (90 mg, yield: 29.5%) as a pale yellow solid. $^1$H NMR (400 MHz, DMSO-d$_6$): δ 8.58 (s, 1H), 8.02 (d, J=9.3 Hz, 2H), 7.86 (d, J=3.0 Hz, 1H), 7.56-7.42 (m, 2H), 7.35 (dd, J=9.1, 3.1 Hz, 1H), 7.20 (t, J=7.8 Hz, 2H), 4.34 (t, J=6.3 Hz, 2H), 3.68 (t, J=6.2 Hz, 2H), 3.47 (q, J=12.6, 12.0 Hz, 1H), 3.32 (s, 3H), 2.85 (d, J=10.6 Hz, 2H), 2.71 (s, 3H), 2.19 (s, 3H), 2.03 (s, 2H), 1.79-1.63 (m, 2H), 1.58 (d, J=11.5 Hz, 2H). MS [ESI, MH⁺]=535.29.

Synthesis of Compound 130

Synthesis of Compound 131

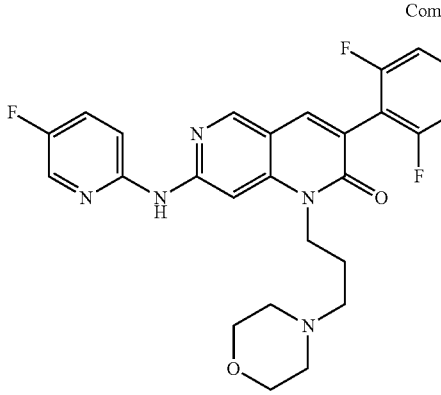

Compound 131

Compound 131, 3-(2,6-difluorophenyl)-7-((5-fluoropyridin-2-yl)amino)-1-(3-morpholinopropyl)-1,6-naphthyridin-2(1H)-one was prepared in a manner similar to Compound 125 using 3-morpholinopropan-1-amine in the first step (and omitting the protection and deprotection steps specific to the hydroxyl group) to obtain Compound 131 (60 mg, yield: 13%). $^1$H NMR (400 MHz, CD$_3$OD): δ 8.60 (s, 1H), 8.22 (d, J=2.9 Hz, 1H), 8.19 (s, 1H), 7.98 (s, 1H), 7.61-7.33 (m, 3H), 7.07 (t, J=7.9 Hz, 2H), 4.40 (t, J=7.1 Hz, 2H), 3.65 (t, J=4.7 Hz, 4H), 2.63 (d, J=36.0 Hz, 6H), 2.11 (m, 2H). MS [ESI, MH⁺]=496.20.

Synthesis of Compound 132

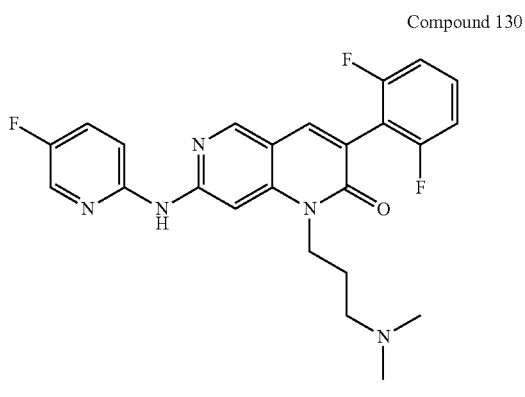 [SMILES: CN(C)CCCn1c(=O)c(-c2c(F)cccc2F)cc2cnc(Nc3ccc(F)cn3)cc21]

Compound 130

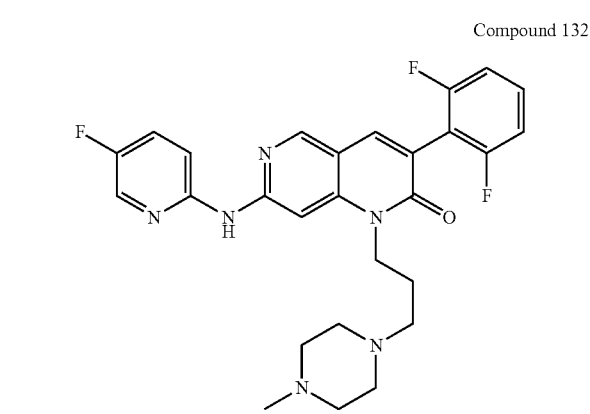 [SMILES: CN1CCN(CCCn2c(=O)c(-c3c(F)cccc3F)cc3cnc(Nc4ccc(F)cn4)cc32)CC1]

Compound 132

Compound 130, 3-(2,6-difluorophenyl)-1-(3-(dimethylamino)propyl)-7-((5-fluoropyridin-2-yl)amino)-1,6-naphthyridin-2(1H)-one was prepared in a manner similar to Compound 125 using N,N-dimethylpropane-1,3-diamine in the first step (and omitting the protection and deprotection steps specific to the hydroxyl group) to obtain Compound 130 (75 mg, yield: 15%). $^1$H NMR (400 MHz, CDCl$_3$): δ 8.48 (s, 1H), 8.18 (d, J=2.9 Hz, 1H), 8.03 (s, 1H), 7.75 (s, 1H), 7.60 (d, J=5.8 Hz, 1H), 7.42 (m, 1H), 7.38-7.27 (m, 2H), 6.99 (t, J=7.9 Hz, 2H), 4.40-4.30 (m, 2H), 2.47 (t, J=7.0 Hz, 2H), 2.27 (s, 6H), 1.99 (p, J=7.2 Hz, 2H). MS [ESI, MH⁺]=454.10.

Compound 132, 3-(2,6-difluorophenyl)-7-((5-fluoropyridin-2-yl)amino)-1-(3-(4-methylpiperazin-1-yl)propyl)-1,6-naphthyridin-2(1H)-one was prepared in a manner similar to Compound 125 using 3-(4-methylpiperazin-1-yl)propan-1-amine in the first step (and omitting the protection and deprotection steps specific to the hydroxyl group) to obtain Compound 132 (50 mg, yield: 17%). $^1$H NMR (400 MHz, DMSo-d$_6$): δ 10.21 (s, 1H), 8.65 (s, 1H), 8.29 (d, J=3.0 Hz, 1H), 8.05 (d, J=18.2 Hz, 2H), 7.69 (m, 2H), 7.51 (m, 1H), 7.20 (t, J=7.9 Hz, 2H), 4.19 (t, J=7.1 Hz, 2H), 2.53-2.39 (m, 4H), 2.39-2.13 (m, 6H), 2.09 (s, 3H), 1.86 (m, 2H). MS [ESI, MH⁺]=509.23.

Synthesis of Compound 133

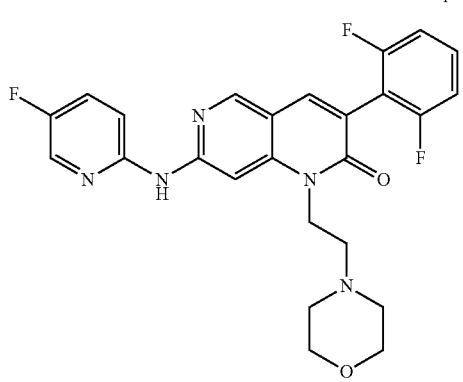

Compound 133

Compound 133, 3-(2,6-difluorophenyl)-7-((5-fluoropyridin-2-yl)amino)-1-(2-morpholinoethyl)-1,6-naphthyridin-2(1H)-one was prepared in a manner similar to Compound 125 using 2-morpholinoethanamine in the first step (and omitting the protection and deprotection steps specific to the hydroxyl group) to obtain Compound 133 (50 mg, yield: 15%). $^1$H NMR (400 MHz, CDCl$_3$): δ 8.48 (s, 1H), 8.13 (d, J=3.4 Hz, 2H), 7.75 (s, 1H), 7.53 (d, J=5.6 Hz, 1H), 7.42 (m, 1H), 7.38-7.30 (m, 1H), 7.23-7.15 (m, 1H), 6.99 (dd, J=9.4, 6.3 Hz, 2H), 4.47 (t, J=7.5 Hz, 2H), 3.72 (t, J=4.6 Hz, 4H), 2.79 (t, J=7.5 Hz, 2H), 2.66 (t, J=4.5 Hz, 4H). MS [ESI, MH$^+$]=482.22.

Synthesis of Compound 134

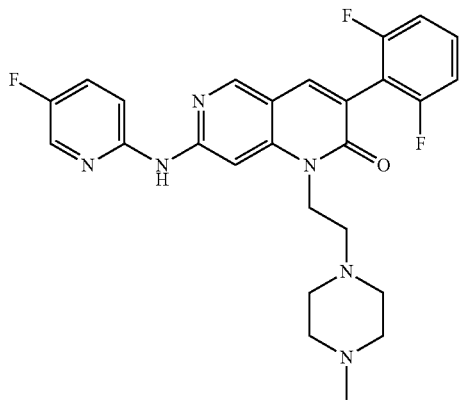

Compound 134

Compound 134, 3-(2,6-difluorophenyl)-7-((5-fluoropyridin-2-yl)amino)-1-(2-(4-methylpiperazin-1-yl)ethyl)-1,6-naphthyridin-2(1H)-one was prepared in a manner similar to Compound 125 using 2-(4-methylpiperazin-1-yl)ethanamine in the first step (and omitting the protection and deprotection steps specific to the hydroxyl group) to obtain Compound 134 (60 mg, yield: 15%). $^1$H NMR (400 MHz, DMSO-d$_6$): δ 10.26 (s, 1H), 8.65 (s, 1H), 8.20 (d, J=3.0 Hz, 1H), 8.08 (d, J=9.2 Hz, 2H), 7.72 (m, 1H), 7.64 (dd, J=9.2, 4.0 Hz, 1H), 7.51 (tt, J=8.5, 6.6 Hz, 1H), 7.20 (t, J=7.8 Hz, 2H), 4.29 (t, J=7.5 Hz, 2H), 2.72-2.51 (m, 6H), 2.40-2.22 (m, 4H), 2.14 (s, 3H). MS [ESI, MH$^+$]=495.20.

Synthesis of Compound 135

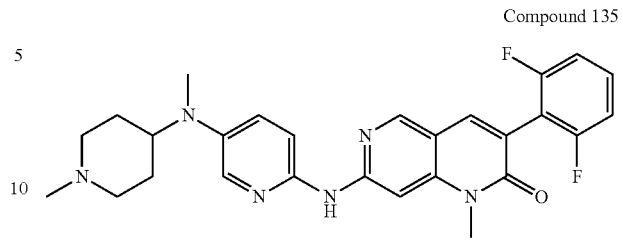

Compound 135

Compound 135, 3-(2,6-difluorophenyl)-1-methyl-7-((5-(methyl(1-methylpiperidin-4-yl)amino)pyridin-2-yl)amino)-1,6-naphthyridin-2(1H)-one was prepared in a manner similar to Compound 125 using methanamine in the first step and N$^5$-methyl-N$^5$-(1-methylpiperidin-4-yl)pyridine-2,5-diamine in the cross-coupling step (and omitting the protection and deprotection steps specific to the hydroxyl group) to obtain Compound 135 (50 mg, yield: 12%). $^1$H NMR (400 MHz, DMSO-d$_6$): δ 9.84 (s, 1H), 8.58 (s, 1H), 8.10-7.86 (m, 3H), 7.50 (m, 1H), 7.43 (d, J=9.1 Hz, 1H), 7.34 (dd, J=9.2, 3.1 Hz, 1H), 7.20 (t, J=7.7 Hz, 2H), 3.58 (s, 3H), 3.50 (t, J=11.8 Hz, 1H), 2.84 (d, J=10.8 Hz, 2H), 2.72 (s, 3H), 2.18 (s, 3H), 2.08-1.93 (m, 2H), 1.71 (m, 2H), 1.58 (d, J=12.8 Hz, 2H). MS [ESI, MH$^+$]=491.16.

Synthesis of Compound 136

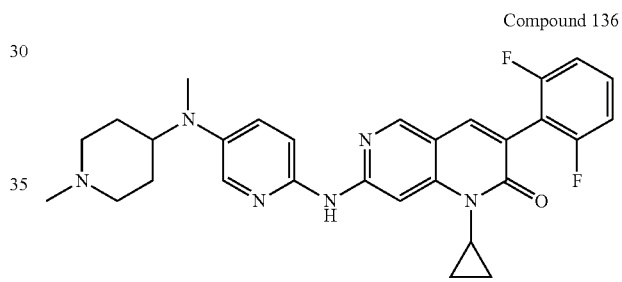

Compound 136

Compound 136, 1-cyclopropyl-3-(2,6-difluorophenyl)-7-((5-(methyl(1-methylpiperidin-4-yl)amino)pyridin-2-yl)amino)-1,6-naphthyridin-2(1H)-one was prepared in a manner similar to Compound 125 using cyclopropanamine in the first step and N$^5$-methyl-N$^5$-(1-methylpiperidin-4-yl)pyridine-2,5-diamine in the cross-coupling step (and omitting the protection and deprotection steps specific to the hydroxyl group) to obtain Compound 136 (60 mg, yield: 13%). $^1$H NMR (400 MHz, DMSO-d$_6$): δ 8.53 (s, 1H), 8.39 (s, 1H), 7.99-7.90 (m, 2H), 7.55-7.39 (m, 2H), 7.34 (dd, J=9.2, 3.0 Hz, 1H), 7.19 (t, J=7.8 Hz, 2H), 3.49 (m, 1H), 2.93 (m, 1H), 2.83 (d, J=10.9 Hz, 2H), 2.71 (s, 3H), 2.17 (s, 3H), 2.00 (t, J=11.2 Hz, 2H), 1.71 (m, 2H), 1.58 (d, J=11.5 Hz, 2H), 1.32 (d, J=6.9 Hz, 2H), 0.82 (t, J=3.6 Hz, 2H). MS [ESI, MH$^+$]=517.31.

Synthesis of Compound 137

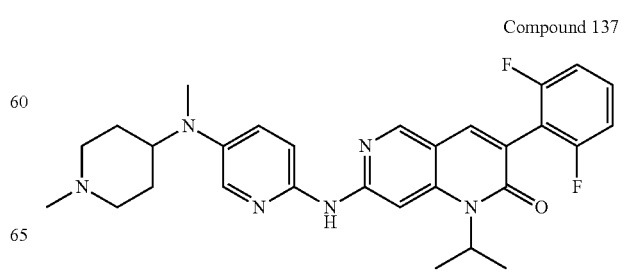

Compound 137

Compound 137, 3-(2,6-difluorophenyl)-1-isopropyl-7-((5-(methyl(1-methylpiperidin-4-yl)amino)pyridin-2-yl)amino)-1,6-naphthyridin-2(1H)-one was prepared in a manner similar to Compound 125 using isopropylamine in the first step and $N^5$-methyl-$N^5$-(1-methylpiperidin-4-yl)pyridine-2,5-diamine in the cross-coupling step (and omitting the protection and deprotection steps specific to the hydroxyl group) to obtain Compound 137 (60 mg, yield: 13%). $^1$H NMR (400 MHz, DMSO-$d_6$): δ 9.78 (s, 1H), 8.56 (s, 1H), 8.27 (s, 1H), 7.95 (s, 1H), 7.89 (d, J=3.1 Hz, 1H), 7.49 (m, 2H), 7.35 (dd, J=9.3, 3.0 Hz, 1H), 7.18 (t, J=7.8 Hz, 2H), 5.42 (s, 1H), 3.59-3.42 (m, 1H), 2.90 (d, J=11.2 Hz, 2H), 2.72 (s, 3H), 2.24 (s, 3H), 2.10 (d, J=18.1 Hz, 3H), 1.72 (m, 3H), 1.60 (d, J=7.1 Hz, 7H). MS [ESI, MH$^+$]=519.24.

Example 69

Synthesis of Compound 127

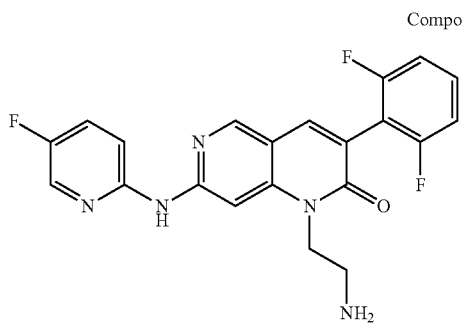

Compound 127

Compound 127, 1-(2-aminoethyl)-3-(2,6-difluorophenyl)-7-((5-fluoropyridin-2-yl)amino)-1,6-naphthyridin-2(1H)-one was synthesized as shown in Scheme 63.

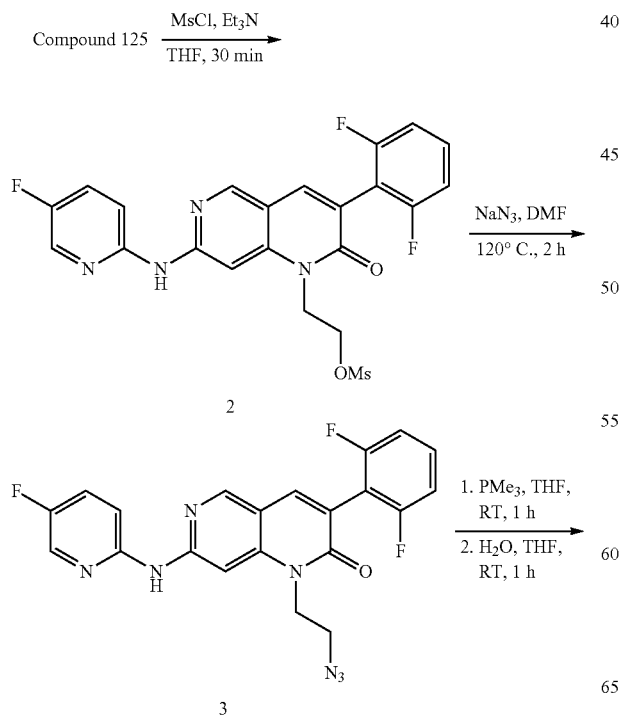

Scheme 63

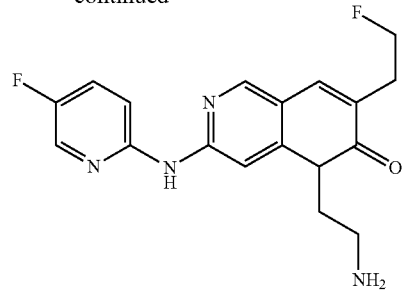

4

A mixture of Compound 125 (230 mg, 0.55 mmol), Et$_3$N (169 mg, 1.67 mmol) and methane sulfonyl chloride (190 mg, 1.67 mmol) in THF (15 mL) was stirred at RT for 30 min. After TLC showed the starting material was completely consumed, the reaction mixture was diluted with ice water (10 mL) and extracted with EtOAc (2×20 mL). The organic layer was washed with brine (20 mL), dried over Na$_2$SO$_4$ then filtered and concentrated to give Scheme 63 compound 2 (250 mg, 91%,) as a yellow solid. MS [ESI, MH$^+$]=491.10.

A mixture of Scheme 63 compound 2 (250 mg, 0.51 mmol) and sodium azide (331 mg, 5.10 mmol) in DMF (20 mL) was stirred at 120° C. for 2 h. After TLC showed the starting material was completely consumed, the reaction mixture was diluted with ice water (10 mL) and extracted with EtOAc (2×20 mL). The organic layer was washed with brine (20 mL), dried over Na$_2$SO$_4$ then filtered and concentrated to give Scheme 63 compound 3 (150 mg, 67%,) as a yellow solid. MS [ESI, MH$^+$]=437.10.

To a solution of Scheme 63 compound 3 (150 mg, 0.34 mmol) in THF (10 mL) was added trimethylphosphine (130 mg, 1.71 mmol) and the reaction mixture was stirred at RT for 1 h after which time water (0.3 mL) was added and the reaction mixture was stirred for an additional 2 h. After TLC showed the starting material was completely consumed, the reaction mixture was diluted with ice water (10 mL) and extracted with EtOAc (2×20 mL). The organic layer was washed with brine (20 mL), dried over Na$_2$SO$_4$ then filtered and concentrated to give a residue which was purified by prep-HPLC to give Compound 127 (50 mg, yield: 35%,) as a yellow solid. $^1$H NMR (400 MHz, DMSO-$d_6$): δ 10.16 (s, 1H), 8.64 (s, 1H), 8.34 (s, 1H), 8.06 (d, J=5.8 Hz, 2H), 7.71 (d, J=5.3 Hz, 2H), 7.52 (m, 1H), 7.20 (t, J=7.8 Hz, 2H), 4.18 (t, J=7.2 Hz, 2H), 2.88 (t, J=7.2 Hz, 2H), 1.69 (s, 2H). MS [ESI, MH$^+$]=411.1.

Example 70

Synthesis of Compound 128

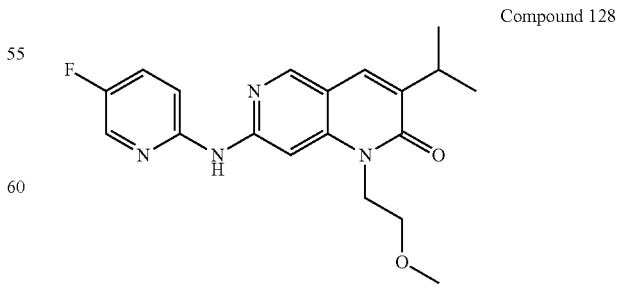

Compound 128

Compound 128, 7-((5-fluoropyridin-2-yl)amino)-3-isopropyl-1-(2-methoxyethyl)-1,6-naphthyridin-2(1H)-one was synthesized following Scheme 64.

Scheme 64

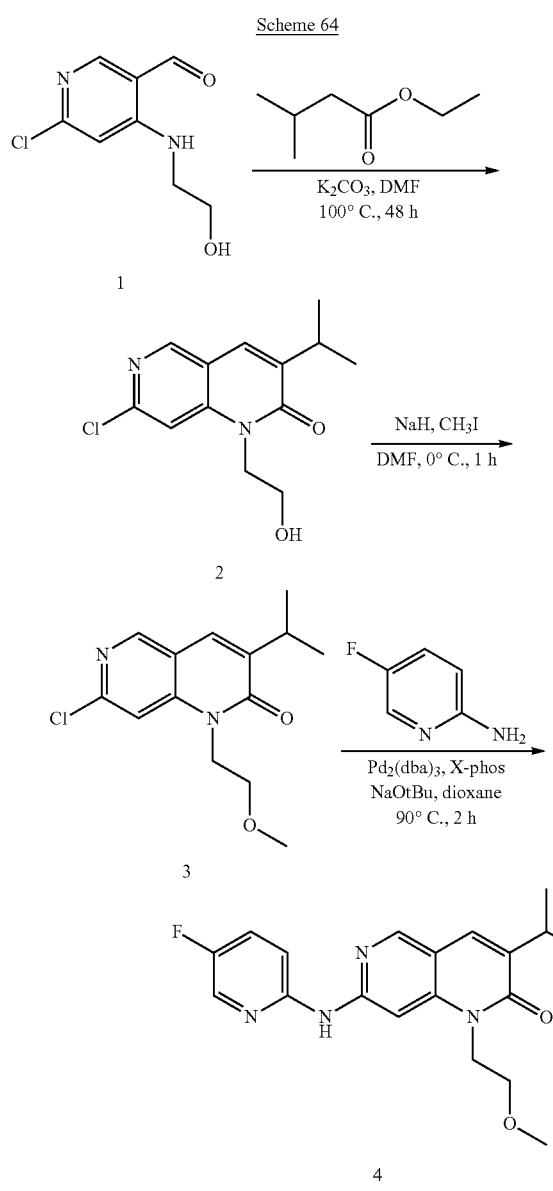

A mixture of Scheme 64 compound 1 (2.0 g, 10 mmol), ethyl 3-methylbutanoate (4.5 mL, 30 mmol) and $K_2CO_3$ (8.2 g, 60 mmol) in dry DMF (20 mL) was heated to 100° C. under nitrogen atmosphere for 48 h. After TLC showed the starting material was completely consumed, the reaction mixture was cooled to RT, diluted with EtOAc (100 mL), washed with water (2×30 mL) and brine (20 mL) then dried over $Na_2SO_4$, filtered and concentrated to give a residue which was purified by flash chromatography on silica gel (eluting with petroleum ether/EtOAc 100/0 gradually increasing to 80/20) to give Scheme 64 compound 2 (380 mg, 14%) as an off-white solid. $^1$H NMR (400 MHz, DMSO-$d_6$): δ 8.70 (d, J=1.5 Hz, 1H), 7.88 (s, 1H), 7.69 (s, 1H), 4.88 (t, J=5.8 Hz, 1H), 4.28 (dd, J=6.4, 5.0 Hz, 2H), 3.66 (m, 2H), 2.22-2.10 (m, 1H), 1.19 (dd, J=6.8, 1.5 Hz, 6H). MS [ESI, MH$^+$]=267.5.

A mixture of NaH (100 mg, 2.84 mmol, 50-60% in oil), Scheme 64 compound 2 (380 mg, 1.42 mmol) and MeI (0.3 mL, 5.69 mmol) in dry DMF (4 mL) was stirred at 0° C. under nitrogen atmosphere for 1 h. After TLC showed the starting material was completely consumed, the reaction mixture was quenched with water (10 mL) and diluted with EtOAc (30 mL). The organic layer was washed with water (2×10 mL) and brine (10 mL) then dried over $Na_2SO_4$, filtered and concentrated to give a residue which was purified by flash chromatography on silica gel (eluting with petroleum ether/EtOAc 100/0 gradually increasing to 70/30) to give Scheme 64 compound 3 (250 mg, 62%) as an off-white solid. $^1$H NMR (400 MHz, DMSO-$d_6$): δ 8.71 (s, 1H), 7.88 (s, 1H), 7.67 (s, 1H), 4.43 (t, J=5.5 Hz, 2H), 3.61 (t, J=5.5 Hz, 2H), 3.22 (s, 3H), 3.11 (m, 1H), 1.19 (d, J=6.9 Hz, 6H). MS [ESI, MH$^+$]=281.5.

Scheme 64 compound 3 (200 mg, 0.714 mmol) and 5-fluoropyridin-2-amine (120 mg, 1.071 mmol) were dissolved in anhydrous dioxane (10 mL). To this mixture was added tBuONa (205 mg, 2.140 mmol), X-PHOS (82 mg, 0.142 mmol) and $Pd_2(dba)_3$ (65 mg, 0.071 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$ then filtered and concentrated to give a residue which was purified by prep-HPLC to give Compound 128 (140 mg, yield: 55%) as a white solid. $^1$H NMR (400 MHz, DMSO-$d_6$): δ 10.00 (s, 1H), 8.57 (s, 1H), 8.23 (d, J=2.9 Hz, 1H), 7.90 (s, 1H), 7.75-7.62 (m, 3H), 4.33 (t, J=6.3 Hz, 2H), 3.64 (t, J=6.2 Hz, 2H), 3.31 (s, 3H), 3.08 (m, 1H), 1.18 (d, J=6.9 Hz, 6H). MS [ESI, MH$^+$]=357.20.

Example 71

Synthesis of Compound 138

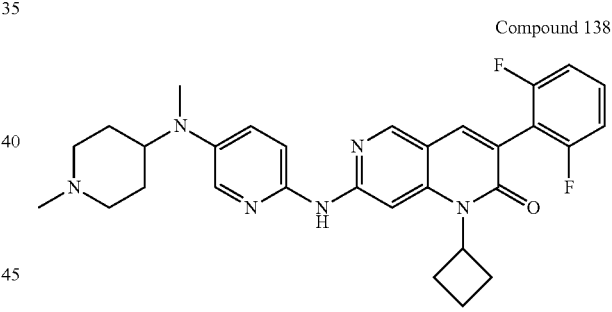

Compound 138

Compound 138, 1-cyclobutyl-3-(2,6-difluorophenyl)-7-((5-(methyl(1-methylpiperidin-4-yl)amino)pyridin-2-yl)amino)-1,6-naphthyridin-2(1H)-one was prepared according to Scheme 65.

Scheme 65

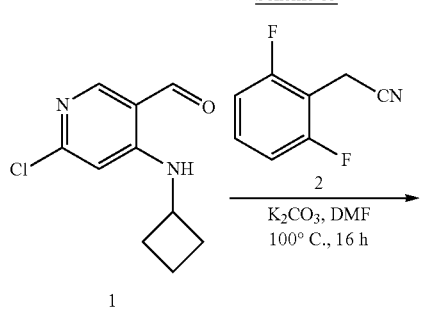

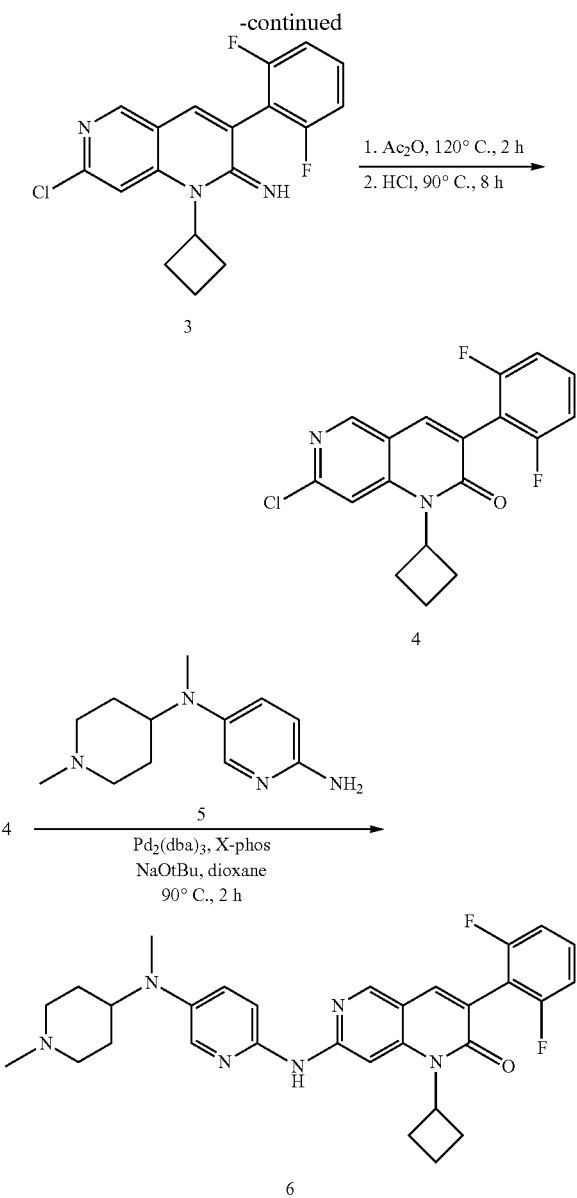

A mixture of Scheme 65 compound 1 (1.80 g, 8.57 mmol), 2-(2,6-difluorophenyl)acetonitrile (1.96 g, 12.85 mmol) and $K_2CO_3$ (3.54 g, 25.71 mmol) in dry DMF (20 mL) was heated to 100° C. under nitrogen atmosphere for 16 h. After TLC showed the starting material was completely consumed, the reaction mixture was cooled to RT, diluted with EtOAc (100 mL), washed with water (2×30 mL) and brine (20 mL) then dried over $Na_2SO_4$, filtered and concentrated to give a residue which was purified by flash chromatography on silica gel (eluting with petroleum ether/EtOAc 100/0 gradually increasing to 70/30) to give Scheme 65 compound 3 (1.0 g, 33%) as an off-white solid. $^1$H NMR (400 MHz, $CDCl_3$): δ 8.28 (s, 1H), 7.41 (m, 1H), 7.17 (s, 1H), 7.07-7.00 (m, 2H), 6.96 (s, 1H), 4.80 (m, 1H), 2.79 (m, 2H), 2.34 (m, 2H), 1.87 (m, 2H). MS [ESI, $MH^+$]=346.5.

A solution of Scheme 65 compound 3 (1.0 g, 2.89 mmol) in $Ac_2O$ (10 mL) was stirred at 120° C. for 2 h. The reaction mixture was cooled to RT and concentrated under reduced pressure to give a crude compound which was dissolved in 6N aqueous HCl (10 mL) and stirred at 90° C. for 8 h. After TLC showed the starting material was completely consumed, the reaction mixture was neutralized with saturated aqueous $NaHCO_3$ (up to pH 3) and extracted with EtOAc (50 mL). The organic layer was washed with water (20 mL) and brine (10 mL) then dried over $Na_2SO_4$, filtered and concentrated to give a residue which was purified by flash chromatography on silica gel (eluting with petroleum ether/EtOAc 100/0 gradually increasing to 80/20) to give Scheme 65 compound 4 (400 mg, 40%) as a yellow solid. MS [ESI, $MH^+$]=347.3.

Scheme 65 compound 4 (300 mg, 0.860 mmol) and $N^5$-methyl-$N^5$-(1-methylpiperidin-4-yl)pyridine-2,5-diamine (Scheme 43 compound 4) (228 mg, 1.040 mmol) were dissolved in anhydrous dioxane (10 mL). To this mixture was added tBuONa (250 mg, 2.600 mmol), X-PHOS (100 mg, 0.173 mmol) and $Pd_2(dba)_3$ (79 mg, 0.086 mmol, 10 mol %) under nitrogen atmosphere. The reaction mixture was stirred at 90° C. under nitrogen atmosphere for 2 h. After TLC showed the starting material was completely consumed, the mixture was quenched with water (20 mL) and extracted with ethyl acetate (2×30 mL). The organic layer was washed with brine (10 mL), dried over anhydrous $Na_2SO_4$ then filtered and concentrated to give a residue which was purified by flash chromatography on silica gel (eluting with $CH_2Cl_2$/MeOH 100/0 gradually increasing to 90/10) to give Compound 138 (50 mg, yield: 11%) as a yellow solid. $^1$H NMR (400 MHz, $CDCl_3$): δ 8.40 (s, 1H), 8.11 (s, 1H), 7.95 (d, J=3.1 Hz, 1H), 7.64 (s, 1H), 7.38-7.28 (m, 1H), 7.22 (dd, J=8.9, 3.1 Hz, 2H), 7.04-6.86 (m, 3H), 5.16 (m, 1H), 3.43 (m, 1H), 2.97 (d, J=11.3 Hz, 2H), 2.85-2.68 (m, 6H), 2.32 (s, 3H), 2.06 (t, J=11.7 Hz, 3H), 2.00-1.80 (m, 3H), 1.75 (d, J=12.2 Hz, 2H). MS [ESI, $MH^+$]=531.28.

Scheme 64 compound 1 was prepared in a similar manner to Scheme 60 compound 4 using cyclobutanamine instead of 2-aminoethanol. $^1$H NMR (400 MHz, $CDCl_3$): δ 9.83 (s, 1H), 8.68 (s, 1H), 8.29 (s, 1H), 6.47 (s, 1H), 4.08-3.91 (m, 1H), 2.57-2.40 (m, 2H), 2.09-1.97 (m, 2H), 1.96-1.79 (m, 2H). MS [ESI, $MH^+$]=211.4.

Synthesis of Compound 139

Compound 139

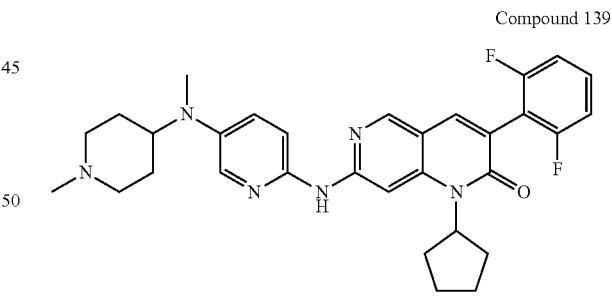

Compound 139, 1-cyclopentyl-3-(2,6-difluorophenyl)-7-((5-(methyl(1-methylpiperidin-4-yl)amino)pyridin-2-yl)amino)-1,6-naphthyridin-2(1H)-one was prepared in a manner similar to Compound 138 using cyclopentanamine instead of cyclobutanamine in the synthesis of the precursor of the naphtyridinime to obtain Compound 139 (100 mg, yield: 22%). $^1$H NMR (400 MHz, $CDCl_3$): δ 8.42 (s, 1H), 8.05 (s, 1H), 7.92 (d, J=3.0 Hz, 1H), 7.66 (s, 1H), 7.37-7.27 (m, 1H), 7.22 (dd, J=9.1, 3.3 Hz, 1H), 7.03-6.91 (m, 3H), 5.77 (t, J=9.3 Hz, 1H), 3.48-3.37 (m, 1H), 3.04-2.91 (m, 2H), 2.80 (s, 3H), 2.32 (s, 5H), 2.18 (dd, J=9.5, 5.6 Hz, 2H), 2.06 (t, J=11.7 Hz, 4H), 1.94-1.69 (m, 6H). MS [ESI, $MH^+$]=545.39.

Example 72

Synthesis of Compound 140

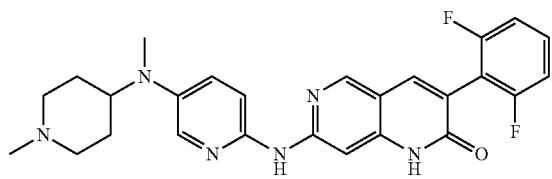

Compound 140

Compound 140, 3-(2,6-difluorophenyl)-7-((5-(methyl(1-methylpiperidin-4-yl)amino)pyridin-2-yl)amino)-1,6-naphthyridin-2(1H)-one was synthesized following Scheme 66.

Scheme 66

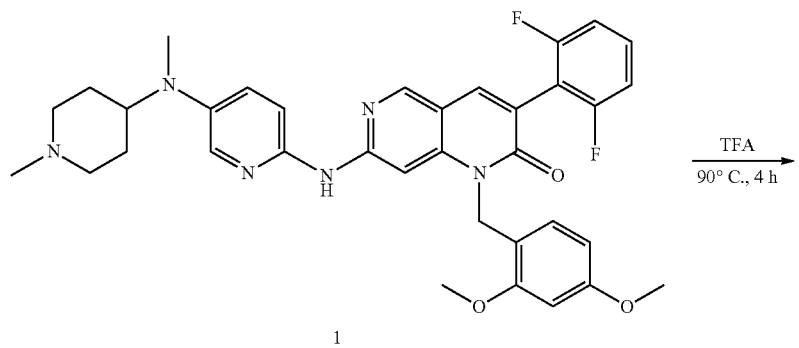

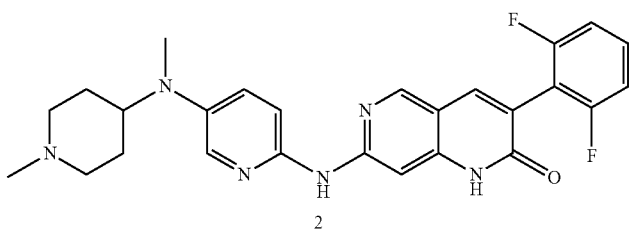

A mixture of Scheme 66 compound 1 (800 mg, 3.05 mmol) and TFA (3 mL) was stirred at 90° C. for 4 h. After TLC showed the starting material was completely consumed, the reaction mixture was neutralized with aqueous NaHCO$_3$ (up to pH 9) and extracted with EtOAc (2×100 mL). The organic layer was washed with brine (20 mL), dried over Na$_2$SO$_4$ then filtered and concentrated to give a residue which was purified by flash chromatography on silica gel (eluting with CH$_2$Cl$_2$/MeOH 100/0 gradually increasing to 90/10) to give Compound 140 (80 mg, yield: 13%) as a yellow solid. $^1$H NMR (400 MHz, DMSO-d$_6$): δ 11.93 (s, 1H), 9.68 (s, 1H), 8.52 (s, 1H), 7.97 (s, 1H), 7.85 (s, 1H), 7.74 (s, 1H), 7.49 (m, 1H), 7.34 (s, 2H), 7.18 (t, J=7.8 Hz, 2H), 3.51-3.40 (m, 1H), 2.83 (d, J=10.8 Hz, 2H), 2.71 (s, 3H), 2.17 (s, 3H), 1.99 (t, J=11.2 Hz, 2H), 1.70 (m, 2H), 1.58 (d, J=11.0 Hz, 2H). MS [ESI, MH$^+$]=477.24.

Scheme 66 intermediate 1 was prepared in a manner similar to Compound 138 using (2,4-dimethoxyphenyl)methanamine instead of cyclobutanamine in the synthesis of the precursor of the naphthyridinone. $^1$H NMR (400 MHz, CDCl$_3$): δ 8.56 (s, 1H), 7.84 (s, 1H), 7.54 (s, 1H), 7.39 (m, 1H), 7.13 (d, J=8.4 Hz, 1H), 7.06-6.97 (m, 2H), 6.51 (d, J=2.4 Hz, 1H), 6.42 (dd, J=8.5, 2.4 Hz, 1H), 5.45 (s, 2H), 3.99 (s, 3H), 3.78 (s, 3H). MS [ESI, MH$^+$]=627.36.

Example 73

Synthesis of Compound 141

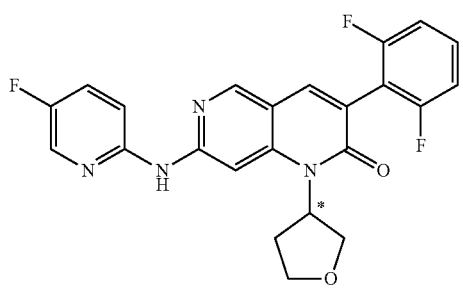

Compound 141

Compound 141, (S or R)-3-(2,6-difluorophenyl)-7-((5-fluoropyridin-2-yl)amino)-1-(tetrahydrofuran-3-yl)-1,6-naphthyridin-2(1H)-one was prepared in a similar manner to Compound 125 using racemic tetrahydrofuran-3-amine in the first step (and omitting the protection and deprotection steps specific to the hydroxyl group) to obtain the racemic mixture of Compound 141 and its enantiomer (350 mg, yield: 58%). Compound 141 and its enantiomer were separated by chiral preparative HPLC following the final synthetic step; therefore the absolute chirality is unknown. $^1$H NMR (400 MHz, DMSO-d$_6$): δ 10.21 (s, 1H), 8.65 (s, 1H), 8.42-8.20 (m, 2H), 8.06 (s, 1H), 7.70 (m, 1H), 7.50 (m, 2H), 7.21 (t, J=8.7 Hz, 2H), 6.29-5.93 (m, 1H), 4.40 (m, 1H), 4.02 (dd, J=9.4, 5.5 Hz, 1H), 3.94 (t, J=9.3 Hz, 1H), 3.82 (m, 1H), 2.49 (s, 1H), 2.30-2.19 (m, 1H). MS [ESI, MH$^+$]=439.16.

Synthesis of Compound 142

Compound 142

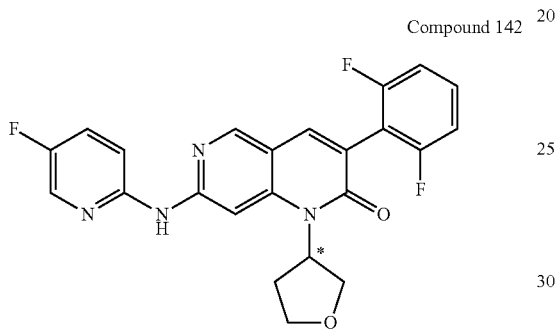

Compound 142, (R or S)-3-(2,6-difluorophenyl)-7-((5-fluoropyridin-2-yl)amino)-1-(tetrahydrofuran-3-yl)-1,6-naphthyridin-2(1H)-one was separated from Compound 141 by chiral preparative HPLC as described above: the absolute chirality is unknown. $^1$H NMR (400 MHz, DMSO-d$_6$): δ 10.21 (s, 1H), 8.65 (s, 1H), 8.34-8.22 (m, 2H), 8.06 (s, 1H), 7.70 (m, 1H), 7.60-7.39 (m, 2H), 7.21 (t, J=8.6 Hz, 2H), 6.19-5.96 (m, 1H), 4.40 (m, 1H), 4.02 (dd, J=9.3, 5.6 Hz, 1H), 3.94 (t, J=9.3 Hz, 1H), 3.87-3.77 (m, 1H), 2.49 (s, 3H), 2.29-2.16 (m, 1H). MS [ESI, MH$^+$]=439.22.

Example 74

Synthesis of Compound 143

Compound 143

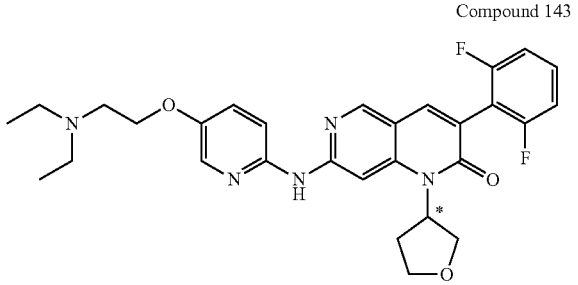

Compound 143, (S or R)-7-((5-(2-(diethylamino)ethoxy)pyridin-2-yl)amino)-3-(2,6-difluoro phenyl)-1-(tetrahydrofuran-3-yl)-1,6-naphthyridin-2(1H)-one was prepared in a manner similar to Compound 138 using racemic tetrahydrofuran-3-amine in the synthesis of the precursor of the napthyridinime and 5-(2-(diethylamino)ethoxy)pyridin-2-amine in the cross-coupling step (and omitting the protection and deprotection steps specific to the hydroxyl group)) to obtain the racemic mixture of Compound 143 and its enantiomer (140 mg, yield: 28%). Compound 143 and its enantiomer were separated by chiral preparative HPLC following the final synthetic step; therefore the absolute chirality is unknown. $^1$H NMR (400 MHz, CDCl$_3$): δ 8.44 (s, 1H), 8.09-7.91 (m, 2H), 7.67 (s, 1H), 7.41-7.26 (m, 4H), 6.97 (t, J=8.6 Hz, 2H), 6.38-6.15 (m, 1H), 4.54-4.38 (m, 1H), 4.21 (dd, J=10.0, 5.0 Hz, 1H), 4.13-3.97 (m, 3H), 3.85 (m, 1H), 2.88 (t, J=6.2 Hz, 2H), 2.65 (m, 4H), 2.58-2.40 (m, 1H), 2.34 (dd, J=13.3, 7.1 Hz, 1H), 1.07 (t, J=7.1 Hz, 6H). MS [ESI, MH$^+$]=536.29.

Synthesis of Compound 144

Compound 144

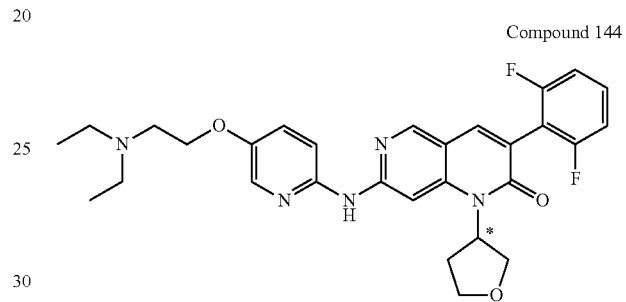

Compound 144, (R or S)-7-((5-(2-(diethylamino)ethoxy)pyridin-2-yl)amino)-3-(2,6-difluoro phenyl)-1-(tetrahydrofuran-3-yl)-1,6-naphthyridin-2(1H)-one was separated from Compound 143 by chiral preparative HPLC as described above: the absolute chirality is unknown. $^1$H NMR (400 MHz, CDCl$_3$): δ 8.45 (s, 1H), 8.09-7.93 (m, 2H), 7.68 (s, 1H), 7.44 (s, 1H), 7.40-7.26 (m, 3H), 6.98 (t, J=8.6 Hz, 2H), 6.29 (dd, J=13.9, 7.5 Hz, 1H), 4.47 (m, 1H), 4.22 (dd, J=9.8, 5.0 Hz, 1H), 4.15-3.96 (m, 3H), 3.91-3.80 (m, 1H), 2.90 (t, J=6.1 Hz, 2H), 2.67 (m, 4H), 2.51 (m, 1H), 2.33 (m, 1H), 1.09 (t, J=7.1 Hz, 6H). MS [ESI, MH$^+$]=536.22.

Synthesis of Compound 145

Compound 145

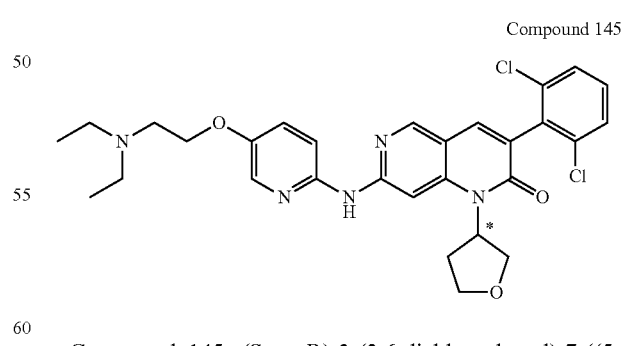

Compound 145, (S or R)-3-(2,6-dichlorophenyl)-7-((5-(2-(diethylamino)ethoxy)pyridin-2-yl)amino)-1-(tetrahydrofuran-3-yl)-1,6-naphthyridin-2(1H)-one was prepared in a manner similar to Compound 143 using 2-(2,6-dichlorophenyl)acetonitrile instead of its difluoro analogue to obtain the racemic mixture of Compound 141 and its enantiomer (270 mg, yield: 19%). Compound 145 and its enantiomer were separated by chiral preparative HPLC following the final synthetic step; therefore the absolute chirality is unknown. ¹H NMR (400 MHz, CDCl₃): δ 8.47 (s, 1H), 8.05 (d, J=3.1 Hz, 2H), 7.57 (s, 1H), 7.41 (d, J=8.3 Hz, 3H), 7.35 (d, J=9.0 Hz, 1H), 7.29 (dd, J=6.5, 3.9 Hz, 1H), 7.25 (s, 1H), 6.24 (td, J=9.7, 4.9 Hz, 1H), 4.48 (m, 1H), 4.23 (dd, J=9.8, 5.2 Hz, 1H), 4.15-4.00 (m, 3H), 3.88 (m, 1H), 2.89 (t, J=6.1 Hz, 2H), 2.66 (m, 4H), 2.54 (m, 1H), 2.35 (m, 1H), 1.09 (t, J=7.1 Hz, 6H). MS [ESI, MH⁺]=568.15.

Synthesis of Compound 146

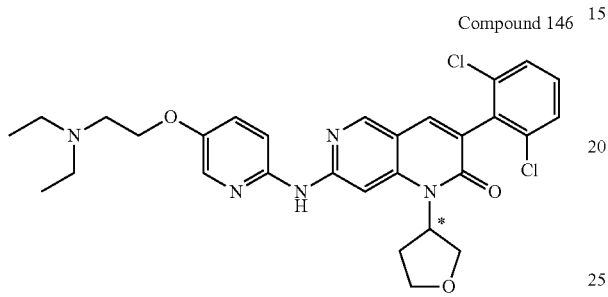

Compound 146

Compound 146, (R or S)-3-(2,6-dichlorophenyl)-7-((5-(2-(diethylamino)ethoxy)pyridin-2-yl)amino)-1-(tetrahydrofuran-3-yl)-1,6-naphthyridin-2(1H)-one was separated from Compound 145 by chiral preparative HPLC as described above: the absolute chirality is unknown. ¹H NMR (400 MHz, CDCl₃): δ 8.47 (s, 1H), 8.05 (d, J=3.0 Hz, 2H), 7.57 (s, 1H), 7.42 (d, J=8.2 Hz, 3H), 7.35 (d, J=9.1 Hz, 1H), 7.32-7.28 (m, 1H), 7.26 (s, 1H), 6.33-6.16 (m, 1H), 4.48 (td, J=8.7, 3.5 Hz, 1H), 4.23 (dd, J=9.7, 5.2 Hz, 1H), 4.12-3.99 (m, 3H), 3.88 (m, 1H), 2.89 (t, J=6.1 Hz, 2H), 2.66 (m, 4H), 2.54 (m, 1H), 2.36 (m, 1H), 1.09 (t, J=7.1 Hz, 6H). MS [ESI, MH⁺]=568.15.

Synthesis of Compound 147

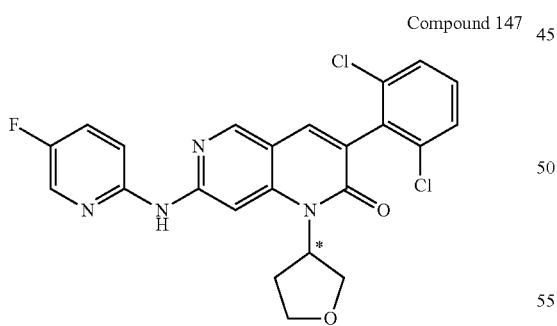

Compound 147

Compound 147, (S or R)-3-(2,6-dichlorophenyl)-7-((5-fluoropyridin-2-yl)amino)-1-(tetrahydrofuran-3-yl)-1,6-naphthyridin-2(1H)-one was prepared in a manner similar to Compound 145 using 5-fluoropyridin-2-amine in the cross-coupling step to obtain the racemic mixture of Compound 147 and its enantiomer (300 mg, yield: 25%). Compound 147 and its enantiomer were separated by chiral preparative HPLC following the final synthetic step; therefore the absolute chirality is unknown. ¹H NMR (400 MHz, CDCl₃): δ 8.50 (s, 1H), 8.21 (d, J=3.0 Hz, 1H), 8.04 (s, 1H), 7.58 (d, J=8.5 Hz, 2H), 7.49 (dd, J=9.0, 3.7 Hz, 1H), 7.42 (d, J=7.9 Hz, 3H), 7.29 (d, J=8.4 Hz, 1H), 6.30 (s, 1H), 4.49 (m, 1H), 4.24 (dd, J=9.9, 4.9 Hz, 1H), 4.06 (t, J=9.6 Hz, 1H), 3.88 (d, J=6.8 Hz, 1H), 2.61-2.46 (m, 1H), 2.44-2.31 (m, 1H). MS [ESI, MH⁺]=471.13.

Synthesis of Compound 148

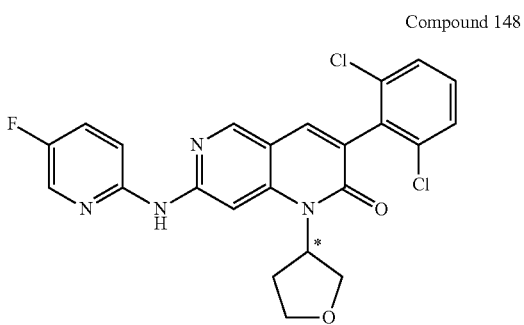

Compound 148

Compound 148, (R or S)-3-(2,6-dichlorophenyl)-7-((5-fluoropyridin-2-yl)amino)-1-(tetrahydrofuran-3-yl)-1,6-naphthyridin-2(1H)-one was separated from Compound 147 by chiral preparative HPLC as described above: the absolute chirality is unknown. ¹H NMR (400 MHz, CDCl₃): δ 8.49 (s, 1H), 8.21 (d, J=2.9 Hz, 1H), 8.05 (s, 1H), 7.59 (d, J=2.7 Hz, 2H), 7.49 (dd, J=9.1, 3.7 Hz, 1H), 7.46-7.38 (m, 2H), 7.29 (d, J=8.3 Hz, 1H), 6.36-6.22 (m, 1H), 4.49 (m, 1H), 4.24 (dd, J=9.9, 5.0 Hz, 1H), 4.06 (t, J=9.6 Hz, 1H), 3.88 (m, 1H), 2.61-2.44 (m, 1H), 2.43-2.25 (m, 1H). MS [ESI, MH⁺]=471.13.

Example 75

Synthesis of Compound 149

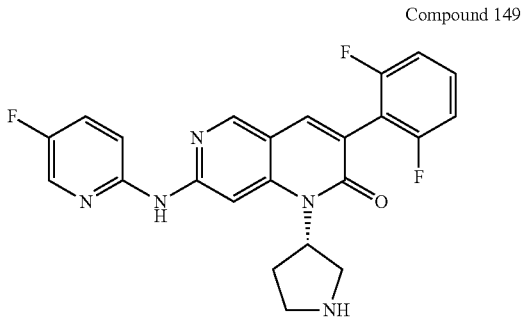 [SMILES: O=c1c(-c2c(F)cccc2F)cc2cnc(Nc3ccc(F)cn3)cc2n1[C@H]1CCNC1]

Compound 149

Compound 149, (S)-3-(2,6-difluorophenyl)-7-((5-fluoropyridin-2-yl)amino)-1-(pyrrolidin-3-yl)-1,6-naphthyridin-2(1H)-one was prepared as shown in Scheme 67 in which intermediate 1 was prepared in a manner similar to Compound 125 using enantiomerically pure (S)-tert-butyl 3-aminopyrrolidine-1-carboxylate instead of cyclobutanamine in the synthesis of the precursor of the naphthyridinime.

Scheme 67

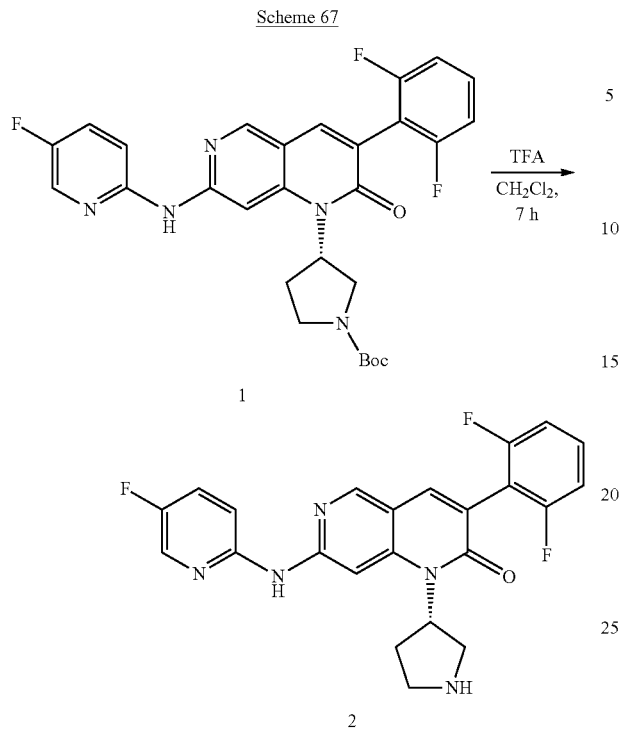

A mixture of Scheme 66 compound 1 (300 mg, 0.56 mmol) and TFA (0.2 mL, 2.80 mmol) in CH$_2$Cl$_2$ (6 mL) was stirred at RT under nitrogen atmosphere for 7 h. After TLC showed the starting material was completely consumed, the mixture was quenched with aqueous NaHCO$_3$ (10 mL) and extracted with ethyl acetate (2×20 mL). The organic layer was washed with brine (10 mL), dried over anhydrous Na$_2$SO$_4$ then filtered and concentrated to give a residue which was purified by flash chromatography on silica gel (eluting with CH$_2$Cl$_2$/MeOH=200/1 to 80/1) to give Compound 149 (32 mg, yield: 13%) as a yellow solid. $^1$H NMR (400 MHz, CD$_3$OD): δ 8.80 (s, 1H), 8.36 (d, J=2.9 Hz, 1H), 8.18 (s, 1H), 7.86 (m, 1H), 7.77 (s, 1H), 7.50 (m, 1H), 7.41 (dd, J=9.2, 3.7 Hz, 1H), 7.10 (t, J=8.5 Hz, 2H), 5.62 (m, 1H), 3.85 (m, 2H), 3.70 (dd, J=13.0, 9.2 Hz, 1H), 3.43 (m, 1H), 2.75 (m, 1H), 2.43 (m, 1H). MS [ESI, MH$^+$]=438.12.

Synthesis of Compound 150

Scheme 68

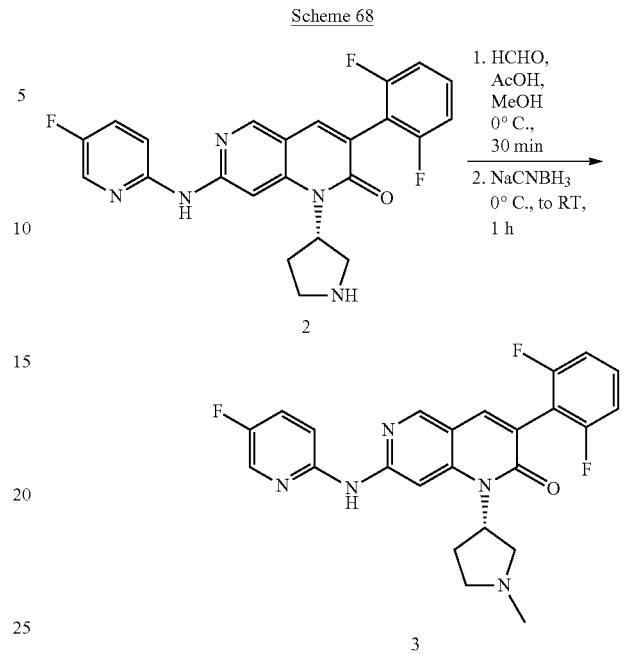

To a cooled (0° C.) solution of Scheme 68 compound 2 (230 mg, 0.53 mmol) in AcOH (0.1 mL) and MeOH (2 mL) was added aqueous HCHO (0.09 mL, 1.05 mmol) and the reaction mixture was stirred at 0° C. for 30 min under nitrogen atmosphere after which NaCNBH$_3$ (67 mg, 1.05 mmol) was added and the temperature was allowed to rise to RT while stirring was continued for 1 h. After TLC showed the starting material was completely consumed, the mixture was quenched with water (10 mL) and extracted with ethyl acetate (2×20 mL). The organic layer was washed with brine (10 mL) and dried over anhydrous Na$_2$SO$_4$ then filtered and concentrated to give a residue which was purified by prep-HPLC to give Compound 150 (80 mg, yield: 33%) as an off-white solid. $^1$H NMR (400 MHz, CD$_3$OD): δ 8.58 (d, J=4.0 Hz, 1H), 8.33 (s, 1H), 8.21 (d, J=2.7 Hz, 1H), 7.92 (d, J=3.8 Hz, 1H), 7.61-7.50 (m, 2H), 7.48-7.37 (m, 1H), 7.06 (t, J=8.7 Hz, 2H), 5.88 (m, 1H), 3.25 (s, 2H), 3.01 (s, 1H), 2.88 (s, 1H), 2.50 (d, J=8.5 Hz, 4H), 2.33 (s, 1H). MS [ESI, (M-H)$^-$]=450.20.

Synthesis of Compound 151

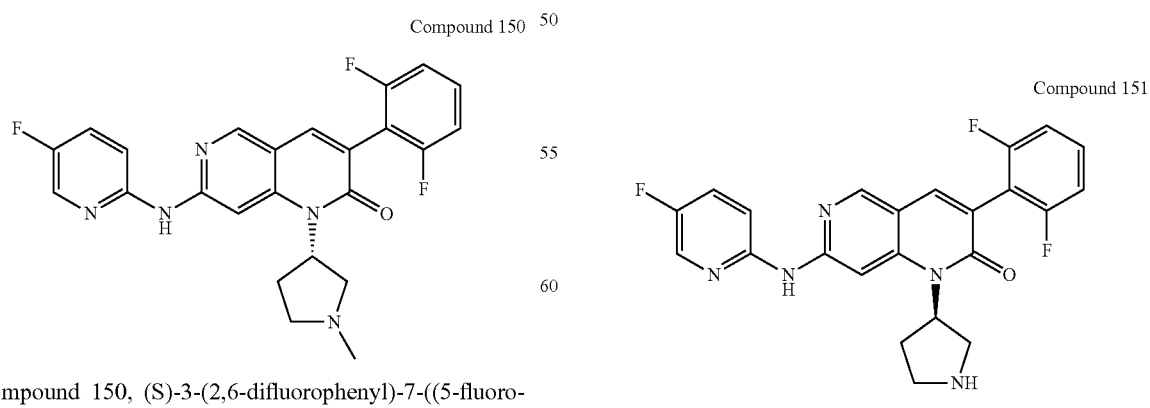

Compound 150, (S)-3-(2,6-difluorophenyl)-7-((5-fluoro-pyridin-2-yl)amino)-1-(1-methylpyrrolidin-3-yl)-1,6-naphthyridin-2(1H)-one was prepared as shown in Scheme 68 from Compound 149

Compound 151, (R)-3-(2,6-difluorophenyl)-7-((5-fluoro-pyridin-2-yl)amino)-1-(pyrrolidin-3-yl)-1,6-naphthyridin-2

(1H)-one was prepared in a manner similar to Compound 149 using enantiomerically pure (R)-tert-butyl 3-aminopyrrolidine-1-carboxylate instead of the (S) enantiomer to obtain Compound 151 (95 mg, yield: 63%). $^1$H NMR (400 MHz, CD$_3$OD): δ 8.73 (s, 1H), 8.32 (d, J=3.0 Hz, 1H), 8.12 (s, 1H), 7.95 (s, 1H), 7.74 (m, 1H), 7.54-7.38 (m, 2H), 7.09 (t, J=8.4 Hz, 2H), 5.64-5.55 (m, 1H), 3.91-3.78 (m, 2H), 3.67 (dd, J=12.9, 9.3 Hz, 1H), 3.48-3.34 (m, 1H), 3.25 (d, J=1.7 Hz, 1H), 2.75 (m, 1H), 2.44 (m, 1H). MS [ESI, MH$^+$]=438.19.

Synthesis of Compound 152

Compound 152

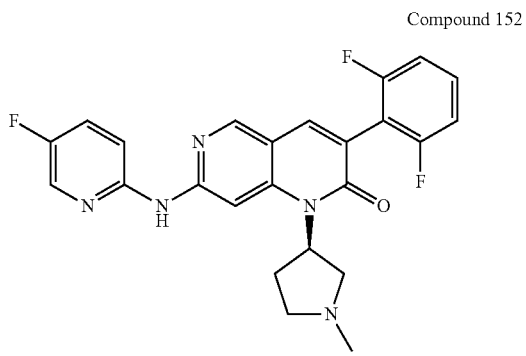 [SMILES: CN1CC[C@@H](n2c(=O)c(-c3c(F)cccc3F)cc3cnc(Nc4ccc(F)cn4)cc32)C1]

Compound 152, (R)-3-(2,6-difluorophenyl)-7-((5-fluoropyridin-2-yl)amino)-1-(1-methylpyrrolidin-3-yl)-1,6-naphthyridin-2(1H)-one was prepared in a manner similar to Compound 150 using enantiomerically pure Compound 151 as a starting material to obtain Compound 152 (80 mg, yield: 41%). $^1$H NMR (400 MHz, CD$_3$OD): δ 8.57 (s, 1H), 8.32 (s, 1H), 8.21 (d, J=2.8 Hz, 1H), 7.92 (s, 1H), 7.61-7.50 (m, 2H), 7.44 (m, 1H), 7.06 (dd, J=9.5, 8.0 Hz, 2H), 5.89 (m, 1H), 3.27-3.13 (m, 2H), 2.98 (t, J=9.6 Hz, 1H), 2.86 (m, 1H), 2.58-2.50 (m, 4H), 2.31 (m, 1H). MS [ESI, MH$^+$]=452.20.

Example 76

Amino Naphthyridinones can Inhibit BTK, SRC, and LYN

Amino naphthyridinones were evaluated in a standard luminescence assay measuring the enzyme's ability to utilize ATP and generate ADP (ADP-GLO™ Kinase Assay, Promega). This luminescent kinase assay is a homogeneous, high-throughput screening method that measures kinase activity by quantifying the amount of ADP produced during a kinase reaction. The assay is performed in three steps; first, the kinase reaction is initiated by incubating kinase, substrate and ATP. After the kinase reaction is completed, the kinase reaction is terminated and depleted of the remaining ATP. Then the Kinase Detection Reagent is added to simultaneously convert ADP to ATP and allow the newly synthesized ATP to be measured using a luciferase/luciferin reaction. The light generated is measured using a luminometer. Luminescence correlates to ADP concentrations. The kinase reaction was performed in a 384 well solid white plate by incubating different amounts of compound with purified enzyme, ATP, and substrate in reaction buffer for 60 minutes. The reaction was stopped, detection reagent added and the plate read on a luminometer.

Table 1 summarizes representative results and shows the identification of several amino naphthyridinones with IC50 potency of <1 uM against BTK, Src, or Lyn. A subset of these amino naphthyridinones showed significant activity (<1 uM) against all three of these kinases, while other subsets showed significant activity against each combination of the 2 of these 3 kinases. Other subsets are apparent in the table in which the IC50 against one, two, or all three of these kinases is <0.1 uM. Thus amino naphthyridinones can inhibit BTK and SFKs in various combinations.

Example 77

Amino Naphthyridinones Inhibit Proliferation of Tumor Cell Lines

The potency of these amino naphthyridinones was evaluated in a standard proliferation/viability assay (CELLTITER-GLO® Luminescent Cell Viability Assay, Promega) to determine their effect on the growth of B cell tumor cell lines. A luminescent cell viability assay measuring metabolism as determined by the amount of ATP in a cell population was used. The assay was performed in a 96 well plate by incubating different amounts of compound with fixed number of cells for 48 hrs. Table 1 summarizes representative results using two B cell tumor lines, namely DoHH2 (DMSZ (The Deutsche Sammlung von Mikroorganismen and Zellkulturen) No: ACC 47) which responds to known drugs such as dasatinib and PCI-32765, and Ramos (ATCC (American Type Culture Collection) No.: CRL-1596) which is resistant to known kinase inhibitors including dasatinib (a polykinase inhibitor), Inno-406 (a LYN inhibitor), AZN0530 (a SRC inhibitor), and PCI-32765 (a BTK inhibitor). Many amino naphthyridinones inhibited the proliferation and viability of DoHH2 cells with EC50 of less than 1 uM. Several of these amino naphthyridinones also inhibited the viability of Ramos cells with significant potency, having EC$_{50}$ of <10 uM, <5 uM, <3 uM, <2 uM, or <1 uM. Thus amino naphthyridinones can inhibit tumor cell lines expressing BTK and SFKs, including a cell line, Ramos, that is resistant to other known drugs targeting these kinases.

Example 78

Biochemical Selectivity

Figure 2:
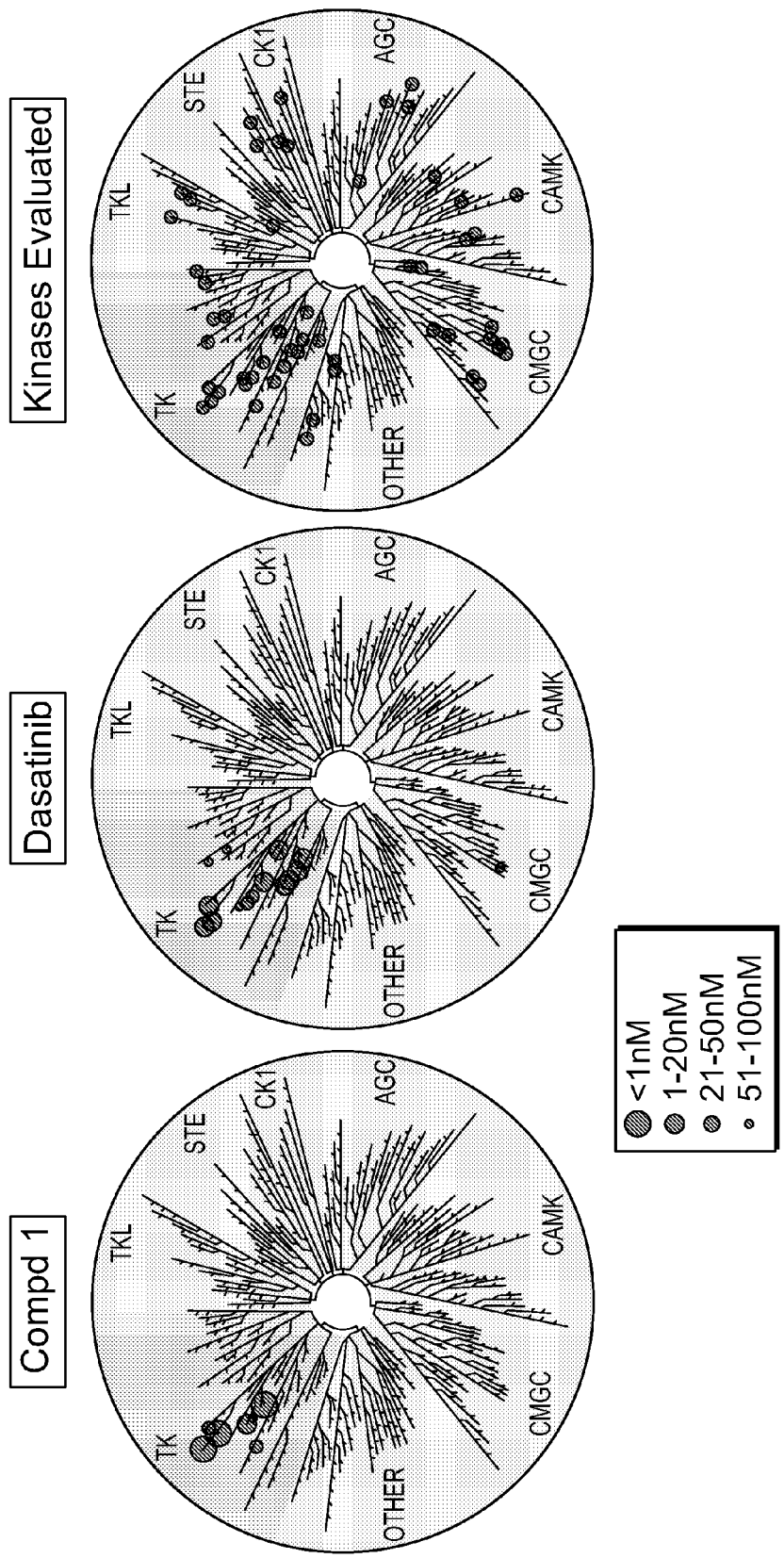
FIG. 2. Kinome maps showing kinase inhibitory activity/selectivity of amino naphthyridinones evaluated in Example 78, the subset of those kinases inhibited by Compound 1 and the subset of those kinases inhibited by dasatinib. Dasatinib data taken from the literature.

In order to determine the relative enzyme selectivity of these amino naphthyridinones, representative amino naphthyridinones were evaluated for their ability to inhibit various kinases. Kinases were selected for a broad representation of the kinome (see FIG. 2: Kinases Evaluated). Compounds were evaluated using the IC$_{50}$ profiler assay (Millipore), which measures substrate phosphorylation via γ-$^{33}$P-ATP transfer by the kinase of interest. The assay directly measures the catalytic incorporation of phosphate onto kinase substrates. The kinase protein is incubated in buffer with substrate and γ-$^{33}$P-ATP. The reaction is initiated by the addition of the Mg-ATP mix. At the end of the reaction incubation time, the reaction is stopped by the addition of phosphoric acid solution and 10 μL of the reaction is spotted onto a filtermat, washed, dried and counted in scintillation fluid.

Table 2 shows that the amino naphthyridinones evaluated have very significant activity (for example IC$_{50}$<100 nM) against specific representative protein tyrosine kinases and not against others. In particular the amino naphthyridinones inhibited Abl and some but not all tested members of the Tec and Src families of tyrosine kinases, but not tyrosine-like kinases or the non-tyrosine kinases tested (See FIG. 2: Compound 1). Even considering kinases for which the compounds have $IC_{50}$ of <500 nM or <1 µM the amino naphthyridinones are focused on a subset of tyrosine kinases to the near exclusion of other kinase families. Other known drugs with activity against BTK and SFKs, such as dasatinib and bosutinib, have activity against a broader array of tyrosine kinases as well as inhibiting non-tyrosine kinases (See FIG. 2: Dasatinib). Thus these amino naphthyridinones are more selective than other known drugs with activity against the presently targeted kinases.

TABLE 2

Kinase selectivity profile

| | | $IC_{50}$ (nM) | |
|---|---|---|---|
| Kinase | Kinase Family | Compound 1 | Compound 2 |
| Abl(h) | TK | <10 | 10-100 |
| Lyn(h) | TK | <10 | <10 |
| Src(1-530)(h) | TK | <10 | 10-100 |
| Lck(h) | TK | <10 | <10 |
| Bmx(h) | TK | <10 | 10-100 |
| Hck(h) activated* | TK | <10 | 100-500 |
| cSRC(h) | TK | <10 | 100-500 |
| FGFR1(h) | TK | <10 | 10-100 |
| BTK(h) | TK | 10-100 | 100-500 |
| Hck(h) | TK | 10-100 | 500-1000 |
| TGFBR1(h) | TKL | 100-500 | 500-1000 |
| Abl (T315I)(h) | TK | 100-500 | 500-1000 |
| KDR(h) | TK | 100-500 | 500-1000 |
| c-RAF(h) | TKL | 100-500 | 100-500 |
| PDGFRβ(h) | TK | 100-500 | 500-1000 |
| c-Kit (h) | TK | 100-500 | 100-500 |
| PDGFRα(h) | TK | 100-500 | 500-1000 |
| c-Kit(D816V)(h) | TK | 100-500 | >1,000 |
| BTK(R28H)(h) | TK | 500-1000 | >1,000 |
| SAPK2a(h) | CMGC | 500-1000 | >1,000 |
| EGFR (h) | TK | 500-1000 | >1,000 |
| Tie2 (h) | TK | 500-1000 | >1,000 |
| CSK(h) | TK | 500-1000 | >1,000 |
| ASK1(h) | STE | >1,000 | >1,000 |
| Aurora-A(h) | MISC | >1,000 | >1,000 |
| CaMKI(h) | CAMK | >1,000 | >1,000 |
| CDK2/cyclinA(h) | CMGC | >1,000 | >1,000 |
| CDK7/cyclinH/MAT1(h) | CMGC | >1,000 | >1,000 |
| CDK9/cyclinT1(h) | CMGC | >1,000 | >1,000 |
| CHK1(h) | CAMK | >1,000 | >1,000 |
| CK1(y) | CK1 | >1,000 | >1,000 |
| CK1δ(h) | CK1 | >1,000 | >1,000 |
| Flt3(h) | TK | >1,000 | >1,000 |
| GSK3α(h) | CMGC | >1,000 | >1,000 |
| GSK3β(h) | CMGC | >1,000 | >1,000 |
| IGF-1R(h) | TK | >1,000 | >1,000 |
| IKKα(h) | MISC | >1,000 | >1,000 |
| IKKβ(h) | MISC | >1,000 | >1,000 |
| Itk(h) | TK | >1,000 | >1,000 |
| JAK2(h) | TK | >1,000 | >1,000 |
| JAK3(h) | TK | >1,000 | >1,000 |
| JNK1α1(h) | CMGC | >1,000 | >1,000 |
| JNK2α2 (h) | CMGC | >1,000 | >1,000 |
| MAPK1(h) | CMGC | >1,000 | >1,000 |
| MAPKAP-K2(h) | CAMK | >1,000 | >1,000 |
| MEK1(h) | STE | >1,000 | >1,000 |
| Met(h) | TK | >1,000 | >1,000 |
| MKK6(h) | STE | >1,000 | >1,000 |
| mTOR(h) | Lipid/Atypical | >1,000 | >1,000 |
| p70S6K(h) | AGC | >1,000 | >1,000 |
| PAK2(h) | STE | >1,000 | >1,000 |
| PDK1(h) | AGC | >1,000 | >1,000 |
| PI3 Kinase (p110α/p85α)(h) | Lipid/Atypical | >1,000 | >1,000 |
| PI3 Kinase (p110β/p85α)(h) | Lipid/Atypical | >1,000 | >1,000 |
| Pim-1(h) | CAMK | >1,000 | >1,000 |
| PKCα(h) | AGC | >1,000 | >1,000 |
| Plk1(h) | MISC | >1,000 | >1,000 |
| SAPK2b(h) | CMGC | >1,000 | >1,000 |
| Syk(h) | TK | >1,000 | >1,000 |

*activated = phosphorylated

Several of the amino naphthyridinones compounds described herein were similarly evaluated or tested at a single concentration of 200 nM to evaluate their relative enzyme activity and selectivity profile using the biochemical assay describe above (data not shown). This class of compounds exhibits a typical profile that can be generally summarized as follows: Significant activity against specific enzymes including Abl, BTK, BMX, Lyn, Lck and Src; moderate activity against another set of enzymes including Kit, KDR, Raf, and PDGFR; very limited activity (meaning the ratio of its % remaining activity after treatment with the compound at 200 nM to that of BTK is typically >20) against a set of enzymes including SAPK2, TGFRβ, GSK3α, GSK3β, and PI3K; and virtually no measurable activity against several other enzymes tested, including MAPK1, MAPKAP-K2, PDK PKG, PKC, and Pim.

Example 79

Cell-Type Selectivity

In order to determine the relative cellular selectivity of these amino naphthyridinones, amino naphthyridinones with demonstrated activity against DoHH2 cells were evaluated in hematologic and non-hematologic cell lines. Results indicate that amino naphthyridinones have a differential effect on proliferation in various cell types, with potency in B cell lymphoma and multiple myeloma lines but not in normal primary epithelial cells (data not shown) or epithelial carcinoma. Most amino naphthyridinones were evaluated against PC3, an epithelial carcinoma, and showed no measurable potency in these cells, confirming their differential effect on B cell lymphoma. In addition, select compounds were evaluated against a T cell lymphoma line, H9, and showed limited effect in this CTCL cell line. Table 3 summarizes data obtained with two amino naphthyridinone compounds. Thus these amino naphthyridinones had activity against cells that express the target kinases, but not in cells expected to not express BTK.

TABLE 3

Cell-based Relative Potency

| | | EC50 | |
|---|---|---|---|
| Cell Line | Cell Type | Compd 1 | Compd 2 |
| DOHH2 | B Lymphoma | <0.1 | 2.1 |
| Ramos | B Lymphoma | 6.7 | 2.8 |
| SuDHL6 | B Lymphoma | 1.3 | 2.4 |
| RPMI | Myeloma | 7.3 | >10 |
| PC3 | Epithelial Ca | >10 | >10 |
| H9 | T Lymphoma | 9.7 | ND |

SuDHL6 (DSMZ #: ACC 572)
RPMI8226 (ATCC #: CCL-155)
PC-3 (ATCC #: CRL-1435)
H9 (ATCC #: HTB-176)

Example 80

Amino Naphthyridinones Effect $G_1$ Arrest in B Cell Lymphoma Cell Lines

The pathways involving the kinases of interest affect biological response by modulating cell survival and progression thru the cell cycle. Several amino naphthyridinones were therefore evaluated for their effect on cell cycle progression. Cell cycle studies were performed in vitro on DoHH2 (see Table 4) and Ramos (data not shown) human tumor cells. Flow cytometry analysis was used to evaluate the ability of amino naphthyridinones to interfere with the cell cycle in these cancer cell lines. The cells were treated with compound for 24 hours, permeabilized and stained with propidium iodide. The cells were analyzed on a BD FACSCalibur flow cytometer using CellQuest Pro software. Treatments with paclitaxel or docetaxel ($G_2$ arrest) or rapamycin ($G_1$ arrest) were used as positive controls for cell cycle inhibition. Treatment of DoHH2 with our amino naphthyridinones resulted with a significant increase in $G_1$ arrest in most cases relative to the untreated control as shown in Table 4. Treatment with amino naphthyridinones with $EC_{50}$ of <1 uM reliably led to $G_1$ arrest and as did some but not all amino naphthyridinones with $EC_{50}$ of 1-10 uM. Amino naphthyridinones that had no measurable $EC_{50}$ on proliferation typically had no effect on cell cycle. Inhibition of BTK is expected to result in $G_1$ arrest.

TABLE 4

Cell cycle analysis of DoHH2 cells by flow cytometry

| Compound No. | $EC_{50}$ (Proliferation) | Effect on Cell Cycle |
|---|---|---|
| 1 | <1 | G1 Arrest |
| 8 | >10 | No Arrest |
| 16 | <1 | G1 Arrest |
| 17 | <1 | G1 Arrest |
| 18 | <1 | G1 Arrest |
| 19 | 1-10 | No Arrest |
| 22 | <1 | G1 Arrest |
| 23 | <1 | G1 Arrest |
| 25 | <1 | G1 Arrest |
| 27 | <1 | G1 Arrest |
| 28 | 1-10 | No Arrest |
| 34 | 1-10 | No Arrest |
| 35 | <1 | G1 Arrest |
| 42 | <1 | G2 Arrest |
| 46 | <1 | G1 Arrest |
| 47 | <1 | G1 Arrest |
| 52 | 1-10 | G1 Arrest |
| 56 | <1 | G1 Arrest |
| 66 | <1 | G1 Arrest |
| 67 | <1 | G1 Arrest |
| 69 | >10 | No Arrest |
| 70 | <1 | G1 Arrest |
| 72 | 1-10 | G1 Arrest |
| 73 | <1 | G1 Arrest |
| 75 | <1 | G1 Arrest |
| 77 | <1 | G1 Arrest |
| 79 | <1 | G1 Arrest |
| 89 | <1 | G1 Arrest |

Example 81

Exposure of Tumor Cell Lines to Amino Naphthyridinones Leads to Apoptosis

Activation of Tec family kinases including BTK, and/or Src kinase family members, regulates cell survival and cell death in normal B cells, lymphomas, and solid tumors. Apoptosis is a programmed cell death characterized by specific changes in cell morphology. Annexin V expression on the outer surface of the cell membrane is an early marker of apoptosis and 7AAD is a marker of late apoptosis. Flow cytometry analysis using Annexin V and 7AAD was used to evaluate the impact of an amino naphthyridinone on apoptosis in DoHH2, Ramos, and control epithelial carcinoma cells. Tumor cell lines were incubated for 6 hours with various concentrations of compound, washed, and stained with Annexin V FITC and 7AAD. Staurosporine was used as a positive control for apoptosis. Representative data is shown in Table 5 and indicate that representative Compound 1 demonstrated a profound effect on DoHH2 and Ramos cell lines, while having little effect on control tumor cells. Table 6 illustrates that several amino naphthyridinones induce significant apoptosis in DoHH2 cells.

TABLE 5

Evaluation of Compound 1-mediated apoptosis in tumor lines

| | Percent Apoptosis | | |
|---|---|---|---|
| | DOHH2 | Ramos | PC3 |
| untreated | 3.65 | 19.34 | 10.41 |
| staurosporine [Compound 1] | 95.86 | 73.74 | 47.16 |
| 1 uM | 4.43 | 35.71 | 7.86 |
| 2 uM | 29.84 | 38.94 | 6.5 |
| 5 uM | 21.76 | 39.09 | 11.74 |
| 10 uM | 37.52 | 51.63 | 6.35 |

TABLE 6

Compound-mediated Apoptosis of DOHH2

| | Percent Apoptosis at | | |
|---|---|---|---|
| Treatment | 0 uM | 2 uM | 5 uM |
| untreated | 8.34 | | |
| Compound 1 | | 26.2 | 32.58 |
| Compound 16 | | 32.57 | 58.99 |
| Compound 22 | | 21.68 | 25.8 |
| Compound 24 | | 34.76 | 46.4 |
| Compound 25 | | 26.94 | 20.29 |
| Compound 27 | | 37.05 | 54.19 |
| Compound 34 | | 19.54 | 46.27 |
| Compound 43 | | 27.26 | 29.38 |
| Compound 56 | | 26.92 | 27.47 |
| Compound 75 | | 35.66 | 39.47 |

Figure 3:
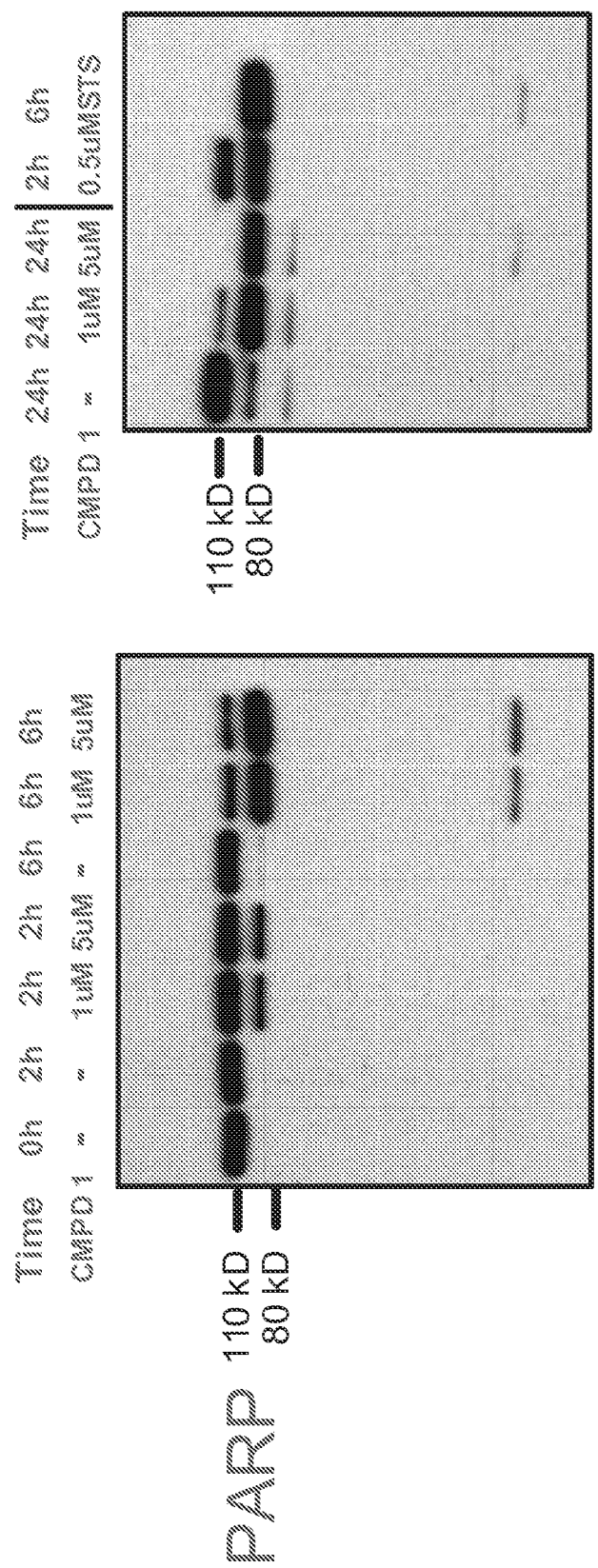
FIG. 3. Analysis of PARP cleavage after treatment with Compound 1.

Additionally, using an exemplary amino naphthyridinones, Compound 1, inhibition of PARP cleavage has been observed. PARP is downstream of the caspase cascade; its cleavage is an indicator or caspase-dependent apoptosis. PARP cleavage was assessed by Western blotting exponentially growing cultures of DoHH-2 cells that had been cultured overnight (18 h) in 1% FBS containing RPMI1640 media. These cells were washed, counted and plated with and without Compound 1 for 2, 6, and 24 hr. Cells were centrifuged and cell pellets were lysed using RIPA buffer from CST. Protein lysates were quantified using the BCA protein assay kit from Pierce and used in a standard Western blotting procedure. Anti-PARP antibody was obtained from CST and used as per the manufacturer's protocol. Results showed that low micromolar concentrations of compound induced the apoptotic pathway as shown by PARP cleavage. This cleavage was seen at the first time point post-treatment and increased with the amount of time that cells were exposed to the compound (See FIG. 3). Thus amino naphthyridinones can be used to induce apoptosis in tumor cells.

Example 82

Exposure of Tumor Cell Lines to Amino Naphthyridinones Leads to Inhibition of Phosphorylation of PLCγ2

Ramos cells were cultured in RPMI 1640 media with 10% FBS and were starved overnight (18 h) in 1% FBS containing media and on the next day pretreated with inhibitor for 2 h before stimulation. Cells were stimulated to induce BTK network dependent signal transduction pathways using mouse anti-human IgM (final concentration 10 ug/ml; Invitrogen) antibodies and 3.3 mM $H_2O_2$ mixture for 2 minutes followed by F(Ab) fragment that cross-linked the anti-IgM antibody (final concentration 10 ug/ml), and 3.3 mM $H_2O_2$ for 8 minutes. Cell lysates were prepared in lysis buffer containing protease and phosphatase inhibitors, quantified using the BCA protein assay kit (Pierce) and used for Western blotting. Antibodies specifically targeted to the molecules of interest, PLCγ2 phosphorylated at $Tyr_{1217}$ and total PLCγ2, (Cell Signaling Technology) were used in a standard Western blotting procedure.

Figure 4:
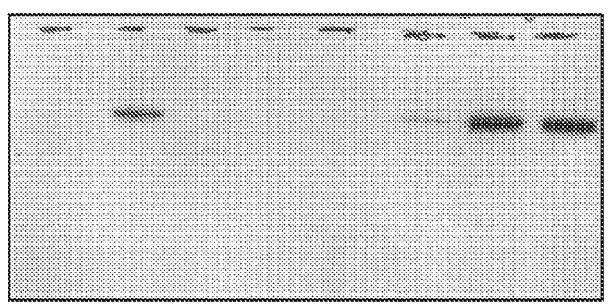
FIG. 4. Compound 1 dose response of inhibition of phosphorylation of PLCg2 by Western blotting.
Figure 4:
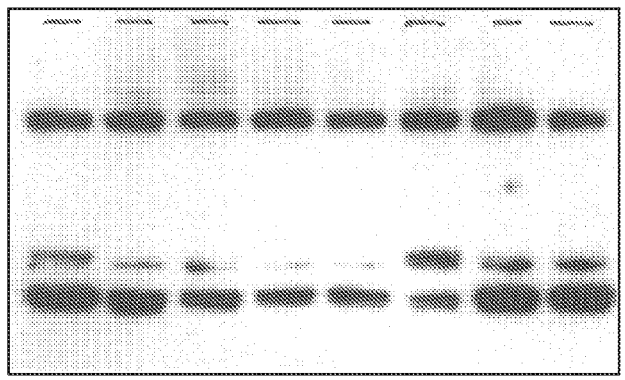
Figure 5:
FIG. 5. comparison of inhibition of PLCg2 by different exemplary compounds.
Figure 5:
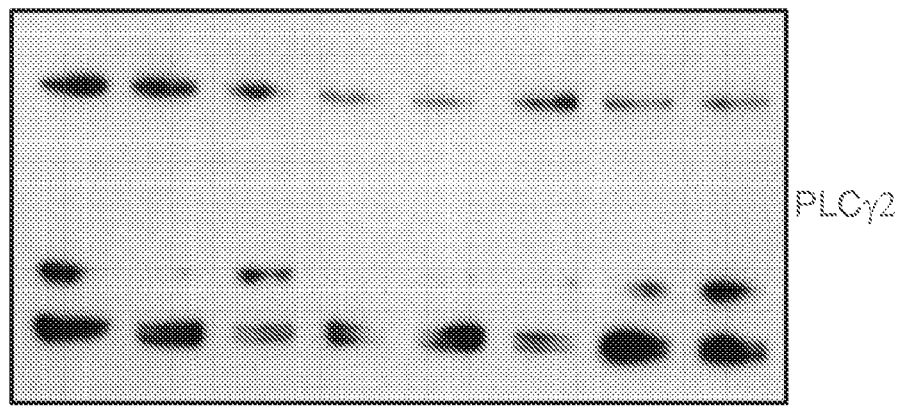

Phosphorylation of PLCγ2 at $Tyr_{1217}$ along with $Tyr_{753}$, $Tyr_{759}$ and $Tyr_{1197}$ is correlated with increased PLCγ2 activity. The readout for BTK network signaling was inhibition of phosphorylation of PLCγ2 induced by the anti-IgM treatment. A dose dependent decrease in PLCγ2 phosphorylation was observed upon treatment with Compound 1 (See FIG. 4). We have observed this inhibition with other amino naphthyridinones such as Compound 56 and Compound 70 as well (see FIG. 5).

Figure 6:
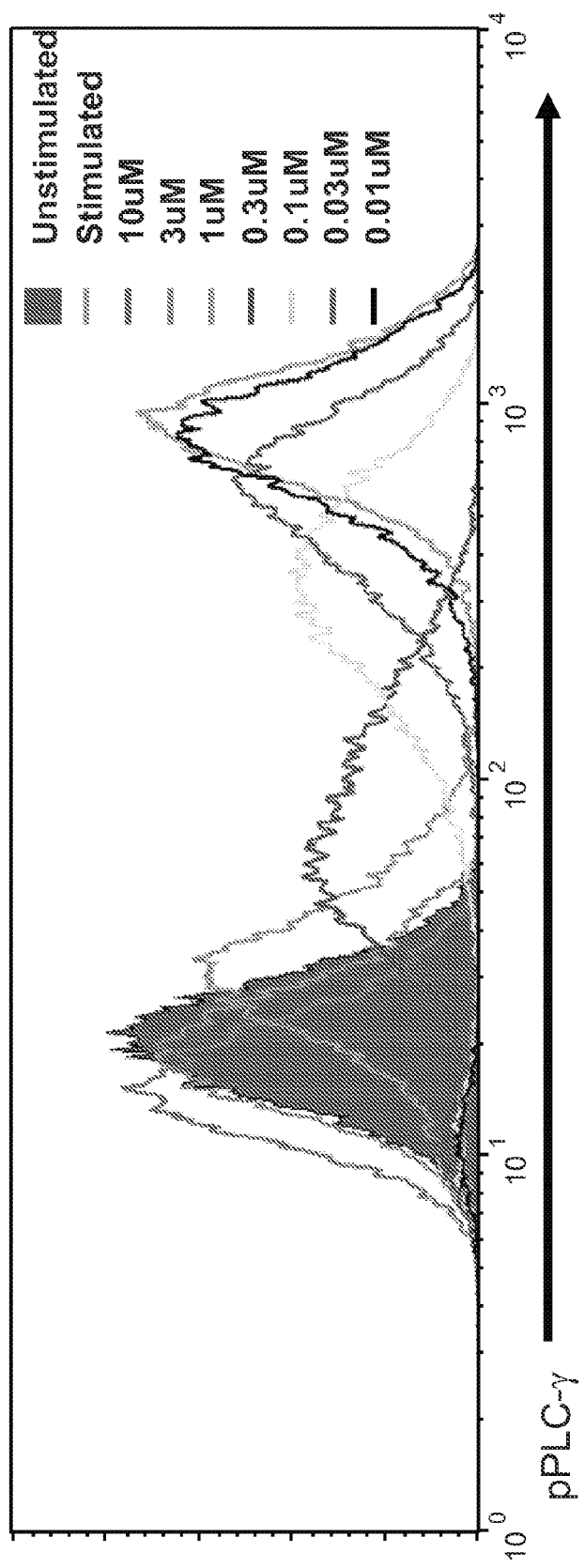
FIG. 6. PLC-γ2 phosphorylation in unstimulated Ramos cells and Ramos cells stimulated with anti IgM antibody and increasing doses of Compound 1.

PLCγ2 phosphorylation was also assessed by flow cytometry. Cells were similarly stimulated and following stimulation, Cytofix buffer (Becton Dickinson) was added, cells were centrifuged and the cell pellets incubated on ice with Phosflow perm buffer III (Becton Dickinson). These cell pellets were washed with Perm/Wash buffer (Becton Dickinson); resuspended and labeled for flow cytometry analysis in a staining mixture containing Perm/Wash buffer and PE-labeled anti-phosphoPCLγa2 ($Tyr_{1217}$) antibody (Becton Dickinson). The samples were washed with Perm/Wash buffer and analyzed on a FACS Calibur flow cytometer using CellQuest Pro software. As mentioned for the Western blot experiments, phosphorylation of PLCγ2 at $Tyr_{1217}$ along with $Tyr_{753}$, $Tyr_{759}$ and $Tyr_{1197}$ is correlated with increased PLCγ2 activity. The readout for BTK network signaling was inhibition of phosphorylation of PLCγ2. Cells were gated to exclude dead or dying cells. Fluorescence signals from the antibody staining were plotted in logarithmic units and data was analyzed using Cellquest Pro software. A dose dependent decrease in PLC-γ2 phosphorylation was observed in DoHH-2 (data not shown) and Ramos cells (FIG. 6) treated with increasing concentrations of Compound 1. Similar results were observed with additional compounds. An $ED_{50}$ was calculated based on the geometric mean of fluorescence intensity observed for treatment for four different concentrations of the inhibitors (see Table 7 and FIG. 6). These results correlate with the results of Western blotting. Thus treatment with amino naphthyridinones inhibits PLCγ2 phosphorylation consistent with inhibition of BTK and/or LYN activity.

TABLE 7

Inhibition of phosphorylation of PLC-γ2 by amino naphthyridinones

| Compound No. | $EC_{50}$ (uM) |
| --- | --- |
| 1 | 0.38 |
| 25 | 0.28 |
| 43 | 0.19 |
| 46 | 0.93 |
| 55 | >3 |
| 70 | 0.33 |
| 83 | 0.45 |

In order to compare the relative potency of various compounds on the inhibition of PLCγ2 phosphorylation, Ramos cells were pretreated with a single concentration of inhibitor, namely 0.3 uM, and stimulated as previously described. Following stimulation, cells were prepared for analysis by flow cytometry as described above. In short, cells were fixed and permeabilized using Cytofix buffer, Phosflow perm buffer and Perm/Wash buffer (Becton Dickinson). The cells were stained with PE-labeled anti-phosphoPCLγ2 (Tyr759) antibody (Becton Dickinson) and analyzed on a FACS Calibur flow cytometer using CellQuest Pro software. Table 8 shows percent inhibition of PLCγ2 phosphorylation as a result of treatment with different compounds. Flow Cytometry results indicate that all of the tested amino naphthyridinones compounds inhibited PLCγ2 phosphorylation, and that differences in their potency in inhibiting the signaling pathway could be observed. Thus aminonaphthyridinones are useful for the indirect inhibition of PLCγ2 phosphorylation.

TABLE 8

Inhibition of phosphorylation of PLC-γ2

| Compound No. | pPLCγ % inhibition |
| --- | --- |
| 1 | 63 |
| 16 | 46 |
| 23 | 32 |
| 25 | 61 |
| 55 | 12 |
| 56 | 60 |
| 78 | 55 |
| 92 | 88 |
| 93 | 79 |
| 94 | 59 |
| 95 | 87 |
| 96 | 86 |
| 99 | 83 |
| 100 | 70 |
| 101 | 92 |
| 107 | 48 |
| 109 | 91 |
| 115 | 97 |
| 120 | 87 |
| 129 | 88 |
| 134 | 80 |
| 135 | 82 |
| 136 | 85 |
| 137 | 98 |
| 138 | 99 |

Example 83

Exposure of Tumor Cell Lines to Amino Naphthyridinones Leads to Inhibition of Phosphorylation of SFKs and BTK

Figure 7A:
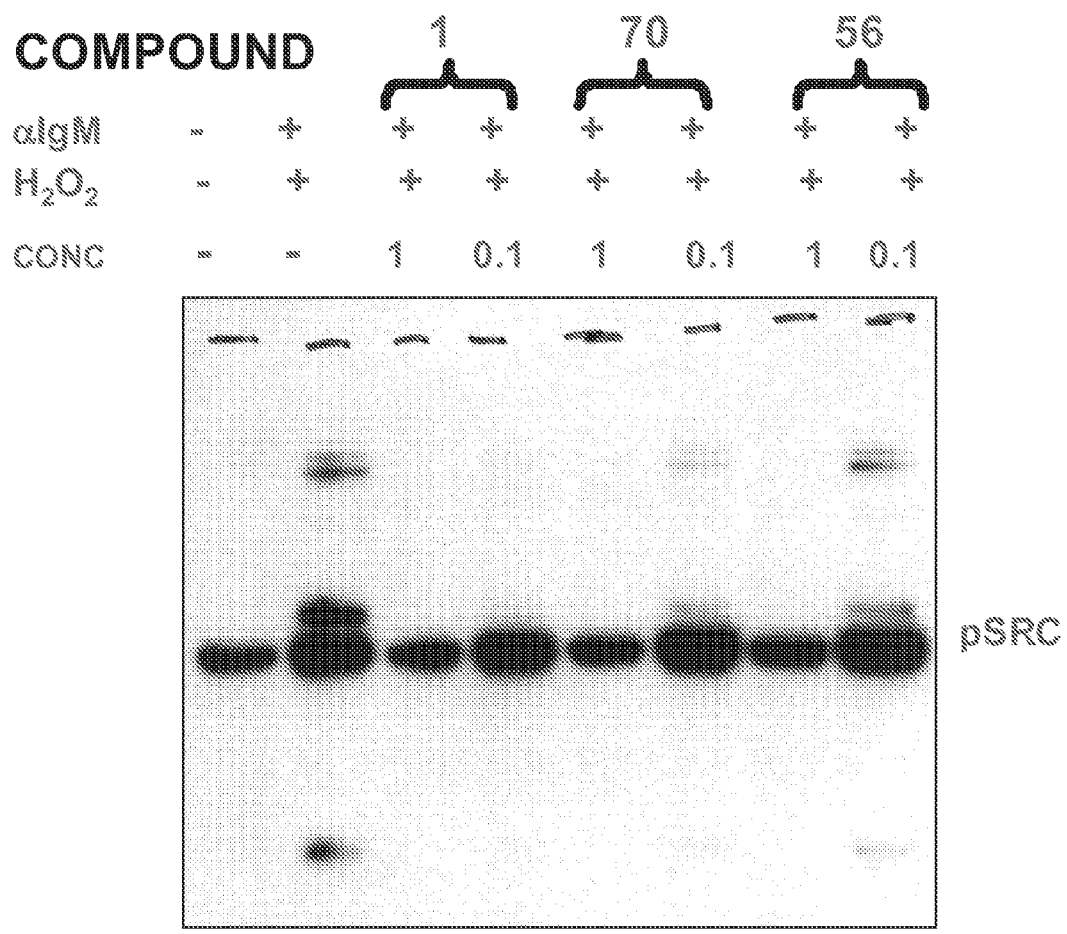
FIG. 7A. Comparison of inhibition of SRC phosphorylation by different exemplary compounds.
Figure 7B:
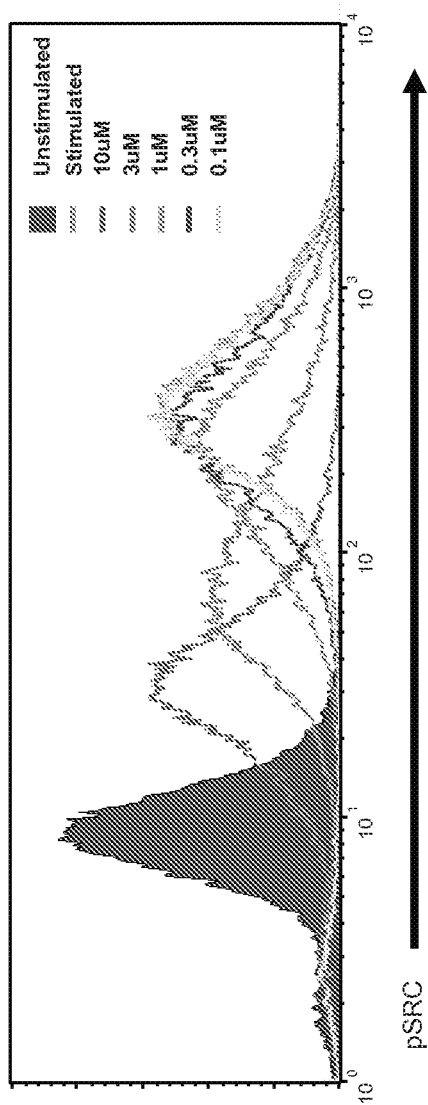
FIG. 7B. Compound 1 inhibition of SFK phosphorylation by measured by flow cytometry. Ramos cells stimulated with $H_2O_2$/anti-IgG/FaB for 10 minutes. Compound 1 incubated for 2 hrs in RPMI media with 5% FBS prior to stimulation. Cells evaluated by FACS analysis us pSRC and FITC-conjugated goat anti-rabbit secondary antibody following overnight storage at 4° C. in BD perm/wash buffer FIG. 8. Comparison of pBTK inhibition by different exemplary compounds. Labeling above gel image indicates compound number, stimulated (S) and unstimulated (U) controls.

Ramos cell lysates from stimulated and unstimulated cells were analyzed for the levels of phosphorylated SRC family members. As described in Example 82 (above), cells were pretreated for 2 hours with an amino naphthyridinones and then stimulated with anti-IgM antibody and $H_2O_2$, protein lysates were prepared, quantified and used for Western blotting. A commercially available antibody that detects Src phosphorylated at Tyr 416 (Cell Signalling) and may cross-react with other Src family members such as Lyn, Fyn, Lck, Yes and Hck when phosphorylated at equivalent sites was used for Western blot analysis. The molecular weights of SFK family members are quite similar (in the 55-60 kDa range) and different family members cannot be resolved by the conditions used for the Western blot. Phosphorylation of Src at Tyr 416, which lies in the activation loop of this molecule as well as equivalent tyrosine residues in other SFK molecules, increases enzyme catalytic activity—hence inhibition of this phosphorylation will cause down-regulation of the downstream catalytic activity. We have observed a dose-dependent decrease of phosphorylation of SFKs in Ramos cells treated with the exemplary amino naphthyridinones compounds 1, 56 and 70 (see FIG. 7A). The procedure can be similarly adapted for flow cytometric analysis as with the PLC-γ2 assay in Example 82. Ramos cells were incubated with Compound 1 for 2 hrs in RPMI media with 5% FBS prior to stimulation stimulated with $H_2O_2$/anti-IgM/F (Ab) for 10 minutes. Cells were evaluated by FACS analysis using anti-pSRC antibody and FITC-conjugated goat anti-rabbit secondary antibody following overnight storage at 4° C. in BD perm/wash buffer. FIG. 7B shows similar dose-dependent inhibition of SFK phosphorylation by Compound 1 measured using the flow cytometric assay.

Figure 8:
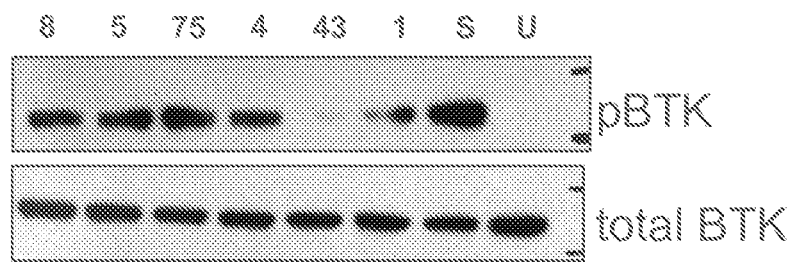

DoHH-2 cell lysates from stimulated and unstimulated cells were analyzed for the levels of phosphorylated BTK. Similar to as described in Example 82 (above), cells were pretreated with 0.1 µM solution of compound for 2 h; stimulated with anti-IgG antibody and $H_2O_2$, protein lysates were prepared, quantified and used for Western blotting. A commercially available antibody that detects BTK phosphorylated at Tyr 223 (Cell Signaling Technology) was used in the Western blot analysis. Autophosphorylation at Tyr 223 of the BTK molecule is required for activation of the molecule and may result from the BTK Tyr 551 phosphorylation by SFK Inhibition of the phosphorylation by compound maybe due to a direct effect on BTK autophosphorylation or due to an indirect inhibition of SFK upstream of this molecule. Thus amino naphthyridinones are able to inhibit the activation of BTK, to varying degree, as seen in FIG. 8.

In order to compare the relative potency of various compounds on the inhibition of SFK phosphorylation, Ramos cells were pretreated with a single concentration of inhibitor, namely 0.3 uM, and stimulated as previously described. Ramos cells were prepared for flow cytometry analysis as described in example 82, and stained with a commercially available antibody that detects SFK phosphorylated at Tyr 416, followed by Alexa Fluor 488 conjugated secondary antibody. Flow Cytometry results shown in table 9 indicate that most of the tested amino naphthyridinones compounds inhibit the phosphorylation of SFKs and that differences in their potency in inhibiting the signaling pathway could be observed. Thus amino naphthyridinones are useful in the inhibition of the phosphorylation of SFKs.

TABLE 9

Inhibition of Phosphorylation

| Compound No. | pSRC % inhibition |
|---|---|
| 1 | 31 |
| 16 | −1 |
| 23 | 5 |
| 25 | 26 |
| 55 | 18 |
| 56 | 25 |
| 78 | 8 |
| 92 | 56 |
| 93 | 39 |
| 94 | 9 |
| 95 | 56 |
| 96 | 51 |
| 99 | 40 |
| 100 | 30 |
| 101 | 70 |
| 107 | 28 |
| 109 | 65 |
| 115 | 80 |
| 120 | 57 |
| 129 | 66 |
| 134 | 44 |
| 135 | 49 |
| 136 | 55 |
| 137 | 81 |
| 138 | 86 |

Example 84

Dual Pathway Inhibition—Increased Control of Tumor Cell Line Growth Thru Inhibition of BTK and SFK

It is observed that inhibiting one individual target at a time using a highly selective compound has only a transient effect on tumor growth and disease progression, as other components of the signaling network compensate for the inhibited target. In contrast, simultaneous inhibition of critical targets can control the tumor-driven signaling network, and prevent a takeover by compensatory mechanisms. Our approach using amino naphthyridinone compounds, such as those in Table 1, aims to inhibit the signaling network, and provide better control the course of tumor growth and disease progression.

Figure 9:
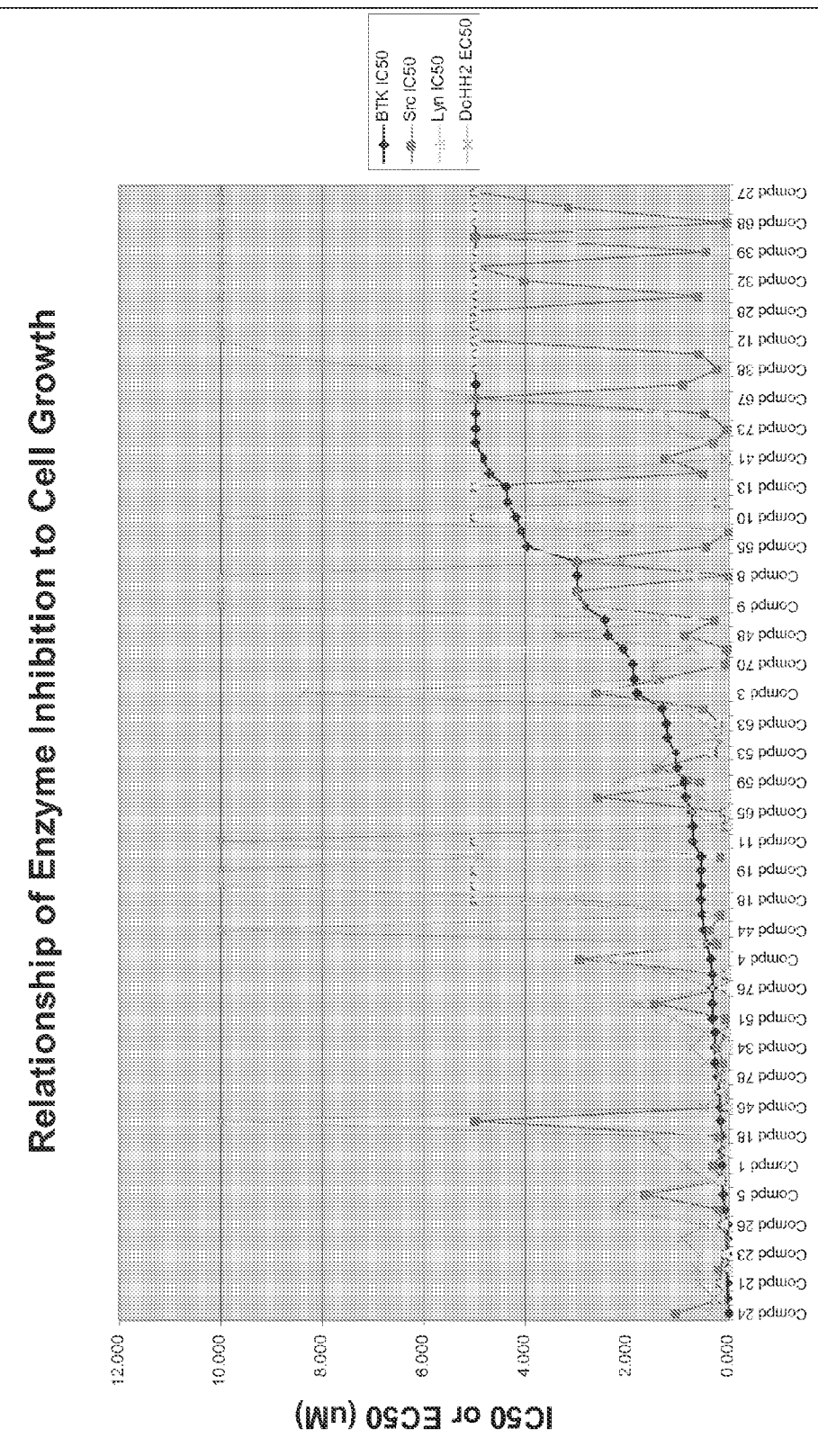
FIG. 9. Amino naphthyridinones that simultaneously inhibit BTK and SFK exhibit relative control over tumor cell growth in culture.

FIG. 9 illustrates that strong inhibition of BTK is important for regulating cell growth, and exhibits a trend indicating that simultaneous inhibition of BTK along with inhibition of SFK provides relative better control over tumor cell growth in culture than inhibiting one pathway alone. That is, as a general though not perfect rule, if there was not a substantial $IC_{50}$ for SRC and LYN (i.e., the $IC_{50}$ was greater than 5 µM as determined using the assay of Example 76) then there was also not a substantial $EC_{50}$ as measured by DoHH2 proliferation (i.e., the $EC_{50}$ was greater than 10 µM as determined using the assay of Example 77). Please note that in FIG. 9 $IC_{50}$ values plotted as 5 µM and EC50 values plotted as 10 µM should be interpreted as exceeding those values by an indeterminate amount.

Additionally, simultaneous inhibition of BTK, SRC, and LYN is more effective than inhibition of these target kinases not in combination. In order to determine whether simultaneous inhibition of BTK and SFK offered increased control of the proliferation of B cell tumor line relative to individual inhibition of BTK, Src or Lyn, cell lines were incubated with specific inhibitors to BTK (PCI-32765), Lyn (Inno-406) or Src (AZN0530) or with a compound shown to inhibit all 3 simultaneously. The same methodology as in Example 77 was used. Briefly, proliferation/viability was determined using a luminescent cell viability assay measuring the amount of ATP in the cell population. Untreated cells were used as control for no inhibition, and PC3 was used as a control for relative cellular specificity. Table 10 shows highly selective compounds have only a limited effect on tumor cell growth while simultaneous inhibition of the 3 kinases has an improved control over tumor cell growth. A similar observation was made in Example 85, where treatment with 62.5 mg/kg of Compound 1 had a more marked effect than treatment with 70 mg/kg of PCI-32765, the selective BTK inhibitor. Thus amino naphthyridinones are useful for the dual inhibition of the BTK and SFK arms of the intracellular signaling network and such dual inhibition is more effective than inhibiting a single arm of the network.

TABLE 10

Effect on Tumor Cell Growth

| | | $EC_{50}$ for Inhibition of | | | |
|---|---|---|---|---|---|
| Cell Line | Cell Type | BTK | Lyn | Src | Compnd 1 |
| DOHH2 | B Lymphoma | 2.8 | 6.9 | 2.4 | 0.85 |
| Ramos | B Lymphoma | >10 | 7.3 | >10 | 5.8 |
| SuDHL6 | B Lymphoma | 5.5 | 5.7 | 2.5 | 0.38 |
| RPMI 8226 | Myeloma | >10 | nd | nd | 2.9 |
| PC3 | Prostate Ca | >10 | >10 | >10 | >10 |

Example 85

In Vivo Tumor Growth Inhibited by an Exemplary Amino Naphthyridinone

Figure 10:
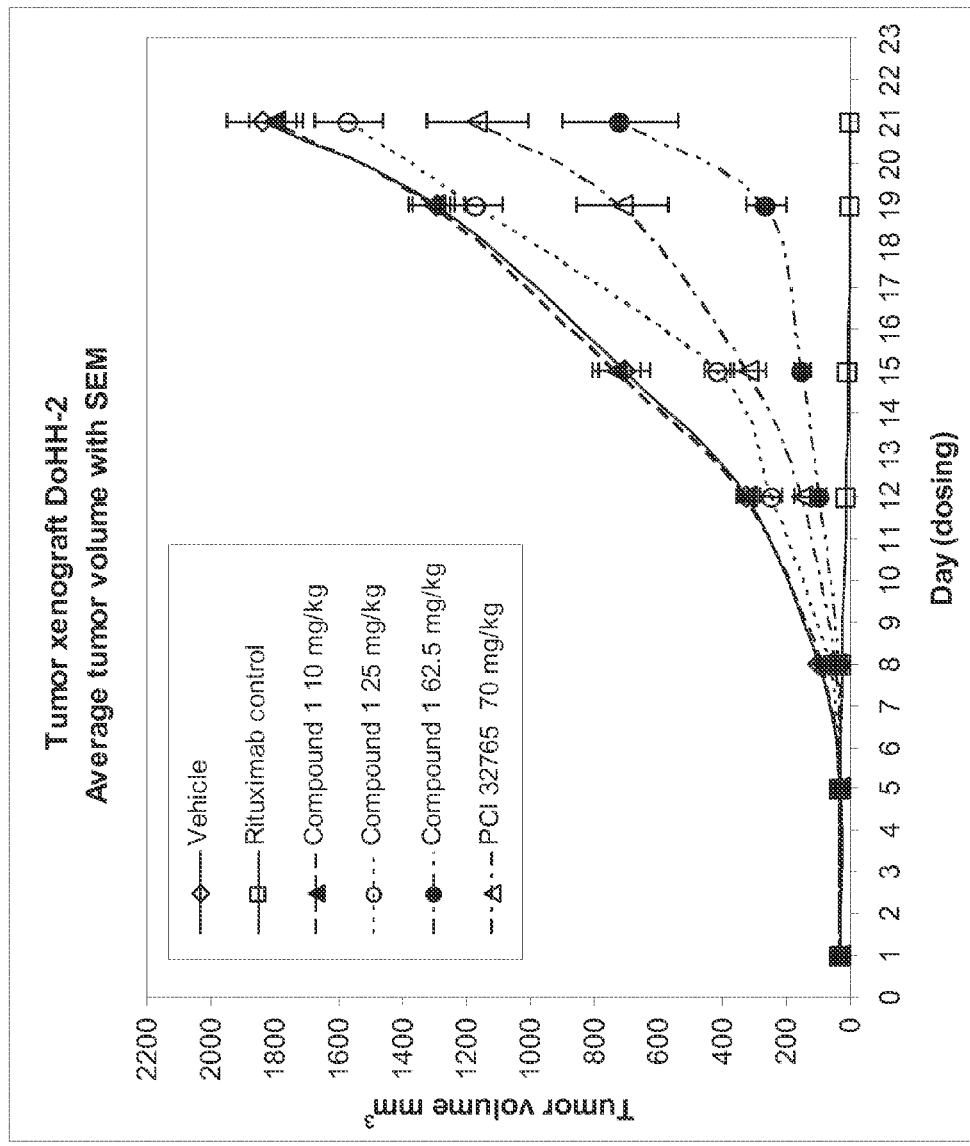
FIG. 10. Graph showing inhibition of tumor xenograft growth by various treatments. Rituximab was dosed intravenously on a bi-weekly schedule at a concentration of 20 mg/kg starting on day 3.

Activity of Compound 1 was evaluated for efficacy in a mouse in vivo tumor model using DoHH-2 cells. Briefly 1 million cells were implanted subcutaneously in 20-25 gm female SCID mice. The mice were allowed to recover and treatment was initiated 3 days later. One group was treated with vehicle alone while the other groups were treated with Compound 1 at 3 doses (10, 25 and 62.5 mg/kg) administered via intraperitoneal (IP) route daily for 21 days. Dosing of the 62.5 mg/kg group was terminated on day 17 due to mortality of 2 animals on this day. For comparison one group was treated with 70 mg/kg of the selective BTK inhibitor, PCI-32765, Vehicle alone and treatment with rituximab were used as negative and positive controls, respectively. Rituximab was dosed intravenously on a bi-weekly schedule at a concentration of 20 mg/kg starting on day 3 Tumor growth was evaluated by measurement with calipers twice weekly and tumor volume was calculated using the formula Volume=length×width (see FIG. 10). The highest dose of the compound used (62.5 mg/kg/day) was at an estimated maximal tolerated dose. The highest dose significantly inhibited tumor growth as shown by the P values for day 15, 19 and 21 (see Table 11). The last 2 measurements for the 62.5 mg/kg group were from the surviving animals that had not received compound from day 17 to 21. Hence, the rapid increase in tumor volume observed at day 21 compared to day 19 may be due to the lack of compound in this high dose group between these days. The tumor volumes for this group on days 19 and 21 are statistically significantly different from the vehicle control. Thus amino naphthyridinones can be used to inhibit tumor growth.

TABLE 11

| | Compound 1 | | |
|---|---|---|---|
| P-value | Vehicle vs. 10 mg/kg | Vehicle vs. 25 mg/kg | Vehicle vs. 62.5 mg/kg |
| Day 12 | NS | NS | *** |
| Day 15 | NS | ** | *** |
| Day 19 | NS | NS | *** |
| Day 21 | NS | NS | *** |

P value > 0.05 Not significant NS
0.01 < P < 0.05 significant *
0.001 < P < 0.01 very significant **
P < 0.001 highly significant ***
n < 10 for 62.5 mg/kg Compound 1 group on day 19 and 21 ***

Example 86

Exposure to Amino Naphthyridinones Leads to Inhibition of Degranulation in Rat Basophilic Cell Line Crosslinking of IgE receptors leads to induction of intracellular signal transduction pathways and degranulation of mast cells and basophils leading to the release of histamine, serotonin and cytokines that constitutes an allergic reaction. Signal transduction pathways involving Lyn and BTK have been demonstrated to be involved in the degranulation of basophilic cells that occurs as a response to IgE-antigen interaction. One of the factors secreted on induction of degranulation is β-hexosaminidase. A colorimetric assay using 4-nitrophenyl N-acetyl-β-D-glucosaminide (Sigma-Aldrich) as a substrate was used to estimate the amount of enzyme secreted upon degranulation. In brief, RBL-2H3 (ATCC # CRL 2256) cells were plated overnight in the presence of IgE (monoclonal anti-dinitrophenyl antibody from Sigma-Aldrich). The next day, cells were treated with compounds in cell culture media, washed and treated with DNP-BSA for 1 hour (Sigma-Aldrich) in Tyrodes's buffer to induce degranulation. The level of β-hexosaminidase was analyzed in cell-free supernates and cell lysates and the amount of β-hexosaminidase released was calculated. $EC_{50}$ values were generated using varying concentrations of inhibitors. Select amino naphthyridinones were tested in this assay and inhibited the secretion of β-hexosaminidase with $EC_{50}$ ranging from <1 uM to >5 uM (Table 12). Thus amino naphthyridinones can be used to inhibit immunologic functions such as degranulation.

TABLE 12

Inhibition of degranulation

| Compound No. | Degranulation EC50 (uM) |
|---|---|
| 78 | >5 |
| 95 | 2.22 |
| 99 | 2.99 |
| 101 | 0.95 |
| 120 | 2.22 |
| 129 | >5 |
| 133 | 5.49 |
| 134 | 3.11 |
| 137 | 1.14 |

TABLE 12-continued

Inhibition of degranulation

| Compound No. | Degranulation EC50 (uM) |
|---|---|
| 142 | >5 |
| 150 | >5 |
| 152 | >5 |

The invention claimed is:

1. A compound having the structural formula of Structural Formula (I):

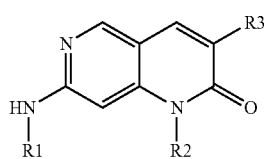

(I)

or a pharmaceutically acceptable salt thereof, wherein:
R1 is a nitrogen-containing five- or six-membered heteroaryl in which at least one ring nitrogen atom is adjacent to the carbon linking R1 to the amino group, optionally substituted with 1, 2, or 3 groups independently selected from the group consisting of:
hydroxyl;
halogen;
C1-C3 alkyl;
hydroxyl (C1-C3)alkylamino, optionally linked to R1 through a carbonyl group;
hydroxyl (C1-C3) dialkylamino, optionally linked to R1 through a carbonyl group;
C1-C3 alkylamino, optionally linked to R1 through a carbonyl group;
C1-C3 dialkylamino, optionally linked to R1 through a carbonyl group;
(C1-C3)alkylamino(C1-C3)alkyl, optionally linked to R1 through a carbonyl group;
(C1-C3)dialkylamino(C1-C3)alkyl, optionally linked to R1 through a carbonyl group;
(C1-C3)alkylamino(C2-C3)alkoxyl, optionally linked to R1 through a carbonyl group;
(C1-C3) dialkylamino(C2-C3)alkoxyl, optionally linked to R1 through a carbonyl group;
(C1-C3)alkylamino(C2-C3)alkylamino, optionally linked to R1 through a carbonyl group;
(C1-C3)dialkylamino(C2-C3)alkylamino, optionally linked to R1 through a carbonyl group;
(C1-C3)alkylamino(C2-C3)dialkylamino, optionally linked to R1 through a carbonyl group;
(C1-C3)dialkylamino(C2-C3)dialkylamino, optionally linked to R1 through a carbonyl group;
(C1-C3)alkoxyl(C2-C3)alkylamino, optionally linked to R1 through a carbonyl group;
(C1-C3)alkoxyl(C2-C3)dialkylamino, optionally linked to R1 through a carbonyl group; and
a three- to six-member heterocyclic ring containing 1 or 2 heteroatoms selected from O, N, and S; and, independently,
(1) optionally is substituted with (C1-C3) alkyl, (C1-C3) hydroxylalkyl, (C1-C3) alkoxyl (C1-C3) alkyl, or (C1-C3)alkylamino(C1-C3)alkyl, and (2) optionally is linked to the five- or six-member heteroaryl through a carbonyl group;
when R1 is substituted then R2 is:
hydrogen;
C1-C6 alkyl, optionally substituted with 1, 2, or 3 groups selected from hydroxyl, methoxyl, ethoxyl, methylamino, N,N-dimethyl amino, ethylamino, N,N-diethylamino, and methylsulfanyl;
a three- to six-member cycloalkyl, optionally substituted with 1, 2, or 3 groups selected from hydroxyl, methoxyl, ethoxyl, methylamino, N,N-dimethyl amino, ethylamino, N,N-diethylamino, and methylsulfanyl;
a three- to six-member heterocyclic ring, optionally substituted with 1, 2, or 3 groups selected from hydroxyl, C1-C3 alkyl, methoxyl, ethoxyl, methylamino, N,N-dimethyl amino, ethylamino, N,N-diethylamino, and methylsulfanyl;
phenyl, optionally substituted with 1, 2, or 3 groups selected from hydroxyl, methoxyl, ethoxyl, methylamino, N,N-dimethyl amino, ethylamino, N,N-diethylamino, and methylsulfanyl; or
heteroaryl, optionally substituted with 1, 2, or 3 groups selected from hydroxyl, methoxyl, ethoxyl, methylamino, N,N-dimethyl amino, ethylamino, N,N-diethylamino, and methylsulfanyl;
when R1 is unsubstituted then R2 is:
hydrogen;
C2-C6 alkyl, optionally substituted with 1, 2, or 3 groups selected from hydroxyl, methoxyl, ethoxyl, methylamino, N,N-dimethyl amino, ethylamino, N,N-diethylamino, and methylsulfanyl;
a three- to six-member cycloalkyl, optionally substituted with 1, 2, or 3 groups selected from hydroxyl, methoxyl, ethoxyl, methylamino, N,N-dimethyl amino, ethylamino, N,N-diethylamino, and methylsulfanyl;
a three- to six-member heterocyclic ring, optionally substituted with 1, 2, or 3 groups selected from hydroxyl, C1-C3 alkyl, methoxyl, ethoxyl, methylamino, N,N-dimethyl amino, ethylamino, N,N-diethylamino, and methylsulfanyl;
phenyl, optionally substituted with 1, 2, or 3 groups selected from hydroxyl, methoxyl, ethoxyl, methylamino, N,N-dimethyl amino, ethylamino, N,N-diethylamino, and methylsulfanyl; or
heteroaryl, optionally substituted with 1, 2, or 3 groups selected from hydroxyl, methoxyl, ethoxyl, methylamino, N,N-dimethyl amino, ethylamino, N,N-diethylamino, and methylsulfonyl; and
R3 is:
halogen;
C1-C6 alkyl;
C1-C6 hydroxylalkyl;
C1-C6 alkylcarbonyl;
C1-C6 perfluoroalkyl;
C3-C6 cycloalkyl;
C2-C6 alkenyl, optionally substituted with 1, 2, or 3 substituents selected from the group consisting of C1-C3 alkoxyl, C1-C3 alkoxylcarbonyl, and trifluoromethyl;
C2-C6 alkynyl, optionally substituted with 1, 2, or 3 substituents selected from the group consisting of C1-C3 alkoxyl, hydroxyl, C1-C6 alkyl, trifluoromethyl;

phenyl, optionally substituted with 1, 2, or 3 substituents selected from the group consisting of halogen, C1-C3 alkoxyl, and trifluoromethyl; and
a five- to six-member heteroaryl, optionally substituted with 1, 2, or 3 substituents selected from the group consisting of halogen, C1-C3 alkoxyl, and trifluoromethyl.

2. The compound of claim 1 having an $IC_{50} \leq 1$ µM for at least one tyrosine kinase selected from BTK, SRC, and LYN.

3. The compound of claim 2 having an $IC_{50} \leq 1$ µM for at least two tyrosine kinases selected from BTK, SRC, and LYN.

4. The compound of claim 3 having an $IC_{50} \leq 1$ µM for BTK, SRC, and LYN.

5. The compound of claim 2 having an $IC_{50} \leq 0.1$ µM for at least one tyrosine kinase selected from BTK, SRC, and LYN.

6. The compound of claim 5 having an $IC_{50} \leq 0.1$ µM for at least two tyrosine kinases selected from BTK, SRC, and LYN.

7. The compound of claim 6 having an $IC_{50} \leq 0.1$ µM for BTK, SRC, and LYN.

8. The compound of claim 2, wherein $IC_{50}$ is determined by measuring consumption of ATP or using an isotopic detection of phosphorylation.

9. The compound of claim 8, wherein $IC_{50}$ is determined by measuring consumption of ATP and the consumption of ATP determined through luminescence.

10. The compound of claim 8, wherein $IC_{50}$ is determined using an isotopic detection of phosphorylation and wherein said isotopic detection comprises radiologic detection of $^{32}P$.

11. The compound of claim 1 having a tissue culture $EC_{50} \leq 10$ µM or having a tissue culture $EC_{50} \leq 1$ µM.

12. The compound of claim 11, wherein the $EC_{50}$ is determined:
    (a) using a dasatinib-resistant cell line; or
    (b) using a dasatinib-resistant cell line, wherein the dasatinib-resistant cell line is Ramos;
    (c) using a dasatinib-sensitive cell line; or
    (d) using a dasatinib-sensitive cell line, wherein the dasatinib-sensitive cell line is DoHH2.

13. The compound of claim 2 having $IC_{50} \leq 1$ µM for non-tyrosine kinases.

14. The compound of claim 2 having $IC_{50} \leq 1$ µM for Aurora kinases, MAPP kinases, and CDK kinases.

15. The compound of claim 1 capable of inducing G1 arrest.

16. A pharmaceutical composition comprising:
    (a) a pharmaceutically acceptable vehicle; and
    (b) a compound of claim 1 or a pharmaceutically acceptable salt thereof.

17. A method of inhibiting kinase activity, comprising contacting a Bruton's tyrosine kinase with a compound of claim 1 or a pharmaceutically acceptable salt thereof, whereby kinase activity of the Bruton's tyrosine kinase is inhibited.

18. The method of claim 17, wherein the contacting occurs:
    (a) in a cell-free system;
    (b) in a cell;
    (c) in a cell in vitro; or
    (d) in a cell in a patient.

19. The compound of claim 1, wherein R1 is optionally substituted pyridinyl, optionally substituted pyrimidinyl, optionally substituted pyridazinyl, optionally substituted thiazolyl or optionally substituted imidazolyl.

20. The compound of claim 19, wherein R1 is substituted with 1, 2 or 3 groups selected from halogen, C1-C3 alkyl or (C1-C3)dialkylamino(C2-C3)alkoxyl.

21. The compound of claim 1, wherein R2 is H, optionally substituted C1-C3 alkyl, an optionally substituted 3-6 membered cycloalkyl ring, an optionally substituted 3-6 membered heterocyclic ring, optionally substituted phenyl or optionally substituted pyridinyl.

22. The compound of claim 21, wherein the C1-C3 alkyl is substituted with methoxyl or N,N-dimethylamino.

23. The compound of claim 1, wherein R3 is phenyl, optionally substituted with 1, 2 or 3 substituents selected from the group consisting of halogen, C1-C3 alkoxyl and trifluoromethyl.

24. The compound of claim 1, wherein the compound has one of the following structures:

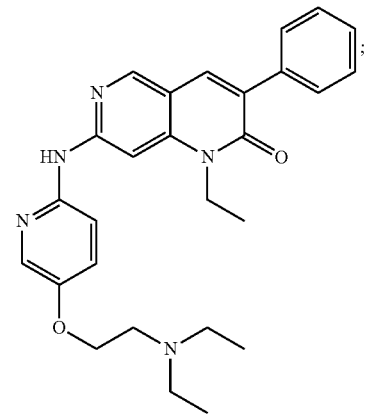

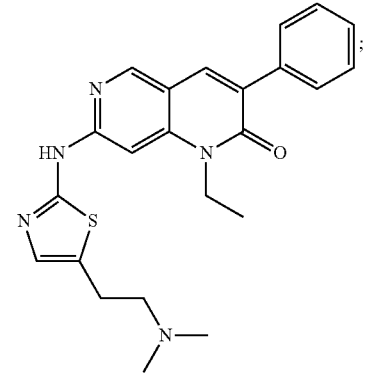

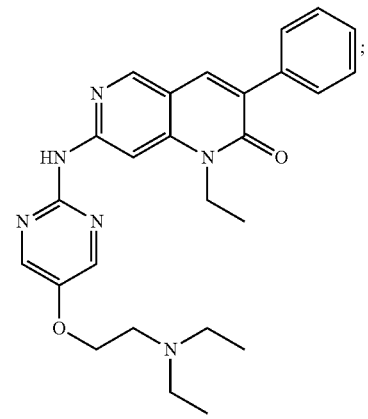

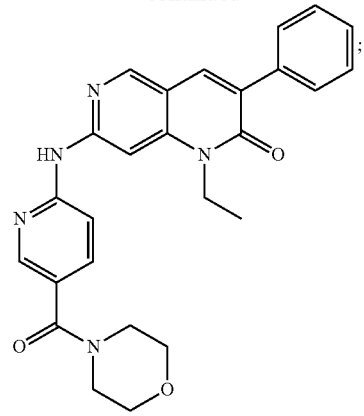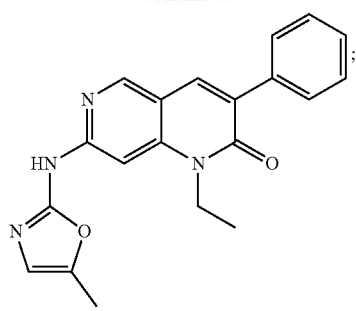

327
-continued
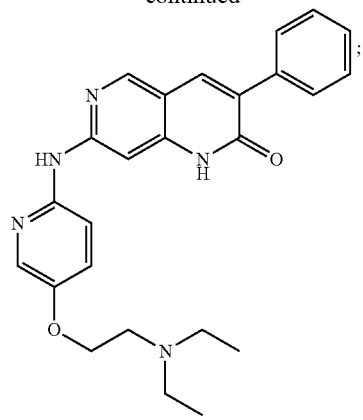
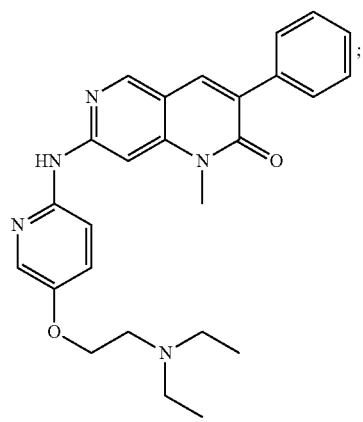
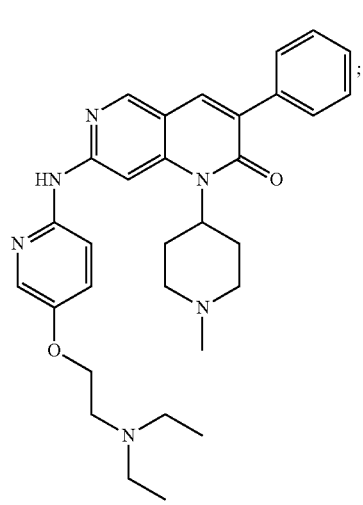
328
-continued
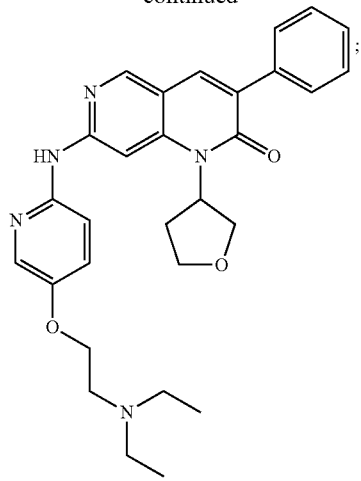
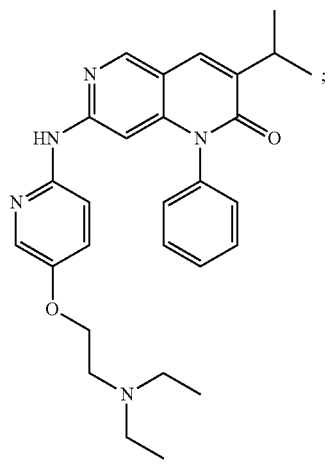
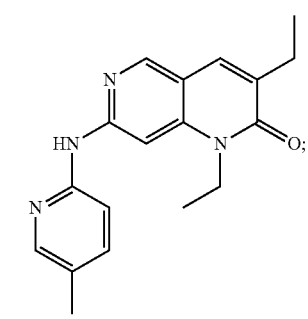
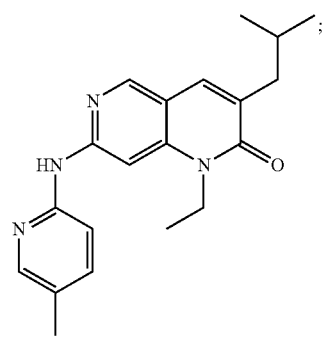

329
-continued
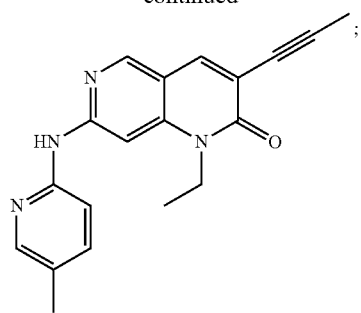
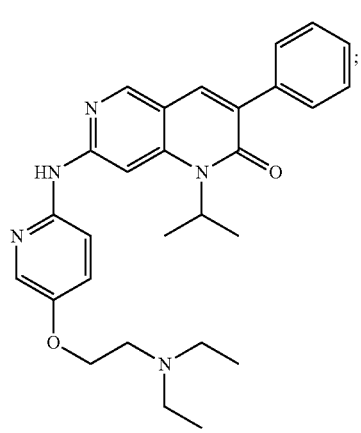
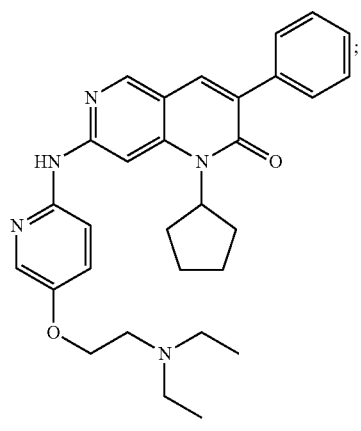
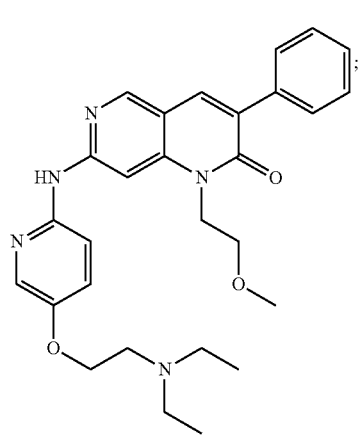
330
-continued
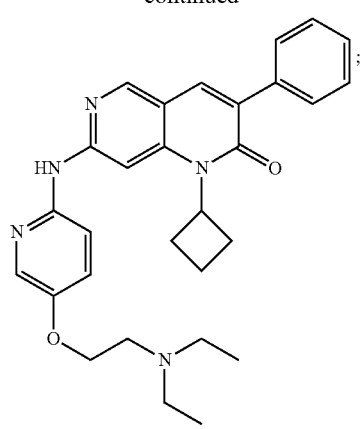
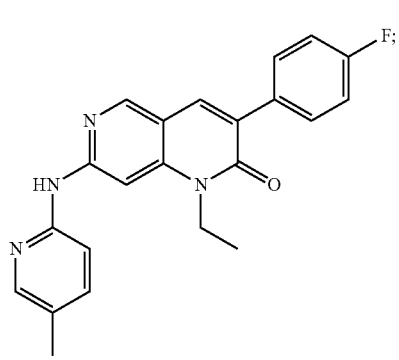
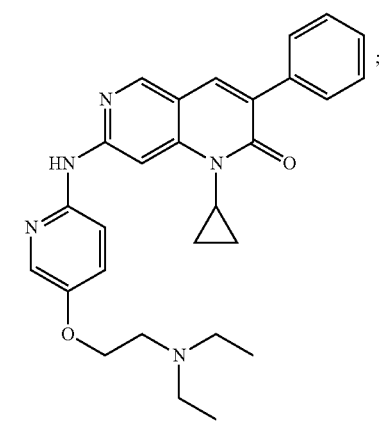
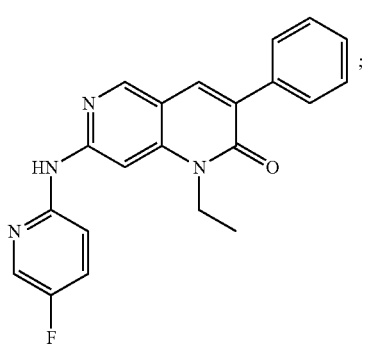

331
-continued
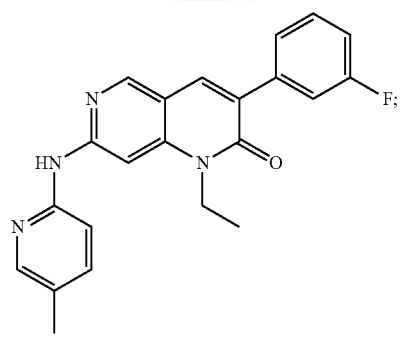
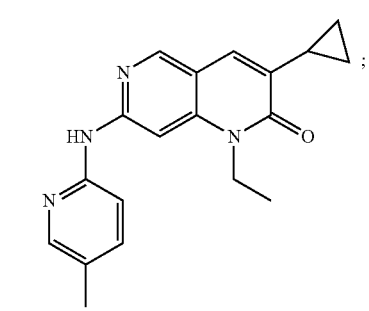
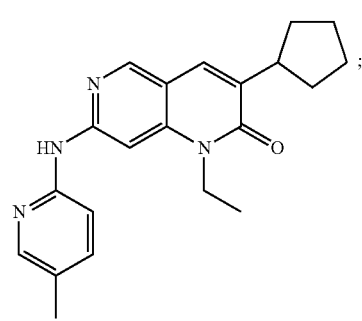
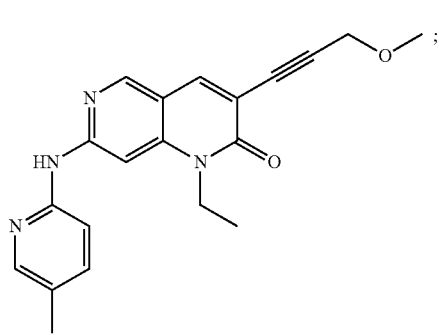
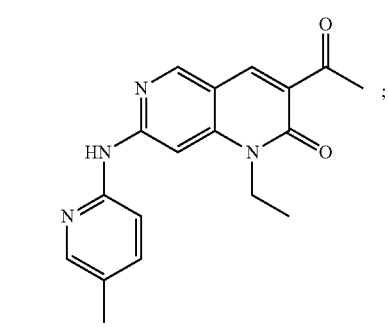
332
-continued
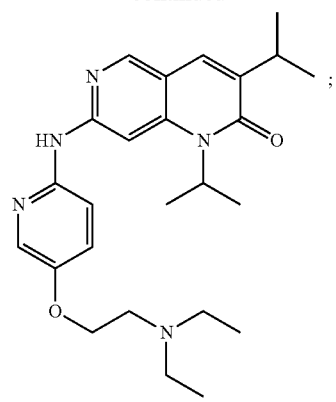
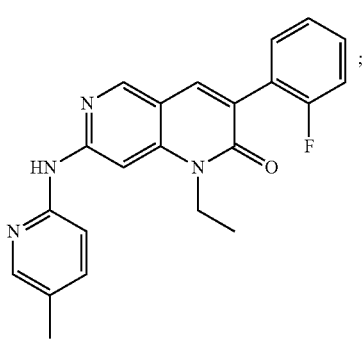
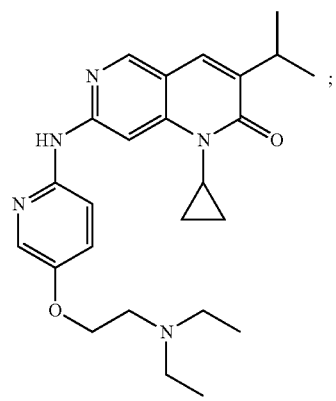
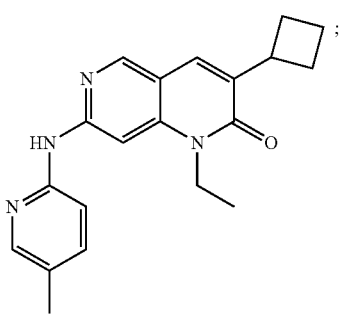

333
-continued
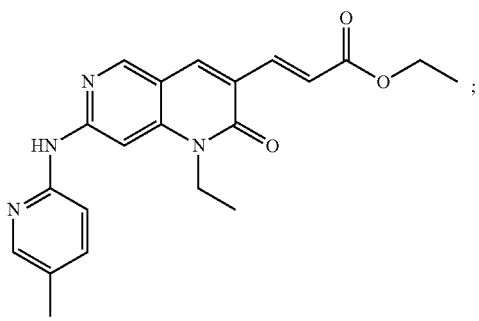
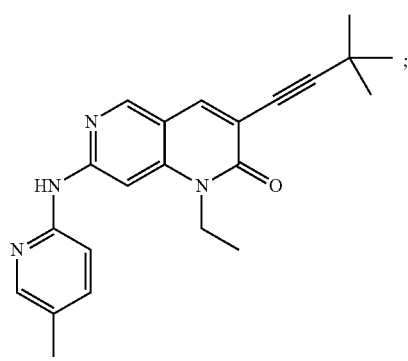
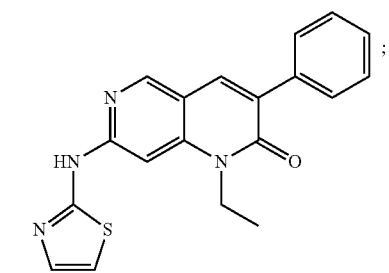
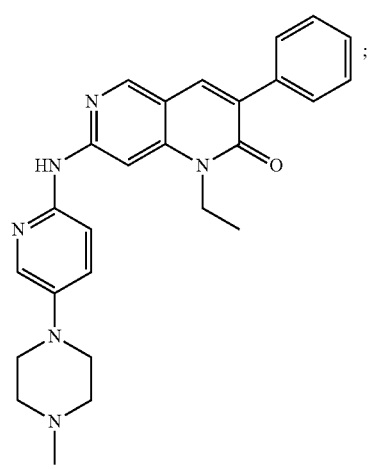
334
-continued
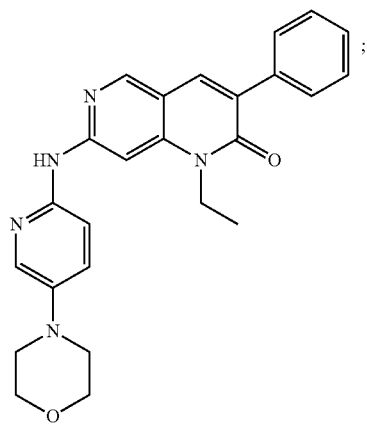
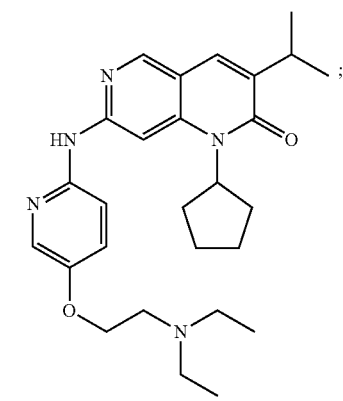
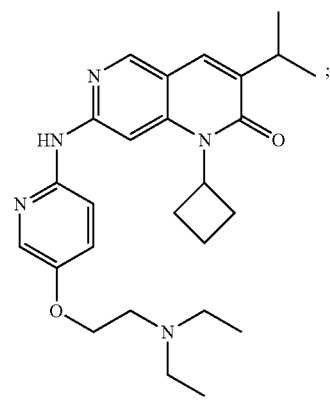
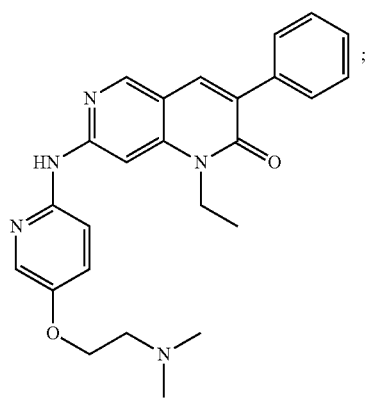

335
-continued
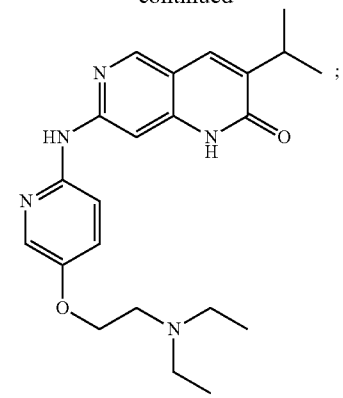
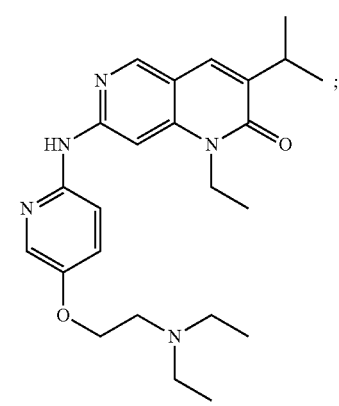
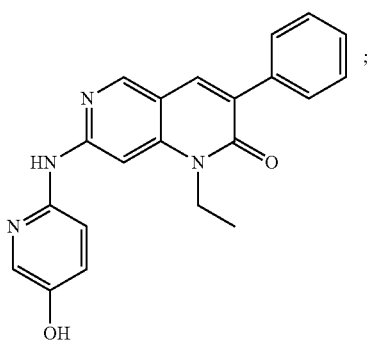
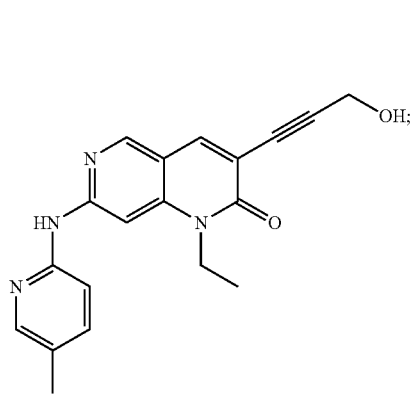
336
-continued
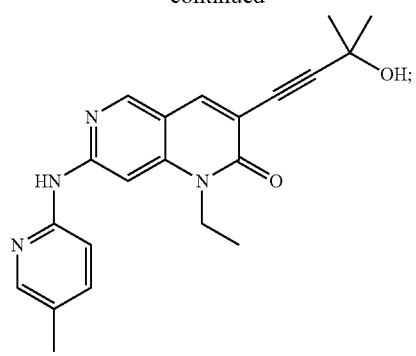
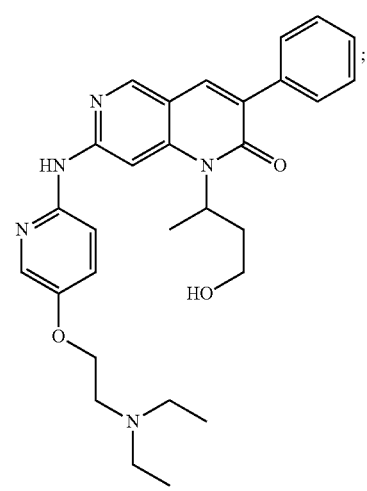
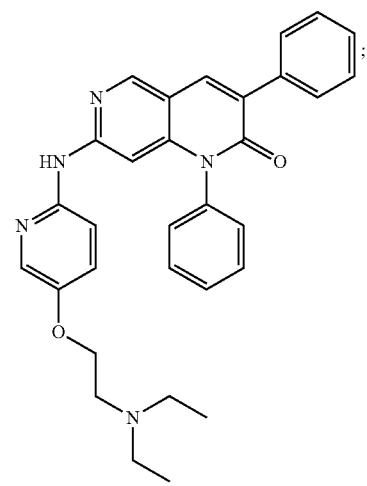
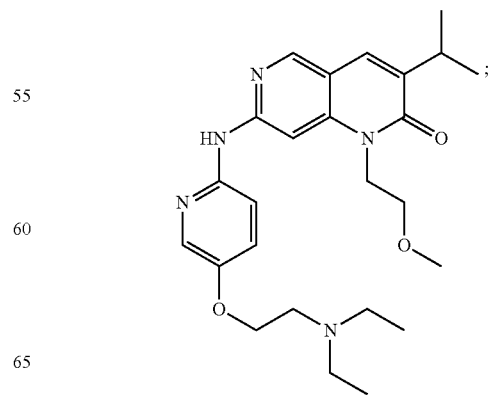

337
-continued
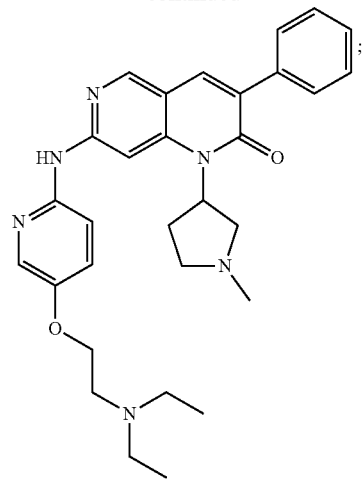
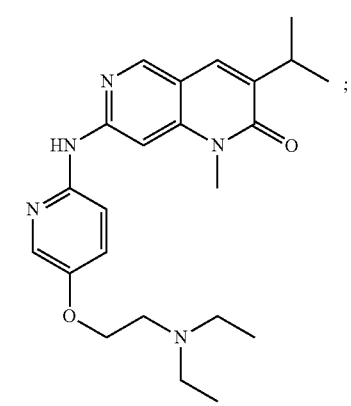
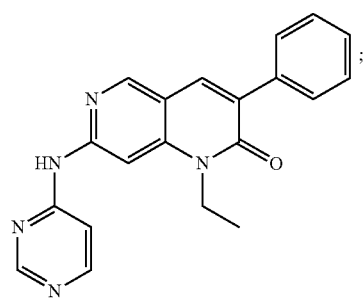
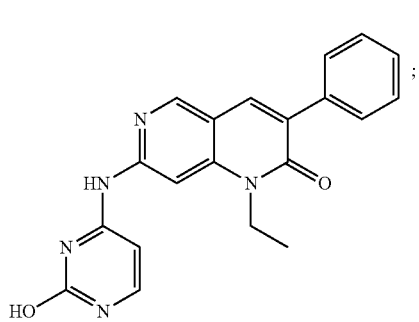
338
-continued
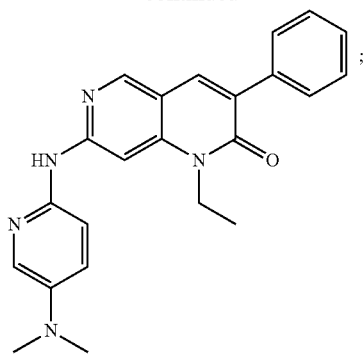
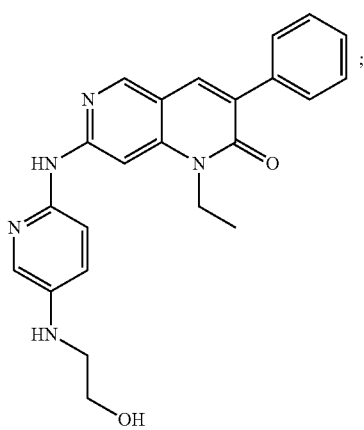
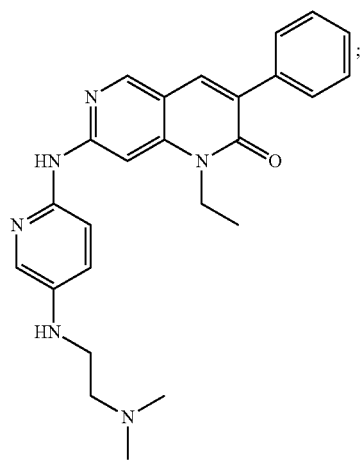
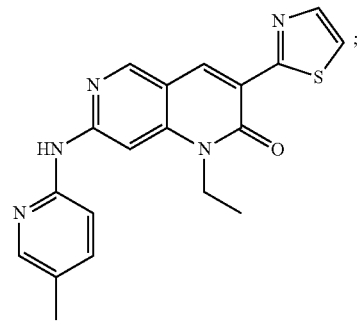

339
-continued

340
-continued

-continued
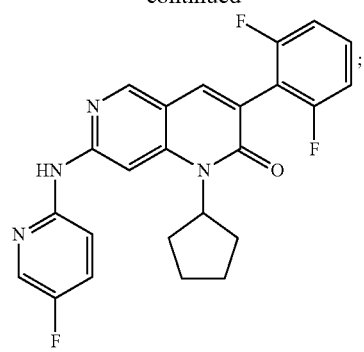
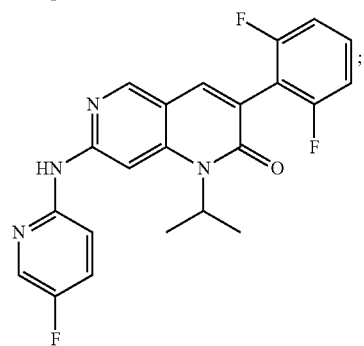
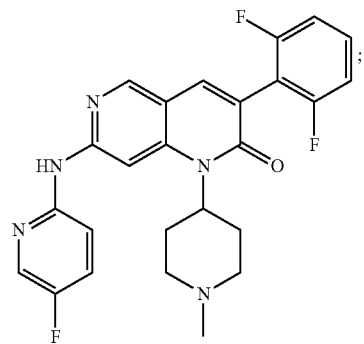
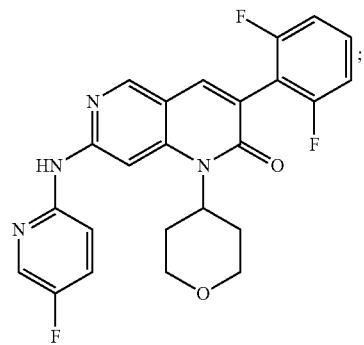
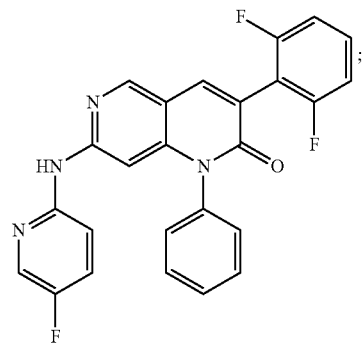
-continued
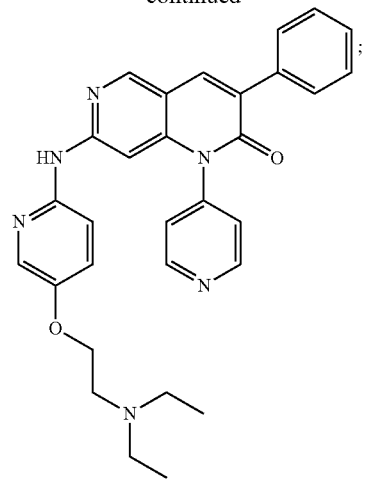
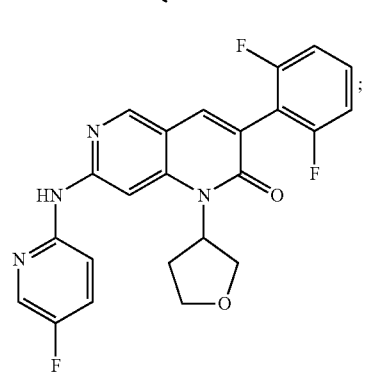
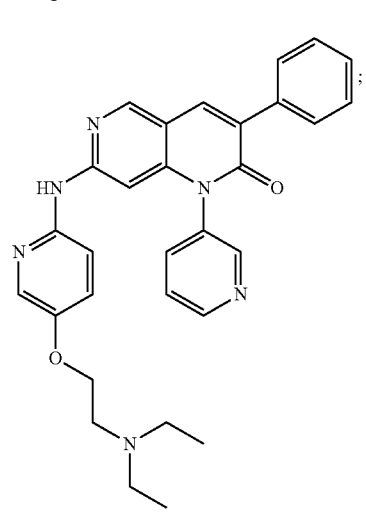
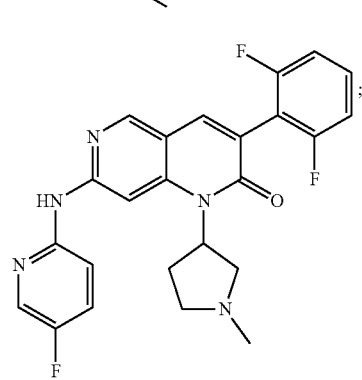

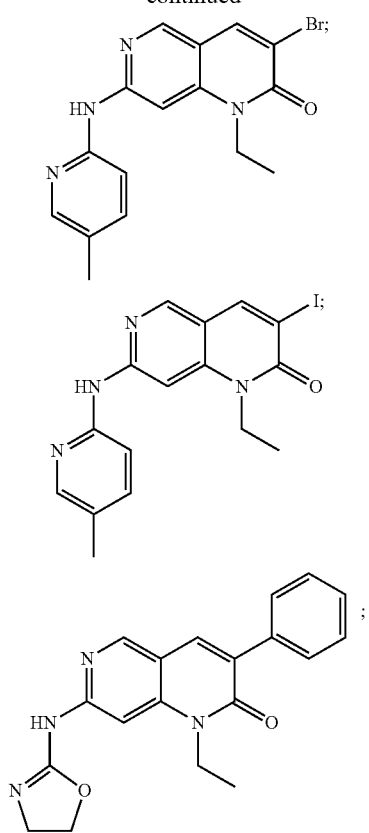
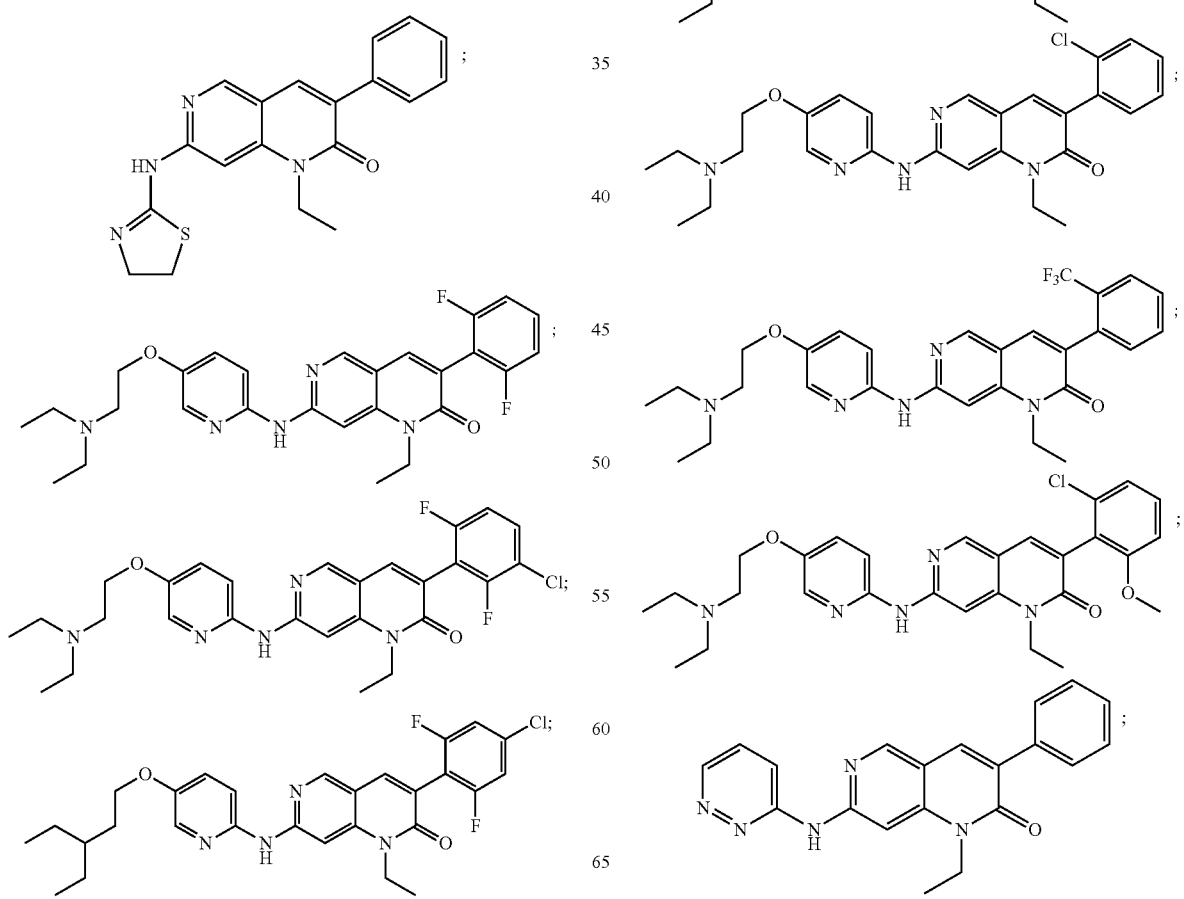

345
-continued
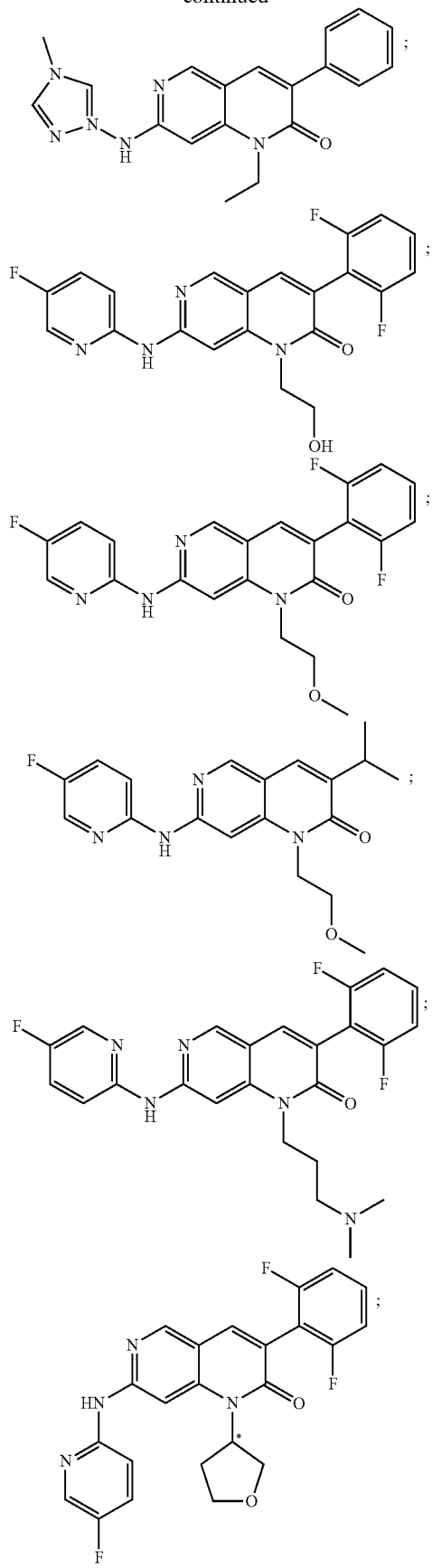
346
-continued
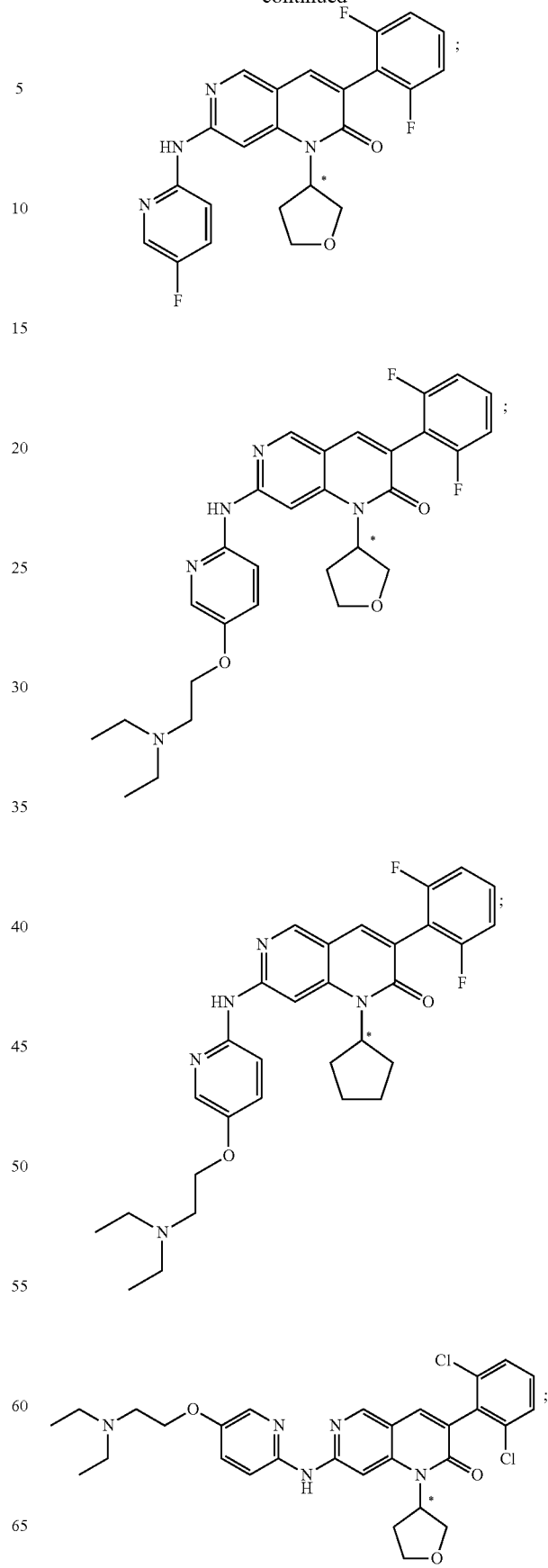

347
-continued
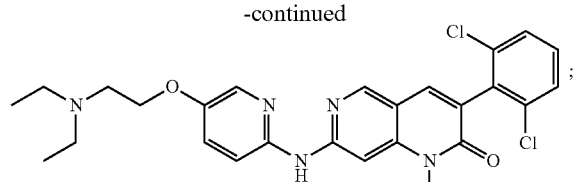
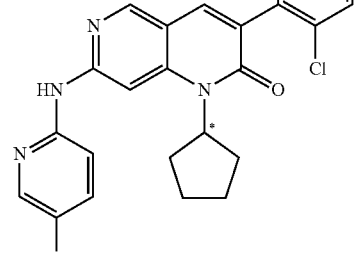
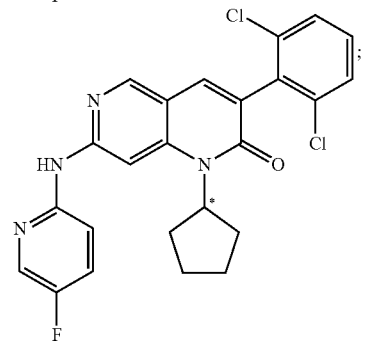
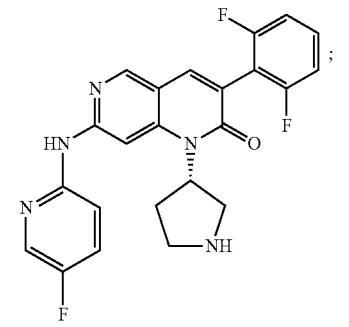
348
-continued
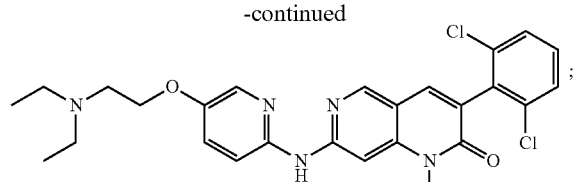
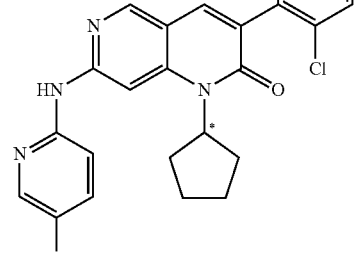
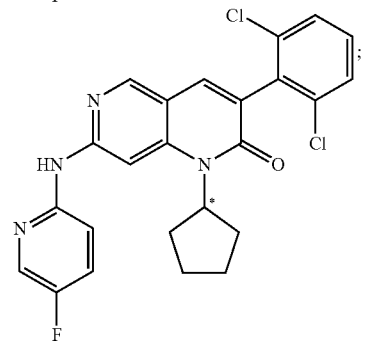
* * * * *

UNITED STATES PATENT AND TRADEMARK OFFICE
CERTIFICATE OF CORRECTION

PATENT NO. : 9,493,454 B2
APPLICATION NO. : 14/431476
DATED : November 15, 2016
INVENTOR(S) : Qingping Zeng et al.

It is certified that error appears in the above-identified patent and that said Letters Patent is hereby corrected as shown below:

In the Claims

Column 343, Lines 60-65:

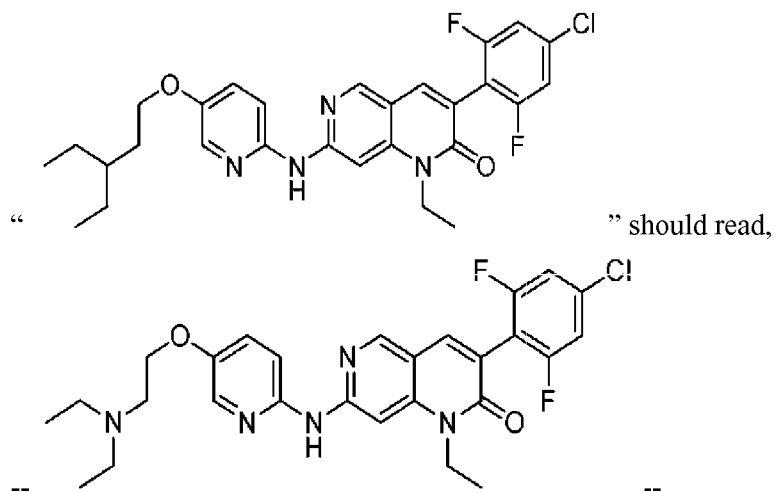

Column 345, Lines 1-10:

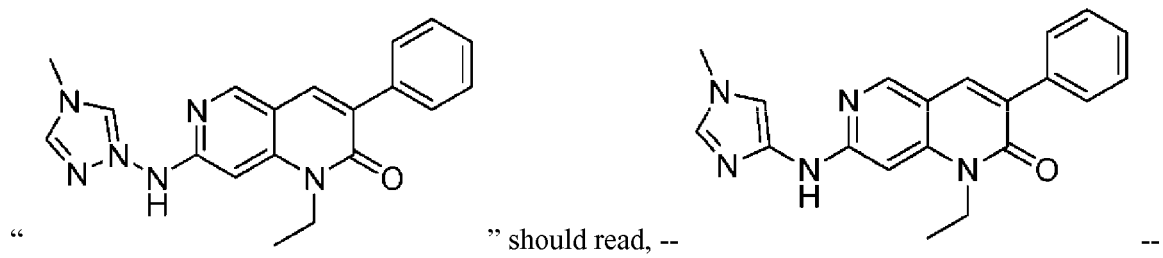

Signed and Sealed this
Sixth Day of June, 2017

Michelle K. Lee
*Director of the United States Patent and Trademark Office*

CERTIFICATE OF CORRECTION (continued)
U.S. Pat. No. 9,493,454 B2

Page 2 of 2

Column 346, Lines 37-55:

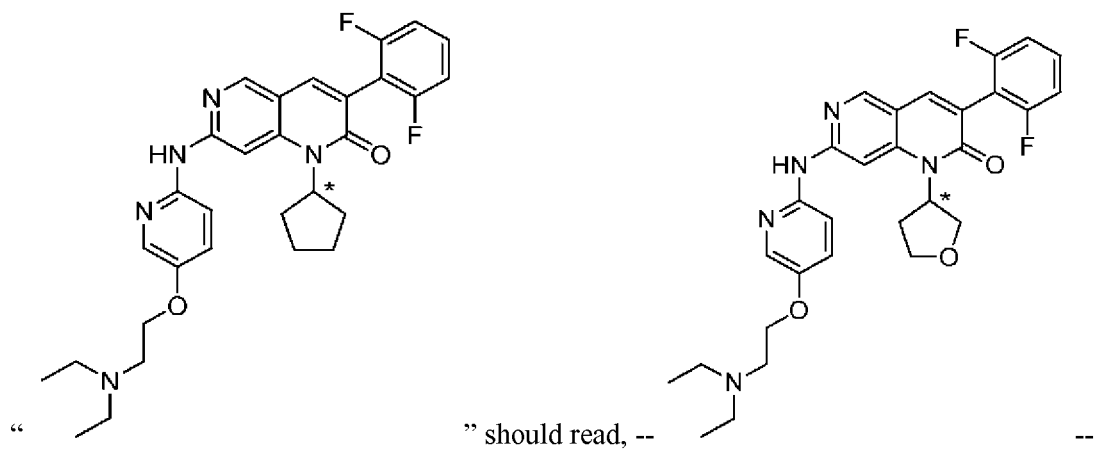

" should read, --  --

Column 347, Lines 25-35:

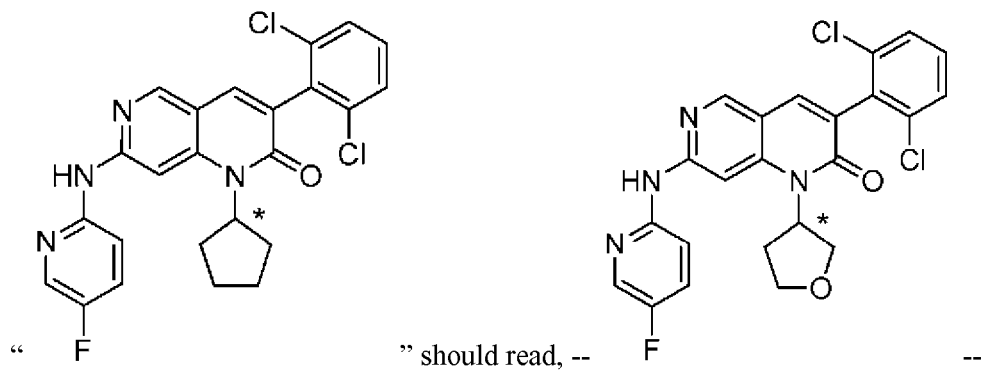

" should read, --  --